United States Patent
Singh et al.

(10) Patent No.: US 9,682,976 B2
(45) Date of Patent: Jun. 20, 2017

(54) PROTEIN KINASE C INHIBITORS AND USES THEREOF

(71) Applicant: Rigel Pharmaceuticals, Inc., South San Francisco, CA (US)

(72) Inventors: Rajinder Singh, Belmont, CA (US); Matthew Duncton, San Bruno, CA (US); Jing Zhang, Mercer Island, WA (US); Salvador Alvarez, Fremont, CA (US); Kin Tso, San Francisco, CA (US); Sacha Holland, San Francisco, CA (US); Rose Yen, San Francisco, CA (US); Rao Kolluri, Foster City, CA (US); Thilo Heckrodt, San Francisco, CA (US); Yan Chen, Foster City, CA (US); Esteban Masuda, Menlo Park, CA (US); Hui Li, Santa Clara, CA (US); Donald G. Payan, Hillsborough, CA (US); Ryan Kelley, Pacifica, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/056,535

(22) Filed: Feb. 29, 2016

(65) Prior Publication Data
US 2016/0257681 A1    Sep. 8, 2016

Related U.S. Application Data

(62) Division of application No. 13/857,028, filed on Apr. 4, 2013, now Pat. No. 9,321,763.

(60) Provisional application No. 61/620,232, filed on Apr. 4, 2012, provisional application No. 61/783,647, filed on Mar. 14, 2013.

(51) Int. Cl.
| | |
|---|---|
| *A61K 31/5383* | (2006.01) |
| *A61K 31/5386* | (2006.01) |
| *A61K 31/506* | (2006.01) |
| *A61K 31/553* | (2006.01) |
| *A61K 31/538* | (2006.01) |
| *A61K 31/5377* | (2006.01) |
| *C07D 519/00* | (2006.01) |
| *C07D 471/04* | (2006.01) |
| *C12Q 1/48* | (2006.01) |
| *C12N 9/12* | (2006.01) |

(52) U.S. Cl.
CPC .......... *C07D 471/04* (2013.01); *A61K 31/506* (2013.01); *A61K 31/538* (2013.01); *A61K 31/5377* (2013.01); *A61K 31/5383* (2013.01); *A61K 31/5386* (2013.01); *A61K 31/553* (2013.01); *C07D 519/00* (2013.01); *C12N 9/12* (2013.01); *C12Q 1/485* (2013.01); *C12Y 207/11013* (2013.01)

(58) Field of Classification Search
CPC ............ A61K 31/5383; A61K 31/5386; A61K 31/5377; A61K 31/506; A61K 31/538; C07D 519/00; C07D 471/04; C12N 9/12; C12Q 1/48
See application file for complete search history.

(56) References Cited

U.S. PATENT DOCUMENTS

| | | | |
|---|---|---|---|
| 5,843,935 A | 12/1998 | Heath et al. | |
| 6,235,746 B1 | 5/2001 | Davis et al. | |
| 7,329,671 B2 * | 2/2008 | Singh .................. | A61K 31/519 514/275 |
| 9,149,475 B2 * | 10/2015 | Singh .................. | C07D 401/12 |
| 9,169,249 B2 * | 10/2015 | Singh .................. | C07D 471/04 |
| 9,181,222 B2 * | 11/2015 | Holland .............. | C07D 401/14 |
| 9,321,763 B2 * | 4/2016 | Singh .................. | C07D 471/04 |
| 2005/0054701 A1 | 3/2005 | Wallace et al. | |
| 2010/0130486 A1 | 5/2010 | Singh et al. | |
| 2010/0130501 A1 | 5/2010 | Li et al. | |
| 2010/0204208 A1 | 8/2010 | Singh et al. | |
| 2011/0130415 A1 | 6/2011 | Singh et al. | |
| 2012/0022092 A1 | 1/2012 | Holland et al. | |
| 2012/0028923 A1 | 2/2012 | Li et al. | |
| 2014/0275055 A1 | 9/2014 | Singh et al. | |

FOREIGN PATENT DOCUMENTS

| | | |
|---|---|---|
| WO | 2010083207 | 7/2010 |
| WO | 2010090875 | 8/2010 |
| WO | 2011068898 | 9/2011 |
| WO | 2012012619 | 1/2012 |
| WO | 2013152198 | 10/2013 |

OTHER PUBLICATIONS

King et al., (1986) "Synthesis of quinolizidines and indolizidines via an intramolecular Mannich reaction," J. Chem. Soc., Perkin Trans. 1:447-453.
Strong et al., (1973) "In Vitro Stimulation of Murine Spleen Cells Usings a Microculture System and a Multiple Automated Sample Harvester," J. Immunol. Methods, 2:279-291.
Fellah et al., (2012) "Total Synthesis of Indolizidine," Eur. J. Org. Chem, 463-465.

* cited by examiner

*Primary Examiner* — Alexander R Pagano
*Assistant Examiner* — Ebenezer O Sackey
(74) *Attorney, Agent, or Firm* — Rudy J. Ng; Carol L. Francis; Bozicevic, Field & Francis LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

55 Claims, No Drawings

PROTEIN KINASE C INHIBITORS AND USES THEREOF

CROSS-REFERENCE TO RELATED APPLICATIONS

This application is a divisional of U.S. application Ser. No. 13/857,028, filed Apr. 4, 2013, which claims priority pursuant to 35 U.S.C. §119(e) to the filing date of U.S. Provisional Application No. 61/620,232, filed Apr. 4, 2012, and U.S. Provisional Application No. 61/783,647, filed Mar. 14, 2013, the disclosures of each of which are herein incorporated by reference.

BACKGROUND

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC α, $β_i$, $β_{ii}$ and γ, contain four homologous domains (C1, C2, C3 and C4) and require calcium, phosphatidylserine, and diacylglycerol or phorbol esters for activation. Members of the "novel" or "nPKC" subfamily, PKC δ, ε, η and θ, lack the C2 homologous domain and do not require calcium for activation. Finally, members of the "atypical" or "αPKC" subfamily, PKC ζ and λ/ι, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Exemplary chemical structures are provided throughout the disclosure. By way of example, such compounds are represented by the following formula (VI):

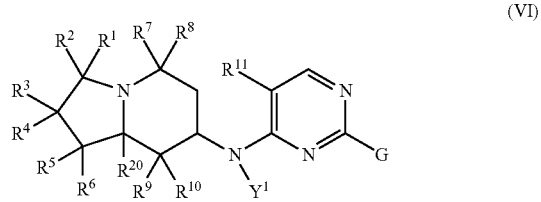

(VI)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, cycloalkyl, substituted cycloalkyl, hydroxy, alkoxy, substituted alkoxy, amino, substituted amino, carboxyl, carboxyl ester, cyano, halogen, thiol, thioalkoxy, substituted thioalkoxy, acyl, aminoacyl, nitro, alkenyl, substituted alkenyl, alkynyl, substituted alkynyl, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl;

$R^{20}$ is selected from hydrogen, alkyl, and substituted alkyl;

G is halogen or —$NY^2Ar^1$;

$Y^1$ and $Y^2$ are independently selected from hydrogen, alkyl and substituted alkyl; and $Ar^1$ is selected from aryl, substituted aryl, heteroaryl, and substituted heteroaryl;

or a salt or stereoisomer thereof.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

TERMS

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3C$—$CH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as difluoromethoxy, trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene- S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, N R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$, R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)

$NR^{80}R^{80}$, —$C(NR^{70})NR^{80}R^{80}$, —$OC(O)R^{70}$, —$OC(S)R^{70}$, —$OC(O)$ $O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of formulae I-X, shown below. Pharmaceutical compositions and methods of the present disclosure also contemplate compounds of formulae I-X.

Formula I

In one of its composition aspects, the present embodiments provide a compound of formula (I):

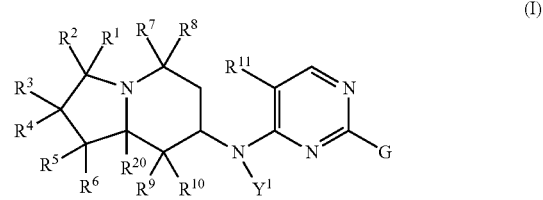

(I)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

G is halogen or —NY$^2$Ar$^1$;

$Y^1$ and $Y^2$ are independently selected from hydrogen and alkyl; and

Ar$^1$ is selected from aryl, substituted aryl, heteroaryl, and substituted heteroaryl;

or a salt or stereoisomer thereof.

In formula (I), G is halogen or —NY$^2$Ar$^1$. In certain embodiments, G is halogen. In certain embodiments, G is —NY$^2$Ar$^1$.

In formula (I), Ar$^1$ is selected from aryl, substituted aryl, heteroaryl, and substituted heteroaryl. In certain embodiments, Ar$^1$ is aryl or substituted aryl. In certain embodiments, Ar$^1$ is aryl. In certain embodiments, Ar$^1$ is substituted aryl. In certain embodiments, Ar$^1$ is heteroaryl or substituted heteroaryl. In certain embodiments, Ar$^1$ is heteroaryl. In certain embodiments, Ar$^1$ is substituted heteroaryl.

In certain embodiments, a compound of formula (I) is of the formula:

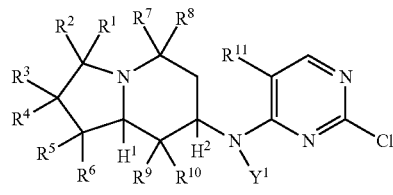

wherein
H¹ and H² are hydrogen.

In certain embodiments, H¹ and H² are hydrogen with cis relative configuration. In certain embodiments, H¹ and H² are hydrogen with trans relative configuration.

Formula II

In one of its composition aspects, the present embodiments provide a compound of formula (II):

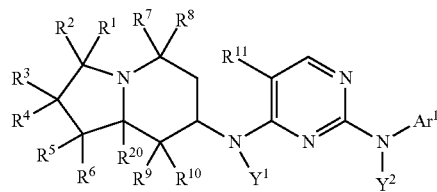

wherein
$R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $Ar^1$ is selected from aryl, substituted aryl, heteroaryl, and substituted heteroaryl;

or a salt or stereoisomer thereof.

In one of its composition aspects, the present embodiments provide a compound of formula (IIa):

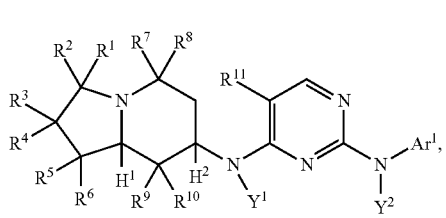

wherein
$R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$Ar^1$ is selected from aryl, substituted aryl, heteroaryl, and substituted heteroaryl; and H¹ and H² are hydrogen with cis relative configuration;

or a salt or stereoisomer thereof.

In one of its composition aspects, the present embodiments provide a compound of formula (IIb):

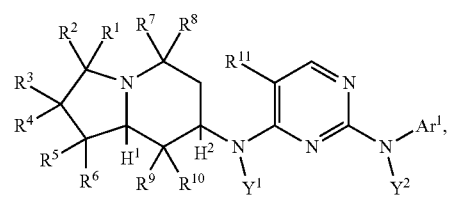

wherein
$R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y$^1$ and Y$^2$ are independently selected from hydrogen and alkyl;

Ar$^1$ is selected from aryl, substituted aryl, heteroaryl, and substituted heteroaryl; and H$^1$ and H$^2$ are hydrogen with trans relative configuration. or a salt or stereoisomer thereof.

Reference to formula (II) is meant to include compounds of formula (II) and (IIa)-(IIb).

In formulae (II), Ar$^1$ is selected from aryl, substituted aryl, heteroaryl, and substituted heteroaryl. In certain embodiments, Ar$^1$ is aryl or substituted aryl. In certain embodiments, Ar$^1$ is aryl. In certain embodiments, Ar$^1$ is substituted aryl. In certain embodiments, Ar$^1$ is heteroaryl or substituted heteroaryl. In certain embodiments, Ar$^1$ is heteroaryl. In certain embodiments, Ar$^1$ is substituted heteroaryl.

In formula (IIa) and (IIb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula III

In one of its composition aspects, the present embodiments provide a compound of formula (III):

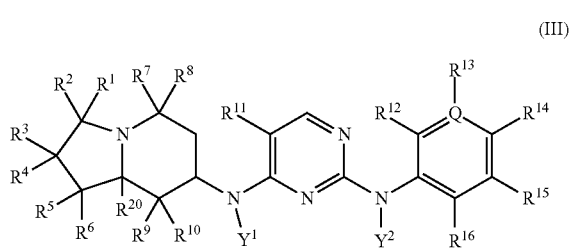

(III)

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

R$^{20}$ is selected from hydrogen, alkyl, and substituted alkyl;

Y$^1$ and Y$^2$ are independently selected from hydrogen and alkyl;

Q is C or N; and

R$^{12}$, R$^{13}$, R$^{14}$, R$^{15}$, and R$^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or R$^{14}$ and R$^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (IIIa):

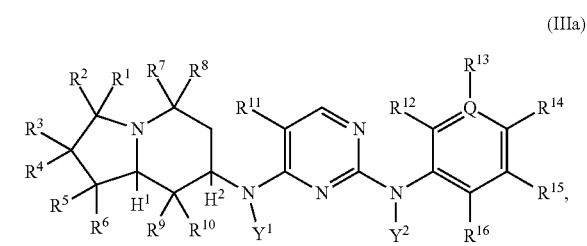

(IIIa)

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

Q is C or N;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration; or a salt or stereoisomer thereof.

In one of its composition aspects, the present embodiments provide a compound of formula (IIIb):

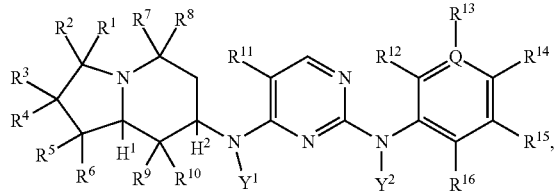

(IIIb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

Q is C or N;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration; or a salt or stereoisomer thereof.

Reference to formula (III) is meant to include compounds of formula (III) and (IIIa)-(IIIb).

In formula (III), Q is C or N. In certain embodiments, Q is C. In certain embodiments, Q is N.

In formula (IIIa) and (IIIb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula IV

In one of its composition aspects, the present embodiments provide a compound of formula (IV):

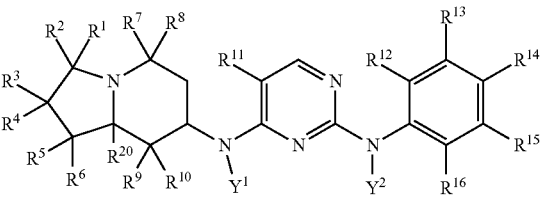

(IV)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (IVa):

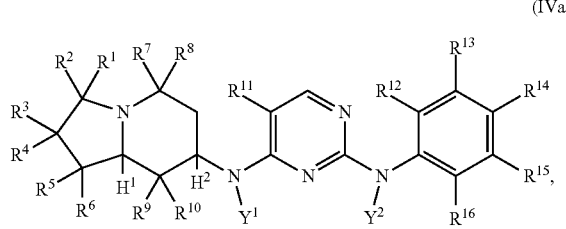

(IVa)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration;

or a salt or stereoisomer thereof.

In one of its composition aspects, the present embodiments provide a compound of formula (IVb):

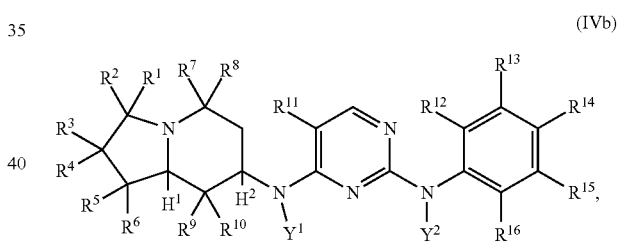

(IVb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration;

or a salt or stereoisomer thereof.

Reference to formula (IV) is meant to include compounds of formula (IV) and (IVa)-(IVb).

In formula (IVa) and (IVb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula V

In one of its composition aspects, the present embodiments provide a compound of formula (V):

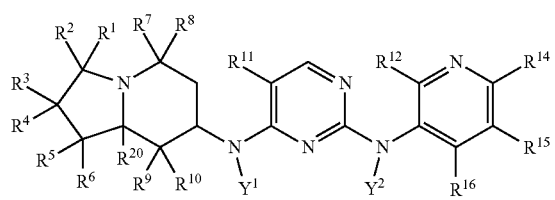

(V)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (Va):

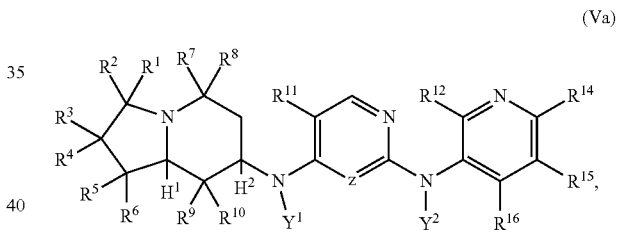

(Va)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration; or a salt or stereoisomer thereof.

In one of its composition aspects, the present embodiments provide a compound of formula (Vb):

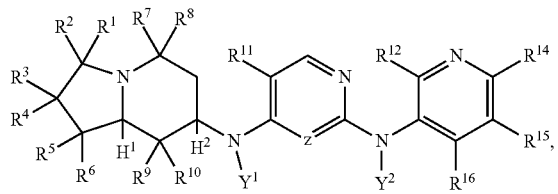

(Vb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen and alkyl;

$R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration; or a salt or stereoisomer thereof.

Reference to formula (V) is meant to include compounds of formula (V) and (Va)-(Vb)

In formula (Va) and (Vb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula VI

In one of its composition aspects, the present embodiments provide a compound of formula (VI):

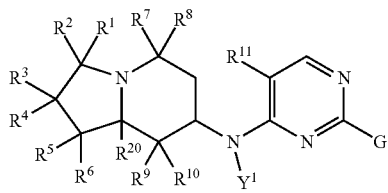

(VI)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, cycloalkyl, substituted cycloalkyl, hydroxy, alkoxy, substituted alkoxy, amino, substituted amino, carboxyl, carboxyl ester, cyano, halogen, thiol, thioalkoxy, substituted thioalkoxy, acyl, aminoacyl, nitro, alkenyl, substituted alkenyl, alkynyl, substituted alkynyl, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

R$^{20}$ is selected from hydrogen, alkyl, and substituted alkyl;

G is halogen or —NY$^2$Ar$^1$;

Y$^1$ and Y$^2$ are independently selected from hydrogen, alkyl and substituted alkyl; and Ar$^1$ is selected from aryl, substituted aryl, heteroaryl, and substituted heteroaryl;

or a salt or stereoisomer thereof.

In formula (VI), G is halogen or —NY$^2$Ar$^1$. In certain embodiments, G is halogen. In certain embodiments, G is —NY$^2$Ar$^1$.

In formula (VI), Ar$^1$ is selected from aryl, substituted aryl, heteroaryl, and substituted heteroaryl. In certain embodiments, Ar$^1$ is aryl or substituted aryl. In certain embodiments, Ar$^1$ is aryl. In certain embodiments, Ar$^1$ is substituted aryl. In certain embodiments, Ar$^1$ is heteroaryl or substituted heteroaryl. In certain embodiments, Ar$^1$ is heteroaryl. In certain embodiments, Ar$^1$ is substituted heteroaryl.

In certain embodiments, a compound of formula (VI) is of the formula:

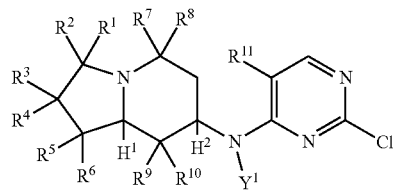

wherein

H$^1$ and H$^2$ are hydrogen.

In certain embodiments, H$^1$ and H$^2$ are hydrogen with cis relative configuration. In certain embodiments, H$^1$ and H$^2$ are hydrogen with trans relative configuration.

Formula VII

In one of its composition aspects, the present embodiments provide a compound of formula (VII):

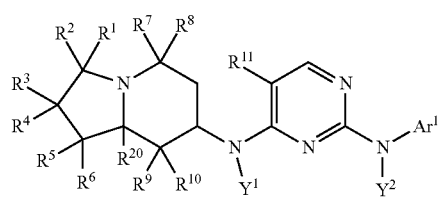

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

R$^{20}$ is selected from hydrogen, alkyl, and substituted alkyl;

Y$^1$ and Y$^2$ are independently selected from hydrogen, alkyl and substituted alkyl; and Ar$^1$ is selected from aryl, substituted aryl, heteroaryl, and substituted heteroaryl;

or a salt or stereoisomer thereof.

In one of its composition aspects, the present embodiments provide a compound of formula (VIIa):

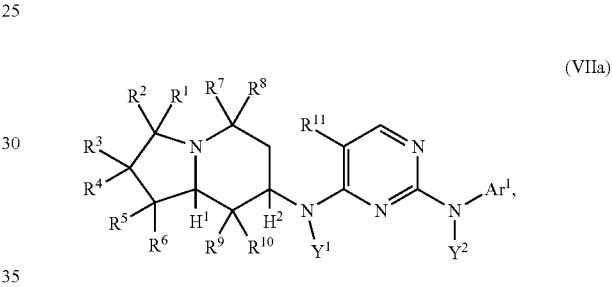

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y$^1$ and Y$^2$ are independently selected from hydrogen, alkyl and substituted alkyl;

Ar$^1$ is selected from aryl, substituted aryl, heteroaryl, and substituted heteroaryl; and H$^1$ and H$^2$ are hydrogen with cis relative configuration;

or a salt or stereoisomer thereof.

In one of its composition aspects, the present embodiments provide a compound of formula (VIIb):

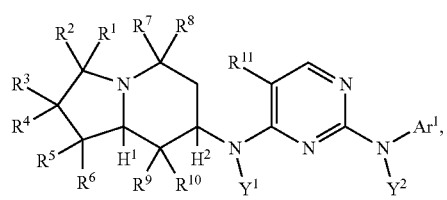

(VIIb)

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y$^1$ and Y$^2$ are independently selected from hydrogen, alkyl and substituted alkyl;

Ar$^1$ is selected from aryl, substituted aryl, heteroaryl, and substituted heteroaryl; and H$^1$ and H$^2$ are hydrogen with trans relative configuration.

or a salt or stereoisomer thereof.

Reference to formula (VII) is meant to include compounds of formula (VII) and (VIIa)-(VIIb).

In formulae (VII), Ar$^1$ is selected from aryl, substituted aryl, heteroaryl, and substituted heteroaryl. In certain embodiments, Ar$^1$ is aryl or substituted aryl. In certain embodiments, Ar$^1$ is aryl. In certain embodiments, Ar$^1$ is substituted aryl. In certain embodiments, Ar$^1$ is heteroaryl or substituted heteroaryl. In certain embodiments, Ar$^1$ is heteroaryl. In certain embodiments, Ar$^1$ is substituted heteroaryl.

In formula (VIIa) and (VIIb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula VIII

In one of its composition aspects, the present embodiments provide a compound of formula (VIII):

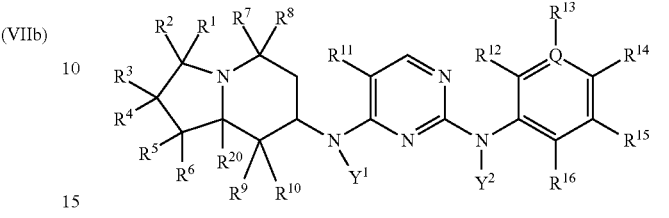

(VIII)

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

R$^{20}$ is selected from hydrogen, alkyl, and substituted alkyl;

Y$^1$ and Y$^2$ are independently selected from hydrogen, alkyl and substituted alkyl;

Q is C or N; and

R$^{12}$, R$^{13}$, R$^{14}$, R$^{15}$, and R$^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or R$^{14}$ and R$^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (VIIIa):

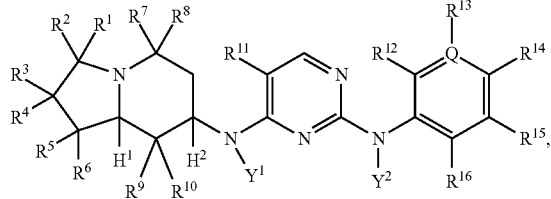

(VIIIa)

wherein

R¹, R², R³, R⁴, R⁵, and R⁶ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl; or R¹ and R² together form an oxo group; or R³ and R⁴ together form an oxo group; or R⁵ and R⁶ together form an oxo group;

R⁷, R⁸, R⁹, and R¹⁰ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl; or R⁷ and R⁸ together form an oxo group; or R⁹ and R¹⁰ together form an oxo group;

R¹¹ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y¹ and Y² are independently selected from hydrogen, alkyl and substituted alkyl;

Q is C or N;

R¹², R¹³, R¹⁴, R¹⁵ and R¹⁶ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or R¹⁴ and R¹⁵ together with the carbon atoms to which they are attached form aryl, substituted aryl, heteroaryl, substituted heteroaryl, heterocyclyl, or substituted heterocyclyl; and H¹ and H² are hydrogen with cis relative configuration;

or a salt or stereoisomer thereof.

In one of its composition aspects, the present embodiments provide a compound of formula (VIIIb):

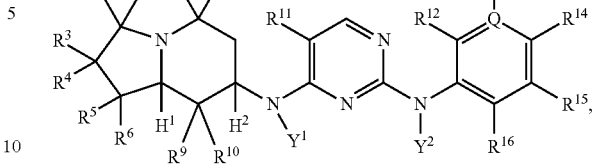

(VIIIb)

wherein

R¹, R², R³, R⁴, R⁵, and R⁶ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl; or R¹ and R² together form an oxo group; or R³ and R⁴ together form an oxo group; or R⁵ and R⁶ together form an oxo group;

R⁷, R⁸, R⁹, and R¹⁰ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl; or R⁷ and R⁸ together form an oxo group; or R⁹ and R¹⁰ together form an oxo group;

R¹¹ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y¹ and Y² are independently selected from hydrogen, alkyl and substituted alkyl;

Q is C or N;

R¹², R¹³, R¹⁴, R¹⁵ and R¹⁶ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or R¹⁴ and R¹⁵ together with the carbon atoms to which they are attached form aryl, substituted aryl, heteroaryl, substituted heteroaryl, heterocyclyl, or substituted heterocyclyl; and H¹ and H² are hydrogen with trans relative configuration;

or a salt or stereoisomer thereof.

Reference to formula (VIII) is meant to include compounds of formula (VIII) and (VIIIa)-(VIIIb).

In formula (VIII), Q is C or N. In certain embodiments, Q is C. In certain embodiments, Q is N.

In formula (VIIIa) and (VIIIb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula IX

In one of its composition aspects, the present embodiments provide a compound of formula (IX):

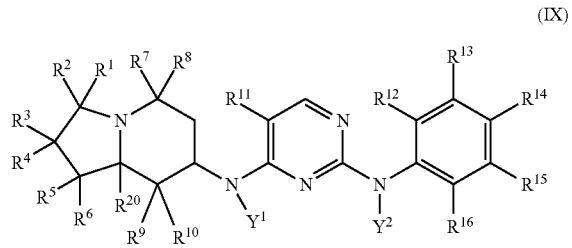

(IX)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen, alkyl and substituted alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (IXa):

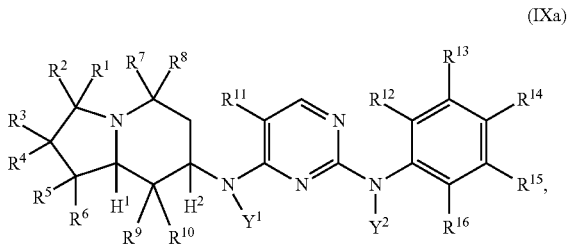

(IXa)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl and substituted alkyl;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration;

or a salt or stereoisomer thereof.

In one of its composition aspects, the present embodiments provide a compound of formula (IXb):

(IXb)

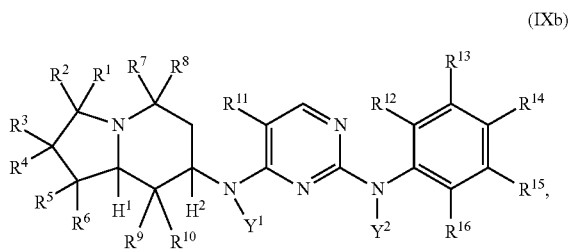

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl and substituted alkyl;

$R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration; or a salt or stereoisomer thereof.

Reference to formula (IX) is meant to include compounds of formula (IX) and (IXa)-(IXb).

In formula (IXa) and (IXb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Formula X

In one of its composition aspects, the present embodiments provide a compound of formula (X):

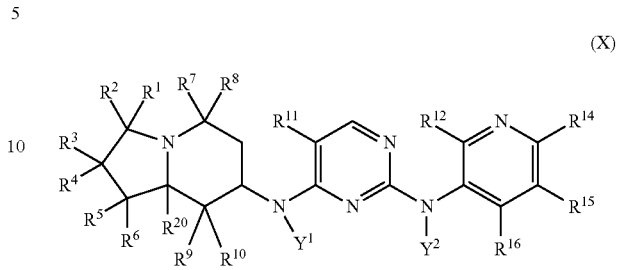

(X)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen, alkyl and substituted alkyl; and $R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

In one of its composition aspects, the present embodiments provide a compound of formula (Xa):

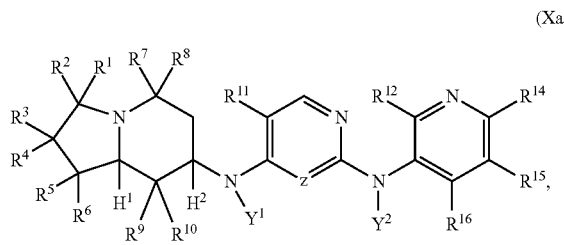

(Xa)

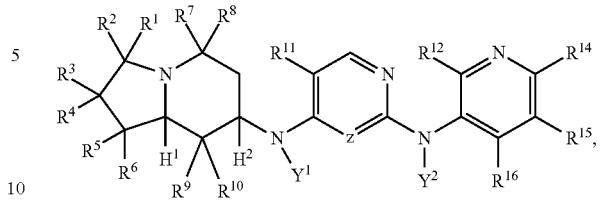

(Xb)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl and substituted alkyl;

$R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with cis relative configuration;

or a salt or stereoisomer thereof.

In one of its composition aspects, the present embodiments provide a compound of formula (Xb):

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl and substituted alkyl;

$R^{12}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl; and $H^1$ and $H^2$ are hydrogen with trans relative configuration;

or a salt or stereoisomer thereof.

Reference to formula (X) is meant to include compounds of formula (X) and (Xa)-(Xb)

In formula (Xa) and (Xb), in certain embodiments, the compound is optically active. In certain embodiments, there is an enantiomeric excess of 90% or more. In certain embodiments, there is an enantiomeric excess of 95% or more. In certain embodiments, there is an enantiomeric excess of 99% or more.

Certain Embodiments of Formulae I-X
With reference to formulae I-X, the formula

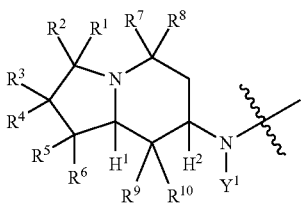

includes at least two chiral centers, and thus at least four stereoisomers. For clarity the numbering of the ring system is shown below with optional substituents omitted.

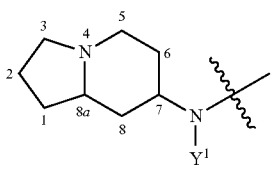

With continued reference to formulae I-X, (7,8a) cis diastereomer has the structure:

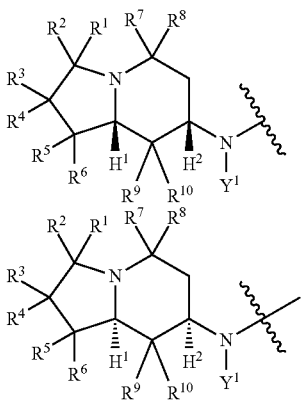

and the (7,8a) trans diastereomer:

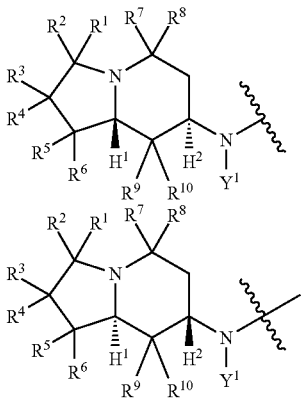

In certain embodiments of formulae I-X, $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group.

In certain embodiments of formulae I-X, $R^1$, $R^2$, $R^3$, $R^4$, $R^5$, and $R^6$ are independently selected from hydrogen, alkyl, substituted alkyl, cyano, halogen, hydroxyl, acyl, aminoacyl, and nitro; or $R^1$ and $R^2$ together form an oxo group; or $R^3$ and $R^4$ together form an oxo group; or $R^5$ and $R^6$ together form an oxo group.

In certain embodiments of formulae I-X, $R^1$, $R^2$, $R^3$, $R^4$, $R^5$, and $R^6$ are independently selected from hydrogen, alkyl, substituted alkyl, halogen, and hydroxyl; or $R^1$ and $R^2$ together form an oxo group; or $R^3$ and $R^4$ together form an oxo group; or $R^5$ and $R^6$ together form an oxo group.

In certain embodiments of formulae I-X, $R^1$ and $R^2$ are each hydrogen. In certain embodiments of formulae I-X, $R^1$ and $R^2$ are each alkyl, such as $C_1$-$C_6$ alkyl, or $C_1$-$C_3$ alkyl. In certain embodiments of formulae I-X, $R^1$ and $R^2$ are each methyl.

In certain embodiments of formulae I-X, at least one of $R^3$ and $R^4$ is hydrogen. In certain embodiments of formulae I-X, $R^3$ and $R^4$ are each hydrogen. In certain embodiments of formulae I-X, at least one of $R^3$ and $R^4$ is halogen or hydroxyl. In certain embodiments of formulae I-X, at least one of $R^3$ and $R^4$ is halogen. In certain embodiments of formulae I-X, one of $R^3$ and $R^4$ is halogen. In certain embodiments of formulae I-X, at least one of $R^3$ and $R^4$ is F. In certain embodiments of formulae I-X, one of $R^3$ and $R^4$ is F. In certain embodiments of formulae I-X, $R^3$ and $R^4$ are each halogen. In certain embodiments of formulae I-X, $R^3$ and $R^4$ are each F. In certain embodiments of formulae I-X, at least one of $R^3$ and $R^4$ is hydroxyl. In certain embodiments of formulae I-X, one of $R^3$ and $R^4$ is hydroxyl.

In certain embodiments of formulae I-X, at least one of $R^5$ and $R^6$ is hydrogen. In certain embodiments of formulae I-X, $R^5$ and $R^6$ are each hydrogen.

In certain embodiments of formulae I-X, $R^1$ and $R^2$ together form an oxo group; or $R^3$ and $R^4$ together form an oxo group; or $R^5$ and $R^6$ together form an oxo group. In certain embodiments of formulae I-X, $R^1$ and $R^2$ together form an oxo group. In certain embodiments of formulae I-X, $R^3$ and $R^4$ together form an oxo group. In certain embodiments of formulae I-X, $R^5$ and $R^6$ together form an oxo group.

In certain embodiments of formulae I-X, $R^1$, $R^2$, $R^3$, $R^4$, $R^5$, and $R^6$ are each hydrogen.

In certain embodiments of formulae I-X, $R^1$, $R^2$, $R^3$, $R^4$, $R^5$, and $R^6$ are independently selected from hydrogen, alkyl, and substituted alkyl. In certain embodiments of formulae I-X, $R^1$, $R^2$, $R^3$, $R^4$, $R^5$, and $R^6$ are independently selected from hydrogen, alkoxy, substituted alkoxy, aryloxy, hydroxyamino, alkoxyamino, and nitro. In certain embodiments of formulae I-X, $R^1$, $R^2$, $R^3$, $R^4$, $R^5$, and $R^6$ are independently selected from hydrogen, acyl, acylamino, acyloxy, amino, substituted amino, aminoacyl, aminoacyloxy, oxyaminoacyl, and azido. In certain embodiments of formulae I-X, $R^1$, $R^2$, $R^3$, $R^4$, $R^5$, and $R^6$ are independently selected from hydrogen, cyano, halogen, and hydroxyl. In certain embodiments of formulae I-X, $R^1$, $R^2$, $R^3$, $R^4$, $R^5$, and $R^6$ are independently selected from hydrogen, carboxyl, carboxylalkyl, thiol, thioalkoxy, and substituted thioalkoxy. In certain embodiments of formulae I-X, $R^1$, $R^2$, $R^3$, $R^4$, $R^5$, and $R^6$ are independently selected from hydrogen and aryl. In certain embodiments of formulae I-X, $R^1$, $R^2$, $R^3$, $R^4$, $R^5$, and $R^6$ are independently selected from hydrogen, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. In certain embodiments of formulae I-X, $R^1$ and $R^2$ together form an oxo group; or $R^3$ and $R^4$ together form an oxo group; or $R^5$ and $R^6$ together form an oxo group.

In certain embodiments of formulae I-X, $R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group.

In certain embodiments of formulae I-X, $R^7$, $R^8$, $R^9$, and $R^{10}$ are independently selected from hydrogen, alkyl, substituted alkyl, alkoxy, substituted alkoxy, cyano, halogen, acyl, aminoacyl, and nitro; or $R^7$ and $R^8$ together form an oxo group. In certain embodiments of formulae I-X, $R^7$, $R^8$, $R^9$, and $R^{10}$ are independently selected from hydrogen, alkyl, substituted alkyl, and halogen; or $R^7$ and $R^8$ together form an oxo group.

In certain embodiments of formulae I-X, $R^7$ and $R^8$ are each hydrogen. In certain embodiments of formulae I-X, $R^7$ and $R^8$ are each alkyl, such as $C_1$-$C_6$ alkyl, or $C_1$-$C_3$ alkyl. In certain embodiments of formulae I-X, $R^7$ and $R^8$ are each methyl. In certain embodiments of formulae I-X, $R^7$ and $R^8$ together form an oxo group.

In certain embodiments of formulae I-X, at least one of $R^9$ and $R^{10}$ is hydrogen. In certain embodiments of formulae I-X, $R^9$ and $R^{10}$ are each hydrogen. In certain embodiments of formulae I-X, at least one of $R^9$ and $R^{10}$ is alkyl, such as $C_1$-$C_6$ alkyl, or $C_1$-$C_3$ alkyl. In certain embodiments of formulae I-X, at least one of $R^9$ and $R^{10}$ is methyl. In certain embodiments of formulae I-X, one of $R^9$ and $R^{10}$ is methyl. In certain embodiments of formulae I-X, $R^9$ and $R^{10}$ together form an oxo group.

In certain embodiments of formulae I-X, $R^7$, $R^8$, $R^9$, and $R^{10}$ are independently selected from hydrogen, alkyl, and substituted alkyl. In certain embodiments of formulae I-X, $R^7$, $R^8$, $R^9$, and $R^{10}$ are independently selected from hydrogen, alkoxy, substituted alkoxy, aryloxy, hydroxyamino, alkoxyamino, and nitro. In certain embodiments of formulae I-X, $R^7$, $R^8$, $R^9$, and $R^{10}$ are independently selected from hydrogen, acyl, acylamino, acyloxy, amino, substituted amino, aminoacyl, aminoacyloxy, oxyaminoacyl, and azido. In certain embodiments of formulae I-X, $R^7$, $R^8$, $R^9$, and $R^{10}$ are independently selected from hydrogen, cyano, halogen, and hydroxyl. In certain embodiments of formulae I-X, $R^7$, $R^8$, $R^9$, and $R^{10}$ are independently selected from hydrogen, carboxyl, carboxylalkyl, thiol, thioalkoxy, and substituted thioalkoxy. In certain embodiments of formulae I-X, $R^7$, $R^8$, $R^9$, and $R^{10}$ are independently selected from hydrogen and aryl. In certain embodiments of formulae I-X, $R^7$, $R^8$, $R^9$, and $R^{10}$ are independently selected from hydrogen, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. In certain embodiments of formulae I-X, $R^7$ and $R^8$ together form an oxo group; or $R^9$ and $R^{10}$ together form an oxo group.

In certain embodiments of formulae I-X, $R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl.

In certain embodiments of formulae I-X, $R^{11}$ is selected from alkoxy, substituted alkoxy, cyano, halogen, acyl, aminoacyl, and nitro. In certain embodiments of formulae I-X, $R^{11}$ is cyano, halogen, acyl, aminoacyl, or nitro. In certain embodiments of formulae I-X, $R^{11}$ is fluoro or cyano. In certain embodiments of formulae I-X, $R^{11}$ is fluoro. In certain embodiments of formulae I-X, $R^{11}$ is cyano. In certain embodiments of formulae I-X, $R^{11}$ is acyl or aminoacyl. In certain embodiments of formulae I-X, $R^{11}$ is nitro.

In certain embodiments of formulae I-X, $R^{11}$ is selected from alkyl, substituted alkyl, cycloalkyl, substituted cycloalkyl, hydroxy, alkoxy, substituted alkoxy, amino, substituted amino, carboxyl, carboxyl ester, cyano, halogen, thiol, thioalkoxy, substituted thioalkoxy, acyl, aminoacyl, nitro, alkenyl, substituted alkenyl, alkynyl, substituted alkynyl, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

In certain embodiments of formulae I-X, $R^{11}$ is selected from alkoxy, substituted alkoxy, cyano, halogen, acyl, aminoacyl, and nitro. In certain embodiments of formulae I-X, $R^{11}$ is cyano, halogen, acyl, aminoacyl, or nitro. In certain embodiments of formulae I-X, $R^{11}$ is fluoro or cyano. In certain embodiments of formulae I-X, $R^{11}$ is fluoro. In certain embodiments of formulae I-X, $R^{11}$ is cyano. In certain embodiments of formulae I-X, $R^{11}$ is acyl or aminoacyl. In certain embodiments of formulae I-X, $R^{11}$ is nitro.

In certain embodiments of formulae I-X, $R^{11}$ is selected from alkyl, substituted alkyl, cycloalkyl, substituted cycloalkyl, thiol, thioalkoxy, substituted thioalkoxy, alkenyl, substituted alkenyl, alkynyl, substituted alkynyl, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. In certain embodiments of formulae I-X, $R^{11}$ is alkyl or substituted alkyl. In certain embodiments of formulae I-X, $R^{11}$ is cycloalkyl or substituted cycloalkyl. In certain embodiments of formulae I-X, $R^{11}$ is thiol, thioalkoxy, or substituted thioalkoxy. In certain embodiments of formulae I-X, $R^{11}$ is alkenyl or substituted alkenyl. In certain embodiments of formulae I-X, $R^{11}$ is alkynyl or substituted alkynyl. In certain embodiments of formulae I-X, $R^{11}$ is —SO-alkyl, —SO-substituted alkyl. In certain embodiments of formulae I-X, $R^{11}$ is —SO-aryl or —SO-heteroaryl. In certain embodiments of formulae I-X, $R^{11}$ is —SO$_2$-alkyl or —SO$_2$-substituted alkyl. In certain embodiments of formulae I-X, $R^{11}$ is —SO$_2$-aryl or —SO$_2$-heteroaryl.

In certain embodiments of formulae I-X, $R^{20}$ is selected from hydrogen, alkyl, and substituted alkyl. In certain embodiments of formulae I-X, $R^{20}$ is hydrogen. In certain embodiments of formulae I-X, $R^{20}$ is alkyl. In certain embodiments of formulae I-X, $R^{20}$ is substituted alkyl.

In certain embodiments of formulae I-X, $Y^1$ and $Y^2$ are independently selected from hydrogen, alkyl and substituted alkyl. In certain embodiments of formulae I-X, $Y^1$ is hydrogen. In certain embodiments of formulae I-X, $Y^2$ is hydrogen. In certain embodiments of formulae I-X, $Y^1$ and $Y^2$ are hydrogen. In certain embodiments of formulae I-X, $Y^1$ is alkyl. In certain embodiments of formulae I-X, $Y^2$ is alkyl. In certain embodiments of formulae I-X, $Y^1$ and $Y^2$ are alkyl. In certain embodiments of formulae I-X, $Y^1$ is substituted alkyl. In certain embodiments of formulae I-X, $Y^2$ is substituted alkyl. For example, $Y^1$ and $Y^2$ may be independently selected from substituted $C_1$-$C_6$ alkyl, such as substituted $C_1$-$C_4$ alkyl, or substituted $C_1$-$C_3$ alkyl. In certain embodiments of formulae I-X, $Y^1$ and $Y^2$ may be independently selected from an alkyl substituted with one or more groups, such as, but not limited to, alkyl, hydroxyl, amino, substituted amino, alkoxy and substituted alkoxy.

In certain embodiments of formulae I-X, $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments of formulae I-X, $R^{12}$, $R^{13}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments of formulae I-X, $R^{12}$, $R^{13}$, $R^{14}$, $R^{15}$, and $R^{16}$ are independently selected from hydrogen, alkyl, halogen, cyano, hydroxyl, alkoxy, substituted alkoxy, acylamino, aminocarbonylamino, sulfur pentafluoride, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

In certain embodiments of formulae IX, $R^{12}$, $R^{13}$, $R^{14}$, $R^{15}$, and $R^{16}$ are independently selected from hydrogen, halogen, cycloalkyl, substituted cycloalkyl, heteroaryl, and substituted heteroaryl. In certain embodiments of formulae I-X, $R^{12}$, $R^{13}$, $R^{14}$, $R^{15}$, and $R^{16}$ are independently selected from hydrogen, alkoxy, substituted alkoxy, heteroaryl, and substituted heteroaryl. In certain embodiments of formulae I-X, $R^{12}$, $R^{13}$, $R^{14}$, $R^{15}$, and $R^{16}$ are independently selected from hydrogen, alkyl, alkoxy, substituted alkoxy, and cyano. In certain embodiments of formulae I-X, $R^{12}$, $R^{13}$, $R^{14}$, $R^{15}$, and $R^{16}$ are independently selected from hydrogen, alkyl, heteroaryl, and substituted heteroaryl.

In certain embodiments of formulae I-X, $R^{12}$, $R^{13}$, $R^{14}$, $R^{15}$, and $R^{16}$ are independently selected from hydrogen, alkyl, and substituted alkyl. In certain embodiments of formulae I-X, at least one of $R^{12}$, $R^{13}$, $R^{14}$, $R^{15}$, and $R^{16}$ are hydrogen. In certain embodiments of formulae I-X, one of $R^{12}$, $R^{13}$, $R^{14}$, $R^{15}$, and $R^{16}$ is hydrogen. In certain embodiments of formulae I-X, two of $R^{12}$, $R^{13}$, $R^{14}$, $R^{15}$, and $R^{16}$ are hydrogen. In certain embodiments of formulae I-X, three of $R^{12}$, $R^{13}$, $R^{14}$, $R^{15}$, and $R^{16}$ are hydrogen. In certain embodiments of formulae I-X, $R^{12}$ and $R^{16}$ are hydrogen. In certain embodiments of formulae I-X, $R^{12}$, $R^{13}$, and $R^{16}$ are hydrogen. In certain embodiments of formulae I-X, $R^{12}$, $R^{13}$, $R^{14}$, $R^{15}$, and $R^{16}$ are independently selected from alkyl and substituted alkyl. In certain embodiments of formulae I-X, $R^{12}$, $R^{13}$, $R^{14}$, $R^{15}$, and $R^{16}$ are independently selected from alkyl, such as $C_1$-$C_6$ alkyl, or $C_1$-$C_3$ alkyl. In certain embodiments of formulae I-X, $R^{12}$, $R^{13}$, $R^{14}$, $R^{15}$, and $R^{16}$ are independently selected from methyl. In certain embodiments of formulae I-X, $R^{12}$, $R^{13}$, $R^{14}$, $R^{15}$, and $R^{16}$ are independently selected from alkenyl, substituted alkenyl, alkynyl, and substituted alkynyl.

In certain embodiments of formulae I-X, $R^{12}$, $R^{13}$, $R^{14}$, $R^{15}$, and $R^{16}$ are independently selected from halogen, cyano, hydroxyl, alkoxy, and substituted alkoxy. In certain embodiments of formulae I-X, $R^{12}$, $R^{13}$, $R^{14}$, $R^{15}$, and $R^{16}$ are independently selected from halogen. In certain embodiments of formulae I-X, $R^{12}$, $R^{13}$, $R^{14}$, $R^{15}$, and $R^{16}$ are independently selected from fluoro. In certain embodiments of formulae I-X, $R^{12}$, $R^{13}$, $R^{14}$, $R^{15}$, and $R^{16}$ are independently selected from cyano. In certain embodiments of formulae I-X, $R^{12}$, $R^{13}$, $R^{14}$, $R^{15}$, and $R^{16}$ are independently selected from hydroxyl. In certain embodiments of formulae I-X, $R^{12}$, $R^{13}$, $R^{14}$, $R^{15}$, and $R^{16}$ are independently selected from alkoxy. In certain embodiments of formulae I-X, $R^{12}$, $R^{13}$, $R^{14}$, $R^{15}$, and $R^{16}$ are independently selected from $C_1$-$C_6$ alkoxy. In certain embodiments of formulae I-X, $R^{12}$, $R^{13}$, $R^{14}$, $R^{15}$, and $R^{16}$ are independently selected from $C_1$-$C_3$ alkoxy, such as methoxy, isopropoxy, and the like. In certain embodiments of formulae I-X, $R^{12}$, $R^{13}$, $R^{14}$, $R^{15}$, and $R^{16}$ are independently selected from substituted alkoxy. In certain embodiments of formulae I-X, $R^{12}$, $R^{13}$, $R^{14}$, $R^{15}$, and $R^{16}$ are independently selected from $C_1$-$C_6$ substituted alkoxy. In certain embodiments of formulae I-X, $R^{12}$, $R^{13}$, $R^{14}$, $R^{15}$, and $R^{16}$ are independently selected from $C_1$-$C_3$ substituted alkoxy. In certain embodiments of formulae I-X, the substituted alkoxy group is substituted with one or more groups selected from halogen, hydroxyl, alkyl (e.g., $C_1$-$C_6$ alkyl, such as $C_1$-$C_3$ alkyl, including methyl).

In certain embodiments of formulae I-X, $R^{12}$, $R^{13}$, $R^{14}$, $R^{15}$, and $R^{16}$ are independently selected from amino and substituted amino. In certain embodiments of formulae I-x, $R^{12}$, $R^{13}$, $R^{14}$, $R^{15}$, and $R^{16}$ are independently selected from acylamino, aminocarbonylamino, alkoxycarbonylamino, acyl, carboxyl, carboxyl ester, aminoacyl, and aminocarbonyloxy. In certain embodiments of formulae I-X, $R^{12}$, $R^{13}$, $R^{14}$, $R^{15}$, and $R^{16}$ are independently selected from acylamino and aminocarbonylamino. In certain embodiments of formulae I-X, $R^{12}$, $R^{13}$, $R^{14}$, $R^{15}$, and $R^{16}$ are independently selected from acylamino. In certain embodiments of formulae I-X, $R^{12}$, $R^{13}$, $R^{14}$, $R^{15}$, and $R^{16}$ are independently selected from aminocarbonylamino.

In certain embodiments of formulae I-X, $R^{12}$, $R^{13}$, $R^{14}$, $R^{15}$, and $R^{16}$ are independently selected from nitro, sulfonyl, sulfonylamino, aminosulfonyl, and sulfur pentafluoride. In certain embodiments of formulae I-X, $R^{12}$, $R^{13}$, $R^{14}$, $R^{15}$, and $R^{16}$ are independently selected from sulfur pentafluoride.

In certain embodiments of formulae I-X, $R^{12}$, $R^{13}$, $R^{14}$, $R^{15}$, and $R^{16}$ are independently selected from aryl, substituted aryl, cycloalkyl, substituted cycloalkyl, heteroaryl, substituted heteroaryl, heterocyclyl, substituted heterocyclyl, heterocyclyloxy, and substituted heterocyclyloxy. In certain embodiments of formulae I-X, $R^{12}$, $R^{13}$, $R^{14}$, $R^{15}$, and $R^{16}$ are independently selected from aryl and substituted aryl. In certain embodiments of formulae I-X, $R^{12}$, $R^{13}$, $R^{14}$, $R^{15}$, and $R^{16}$ are independently selected from cycloalkyl and substituted cycloalkyl. In certain embodiments of formulae I-X, $R^{12}$, $R^{13}$, $R^{14}$, $R^{15}$, and $R^{16}$ are independently selected from cycloalkyl. For example, cycloalkyl groups may include, but are not limited to, $C_3$-$C_8$ cycloalkyl, including $C_3$-$C_6$ cycloalkyl, such as cyclohexyl, cyclopentyl, cyclobutyl, cyclopropyl. In certain embodiments of formulae I-X, $R^{12}$, $R^{13}$, $R^{14}$, $R^{15}$, and $R^{16}$ are independently selected from cyclopropyl.

In certain embodiments of formulae I-X, $R^{12}$, $R^{13}$, $R^{14}$, $R^{15}$, and $R^{16}$ are independently selected from heteroaryl, substituted heteroaryl, heterocyclyl and substituted heterocyclyl. In certain embodiments of formulae I-X, $R^{12}$, $R^{13}$, $R^{14}$, $R^{15}$, and $R^{16}$ are independently selected from heteroaryl. In certain embodiments of formulae I-X, $R^{12}$, $R^{13}$, $R^{14}$, $R^{15}$, and $R^{16}$ are independently selected from substituted heteroaryl. In certain embodiments of formulae I-X, $R^{12}$, $R^{13}$, $R^{14}$, $R^{15}$, and $R^{16}$ are independently selected from heterocyclyl. In certain embodiments of formulae I-X, $R^{12}$, $R^{13}$, $R^{14}$, $R^{15}$, and $R^{16}$ are independently selected from substituted heterocyclyl. Examples of heterocycles and heteroaryls include, but are not limited to, tetrazolone, substituted tetrazolone, tetrazolyl, and substituted tetrazolyl. For example, a tetrazolyl or a tetrazolonyl group may be substituted with one or more groups, such as an alkyl, e.g., $C_1$-$C_6$ alkyl, including $C_1$-$C_3$ alkyl, such as methyl, and the like. In certain embodiments of formulae I-X, tetrazolyl substituents have the formula

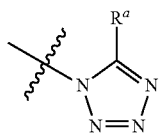

wherein $R^a$ is selected from hydrogen, alkyl, substituted alkyl, cycloalkyl and substituted cycloalkyl. In certain embodiments of formulae I-X, $R^a$ is hydrogen, alkyl (e.g., $C_1$-$C_6$ alkyl, or $C_1$-$C_3$ alkyl, such as, but not limited to methyl), or haloalkyl, such as difluoromethyl or trifluoromethyl, and the like. Tetrazolonyl substituents in certain embodiments of formulae I-X have the formula

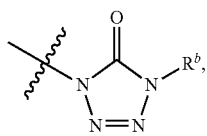

where $R^b$ is selected from hydrogen, alkyl, substituted alkyl, cycloalkyl and substituted cycloalkyl. In certain embodiments of formulae I-X, $R^b$ is alkyl or substituted alkyl, such as $C_1$-$C_6$ alkyl or substituted alkyl, or $C_1$-$C_3$ alkyl or substituted alkyl. In certain embodiments of formulae I-X, $R^b$ is cycloalkyl or substituted cycloalkyl, such as $C_3$-$C_8$ cycloalkyl or substituted cycloalkyl, or $C_3$-$C_6$ cycloalkyl or substituted cycloalkyl. In certain embodiments of formulae I-X, where one of $R^{12}$, $R^{13}$, $R^{14}$, $R^{15}$, and $R^{16}$ is tetrazolonyl, $R^b$ is methyl, trifluoromethyl or cyclopropyl.

In certain embodiments of formulae I-X, $R^{12}$, $R^{13}$, $R^{14}$, $R^{15}$, and $R^{16}$ are independently selected from heterocyclyloxy and substituted heterocyclyloxy. In certain embodiments of formulae I-X, $R^{12}$, $R^{13}$, $R^{14}$, $R^{15}$, and $R^{16}$ are independently selected from heterocyclyloxy. In certain embodiments of formulae I-X, $R^{12}$, $R^{13}$, $R^{14}$, $R^{15}$, and $R^{16}$ are independently selected from substituted heterocyclyloxy. In certain embodiments of formulae I-X, heterocyclyloxy and substituted heterocyclyloxy groups include a 3 to 8-membered ring, such as a 3 to 6-membered ring, that includes 1 to 5 heteroatoms, or 1 to 3 heteroatoms, such as 1 heteroatom (e.g., oxygen, nitrogen or sulfur). For example, heterocyclyloxy and substituted heterocyclyloxy groups may include rings such as, but not limited to, tetrahydropyran, tetrahydrofuran, oxetane, piperidine, and the like. Substituted heterocyclyloxy groups may be substituted with one or more groups, such as alkyl, e.g., $C_1$-$C_6$ alkyl, including $C_1$-$C_3$ alkyl, such as methyl, isopropyl, and the like.

In certain embodiments of formulae I-X, $R^{14}$ and $R^{15}$ together with the carbon atoms to which they are attached form aryl, substituted aryl, heteroaryl, substituted heteroaryl, heterocyclyl, or substituted heterocyclyl. In certain embodiments of formulae I-X, $R^{14}$ and $R^{15}$ together with the carbon atoms to which they are attached form an aryl or heteroaryl 5 to 10-membered ring. In certain embodiments of formulae I-X, $R^{14}$ and $R^{15}$ together with the carbon atoms to which they are attached form a heterocyclyl or substituted heterocyclyl 5 to 10-membered ring. For example, $R^{14}$ and $R^{15}$ together with the carbon atoms to which they are attached may form a tetrazolooxazinyl group, which may be substituted with one or more groups, such as alkyl, e.g., $C_1$-$C_6$ alkyl, including $C_1$-$C_3$ alkyl, such as methyl.

As is understood by those of skill in the art, the embodiments described herein with respect to formulae I-X may be used in combination with other embodiments. Accordingly, features may be included in a compound according to formulae I-X. By way of example, a compound may have features, such that, for example, $R^{14}$ and $R^{15}$, are one cycloalkyl and one heterocycloalkyl, such as in a compound according to any one of formulae I-X wherein $R^{14}$ is cycloalkyl and $R^{15}$ is heterocycloalkyl. Likewise, compounds may include features—an example of such a compound may have $R^{12}$ being halogen, such as fluoro, $R^{14}$ being heterocyclyloxy or substituted heterocyclyloxy and $R^{15}$ being heteroaryl or substituted heteroaryl. Similarly, certain embodiments of formulae I-X include one or more features.

In certain embodiments of formulae I-X, $R^{12}$, $R^{13}$, $R^{14}$, $R^{15}$ and $R^{16}$ are independently selected from hydrogen, methyl, fluoro, hydroxyl, methoxy, isopropoxy, cyano, sulfur pentafluoride, —OCHF$_2$, —OCH$_2$CH$_2$OH, —OCH$_2$CH(OH)CH$_3$, —OCH$_2$C(CH$_3$)$_2$OH, —OCH$_2$CH(CH$_3$)OH, —OC(CH$_3$)$_2$CH$_2$OH,

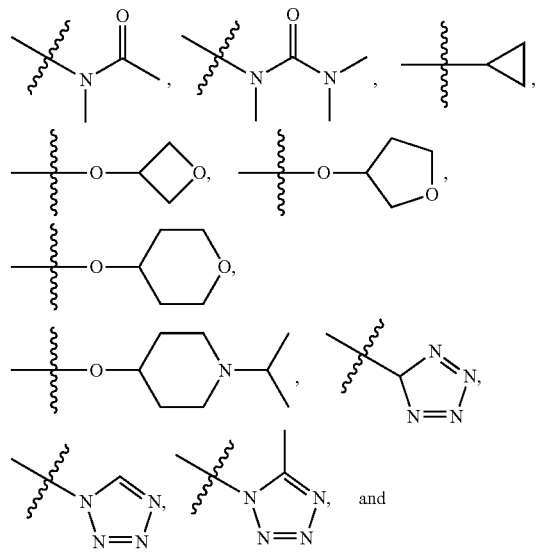 and

-continued

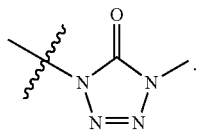

For example, in one embodiment of formulae I-X, $R^{12}$ is halogen, such as fluorine.

For example, in one embodiment of formulae I-X, at least one of $R^{12}$, $R^{13}$, $R^{14}$, $R^{15}$, and $R^{16}$ is selected from cycloalkyl and substituted cycloalkyl.

For example, in one embodiment of formulae I-X, at least one of $R^{14}$ and $R^{15}$ is selected from halogen and cycloalkyl.

For example, in one embodiment of formulae I-X, $R^{14}$ and $R^{15}$ independently are selected from alkoxy, substituted alkoxy, halogen, heterocyclyloxy, heterocyclyl, substituted heterocyclyl, heteroaryl and substituted heteroaryl.

For example, in one embodiment of formulae I-X, at least one of $R^{14}$ and $R^{15}$ is selected from

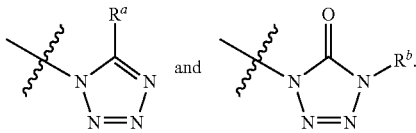

For example, in one embodiment of formulae I-X, $R^{12}$ is selected from hydrogen, halogen, alkoxy and substituted alkoxy and $R^{14}$ is selected from alkoxy, substituted alkoxy, cycloalkyl, halogen, heterocyclyloxy, substituted heterocyclyloxy, heterocyclyl, substituted heterocyclyl, heteroaryl and substituted heteroaryl.

Particular compounds of interest are shown illustrated the following table.

TABLE 1
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 1 | H/H | H/H | H/H | CH₃/CH₃ | H/H | F | H | H | 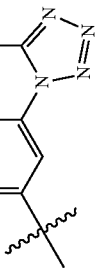 | mixture of diastereomers |
| 2 | H/H | H/H | H/H | CH₃/CH₃ | H/H | F | H | H | 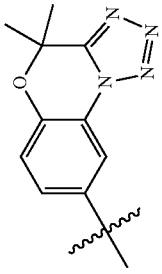 | single enantiomer |
| 3 | H/H | H/H | H/H | CH₃/CH₃ | H/H | F | H | H | 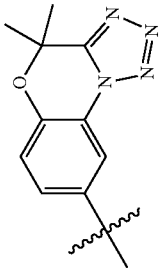 | single enantiomer |
| 4 | H/H | H/H | H/H | CH₃/CH₃ | H/H | F | H | H |  | Racemic (single diastereomer) |

TABLE 1-continued
| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 5 | H/H | H/H | H/H | CH$_3$/CH$_3$ | H/H | F | H | H | 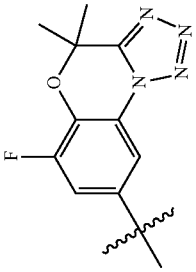 | Racemic cis diastereomer |
| 6 | H/H | H/H | H/H | CH$_3$/CH$_3$ | H/H | F | H | H | 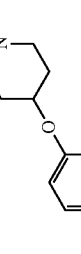 | mixture of diastereomers |
| 7 | H/H | H/H | H/H | CH$_3$/CH$_3$ | H/H | F | H | H | 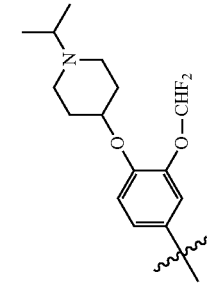 | single enantiomer |
| 8 | H/H | H/H | H/H | CH$_3$/CH$_3$ | H/H | F | H | H | | single enantiomer |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 9 | H/H | H/H | H/H | CH₃/CH₃ | H/H | F | H | H | 4-(1-isopropylpiperidin-4-yloxy)-3-(difluoromethoxy)phenyl | single enantiomer |
| 10 | H/H | H/H | H/H | CH₃/CH₃ | H/H | F | H | H | 4-(1-isopropylpiperidin-4-yloxy)-3-(difluoromethoxy)phenyl | single enantiomer |
| 11 | H/H | H/H | H/H | CH₃/CH₃ | H/H | F | H | H | 3-methoxy-5-(5-methyltetrazol-1-yl)phenyl | single enantiomer |
| 12 | H/H | H/H | H/H | CH₃/CH₃ | H/H | F | H | H | 3-methoxy-5-(5-methyltetrazol-1-yl)phenyl | single enantiomer |

TABLE 1-continued

| | R$^1$/R$^2$ | R$^3$/R$^4$ | R$^5$/R$^6$ | R$^7$/R$^8$ | R$^9$/R$^{10}$ | R$^{11}$ | Y$^1$ | Y$^2$ | Ar$^1$ | H$^1$/H$^2$ |
|---|---|---|---|---|---|---|---|---|---|---|
| 13 | H/H | H/H | H/H | CH$_3$/CH$_3$ | H/H | F | H | H | 3-OCH$_3$, 5-substituted phenyl with methyl-tetrazolyl | single enantiomer |
| 14 | H/H | H/H | H/H | CH$_3$/CH$_3$ | H/H | F | H | H | 3-OCH$_3$, 5-substituted phenyl with methyl-tetrazolyl | single enantiomer |
| 15 | H/H | H/H | H/H | CH$_3$/CH$_3$ | H/H | F | H | H | 2-methyl-pyridyl with methyl-tetrazolyl | H/H |
| 16 | H/H | H/H | H/H | CH$_3$/CH$_3$ | H/H | F | H | H | 2-cyclopropyl-4-F phenyl with N-methyl-tetrazolone | racemic |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 17 | H/H | H/H | H/H | CH₃/CH₃ | H/H | F | H | H | (2-cyclopropyl-4-fluoro-5-(4-methyl-5-oxo-4,5-dihydro-1H-tetrazol-1-yl)phenyl) | H▼/▲H 7R, 8aS |
| 18 | H/H | H/H | H/H | CH₃/CH₃ | H/H | F | H | H | (2-cyclopropyl-4-fluoro-5-(4-methyl-5-oxo-4,5-dihydro-1H-tetrazol-1-yl)phenyl) | ⋯H/⋯H 7S, 8aR |
| 19 | H/H | H/H | H/H | CH₃/CH₃ | H/H | F | H | H | (2-cyclopropyl-4-fluoro-5-(4-methyl-5-oxo-4,5-dihydro-1H-tetrazol-1-yl)phenyl) | trans |
| 20 | H/H | H/H | H/H | CH₃/CH₃ | H/H | F | H | H | (2-cyclopropyl-4-fluoro-5-(4-methyl-5-oxo-4,5-dihydro-1H-tetrazol-1-yl)phenyl) | single enantiomer |

TABLE 1-continued
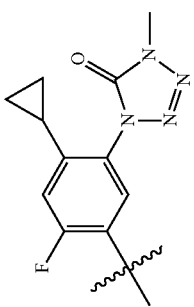
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 21 | H/H | H/H | H/H | CH₃/CH₃ | H/H | F | H | H | 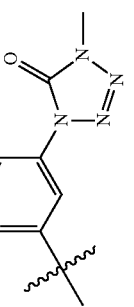 | single enantiomer |
| 22 (p-toluene-sulfonic salt) | H/H | H/H | H/H | CH₃/CH₃ | H/H | F | H | H | 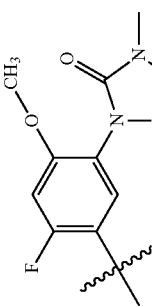 | 7R, 8aS |
| 23 (p-toluene-sulfonic salt) | H/H | H/H | H/H | CH₃/CH₃ | H/H | F | H | H | 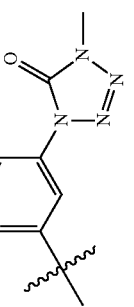 | 7R, 8aS |
| 24 | H/H | H/H | H/H | H/H | H/H | F | H | H | 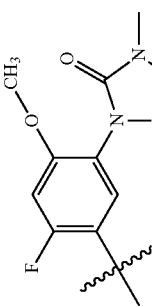 | racemic (single diastereomer) |

TABLE 1-continued

[Structure shown: pyrrolidine-piperidine fused bicyclic system with R¹-R¹¹ substituents connected via NH-Y¹ to a pyrimidine bearing NH-Ar¹ and Y²]

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 25 | CH₃/CH₃ | H/H | H/H | H/H | H/H | F | H | H | [2-cyclopropyl-4-fluoro-5-(4-methyl-5-oxo-4,5-dihydro-tetrazol-1-yl)phenyl] | racemic (single diastereomer) |
| 26 | CH₃/CH₃ | H/H | H/H | H/H | H/H | F | H | H | [2-cyclopropyl-4-fluoro-5-(4-methyl-5-oxo-4,5-dihydro-tetrazol-1-yl)phenyl] | racemic (single diastereomer) |
| 27 | H/H | H/H | H/H | H/H | H/H | F | H | H | [2-cyclopropyl-4-fluoro-5-(4-methyl-5-oxo-4,5-dihydro-tetrazol-1-yl)phenyl] | racemic (single diastereomer) |
| 28 | H/H | | | | | F | | | [2-cyclopropyl-4-fluoro-5-(5-methyl-tetrazol-1-yl)phenyl] | |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 29 | H/H | H/H | H/H | H/H | H/H | F | H | H | cyclopropyl-4-fluoro-5-(4-methyl-5-oxo-4,5-dihydro-1H-tetrazol-1-yl)phenyl | racemic (single diastereomer) |
| 30 | CH₃/CH₃ | H/H | H/H | =O | H/H | F | H | H | cyclopropyl-4-fluoro-5-(4-methyl-5-oxo-4,5-dihydro-1H-tetrazol-1-yl)phenyl | racemic (single diastereomer) |
| 31 | =O | H/H | H/H | CH₃/CH₃ | H/H | F | H | H | cyclopropyl-4-fluoro-5-(4-methyl-5-oxo-4,5-dihydro-1H-tetrazol-1-yl)phenyl | racemic (7, 8a cis) |
| 32 | =O | H/H | H/H | CH₃/CH₃ | H/H | F | H | H | cyclopropyl-4-fluoro-5-(4-methyl-5-oxo-4,5-dihydro-1H-tetrazol-1-yl)phenyl | racemic (7, 8a trans) |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 33 (formic salt) | =O | H/H | H/H | CH₃/CH₃ | H/H | F | H | H |  | racemic (7, 8a trans) |
| 34 | CH₃/CH₃ | H/H | H/H | H/H | H/H | F | H | H | 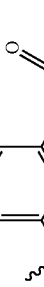 | single enantiomer |
| 35 | CH₃/CH₃ | H/H | H/H | H/H | H/H | F | H | H |  | single enantiomer |
| 36 | CH₃/CH₃ | H/H | H/H | H/H | H/H | F | H | H |  | single enantiomer |

TABLE 1-continued
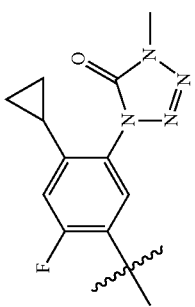
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 37 | CH₃/CH₃ | H/H | H/H | H/H | H/H | F | H | H | 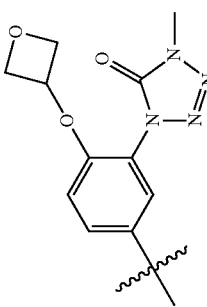 | single enantiomer |
| 38 | H/H | H/H | H/H | CH₃/CH₃ | H/H | F | H | H | 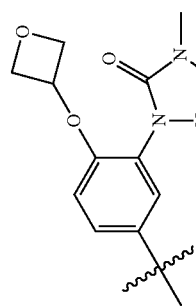 | racemic (single diastereomer) |
| 39 | H/H | H/H | H/H | CH₃/CH₃ | H/H | F | H | H |  | single enantiomer |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 40 | H/H | H/H | H/H | CH₃/CH₃ | H/H | F | H | H | (4-oxetan-3-yloxy-2-(4-methyl-5-oxo-tetrazol-1-yl)phenyl) | single enantiomer |
| 41 | H/H | H/H | H/H | CH₃/CH₃ | H/H | F | H | H | (4-(tetrahydropyran-4-yloxy)-2-cyanophenyl) | racemic (single diastereomer) |
| 42 | H/H | F/F | H/H | CH₃/CH₃ | H/H | F | H | H | (2-cyclopropyl-4-fluoro-5-(4-methyl-5-oxo-tetrazol-1-yl)phenyl) | trans (7S, 8aR) |
| 43 | H/H | F/F | H/H | CH₃/CH₃ | H/H | F | H | H | (2-cyclopropyl-4-fluoro-5-(tetrazol-1-yl)phenyl) | trans (7S, 8aR) |

TABLE 1-continued
| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 44 | H/H | F/F | H/H | CH₃/CH₃ | H/H | F | H | H | 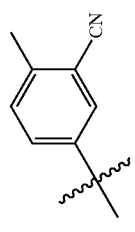 | trans |
| 45 | H/H | F/F | H/H | CH₃/CH₃ | H/H | F | H | H | 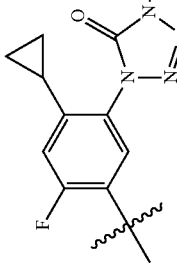 | cis |
| 46 | H/H | F/F | H/H | CH₃/CH₃ | H/H | F | H | H | 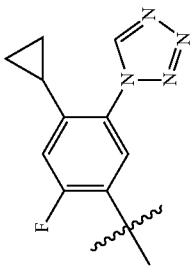 | cis |
| 47 | H/H | H/H | H/H | CH₃/CH₃ | H/H | F | H | H | 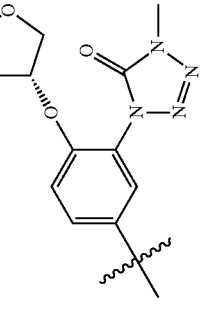 | mixture of two diastereomers |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 48 | H/H | H/H | H/H | CH₃/CH₃ | H/H | F | H | H | 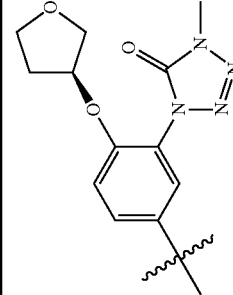 | 7R, 8aS |
| 49 | H/H | H/H | H/H | CH₃/CH₃ | H/H | F | H | H | 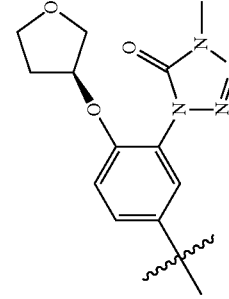 | two diastereomers |
| 50 | H/H | H/H | H/H | CH₃/CH₃ | H/H | F | H | H | 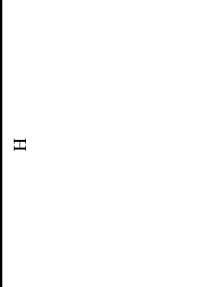 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 51 | H/H | H/H | H/H | CH₃/CH₃ | H/H | F | H | H | tetrahydropyran-oxy phenyl with 4-methyl-5-oxo-tetrazole | racemic |
| 52 | H/H | H/H | H/H | CH₃/CH₃ | H/H | F | H | H | tetrahydropyran-oxy phenyl with 4-methyl-5-oxo-tetrazole | H/H 7R, 8aS |
| 53 | H/H | H/H | H/H | CH₃/CH₃ | H/H | F | H | H | cyclopropyl-fluoro-phenyl with tetrazole | cis racemic (single diastereomer) |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 54 | H/H | H/H | H/H | CH₃/CH₃ | H/H | F | H | H | 5-cyclopropyl-4-fluoro-2-(tetrazol-2-yl)phenyl | single enantiomer |
| 55 | H/H | H/H | H/H | CH₃/CH₃ | H/H | F | H | H | 5-cyclopropyl-4-fluoro-2-(tetrazol-2-yl)phenyl | single enantiomer |
| 56 | H/H | H/H | H/H | CH₃/CH₃ | H/H | CN | H | H | 5-cyclopropyl-4-fluoro-2-(tetrazol-2-yl)phenyl | cis racemic (single diastereomer) |
| 57 | H/H | H/H | H/H | CH₃/CH₃ | H/H | F | H | H | 2-cyano-4-((tetrahydrofuran-3-yl)oxy)phenyl | two diastereomers (7, 8a-cis) |

TABLE 1-continued
| | R$^1$/R$^2$ | R$^3$/R$^4$ | R$^5$/R$^6$ | R$^7$/R$^8$ | R$^9$/R$^{10}$ | R$^{11}$ | Y$^1$ | Y$^2$ | Ar$^1$ | H$^1$/H$^2$ |
|---|---|---|---|---|---|---|---|---|---|---|
| 58 | H/H | H/H | H/H | CH$_3$/CH$_3$ | H/H | F | H | H | 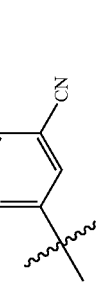 | single enantiomer (7, 8a-cis) |
| 59 | H/H | H/H | H/H | CH$_3$/CH$_3$ | H/H | F | H | H |  | single enantiomer |
| 60 | H/H | H/H | H/H | CH$_3$/CH$_3$ | H/H | F | H | H |  | two diastereomers (7, 8a-cis) |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 61 | H/H | H/H | H/H | CH₃/CH₃ | H/H | F | H | H | 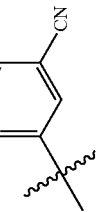 | single enantiomer |
| 62 | H/H | H/H | H/H | CH₃/CH₃ | H/H | F | H | H | 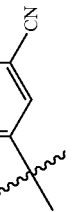 | single enantiomer |
| 63 | H/H | H/H | H/H | CH₃/CH₃ | H/H | F | H | H | 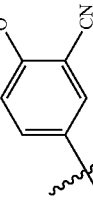 | racemic (single diastereomer) |
| 64 | H/H | H/▼F (R) | H/H | CH₃/CH₃ | H/H | F | H | H | 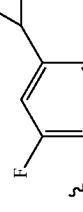 | ▼H/H 7R, 8aR |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 65 | H/H | H/▼F (R) | H/H | CH₃/CH₃ | H/H | F | H | H | (2-cyclopropyl-4-fluoro-5-(4-methyl-5-oxo-4,5-dihydro-1H-tetrazol-1-yl)phenyl) | H/⦁⦁⦁H 7S, 8aR |
| 66 | H/H | H/H | H/H | CH₃/CH₃ | H/H | CN | H | H | (2-cyclopropyl-4-fluoro-5-(4-methyl-5-oxo-4,5-dihydro-1H-tetrazol-1-yl)phenyl) | (cis) racemic |
| 67 | H/H | H/⦁⦁⦁F (S) | H/H | CH₃/CH₃ | H/H | F | H | H | (2-cyclopropyl-4-fluoro-5-(4-methyl-5-oxo-4,5-dihydro-1H-tetrazol-1-yl)phenyl) | H/▼H 7R, 8aR |
| 68 | H/H | H/▼OH (R) | H/H | CH₃/CH₃ | H/H | F | H | H | (2-cyclopropyl-4-fluoro-5-(4-methyl-5-oxo-4,5-dihydro-1H-tetrazol-1-yl)phenyl) | H/▼H 7R, 8aR |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 69 (p-toluene-sulfonic salt) | H/H | H/H | H/H | CH₃/CH₃ | H/CH₃ | F | H | H | 2-cyclopropyl-4-fluoro-5-(4-methyl-5-oxo-4,5-dihydro-1H-tetrazol-1-yl)phenyl | racemic (single diastereomer) |
| 70 (formic acid) | H/H | H/H | H/H | CH₃/CH₃ | H/CH₃ | F | H | H | 2-fluoro-5-(5-methyl-tetrazol-2-yl)phenyl | racemic (single diastereomer) |
| 71 | H/H | H/H | H/H | CH₃/CH₃ | H/H | F | H | H | 4-fluoro-3-(SF₅)phenyl | H/H 7R, 8aS |
| 72 | H/H | H/H | H/H | CH₃/CH₃ | H/H | F | H | H | 4-fluoro-3-(SF₅)phenyl | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 73 (formic acid) | H/H | H/H | H/H | CH₃/CH₃ | H/H | F | H | H | 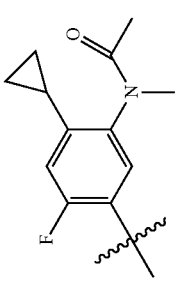 | H/H 7R, 8aS |
| 74 (formic acid) | H/H | H/H | H/H | CH₃/CH₃ | H/H | F | H | H | 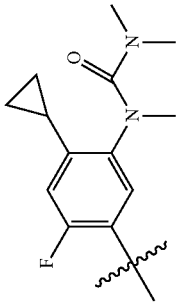 | H/H 7R, 8aS |
| 75 (formic acid) | H/H | H/H | H/H | CH₃/CH₃ | H/H | F | H | H | 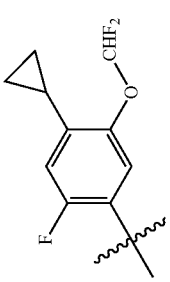 | H/H 7R, 8aS |
| 76 | H/H | H/H | H/H | CH₃/CH₃ | H/H | CN | H | H | 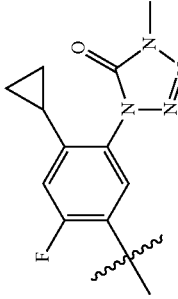 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 77 | H/H | H/H | H/H | CH₃/CH₃ | H/H | F | H | H | (2-(2-hydroxyethoxy)-4-fluoro-5-(4-methyl-5-oxo-tetrazol-1-yl)phenyl) | H/H 7R, 8aS |
| 78 | H/H | H/H | H/H | CH₃/CH₃ | H/H | CN | H | H | (2-(2-hydroxyethoxy)-4-fluoro-5-(4-methyl-5-oxo-tetrazol-1-yl)phenyl) | H/H 7R, 8aS |
| 79 | H/H | H/H | H/H | CH₃/CH₃ | H/H | CN | H | H | (2-((2-hydroxypropyl)oxy)-4-fluoro-5-(4-methyl-5-oxo-triazol-1-yl)phenyl) | H/H 7R, 8aS |

TABLE 1-continued
| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 80 | H/H | H/H | H/H | CH$_3$/CH$_3$ | H/H | CN | H | H | 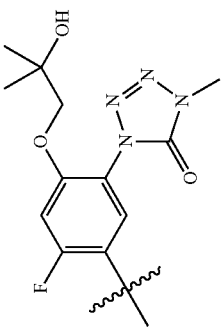 | <br>7R, 8aS |
| 81 | H/H | H/H | H/H | CH$_3$/CH$_3$ | H/H | F | H | H | 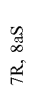 | 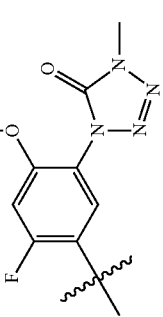<br>7R, 8aS |
| 82 | H/H | H/H | H/H | CH$_3$/CH$_3$ | H/H | F | H | H |  | <br>7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 83 | H/H | H/H | H/H | CH₃/CH₃ | H/H | CN | H | H | 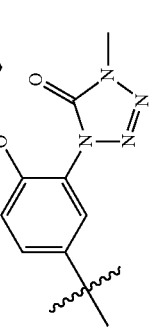 | H/H 7R, 8aS |
| 84 | H/H | H/H | H/H | CH₃/CH₃ | H/H | CN | H | H | 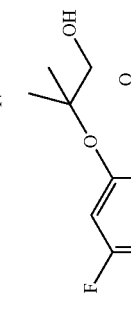 | H/H 7R, 8aS |
| 85 | H/H | H/H | H/H | CH₃/CH₃ | H/H | F | H | H | 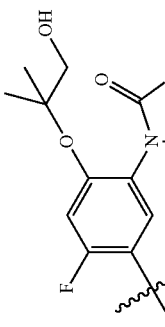 | H/H 7R, 8aS |

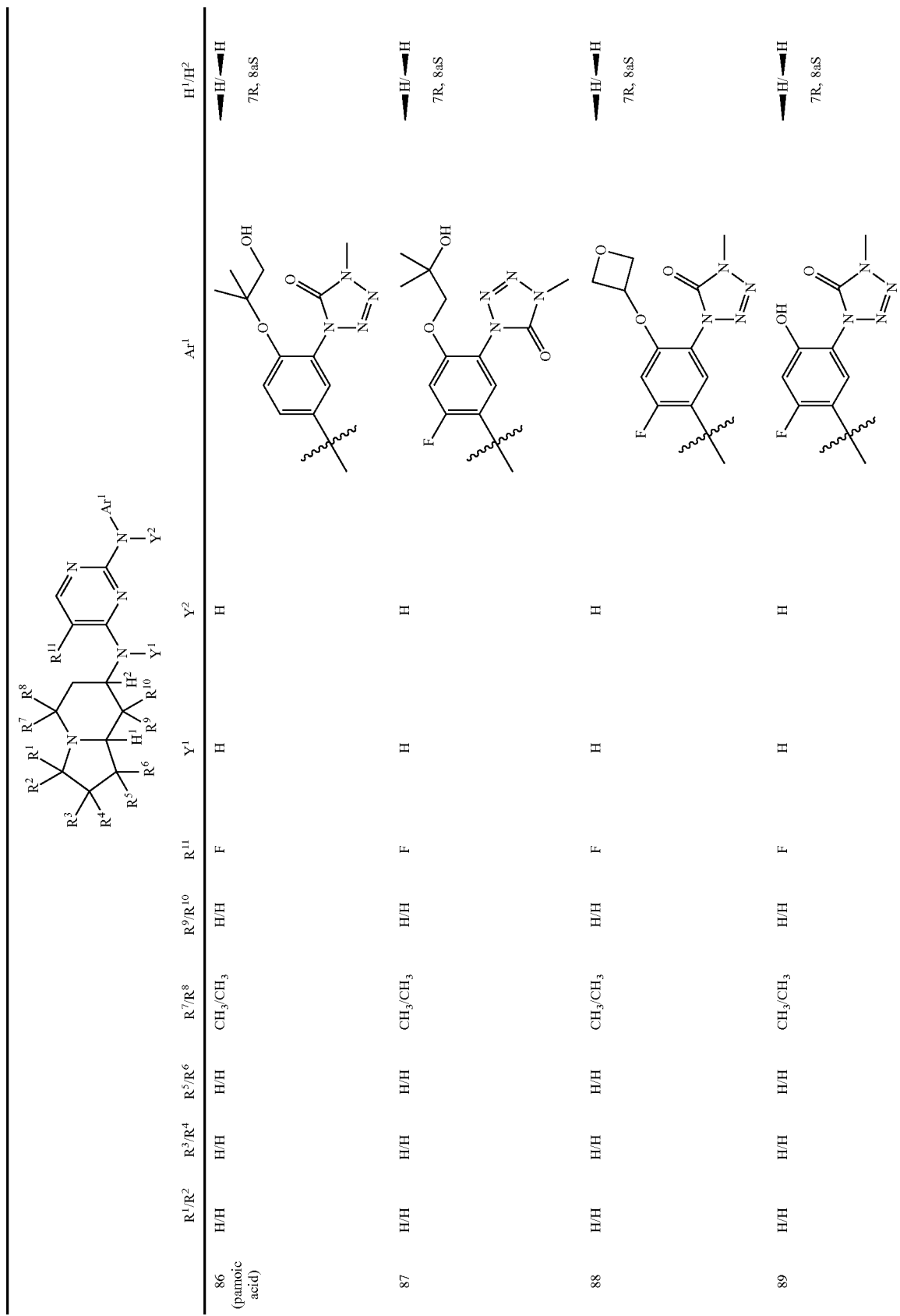

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 90 | H/H | H/H | H/H | CH₃/CH₃ | H/H | CN | H | H | 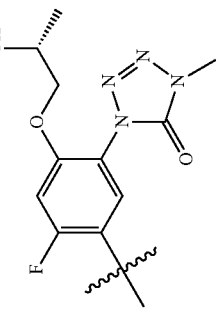 | H/H 7R, 8aS |
| 91 | H/H | H/H | H/H | CH₃/CH₃ | H/H | F | H | H | 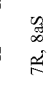 | H/H 7R, 8aS |
| 92 | H/H | H/H | H/H | CH₃/CH₃ | H/H | F | H | H | 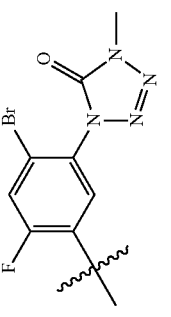 | H/H 7R, 8aS |

TABLE 1-continued

| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 93 | H/H | H/H | H/H | CH₃/CH₃ | H/H | F | H | H | 2-(hydroxyethyl)-4-fluoro-5-(4-methyl-5-oxo-tetrazol-1-yl)phenyl | H/H; 7R, 8aS |
| 94 | H/H | H/H | H/H | CH₃/CH₃ | H/H | F | H | H | 2-(1-hydroxyethyl)-4-fluoro-5-(4-methyl-5-oxo-tetrazol-1-yl)phenyl | H/H; 7R, 8aS; 1:1 mixture of diastereomers at the benzylic alcohol center. |
| 95 | H/H | H/H | H/H | CH₃/CH₃ | H/H | F | H | H | 2-ethyl-4-fluoro-5-(4-methyl-5-oxo-tetrazol-1-yl)phenyl | H/H; 7R, 8aS |
| 96 | H/H | H/H | H/H | CH₃/CH₃ | H/H | F | H | H | 2-(3-hydroxypropynyl)-4-fluoro-5-(4-methyl-5-oxo-tetrazol-1-yl)phenyl | H/H; 7R, 8aS |

TABLE 1-continued

| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 97 | H/H | H/H | H/H | CH$_3$/CH$_3$ | H/H | F | H | H | 2-(3-hydroxypropyl)-4-fluoro-5-(4-methyl-5-oxo-4,5-dihydro-1H-tetrazol-1-yl)phenyl | H/H 7R, 8aS |
| 98 | H/H | H/H | H/H | CH$_3$/CH$_3$ | H/H | F | H | H | 2-cyano-4-fluoro-5-(4-methyl-5-oxo-4,5-dihydro-1H-tetrazol-1-yl)phenyl | H/H 7R, 8aS |
| 99 | H/H | H/H | H/H | CH$_3$/CH$_3$ | H/H | F | H | H | 2-((1-hydroxypropan-2-yl)oxy)-4-fluoro-5-(4-methyl-5-oxo-4,5-dihydro-1H-tetrazol-1-yl)phenyl | single diastereomer |

TABLE 1-continued

| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 100 | H/H | H/H | H/H | CH$_3$/CH$_3$ | H/H | F | H | H | oxetane-spiro-piperidine-phenyl-CN | H/H; 7R, 8aS |
| 101 | H/H | H/H | H/H | CH$_3$/CH$_3$ | H/H | F | H | H | oxetane-spiro-azetidine-phenyl-CN | H/H; 7R, 8aS |
| 102 | H/H | H/H | H/H | CH$_3$/CH$_3$ | H/H | F | H | H | dimethyl-chromeno-tetrazole | ⋯H/⋯H; 7S, 8aR |
| 103 | H/H | H/H | H/H | CH$_3$/CH$_3$ | H/H | F | H | H | methylsulfonyl-piperazine-phenyl-CN | H/H; 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 104 | H/H | H/H | H/H | CH₃/CH₃ | H/H | F | H | H | 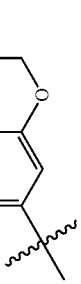 | H/H 7R, 8aS |
| 105 | H/H | H/H | H/H | CH₃/CH₃ | H/H | F | H | H | 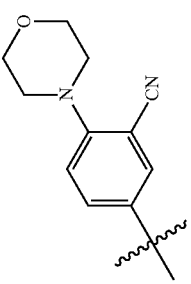 | H/H 7R, 8aS |
| 106 | H/H | H/H | H/H | CH₃/CH₃ | H/H | F | H | H | 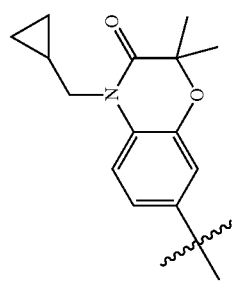 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 107 | H/H | H/H | H/H | CH₃/CH₃ | H/H | F | H | H | 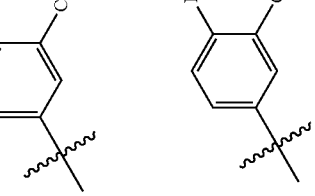 | H/H 7R, 8aS |
| 108 (formate salt) | H/H | H/H | H/H | CH₃/CH₃ | H/H | F | H | H | 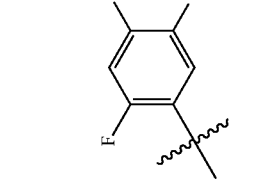 | H/H 7R, 8aS |
| 109 | H/H | H/H | H/H | CH₃/CH₃ | H/H | F | H | H | 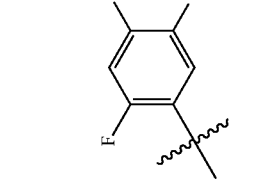 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 110 | H/H | H/H | H/H | CH₃/CH₃ | H/H | F | H | H | | H/H 7R, 8aS |
| 111 | H/H | H/H | H/H | CH₃/CH₃ | H/H | CN | H | H | | H/H 7R, 8aS |
| 112 | H/H | H/H | H/H | CH₃/CH₃ | H/H | CN | H | H | | H/H 7R, 8aS |

TABLE 1-continued
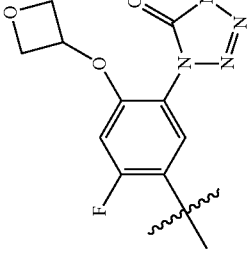
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 113 | H/H | H/H | H/H | CH₃/CH₃ | H/H | CN | H | H | 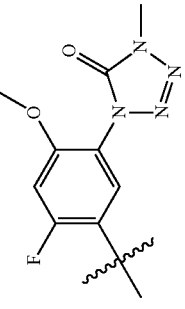 | H/H 7R, 8aS |
| 114 | H/H | H/H | H/H | CH₃/CH₃ | H/H | F | H | H | 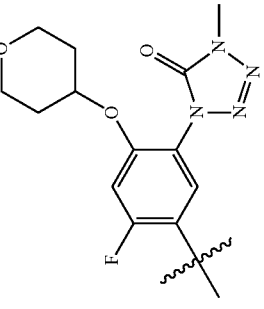 | H/H 7R, 8aS |
| 115 | H/H | H/H | H/H | CH₃/CH₃ | H/H | CN | H | H | | H/H 7R, 8aS |

TABLE 1-continued
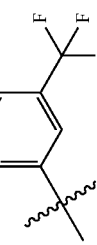
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 116 | H/H | H/H | H/H | CH₃/CH₃ | H/H | F | H | H |  | H/H 7R, 8aS |
| 117 | H/H | H/H | H/H | CH₃/CH₃ | H/H | F | H | H | 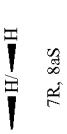 | H/H 7R, 8aS |
| 118 | H/H | H/H | H/H | CH₃/CH₃ | H/H | F | H | H |  | H/H 7R, 8aS |

TABLE 1-continued

| | R$^1$/R$^2$ | R$^3$/R$^4$ | R$^5$/R$^6$ | R$^7$/R$^8$ | R$^9$/R$^{10}$ | R$^{11}$ | Y$^1$ | Y$^2$ | Ar$^1$ | H$^1$/H$^2$ |
|---|---|---|---|---|---|---|---|---|---|---|
| 119 | H/H | H/H | H/H | CH$_3$/CH$_3$ | H/H | F | H | H | 3-fluoro-4-(4-trifluoromethylphenoxy)piperidine | H/H 7R, 8aS |
| 120 | H/H | H/H | H/H | CH$_3$/CH$_3$ | H/H | F | H | H | 1-(oxetan-3-yl)-4-(4-trifluoromethylphenoxy)piperidine | H/H 7R, 8aS |
| 121 | H/H | H/H | H/H | CH$_3$/CH$_3$ | H/H | F | H | H | 3-fluoro-4-(4-trifluoromethylphenoxy)piperidine | H/H 7R, 8aS |
| 122 | H/H | H/H | H/H | CH$_3$/CH$_3$ | H/H | F | | | 1-(oxetan-3-yl)-3-fluoro-4-(4-trifluoromethylphenoxy)piperidine | single diastereomer |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 123 | H/H | H/H | H/H | CH₃/CH₃ | H/H | F | H | H | 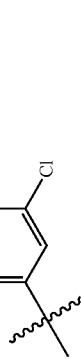 | H/H; 7R, 8aS |
| 124 | H/H | H/H | H/H | CH₃/CH₃ | H/H | F | H | H | 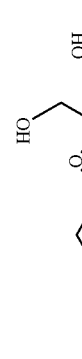 | H/H; 7R, 8aS; diastereomers at 3- and 4-positions of piperidine. Each diastereomer is trans with respect to C3 and C4 substituent. |
| 125 | H/H | H/H | H/H | CH₃/CH₃ | H/H | F | H | H | 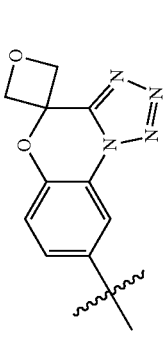 | H/H; 7R, 8aS |
| 126 (TFA salt) | H/H | H/H | H/H | CH₃/CH₃ | H/H | F | H | H | | H/H; 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 127 | H/H | H/H | H/H | CH₃/CH₃ | H/H | F | H | H | 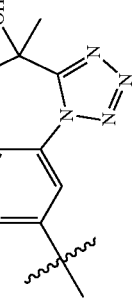 | H/H; 7R, 8aS; mixture of diastereomers at tertiary alcohol carbon. |
| 128 | H/H | H/H | H/H | CH₃/CH₃ | H/H | F | H | H | 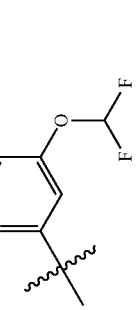 | H/H; 7R, 8aS |
| 129 | H/H | H/H | H/H | CH₃/CH₃ | H/H | F | H | H | 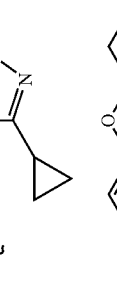 | H/H; 7R, 8aS |
| 130 | H/H | H/H | H/H | CH₃/CH₃ | H/H | F | H | H |  | H/H; 7R, 8aS |

TABLE 1-continued

| | R$^1$/R$^2$ | R$^3$/R$^4$ | R$^5$/R$^6$ | R$^7$/R$^8$ | R$^9$/R$^{10}$ | R$^{11}$ | Y$^1$ | Y$^2$ | Ar$^1$ | H$^1$/H$^2$ |
|---|---|---|---|---|---|---|---|---|---|---|
| 131 | H/H | H/H | H/H | CH$_3$/CH$_3$ | H/H | F | H | H | 4-(2-hydroxyethoxy)-3-trifluoromethylphenyl | H/H, 7R, 8aS |
| 132 | H/H | H/H | H/H | CH$_3$/CH$_3$ | H/H | F | H | H | 4-(2-hydroxyethoxy)-3-(4-methyl-5-oxo-4,5-dihydro-tetrazol-1-yl)phenyl | H/H, 7R, 8aS |
| 133 | H/H | H/H | H/H | CH$_3$/CH$_3$ | H/H | F | H | H | 4-(2-hydroxyethoxy)-3-chlorophenyl | H/H, 7R, 8aS |
| 134 | H/H | H/H | H/H | CH$_3$/CH$_3$ | H/H | F | H | H | 4-(2-hydroxyethoxy)-3-methylphenyl | H/H, 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 135 | H/H | H/H | H/H | CH₃/CH₃ | H/H | F | H | H | (2-(1-hydroxypropan-2-yloxy)-5-yl phenyl with N-methyl tetrazolone) | H/H 7R, 8aS |
| 136 | H/H | H/H | H/H | CH₃/CH₃ | H/H | F | H | H | (4,4-dimethyl-chromeno-tetrazole) | H/H 7R, 8aS |
| 137 (formic acid) | H/H | H/H | H/H | CH₃/CH₃ | H/H | F | H | H | (spiro tetrahydropyran-chromeno-tetrazole) | H/H 7R, 8aS |
| 138 | H/H | H/H | H/H | CH₃/CH₃ | H/H | F | H | H | (2-(4-isopropylpiperazin-1-yl)-5-cyanophenyl) | H/H 7R, 8aS |

TABLE 1-continued
| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 139 | H/H | H/H | H/H | CH₃/CH₃ | H/H | F |  | H |  | H/H 7R, 8aS |
| 140 (bis-formate salt) | H/H | H/H | H/H | CH₃/CH₃ | H/H | F | H | H |  | H/H 7R, 8aS |
| 141 (bis-formate salt) | H/H | H/H | H/H | CH₃/CH₃ | H/H | F | H | H |  | H/H 7R, 8aS |
| 142 (bis-formate salt) | H/H | H/H | H/H | CH₃/CH₃ | H/H | F | H | H |  | H/H 7R, 8aS |

TABLE 1-continued
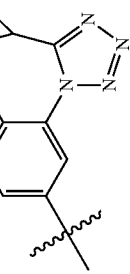
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 143 (bis-formate salt) | H/H | H/H | H/H | CH₃/CH₃ | H/H | F | H | H | 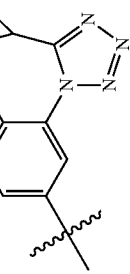 | H/H 7R, 8aS |
| 144 (bis-formate salt) | H/H | H/H | H/H | CH₃/CH₃ | H/H | F | H | H | 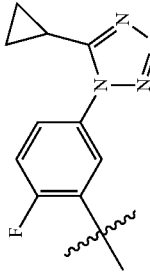 | H/H 7R, 8aS |
| 145 (bis-formate salt) | H/H | H/H | H/H | CH₃/CH₃ | H/H | F | H | H | 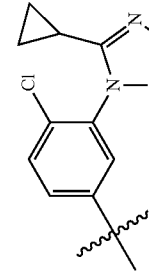 | H/H 7R, 8aS |
| 146 (bis-formate salt) | H/H | H/H | H/H | CH₃/CH₃ | H/H | Cl | H | H | 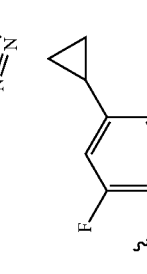 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 147 (bis-formate salt) | H/H | H/H | H/H | CH₃/CH₃ | H/H | Cl | H | H | 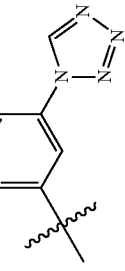 | H/H 7R, 8aS |
| 148 (formate salt) | H/H | H/H | H/H | CH₃/CH₃ | H/H | Cl | H | H | 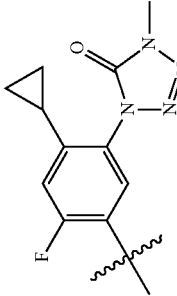 | H/H 7R, 8aS |
| 149 (bis-formate salt) | H/H | H/H | H/H | CH₃/CH₃ | H/H | Cl | H | H | 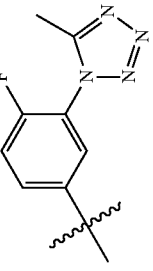 | H/H 7R, 8aS |
| 150 (bis-formate salt) | H/H | H/H | H/H | CH₃/CH₃ | H/H | Cl | H | H | 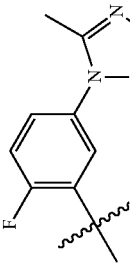 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 151 (bis-formate salt) | H/H | H/H | H/H | CH₃/CH₃ | H/H | Cl | H | H | 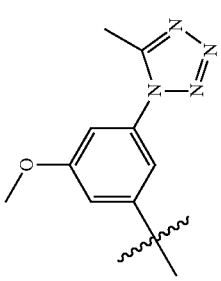 | H/H 7R, 8aS |
| 152 (bis-formate salt) | H/H | H/H | H/H | CH₃/CH₃ | H/H | Cl | H | H | 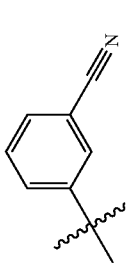 | H/H 7R, 8aS |
| 153 | H/H | H/H | H/H | CH₃/CH₃ | H/H | Cl | H | H | 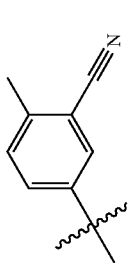 | H/H 7R, 8aS |
| 154 | H/H | H/H | H/H | CH₃/CH₃ | H/H | Cl | H | H |  | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 155 | H/H | H/H | H/H | CH₃/CH₃ | H/H | Cl | H | H | 2-cyclopropyl-5-cyanophenyl | H/H, 7R, 8aS |
| 156 | H/H | H/H | H/H | CH₃/CH₃ | H/H | F | H | H | 3,4,5-trimethoxyphenyl | H/H, 7R, 8aS |
| 157 | H/H | H/H | H/H | CH₃/CH₃ | H/H | F | H | H | benzo[1,3]dioxol-5-yl | H/H, 7R, 8aS |
| 158 | H/H | H/H | H/H | CH₃/CH₃ | H/H | F | H | H | 4-fluoro-2-(2-methoxyethoxy)-5-(4-methyl-5-oxotetrazol-1-yl)phenyl | H/H, 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 159 | H/H | H/H | H/H | CH₃/CH₃ | H/H | F | H | H | 2-(oxetan-3-ylmethoxy)-4-fluoro-5-(4-methyl-5-oxo-tetrazol-1-yl)phenyl | H/H 7R, 8aS |
| 160 (bis-TFA salt) | H/H | H/H | H/H | CH₃/CH₃ | H/H | F | H | H | 2,3-bis(2-methoxyethoxy)phenyl | H/H 7R, 8aS |
| 161 (bis-TFA salt) | H/H | H/H | H/H | CH₃/CH₃ | H/H | F | H | H | 3,5-dimethoxyphenyl | H/H 7R, 8aS |
| 162 (bis-TFA salt) | H/H | H/H | H/H | CH₃/CH₃ | H/H | Cl | H | H | 3,5-dimethoxyphenyl | H/H 7R, 8aS |

TABLE 1-continued
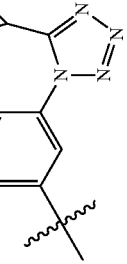
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 163 (bis-TFA salt) | H/H | H/H | H/H | CH₃/CH₃ | H/H | Cl | H | H |  | H/H 7R, 8aS |
| 164 (bis-formate salt) | H/H | H/H | H/H | CH₃/CH₃ | H/H | Cl | H | H | 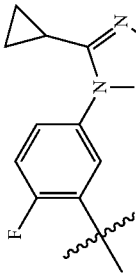 | H/H 7R, 8aS |
| 165 (bis-formate salt) | H/H | H/H | H/H | CH₃/CH₃ | H/H | F | H | H |  | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 166 (bis-formate salt) | H/H | H/H | H/H | CH₃/CH₃ | H/H | F | H | H | 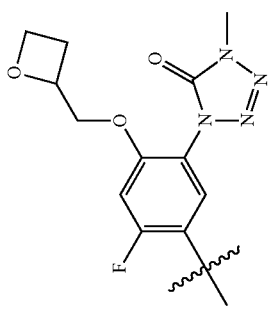 | H/H 7R, 8aS |
| 167 (bis-formate salt) | H/H | H/H | H/H | CH₃/CH₃ | H/H | F | H | H |  | H/H 7R, 8aS |
| 168 | H/H | H/H | H/H | CH₃/CH₃ | H/H | F | H | H |  | H/H 7R, 8aS |

TABLE 1-continued
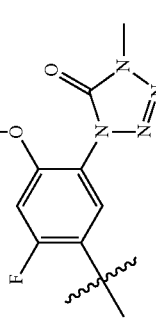
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 169 (bis-TFA salt) | H/H | H/H | H/H | CH₃/CH₃ | H/H | F | H | H | 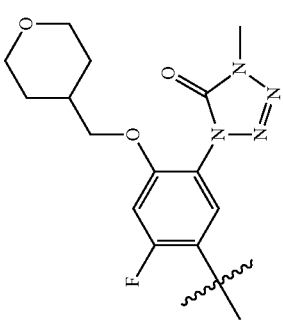 | racemic |
| 170 (bis-TFA salt) | H/H | H/H | H/H | CH₃/CH₃ | H/H | F | H | H | 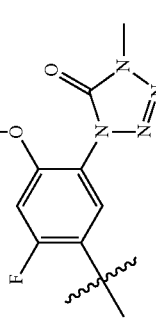 | H/̄H 7R, 8aS |

TABLE 1-continued
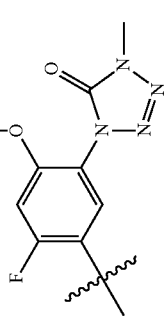
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 171 (bis-TFA salt) | H/H | H/H | H/H | CH₃/CH₃ | H/H | F | H | H | 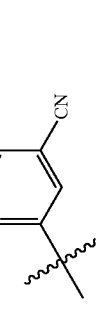 | H/H 7R, 8aS |
| 172 | H/H | H/H | H/H | CH₃/CH₃ | H/H | F | H | H | 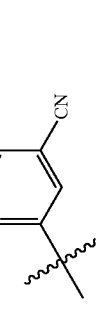 | H/H 7R, 8aS |
| 173 | H/H | H/H | H/H | CH₃/CH₃ | H/H | F | H | H | 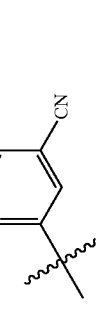 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 174 | H/H | H/H | H/H | CH₃/CH₃ | H/H | F | H | H |  | H/H 7R, 8aS |
| 175 | H/H | H/H | H/H | CH₃/CH₃ | H/H | F | H | H |  | H/H 7R, 8aS |
| 176 | H/H | H/H | H/H | CH₃/CH₃ | H/H | F | H | H |  | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 177 | H/H | H/H | H/H | CH₃/CH₃ | H/H | F | H | H | (1,3-dioxan-2-ylmethoxy)-cyanophenyl | H/H 7R, 8aS |
| 178 | H/H | H/H | H/H | CH₃/CH₃ | H/H | F | H | H | (tetrahydropyran-4-ylmethoxy)-cyanophenyl | H/H 7R, 8aS |
| 179 (formate salt) | H/H | H/H | H/H | CH₃/CH₃ | H/H | F | H | H | (oxetan-3-yloxy)-cyanophenyl | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 180 | H/H | H/H | H/H | CH₃/CH₃ | H/H | F | H | H | 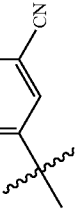 | H/H 7R, 8aS |
| 181 | H/H | H/H | H/H | CH₃/CH₃ | H/H | Cl | H | H | 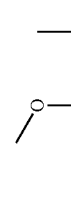 | H/H 7R, 8aS |
| 182 | H/H | H/H | H/H | CH₃/CH₃ | H/H | Cl | H | H | 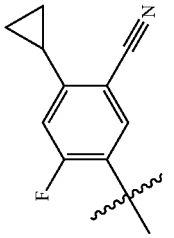 | H/H 7R, 8aS |
| 183 | H/H | H/H | H/H | CH₃/CH₃ | H/H | Cl | H | H | 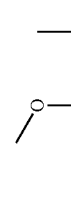 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 184 | H/H | H/H | H/H | CH₃/CH₃ | H/H | F | H | H | (ethyl ester tetrazolone aryl group) | H/H 7R, 8aS |
| 185 (formate salt) | H/H | H/H | H/H | CH₃/CH₃ | H/H | F | H | H | (lactone tetrazolone aryl group) | H/H 7R, 8aS |
| 186 (formate salt) | H/H | H/H | H/H | CH₃/CH₃ | H/H | F | H | H | (hydroxyethoxy tetrazolone aryl group) | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 187 (TFA salt) | H/H | H/H | H/H | CH₃/CH₃ | H/H | F | H | H | 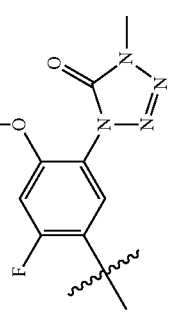 | H/H 7R, 8aS |
| 188 (TFA salt) | H/H | H/H | H/H | CH₃/CH₃ | H/H | F | H | H | 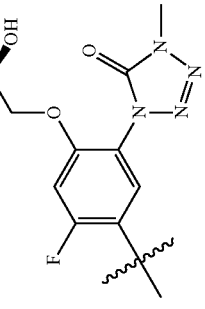 | H/H 7R, 8aS |
| 189 (formate salt) | H/H | H/H | H/H | CH₃/CH₃ | H/H | F | H | H | 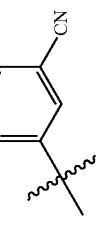 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 190 (formate salt) | H/H | H/H | H/H | CH₃/CH₃ | H/H | F | H | H | 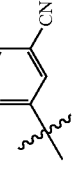 | H/H 7R, 8aS |
| 191 | H/H | H/H | H/H | CH₃/CH₃ | H/H | F | H | H |  | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 192 | H/H | H/H | H/H | CH₃/CH₃ | H/H | F | H | H | 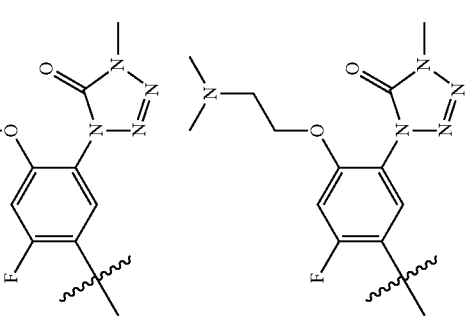 | H/H 7R, 8aS |
| 193 | H/H | H/H | H/H | CH₃/CH₃ | H/H | F | H | 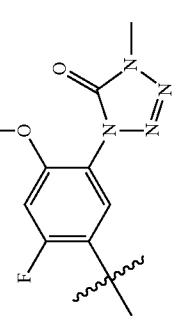 |  | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 194 (TFA salt) | H/H | H/H | H/H | CH₃/CH₃ | H/H | F | H | H | (diethylaminoethoxy-fluoro-(4-methyl-5-oxo-tetrazolyl)phenyl) | H/H 7R, 8aS |
| 195 | H/H | H/H | H/H | CH₃/CH₃ | H/H | F | H | H | (morpholinoethoxy-fluoro-(4-methyl-5-oxo-tetrazolyl)phenyl) | H/H 7R, 8aS |
| 196 | H/H | H/H | H/H | CH₃/CH₃ | H/H | F | H | H | (hydroxy-(tetrazolyl)phenyl) | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 197 | H/H | H/H | H/H | CH₃/CH₃ | H/H | F | H | H | (2,3,4-triacetoxy-tetrahydropyran-yloxy)-cyanophenyl group | H/H 7R, 8aS |
| 198 (TFA salt) | H/H | H/H | H/H | CH₃/CH₃ | H/H | F | H | H | 2-(2-methoxyethoxy)-4-fluoro-5-(4-methyl-5-oxo-tetrazol-1-yl)phenyl | H/H 7R, 8aS |
| 199 (bis-TFA salt) | H/H | H/H | H/H | CH₃/CH₃ | H/H | F | H | H | 2-(2,3-dihydroxypropoxy)-4-fluoro-5-(4-methyl-5-oxo-tetrazol-1-yl)phenyl | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 200 (TFA salt) | H/H | H/H | H/H | CH₃/CH₃ | H/H | F | H | H | 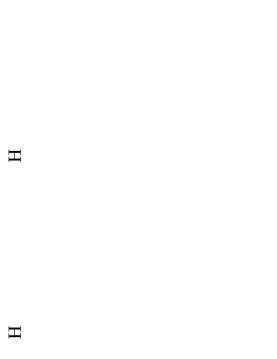 | H/H 7R, 8aS |
| 201 (formate salt) | H/H | H/H | H/H | CH₃/CH₃ | H/H | F | H | H |  | H/H 7R, 8aS |
| 202 (formate salt) | H/H | H/H | H/H | CH₃/CH₃ | H/H | F | H | H | 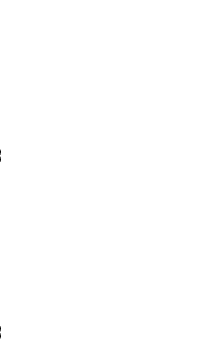 | H/H 7R, 8aS |

TABLE 1-continued
| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 203 (formate salt) | H/H | H/H | H/H | CH₃/CH₃ | H/H | F | H | H | 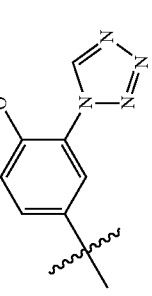 | H/H 7R, 8aS |
| 204 (formate salt) | H/H | H/H | H/H | CH₃/CH₃ | H/H | F | H | H | 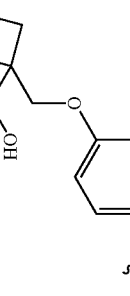 | H/H 7R, 8aS |
| 205 | H/H | H/H | H/H | CH₃/CH₃ | H/H | F | H | H | 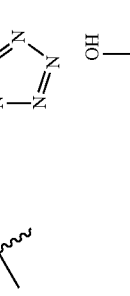 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 206 (formate salt) | H/H | H/H | H/H | CH₃/CH₃ | H/H | F | H | H | 5-(2-hydroxypropoxy)phenyl | H/H 7R, 8aS |
| 207 | H/H | H/H | H/H | CH₃/CH₃ | H/H | F | H | H | 2-(2-methoxyethoxy)-5-(tetrazolyl)phenyl | H/H 7R, 8aS |
| 208 | H/H | H/H | H/H | CH₃/CH₃ | H/H | F | H | H | 4-hydroxy-3-methoxyphenyl | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 209 (formate salt) | H/H | H/H | H/H | CH₃/CH₃ | H/H | F | H | H | 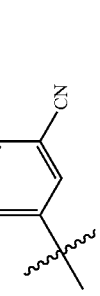 |  7R, 8aS |
| 210 (formate salt) | H/H | H/H | H/H | CH₃/CH₃ | H/H | F | H | H |  | 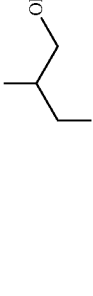 7R, 8aS |
| 211 (TFA salt) | H/H | H/H | H/H | CH₃/CH₃ | H/H | F | 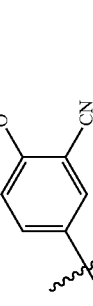 | H | 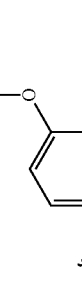 | 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 212 (TFA salt) | H/H | H/H | H/H | CH₃/CH₃ | H/H | F | H | H | 3-(2-cyano-4-yl-phenoxy)propane-1,2-diol substituent | racemic |
| 213 (TFA salt) | H/H | H/H | H/H | CH₃/CH₃ | H/H | F | H | H | 3-(2-cyano-4-yl-phenoxy)propan-1-ol substituent | H/H 7R, 8aS |
| 214 (TFA salt) | H/H | H/H | H/H | CH₃/CH₃ | H/H | F | H | H | 3-(2-(tetrazol-1-yl)-4-yl-phenoxy)propane-1,2-diol substituent | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 215 (TFA salt) | H/H | H/H | H/H | CH₃/CH₃ | H/H | F | H | H | 3-(tetrazol-1-yl)-4-(3-hydroxypropoxy)phenyl | H/H 7R, 8aS |
| 216 | H/H | H/H | H/H | CH₃/CH₃ | H/H | F | H | H | 4-(2-hydroxyethoxy)-3-methoxyphenyl | H/H 7R, 8aS |
| 217 | H/H | H/H | H/H | CH₃/CH₃ | H/H | F | H | H | 4-(2-hydroxy-d4-ethoxy)-3-methoxyphenyl | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 218 | H/H | H/H | H/H | CH₃/CH₃ | H/H | F | H | H | (3-hydroxypropoxy phenyl with tetrazole) | H/H 7R, 8aS |
| 219 | H/H | H/H | H/H | CH₃/CH₃ | H/H | F | H | H | (deuterated hydroxyethoxy phenyl with CN) | H/H 7R, 8aS |
| 220 | H/H | H/H | H/H | CH₃/CH₃ | H/H | F | H | H | (hydroxypropoxy fluorophenyl with methyl-oxo-tetrazole) | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 221 | H/H | H/H | H/H | CH₃/CH₃ | H/H | F | H | H | (structure with OH, D, D, D, F, tetrazolone) | H/H 7R, 8aS |
| 222 | H/H | H/H | H/H | CH₃/CH₃ | H/H | F | H | H | (structure with OH, methyl, F, tetrazolone) | (R)-configuration |
| 223 | H/H | H/H | H/H | CH₃/CH₃ | H/H | Cl | H | H | (structure with OH, tetrazole) | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 224 (formate salt) | H/H | H/H | H/H | CH₃/CH₃ | H/H | F | H | H | 3-(3-hydroxypropoxy)-4-tetrazolyl-phenyl | H/H 7R, 8aS |
| 225 | H/H | H/H | H/H | CH₃/CH₃ | H/H | F | H | H | benzyloxy-cyclobutoxy-fluoro-methyltetrazolone-phenyl | trans |
| 226 | H/H | H/H | H/H | CH₃/CH₃ | H/H | F | H | H | Boc-aminoethoxy-fluoro-methyltetrazolone-phenyl | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 227 | H/H | H/H | H/H | CH₃/CH₃ | H/H | F | H | H | (cyclobutyl-OH / F-phenyl-O-tetrazolinone) | trans |
| 228 | H/H | H/H | H/H | CH₃/CH₃ | H/H | F | H | H | (NH₂-ethyl / F-phenyl-O-tetrazolinone) | H/H, 7R, 8aS |
| 229 (formate salt) | H/H | H/H | H/H | CH₃/CH₃ | H/H | Cl | H | H | (OH-isopropyl-O / CN-phenyl) | H/H, 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 230 (formate salt) | H/H | H/H | H/H | CH₃/CH₃ | H/H | F | H | H | (2-hydroxy-3,3,3-trifluoropropoxy, 4-F, 5-(4-methyl-5-oxo-tetrazol-1-yl)phenyl) | H/H 7R, 8aS |
| 231 (formate salt) | H/H | H/H | H/H | CH₃/CH₃ | H/H | F | H | H | (2-aminoethoxy, 4-F, 5-(4-methyl-5-oxo-tetrazol-1-yl)phenyl) | H/H 7R, 8aS |
| 232 | H/H | H/H | H/H | CH₃/CH₃ | H/H | Cl | H | H | (2-OH, 4-F, 5-(4-methyl-5-oxo-tetrazol-1-yl)phenyl) | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 233 | H/H | H/H | H/H | CH₃/CH₃ | H/H | F | H | H | 5-fluoro-2-[(2S)-2-methoxypropoxy]-4-(4-methyl-5-oxo-4,5-dihydro-1H-tetrazol-1-yl)phenyl | H/H 7R, 8aS |
| 234 | H/H | H/H | H/H | CH₃/CH₃ | H/H | F | (R)-CH(CH₃)CH₂OCH₃ | H | 5-fluoro-2-[(2S)-2-methoxypropoxy]-4-(4-methyl-5-oxo-4,5-dihydro-1H-tetrazol-1-yl)phenyl | 7R, 8aS |
| 235 (formate salt) | H/H | H/H | H/H | CH₃/CH₃ | H/H | Cl | H | H | 5-fluoro-2-[(2S)-2-hydroxypropoxy]-4-(4-methyl-5-oxo-4,5-dihydro-1H-tetrazol-1-yl)phenyl | (S)-configuration |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 236 (formate salt) | H/H | H/H | H/H | CH₃/CH₃ | H/H | Cl | H | H | ![Ar1 structure with OH-propyl-O-phenyl(F)-N-methyltetrazolone] | racemic |
| 237 (formate salt) | H/H | H/H | H/H | CH₃/CH₃ | H/H | Cl | H | H | ![Ar1 structure with OH-ethyl-O-phenyl(F)-N-methyltetrazolone] | H/▬H 7R, 8aS |
| 238 (formate salt) | H/H | H/H | H/H | CH₃/CH₃ | H/H | Cl | H | H | ![Ar1 structure with OMe-propyl-O-phenyl(F)-N-methyltetrazolone] | H/▬H 7R, 8aS |

TABLE 1-continued

| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 239 (formate salt) | H/H | H/H | H/H | CH₃/CH₃ | H/H | Cl | *methoxyisopropyl group* | H | *4-fluoro-2-(methoxyisopropoxy)-5-(4-methyl-5-oxo-tetrazolyl)phenyl* | 7R, 8aS |
| 240 | H/H | H/H | H/H | CH₃/CH₃ | H/H | Cl | H | H | *4-fluoro-2-(methoxyisopropoxy)-5-(4-methyl-5-oxo-tetrazolyl)phenyl* | H/H 7R, 8aS |
| 241 (TFA salt) | H/H | H/H | H/H | CH₃/CH₃ | H/H | F | H | H | *2-fluoro-5-methoxy-3-(5-methyltetrazol-1-yl)phenyl* | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 242 (TFA salt) | H/H | H/H | H/H | CH₃/CH₃ | H/H | F | H | H | 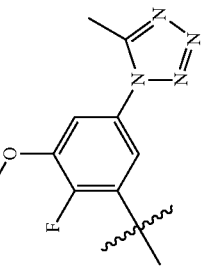 | H/H 7R, 8aS |
| 243 (TFA salt) | H/H | H/H | H/H | CH₃/CH₃ | H/H | F | H | H | 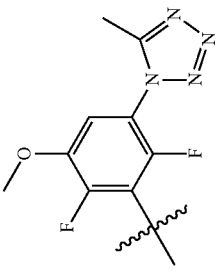 | H/H 7R, 8aS |
| 248 | H/H | H/H | H/H | CH₃/CH₃ | H/H | F | H | H | 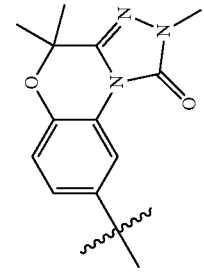 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 249 | H/H | H/H | H/H | CH₃/CH₃ | H/H | F | H | H | | H/H 7R, 8aS |
| 250 | H/H | H/H | H/H | CH₃/CH₃ | H/H | F | H | H | | mixture of diastereomers |
| 251 | H/H | H/H | H/H | CH₃/CH₃ | H/H | F | H | H | | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 252 (besylate salt) | H/H | H/H | H/H | CH₃/CH₃ | H/H | F | H | H | | H/H 7R, 8aS |
| 253 (formate salt) | H/H | H/H | H/H | CH₃/CH₃ | H/H | F | H | H | | H/H 7R, 8aS |
| 254 (besylate salt) | H/H | H/H | H/H | CH₃/CH₃ | H/H | F | H | H | | H/H 7R, 8aS |
| 255 | H/H | H/H | H/H | CH₃/CH₃ | H/H | F | H | H | | H/H 7R, 8aS |

TABLE 1-continued
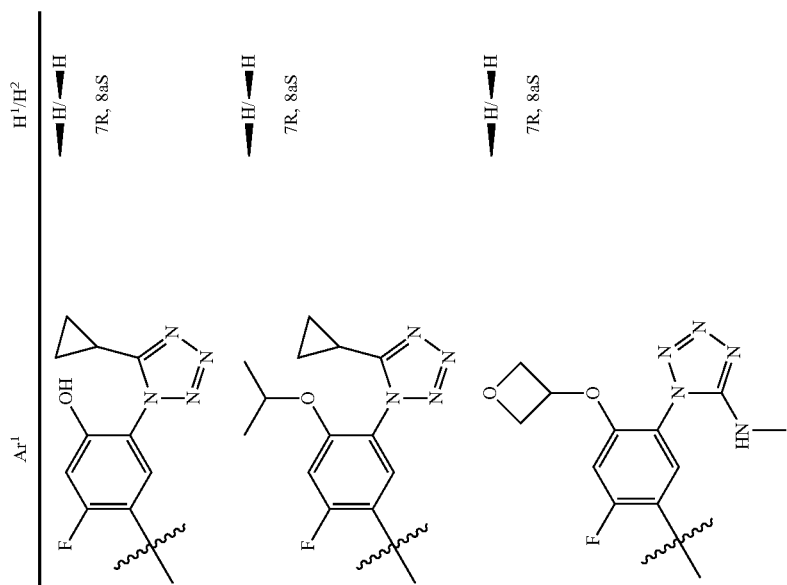
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 256 (TFA salt) | H/H | H/H | H/H | CH₃/CH₃ | H/H | F | H | H | cyclopropyl-tetrazole, OH, F phenyl | H/H 7R, 8aS |
| 257 (TFA salt) | H/H | H/H | H/H | CH₃/CH₃ | H/H | F | H | H | cyclopropyl-tetrazole, isopropoxy, F phenyl | H/H 7R, 8aS |
| 258 | H/H | H/H | H/H | CH₃/CH₃ | H/H | F | H | H | methylamino-tetrazole, oxetanyloxy, F phenyl | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 259 (formate salt) | H/H | H/H | H/H | CH₃/CH₃ | H/H | F | H | H | 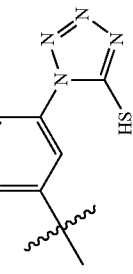 | H/H 7R, 8aS |
| 260 | H/H | H/H | H/H | CH₃/CH₃ | H/H | F | H | H | 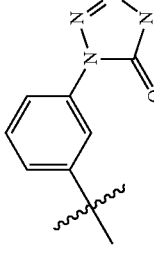 | H/H 7R, 8aS |
| 261 | H/H | H/H | H/H | CH₃/CH₃ | H/H | F | H | H | 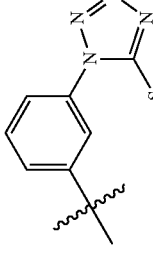 | H/H 7R, 8aS |
| 262 | H/H | H/H | H/H | CH₃/CH₃ | H/H | F | H | H | 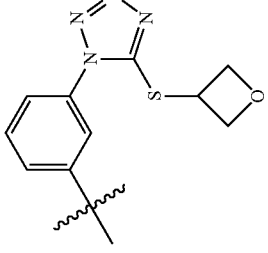 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 263 | H/H | H/H | H/H | CH₃/CH₃ | H/H | F | H | H | (3-substituted phenyl with 1-aryl-tetrazol-5-yl-S-CH(CH₂OH)₂) | H/H 7R, 8aS |
| 264 (besylate salt) | H/H | H/H | H/H | CH₃/CH₃ | H/H | F | H | H | (3-substituted phenyl with 1-aryl-tetrazol-5-yl-S-CH(CH₂OH)(CH₂NH₂)) | mixture of diastereomers |
| 265 (formate salt) | H/H | H/H | H/H | CH₃/CH₃ | H/H | F | H | H | (3-substituted phenyl with tetrazol-5(4H)-one N-oxetanyl) | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 266 (besylate salt) | H/H | H/H | H/H | CH₃/CH₃ | H/H | F | H | H | 3-(1-(2-hydroxyethylthio)tetrazol-5-yl)phenyl | H/H 7R, 8aS |
| 267 (formate salt) | H/H | H/H | H/H | CH₃/CH₃ | H/H | F | H | H | 3-(4-(2-hydroxyethyl)-5-oxo-tetrazol-1-yl)phenyl | H/H 7R, 8aS |
| 268 | H/H | H/H | H/H | CH₃/CH₃ | H/H | F | H | H | benzoxazine-triazinone with hydroxyethyl | H/H 7R, 8aS |

TABLE 1-continued

| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 269 (TFA salt) | H/H | H/H | H/H | CH₃/CH₃ | H/H | F | H | H | 3-(1-(methylsulfonyl)tetrazol-1-yl)phenyl | H/H 7R, 8aS |
| 270 (TFA salt) | H/H | H/H | H/H | CH₃/CH₃ | H/H | F | H | H | 3-(1-(methylsulfinyl)tetrazol-1-yl)phenyl | H/H 7R, 8aS |
| 271 | H/H | H/H | H/H | CH₃/CH₃ | H/H | F | H | H | 3-(1-(2-hydroxyethylthio)tetrazol-1-yl)phenyl | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 272 (besylate salt) | H/H | H/H | H/H | CH₃/CH₃ | H/H | F | H | H | 2-methyl-5-(4-oxo-4,5-dihydro-1H-tetrazol-1-yl)phenyl | H/H, 7R, 8aS |
| 273 (HCl salt) | H/H | H/H | H/H | CH₃/CH₃ | H/H | F | H | H | 2-methyl-5-(4-methyl-5-oxo-4,5-dihydro-1H-tetrazol-1-yl)phenyl | H/H, 7R, 8aS |
| 274 | H/H | H/H | H/H | CH₃/CH₃ | H/H | F | H | H | 2-methyl-5-(1-methyl-5-oxo-1H-tetrazol-4(5H)-yl)phenyl | H/H, 7R, 8aS |
| 275 | H/H | H/H | H/H | CH₃/CH₃ | H/H | F | H | H | 5-(4-(2-hydroxyethyl)-5-oxo-4,5-dihydro-1H-tetrazol-1-yl)-2-methylphenyl | H/H, 7R, 8aS |

TABLE 1-continued
| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 276 (formate salt) | H/H | H/H | H/H | $CH_3/CH_3$ | H/H | F | H | H | 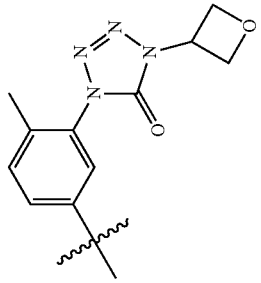 | H/H 7R, 8aS |
| 277 | H/H | H/H | H/H | $CH_3/CH_3$ | H/H | F | H | H | 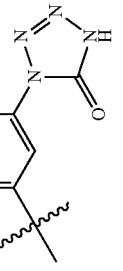 | H/H 7R, 8aS |
| 278 (HCl salt) | H/H | H/H | H/H | $CH_3/CH_3$ | H/H | F | H | H | 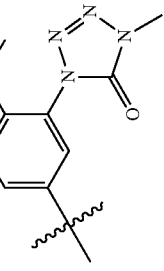 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 279 | H/H | H/H | H/H | CH₃/CH₃ | H/H | F | H | H | 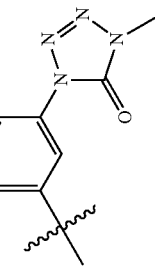 | H/H 7R, 8aS |
| 280 | H/H | H/H | H/H | CH₃/CH₃ | H/H | F | H | H | 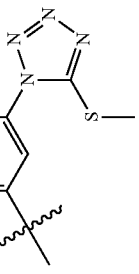 | H/H 7R, 8aS |
| 281 | H/H | H/H | H/H | CH₃/CH₃ | H/H | F | H | H | 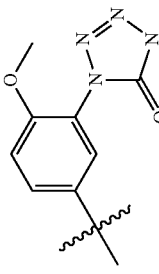 | H/H 7R, 8aS |

TABLE 1-continued

| | R$^1$/R$^2$ | R$^3$/R$^4$ | R$^5$/R$^6$ | R$^7$/R$^8$ | R$^9$/R$^{10}$ | R$^{11}$ | Y$^1$ | Y$^2$ | Ar$^1$ | H$^1$/H$^2$ |
|---|---|---|---|---|---|---|---|---|---|---|
| 282 | H/H | H/H | H/H | CH$_3$/CH$_3$ | H/H | F | H | H | | H/H 7R, 8aS |
| 283 (TFA salt) | H/H | H/H | H/H | CH$_3$/CH$_3$ | H/H | F | H | H | | H/H 7R, 8aS |
| 284 (formate salt) | H/H | H/H | H/H | CH$_3$/CH$_3$ | H/H | F | H | H | | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 285 (formate salt) | H/H | H/H | H/H | CH₃/CH₃ | H/H | F | H | H | | H/H 7R, 8aS |
| 286 (TFA salt) | H/H | H/H | H/H | CH₃/CH₃ | H/H | F | H | H | | H/H 7R, 8aS |
| 287 (besylate salt) | H/H | H/H | H/H | CH₃/CH₃ | H/H | F | H | H | | mixture of diastereomers |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 288 (besylate salt) | H/H | H/H | H/H | CH₃/CH₃ | H/H | F | H | H | | H/H 7R, 8aS |
| 289 (formate salt) | H/H | H/H | H/H | CH₃/CH₃ | H/H | F | H | H | | H/H 7R, 8aS |
| 290 | H/H | H/H | H/H | CH₃/CH₃ | H/H | F | H | H | | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 291 | H/H | H/H | H/H | CH₃/CH₃ | H/H | F | H | H | 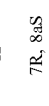 | H/H 7R, 8aS |
| 292 | H/H | H/H | H/H | CH₃/CH₃ | H/H | F | H | H | 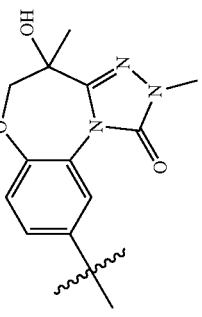 | mixture of diastereomers |
| 293 | H/H | H/H | H/H | CH₃/CH₃ | H/H | F | H | H | 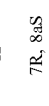 | H/H 7R, 8aS |
| 294 | H/H | H/H | H/H | CH₃/CH₃ | H/H | F | H | H | 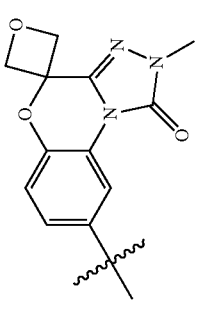 | H/H 7R, 8aS |

TABLE 1-continued

| | $R^1/R^2$ | $R^3/R^4$ | $R^5/R^6$ | $R^7/R^8$ | $R^9/R^{10}$ | $R^{11}$ | $Y^1$ | $Y^2$ | $Ar^1$ | $H^1/H^2$ |
|---|---|---|---|---|---|---|---|---|---|---|
| 295 | H/H | H/H | H/H | CH₃/CH₃ | H/H | F | H | H | | H/H, 7R, 8aS |
| 296 | H/H | H/H | H/H | CH₃/CH₃ | H/H | F | H | H | | H/H, 7R, 8aS |
| 297 | H/H | H/H | H/H | CH₃/CH₃ | H/H | F | H | H | | H/H, 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 298 (formate salt) | H/H | H/H | H/H | CH₃/CH₃ | H/H | F | H | H | 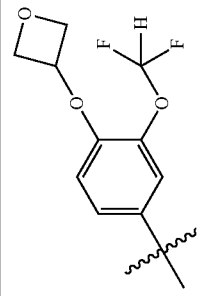 | H/H 7R, 8aS |
| 299 | H/H | H/H | H/H | CH₃/CH₃ | H/H | F | H | H | 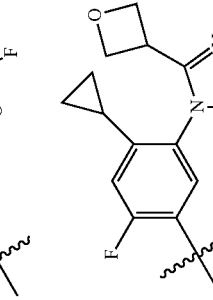 | H/H 7R, 8aS |
| 300 | H/H | H/H | H/H | CH₃/CH₃ | H/H | F | H | H | 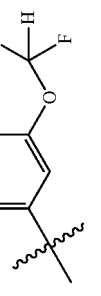 | H/H 7R, 8aS; 2,6-dimethyl on morpholine ring is cis. |
| 301 (formate salt) | H/H | H/H | H/H | CH₃/CH₃ | H/H | F | H | H | 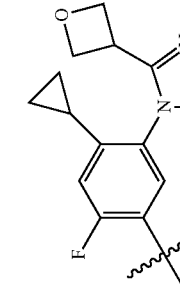 | H/H 7R, 8aS |

TABLE 1-continued
| | R$^1$/R$^2$ | R$^3$/R$^4$ | R$^5$/R$^6$ | R$^7$/R$^8$ | R$^9$/R$^{10}$ | R$^{11}$ | Y$^1$ | Y$^2$ | Ar$^1$ | H$^1$/H$^2$ |
|---|---|---|---|---|---|---|---|---|---|---|
| 302 (formate salt) | H/H | H/H | H/H | CH$_3$/CH$_3$ | H/H | F | H | H |  | H/H 7R, 8aS |
| 303 (formate salt) | H/H | H/H | H/H | CH$_3$/CH$_3$ | H/H | F | H | H |  | H/H 7R, 8aS |
| 304 (formate salt) | H/H | H/H | H/H | CH$_3$/CH$_3$ | H/H | F | H | H |  | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 305 (formate salt) | H/H | H/H | H/H | CH₃/CH₃ | H/H | F | H | H | 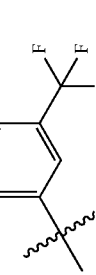 | H/H 7R, 8aS |
| 306 (formate salt) | H/H | H/H | H/H | CH₃/CH₃ | H/H | F | H | H | 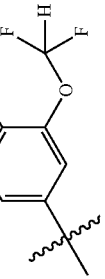 | H/H 7R, 8aS |
| 307 (formate salt) | H/H | H/H | H/H | CH₃/CH₃ | H/H | F | H | H | 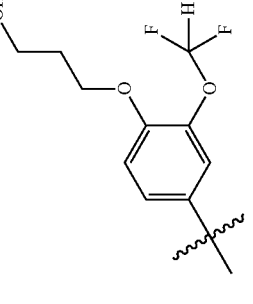 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 308 (formate salt) | H/H | H/H | H/H | CH₃/CH₃ | H/H | F | H | H | 3-hydroxyazetidinyl-2-(difluoromethoxy)phenyl | H/H 7R, 8aS |
| 309 (formate salt) | H/H | H/H | H/H | CH₃/CH₃ | H/H | F | H | H | 5-(3-hydroxycyclobutoxy)-4-fluoro-2-(4-methyl-5-oxo-tetrazolyl)phenyl | H/H 7R, 8aS |
| 310 | H/H | H/H | H/H | CH₃/CH₃ | H/H | F | H | H | 3-(benzyloxy)cyclobutoxy-2-chlorophenyl | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 311 | H/H | H/H | H/H | CH₃/CH₃ | H/H | F | H | H | 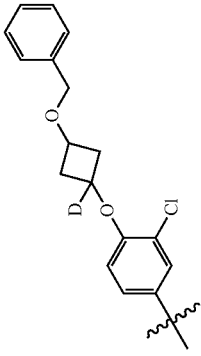 | H/H 7R, 8aS |
| 312 (formate salt) | H/H | H/H | H/H | CH₃/CH₃ | H/H | F | H | H |  | H/H 7R, 8aS |
| 313 (formate salt) | H/H | H/H | H/H | CH₃/CH₃ | H/H | F | H | H | 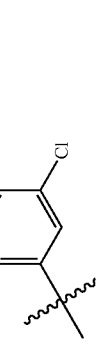 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 314 (formate salt) | H/H | H/H | H/H | CH₃/CH₃ | H/H | CN | H | H | 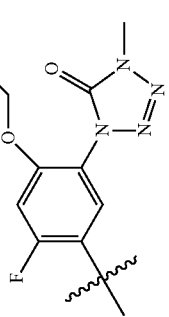 | H/H, 7R, 8aS |
| 315 (formate salt) | H/H | H/H | H/H | CH₃/CH₃ | H/H | F | H | H | 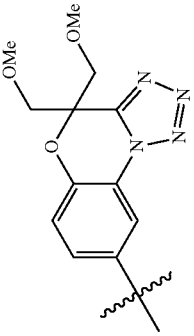 | H/H, 7R, 8aS |
| 316 | H/H | H/H | H/H | CH₃/CH₃ | H/H | F | H | H | 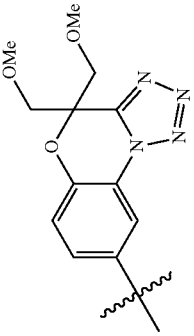 | H/H, 7R, 8aS |
| 317 (formate salt) | H/H | H/H | H/H | CH₃/CH₃ | H/H | F | H | H | 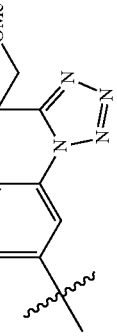 | H/H, 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 318 (p-toluene-sulfonic salt) | H/H | H/H | H/H | CH₃/CH₃ | H/H | F | H | H | 2,2-dimethyl-4-oxo-4H-benzo[1,4]oxazin-3-yl with N-methyl | H/H, 7R, 8aS |
| 319 (p-toluene-sulfonic salt) | H/H | H/H | H/H | CH₃/CH₃ | H/H | F | H | H | 2,2-dimethyl-4-oxo-benzoxazine N-(2-methoxyethyl) | H/H, 7R, 8aS |
| 320 (formate salt) | H/H | H/H | H/H | CH₃/CH₃ | H/H | F | H | H | methyl 2-(trifluoromethyl)benzoate | H/H, 7R, 8aS |
| 321 (formate salt) | H/H | H/H | H/H | CH₃/CH₃ | H/H | F | H | H | 1-chloro-3-[(2-(trifluoromethyl)phenyl)amino]propan-2-ol | mixture of diastereomers |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 322 (formate salt) | H/H | H/H | H/H | CH₃/CH₃ | H/H | F | H | H | (structure with NH₂, methyltetrazolone, fluorophenyl ether) | H/H 7R, 8aS |
| 323 (p-toluenesulfonic salt) | H/H | H/H | H/H | CH₃/CH₃ | H/H | F | H | H | (structure with isopropyl ester, methyltetrazolone, fluorophenyl ether) | H/H 7R, 8aS |
| 324 (formate salt) | H/H | H/H | H/H | CH₃/CH₃ | H/H | F | H | H | (azetidine carboxamide with trifluoromethyl phenyl) | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 325 (p-toluene-sulfonic salt) | H/H | H/H | H/H | CH₃/CH₃ | H/H | F | H | H | (chloroacetamide with CF₃-aniline substituent) | mixture of diastereomers |
| 326 (formate salt) | H/H | H/H | H/H | CH₃/CH₃ | H/H | F | H | H | (3-hydroxyazetidinyl-CF₃-phenyl) | H/H 7R, 8aS |
| 327 (p-toluene-sulfonic salt) | H/H | H/H | H/H | CH₃/CH₃ | H/H | F | H | H | (N-methylbenzamide-Cl-phenyl) | H/H 7R, 8aS |
| 328 (formate salt) | H/H | H/H | H/H | CH₃/CH₃ | H/H | F | H | H | (3-hydroxyazetidinyl-methyltetrazolone-phenyl) | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 329 | H/H | H/H | H/H | CH₃/CH₃ | H/H | F | H | H | 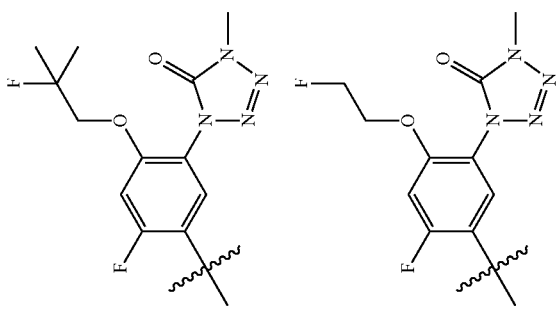 | H/H 7R, 8aS |
| 330 | H/H | H/H | H/H | CH₃/CH₃ | H/H | F | H | H | 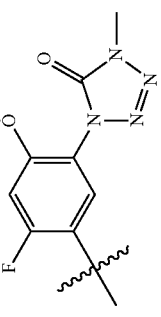 | H/H 7R, 8aS |
| 331 | H/H | H/H | H/H | CH₃/CH₃ | H/H | F | H | H | 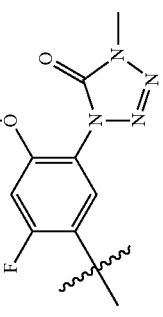 | H/H 7R, 8aS |

TABLE 1-continued
| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 332 | H/H | H/H | H/H | CH₃/CH₃ | H/H | F | H | H | 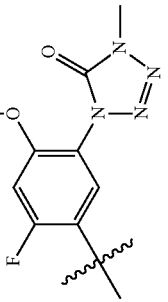 | H/H 7R, 8aS |
| 333 | H/H | H/H | H/H | CH₃/CH₃ | H/H | CN | H | H | 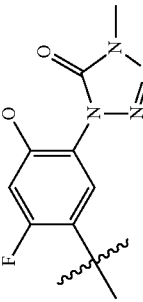 | H/H 7R, 8aS |
| 334 | H/H | H/H | H/H | CH₃/CH₃ | H/H | CN | H | H | 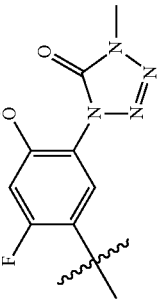 | H/H 7R, 8aS |

TABLE 1-continued

| | R¹/R² | R³/R⁴ | R⁵/R⁶ | R⁷/R⁸ | R⁹/R¹⁰ | R¹¹ | Y¹ | Y² | Ar¹ | H¹/H² |
|---|---|---|---|---|---|---|---|---|---|---|
| 335 | H/H | H/H | H/H | CH₃/CH₃ | H/H | CN | H | H | (structure) | H/H, 7R, 8aS |
| 336 | H/H | H/H | H/H | CH₃/CH₃ | H/H | CN | H | H | (structure) | H/H, 7R, 8aS |

Particular compounds of interest, and salts or solvates or stereoisomers thereof, include:

Compounds 1-4: N2-(4,4-dimethyl-4H-benzo[b]tetrazolo[1,5-d][1,4]oxazin-8-yl)-5-fluoro-N4-(octahydro-5, 5-dimethylindolizin-7-amine)pyrimidine-2,4-diamine;

Compound 5: N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine;

Compounds 6-10: (R/S, S/R, R/R, S/S)-$N^2$-(4-(1-isopropylpiperidin-4-yloxy)-3-(difluoromethoxy)phenyl)-5-fluoro-$N^4$-(octahydro-5,5-dimethylindolizin-7-yl)pyrimidine-2,4-diamine;

Compounds 11-14: (R/S, S/R, R/R, S/S)-5-fluoro-N4-(octahydro-5,5-dimethylindolizin-7-yl)N2-(3-methoxy-5-(5-methyl-1H-tetrazol-1-yl)phenyl)pyrimidine-2,4-diamine;

Compounds 16-21: octahydro-5,5-dimethylindolizin-7ylamino)-5-fluoropyrimidin-2-yl-amino)-2-cyclopropyl-4-fluorophenyl)-4-methyl-1H-tetrazol-5(4H)-one;

Compound 17: 1-(5-(4-((7R,8aS)-octahydro-5,5-dimethylindolizin-7ylamino)-5-fluoropyrimidin-2-yl-amino)-2-cyclopropyl-4-fluorophenyl)-4-methyl-1H-tetrazol-5(4H)-one;

Compound 18: 1-(5-(4-((7S,8aR)-octahydro-5,5-dimethylindolizin-7ylamino)-5-fluoropyrimidin-2-yl amino)-2-cyclopropyl-4-fluorophenyl)-4-methyl-1H-tetrazol-5(4H)-one;

Compound 22: 1-(5-(4-((7R,8aS)-5,5-dimethyl-octahydroindolizin-7-ylamino)-5-fluoropyrimidin-2-ylamino)-4-fluoro-2-methoxyphenyl)-4-methyl-1H-tetrazol-5(4H)-one;

Compound 23: 1-(5-(4-((7R,8aS)-5,5-dimethyl-octahydroindolizin-7-ylamino)-5-fluoropyrimidin-2-ylamino)-4-fluoro-2-isopropoxyphenyl)-4-methyl-1H-tetrazol-5(4H)-one;

Compound 24: (±)-$N^2$-(4-cyclopropyl-2-fluoro-5-(1H-tetrazol-1-yl)phenyl)-5-fluoro-$n^4$-(octahydroindolizin-7-yl)pyrimidine-2,4-diamine;

Compound 26: N2-(4-cyclopropyl-2-fluoro-5-(4,5-dihydro-4-methyl-5-oxotetrazol-yl)phenylamino)-5-fluoro-N4-(octahydro-5,5-dimethylindolizin-7-ylamino) pyrimidine-2,4-diamine;

Compound 27: (±)-1-(5-(5-fluoro-4-(octahydroindolizin-7-ylamino)pyrimidin-2-ylamino)-2-cyclopropyl-4-fluorophenyl)-4-methyl-1H-tetrazol-5(4H)one;

Compound 28: (±)-$N^2$-(4-cyclopropyl-2-fluoro-5-(5-methyl-1H-tetrazol-1-yl)phenyl)-5-fluoro-$n^4$-(octahydroindolizin-7-yl)pyrimidine-2,4-diamine;

Compound 30: N2-{4-cyclopropyl-6-fluoro-[3-(4-methyl)-1,2,3,4-tetrazol-5-one-1-yl]}phenyl-5-fluoro-N4(7-amino-hexahydro-3, 3-dimethylindolizin-5 (1H)-one))2,4-pyrimidinediamine;

Compounds 31-33: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5 (4H)-one;

Compound 31: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 32: 1-(5-(4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 33: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one formate;

Compounds 34 and 35: 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one;

Compound 38: 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one;

Compounds 39-40: 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one;

Compound 41: 5-(5-fluoro-4-(octahydro-5,5-dimethylindolizin-7-ylamino)pyrimidin-2-ylamino)-2-(tetrahydro-2H-pyran-4-yloxy)benzonitrile;

Compound 42: 1-(5-(4-((7S,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 43: $N^2$-(4-cyclopropyl-2-fluoro-5-(1H-tetrazol-1-yl)phenyl)-5-fluoro-$N^4$-((7S,8aR)-2,2-difluoro-octahydro-5,5-dimethylindolizin-7-yl)pyrimidine-2,4-diamine;

Compound 44: (4-((7S,8aR)-2,2-difluoro-octahydro-5,5-dimethylindolizin-7-ylamino)-5-fluoropyrimidin-2-ylamino)-2-methylbenzonitrile;

Compound 45: 1-(5-(4-((7R,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 46: $N^2$-(4-cyclopropyl-2-fluoro-5-(1H-tetrazol-1-yl)phenyl)-5-fluoro-$N^4$-((7R,8aR)-2,2-difluoro-octahydro-5,5-dimethylindolizin-7-yl)pyrimidine-2,4-diamine;

Compound 47: 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 48: 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 49: 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 50: 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 51: 1-(5-(5-fluoro-4-(octahydro-5,5-dimethylindolizin-7-ylamino)pyrimidin-2-ylamino)-2-(tetrahydro-2H-pyran-4-oxy)phenyl)-4-methyl-1H-tetrazol-5(4H)-one;

Compound 52: 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one;

Compound 53: (±)-$N^2$-(4-cyclopropyl-2-fluoro-5-(1H-tetrazol-1-yl)phenyl)-5-fluoro-$n^4$-(octahydro-5,5-dimethylindolizin-7-yl)pyrimidine-2,4-diamine;

Compounds 54 and 55: (±)-$N^2$-(4-cyclopropyl-2-fluoro-5-(1H-tetrazol-1-yl)phenyl)-5-fluoro-$n^4$-(octahydro-5,5-dimethylindolizin-7-yl)pyrimidine-2,4-diamine;

Compound 56: (±)-2-(4-cyclopropyl-2-fluoro-5-(1H-tetrazol-1-yl)phenylamino)-4-(octahydro-5,5-dimethylindolizin-7-ylamino)pyrimidine-5-carbonitrile;

Compound 57: 2-((R)-tetrahydrofuran-3-yloxy)-5-(5-fluoro-4-(octahydro-5,5-dimethylindolizin-7-ylamino)pyrimidin-2-ylamino)benzonitrile;

Compounds 58-59: 2-((R)-tetrahydrofuran-3-yloxy)-5-(5-fluoro-4-(octahydro-5,5-dimethylindolizin-7-ylamino)pyrimidin-2-ylamino)benzonitrile;

Compound 60: 2-((S)-tetrahydrofuran-3-yloxy)-5-(5-fluoro-4-(octahydro-5,5-dimethylindolizin-7-ylamino)pyrimidin-2-ylamino)benzonitrile;

Compounds 61-62: 2-((S)-tetrahydrofuran-3-yloxy)-5-(5-fluoro-4-(octahydro-5,5-dimethylindolizin-7-ylamino)pyrimidin-2-ylamino)benzonitrile;

Compound 63: 5-(5-fluoro-4-(octahydro-5,5-dimethylindolizin-7-ylamino)pyrimidin-2-ylamino)-2-(oxetan-3-yloxy)benzonitrile;

Compound 64: 1-(5-(4-((2R,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 65: 1-(5-(4-((2R,7S,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 66: 4-((R/S,S/R)-Octahydro-5,5-dimethylindolizin-7-ylamino)-2-(4-cyclopropyl-2-fluoro-5-(4,5-dihydro-4-methyl-5-oxotetrazol-yl)phenylamino) pyrimidine-5-carbonitrile;

Compound 67: 1-(5-(4-((2S,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 68: 1-(5-(4-((2R,7R,8aR)-2-hydroxy-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compounds 69-70: 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine;

Compound 69: 1-(5-(5-Fluoro-4-(octahydro-5,5,8-trimethylindolizin-7-ylamino)pyrimidin-2-ylamino)-2-cyclopropyl-4-fluorophenyl)-4-methyl-1H-tetrazol-5(4H)-one;

Compound 70: 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine;

Compound 76: 4-(R,S)-Octahydro-5,5-dimethylindolizin-7-ylamino)-2-(4-cyclopropyl-2-fluoro-5-(4,5-dihydro-4-methyl-5-oxotetrazol-yl)phenylamino) pyrimidine-5-carbonitrile;

Compound 77: 1-(2-(2-hydroxyethoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;

Compound 78: 4-((7R,8aS)-octahydro-5,5-dimethylindolizin-7-ylamino)-2-(4-(2-hydroxyethoxy)-2-fluoro-5-(4,5-dihydro-4-methyl-5-oxotetrazol-1-yl)phenylamino)pyrimidine-5-carbonitrile;

Compound 79: 4-((7R,8aS)-octahydro-5,5-dimethylindolizin-7-ylamino)-2-(4-((S)-2-hydroxypropoxy)-2-fluoro-5-(4,5-dihydro-4-methyl-5-oxotetrazol-1-yl)phenylamino)pyrimidine-5-carbonitrile;

Compound 80: 4-((7R,8aS)-octahydro-5,5-dimethylindolizin-7-ylamino)-2-(4-(2-hydroxy-2-methylpropoxy)-2-fluoro-5-(4,5-dihydro-4-methyl-5-oxotetrazol-1-yl)phenylamino)pyrimidine-5-carbonitrile;

Compound 81: 1-(2-((S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;

Compound 82: 1-(5-(4-((7R,8aS)-5,5-dimethyloctahydroindolizin-7-ylamino)-5-fluoropyrimidin-2-ylamino)-4-fluoro-2-((R)-2-hydroxypropoxy)phenyl)-4-methyl-1H-tetrazol-5(4H)-one;

Compound 83: 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile;

Compound 84: 4-((7R,8aS)-5,5-dimethyloctahydroindolizin-7-ylamino)-2-(2-fluoro-4-(1-hydroxy-2-methylpropan-2-yloxy)-5-(4-methyl-5-oxo-4,5-dihydro-1H-tetrazol-1-yl)phenylamino)pyrimidine-5-carbonitrile;

Compound 85: 1-(5-(4-((7R,8aS)-5,5-dimethyloctahydroindolizin-7-ylamino)-5-fluoropyrimidin-2-ylamino)-4-fluoro-2-(1-hydroxy-2-methylpropan-2-yloxy)phenyl)-4-methyl-1H-tetrazol-5(4H)-one;

Compound 86: 1-(5-(4-((7R,8aS)-5,5-dimethyloctahydroindolizin-7-ylamino)-5-fluoropyrimidin-2-ylamino)-2-(1-hydroxy-2-methylpropan-2-yloxy)phenyl)-4-methyl-1H-tetrazol-5(4H)-one;

Compound 87: 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5(4H)-one;

Compound 88: 1-(5-(4-((7R,8aS)-octahydro-5,5-dimethylindolizin-7-ylamino)-5-fluoropyrimidin-2-ylamino)-4-fluoro-2-(oxetan-3-yloxy)phenyl)-4-methyl-1H-tetrazol-5(4H)-one;

Compound 89: 1-(5-(4-((7R,8aS)-5,5-dimethyloctahydroindolizin-7-ylamino)-5-fluoropyrimidin-2-ylamino)-4-fluoro-2-hydroxyphenyl)-4-methyl-1H-tetrazol-5(4H)-one;

Compound 90: 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimidine-5-carbonitrile;

Compound 91: 1-(5-(4-((7R,8aS)-5,5-dimethylindolizin-7-ylamino)-5-fluoropyrimidin-2-ylamino)-2-bromo-4-fluorophenyl)-4-methyl-1H-tetrazol-5(4H)-one;

Compound 92: 1-(5-(4-((7R,8aS)-5,5-dimethylindolizin-7-ylamino)-5-fluoropyrimidin-2-ylamino)-4-fluoro-2-vinylphenyl)-4-methyl-1H-tetrazol-5(4H)-one;

Compound 93: 1-(5-(4-((7R,8aS)-5,5-dimethylindolizin-7-ylamino)-5-fluoropyrimidin-2-ylamino)-4-fluoro-2-(2-hydroxyethyl)phenyl)-4-methyl-1H-tetrazol-5(4H)-one;

Compound 94: 1-(5-(4-((7R,8aS)-octahydro-5,5-dimethylindolizin-7-ylamino)-5-fluoropyrimidin-2-ylamino)-4-fluoro-2-(1-hydroxyethyl)phenyl)-4-methyl-1H-tetrazol-5(4H)-one;

Compound 95: 1-(5-(4-((7R,8aS)-octahydro-5,5-dimethylindolizin-7-ylamino)-5-fluoropyrimidin-2-ylamino)-2-ethyl-4-fluorophenyl)-4-methyl-1H-tetrazol-5(4H)-one;

Compound 96: 1-(5-(4-((7R,8aS)-octahydro-5,5-dimethylindolizin-7-ylamino)-5-fluoropyrimidin-2-ylamino)-4-fluoro-2-(3-hydroxyprop-1-ynyl)phenyl)-4-methyl-1H-tetrazol-5(4H)-one;

Compound 97: 1-(5-(4-((7R,8aS)-octahydro-5,5-dimethylindolizin-7-ylamino)-5-fluoropyrimidin-2-ylamino)-4-fluoro-2-(3-hydroxypropyl)phenyl)-4-methyl-1H-tetrazol-5(4H)-one;

Compound 98: 4-(4-((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)benzonitrile;

Compound 99: 1-(2-((R)-1-hydroxypropan-2-yloxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;

Compound 100: 5-(4-(((7R,8aS)-5,5-dimethyloctahydroindolizin-7-ylamino)-5-fluoropyrimidin-2-ylamino)-2-(2-oxa-7-azaspiro[3.5]nonan-7-yl)benzonitrile;

Compound 101: 5-(4-(((7R,8aS)-5,5-dimethyloctahydroindolizin-7-ylamino)-5-fluoropyrimidin-2-ylamino)-2-(2-oxa-6-azaspiro[3.3]heptan-6-yl)benzonitrile;

Compound 102: N2-(4,4-dimethyl-4H-benzo[b]tetrazolo[1,5-d][1,4]oxazin-8-yl)-N4-((7S,8aR)-5,5-dimethyloctahydroindolizin-7-yl)-5-fluoropyrimidine-2,4-diamine;

Compound 103: 5-((4-(((7R,8aS)-5,5-Dimethyloctahydroindolizin-7-yl)amino)-5-fluoropyrimidin-2-yl)amino)-2-(4-(methylsulfonyl)piperazin-1-yl)benzonitrile;

Compound 104: 4-(cyclopropylmethyl)-7-((4-(((7R,8aS)-5,5-dimethyloctahydroindolizin-7-yl)amino)-5-fluoropyrimidin-2-yl)amino)-2H-benzo[b][1,4]oxazin-3(4H)-one;

Compound 105: 4-(cyclopropylmethyl)-7-((4-(((7R,8aS)-5,5-dimethyloctahydroindolizin-7-yl)amino)-5-fluoropyrimidin-2-yl)amino)-2,2-dimethyl-2H-benzo[b][1,4]oxazin-3(4H)-one;

Compound 106: 5-((4-(((7R,8aS)-5,5-dimethyloctahydroindolizin-7-yl)amino)-5-fluoropyrimidin-2-yl)amino)-2-morpholinobenzonitrile;

Compound 107: 5-((4-(((7R,8aS)-5,5-dimethyloctahydroindolizin-7-yl)amino)-5-fluoropyrimidin-2-yl)amino)-2-(4-hydroxypiperidin-1-yl)benzonitrile;

Compound 108: 5-((4-(((7R,8aS)-5,5-dimethyloctahydroindolizin-7-yl)amino)-5-fluoropyrimidin-2-yl)amino)-2-(4-methylpiperazin-1-yl)benzonitrile, formate salt;

Compound 109: 1-(5-((4-(((7R,8aS)-5,5-dimethyloctahydroindolizin-7-yl)amino)-5-fluoropyrimidin-2-yl)amino)-4-fluoro-2-(((R)-tetrahydrofuran-3-yl)oxy)phenyl)-4-methyl-1,4-dihydro-5H-tetrazol-5-one;

Compound 110: 1-(5-((4-(((7R,8aS)-5,5-dimethyloctahydroindolizin-7-yl)amino)-5-fluoropyrimidin-2-yl)amino)-4-fluoro-2-(((S)-tetrahydrofuran-3-yl)oxy)phenyl)-4-methyl-1,4-dihydro-5H-tetrazol-5-one;

Compound 111: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-(((R)-tetrahydrofuran-3-yl)oxy)phenyl)amino)pyrimidine-5-carbonitrile;

Compound 112: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-(((S)-tetrahydrofuran-3-yl)oxy)phenyl)amino)pyrimidine-5-carbonitrile;

Compound 113: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-(oxetan-3-yloxy)phenyl)amino)pyrimidine-5-carbonitrile;

Compound 114: 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)oxy)phenyl)-4-methyl-1,4-dihydro-5H-tetrazol-5-one;

Compound 115: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-((tetrahydro-2H-pyran-4-yl)oxy)phenyl)amino)pyrimidine-5-carbonitrile;

Compound 116: 5-(4-(((7R,8aS)-5,5-dimethyloctahydroindolizin-7-yl)amino)-5-fluoropyrimidin-2-yl)amino)-2-(4-(oxetan-3-yl)piperazin-1-yl)benzonitrile;

Compound 117: 1-(5-((4-(((7R,8aS)-5,5-dimethyloctahydroindolizin-7-yl)amino)-5-fluoropyrimidin-2-yl)amino)-2-(4-(oxetan-3-yl)piperazin-1-yl)phenyl)-4-methyl-1,4-dihydro-5H-tetrazol-5-one;

Compound 118: $N^4$-((7R,8aS)-5,5-dimethyloctahydroindolizin-7-yl)-5-fluoro-$N^2$-(4-(piperidin-4-yloxy)-3-(trifluoromethyl)phenyl)pyrimidine-2,4-diamine;

Compound 119: $N^4$-((7R,8aS)-5,5-dimethyloctahydroindolizin-7-yl)-5-fluoro-$N^2$-(4-(((3R,4R)-3-fluoropiperidin-4-yl)oxy)-3-(trifluoromethyl)phenyl)pyrimidine-2,4-diamine;

Compound 120: $N^4$-((7R,8aS)-5,5-dimethyloctahydroindolizin-7-yl)-5-fluoro-$N^2$-(4-((1-(oxetan-3-yl)piperidin-4-yl)oxy)-3-(trifluoromethyl)phenyl)pyrimidine-2,4-diamine;

Compound 121: $N^4$-((7R,8aS)-5,5-dimethyloctahydroindolizin-7-yl)-5-fluoro-$N^2$-(4-(((3S,4S)-3-fluoropiperidin-4-yl)oxy)-3-(trifluoromethyl)phenyl)pyrimidine-2,4-diamine;

Compound 122: $N^4$-((7R,8aS)-5,5-dimethyloctahydroindolizin-7-yl)-5-fluoro-$N^2$-(4-(((3R,4R)-3-fluoro-1-(oxetan-3-yl)piperidin-4-yl)oxy)-3-(trifluoromethyl)phenyl)pyrimidine-2,4-diamine;

Compound 123: $N^2$-(3-chloro-4-(((3S,4S)-3-fluoropiperidin-4-yl)oxy)phenyl)-$N^4$-((7R,8aS)-5,5-dimethyloctahydroindolizin-7-yl)-5-fluoropyrimidine-2,4-diamine;

Compound 124: 4-(2-chloro-4-((4-(((7R,8aS)-5,5-dimethyloctahydroindolizin-7-yl)amino)-5-fluoropyrimidin-2-yl)amino)phenoxy)piperidin-3-ol;

Compound 125: 8-((4-(((7R,8aS)-5,5-dimethyloctahydroindolizin-7-yl)amino)-5-fluoropyrimidin-2-yl)amino)-4H-benzo[b]tetrazolo[1,5-d][1,4]oxazine-4,4-diyl)dimethanol;

Compound 126: 9-(4-(((7R,8aS)-5,5-dimethyloctahydroindolizin-7-ylamino)-5-fluoropyrimidin-2-ylamino)-4-methyl-4,5-dihydrobenzo[b]tetrazolo[1,5-d][1,4]oxazepin-4-ol;

Compound 127: 9-((4-(((7R,8aS)-5,5-dimethyloctahydroindolizin-7-yl)amino)-5-fluoropyrimidin-2-yl)amino)-4-methyl-4,5-dihydrobenzo[b]tetrazolo[1,5-d][1,4]oxazepin-4-ol;

Compound 128: $N^2$-(3-(difluoromethoxy)-4-(piperidin-4-yloxy)phenyl)-$N^4$-((7R,8aS)-5,5-dimethyloctahydroindolizin-7-yl)-5-fluoropyrimidine-2,4-diamine;

Compound 129: 2-(2-(5-cyclopropyl-1H-tetrazol-1-yl)-4-((4-(((7R,8aS)-5,5-dimethyloctahydroindolizin-7-yl)amino)-5-fluoropyrimidin-2-yl)amino)phenoxy)ethan-1-ol;

Compound 130: 2-(4-((4-(((7R,8aS)-5,5-dimethyloctahydroindolizin-7-yl)amino)-5-fluoropyrimidin-2-yl)amino)-2-fluorophenoxy)ethan-1-ol;

Compound 131: 2-(4-((4-(((7R,8aS)-5,5-dimethyloctahydroindolizin-7-yl)amino)-5-fluoropyrimidin-2-yl)amino)-2-(trifluoromethyl)phenoxy)ethan-1-ol;

Compound 132: 1-(5-((4-(((7R,8aS)-5,5-dimethyloctahydroindolizin-7-yl)amino)-5-fluoropyrimidin-2-yl)amino)-2-(2-hydroxyethoxy)phenyl)-4-methyl-1,4-dihydro-5H-tetrazol-5-one;

Compound 133: 2-(2-chloro-4-((4-(((7R,8aS)-5,5-dimethyloctahydroindolizin-7-yl)amino)-5-fluoropyrimidin-2-yl)amino)phenoxy)ethan-1-ol;

Compound 134: 2-(4-((4-(((7R,8aS)-5,5-dimethyloctahydroindolizin-7-yl)amino)-5-fluoropyrimidin-2-yl)amino)-2-(methyl)phenoxy)ethan-1-ol;

Compound 135: 1-(5-((4-(((7R,8aS)-5,5-dimethyloctahydroindolizin-7-yl)amino)-5-fluoropyrimidin-2-yl)amino)-2-(((S)-1-hydroxypropan-2-yl)oxy)phenyl)-4-methyl-1,4-dihydro-5H-tetrazol-5-one;

Compound 136: N2-(4,4-dimethyl-4H-benzo[b]tetrazolo[1,5-d][1,4]oxazin-8-yl)-N4-((7R,8aS)-5,5-dimethyloctahydroindolizin-7-yl)-5-fluoropyrimidine-2,4-diamine;

Compound 137: N4-((7R,8aS)-5,5-dimethyloctahydroindolizin-7-yl)-5-fluoro-N2-(2',3',5',6'-tetrahydrospiro[benzo[b]tetrazolo[1,5-d][1,4]oxazine-4,4'-pyran]-8-yl)pyrimidine-2,4-diamine, formate salt;

Compound 138: 5-(4-((7R,8aS)-octahydro-5,5-dimethylindolizin-7-ylamino)-5-fluoropyrimidin-2-ylamino)-2-(4-isopropylpiperazin-1-yl)benzonitrile;

Compound 139: 1-(5-(4-(((7R,8aS)-5,5-dimethyloctahydroindolizin-7-yl)(2-hydroxy-2-methylpropyl)amino)-5-fluoropyrimidin-2-ylamino)-4-fluoro-2-(2-hydroxy-2-methylpropoxy)phenyl)-4-methyl-1H-tetrazol-5(4H)-one;

Compound 140: N4-((7R,8aS)-5,5-dimethyloctahydroindolizin-7-yl)-5-fluoro-N2-(4-methoxy-3-(5-methyl-1H-tetrazol-1-yl)phenyl)pyrimidine-2,4-diamine, bis-formate salt;

Compound 141: N4-((7R,8aS)-5,5-dimethyloctahydroindolizin-7-yl)-5-fluoro-N2-(4-fluoro-3-(5-methyl-1H-tetrazol-1-yl)phenyl)pyrimidine-2,4-diamine, bis-formate salt;

Compound 142: N4-((7R,8aS)-5,5-dimethyloctahydroindolizin-7-yl)-5-fluoro-N2-(2-fluoro-5-(5-methyl-1H-tetrazol-1-yl)phenyl)pyrimidine-2,4-diamine, formate salt;

Compound 143: N2-(3-(5-cyclopropyl-1H-tetrazol-1-yl)-4-fluorophenyl)-N4-((7R,8aS)-5,5-dimethyloctahydroindolizin-7-yl)-5-fluoropyrimidine-2,4-diamine, bis-formate salt;

Compound 144: N2-(5-(5-cyclopropyl-1H-tetrazol-1-yl)-2-fluorophenyl)-N4-((7R,8aS)-5,5-dimethyloctahydroindolizin-7-yl)-5-fluoropyrimidine-2,4-diamine, bis-formate salt;

Compound 145: N2-(4-chloro-3-(5-cyclopropyl-1H-tetrazol-1-yl)phenyl)-N4-((7R,8aS)-5,5-dimethyloctahydroindolizin-7-yl)-5-fluoropyrimidine-2,4-diamine, bis-formate salt;

Compound 146: 5-chloro-N2-(4-cyclopropyl-2-fluoro-5-(1H-tetrazol-1-yl)phenyl)-N4-((7R,8aS)-5,5-dimethyloctahydroindolizin-7-yl)pyrimidine-2,4-diamine, bis-formate salt;

Compound 147: 5-chloro-N4-((7R,8aS)-5,5-dimethyloctahydroindolizin-7-yl)-N2-(4-methyl-3-(1H-tetrazol-1-yl)phenyl)pyrimidine-2,4-diamine, bis-formate salt;

Compound 148: 1-(5-((5-chloro-4-(((7R,8aS)-5,5-dimethyloctahydroindolizin-7-yl)amino)pyrimidin-2-yl)amino)-2-cyclopropyl-4-fluorophenyl)-4-methyl-1,4-dihydro-5H-tetrazol-5-one, formate salt;

Compound 149: 5-chloro-N4-((7R,8aS)-5,5-dimethyloctahydroindolizin-7-yl)-N2-(4-fluoro-3-(5-methyl-1H-tetrazol-1-yl)phenyl)pyrimidine-2,4-diamine, bis-formate salt;

Compound 150: 5-chloro-N4-((7R,8aS)-5,5-dimethyloctahydroindolizin-7-yl)-N2-(2-fluoro-5-(5-methyl-1H-tetrazol-1-yl)phenyl)pyrimidine-2,4-diamine, bis-formate salt;

Compound 151: 5-chloro-N4-((7R,8aS)-5,5-dimethyloctahydroindolizin-7-yl)-N2-(4-methoxy-3-(5-methyl-1H-tetrazol-1-yl)phenyl)pyrimidine-2,4-diamine, bis-formate salt;

Compound 152: 5-chloro-N4-((7R,8aS)-5,5-dimethyloctahydroindolizin-7-yl)-N2-(3-methoxy-5-(5-methyl-1H-tetrazol-1-yl)phenyl)pyrimidine-2,4-diamine, bis-formate salt;

Compound 153: 3-((5-chloro-4-(((7R,8aS)-5,5-dimethyloctahydroindolizin-7-yl)amino)pyrimidin-2-yl)amino)benzonitrile;

Compound 154: 5-((5-chloro-4-(((7R,8aS)-5,5-dimethyloctahydroindolizin-7-yl)amino)pyrimidin-2-yl)amino)-2-methylbenzonitrile;

Compound 155: 5-((5-chloro-4-(((7R,8aS)-5,5-dimethyloctahydroindolizin-7-yl)amino)pyrimidin-2-yl)amino)-2-cyclopropylbenzonitrile;

Compound 156: N4-((7R,8aS)-5,5-dimethyloctahydroindolizin-7-yl)-5-fluoro-N2-(3,4,5-trimethoxyphenyl)pyrimidine-2,4-diamine;

Compound 157: N2-(2,2-dimethylbenzo[d][1,3]dioxol-5-yl)-N4-((7R,8aS)-5,5-dimethyloctahydroindolizin-7-yl)-5-fluoropyrimidine-2,4-diamine;

Compound 158: 1-(5-((4-(((7R,8aS)-5,5-dimethyloctahydroindolizin-7-yl)amino)-5-fluoropyrimidin-2-yl)amino)-4-fluoro-2-(2-methoxyethoxy)phenyl)-4-methyl-1,4-dihydro-5H-tetrazol-5-one;

Compound 159: 1-(5-((4-(((7R,8aS)-5,5-dimethyloctahydroindolizin-7-yl)amino)-5-fluoropyrimidin-2-yl)amino)-4-fluoro-2-((3-methyloxetan-3-yl)methoxy)phenyl)-4-methyl-1,4-dihydro-5H-tetrazol-5-one;

Compound 160: N4-((7R,8aS)-5,5-dimethyloctahydroindolizin-7-yl)-5-fluoro-N2-(2-fluoro-3,4-bis(2-methoxyethoxy)phenyl)pyrimidine-2,4-diamine, bis-TFA salt;

Compound 161: N2-(3,5-dimethoxyphenyl)-N4-((7R,8aS)-5,5-dimethyloctahydroindolizin-7-yl)-5-fluoropyrimidine-2,4-diamine, bis-TFA salt;

Compound 162: 5-chloro-N2-(3,5-dimethoxyphenyl)-N4-((7R,8aS)-5,5-dimethyloctahydroindolizin-7-yl)pyrimidine-2,4-diamine, bis-TFA salt;

Compound 163: 5-chloro-N2-(3-(5-cyclopropyl-1H-tetrazol-1-yl)-4-fluorophenyl)-N4-((7R,8aS)-5,5-dimethyloctahydroindolizin-7-yl)pyrimidine-2,4-diamine, bis-TFA salt;

Compound 164: 5-chloro-N2-(5-(5-cyclopropyl-1H-tetrazol-1-yl)-2-fluorophenyl)-N4-((7R,8aS)-5,5-dimethyloctahydroindolizin-7-yl)pyrimidine-2,4-diamine, bis-formate salt;

Compound 165: 1-(5-((4-(((7R,8aS)-5,5-dimethyloctahydroindolizin-7-yl)amino)-5-fluoropyrimidin-2-yl)amino)-4-fluoro-2-((3-(hydroxymethyl)oxetan-3-yl)methoxy)phenyl)-4-methyl-1,4-dihydro-5H-tetrazol-5-one, bis-formate salt;

Compound 166: 1-(5-((4-(((7R,8aS)-5,5-dimethyloctahydroindolizin-7-yl)amino)-5-fluoropyrimidin-2-yl)amino)-4-fluoro-2-(oxetan-3-ylmethoxy)phenyl)-4-methyl-1,4-dihydro-5H-tetrazol-5-one, bis-formate salt;

Compound 167: 1-(5-((4-(((7R,8aS)-5,5-dimethyloctahydroindolizin-7-yl)amino)-5-fluoropyrimidin-2-yl)amino)-4-fluoro-2-(oxetan-2-ylmethoxy)phenyl)-4-methyl-1,4-dihydro-5H-tetrazol-5-one, bis-formate salt;

Compound 168: 5-((4-(((7R,8aS)-5,5-dimethyloctahydroindolizin-7-yl)amino)-5-fluoropyrimidin-2-yl)amino)-2-hydroxybenzonitrile;

Compound 169: 1-(2-((1,4-dioxan-2-yl)methoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, bis-TFA salt;

Compound 170: 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)methoxy)phenyl)-4-methyl-1,4-dihydro-5H-tetrazol-5-one, bis-TFA salt;

Compound 171: 3-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)-2-oxopropanoic acid, bis-TFA salt;

Compound 172: 5-((4-(((7R,8aS)-5,5-dimethyloctahydroindolizin-7-yl)amino)-5-fluoropyrimidin-2-yl)amino)-2-(2-methoxyethoxy)benzonitrile;

Compound 173: 5-(4-((7R,8aS)-5,5-dimethyloctahydroindolizin-7-ylamino)-5-fluoropyrimidin-2-ylamino)-2-((3-methyloxetan-3-yl)methoxy)benzonitrile;

Compound 174: 5-(4-((7R,8aS)-5,5-dimethyloctahydroindolizin-7-ylamino)-5-fluoropyrimidin-2-ylamino)-2-((3-(hydroxymethyl)oxetan-3-yl)methoxy)benzonitrile;

Compound 175: 5-(4-((7R,8aS)-5,5-dimethyloctahydroindolizin-7-ylamino)-5-fluoropyrimidin-2-ylamino)-2-(oxetan-3-ylmethoxy)benzonitrile;

Compound 176: 5-(4-((7R,8aS)-5,5-dimethyloctahydroindolizin-7-ylamino)-5-fluoropyrimidin-2-ylamino)-2-(oxetan-2-ylmethoxy)benzonitrile;

Compound 177: 2-((1,4-dioxan-2-yl)methoxy)-5-(4-((7R,8aS)-5,5-dimethyloctahydroindolizin-7-ylamino)-5-fluoropyrimidin-2-ylamino)benzonitrile;

Compound 178: 5-(4-((7R,8aS)-5,5-dimethyloctahydroindolizin-7-ylamino)-5-fluoropyrimidin-2-ylamino)-2-((tetrahydro-2H-pyran-4-yl)methoxy)benzonitrile;

Compound 179: 5-(4-((7R,8aS)-5,5-dimethyloctahydroindolizin-7-ylamino)-5-fluoropyrimidin-2-ylamino)-2-(oxetan-3-yloxy)benzonitrile, formate salt;

Compound 180: 2-bromo-5-((4-(((7R,8aS)-5,5-dimethyloctahydroindolizin-7-yl)amino)-5-fluoropyrimidin-2-yl)amino)benzonitrile;

Compound 181: 5-((5-chloro-4-(((7R,8aS)-5,5-dimethyloctahydroindolizin-7-yl)amino)pyrimidin-2-yl)amino)-2-cyclopropyl-4-fluorobenzonitrile;

Compound 182: 5-chloro-N2-(4-chloro-3-(5-cyclopropyl-1H-tetrazol-1-yl)phenyl)-N4-((7R,8aS)-5,5-dimethyloctahydroindolizin-7-yl)pyrimidine-2,4-diamine;

Compound 183: 5-chloro-N4-((7R,8aS)-5,5-dimethyloctahydroindolizin-7-yl)-N2-(3,4,5-trimethoxyphenyl)pyrimidine-2,4-diamine;

Compound 184: ethyl 2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)propanoate;

Compound 185: 1-(5-((4-(((7R,8aS)-5,5-dimethyloctahydroindolizin-7-yl)amino)-5-fluoropyrimidin-2-yl)amino)-4-fluoro-2-((2-oxotetrahydrofuran-3-yl)oxy)phenyl)-4-methyl-1,4-dihydro-5H-tetrazol-5-one, formate salt;

Compound 186: 1-(5-((4-(((7R,8aS)-5,5-dimethyloctahydroindolizin-7-yl)amino)-5-fluoropyrimidin-2-yl)amino)-4-fluoro-2-(2-hydroxyethoxy)phenyl)-4-methyl-1,4-dihydro-5H-tetrazol-5-one, formate salt;

Compound 187: 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)methoxy)phenyl)-4-methyl-1,4-dihydro-5H-tetrazol-5-one, TFA salt;

Compound 188: 1-(2-((R)-2,3-dihydroxypropoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, TFA salt;

Compound 189: 5-((4-(((7R,8aS)-5,5-dimethyloctahydroindolizin-7-yl)amino)-5-fluoropyrimidin-2-yl)amino)-2-(2-hydroxyethoxy)benzonitrile, formate salt;

Compound 190: 5-((4-(((7R,8aS)-5,5-dimethyloctahydroindolizin-7-yl)amino)-5-fluoropyrimidin-2-yl)amino)-2-(2-(2-methoxyethoxy)ethoxy)benzonitrile, formate salt;

Compound 191: (3S,4R,5R)-2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)tetrahydro-2H-pyran-3,4,5-triyl triacetate;

Compound 192: 1-(2-(2-(dimethylamino)ethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 193: 1-(2-(2-(dimethylamino)ethoxy)-(2-(dimethylamino)ethyl)(4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 194: 1-(2-(2-(diethylamino)ethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, TFA salt;

Compound 195: 1-(5-((4-(((7R,8aS)-5,5-dimethyloctahydroindolizin-7-yl)amino)-5-fluoropyrimidin-2-yl)amino)-4-fluoro-2-(2-morpholinoethoxy)phenyl)-4-methyl-1,4-dihydro-5H-tetrazol-5-one;

Compound 196: 4-((4-(((7R,8aS)-5,5-dimethyloctahydroindolizin-7-yl)amino)-5-fluoropyrimidin-2-yl)amino)-2-(1H-tetrazol-1-yl)phenol;

Compound 197: (3S,4R,5R)-2-(2-cyano-4-((4-(((7R,8aS)-5,5-dimethyloctahydroindolizin-7-yl)amino)-5-fluoropyrimidin-2-yl)amino)phenoxy)tetrahydro-2H-pyran-3,4,5-triyl triacetate;

Compound 198: 1-(5-((4-(((7R,8aS)-5,5-dimethyloctahydroindolizin-7-yl)amino)-5-fluoropyrimidin-2-yl)amino)-4-fluoro-2-(2-(2-methoxyethoxy)ethoxy)phenyl)-4-methyl-1,4-dihydro-5H-tetrazol-5-one, TFA salt;

Compound 199: 1-(2-(2,3-dihydroxypropoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, bis-TFA salt;

Compound 200: 1-(5-((4-(((7R,8aS)-5,5-dimethyloctahydroindolizin-7-yl)amino)-5-fluoropyrimidin-2-yl)amino)-4-fluoro-2-(2-hydroxypropoxy)phenyl)-4-methyl-1,4-dihydro-5H-tetrazol-5-one, TFA salt;

Compound 201: 5-((4-(((7R,8aS)-5,5-dimethyloctahydroindolizin-7-yl)amino)-5-fluoropyrimidin-2-yl)amino)-2-(2-hydroxypropoxy)benzonitrile, formate salt;

Compound 202: N4-((7R,8aS)-5,5-dimethyloctahydroindolizin-7-yl)-5-fluoro-N2-(4-(2-methoxyethoxy)-3-(1H-tetrazol-1-yl)phenyl)pyrimidine-2,4-diamine, formate salt;

Compound 203: N4-((7R,8aS)-5,5-dimethyloctahydroindolizin-7-yl)-5-fluoro-N2-(4-((3-methyloxetan-3-yl)methoxy)-3-(1H-tetrazol-1-yl)phenyl)pyrimidine-2,4-diamine, formate salt;

Compound 204: (3-((4-((4-(((7R,8aS)-5,5-dimethyloctahydroindolizin-7-yl)amino)-5-fluoropyrimidin-2-yl)amino)-2-(1H-tetrazol-1-yl)phenoxy)methyl)oxetan-3-yl)methanol, formate salt;

Compound 205: 2-(4-((4-(((7R,8aS)-5,5-dimethyloctahydroindolizin-7-yl)amino)-5-fluoropyrimidin-2-yl)amino)-2-(1H-tetrazol-1-yl)phenoxy)ethan-1-ol;

Compound 206: 1-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-2-ol, formate salt;

Compound 207: N4-((7R,8aS)-5,5-dimethyloctahydroindolizin-7-yl)-5-fluoro-N2-(4-(2-(2-methoxyethoxy)ethoxy)-3-(1H-tetrazol-1-yl)phenyl)pyrimidine-2,4-diamine;

Compound 208: 4-((4-(((7R,8aS)-5,5-dimethyloctahydroindolizin-7-yl)amino)-5-fluoropyrimidin-2-yl)amino)-2-methoxyphenol;

Compound 209: 5-((4-(((7R,8aS)-5,5-dimethyloctahydroindolizin-7-yl)amino)-5-fluoropyrimidin-2-yl)amino)-2-(3,3,3-trifluoro-2-hydroxy-2-(trifluoromethyl)propoxy)benzonitrile, formate salt;

Compound 210: 5-((4-(((7R,8aS)-5,5-dimethyloctahydroindolizin-7-yl)amino)-5-fluoropyrimidin-2-yl)amino)-2-(2-hydroxyethoxy-1,1,2,2-d4)benzonitrile, formate salt;

Compound 211: 2-(2,3-dihydroxypropoxy)-5-(((4-(((2,3-dihydroxypropyl)((7R,8aS)-5,5-dimethyloctahydroindolizin-7-yl)amino)-5-fluoropyrimidin-2-yl)amino)benzonitrile, TFA salt;

Compound 212: 2-(2,3-dihydroxypropoxy)-5-((4-(((7R,8aS)-5,5-dimethyloctahydroindolizin-7-yl)amino)-5-fluoropyrimidin-2-yl)amino)benzonitrile, TFA salt;

Compound 213: 5-((4-(((7R,8aS)-5,5-dimethyloctahydroindolizin-7-yl)amino)-5-fluoropyrimidin-2-yl)amino)-2-(3-hydroxypropoxy)benzonitrile, TFA salt;

Compound 214: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propane-1,2-diol, TFA salt;

Compound 215: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol, TFA salt;

Compound 216: 2-(4-((4-(((7R,8aS)-5,5-dimethyloctahydroindolizin-7-yl)amino)-5-fluoropyrimidin-2-yl)amino)-2-methoxyphenoxy)ethan-1-ol;

Compound 217: 2-(4-((4-(((7R,8aS)-5,5-dimethyloctahydroindolizin-7-yl)amino)-5-fluoropyrimidin-2-yl)amino)-2-methoxyphenoxy)ethan-1,1,2,2-d4-1-ol;

Compound 218: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol;

Compound 219: 5-((4-(((7R,8aS)-5,5-dimethyloctahydroindolizin-7-yl)amino)-5-fluoropyrimidin-2-yl)amino)-2-(2-hydroxyethoxy-1,1,2,2-d4)benzonitrile;

Compound 220: 1-(5-((4-(((7R,8aS)-5,5-dimethyloctahydroindolizin-7-yl)amino)-5-fluoropyrimidin-2-yl)amino)-4-fluoro-2-(2-hydroxypropoxy)phenyl)-4-methyl-1,4-dihydro-5H-tetrazol-5-one;

Compound 221: 1-(5-((4-(((7R,8aS)-5,5-dimethyloctahydroindolizin-7-yl)amino)-5-fluoropyrimidin-2-yl)amino)-4-fluoro-2-(2-hydroxyethoxy-1,1,2,2-d4)phenyl)-4-methyl-1,4-dihydro-5H-tetrazol-5-one;

Compound 222: 1-(5-((4-(((7R,8aS)-5,5-dimethyloctahydroindolizin-7-yl)amino)-5-fluoropyrimidin-2-yl)amino)-4-fluoro-2-((R)-3-hydroxy-2-methylpropoxy)phenyl)-4-methyl-1,4-dihydro-5H-tetrazol-5-one;

Compound 223: 2-(4-((5-chloro-4-(((7R,8aS)-5,5-dimethyloctahydroindolizin-7-yl)amino)pyrimidin-2-yl)amino)-2-(1H-tetrazol-1-yl)phenoxy)ethan-1-ol;

Compound 224: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol, formate salt;

Compound 225: 1-(2-(3-(benzyloxy)cyclobutoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 226: tert-butyl (2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)ethyl)carbamate;

Compound 227: 1-(5-((4-(((7R,8aS)-5,5-dimethyloctahydroindolizin-7-yl)amino)-5-fluoropyrimidin-2-yl)amino)-4-fluoro-2-(3-hydroxycyclobutoxy)phenyl)-4-methyl-1,4-dihydro-5H-tetrazol-5-one;

Compound 228: 1-(2-(2-aminoethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 229: 5-((5-chloro-4-(((7R,8aS)-5,5-dimethyloctahydroindolizin-7-yl)amino)pyrimidin-2-yl)amino)-2-(2-hydroxypropoxy)benzonitrile, formate salt;

Compound 230: 1-(5-((4-(((7R,8aS)-5,5-dimethyloctahydroindolizin-7-yl)amino)-5-fluoropyrimidin-2-yl)amino)-4-fluoro-2-(3,3,3-trifluoro-2-hydroxypropoxy)phenyl)-4-methyl-1,4-dihydro-5H-tetrazol-5-one, formate salt;

Compound 231: 1-(2-(2-aminoethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, formate salt;

Compound 232: 1-(5-((5-chloro-4-(((7R,8aS)-5,5-dimethyloctahydroindolizin-7-yl)amino)pyrimidin-2-yl)amino)-4-fluoro-2-hydroxyphenyl)-4-methyl-1,4-dihydro-5H-tetrazol-5-one;

Compound 233: 1-(5-((4-(((7R,8aS)-5,5-dimethyloctahydroindolizin-7-yl)amino)-5-fluoropyrimidin-2-yl)amino)-4-fluoro-2-((S)-2-methoxypropoxy)phenyl)-4-methyl-1,4-dihydro-5H-tetrazol-5-one;

Compound 234: 1-(5-((4-(((7R,8aS)-5,5-dimethyloctahydroindolizin-7-yl)((S)-2-methoxypropyl)amino)-5-fluoropyrimidin-2-yl)amino)-4-fluoro-2-((S)-2-methoxypropoxy)phenyl)-4-methyl-1,4-dihydro-5H-tetrazol-5-one;

Compound 235: 1-(5-((5-chloro-4-(((7R,8aS)-5,5-dimethyloctahydroindolizin-7-yl)amino)pyrimidin-2-yl)amino)-4-fluoro-2-((S)-2-hydroxypropoxy)phenyl)-4-methyl-1,4-dihydro-5H-tetrazol-5-one, formate salt;

Compound 236: 1-(5-((5-chloro-4-(((7R,8aS)-5,5-dimethyloctahydroindolizin-7-yl)amino)pyrimidin-2-yl)amino)-4-fluoro-2-(2-hydroxypropoxy)phenyl)-4-methyl-1,4-dihydro-5H-tetrazol-5-one, formate salt, mixture of diastereomers;

Compound 237: 1-(5-((5-chloro-4-(((7R,8aS)-5,5-dimethyloctahydroindolizin-7-yl)amino)pyrimidin-2-yl)amino)-4-fluoro-2-(2-hydroxyethoxy)phenyl)-4-methyl-1,4-dihydro-5H-tetrazol-5-one, formate salt;

Compound 238: 1-(5-((5-chloro-4-(((7R,8aS)-5,5-dimethyloctahydroindolizin-7-yl)amino)pyrimidin-2-yl)amino)-4-fluoro-2-((S)-2-methoxypropoxy)phenyl)-4-methyl-1,4-dihydro-5H-tetrazol-5-one, formate salt;

Compound 239: 1-(5-((5-chloro-4-(((7R,8aS)-5,5-dimethyloctahydroindolizin-7-yl)((S)-2-methoxypropyl)amino)pyrimidin-2-yl)amino)-4-fluoro-2-((S)-2-methoxypropoxy)phenyl)-4-methyl-1,4-dihydro-5H-tetrazol-5-one, formate salt;

Compound 240: 1-(5-((5-chloro-4-(((7R,8aS)-5,5-dimethyloctahydroindolizin-7-yl)amino)pyrimidin-2-yl)amino)-4-fluoro-2-(2-hydroxy-2-methylpropoxy)phenyl)-4-methyl-1,4-dihydro-5H-tetrazol-5-one;

Compound 241: 5-fluoro-N2-(2-fluoro-5-methoxy-3-(5-methyl-1H-tetrazol-1-yl)phenyl)-N4-((7R,8aS)-octahydro-5,5-dimethylindolizin-7-yl)pyrimidine-2,4-diamine, TFA salt;

Compound 242: 5-fluoro-N2-(2-fluoro-3-methoxy-5-(5-methyl-1H-tetrazol-1-yl)phenyl)-N4-((7R,8aS)-octahydro-5,5-dimethylindolizin-7-yl)pyrimidine-2,4-diamine, TFA salt;

Compound 243: 5-fluoro-N2-(2,6-difluoro-3-methoxy-5-(5-methyl-1H-tetrazol-1-yl)phenyl)-N4-((7R,8aS)-octahydro-5,5-dimethylindolizin-7-yl)pyrimidine-2,4-diamine, TFA salt;

Compound 248: 5-fluoro-N2-(1H-2,4-dihydron-2,4,4-trimethyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 249: 5-fluoro-N2-(2-fluoro-5-(5-methyl-1H-tetrazol-1-yl)-4-(oxetan-3-yloxy)phenyl)-N4-((7R,8aS)-octahydro-5,5-dimethylindolizin-7-yl)pyrimidine-2,4-diamine;

Compound 250: 5-fluoro-N2-(1H-2,4-dihydron-4,4-dimethyl-2-(3-chloropropanol-2-yl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 251: 5-fluoro-N2-(1H-2,4-dihydron-4,4-dimethyl-2-(oxetan-3-yl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 252: 4-(4-((7R,8aS)-octahydro-5,5-dimethylindolizin-7-ylamino)-5-fluoropyrimidin-2-ylamino)-5-fluoro-2-(5-methyl-1H-tetrazol-1-yl)phenol, besylate salt;

Compound 253: N5-(4-((7R,8aS)-octahydro-5,5-dimethylindolizin-7-ylamino)-5-fluoropyrimidin-2-yl)-6-fluoro-N2-methylbenzo[d]oxazole-2,5-diamine, formate salt;

Compound 254: N5-(4-((7R,8aS)-octahydro-5,5-dimethylindolizin-7-ylamino)-5-fluoropyrimidin-2-yl)-6-fluoro-N2-methylbenzo[d]oxazole-2,5-diamine, besylate salt;

Compound 255: N2-(5-(5-cyclopropyl-1H-tetrazol-1-yl)-2-fluoro-4-(oxetan-3-yloxy)phenyl)-5-fluoro-N4-((7R,8aS)-octahydro-5,5-dimethylindolizin-7-yl)pyrimidine-2,4-diamine;

Compound 256: 4-(4-((7R,8aS)-octahydro-5,5-dimethylindolizin-7-ylamino)-5-fluoropyrimidin-2-ylamino)-2-(5-cyclopropyl-1H-tetrazol-1-yl)-5-fluorophenol, TFA salt;

Compound 257: N2-(5-(5-cyclopropyl-1H-tetrazol-1-yl)-2-fluoro-4-isopropoxyphenyl)-5-fluoro-N4-((7R,8aS)-octahydro-5,5-dimethylindolizin-7-yl)pyrimidine-2,4-diamine, TFA salt;

Compound 258: 5-fluoro-N2-(2-fluoro-5-(5-(methylamino)-1H-tetrazol-1-yl)-4-(oxetan-3-yloxy)phenyl)-N4-((7R,8aS)-octahydro-5,5-dimethylindolizin-7-yl)pyrimidine-2,4-diamine;

Compound 259: 1-(3-(4-((7R,8aS)-octahydro-5,5-dimethylindolizin-7-ylamino)-5-fluoropyrimidin-2-ylamino)phenyl)-1H-tetrazole-5-thiol, formate salt;

Compound 260: 1-(3-(4-((7R,8aS)-octahydro-5,5-dimethylindolizin-7-ylamino)-5-fluoropyrimidin-2-ylamino)phenyl)-1H-tetrazol-5(4H)-one;

Compound 261: 5-fluoro-N4-((7R,8aS)-octahydro-5,5-dimethylindolizin-7-yl)-N2-(3-(5-(methylthio)-1H-tetrazol-1-yl)phenyl)pyrimidine-2,4-diamine;

Compound 262: 5-fluoro-N4-((7R,8aS)-octahydro-5,5-dimethylindolizin-7-yl)-N2-(3-(5-(oxetan-3-ylthio)-1H-tetrazol-1-yl)phenyl)pyrimidine-2,4-diamine;

Compound 263: 2-(1-(3-(4-((7R,8aS)-octahydro-5,5-dimethylindolizin-7-ylamino)-5-fluoropyrimidin-2-ylamino)phenyl)-1H-tetrazol-5-ylthio)propane-1,3-diol;

Compound 264: 2-(1-(3-(4-((7R,8aS)-octahydro-5,5-dimethylindolizin-7-ylamino)-5-fluoropyrimidin-2-ylamino)phenyl)-1H-tetrazol-5-ylthio)-3-aminopropan-1-ol, besylate salt;

Compound 265: 1-(3-(4-((7R,8aS)-octahydro-5,5-dimethylindolizin-7-ylamino)-5-fluoropyrimidin-2-ylamino)phenyl)-4-(oxetan-3-yl)-1H-tetrazol-5(4H)-one, formate salt;

Compound 266: 2-(1-(3-(4-((7R,8aS)-octahydro-5,5-dimethylindolizin-7-ylamino)-5-fluoropyrimidin-2-ylamino)phenyl)-1H-tetrazol-5-ylthio)ethanol, besylate salt;

Compound 267: 1-(3-(4-((7R,8aS)-octahydro-5,5-dimethylindolizin-7-ylamino)-5-fluoropyrimidin-2-ylamino)phenyl)-4-(2-hydroxyethyl)-1H-tetrazol-5(4H)-one, formate salt;

Compound 268: 5-fluoro-N2-(1H-2,4-dihydron-2-(2-hydroxyethyl)-4,4-dimethyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 269: 5-fluoro-N4-((7R,8aS)-octahydro-5,5-dimethylindolizin-7-yl)-N2-(3-(5-(methylsulfonyl)-1H-tetrazol-1-yl)phenyl)pyrimidine-2,4-diamine, TFA salt;

Compound 270: 5-fluoro-N4-((7R,8aS)-octahydro-5,5-dimethylindolizin-7-yl)-N2-(3-(5-(methylsulfinyl)-1H-tetrazol-1-yl)phenyl)pyrimidine-2,4-diamine, TFA salt;

Compound 271: 2-(1-(3-(4-((7R,8aS)-octahydro-5,5-dimethylindolizin-7-ylamino)-5-fluoropyrimidin-2-ylamino)phenyl)-1H-tetrazol-5-ylthio)ethanol;

Compound 272: 1-(5-(4-((7R,8aS)-octahydro-5,5-dimethylindolizin-7-ylamino)-5-fluoropyrimidin-2-ylamino)-2-methylphenyl)-1H-tetrazol-5(4H)-one, besylate salt;

Compound 273: 1-(5-(4-((7R,8aS)-octahydro-5,5-dimethylindolizin-7-ylamino)-5-fluoropyrimidin-2-ylamino)-2-methylphenyl)-4-methyl-1H-tetrazol-5(4H)-one, HCl salt;

Compound 274: 1-(5-(4-((7R,8aS)-octahydro-5,5-dimethylindolizin-7-ylamino)-5-fluoropyrimidin-2-ylamino)-2-methylphenyl)-4-methyl-1H-tetrazol-5(4H)-one;

Compound 275: 1-(5-(4-((7R,8aS)-octahydro-5,5-dimethylindolizin-7-ylamino)-5-fluoropyrimidin-2-ylamino)-2-methylphenyl)-4-(2-hydroxyethyl)-1H-tetrazol-5(4H)-one;

Compound 276: 1-(5-(4-((7R,8aS)-octahydro-5,5-dimethylindolizin-7-ylamino)-5-fluoropyrimidin-2-ylamino)-2-methylphenyl)-4-(oxetan-3-yl)-1H-tetrazol-5(4H)-one, formate salt;

Compound 277: 1-(5-(4-((7R,8aS)-octahydro-5,5-dimethylindolizin-7-ylamino)-5-fluoropyrimidin-2-ylamino)-2-methoxyphenyl)-1H-tetrazol-5(4H)-one;

Compound 278: 1-(5-(4-((7R,8aS)-octahydro-5,5-dimethylindolizin-7-ylamino)-5-fluoropyrimidin-2-ylamino)-2-methoxyphenyl)-4-methyl-1H-tetrazol-5(4H)-one, HCl salt;

Compound 279: 1-(5-(4-((7R,8aS)-octahydro-5,5-dimethylindolizin-7-ylamino)-5-fluoropyrimidin-2-ylamino)-2-methoxyphenyl)-4-methyl-1H-tetrazol-5(4H)-one;

Compound 280: 1-(5-(4-((7R,8aS)-octahydro-5,5-dimethylindolizin-7-ylamino)-5-fluoropyrimidin-2-ylamino)-2-methoxyphenyl)-4-(2-hydroxyethyl)-1H-tetrazol-5(4H)-one;

Compound 281: 5-fluoro-N4-((7R,8aS)-octahydro-5,5-dimethylindolizin-7-yl)-N2-(4-methyl-3-(5-(methylthio)-1H-tetrazol-1-yl)phenyl)pyrimidine-2,4-diamine;

Compound 282: 2-(1-(5-(4-((7R,8aS)-octahydro-5,5-dimethylindolizin-7-ylamino)-5-fluoropyrimidin-2-ylamino)-2-methylphenyl)-1H-tetrazol-5-ylthio)ethanol;

Compound 283: 5-fluoro-N2-(1H-2,4-dihydron-spiro(2H-1,4-benzoxazine-4,4'-[4H]pyran)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, TFA salt;

Compound 284: 5-fluoro-N4-((7R,8aS)-octahydro-5,5-dimethylindolizin-7-yl)-N2-(4-methoxy-3-(5-(oxetan-3-yloxy)-1H-tetrazol-1-yl)phenyl)pyrimidine-2,4-diamine, formate salt;

Compound 285: 1-(5-(4-((7R,8aS)-octahydro-5,5-dimethylindolizin-7-ylamino)-5-fluoropyrimidin-2-ylamino)-2-methoxyphenyl)-4-(oxetan-3-yl)-1H-tetrazol-5(4H)-one, formate salt;

Compound 286: 5-fluoro-N4-((7R,8aS)-octahydro-5,5-dimethylindolizin-7-yl)-N2-(4-methyl-3-(5-(methylsulfonyl)-1H-tetrazol-1-yl)phenyl)pyrimidine-2,4-diamine, TFA salt;

Compound 287: 5-fluoro-N2-(1H-2,4-dihydron-4-(hydroxymethyl)-4-(((1,1-dimethylethyl)dimethylsilyl)oxymethyl)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, besylate salt;

Compound 288: 5-fluoro-N2-(1H-2,4-dihydron-4,4-di(hydroxymethyl)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, besylate salt;

Compound 289: 1-(5-(4-((7R,8aS)-octahydro-5,5-dimethylindolizin-7-ylamino)-5-fluoropyrimidin-2-ylamino)-2-methylphenyl)-4-(2-hydroxy-2-methylpropyl)-1H-tetrazol-5(4H)-one, formate salt;

Compound 290: 1-(5-(4-((7R,8aS)-octahydro-5,5-dimethylindolizin-7-ylamino)-5-fluoropyrimidin-2-ylamino)-2-methoxyphenyl)-4-(2-hydroxy-2-methylpropyl)-1H-tetrazol-5(4H)-one;

Compound 291: 5-fluoro-N2-(1H-2,4-dihydron-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 292: 5-fluoro-N2-(1H-2,3,4,5-tetrahydro-2,4-dimethyl-4-hydroxy-[1,2,4]triazolo[4,5-c][1,5]benzoxazepin-1-one-9-yl)-N4-((7R,8aS)-octahydro-5,5-dimethyl-indolizin-7-yl)pyrimidine-2,4-diamine;

Compound 293: 5-fluoro-N2-(1H-2,4-dihydron-spiro(2H-1,4-benzoxazine-4,3'-[3H]oxetan)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 294: 5-fluoro-N2-(1H-2,3,4,5-tetrahydron-2,4-dimethyl-4-hydroxy-[1,2,4]triazolo[4,5-c][1,5]benzoxazepin-1-one-9-yl)-N4-((7R,8aS)-octahydro-5,5-dimethyl-indolizin-7-yl)pyrimidine-2,4-diamine;

Compound 295: 5-fluoro-N2-(1H-2,3,4,5-tetrahydron-2,4-dimethyl-4-hydroxy-[1,2,4]triazolo[4,5-c][1,5]benzoxazepin-1-one-9-yl)-N4-((7R,8aS)-octahydro-5,5-dimethyl-indolizin-7-yl)pyrimidine-2,4-diamine;

Compound 296: 5-fluoro-N2-(1H-2,4-dihydron-2-methyl-4,4-di(methoxymethyl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 297: N2-(3-(Difluoromethoxy)-4-morpholinophenyl)-N4-((7S,8aS)-3,3-dimethyloctahydroindolizin-7-yl)-5-fluoropyrimidine-2,4-diamine;

Compound 298: N2-(3-(Difluoromethoxy)-4-(oxetan-3-yloxy)phenyl)-N4-((7S,8aS)-3,3-dimethyloctahydroindolizin-7-yl)-5-fluoropyrimidine-2,4-diamine, formate salt;

Compound 299: N2-(3-(Difluoromethoxy)-4-methoxyphenyl)-N4-((7S,8aS)-3,3-dimethyloctahydroindolizin-7-yl)-5-fluoropyrimidine-2,4-diamine;

Compound 300: N2-(3-(Difluoromethoxy)-4-(2,6-dimethylmorpholino)phenyl)-N4-((7S,8aS)-3,3-dimethyloctahydroindolizin-7-yl)-5-fluoropyrimidine-2,4-diamine;

Compound 301: N2-(4-Cyclopropyl-2-fluoro-5-(5-(oxetan-3-yl)-1H-tetrazol-1-yl)phenyl)-N4-((7S,8aS)-3,3-dimethyloctahydroindolizin-7-yl)-5-fluoropyrimidine-2,4-diamine, formate salt;

Compound 302: N2-(3-(Difluoromethoxy)-4-(2-oxa-6-azaspiro[3.3]heptan-6-yl)phenyl)-N4-((7S,8aS)-3,3-dimethyloctahydroindolizin-7-yl)-5-fluoropyrimidine-2,4-diamine, formate salt;

Compound 303: 2-(2-(Difluoromethoxy)-4-((4-(((7S,8aS)-3,3-dimethyloctahydroindolizin-7-yl)amino)-5-fluoropyrimidin-2-yl)amino)phenoxy)ethan-1-ol, formate salt;

Compound 304: 5-((4-(((7S,8aS)-3,3-Dimethyloctahydroindolizin-7-yl)amino)-5-fluoropyrimidin-2-yl)amino)-2-(3-hydroxycyclobutoxy)benzonitrile, formate salt;

Compound 305: 3-(4-((4-(((7S,8aS)-3,3-Dimethyloctahydroindolizin-7-yl)amino)-5-fluoropyrimidin-2-yl)amino)-2-(trifluoromethyl)phenoxy)cyclobutan-1-ol, formate salt;

Compound 306: 3-(2-(Difluoromethoxy)-4-((4-(((7S,8aS)-3,3-dimethyloctahydroindolizin-7-yl)amino)-5-fluoropyrimidin-2-yl)amino)phenoxy)cyclobutan-1-ol, formate salt;

Compound 307: 3-(2-(Difluoromethoxy)-4-((4-(((7S,8aS)-3,3-dimethyloctahydroindolizin-7-yl)amino)-5-fluoropyrimidin-2-yl)amino)phenoxy)propan-1-ol, formate salt;

Compound 308: 1-(2-(Difluoromethoxy)-4-((4-(((7S,8aS)-3,3-dimethyloctahydroindolizin-7-yl)amino)-5-fluoropyrimidin-2-yl)amino)phenyl)azetidin-3-ol, formate salt;

Compound 309: 1-(5-((4-(((7S,8aS)-3,3-Dimethyloctahydroindolizin-7-yl)amino)-5-fluoropyrimidin-2-yl)amino)-2-(3-hydroxycyclobutoxy-1-d)phenyl)-4-methyl-1,4-dihydro-5H-tetrazol-5-one, formate salt;

Compound 310: N2-(4-(3-(Benzyloxy)cyclobutoxy)-3-chlorophenyl)-N4-((7S,8aS)-3,3-dimethyloctahydroindolizin-7-yl)-5-fluoropyrimidine-2,4-diamine;

Compound 311: N2-(4-(3-(benzyloxy)cyclobutoxy-1-d)-3-chlorophenyl)-N4-((7S,8aS)-3,3-dimethyloctahydroindolizin-7-yl)-5-fluoropyrimidine-2,4-diamine;

Compound 312: 3-(2-Chloro-4-((4-(((7S,8aS)-3,3-dimethyloctahydroindolizin-7-yl)amino)-5-fluoropyrimidin-2-yl)amino)phenoxy)cyclobutan-1-ol, formate salt;

Compound 313: 3-(2-Chloro-4-((4-(((7S,8aS)-3,3-dimethyloctahydroindolizin-7-yl)amino)-5-fluoropyrimidin-2-yl)amino)phenoxy)cyclobutan-3-d-1-ol, formate salt;

Compound 314: 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimidine-5-carbonitrile, formate salt;

Compound 315: 4-methyl-N-(5-(4-((7R,8aS)-octahydro-5,5-dimethylindolizin-7-ylamino)-5-fluoropyrimidin-2-ylamino)-2H-1,4-benzoxazine-3(4H)-one, formate salt;

Compound 316: $N^2$-(4,5-dihydro-4,4-bis(methoxymethyl)tetrazolo[5,1-c][1,4]benzoxazin-8-yl)-$N^4$-((7R,8aS)-octahydro-5,5-dimethylindolizin-7-yl)-5-fluoropyrimidin-2,4-diamine;

Compound 317: $N^2$-(4,5-dihydro-4,4-bis(methoxymethyl)tetrazolo[5,1-c][1,4]benzoxazin-8-yl)-$N^4$-((7R,8aS)-octahydro-5,5-dimethylindolizin-7-yl)-5-fluoropyrimidin-2,4-diamine, formate salt;

Compound 318: 2,2,4-trimethyl-N-(5-(4-((7R,8aS)-octahydro-5,5-dimethylindolizin-7-ylamino)-5-fluoropyrimidin-2-ylamino)-2H-1,4-benzoxazine-3(4H)-one, p-toluene sulfonic salt;

Compound 319: 4N-(1-methoxyethyl)-2,2-dimethyl-N-(5-(4-((7R,8aS)-octahydro-5,5-dimethylindolizin-7-ylamino)-5-fluoropyrimidin-2-ylamino)-2H-1,4-benzoxazine-3(4H)-one, p-toluene sulfonic salt;

Compound 320: methyl 2-trifluoromethyl-N-(5-(4-((7R,8aS)-octahydro-5,5-dimethylindolizin-7-ylamino)-5-fluoropyrimidin-2-ylamino)benzoate, formate salt;

Compound 321: 1-(4-(4-((7R,8aS)-octahydro-5,5-dimethylindolizin-7-ylamino)-5-fluoropyrimidin-2-ylamino)-2-(trifluoromethyl)phenylamino)-3-chloropropa-2-ol, formate salt;

Compound 322: 2-(4-(4-((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)phenoxy)acetamide, formate salt;

Compound 323: isopropyl 2-(4-(4-((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)phenoxy)acetate, p-toluene sulfonic salt;

Compound 324: 1-(4-(4-((7R,8aS)-octahydro-5,5-dimethylindolizin-7-ylamino)-5-fluoropyrimidin-2-ylamino)-2-(trifluoromethyl)phenyl)azetidine-3-carboxamide, formate salt;

Compound 325: 1-(4-(4-((7R,8aS)-octahydro-5,5-dimethylindolizin-7-ylamino)-5-fluoropyrimidin-2-ylamino)-2-((2-trifluoromethylphenylamino)methyl)-3-chloropropanamide, p-toluene sulfonic salt;

Compound 326: 1-(4-(4-((7R,8aS)-octahydro-5,5-dimethylindolizin-7-ylamino)-5-fluoropyrimidin-2-ylamino)-2-(trifluoromethyl)phenyl)azetidin-3-ol, formate salt;

Compound 327: 4-(4-((7R,8aS)-octahydro-5,5-dimethylindolizin-7-ylamino)-5-fluoropyrimidin-2-ylamino)-2-chloro-N-methylbenzamide, p-toluene sulfonic salt; and Compound 328: 1-(5-(4-((7R,8aS)-octahydro-5,5-dimethylindolizin-7-ylamino)-5-fluoropyrimidin-2-ylamino)-2-(3-hydroxyazetidin-1-yl)phenyl)-4-methyl-1H-tetrazol-5(4H)-one.

Additional compounds of interest, and salt or solvates or stereoisomers thereof, include:

Compound 329: 1-(5-(4-((7R,8aS)-5,5-dimethyloctahydroindolizin-7-ylamino)-5-fluoropyrimidin-2-ylamino)-4-fluoro-2-(2-fluoro-2-methylpropoxy)phenyl)-4-methyl-1H-tetrazol-5(4H)-one;

Compound 330: 1-(5-(4-((7R,8aS)-5,5-dimethyloctahydroindolizin-7-ylamino)-5-fluoropyrimidin-2-ylamino)-4-fluoro-2-(2-fluoroethoxy)phenyl)-4-methyl-1H-tetrazol-5(4H)-one;

Compound 331: 1-(5-(4-((7R,8aS)-5,5-dimethyloctahydroindolizin-7-ylamino)-5-fluoropyrimidin-2-ylamino)-4-fluoro-2-((S)-2-fluoropropoxy)phenyl)-4-methyl-1H-tetrazol-5(4H)-one;

Compound 332: 1-(5-(4-((7R,8aS)-5,5-dimethyloctahydroindolizin-7-ylamino)-5-fluoropyrimidin-2-ylamino)-4-fluoro-2-((R)-2-fluoropropoxy)phenyl)-4-methyl-1H-tetrazol-5(4H)-one;

Compound 333: 4-(((7R,8aS)-5,5-dimethyloctahydroindolizin-7-yl)amino)-2-((2-fluoro-4-(2-fluoro-2-methylpropoxy)-5-(4-methyl-5-oxo-4,5-dihydro-1H-tetrazol-1-yl)phenyl)amino)pyrimidine-5-carbonitrile;

Compound 334: 4-((7R,8aS)-5,5-dimethyloctahydroindolizin-7-ylamino)-2-(2-fluoro-4-(2-fluoroethoxy)-5-(4-methyl-5-oxo-4,5-dihydro-1H-tetrazol-1-yl)phenylamino)pyrimidine-5-carbonitrile;

Compound 335: 4-((7R,8aS)-5,5-dimethyloctahydroindolizin-7-ylamino)-2-(2-fluoro-4-((S)-2-fluoropropoxy)-5-(4-methyl-5-oxo-4,5-dihydro-1H-tetrazol-1-yl)phenylamino)pyrimidine-5-carbonitrile; and Compound 336: 4-((7R,8aS)-5,5-dimethyloctahydroindolizin-7-ylamino)-2-(2-fluoro-4-((R)-2-fluoropropoxy)-5-(4-methyl-5-oxo-4,5-dihydro-1H-tetrazol-1-yl)phenylamino)pyrimidine-5-carbonitrile.

The present disclosure provides a compound according to the formula (XI):

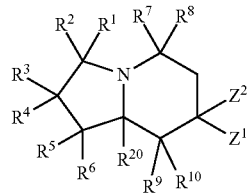

(XI)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{20}$ is selected from hydrogen, alkyl, and substituted alkyl;

$Z^1$ is $OR^{17}$, —$NR^{17}R^{18}$ or X;

$Z^2$ is H, or $Z^1$ and $Z^2$ together form an oxo, =$NR^{19}$ or =$NNR^{20}R^{21}$;

$R^{17}$ is H, alkyl, substituted alkyl, acyl, acylamino, —SO$_2$-alkyl or —SO$_2$-aryl;

$R^{18}$ is H, alkyl, substituted alkyl, acyl, acylamino, —SO$_2$-alkyl, —SO$_2$-aryl, aryl or heteroaryl;

X is halo or azido;

$R^{19}$, $R^{20}$ and $R^{21}$ each independently are selected from alkyl, substituted alkyl, aryl substituted aryl, heteroaryl and substituted heteroaryl; and the compound is optically active.

In certain embodiments, formula (XI), there is an enantiomeric excess of 90% or more. In certain embodiments, formula (XI), there is an enantiomeric excess of 95% or more.

In certain embodiments, in formula (XI), $R^{18}$ comprises the formula

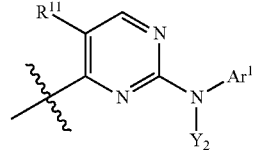

wherein $R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; $Y^1$ and $Y^2$ are independently selected from hydrogen and alkyl; and $Ar^1$ is selected from aryl, substituted aryl, heteroaryl, and substituted heteroaryl.

In certain embodiments, the compound of formula (XI) comprises the formula

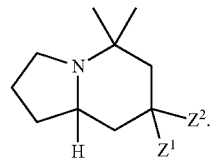

In certain embodiments, the compound of formula (XI) comprises the formula

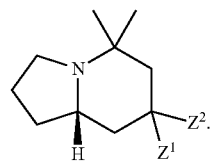

In certain embodiments, the compound of formula (XI) comprises the formula

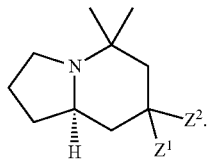

In certain embodiments, the compound of formula (XI) comprises the formula

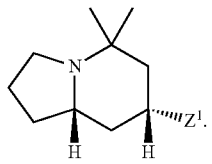

In certain embodiments, the compound of formula (XI) comprises the formula

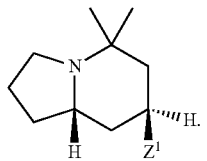

The present disclosure provides a compound according to the formula (XII):

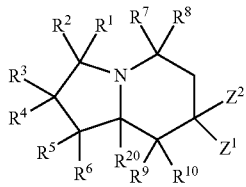

(XII)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl; or $R^7$ and $R^8$ together form an oxo group; or $R^9$ and $R^{10}$ together form an oxo group;

$R^{20}$ is selected from hydrogen, alkyl, and substituted alkyl;

$Z^1$ is $OR^{17}$, —$NR^{17}R^{18}$ or X;

$Z^2$ is H, or $Z^1$ and $Z^2$ together form an oxo, =$NR^{19}$ or =$NNR^{20}R^{21}$;

$R^{17}$ is H, alkyl, substituted alkyl, acyl, acylamino, —SO₂-alkyl or —SO₂-aryl;

$R^{18}$ is H, alkyl, substituted alkyl, acyl, acylamino, —SO₂-alkyl, —SO₂-aryl, aryl or heteroaryl;

X is halo or azido;

$R^{19}$, $R^{20}$ and $R^{21}$ each independently are selected from alkyl, substituted alkyl, aryl substituted aryl, heteroaryl and substituted heteroaryl; and the compound is optically active.

In certain embodiments, formula (XII), there is an enantiomeric excess of 90% or more. In certain embodiments, formula (XII), there is an enantiomeric excess of 95% or more.

In certain embodiments, in formula (XII), $R^{18}$ comprises the formula

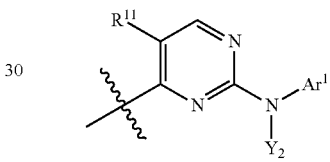

wherein $R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl; $Y^1$ and $Y^2$ are independently selected from hydrogen, alkyl and substituted alkyl; and $Ar^1$ is selected from aryl, substituted aryl, heteroaryl, and substituted heteroaryl.

In certain embodiments, the compound of formula (XII) comprises the formula

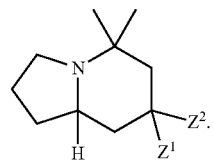

In certain embodiments, the compound of formula (XII) comprises the formula

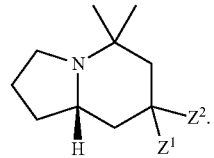

In certain embodiments, the compound of formula (XII) comprises the formula

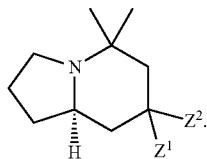

In certain embodiments, the compound of formula (XII) comprises the formula

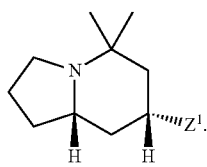

In certain embodiments, the compound of formula (XII) comprises the formula

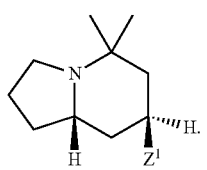

The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Thus, the disclosed compounds may be enriched in one or more of these isotopes relative to the natural abundance of such isotope. By way of example, deuterium ($^2H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

Representative isotopically enriched compounds include the following:

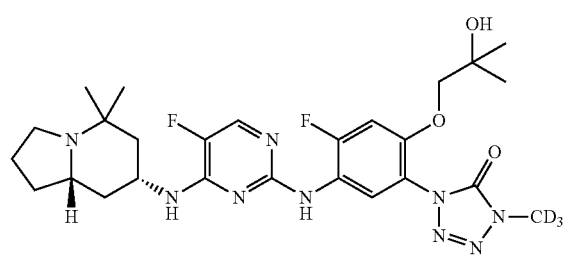

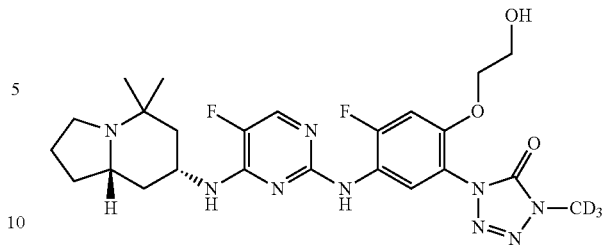

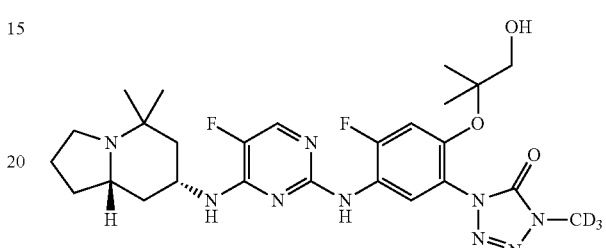

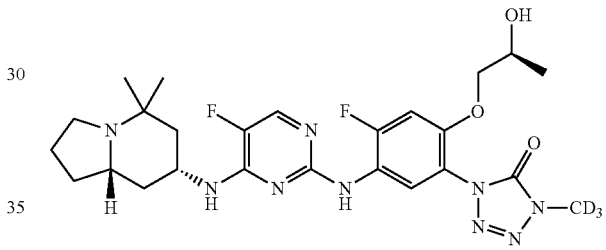

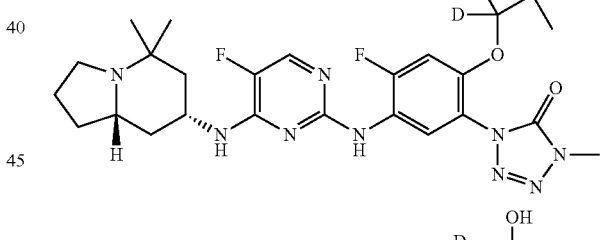

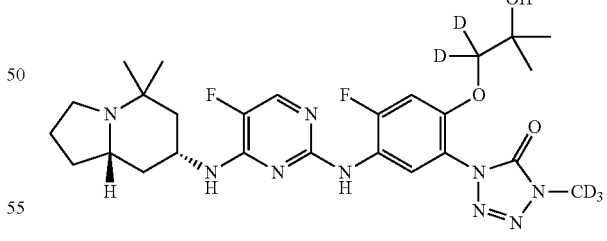

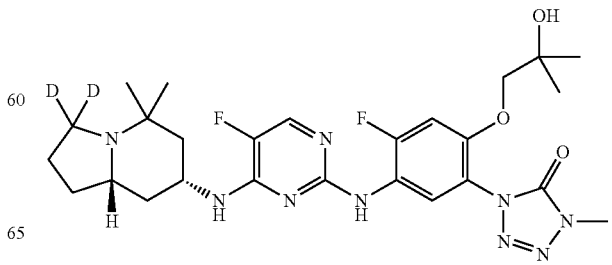

269
-continued
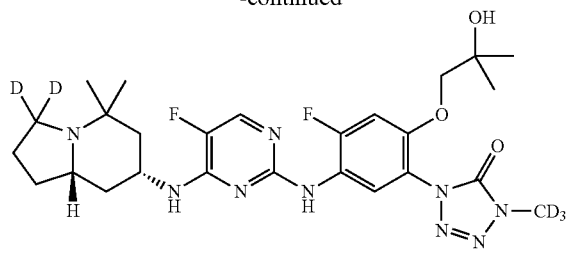
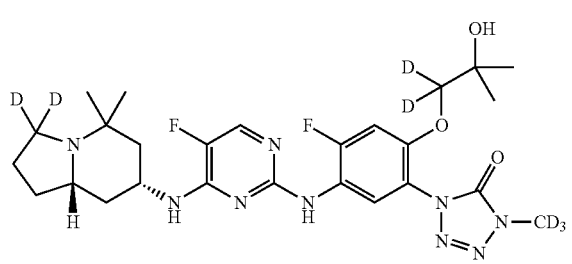
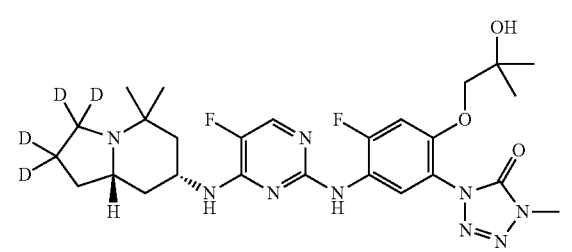
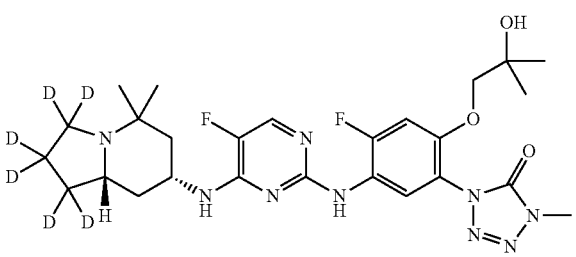
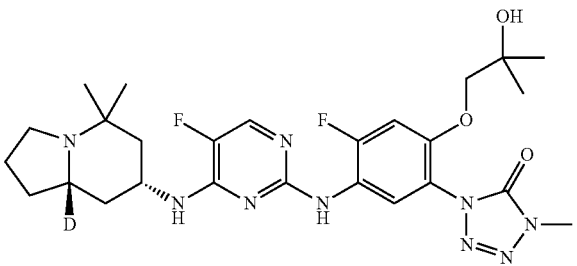
270
-continued
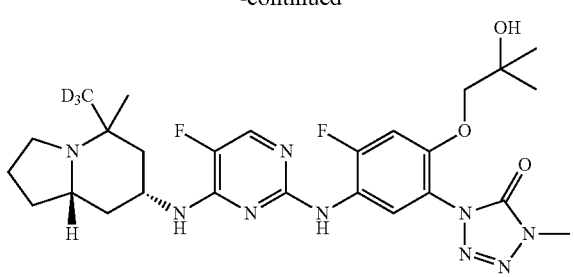
either enantiomer
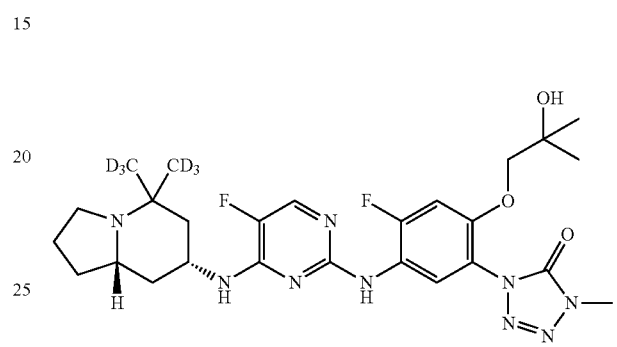
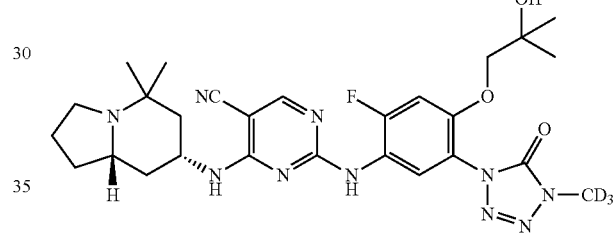
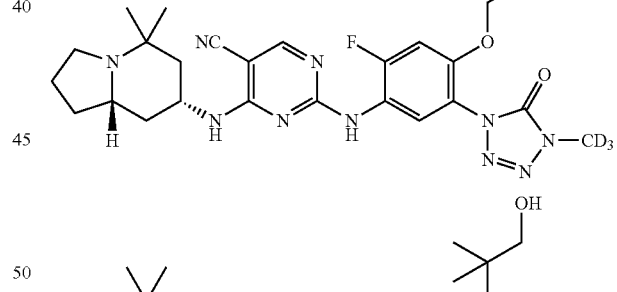
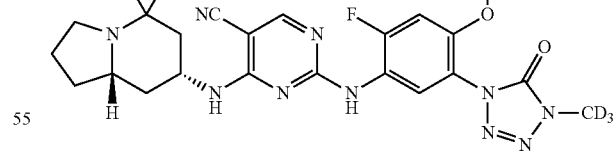
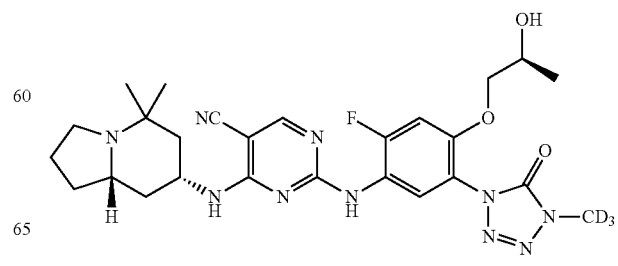

-continued
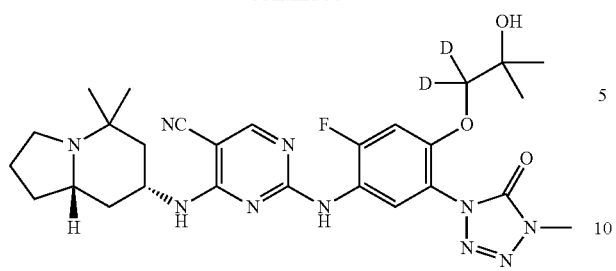
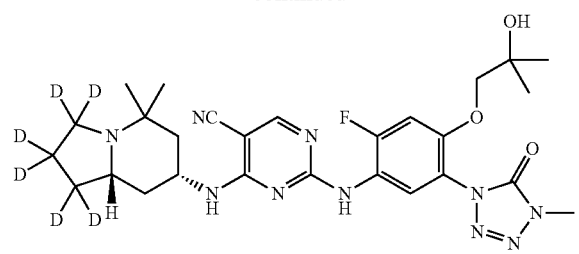
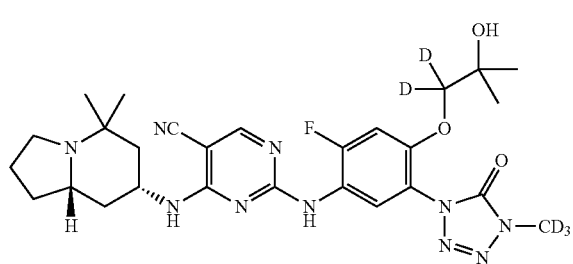
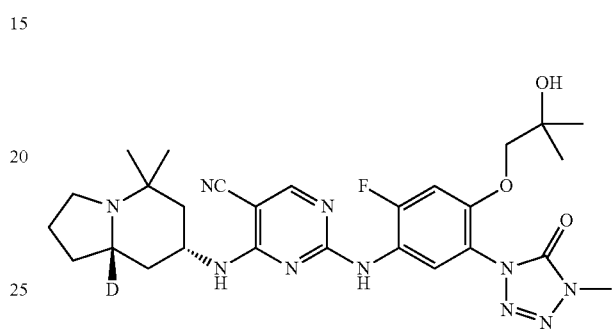
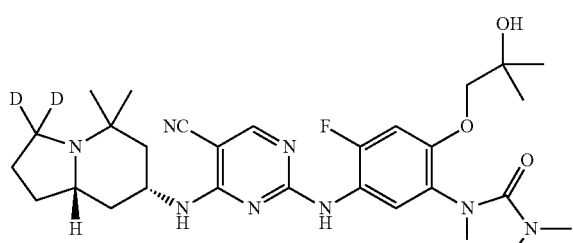
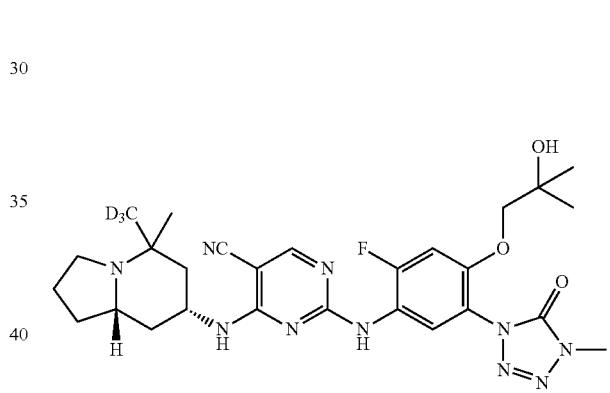
either enantiomer
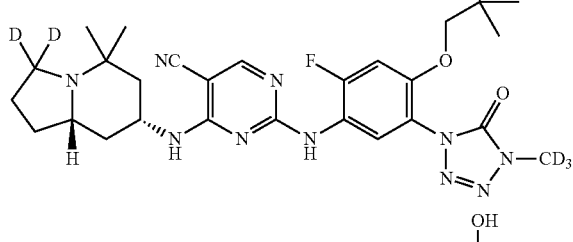
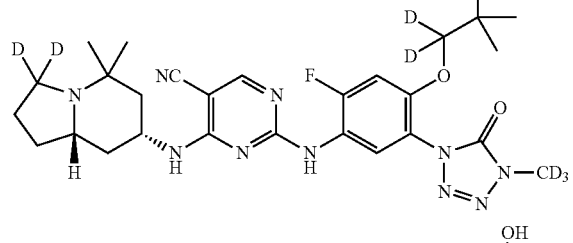
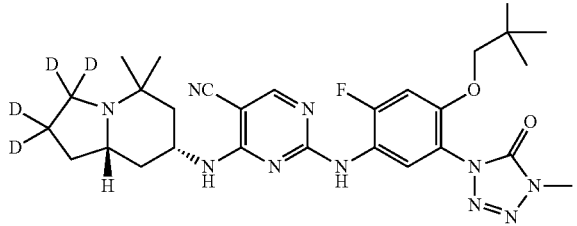
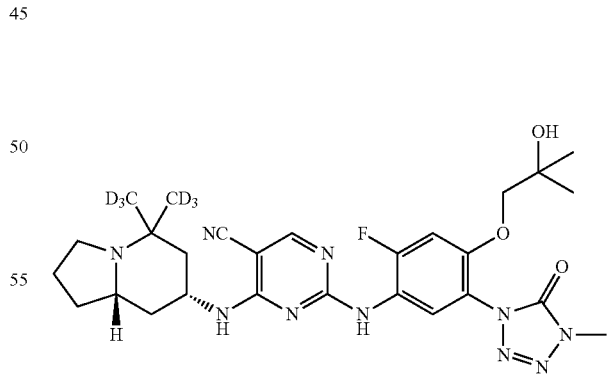
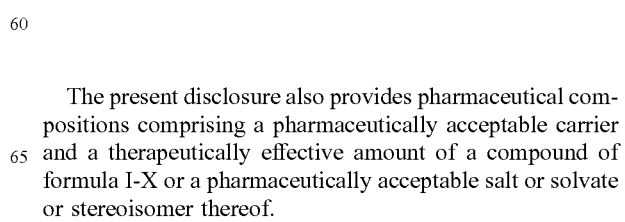
The present disclosure also provides pharmaceutical compositions comprising a pharmaceutically acceptable carrier and a therapeutically effective amount of a compound of formula I-X or a pharmaceutically acceptable salt or solvate or stereoisomer thereof.

A disclosed compound can be administered alone, as the sole active pharmaceutical agent, or in combination with one or more additional compounds of formula I-X or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of formula I-X optionally contain other therapeutic agents. Accordingly, certain embodiments are directed to such pharmaceutical compositions, wherein the composition further comprises a therapeutically effective amount of an agent selected as is known to those of skill in the art.

Since subject compounds possess PKC inhibitory properties, such compounds are also useful as research tools. Accordingly, the disclosure also provides for a method for using a compound of formula I-X or a salt or solvate or stereoisomer thereof as a research tool for studying a biological system or sample, or for discovering new chemical compounds having PKC inhibitory properties.

The embodiments are also directed to a compound of formula I-X or a salt or solvate or stereoisomer thereof, for use in therapy or as a medicament.

Additionally, the embodiments are directed to the use of a compound of formula I-X or a salt or solvate or stereoisomer thereof, for the manufacture of a medicament; especially for the manufacture of a medicament for the inhibition of protein kinase C (PKC) activity. The embodiments are also directed to the use of a compound of formula I-X or a salt or solvate or stereoisomer thereof for the manufacture of a medicament for the treatment of a disease or disorder mediated or sustained through the activity of PKC activity. The embodiments are also directed to the use of a compound of formula I-X or a salt or solvate or stereoisomer thereof for the manufacture of a medicament for the treatment of a disease or disorder associated with the activation of T-cells, including, inflammatory, autoimmune and allergic disorders.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in the U.S. publication No. US2004/0029902A1, the contents of which are incorporated herein by reference. Suitable exemplary methods that can be routinely used and/or adapted to synthesize active 2,4-pyrimidinediamine compounds can also be found in WO 03/063794, U.S. application Ser. No. 10/631,029 filed Jul. 29, 2003, WO2004/014382, U.S. publication No. 2005-0234049 A1, and W0005/016893, the disclosures of which are incorporated herein by reference. All of the compounds described herein (including prodrugs) can be prepared by routine adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of exemplary synthetic routes that can be used to synthesize the 2,4-pyrimidinediamine compounds of the invention are described in scheme below. These methods can be routinely adapted to synthesize the 2,4-pyrimidinediamine compounds and prodrugs described herein.

Synthesis of Compounds

In a certain embodiment, the compounds can be synthesized from substituted or unsubstituted uracils as illustrated in Scheme 1, below:

Scheme 1

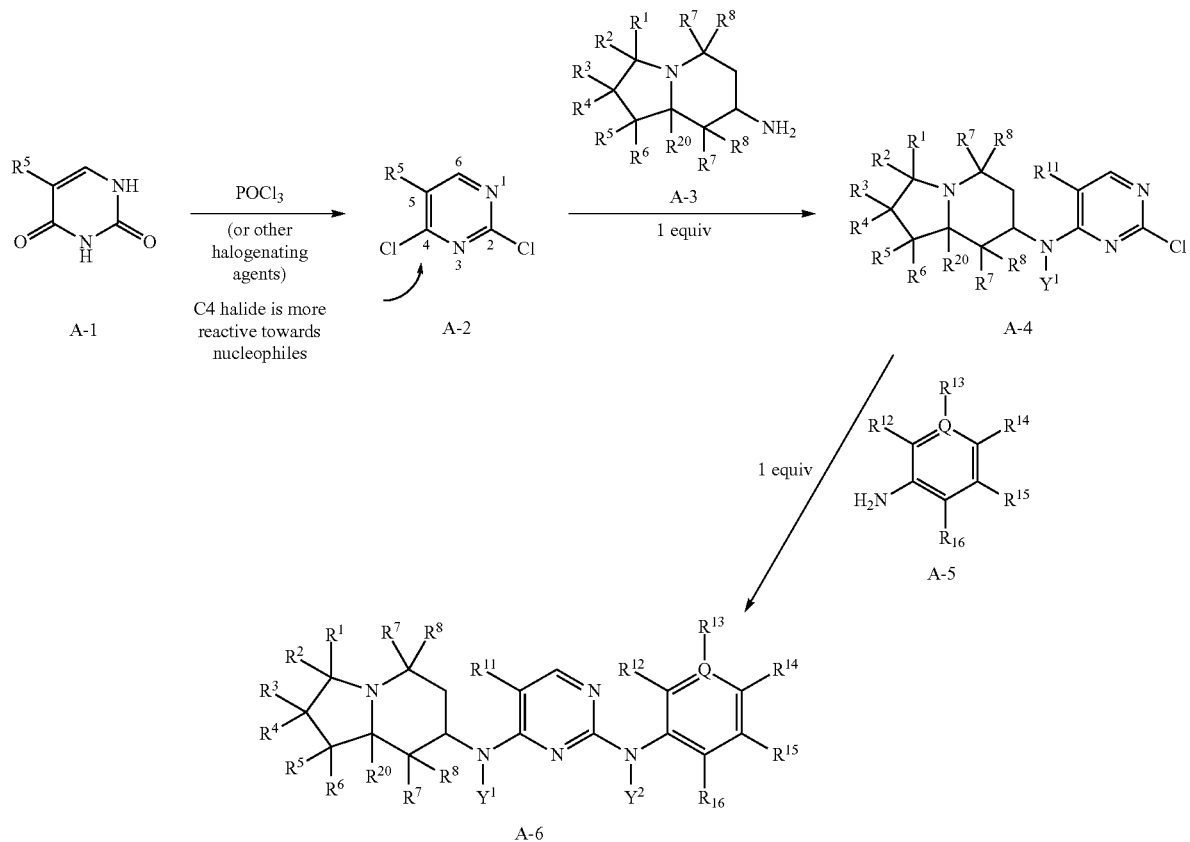

In Scheme 1, $R^1$, $R^2$, $R^3$, $R^4$, $R^5$, $R^6$, $R^7$, $R^8$, $R^9$, $R^{10}$, $R^{11}$, $R^{20}$, $Y^1$, $Y^2$, Q, $R^{12}$, $R^{13}$, $R^{14}$, $R^{15}$, and $R^{16}$ are as set forth hereinbefore.

According to Scheme 1, uracil A-1 is dihalogenated at the 2- and 4-positions using a standard dehydrating-halogenating agent such as $POCl_3$ (phosphorus oxychloride) (or other standard halogenating agent) under standard conditions to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-5 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

The reactions depicted in Scheme 1 may proceed more quickly when the reaction mixtures are heated via microwave. When heating in this fashion, the following conditions can be used: heat to 175° C. in ethanol for 5-20 minutes in a Smith Reactor (Personal Chemistry, Uppsala, Sweden) in a sealed tube (at 20 bar pressure).

A specific embodiment of Scheme 1 utilizing 5-fluorouracil (Aldrich #32,937-1) as a starting material is illustrated in Scheme 2, below.

Scheme 2

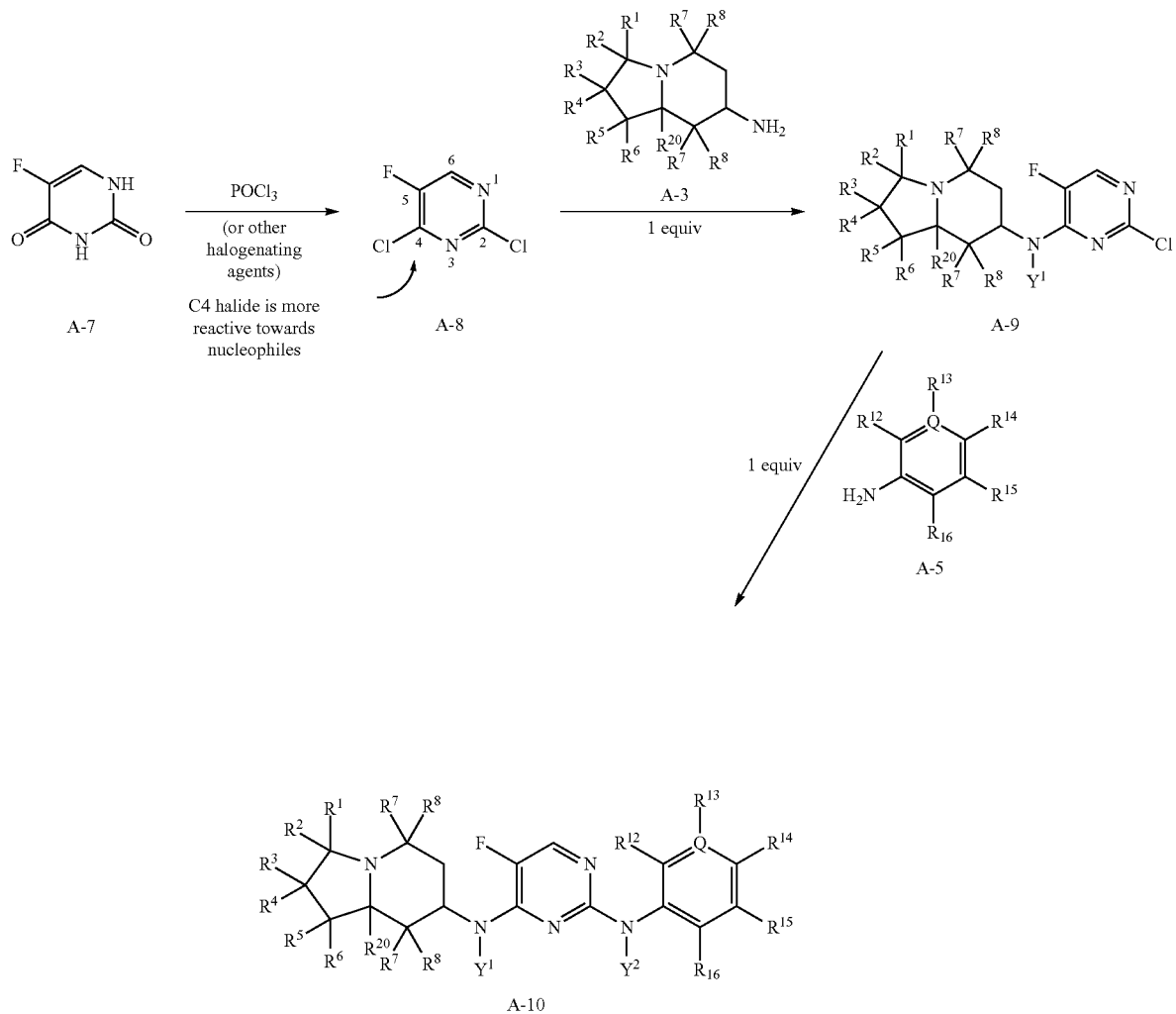

In Scheme 2, $R^1$, $R^2$, $R^3$, $R^4$, $R^5$, $R^6$, $R^7$, $R^8$, $R^9$, $R^{10}$, $R^{11}$, $R^{20}$, $Y^1$, $Y^2$, Q, $R^{12}$, $R^{13}$, $R^{14}$, $R^{15}$, and $R^{16}$ are as set forth hereinbefore.

Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

A specific embodiment of Scheme 1 to form cyano derivatives is illustrated in Scheme 3, below.

Scheme 3

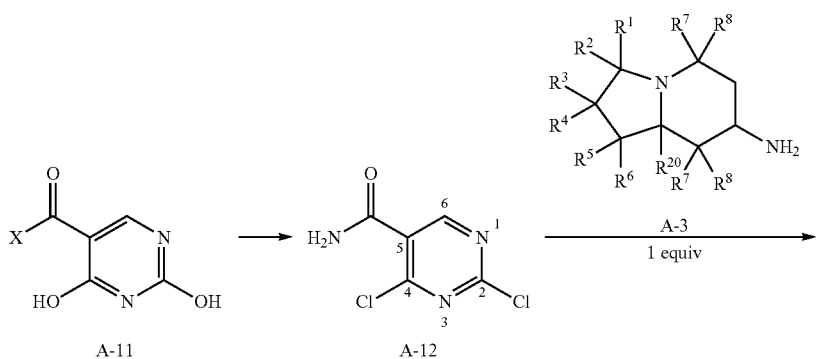

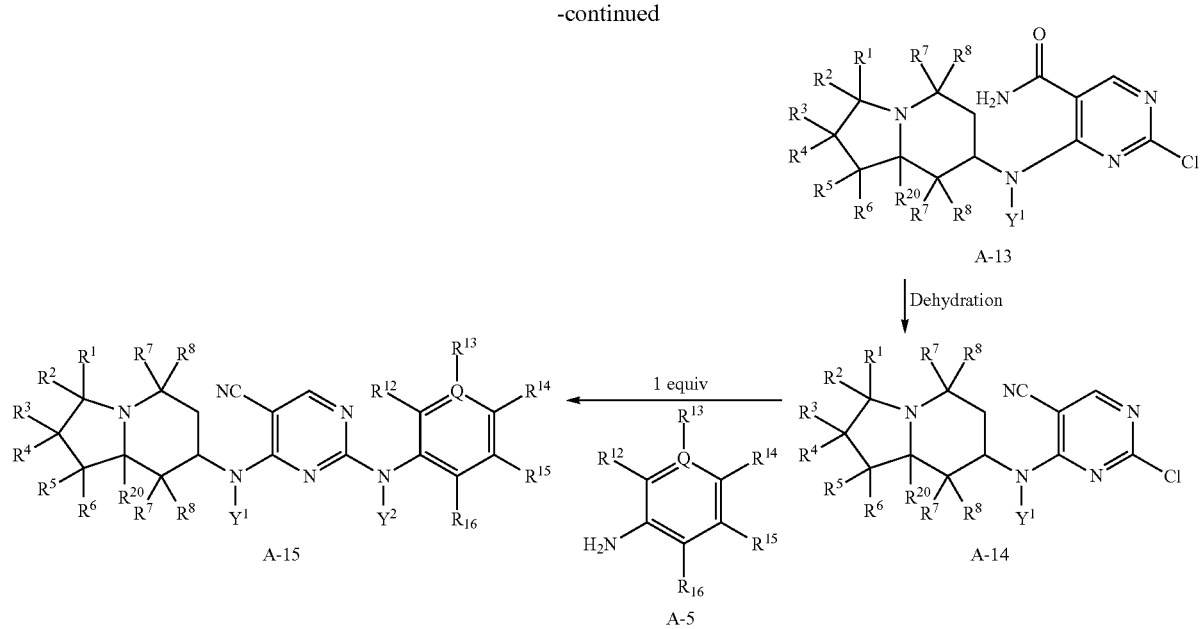

A-13

Dehydration

A-15 ← 1 equiv ← A-5 ← A-14

In Scheme 3, $R^1$, $R^2$, $R^3$, $R^4$, $R^5$, $R^6$, $R^7$, $R^8$, $R^9$, $R^{10}$, $R^{11}$, $R^{20}$, $Y^1$, $Y^2$, Q, $R^{12}$, $R^{13}$, $R^{14}$, $R^{15}$, and $R^{16}$ are as set forth hereinbefore.

Asymmetric 2N,4N-disubstituted-5-cyano-2,4-pyrimidinediamine A-15 can be obtained by reacting 2,4-dichloro-5-carbamoylpyrimidine A-12 with one equivalent of amine A-3 (to yield 2-chloro-N4-substituted-5-carbamoyl-4-pyrimidineamine A-13). The amide group of Compound A-13 is converted to a cyano group to yield Compound A-14, followed by reaction with one or more equivalents of amine A-5. Conversion of the amide group to the cyano group can be accomplished with dehydration, such as with use of Burgess reagent or trifluoroacetic anhydride. As will be recognized by those of skill in the art and exemplified herein, aniline A-5 may also be reacted with intermediate A-13, and the resultant N2,N4-disubstituted diaminopyrimidine-5-carbamoylpyrimidine can be dehydrated to yield the corresponding 5-cyano compound A-15.

Uracil Starting Materials and Intermediates

The uracil A-1, A-7, and A-11 starting materials can be purchased from commercial sources or prepared using standard techniques of organic chemistry. Commercially available uracils that can be used as starting materials in the schemes disclosed herein include, by way of example and not limitation, uracil (Aldrich #13,078-8; CAS Registry 66-22-8); 5 bromouracil (Aldrich #85,247-3; CAS Registry 51-20-7; 5 fluorouracil (Aldrich #85,847-1; CAS Registry 51-21-8); 5 iodouracil (Aldrich #85,785-8; CAS Registry 696-07-1); 5 nitrouracil (Aldrich #85,276-7; CAS Registry 611-08-5); 5 (trifluoromethyl)-uracil (Aldrich #22,327-1; CAS Registry 54-20-6). Additional 5-substituted uracils are available from General Intermediates of Canada, Inc., Edmonton, CA and/or Interchim, Cedex, France, or can be prepared using standard techniques. Myriad textbook references teaching suitable synthetic methods are provided infra.

Amino Starting Materials and Intermediates

Amines, such as A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc. By way of example amines A-5 can be prepared as described in WO 2010/090875, WO 2010-083207, WO 2011/068898 and WO 2012/012619, each of which are incorporated herein by reference.

In a certain embodiment, Compound A-3 can be synthesized as illustrated in Scheme 4, below:

Scheme 4

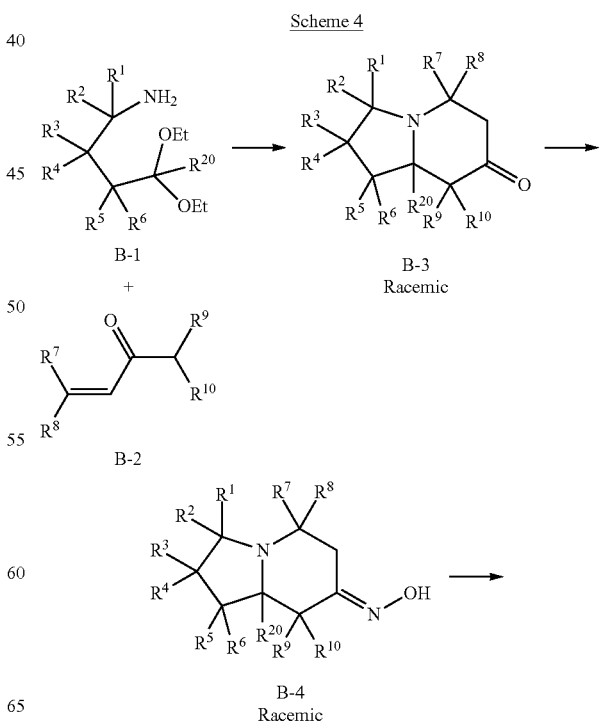

B-1 + B-2 → B-3 Racemic → B-4 Racemic →

-continued

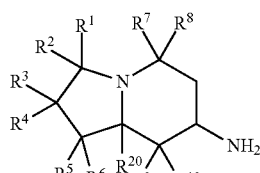

A-3
Mixture of two diastereomers
(each diastereomer is mixture
of two enantiomers)

Referring to Scheme 4, amine Compound B-1 reacts with enone Compound B-2 to form Compound B-3. First, the condensation reaction between Compound B-1 and Compound B-2 occurs by mixing the compounds neat or in a solvent. Then, the intermediate from the reaction between Compound B-1 and Compound B-2 is formed. The protecting groups are removed from intermediate. For example and not meant to be limiting, Scheme 4 shows a diethyl acetal as a protecting group. Conditions to remove the diethyl acetal protecting group include refluxing the intermediate in aqueous acid. After the protecting group is removed, further reaction affords Compound B-3.

With continued reference to Scheme 4, the carbonyl group of Compound B-3 reacts with hydroxylamine to form Compound B-4. Then, reduction of the oxime group of Compound B-4 affords Compound A-3. Suitable conditions for reduction of the oxime group include hydrogenation or reaction with sodium amalgam, borane, or sodium cyanoborohydride. In certain embodiments, the oxime group is hydrogenated with a catalyst. Suitable hydrogenation catalysts include $PtO_2$ and Raney Ni.

The isomers of Compound A-3 can be isolated by procedures known to those skilled in the art. The individual isomers may be obtained, for instance, by a resolution technique or by chiral chromatography techniques.

In a certain embodiment, Compound A-3 can be synthesized as illustrated in Scheme 5, below:

Scheme 5

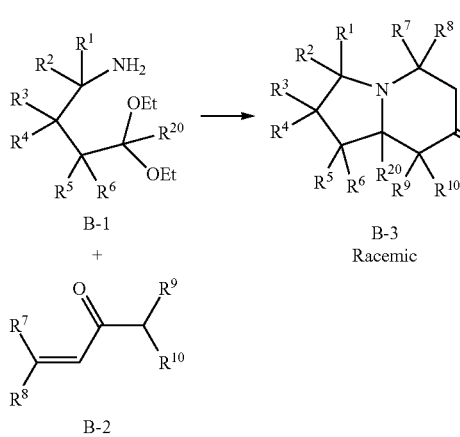

-continued

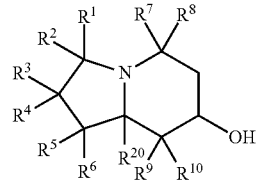

B-5

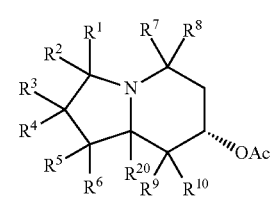

B-6

+

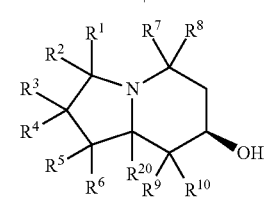

B-7

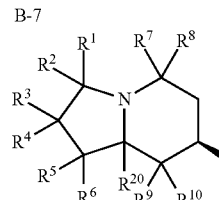

B-7

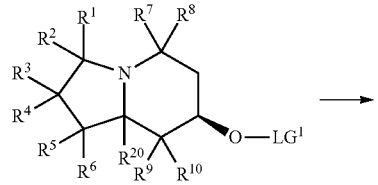

B-8

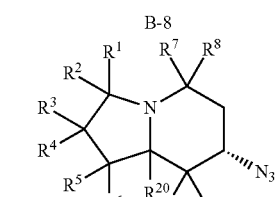

B-9

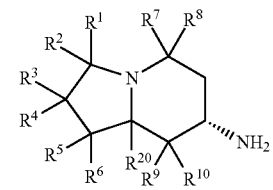

B-10

Referring to Scheme 5, amine Compound B-1 reacts with enone Compound B-2 to form Compound B-3. First, the condensation reaction between Compound B-1 and Compound B-2 occurs by mixing the compounds neat or in a solvent. Then, the intermediate from the reaction between Compound B-1 and Compound B-2 is formed. The protecting groups are removed from intermediate. For example and not meant to be limiting, Scheme 5 shows a diethyl acetal as a protecting group. Conditions to remove the diethyl acetal protecting group include refluxing the intermediate in aqueous acid. After the protecting group is removed, further reaction affords Compound B-3.

With continued reference to Scheme 5, the carbonyl of Compound B-3 is reduced to afford Compound B-5. Suitable conditions for reduction of the carbonyl group include hydrogenation or reaction with a metal hydride. In certain embodiments, the carbonyl group is reduced with metal hydride, such as L-selectride ((sec-Bu)BH)$_3$BHLi), sodium borohydride, lithium aluminum hydride, borane, or aluminum hydride.

Next, the stereoisomers of Compound B-5 are separated. The isomers of Compound B-5 can be isolated by procedures known to those skilled in the art. The individual isomers may be obtained, for instance, by a resolution technique or by chiral chromatography techniques. In certain embodiments, the stereoisomers of Compound B-5 can be isolated with the help of enzyme-catalyzed acylation. Acylation of one of the isomers is performed to differentiate the isomers. Suitable enzymes include Novozym 325 (Aldrich) and subtilisin. For the acylation reagent, an acetate substrate, such as vinylacetate or ethyl acetate, can be used.

Next, for example and not meant to be limiting, Compound B-7 is obtained for further reaction. Alternatively, Compound B-6 can also be obtained for further reaction, depending on which stereoisomer is desired. However, Compound B-7 is shown in the above scheme for further reaction for the purposes of being an example. With continued reference to Scheme 5, the hydroxyl group of Compound B-7 is converted to a leaving group (—O-LG$^1$) to form Compound B-8. Examples of leaving groups include halides, nonaflates, triflates, fluorosulfonates, tosylates, and mesylates. In certain embodiments, the hydroxyl group of Compound B-7 is converted to a tosylate or mesylate. Alternatively the transformation of B-7 to B-9 can be accomplished as is known to those of skill in the art via in situ activation of the B-7 hydroxyl group, such as via a Mitsonobu reaction.

Then, the leaving group of Compound B-8 is displaced with an azide (—N$_3$) to form Compound B-9. Reaction of Compound B-8 with sodium azide can form Compound B-9. Then, conversion of the azide of Compound B-9 to form an amine of Compound B-10 can be performed with reduction. Azides may be reduced to amines by hydrogenolysis or with a phosphine, e.g. triphenylphosphine, in the Staudinger reaction. Hydrogenolysis conditions include reaction with hydrogen and a catalyst, such as Pd(OH)$_2$ or Pd/C.

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine with a suitable progroup. Conditions for carrying out such reactions and for deprotecting the product to yield prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

The embodiments are also directed to processes and novel intermediates useful for preparing compounds of formula I-V or a salt or solvate or stereoisomer thereof.

Accordingly, the present disclosure provides a method for making a compound according to the formula

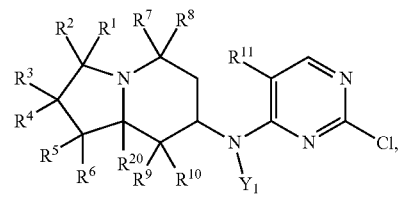

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl, and $Y^1$ is selected from hydrogen and alkyl;

the method comprising contacting a compound of the formula

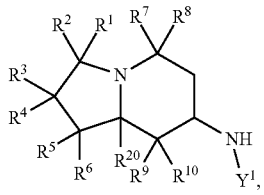

with a compound of the formula:

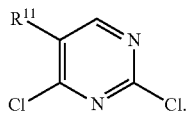

The present disclosure provides a method for making a compound according to the formula

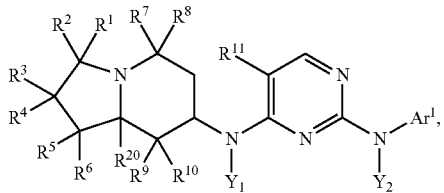

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen and alkyl; and $Ar^1$ is selected from aryl, substituted aryl, heteroaryl, and substituted heteroaryl;

the method comprising contacting a compound of the formula

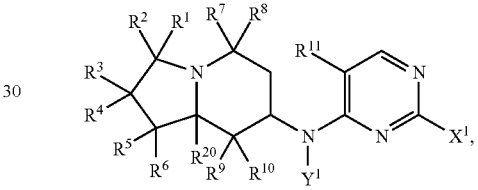

wherein $X^1$ is a halogen;

with a compound of the formula $HNY^2Ar^1$.

In certain embodiments, in the above methods, the method further comprises performing separation of isomers with chiral chromatography. In certain embodiments, in the above methods, the method further comprises performing separation of isomers with a resolution technique.

The present disclosure provides a method for preparing an optically active compound comprising contacting a racemic mixture of compounds of the formula

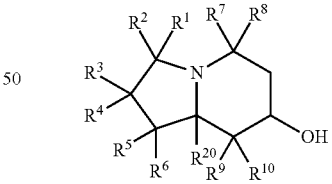

with a lipase; wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group; and $R^{20}$ is selected from hydrogen, alkyl, and substituted alkyl.

In one embodiment, the above process further comprises the step of forming a salt of a compound of formula I-V. Embodiments are directed to the other processes described herein; and to the product prepared by any of the processes described herein.

The embodiments are also directed to processes and novel intermediates useful for preparing compounds of formula VI-X or a salt or solvate or stereoisomer thereof.

Accordingly, the present disclosure provides a method for making a compound according to the formula

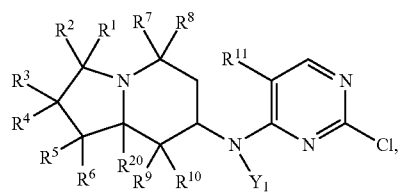

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl, and $Y^1$ is selected from hydrogen, alkyl and substituted alkyl; the method comprising contacting a compound of the formula

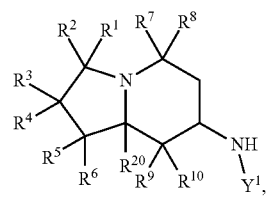

with a compound of the formula:

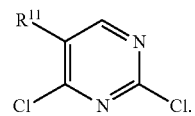

The present disclosure provides a method for making a compound according to the formula

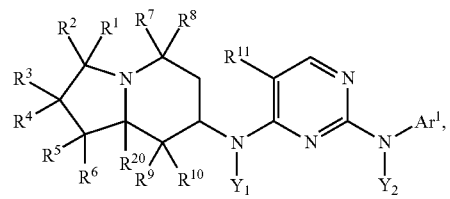

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen, alkyl and substituted alkyl; and $Ar^1$ is selected from aryl, substituted aryl, heteroaryl, and substituted heteroaryl;

the method comprising contacting a compound of the formula

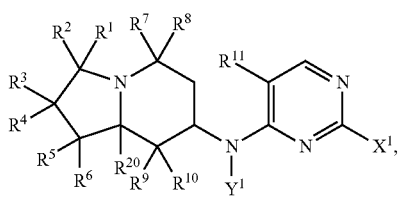

wherein $X^1$ is a halogen;
with a compound of the formula $HNY^2Ar^1$.

In certain embodiments, in the above methods, the method further comprises performing separation of isomers with chiral chromatography. In certain embodiments, in the above methods, the method further comprises performing separation of isomers with a resolution technique.

The present disclosure provides a method for preparing an optically active compound comprising contacting a racemic mixture of compounds of the formula

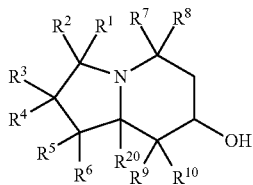

with a lipase; wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group; and $R^{20}$ is selected from hydrogen, alkyl, and substituted alkyl.

In one embodiment, the above process further comprises the step of forming a salt of a compound of formula VI-X. Embodiments are directed to the other processes described herein; and to the product prepared by any of the processes described herein.

Pharmaceutical Compositions

The disclosed compounds are useful, at least, for the inhibition of PKC activity and the treatment of a disease or disorder that is mediated through the activity of a PKC activity. Accordingly, pharmaceutical compositions comprising at least one disclosed compound are also described herein.

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington Science and Practice of Pharmacey 19th-22nd Editions, 1995-2012, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of inorganic acids suitable forming salts with the present compounds are hydrochloric acid, nitric acid, hydrobromic acid, sulfuric acid, hydroiodic acid, and phosphoric acid. Non-limiting examples of suitable organic acids forming salts with the present compounds are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, salicylic acid, formic acid, trichloroacetic acid, gluconic acid, asparagic acid, aspartic acid, benzenesulfonic acid, para-toluenesulfonic acid, naphthalenesulfonic acid, 1-hydroxy-2-napthoic acid, and the like. Lists of other suitable pharmaceutically acceptable salts are found in Remington: the Science and Practice of Pharmacy, 19th, 20th, 21st, and 22nd Edition, Williams & Wilkins, Lippincott Williams & Wilkins Philadelphia, Pa., and Pharmaceutical Press, London, England, 1995-2012. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a protein kinase C activity. Accordingly, the subject compounds are useful for treating a disease or disorder that is mediated through the activity of a PKC activity in a subject. Accordingly, the subject compounds are useful for treating a disease or disorder that is associated with the activation of T-cells in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Protein Kinase C

Protein Kinase C

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and α of PKC over one or more of the other PKC isoforms. In a certain instance, the subject compound possesses selectivity for the isoform θ of PKC over one or more of the other PKC isoforms. In a certain instance, the subject compound possesses selectivity for the isoform α of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In a certain instance, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 µM or less, such as less than about 300 nM, such as from about 1 nM to about 250 nM, less than 100 nM or even less than 10 nM in the assays disclosed herein.

The subject compounds can show a selectivity of the isoforms θ or μ of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC δ and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC (memory and fibroblast growth).

PKC theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory and/or allergic diseases such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC θ inactivation prevented fat-induced defects in insulin signaling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include those characterized by acute inflammation, chronic inflammation or both.

The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, cardiac arrhythmia, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, Parkinson's disease, bipolar disorder, and can be used to induce axon regeneration. Further the compounds can be used to treat cancer, infectious diseases such as: AIDS, malaria, such as by blocking the development of cerebral malaria, septic shock or adult respiratory distress syndrome, ischemia/reperfusion injury, myocardial infarction, stroke, gut ischemia, renal failure, hemorrhagic shock, and traumatic shock, for example traumatic brain injury. In one aspect, the present compounds are useful in treating muscle diseases or disorders, including inflammatory muscle disease and dystrophic disorders, such as Duchenne muscular dystrophy and myotonic muscular dystrophy.

Further diseases or conditions that can be treated with the disclosed compounds according to the present disclosure include, but are not limited to, T-cell mediated acute or chronic inflammatory, allergic, autoimmune diseases or disorders, including, without limitation rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, allergic rhinitis, inflammatory lung injury, inflammatory liver injury, inflammatory glomerular injury, cutaneous manifestations of immunologically-mediated disorders or illnesses, such as cutaneous lupus, including discoid lupus, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies. The disclosed compounds can be used to treat symptoms associated with the disorders described above. In particular the presently disclosed compounds can be used to treat complications of diabetes or insulin resistance and conditions associated therewith, including diabetic cardiomyopathy, glucose intolerance, fatty liver disease, hepatic steatosis, particularly non-alcoholic hepatic steatosis, and can be used to improve insulin sensitivity. Moreover, the present compounds also may be used to improve metabolic efficiency, for example, they can be used to treat exercise intolerance and intermittent claudication caused by, for example, peripheral artery disease.

The subject compounds can also be used for preventing or treating or delaying ocular diseases and disorders involving autoimmune or allergic inflammation and/or neovascularization. Ocular diseases or disorders involving inflammatory and/or neovascular events include, but are not limited to, macular degeneration (AMD), allergic conjunctivitis, diabetic ocular diseases or disorders, including diabetic retinopathy, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders that can be treated using the present compounds include a variety of cancers, including, among others, breast cancer, ovarian cancer, renal cancer, gastrointestinal cancer, including gastrointestinal stromal tumors, Ewing's sarcoma, kidney cancer, bladder cancer, pancreatic cancer, lung cancer, including non-small cell lung cancer, including lung squamous carcinoma, adenocarcinoma and large cell carcinomas.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gammadelta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

Characterization of Functional Properties

The following are exemplary assays useful in characterizing activities of a compound of interest.

A. In Vitro

1. Protein Kinase C Assay

The inhibition of PKC activity is measured by monitoring the production of phosphorylated peptide by fluorescence polarization at different concentrations of the inhibitor. Reactions are carried out in 96-well plate format with a total volume of 20 μL containing 20 mM HEPES, pH 7.4, 5 mM $MgCl_2$, 0.2 mM $CaCl_2$, 1 mM DTT, 0.02% Brij-35, 0.1 mg/ml phosphatidylserine, 0.02 mg/ml dioleoyl-sn-glycerol and 5 μM each of ATP and the peptide substrate. Compounds are first diluted serially in DMSO and then transferred to a solution containing the above concentrations of HEPES, $MgCl_2$, $CaCl_2$, DTT, and Brij-35 to yield 5× compound solutions in 2% DMSO, which is then added to the reaction solution. Reactions are initiated by the addition of PKC at a typical concentration as described in the table below, and then allowed to incubate at room temperature for 20 minutes. At the end of this time, a combination of quench (EDTA) and detection (peptide tracer and antibody) reagents is added using the protocol of Invitrogen P2748 (Carlsbad, Calif.), a Protein Kinase C Fluorescence polarization Assay Kit. After a 30 minute period of incubation, the amount of phosphorylated peptide generated is measured by fluorescence polarization (Ex=485 nm, Em=535 nm) using a Tecan Polarian instrument (Switzerland).

TABLE 2

| | Peptide substrate | SEQ ID | Enzyme source | enzyme concentration |
|---|---|---|---|---|
| PKC theta | RFARKGSLRQKNV | Seq ID No. 1 | Upstate Biotechnologies, Temecula, CA, cat. #14-444 | 40 ng/ml |
| PKC epsilon | RFARKGSLRQKNV | Seq ID No. 1 | Upstate Biotechnologies, Temecula, CA, cat. #14-518 | 50 ng/ml |

2. IL-2 ELISA, Human Primary T Cell, Anti-CD3+CD28+ Assays

Human Primary T Cell Isolation and Culture: Human primary T cells were prepared as follows. Fresh PBMC's from All Cells (Cat # PB002) were re-suspended in RPMI (RPMI-1640 with L-Glutamine; Mediatech, Inc., Herndon Va., cat. #10-040-CM) with 10% FBS and seeded into flasks and incubated at 37° C. for 2 hours to allow the monocytes to adhere. The non-adherent cells were then centrifuged and re-suspended in RPMI medium containing 40 U/ml IL2 and seeded into a flask pre-coated with 1 µg/ml αCD3 and 5 ug/ml αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/ml IL-2.

Primary T Cell Stimulation and IL2 ELISA: Human primary T cells (100,000 cells per well) were pre-incubated with or without test compound in RPMI-1640 with L-Glutamine and 10% FBS for 1 hour at 37° C. Cells were then stimulated by transferring them to round-bottom 96-well plates pre-coated with 1 µm/ml αCD3 and 5 µg/ml αCD28. For counter assay, cells were instead stimulated by adding 8× stock solutions of PMA and ionomycin in RPMI-1640 with L-Glutamine and 10% FBS (for final concentrations of 0.5 ng/ml PMA and 0.1 µM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. # DY202E.

3. Protein Kinase C assay

The subject compounds can be tested for activity on different PKC isoforms according to the following method. Assay is performed in a white with clear bottom 384-well microtiterplate with non-binding surface. The reaction mixture (25 µl) contains 1.5 µM of a tridecapeptide acceptor substrate that mimics the pseudo substrate sequence of PKC α with the Ala→Ser replacement, 10 µM $^{33}$P-ATP, 10 mM $Mg(NO_3)_2$, 0.2 mM $CaCl_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 µl of stop mix (100 mM EDTA, 200 µM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. $IC_{50}$ measurement is performed on a routine basis by incubating a serial dilution of inhibitor at concentrations ranging between 1-1000 µM. $IC_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase C β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C ε Assay

Human recombinant PKC ε is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at room temperature. Plates are blocked after removing the antibodies by incubation with 2% bovine serum albumin (BSA) in PBS (300 µl per well) for 2 hours at room temperature. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% $CO_2$ 100 µl of this mixture containing $1 \times 10^5$ cells are then transferred to the antibody-coated assay plates. In parallel 100 µl are incubated with 40 ng/ml PMA and 2 µM ionomycin. After incubation for 5.5 hours at 37° C. in 5% $CO_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1,2-diaminocyclohexane-N,N,N',N-tetraacetic acid, 10% (v/v) glycerol and 1% (v/v) Triton X-100 is added (20 µl per well). The plates are incubated at room temperature for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 µM coenzyme A, 470 µM luciferin (Chemie Brunschwig AG), 530 µM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves.

11. Bone Marrow Proliferation (BM) Assay

Bone marrow cells from CBA mice ($2.5 \times 10^4$ cells per well in flat bottom tissue culture microtiter plates) are incubated in 100 µl RPMI medium containing 10% FCS, 100 U/ml penicillin, 100 µm/ml streptomycin (Gibco BRL, Basel, Switzerland), 50 tJM 2-mercaptoethanol (Fluke, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 µm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 µm/ml streptomycin (Gibco BRL, Basel, Switzerland), 50 µM 2-mercaptoethanol (Fluka, Buchs, Switzerland) and serially diluted compounds. Seven three-fold dilution steps in duplicates per test compound are performed. After four days of incubation 1 µCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In Vivo

Heart Transplantation Model

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

Graft v. Host Model

Spleen cells ($2 \times 10^7$) from Wistar/F rats are injected subcutaneously into the right hind footpad of (Wistar/F× Fischer 344) $F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

Rat Arthritis Models

Rheumatoid arthritis (RA) is characterized by chronic joint inflammation eventually leading to irreversible cartilage destruction. IgG-containing IC are abundant in the synovial tissue of patients with RA. While it is still debated what role these complexes play in the etiology and pathology of the disease, IC communicate with the hematopoetic cells via the FcγR.

Collagen induced arthritis (CIA) is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

Study Protocol

Syngeneic LOU rats are immunized with native type II collagen on Day 0, and efficacy of a test compound is evaluated in a prevention regimen and a treatment regimen. In the prevention protocol, either vehicle or various doses of a test compound are administered via oral gavage starting on day of immunization (Day 0). In the treatment protocol, after clinical signs of arthritis develop on Day 10, treatment with a test compound is initiated (e.g., 300 mg/kg by oral gavage, qd) and continued until sacrifice on Day 28. In both protocols, clinical scores are obtained daily, and body weights are measured twice weekly. At Day 28, radiographic scores are obtained, and serum levels of collagen II antibody are measured by ELISA.

Determination of Results

By 10 days after immunization, rats can develop clinical CIA, as determined by an increase in their arthritis scores. The mean arthritic score gradually increases in the rats treated with vehicle alone after Day 10, and by Day 28 the mean clinical score can reach about 6.75. Mean clinical scores in animals treated from the day of immunization (Day 0) with a test compound can be significantly reduced on Days 10-28 compared with vehicle controls. In the rats treated with a test compound at disease onset, there can be a significantly lower arthritis score beginning around Day 16, and this difference can be observed until the end of the study on Day 28.

Blinded radiographic scores (scale 0-6) can be obtained on Day 28 of CIA and compared between the animals in the vehicle group, animals in the prevention group, and animals in the treatment group.

The groups administered with a test compound, either prophylactically (at immunization) or after disease onset can preclude the development of erosions and reduced soft tissue swelling. Similarly, the groups administered with a test compound can result in reduction of serum anti-collagen II antibody.

Similar to CIA rat adjuvant induced arthritis (rat AIA) is an accepted model of arthritis. See, e.g., Badger et al., 2000, "Disease-modifying activity of SB242235, a selective inhibitor of p38 mitogen-activated protein kinase, in rat AIA", *Arthritis and Rheumatism* 43: 175-183, the disclosure of which is incorporated herein by reference. The protocol for rat AIA is similar to CIA as described herein.

Mouse Experimental Autoimmune Encephalomyelitis

The in vivo efficacy of a test compound towards autoimmune diseases can be demonstrated in a mouse model of experimental autoimmune encephalomyelitis (EAE).

Model Description

EAE is a useful model for multiple sclerosis (MS), an autoimmune disease of the CNS that is caused by immune-cell infiltration of the CNS white matter. Inflammation and subsequent destruction of myelin cause progressive paralysis. Like the human disease, EAE is associated with peripheral activation of T cells autoreactive with myelin proteins, such as myelin basic protein (MBP), proteolipid protein (PLP), or myelin oligodendrocyte protein (MOG). Activated neuroantigen-specific T cells pass the blood-brain barrier, leading to focal mononuclear cell infiltration and demyelination. EAE can be induced in susceptible mouse strains by immunization with myelin-specific proteins in combination with adjuvant. In the SJL mouse model used in these studies, hind limb and tail paralysis is apparent by Day 10 after immunization, the peak of disease severity can be observed between Days 10 and 14, and a cycle of partial spontaneous remission followed by relapse can be observed up to Day 35. The results can demonstrate the potential of the test compound to suppress disease severity and prevent relapse of disease symptoms that may be the result of FcγR-mediated cytokine release from immune cells.

Study Protocol

In the SJL murine model of EAE, each mouse is sensitized with PLP/CFA. (150 μg PLP139-151 with 200 μg CFA in 0.05 ml of homogenate on four sites of hind flank for a total of 0.2 ml emulsion is used to induce EAE). In a suppression protocol, either vehicle or various doses of a test compound are administered via oral gavage starting on the day of immunization (Day 0). In a treatment protocol, at onset of disease, animals are separated to achieve groups with a similar mean clinical score at onset and administered vehicle or various dose frequencies of test compounds via oral gavage. In both protocols, clinical scores are monitored daily, and body weights are measured twice weekly.

Determination of Results

By 10 days after PLP immunization, SJL mice can develop clinical EAE, as evidenced by an increase in their mean clinical scores. The paralytic score can gradually increase in the animals treated with vehicle only from the day of immunization (Day 0), and by Day 14 the mean score can reach a peak of about 5.1. At disease peak (e.g., Day 14), the mean clinical score in animals treated with either daily or twice daily can be significantly reduced. By Day 16, animals can exhibit a partial remission of mean clinical severity, which is a characteristic of the SJL model. The lower clinical scores in animals treated twice daily with a test compound can remain significant throughout the experiment until the animals are sacrificed on Day 30. These lower scores throughout the treatment period are reflected in the significantly lower cumulative disease index (CDI) and increase in cumulative weight index (CWI).

SJL mice treated with a test compound at disease onset (e.g., Day 11) can show a significant decrease in CDI. Further, there can be a decrease in the number of relapses in animals treated with a test compound compared with the number of relapses in animals treated with vehicle.

Research Applications

Since subject compounds can inhibit a PKC activity, such compounds are also useful as research tools. The present disclosure also provides a method for using subject compounds as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of formula I-X or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. As will be understood, by those of skill in the art of organic synthesis and medicinal chemistry the specific conditions set forth below are exemplary and can be varied or adapted to other reagents and products in routine fashion. Unless indicated otherwise, parts are parts by weight, molecular weight is weight average molecular weight, temperature is in degrees Celsius, and pressure is at or near atmospheric. Standard abbreviations may be used.

As referred to in the Examples, HPLC and LCMS protocols are as follows:

Protocol-1:
HPLC: Waters 2690 Alliance
Diode array detector (210-400 nm)
Column: Phenomenex Gemini 4.6×100 mm, 5 µm, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|---|---|---|
| 0 | 95 | 5 |
| 10 | 0 | 100 (curve = 6) |
| 11.1 | 0 | 100 |
| 11.2 | 95 | 5 |
| 12.1 | 95 | 5 |

Protocol-2:
HPLC: Waters 2690 Alliance
Diode array detector (210-400 nm)
Column: Phenomenex Gemini 4.6×100 mm, 5 µm, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|---|---|---|
| 0 | 95 | 5 |
| 10 | 0 | 100 (curve = 8) |
| 11.1 | 0 | 100 |
| 11.2 | 95 | 5 |
| 12.1 | 95 | 5 |

Protocol-3:
HPLC: Waters 2695 Alliance
Diode array detector (210-400 nm)
Column: Phenomenex Gemini 4.6×100 mm, 5 µm, 110 Å
Column temperature 30° C.
Sample temperature 15° C.
Solvent A—0.05% Formic acid in Water
Solvent B—0.05% Formic acid in Acetonitrile
Flow rate—1.5 ml/min
Gradient:

| Time | A % | B % |
|---|---|---|
| 0 | 95 | 5 |
| 10 | 0 | 100 (curve = 6) |
| 11.1 | 0 | 100 |
| 11.2 | 95 | 5 |
| 12.1 | 95 | 5 |

Chiral HPLC methods:
Protocol-4:
HPLC: Waters 2695 Alliance
Diode array detector (210-400 nm)
Column: Chiralcel-OJ, 4.6×250 mm, with guard
Mobil phase (isocratic): 40% methanol, 40% ethanol, 19.9% Hexane, 0.1% triethylamine
Flow rate: 0.5 ml/min
Injection volume: 3 µL
Concentration: approx 5 mg/ml
Detection: UV at 254 nm
Run Time: 30 minutes Protocol-5:
HPLC: Waters 2695 Alliance
Diode array detector (210-400 nm)
Column: Chiralcel-OJ, 4.6×250 mm, with guard
Mobil phase (isocratic): 89.9% Hexane, 5% methanol, 5% ethanol 0.1% triethylamine
Flow rate: 0.5 ml/min
Injection volume: 3 µL
Concentration: approx 5 mg/ml
Detection: UV at 254 nm
Run Time: 45 minutes

Synthesis of Octahydroindolizine Portions

Example 1

Synthesis of (RS, SR, RR, SS)-N-(2-chloro-5-fluoropyrimidin-4-yl)-octahydro-5,5-dimethylindolizin-7-amine

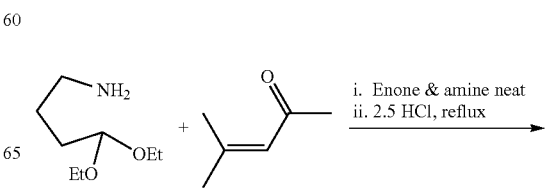

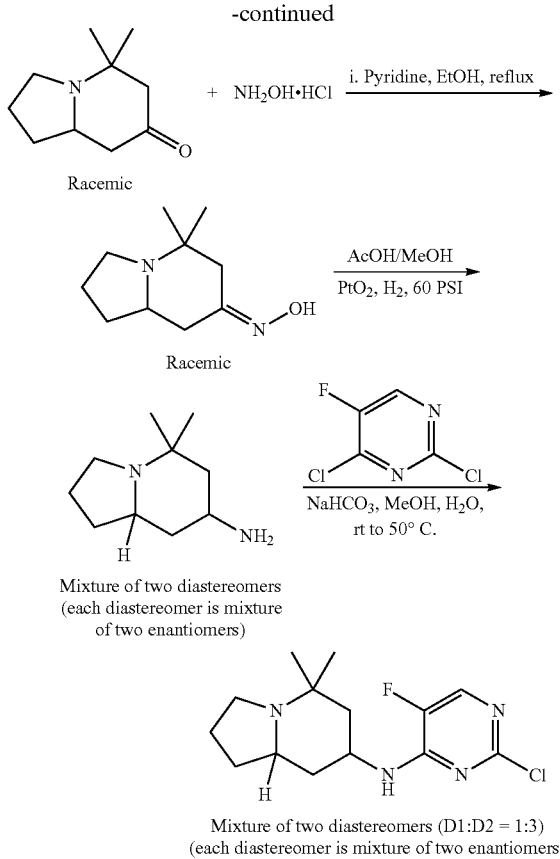

Preparation of (R/S)-Hexahydro-5,5-dimethylindolizin-7(1H)-one

The compound was prepared as described in *J. Chem. Soc., Perkin Trans.* 1 1986, 447-453, which is hereby incorporated by reference in its entirety.

4-Aminobutyraldehyde diethyl acetal (6.4 g, 39.7 mmol) and mesityl oxide (20 ml, 175.2 mmol) were mixed neat and stirred at room temperature for 1 hour. After this time, the reaction mixture was extracted with 2.5 M HCl and the extract washed with ether. The aqueous layer was heated at reflux for 3 hours. The reaction mixture was concentrated in vacuo to reduce the volume by ~50%. The concentrated aqueous layer was cooled on ice and diluted with methylene chloride (~100 ml). The mixture was basified with aqueous potassium hydroxide and the layers separated. The aqueous layer was further extracted with methylene chloride (100 ml) and the combined organic extracts were washed with aqueous potassium carbonate. The organic layer was dried over potassium carbonate, filtered and concentrated. Purification by flash column chromatography, on silica gel, eluting with neat EtOAc provided the product as pale yellow oil, 3.2 g (48% yield). The mixture can also be purified by distillation from $K_2CO_3$ (instead of column chromatography) to afford the ketone in a similar yield.

$^1$H NMR (CDCl$_3$, 300 MHz) δ: 3.02 (dt, J=8.8, 3.6 Hz, 1H), 2.74-2.84 (m, 1H), 2.38-2.54 (m, 3H), 2.09-2.24 (m, 2H), 1.86-2.02 (m, 2H), 1.72-1.82 (m, 1H), 1.45-1.57 (m, 1H), 1.24 (s, 3H), 0.92 (s, 3H).

Preparation of (R/S)-Hexahydro-5,5-dimethylindolizin-7(1H)-one-oxime

The compound was prepared as described in *J. Chem. Soc., Perkin Trans.* 1 1986, 447-453, which is hereby incorporated by reference in its entirety.

Mixture of (R, S)-hexahydro-5, 5-dimethylindolizin-7(1H)-one-oxime (2.9 g, 17.3 mmol) and hydroxylamine hydrochloride (1.2 g, 17.3 mmol) in EtOH (10 ml) and pyridine (10 ml) were heated to reflux and the mixture stirred for 2 hours. A thick precipitate develops. After allowing the reaction mixture to cool to room temperature, the mixture was placed in a −18° C. freezer where it was left for 1 hour. The mixture was then filtered, and the filter cake washed with cold EtOH (2×5 ml) to afford the oxime (3.00 g, 95%) as a solid.

LCMS (m/z): 183 (MH$^+$), RT=0.89 min. (Protocol-1)

Preparation of (R/S, S/R, R/R, S/S)-Octahydro-5,5-dimethylindolizin-7-amine (R, S)-Hexahydro-5, 5-dimethylindolizin-7(1H)-one-oxime (3.2 g, 17.6 mmol) was dissolved in AcOH (30 ml). The clear solution is transferred to a Parr hydrogenation flask and placed under nitrogen. PtO$_2$ (0.5 g) is added to the Parr flask under nitrogen. The mixture was then transferred to a Parr hydrogenation apparatus, evacuated and filled with hydrogen (×3). The mixture was hydrogenated at 55-60 psi (optionally topping-up hydrogen) until LC/MS and TLC indicated complete reaction to the amine. After complete reaction, the mixture was placed under nitrogen and filtered through a small pad of Celite. The filter cake was washed with MeOH (×3) and the filtrate was concentrated under vacuum to leave the octahydro-5, 5-dimethylindolizin-7-amine as a salt—yield assumed quantitative, and amine was used directly in a displacement reaction after drying under high vacuum.

Preparation of (R/S, S/R, R/R, S/S)-N-(2-chloro-5-fluoropyrimidin-4-yl)-octahydro-5,5-dimethylindolizin-7-amine A mixture of octahydro-5, 5-dimethylindolizin-7-amine acetic acid salt (4.1 g, 14.1 mmol) and dichloro-5-fluoropyrimidine (2.83 g, 17 mmol) and NaHCO$_3$ (3.6 g, 42.4 mmol) in MeOH/H$_2$O (50:10) was stirred at 45° C. for 12 hours. Both the diastereomers were detected by LC/MS and TLC. Volatiles were removed and 100 ml of 4 N HCl in dioxane was added to the crude reaction mixture. Volatiles were removed and the crude mixture was adsorbed on silica gel. Combi-flash column chromatography was performed to separate the diastereomers using DCM/2N NH$_3$ in MeOH (90:10) as eluent. Column purification gave the product as a mixture of two diastereomers [each diastereomer is mixture of two enantiomers] in 74% yield (3.1 g).

A note should be made that the desired isomer can be prepared in a ca. 6:1 ratio by use of the Na/pentanol reduction used in *J. Chem. Soc., Perkin Trans.* 1 1986, 447-453, which is hereby incorporated by reference in its entirety.

Example 2

Chromatography of N-(2-chloro-5-fluoropyrimidin-4-yl)-octahydro-5,5-dimethylindolizin-7-amine

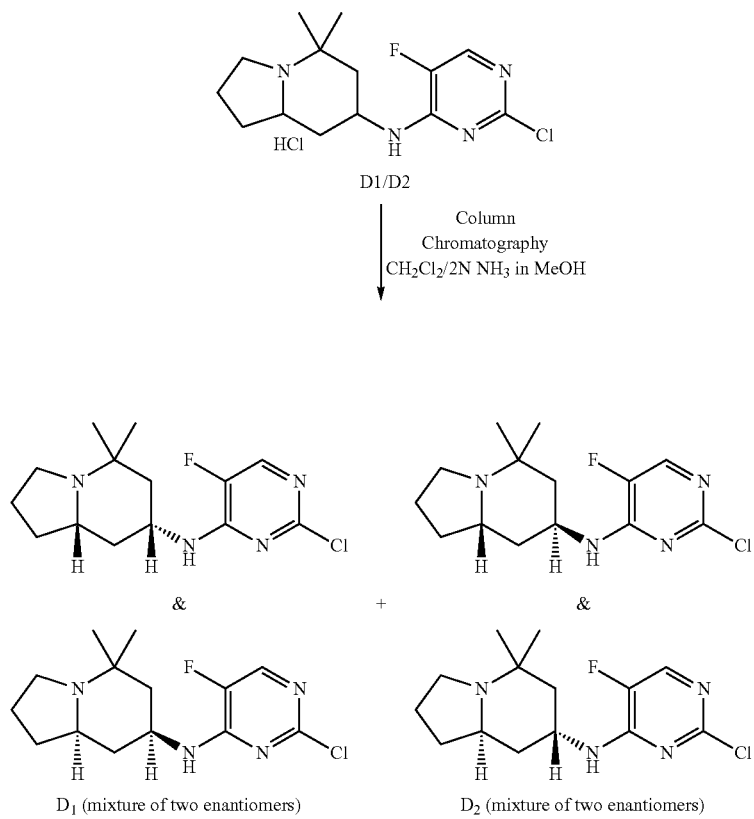 [SMILES: CC1(C)CC(Nc2nc(Cl)ncc2F)CC2CCCN21 ; Cl ; CC1(C)C[C@H](Nc2nc(Cl)ncc2F)C[C@@H]2CCCN21 ; CC1(C)C[C@@H](Nc2nc(Cl)ncc2F)C[C@@H]2CCCN21 ; CC1(C)C[C@@H](Nc2nc(Cl)ncc2F)C[C@H]2CCCN21 ; CC1(C)C[C@H](Nc2nc(Cl)ncc2F)C[C@H]2CCCN21]

Preparation of (R/S, S/R)-N-(2-chloro-5-fluoropyrimidin-4-yl)-octahydro-5,5-dimethylindolizin-7-amine and (S/S & R/R)-N-(2-chloro-5-fluoropyrimidin-4-yl)-octahydro-5,5-dimethylindolizin-7-amine A mixture of octahydro-5,5-dimethylindolizin-7-amine acetic acid salt (4.1 g, 14.1 mmol) and dichloro-5-fluoropyrimidine (2.8 g, 17 mmol) and NaHCO$_3$ (3.6 g, 42.4 mmol) in MeOH/H$_2$O (50:10) was stirred at 45° C. for 12 hours. Both the diastereomers were detected by LC/MS and TLC. Volatiles were removed and 100 ml of 4 N HCl in dioxane was added to the crude reaction mixture. Volatiles were removed and the crude mixture was adsorbed on silica gel. Combiflash column chromatography was performed to separate the diastereomers using DCM/2N NH$_3$ in MeOH (95:5) as eluent. Column purification gave separated diastereomers D1 & D2 in 12% yield (0.5 g) and 62% yield (2.6 g) respectively as HCl salts.

A small quantity of each diastereomer was neutralized with aq. 1N NaOH and analyzed. Aqueous 1N NaOH was added to diastereomeric HCl salt (50 mg) in EtOAc (10 ml) and the layers were separated. Aqueous layer was worked up twice with EtOAc (10 ml) and the combined organic layers were dried over Na$_2$SO$_4$. Removal of the volatiles in vacuo gave the product.

Data for (R/S, S/R)-N-(2-chloro-5-fluoropyrimidin-4-yl)-octahydro-5,5-dimethylindolizin-7-amine (D1): [single diastereomer, mix of enantiomers]

$^1$H NMR (CDCl$_3$, 300 MHz) δ: 7.84 (dd, J=2.8, 1.4 Hz, 1H), 5.02 (br. s, 1H), 4.17-4.27 (m, 1H), 2.97 (dt, J=8.5, 2.8 Hz, 1H), 2.57-2.51 (m, 1H), 2.38 (q, J=8.5 Hz, 1H), 2.26 (dd, J=11.8, 1.6 Hz, 1H), 1.79-1.90 (m, 2H), 1.64-1.78 (m, 2H), 1.33-1.47 (m, 2H), 1.23-1.26 (m, 1H), 1.19 (s, 3H), 1.06 (s, 3H).

$^{19}$F NMR (DMSO) δ: −159.91.

LCMS (m/z): 299 (MH$^+$) (D1 retention time: 4.75 min. see Protocol-2 in general methods).

Data for (S/S, R/R)-N-(2-chloro-5-fluoropyrimidin-4-yl)-octahydro-5,5-dimethylindolizin-7-amine (D2): [single diastereomer, mix of enantiomers]

$^1$H NMR (CDCl$_3$, 300 MHz) δ: 7.86 (d, J=2.8 Hz, 1H), 5.35 (br. d, J=3.6 Hz, 1H), 4.37-4.40 (m, 1H), 3.02 (dt, J=8.5, 2.75 Hz, 1H), 2.58-2.50 (m, 1H), 2.42 (q, J=8.8 Hz, 1H), 2.05 (dd, J=13.8, 2.2 Hz, 1H), 1.86-1.96 (m, 2H), 1.61-1.82 (m, 2H), 1.37-1.61 (m, 3H), 1.18 (s, 3H), 1.08 (s, 3H).

LCMS (m/z): 299 (MH$^+$) (D2 retention time: 3.99 min. (see Protocol-2 in general methods).

Example 3

Synthesis of (7R,8aS)-N-(2-chloro-5-fluoropyrimidin-4-yl)-octahydro-5,5-dimethylindolizin-7-amine

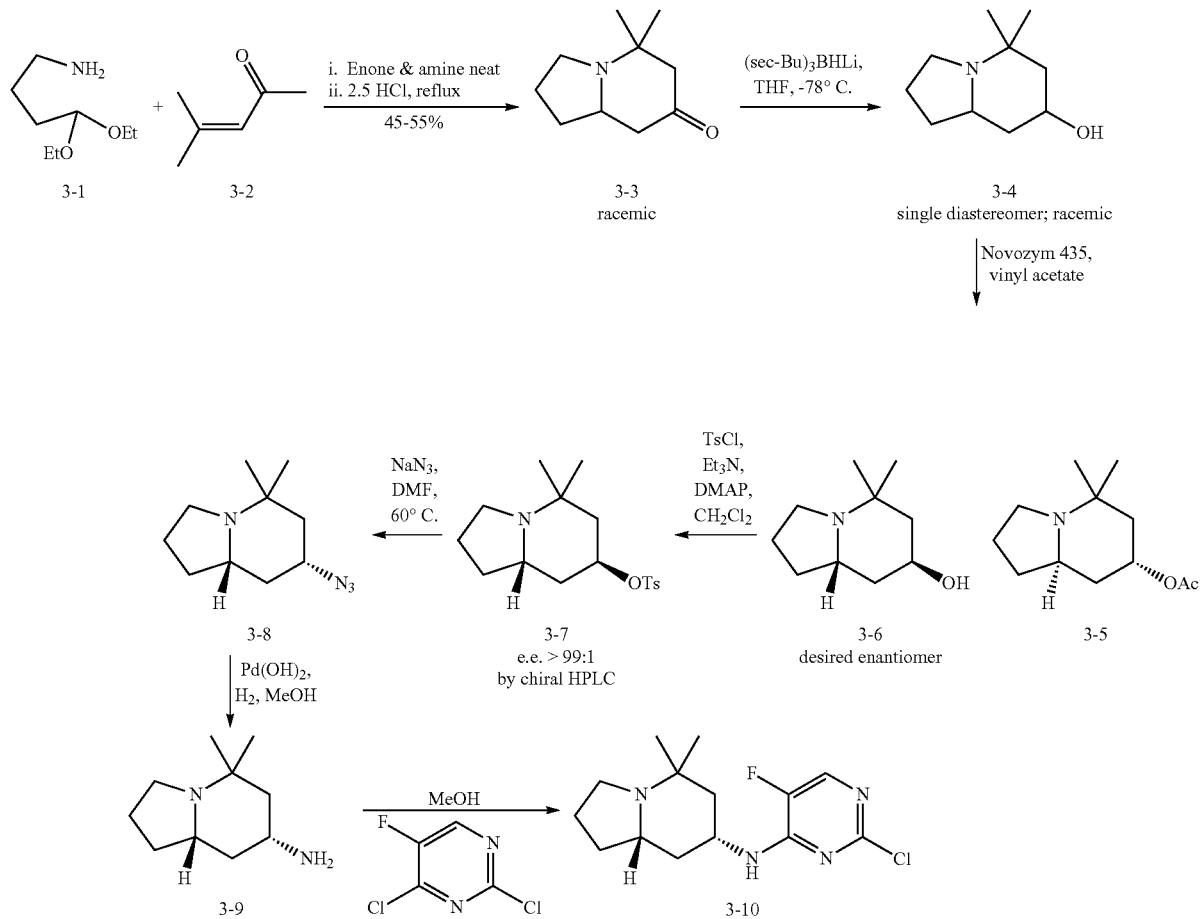

Preparation of Preparation of (±)-hexahydro-5,5-dimethylindolizin-7-(1H)-one (Compound 3-3)

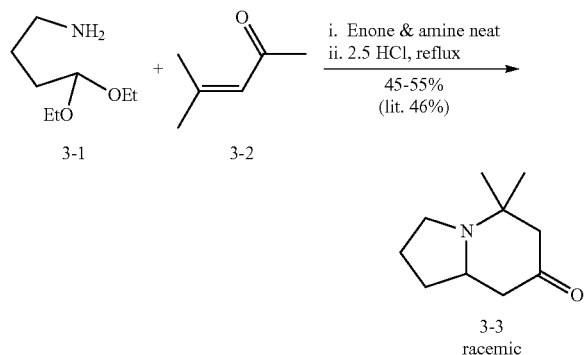

This is based on a literature procedure—see F. D. King *J. Chem. Soc., Perkin Trans.* 1 1986, 447-453, which is hereby incorporated by reference in its entirety.

4-Aminobutyraldehyde diethyl acetal (Compound 3-1) (94 g, 0.58 mol) and mesityl oxide (Compound 3-2) (290 g, 2.95 mol) were mixed neat and stirred at room temperature for 1 hour. After this time, the reaction mixture was extracted with 2.5 M HCl and the extract washed with ether. The aqueous layer was heated at reflux for 3 hours. The reaction mixture was concentrated under vacuum to reduce the volume by ~50%. The concentrated aqueous layer was cooled on ice and diluted with methylene chloride (~300 mL). The mixture was basified with aqueous KOH and the layers separated. The aqueous layer was further extracted with $CH_2Cl_2$ (200 mL) and the combined organic extracts were washed with aqueous $K_2CO_3$. The organic layer was dried over $K_2CO_3$, filtered and concentrated in vacuo to leave a crude residue. The residue was purified by flash column chromatography, on silica gel, eluting with neat methylene chloride to provide the product (45.5 g, 47%) as a pale yellow oil.

$^1$H NMR (CDCl$_3$, 300 MHz): δ 2.96 (dt, J=9.0, 3.0 Hz, 1H), 2.79-2.69 (m, 1H), 2.48-2.32 (m, 3H), 2.18-2.04 (m, 2H), 1.97-1.63 (m, 3H), 1.51-1.41 (m, 1H), 1.18 (s, 3H), 0.87 (s, 3H).

$^{13}$C NMR (CDCl$_3$, 75 MHz): δ 210.1, 56.8, 54.7, 54.1, 47.3, 44.3, 31.5, 30.2, 21.2, 16.6.

It should be noted that, after workup, the reaction mixture can also be purified by distillation from $K_2CO_3$ (instead of column chromatography), to afford the ketone product in a similar yield.

Preparation of (±)-octahydro-5,5-dimethylindolizin-7-ol (Compound 3-4)

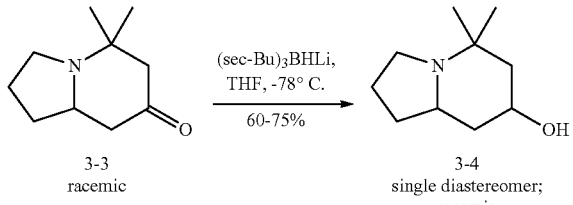

3-3
racemic 3-4
single diastereomer;
racemic

A solution of 1.0 M L-selectride in THF (419.5 mL, 419.5 mmol) was added dropwise over ca. 120 minutes to a mixture of (±)-hexahydro-5,5-dimethylindolizin-7-(1H)-one (Compound 3-3) (50.0 g, 299 mmol) in anhydrous THF (200 mL) at −78° C. The reaction mixture was stirred at −78° C. for a further 4 hours. The mixture was lifted from the bath and allowed to warm to −15° C. over 1 hour. Analysis of the crude reaction by TLC indicated complete conversion to alcohol (Compound 3-4). The reaction mixture was cooled to −78° C. and quenched by the dropwise addition of MeOH (150 mL). The reaction mixture was then allowed to warm to room temperature and stirred overnight. The solvent was then removed in vacuo to leave a crude residue. The residue was dissolved in 3N HCl (200 mL) and extracted with EtOAc (250 mL then 100 mL). The aqueous layer was then basified using 12N NaOH to pH 14, and extracted with $CH_2Cl_2$ (4×500 mL). The combined organic layers were dried ($Na_2SO_4$), filtered and the solvent removed in vacuo to leave a light brown solid. The solid was titurated with $Et_2O$ to give the product (29.2 g). The filtrate was concentrated in vacuo and triturated with $Et_2O$/hexane (1:1) to give a further crop of product (5.8 g). The combined yield of the alcohol product (Compound 3-4) was 35.0 g (70%).

$^1$H NMR ($CDCl_3$, 300 MHz): δ 4.17 (m, 1H), 2.98 (dt, J=8.7, 3.0 Hz, 1H), 2.78-2.68 (m, 1H), 2.43 (q, J=8.7 Hz, 1H), 1.93-1.83 (m, 2H), 1.80-1.54 (m, 5H), 1.46-1.34 (m, 2H), 1.16 (s, 3H), 1.14 (s, 3H).

$^{13}$C NMR ($CDCl_3$, 75 MHz): δ 66.9, 52.5, 50.9, 45.8, 45.1, 39.4, 31.6, 31.0, 20.6, 17.1.

An alternative workup using hydrogen peroxide and NaOH is also possible. (±)-Hexahydro-5,5-dimethylindolizin-7-(1H)-one (Compound 3-3) (30.6 g, 0.18 mol) was dissolved in anhydrous THF and cooled to −78° C. L-Selectride, 1.0 M in THF (260 mL, 0.26 mol) was added dropwise over 90 minutes. The resulting mixture was allowed to stir at −78° C. for 4 hours. The reaction was quenched by dropwise addition of hydrogen peroxide, 30% wt in $H_2O$ (150 mL), followed by dropwise addition of 3N sodium hydroxide solution (150 mL). The cold bath was removed and replaced with a lukewarm water bath—the resulting mixture was allowed to stir for 1 hour after reaching room temperature. A white precipitate formed and was removed by vacuum filtration through a pad of Celite, and the filter cake was rinsed with EtOAc (×3). The filtrate was diluted further with EtOAc and $H_2O$ and the layers were separated. The organic layer was washed with brine, dried ($Na_2SO_4$), filtered and concentrated in vacuo to provide the product (27.6 g) as a solid. Trituration with an $Et_2O$/hexane solution (1:1) provided the product (21.5 g, 71% yield) as an off-white solid.

Preparation of (7S,8aS)-octahydro-5,5-dimethylindolizin-7-ol (Compound 3-6)

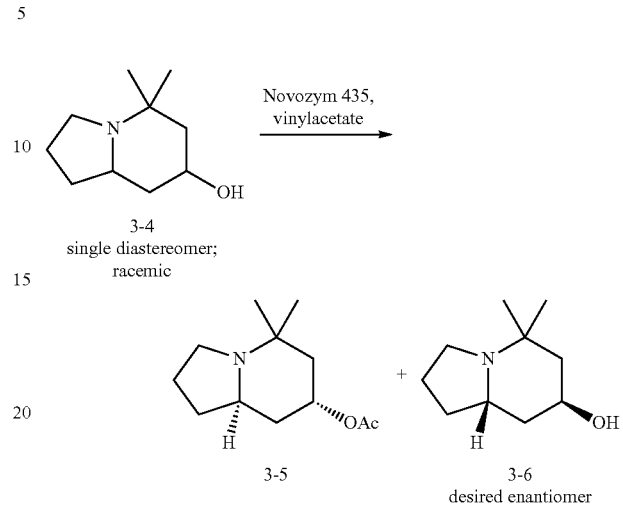

3-4
single diastereomer;
racemic 3-5

3-6
desired enantiomer

A mixture of (±)-octahydro-5,5-dimethylindolizin-7-ol (Compound 3-4) (20.4 g, 118.3 mmol) and Novozym 435 (20.4 g) in vinyl acetate (400 mL) was slowly stirred (150 revolutions per minute) at room temperature for 16 hours. The reaction mixture was then filtered and the filter cake washed with EtOAc (400 mL). The filtrate was concentrated in vacuo to leave a crude residue that was separated by column chromatography on silica gel using $CH_2Cl_2$/2N $NH_3$ in MeOH (95:5) as eluent to give the desired chiral alcohol (Compound 3-6) (9.0 g, 44%)

$[α]_D$=−25.1° (c=0.34 in MeOH).

$^1$H NMR ($CDCl_3$, 300 MHz): δ 4.19-4.17 (m, 1H), 2.98 (td, J=8.7, 3.0 Hz, 1H), 2.78-2.68 (m, 1H), 2.44 (q, J=8.7 Hz, 1H), 1.93-1.82 (m, 2H), 1.80-1.57 (m, 5H), 1.47-1.34 (m, 2H), 1.16 (s, 3H), 1.14 (s, 3H).

$^{13}$C NMR ($CDCl_3$, 75 MHz): δ 66.8, 52.4, 50.8, 45.6, 45.0, 39.2, 31.5, 30.8, 20.5, 16.9.

m/z=170.17 $(M+H)^+$.

Alternatively, the product can be purified by column chromatography on basic alumina using EtOAc/hexane (0:1 to 2:3) or $CH_2Cl_2$/MeOH (1:0 to 95:5) as eluent.

Compounds 3-5 and 3-6 also were separated by liquid-liquid extraction using hexane and water. Hexane washing of aqueous layer resulted in complete removal of Compound 3-5.

The effect of time on the yield and enantiomeric excess from this resolution is shown below.

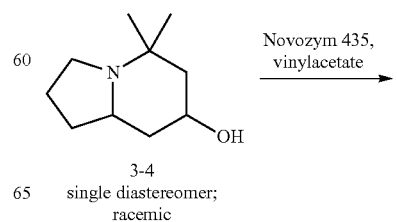

3-4
single diastereomer;
racemic

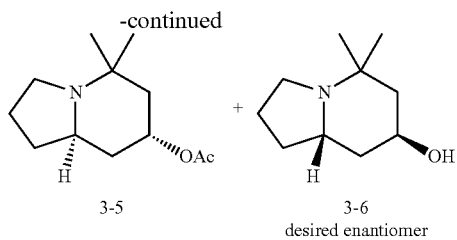

Effect upon yield and enantiomeric excess with variation in time for kinetic resolution of (±)-octahydro-5,5-dimethylindolizin-7-ol (Compound 3-4)

| Time (hours) | Absolute yield of recovered alcohol (Compound 3-6) (theoretical yield) | Enantiomer excess of recovered alcohol (Compound 3-6) |
| --- | --- | --- |
| 8 | 62% | 48% |
| 16 | 44% (88% theoretical) | >99% |
| 24 | 40% (80% theoretical) | >99% |
| 60 | 35% (70% theoretical) | >99% |
| >72 | 21% (42% theoretical) | >99% |

Reactions were undertaken with alcohol 4 (1 equivalent) and Novozym 435 (same weight as alcohol) in vinyl acetate at room temperature while stirring at ca. 150 revolutions per minute.

Enantiomer excess ascertained by measuring enantiomeric excess of tosylate derivative 3-7 by chiral HPLC, after reaction of the alcohol 3-6 with p-TsCl, Et₃N and DMAP in CH₂Cl₂.

Other Procedures for Resolution of Racemic Mixture 3-4
Enzymatic Resolution Using Amano Lipase A, from *Aspergillus niger*

Amano Lipase A, from *Aspergillus niger* (100 mg; Aldrich catalogue number 534781) was added in one portion to a mixture of racemic alcohol (1.0 g, 5.9 mmol) in vinyl acetate (20 mL). The mixture was sealed, then stirred at room temperature overnight. TLC analysis indicated no substantial formation of acetate product.

Attempted Enzymatic Resolution Using Amano Lipase A, from *Aspergillus niger* at 40° C.:

Amano Lipase A, from *Aspergillus niger* (100 mg; Aldrich catalogue number 534781) was added in one portion to a mixture of racemic alcohol (0.5 g, 3.0 mmol) in vinyl acetate (10 mL). The mixture was sealed, then heated to 40° C. and stirred at overnight. TLC analysis indicated no formation of acetate product.

Attempted Enzymatic Resolution Using Amano Lipase M, from *Mucor javanicus*

Amano Lipase M, from *Mucor javanicus* (100 mg; Aldrich catalogue number 534803) was added in one portion to a mixture of racemic alcohol (0.5 g, 3.0 mmol) in vinyl acetate (10 mL) under nitrogen. The mixture was stirred at room temperature overnight. TLC analysis indicated no formation of acetate product.

Resolution of (±)-Octahydro-5,5-dimethylindolizin-7-ol with R-(−)-Mandelic Acid (±)-Octahydro-5,5-dimethylindolizin-7-ol (10 g, 59.1 mmol) was dissolved in acetone (150 mL) with heating (heat gun). R-(−)-Mandelic acid (9.0 g, 59.1 mmol) was dissolved in acetone (50 mL) with heating (heat gun). The two solutions were combined, heated for one minute additional (heat gun) and then concentrated under reduced pressure. The resulting residue was dissolved in methyl isobutyl ketone (30 mL) with heating (heat gun). Upon cooling to room temperature crystals formed and were subsequently collected by vacuum filtration (13.3 g, 70% yield, 40% ee). These crystals (13.0 g) were then dissolved in methyl isobutyl ketone (100 mL) with significant heating (water bath, 86° C.). The solution was slowly cooled to room temperature overnight and a second batch of crystals was collected by vacuum filtration (8.9 g, 68% yield, 70% ee). The resulting crystals (8.6 g) were recrystallized again from methyl isobutyl ketone (70 mL), requiring significant heating (water bath 86° C.) to fully dissolve the sample. The solution was cooled to room temperature overnight and a third batch of crystals was collected by vacuum filtration (6.1 g, 71% yield, 90% ee, melting point 128-129° C.).

Preparation of (7S,8aS)-octahydro-5,5-dimethylindolizin-7-yl-4-methylbenzenesulfonate (Compound 3-7)

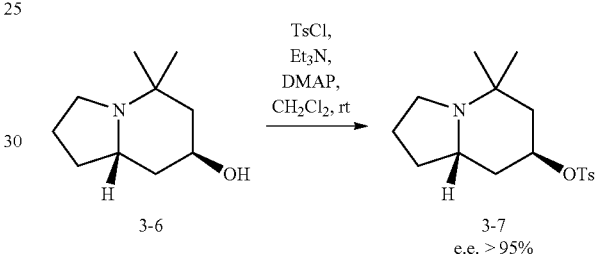

para-Toluenesulfonyl chloride (13.2 g, 69.2 mmol) was added in portions to a mixture of (7S,8aS)-octahydro-5,5-dimethylindolizin-7-ol (Compound 3-6) (9.0 g, 53.25 mmol, 1.0 equiv), 4-N,N-dimethylaminopyridine (9.8 g, 79.9 mmol) and Et₃N (11.1 mL, 79.9 mmol) in CH₂Cl₂ (180 mL) at 0° C. The mixture was allowed to warm to room temperature and then stirred for 4 days. EtOAc (600 mL) was added, and the resulting solid was filtered and washed with EtOAc (ca. 150 mL). The filtrate was washed with water (600 mL) and concentrated in vacuo to leave a crude residue. The residue was purified by column chromatography on silica gel using EtOAc/MeOH (9:1) as eluent to give the product (14.5 g, 84%) as a solid.

$[\alpha]_D = -6.1°$ (c=0.43 in MeOH).

¹H NMR (CDCl₃, 300 MHz): δ 7.75 (d, J=8.4 Hz, 2H), 7.30 (d, J=8.1 Hz, 2H), 4.80-4.78 (m, 1H), 2.92 (td, J=9.0, 3.3 Hz, 1H), 2.69-2.60 (m, 1H), 2.41 (s, 3H), 2.39 (q, J=8.7 Hz, 1H), 2.01-1.96 (m, 1H), 1.88-1.78 (m, 1H), 1.74-1.68 (m, 2H), 1.65-1.56 (m, 1H), 1.55-1.49 (m, 1H), 1.40-1.26 (m, 2H), 1.07 (s, 3H), 1.05 (s, 3H).

¹³C NMR (CDCl₃, 75 MHz): δ 144.5, 134.3, 129.8, 127.6, 78.7, 52.5, 50.9, 44.9, 42.9, 36.7, 31.0, 30.6, 21.6, 20.4, 16.6. m/z=324.42 (M+H)⁺.

Chiral HPLC Conditions:
Column: Daicel Chemical Industries, Chiralcel OJ, 4.6× 250 mm
Mobile phase: 1:1 Methanol/Ethanol 0.1% diethylamine (isocratic)
Flow rate: 0.5 ml/min
Run time: 15 minutes
Temperature: room temperature Detection: Water 996 PDA
HPLC: Waters 2690 Separations Module
Alternatively, Compound 3-7 was prepared as follows:

Preparation of (7S,8aS)-octahydro-5,5-dimethylindolizin-7-yl-4-methanesulfonate

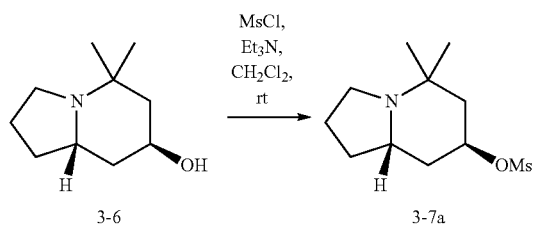 [SMILES: CC1(C)C[C@@H](O)C[C@@H]2CCCN21 ; CC1(C)C[C@@H](OS(C)(=O)=O)C[C@@H]2CCCN21]

Methanesulfonyl chloride (4.2 mL, 53.1 mmol) was added slowly to a solution of alcohol Compound 3-6 (6.0 g, 35.4 mmol) and Et$_3$N (14.8 mL, 106.1 mmol) in DCM (100 mL) at 0° C. The reaction was stirred overnight and had warmed to room temperature. The reaction mixture was diluted with EtOAc (~200 mL) and washed with sat. NaHCO$_3$ and brine. The organic layer was separated, dried (MgSO$_4$) and concentrated to give mesylate Compound 3-7a (~7.3 g) which was directly used in the next step.

$[\alpha]_D$=−8.7 (c=1.20 in MeOH)

$^1$H NMR (CDCl$_3$, 300 MHz): δ 5.08 (t-like, J=3.0, 2.4 Hz, 1H), 3.00 (s, 3H), 2.80-2.65 (m, 1H), 2.47 (q, J=8.7 Hz, 1H), 2.20 (dm, J=14.4 Hz, 1H), 1.98-1.88 (m, 2H), 1.79-1.61 (m, 4H), 1.61-1.40 (m, 2H), 1.18 (s, 3H), 1.13 (s, 3H)

$^{13}$C NMR (CDCl$_3$, 75 MHz): δ 78.5, 52.4, 50.8, 44.9, 43.5, 38.5, 37.3, 31.2, 30.8, 20.5, 16.5 m/z=248.0 (M+H)$^+$

HRMS (EI): [M+H]$^+$ calc'd for C$_{11}$H$_{21}$NO$_3$S m/z 248.1320, found 248.1301.

Preparation of (7R,8aS)-7-azido-octahydro-5,5-dimethylindolizine (Compound 3-8)

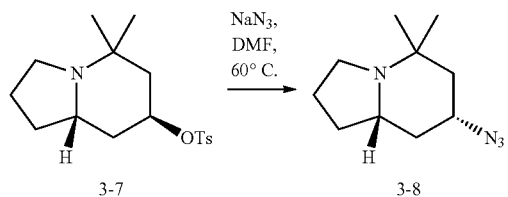 [SMILES: Cc1ccc(S(=O)(=O)O[C@H]2C[C@@H]3CCCN3C(C)(C)C2)cc1 ; CC1(C)C[C@H](N=[N+]=[N-])C[C@@H]2CCCN21]

A mixture of (7S,8aS)-octahydro-5,5-dimethylindolizin-7-yl-4-methylbenzenesulfonate (Compound 3-7) (14.5 g, 44.9 mmol) and NaN$_3$ (8.8 g, 134.7 mmol) in DMF (120 mL) was heated at 80° C. overnight. After cooling, the reaction mixture was diluted with EtOAc (400 mL) and H$_2$O (300 mL). The aqueous and organic layers were separated and the aqueous layer extracted with EtOAc (200 mL). The combined organic layers were washed with H$_2$O (200 mL), dried (MgSO$_4$) and concentrated in vacuo to leave the product which was directly used in the next step—yield assumed quantitative (8.7 g). Mesyl Compound 3-7a can be used in this reaction under analogous conditions.

$[\alpha]_D$=−35.6 (c=1.23 in MeOH)

$^1$H NMR (CDCl$_3$, 300 MHz): δ 3.48-3.40 (m, 1H), 3.00-2.92 (m, 1H), 2.46-2.40 (m, 1H), 2.35 (q, J=8.7 Hz, 1H), 2.01-1.96 (m, 1H), 1.89-1.64 (m, 4H), 1.50-1.40 (m, 2H), 1.20 (s, 3H), 0.96 (s, 3H).

m/z=195.08 (M+H)$^+$.

Preparation of (7R,8aS)-octahydro-5,5-dimethylindolizin-7-amine (Compound 3-9)

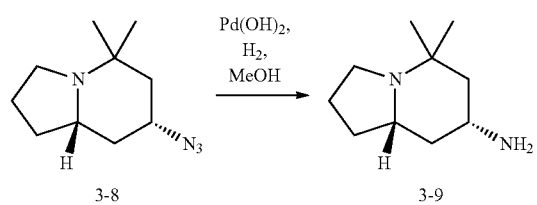

A solution of crude (7R,8aS)-7-azido-octahydro-5,5-dimethylindolizine (Compound 3-8) (assumed 8.7 g) and Pd(OH)$_2$ (20% weight on carbon; 1.7 g) in MeOH (150 mL) was hydrogenated at 30 psi at room temperature for 6 hours. The reaction mixture was filtered through a pad of Celite and the filter cake was washed with MeOH (200 mL). The filtrate was concentrated under vacuum to give the product, which was used directly in the next step—yield assumed quantitative (7.5 g).

$[\alpha]_D$=−16.0° (c=0.175 in MeOH)

$^1$H NMR (CDCl$_3$, 300 MHz): δ 3.03-2.96 (m, 1H), 2.55-2.47 (m, 1H), 2.41 (q, J=8.7 Hz, 1H), 2.08-2.03 (m, 1H), 1.93-1.80 (m, 2H), 1.77-1.65 (m, 2H), 1.37-1.20 (m, 2H), 1.21 (s, 3H), 1.10-1.06 (m, 1H), 0.99 (s, 3H).

m/z=169.10 (M+H)$^+$.

Preparation of (7R,8aS)-N-(2-chloro-5-fluoropyrimidin-4-yl)-octahydro-5,5-dimethylindolizin-7-amine (Compound 3-10)

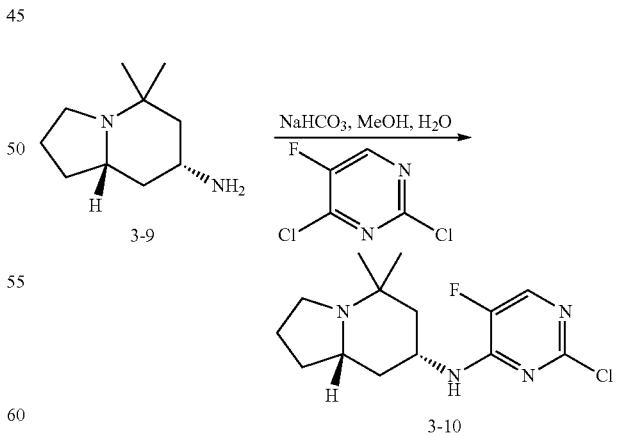

A mixture of crude (7R,8aS)-octahydro-5,5-dimethylindolizin-7-amine (Compound 3-9) (assumed 7.5 g, 44.9 mmol) and dichlorofluoropyrimidine (7.5 g, 44.9 mmol) in MeOH (120 mL) was stirred at room temperature for 20 hours. The solvent was removed in vacuo and the residue was purified by column chromatography on silica gel using CH$_2$Cl$_2$/2N NH$_3$ in MeOH (95:5) as eluent to give the product (10.8 g, 80% over 3 steps).

[α]$_D$=−1.7° (c=0.35 in MeOH).

$^1$H NMR (CDCl$_3$, 300 MHz): δ 7.89 (d, J=2.7 Hz, 1H), 5.83 (d, J=5.7 Hz, 1H), 4.55-4.38 (m, 1H), 3.55-3.45 (m, 1H), 3.25-3.10 (m, 1H), 2.82 (q, J=8.1 Hz, 1H), 2.42-2.38 (m, 1H), 2.32-1.92 (m, 7H), 1.55 (s, 3H), 1.36 (s, 3H).

$^{13}$C NMR (CDCl$_3$, 300 MHz): δ 154.3 (d, J=3.3 Hz), 152.9 (d, J=12.6 Hz), 145.1 (d, J=256.1 Hz), 139.7 (d, J=20.3 Hz), 59.0, 58.2, 44.8, 44.0, 41.6, 33.9, 28.8, 27.7, 20.0, 17.9. $^{19}$F NMR (CDCl$_3$, 282 MHz): δ −158.0 (s).

m/z=299.03 (M+H)$^+$.

Compound 3-10 can be analyzed for chiral purity by high-performance liquid chromatography using the following conditions:

Column: ChiralPak AD-H (250×4.6 mm)
Eluent: hexane: IPA:diethylamine (90:10:0.01)
Flow-rate: 1 mL/min
Detection: 230 nM detection Likewise Compound 3-10 can be analyzed for chiral purity by supercritical fluid chromatography using the following conditions:

Column: Daicel Chemical Industries, Chiralcel AD-H, 4.6×250 mm
Mobile phase: 10% Methanol 0.1% diethylamine (isocratic)/90% CO$_2$
Flow rate: 3 ml/min
Run time: 8 minutes
Temperature: 30° C.
Detection: 254 nm
SFC: TharSFC Investigator Example 4

Synthesis of 7-Amino-hexahydro-3, 3-dimethylindolizin-5 (1H)-one

Synthesis of 7-amino-hexahydro-3, 3-dimethylindolizin-5 (1H)-one is illustrated in scheme below. Although the absolute stereochemistry was not established for any of the intermediates, from the analysis of $^1$H NMR spectral pattern indicates that the final product and the intermediates were single diastereomers (racemic). Absolute stereochemistry of individual enantiomers was not established.

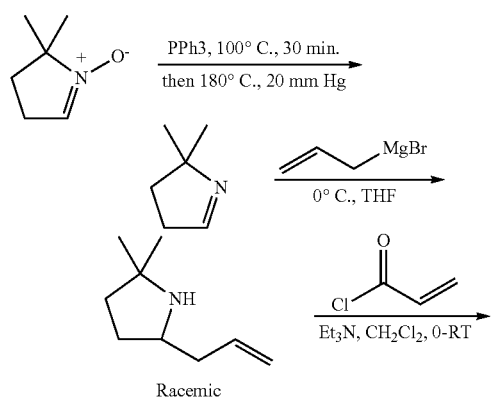

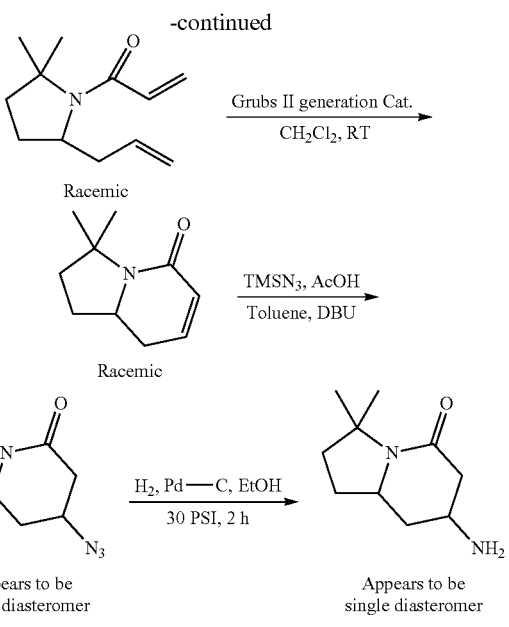

Preparation of 5,5-Dimethyl-1-pyrroline 5,5-Dimethyl-1-pyrroline was prepared with reference to *Can. J. Chem.* 1962, 40, 181, which is hereby incorporated by reference in its entirety.

A suspension of 5, 5-dimethyl-1-pyrroline N-oxide (20 g, 177 mmol) and triphenylphosphine (52.38 g, 200 mmol) were heated at 100° C. for 30 minutes, under a short Vigreux column under argon. The liquid which formed was further heated up to 180° C. under vacuum (20 torr), and the distillate was collected. The boiling point varied from 46° C. to 58° C. at 20 torr (lit. 104° C. 760 torr) to give 5,5-dimethyl-1-pyrroline (8.60 g, 50%) as a colorless liquid which becomes yellowish upon standing, even when kept in the refrigerator.

$^1$H NMR (DMSO d$_6$, 300 MHz) δ 7.31 (s, 1H), 2.48-2.55 (m, 2H), 1.50-1.55 (m, 2H), 1.11-1.15 (m, 6H); m/z=98 (M+H)$^+$.

Preparation of 5-Allyl-2, 2-dimethylpyrrolidine

To a solution of 5,5-dimethyl-1-pyrroline (2.3 g, 23.7 mmol) in anhydrous THF (50 ml) 1.0 M solution of allylmagnesium bromide in diethyl ether (43.3 ml, 47.3 mmol) was added dropwise at 0° C. The reaction mixture was allowed to stir at 0° C. for 1 hour and brought to room temperature and stirred for 3 hours. Analysis of the reaction mixture by LC-MS indicated the completion of the reaction. The reaction mixture was cooled to 0° C. and quenched with 5 ml of 1N aqueous HCl and partitioned with 50 ml of EtOAc. Organic layer was separated and the aqueous layer was worked up with 2×50 ml of EtOAc. Combined organic layers were dried over MgSO$_4$ and concentrated under vacuum gave the product as light yellow oil in 44% yield (1.5 g). The crude product was taken to the next step without further purification.

LCMS (m/z)=140 (M+H)$^+$.

Preparation of 1-(5-Allyl-2, 2-dimethylpyrrolidine-1-yl) prop-2-en-1-one

To a solution of 5-allyl-2, 2-dimethylpyrrolidine (1.5 g, 10.5 mmol) in 50 ml of anhydrous CH$_2$Cl$_2$, triethylamine (3 ml, 21 mmol) and acryloyl chloride (0.94 ml, 11.6 mmol) were added at 0° C. The reaction mixture was stirred at 0° C. for 1 hour and allowed to warm to room temperature and stirred for overnight. Analysis of the reaction mixture by LCMS indicated the completion of the reaction. Saturated aqueous NaHCO$_3$ was added to the reaction mixture and the layers were separated. Aqueous layer was worked up twice with CH$_2$Cl$_2$ and the combined organic layers were dried over Na$_2$SO$_4$. Removal of the volatiles and purification of the crude by column chromatography gave the product in 80% yield (1.60 g) as colorless oil.

$^1$H NMR (CDCl$_3$, 300 MHz) δ 6.33-6.52 (m, 2H), 5.68-5.75 (m, 1H), 5.62 (dd, J=7.0, 2.6 Hz, 1H), 5.09 (s, 1H), 5.06-5.07 (m, 1H), 3.97-4.00 (m, 1H), 2.15-2.33 (m, 2H), 1.88-1.95 (m, 2H), 1.66-1.83 (m, 2H), 1.60 (s, 3H), 1.45 (s, 3H); LCMS (m/z)=194 (M+H)$^+$.

Preparation of 2,3,8,8a-Tetrahydro-3, 3-dimethylindolizin-5-(1H)-one

5-Allyl-2, 2-dimethylpyrrolidine (0.5 g, 2.6 mmol) was taken in a 250 ml RB flask and flushed with nitrogen for three times. To the above flask 100 ml of anhydrous CH$_2$Cl$_2$ and Grubbs 2$^{nd}$ generation catalyst (0.27 g, 0.3 mmol) were added at room temperature. The reaction mixture was stirred for overnight at room temperature. LCMS analysis indicated completion of the reaction. Volatiles were removed in vacuo and the crude was purified by column chromatography to give 0.32 g (yield=74%) of the product as colorless oil.

$^1$H NMR (CDCl$_3$, 300 MHz) δ 6.38-6.46 (m, appears to be dt, 1H), 5.84 (dd, J=9.7, 3.2 Hz, 1H), 3.69-3.80 (m, 1H), 2.40 (td, J=17.3, 6.2 Hz, 1H), 2.07-2.14 (m, 1H), 1.97-2.02 (m, 1H), 1.61-1.84 (m, 3H), 1.56 (s, 3H), 1.44 (s, 3H); LCMS (m/z)=166 (M+H)$^+$.

Preparation of 7-Azido-3, 3-dimethylindolizin-5-(1H)-one

A solution of 2, 3, 8, 8a-tetrahydro-3, 3-dimethylindolizin-5(1H)-one (0.3 g, 1.8 mmol) in 10 ml of toluene was taken a 25 ml RB flask. To the above flask azido-trimethylsilane (2.42 ml, 18.2 mmol), AcOH (1.2 ml, 20 mmol) and DBU (0.27 ml, 1.8 mmol) were added. The reaction mixture was stirred at room temperature for overnight. Volatiles were removed under vacuum and the crude reaction mixture was purified by column chromatography. The product was obtained as colorless oil in 85% yield (0.32 g).

$^1$H NMR (CDCl$_3$, 300 MHz) δ 4.10-4.13 (m, 1H), 3.68-3.78 (m, 1H), 2.58 (dd, J=17.9, 5.6 Hz, 1H), 2.42-2.49 (m, 1H), 2.14-2.20 (m, 1H), 1.90-1.96 (m, 1H), 1.72-1.80 (m, 2H), 1.55 (s, 3H), 1.47-1.49 (m, 2H), 1.42 (s, 3H); LCMS (m/z)=209 (M+H)$^+$.

The product from the above reaction appears to be a single diastereomer—see *Journal of Organic Chemistry*, 71, 6630-6633; 2006, which is hereby incorporated by reference in its entirety, for a similar addition of TMS-N$_3$ to a tetrahydroindolizin-5(1H)-one system to give a single diastereomeric product.

Preparation of 7-amino-hexahydro-3,3-dimethylindolizin-5 (1H)-one

7-Azido-3,3-dimethylindolizin-5 (1H)-one (0.3 g, 1.5 mmol) is dissolved in EtOH (20 ml). The clear solution is transferred to a Parr hydrogenation flask and placed under nitrogen. 10% Pd-C (0.25 g) was added to the Parr flask under nitrogen. The mixture was then transferred to a Parr hydrogenation apparatus, evacuated and filled with hydrogen (×3). The mixture was hydrogenated at 30 psi (optionally topping-up hydrogen) until LC/MS and TLC indicated complete reaction to the amine. After complete reaction, the mixture was placed under nitrogen and filtered through a small pad of Celite. The filter cake was washed with MeOH (×3) and the filtrate was concentrated under vacuum to leave the 7-amino-hexahydro-3, 3-dimethylindolizin-5-(1H)-one in 89% yield (0.25 g).

$^1$H NMR (CDCl$_3$, 300 MHz) δ 3.75-3.92 (m, 1H), 3.50-3.54 (m, 1H), 2.54 (dd, J=16.9, 5.9 Hz, 1H), 2.13 (dd, J=17.6, 1.8 Hz, 1H), 1.87-1.95 (m, 2H), 1.67-1.76 (m, 2H), 1.56 (s, 3H), 1.44-1.53 (m, 2H), 1.42 (s, 3H); LCMS (m/z)=183 (M+H)$^+$.

Example 5

Synthesis of (R/R,S/S)-N-(2-chloro-5-fluoropyrimidin-4-yl)octahydroindolizin-7-amine and (R,S/S,R)—N-(2-chloro-5-fluoropyrimidin-4-yl)octahydroindolizin-7-amine

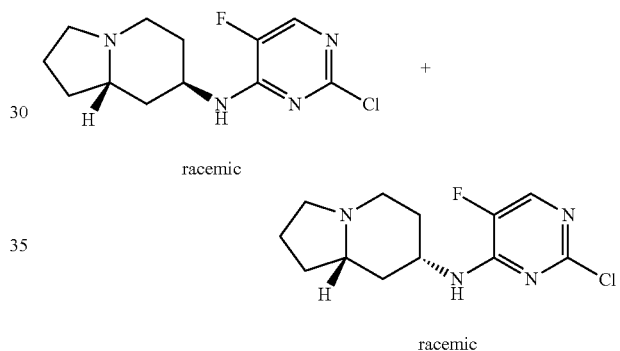

Preparation of (R/S)-octahydroindolizin-7-one

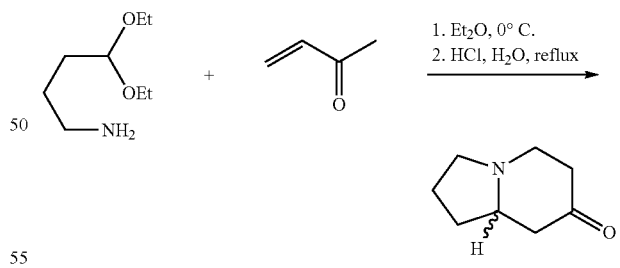

The compound was prepared according to *J. Chem. Soc., Perkin Trans.* 1 1986, 447-453, which is hereby incorporated by reference in its entirety.

A mixture of but-3-en-2-one (5.4 g, 75 mmol) was added dropwise over ca. 10 minutes to a solution of 4,4-diethoxybutan-1-amine (9.6 g, 60 mmol) in Et$_2$O (30 ml) at 0° C. under nitrogen. The mixture was stirred at 0° C. for a further 60 minutes then extracted with 2.5 M HCl (150 ml). The aqueous acid layer was then heated to reflux and stirred for 150 minutes. After allowing to cool to room temperature, the mixture was concentrated in vacuo to about one third of the original volume. The mixture was cooled to 0° C. and CH$_2$Cl$_2$ (200 ml) was added, followed by 3N NaOH until pH>10. The aqueous and organic layers were partitioned and the organic layer was washed with a K$_2$CO$_3$ solution (×1). The combined aqueous layers were extracted with CH$_2$Cl$_2$ (2×150 ml) and then the combined organic layers were dried (K$_2$CO$_3$), filtered and concentrated in vacuo. The residue was dry-loaded on to silica gel and purified by column chromatography on silica gel using CH$_2$Cl$_2$/MeOH (100:0 to 94:6 in increments of 2% MeOH) to give the desired product (2.0 g, 24%) as an oil.

$^1$H NMR (300 MHz; CDCl$_3$) δ 3.37-3.30 (m, 1H), 3.20-3.14 (m, 1H), 2.68-2.51 (m, 2H), 2.40-2.19 (m, 5H), 2.03-1.93 (m, 2H), 1.91-1.80 (m, 1H), 1.60-1.48 (m, 1H).

$^{13}$C NMR (75 MHz; CDCl$_3$) δ 209.3, 64.2, 53.3, 50.3, 47.4, 40.7, 31.5, 22.6.

Preparation of (R/S)-octahydroindolizin-7-one oxime

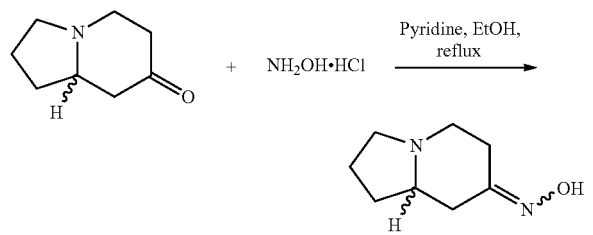

The compound was prepared according to *J. Chem. Soc., Perkin Trans.* 1 1986, 447-453, which is hereby incorporated by reference in its entirety.

A mixture of octahydroindolizin-7-one (1.8 g, 12.9 mmol) and hydroxylamine hydrochloride (0.8 g, 12.9 mmol) in EtOH (10 ml) and pyridine (10 ml) was heated to reflux and stirred for 90 minutes. After allowing to cool, the mixture was concentrated in vacuo to leave a crude solid (a bath temperature of 50° C. was used to remove solvent). The solid was triturated with cold (−18° C.) EtOH and filtered and the filter cake was washed with a further small portion of cold (−18° C.) EtOH. The solid was used directly in the next step and the yield was assumed quantitative=2.0 g. m/z=155.01 (M+H)$^+$; rt=0.90 min (HPLC protocol-1).

Preparation of (R/R,R/S,S/R,S/S)-octahydroindolizin-7-amine

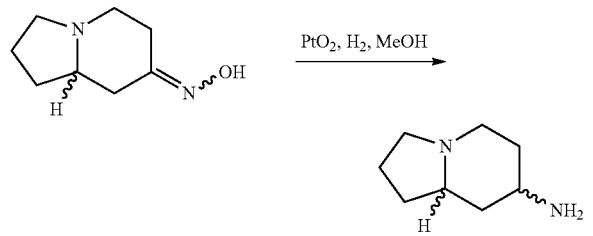

A mixture of octahydroindolizin-7-one oxime (2.0 g, 12.9 mmol) and platinum(IV) oxide (0.5 g) in AcOH (30 ml) was hydrogenated at 60 psi overnight. The mixture was filtered through Celite and the filter cake washed with EtOH (3×30 ml). The filtrate was concentrated in vacuo to give the product as an acetate salt. The yield was assumed to be quantitative=1.81 g of the free amine.

Synthesis of (R/R,S/S)-N-(2-chloro-5-fluoropyrimidin-4-yl)octahydroindolizin-7-amine and (R,S/S,R)-N-(2-chloro-5-fluoropyrimidin-4-yl)octahydroindolizin-7-amine

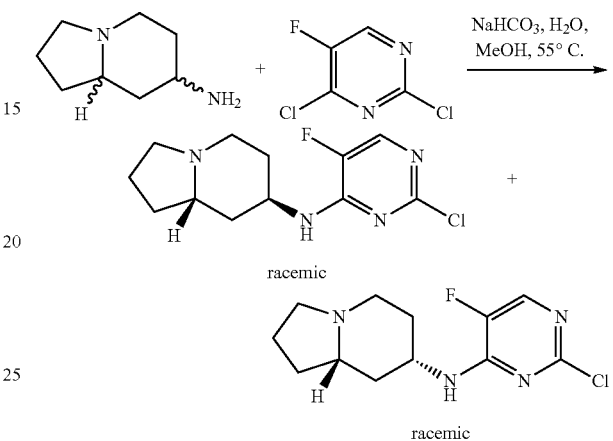

A mixture of 2,4-dichloro-5-fluoropyrimidine (3.45 g, 20.7 mmol), (R/R,R/S,S/R,S/S)-octahydroindolizin-7-amine (1.81 g, 12.9 mmol) and NaHCO$_3$ (2.71 g, 32.3 mmol) in MeOH (66 ml) and H$_2$O (22 ml) was heated at 55° C. and stirred for 5 hours. After cooling, the MeOH was removed in vacuo. CH$_2$Cl$_2$ (100 ml) and H$_2$O (100 ml) was added to the residue and the organic and aqueous layers were partitioned. The aqueous layer was extracted with CH$_2$Cl$_2$ (2×50 ml) and the combined organic layers were dried (MgSO$_4$), filtered and the solvent removed in vacuo to leave a crude oil. The crude residue was dry-loaded on to silica gel and purified by column chromatography on silica gel (ISCO Redisep Rf Gold column) using a 2M NH$_3$ in MeOH/CH$_2$Cl$_2$ gradient system to give a pure first-eluting diastereomer (small quantity), mixed fractions, a second-eluting pure diastereomer and mixed fractions.

Data for second-eluting pure diastereomer: $^1$H NMR (300 MHz; CDCl$_3$) δ 7.86 (t, J=2.6 Hz, 1H), 5.33 (br. d, J=7.4 Hz, 1H), 4.20-4.07 (m, 1H), 3.25-3.12 (m, 2H), 2.32-2.10 (m, 5H), 1.99-1.46 (m, 5H), 1.30 (q, J=11.5 Hz, 1H); $^{13}$C NMR (75 MHz; CDCl$_3$) δ 154.6 (d, J=4.4 Hz), 153.1 (d, J=12.0 Hz), 143.4 (d, J=254.8 Hz), 139.5 (d, J=20.1 Hz), 63.3, 53.4, 50.4, 48.4, 37.0, 31.6, 30.1, 21.5; $^{19}$F NMR (282 MHz; CDCl$_3$) δ −159.4; m/z=271.08 (M+H)$^+$ for $^{35}$Cl; rt=1.91 min (HPLC protocol-1).

The mixed fractions from the first column were combined and re-columned using the same silica gel and gradient system to give a pure first-eluting diastereomer, a pure second-eluting diastereomer and mixed fractions.

Data for pure first-eluting diastereomer from the above column: m/z=271.04 (M+H)$^+$ for $^{35}$Cl; rt=2.35 min (HPLC protocol-1).

Data for pure second-eluting diastereomer from the above column: m/z=269.05 (M−H)$^+$ for $^{35}$Cl; rt=1.97 min (HPLC protocol-1).

Example 6

Synthesis of (±)-2-chloro-4-(octahydro-5,5-dimethylindolizin-7-ylamino)pyrimidine-5-carboxamide

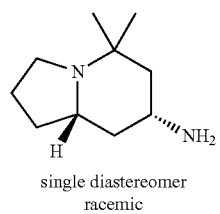

single diastereomer
racemic

+

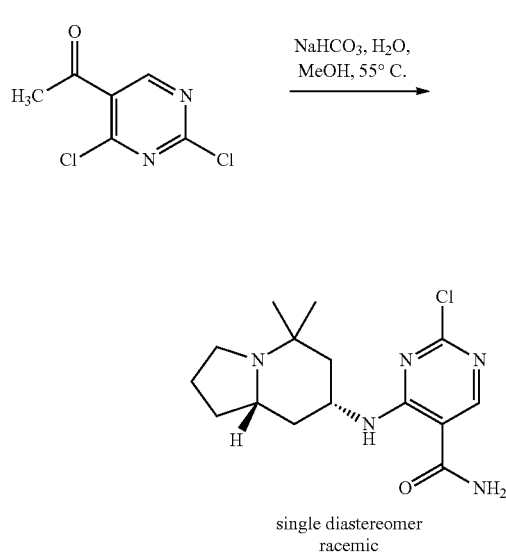

NaHCO₃, H₂O,
MeOH, 55° C.

single diastereomer
racemic

A mixture of (±)-octahydro-5,5-dimethylindolizin-7-amine (0.65 g, 3.9 mmol) in MeOH (10 ml) was added to a stirred solution of 2,4-dichloropyrimidine-5-carboxamide (0.75 g, 3.9 mmol; prepared according to the procedure set forth in US patent application publication US20110130415, page 41) in MeOH (30 ml) and H₂O (4 ml) at 0° C. under nitrogen. After complete addition, the mixture was slowly warmed to room temperature and stirred at room temperature overnight. The mixture was then concentrated in vacuo and the residue partitioned between EtOAc (150 ml) and 1N NaOH (100 ml). The aqueous layer was extracted with EtOAc (1×100 ml) and the combined organic extracts were dried (Na₂SO₄), filtered and the solvent removed in vacuo. The residue was dry-loaded on to basic alumina (Brockmann grade IV) and then purified by column chromatography on basic alumina (Brockmann grade IV) using CH₂Cl₂/MeOH (1:0 to 95:5) as eluent to give the product (550 mg).

Note: the product eluted very quickly from the basic alumina column, and a by-product also co-eluted with the desired compound. This by-product is believed to be (±)-2-methoxy-4-(octahydro-5,5-dimethylindolizin-7-ylamino)pyrimidine-5-carboxamide. However, the mixture (550 mg) was used directly in the next step without further purification.

Example 7

Synthesis of (±)-2-chloro-4-(octahydro-5,5-dimethylindolizin-7-ylamino)pyrimidine-5-carbonitrile

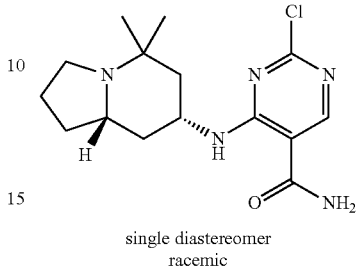

TFAA, Et₃N,
THF, -40° C.

single diastereomer
racemic

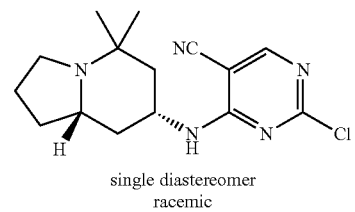

single diastereomer
racemic

Trifluoroacetic anhydride (460 µL, 3.24 mmol) was added dropwise over 5-10 minutes to a stirred mixture of (±)-2-chloro-4-(octahydro-5,5-dimethylindolizin-7-ylamino)pyrimidine-5-carboxamide (500 mg; contaminated with (±)-2-methoxy-4-(octahydro-5,5-dimethylindolizin-7-ylamino)pyrimidine-5-carboxamide) and Et₃N (970 µL, 7.0 mmol) in THF (15 ml) at −40° C. (internal temperature) under nitrogen. The mixture was stirred at −40 to −50° C. (internal temperature) for 30 minutes, then allowed to warm to −30° C. (internal temperature) and the mixture stirred for 15 minutes. TLC analysis indicated completion of the reaction, so the mixture was worked-up by pouring in to an ice-H₂O mixture (50 ml) and EtOAc (50 ml). The aqueous and organic layers were partitioned and the aqueous layer was extracted with EtOAc (1×50 ml). The combined organic extracts were dried (MgSO₄), filtered and the solvent removed in vacuo to leave a crude residue. The residue was dry-loaded on to basic alumina (Brockmann grade IV) and purified by column chromatography on basic alumina (Redisep 24 g basic alumina column) using CH₂Cl₂/MeOH (gradient from 1:0 to 93:7) as eluent to give the product (128 mg). LC/MS indicated the product to be of about 70% purity and it was used directly in the next step (the contaminant was N-(5-cyano-2-methoxypyrimidin-4-yl)-octahydro-5,5-dimethylindolizin-7-amine). m/z=306.13 (M+H)⁺ for ³⁵Cl; rt=2.64 min (HPLC protocol-1).

Also obtained from the column was a sample containing mostly N-(5-cyano-2-methoxypyrimidin-4-yl)-octahydro-5,5-dimethylindolizin-7-amine (100 mg). This was purified by high-performance liquid chromatography in order to confirm identity. m/z=302.17 (M+H)⁺; rt=2.87 min (HPLC protocol-1).

Example 8

Synthesis of 7-(2-Chloro-5-fluoropyrimidin-4-ylamino)-hexahydro-5,5-dimethylindolizin-3(5H)-one

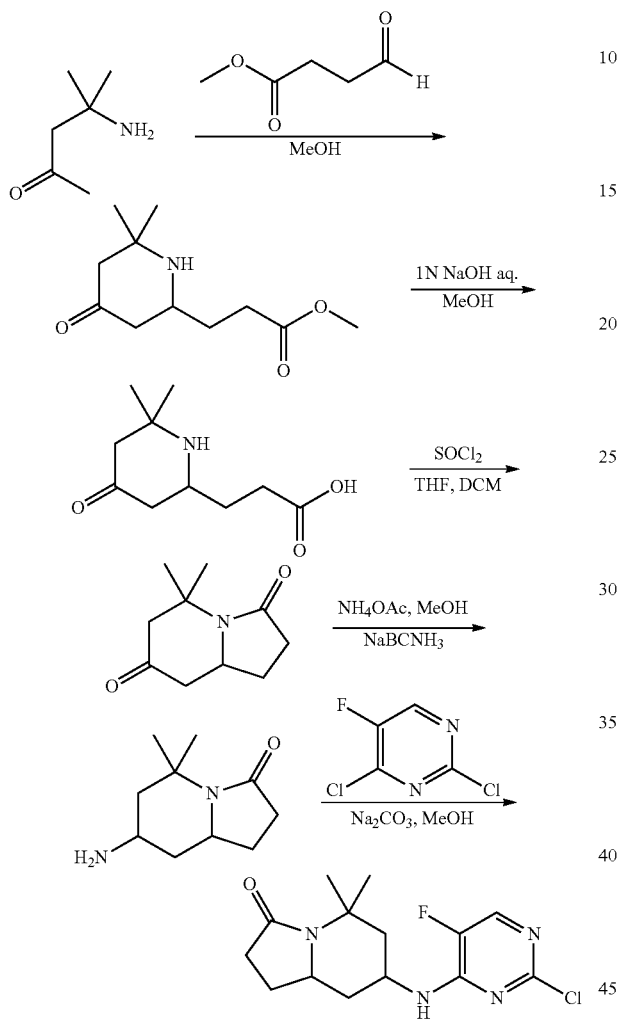

Preparation of Methyl 3-(6,6-dimethyl-4-oxopiperidin-2-yl)propanoate

Diacetoneamine hydrogen oxalate (4.25 g) and methyl 4-oxobutanoate (2 g) were suspended in methanol (20 ml). The reaction mixture were stirred at 100° C. for three hours and then at room temperature overnight. It was then evaporated and the residue was purified by Combiflash chromatography (2.0 M ammonia methanol in dichloromethane=0-30%) to give methyl 3-(6,6-dimethyl-4-oxopiperidin-2-yl)propanoate (1.35 g, 37%).

$^1$H NMR (300 MHz; CDCl3) δ 3.62 (s, 3H), 3.21-3.16 (m, 1H), 2.41-2.32 (m, 4H), 2.20 (dd, J=1.8, 13.8 Hz, 2H), 1.85 (p, J=6.6 Hz, 2H), 1.28 (s, 3H), 1.09 (s, 3H).

Preparation of Hexahydro-5,5-dimethylindolizine-3,7-dione

Methyl 3-(6,6-dimethyl-4-oxopiperidin-2-yl)propanoate (1.35 g) was dissolved in methanol (25 ml) and 1.0 N sodium hydroxide aqueous solution was added (7.6 ml, 1.2 eq.). The reaction mixture was stirred at room temperature overnight. It was then evaporated and pumped to dryness to give the acid.

The acid was dissolved in THF (20 ml) and dichloromethane (100 ml). To this solution, was added thionyl chloride (0.69 ml, 1.5 eq.) dropwise. It was then stirred at 40° C. for three hours and evaporated. The residue was purified by Combiflash chromatography (2.0 M ammonia methanol in dichloromethane=0-30%) to give hexahydro-5,5-dimethylindolizine-3,7-dione.

$^1$H NMR (300 MHz; d$_6$-DMSO) δ 3.24 (m, 1H), 2.59 (dd, J=3.6, 18.0 Hz, 1H), 2.34-2.10 (m, 5H), 1.54-1.47 (m, 2H), 1.41 (s, 3H), 1.32 (s, 3H).

Preparation of 7-(2-Chloro-5-fluoropyrimidin-4-ylamino)-hexahydro-5,5-dimethylindolizin-3(5H)-one Hexahydro-5,5-dimethylindolizine-3,7-dione (230 mg) and ammonium acetate (990 mg, 10 eq.) were dissolved in methanol (5 ml). To the reaction mixture, was added sodium cyanoborohydride (56 mg, 0.7 eq.). The reaction mixture was stirred at room temperature overnight. LC-MS showed the formation of the amine. The reaction mixture was quenched with 10 N. HCl aqueous solution to pH 2. Then it was stirred for two hours.

To the reaction mixture, was added sodium carbonate to pH 7. Then 2,4-dichloro-5-fluoropyrimidine (500 mg) was added. It was then stirred at room temperature for three days and evaporated. The residue was purified by Combiflash chromatography (2.0 M ammonia methanol in dichloromethane=0-30%) to give two isomers of 7-(2-chloro-5-fluoropyrimidin-4-ylamino)-hexahydro-5,5-dimethylindolizin-3(5H)-one (a: 55 mg; b. 110 mg).

Example 9

Synthesis of N-(2-Chloro-5-fluoropyrimidin-4-yl)-2,2-difluoro-5,5-dimethyloctahydroindolizin-7-amine

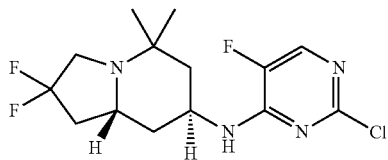

Diastereomer-1 (D-1)

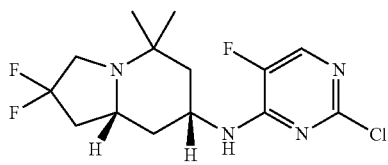

Diastereomer-2 (D-2)

Preparation of (S)-tert-butyl 4,4-difluoro-2-(hydroxymethyl)pyrrolidine-1-carboxylate

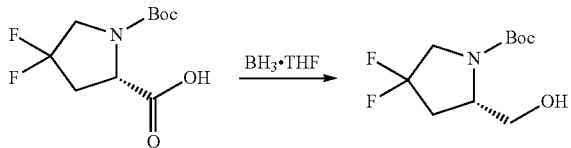 [SMILES: CC(C)(C)OC(=O)N1CC(F)(F)C[C@H]1C(=O)O ; CC(C)(C)OC(=O)N1CC(F)(F)C[C@H]1CO ; "BH3·THF"]

To a THF (30 ml) solution of (S)-1-(tert-butoxycarbonyl)-4,4-difluoropyrrolidine-2-carboxylic acid (3.77 g, 15 mmol) at 0° C., BH$_3$.THF solution (1.0 M in THF, 45 ml) was added dropwise over 20 minutes. The reaction mixture was allowed to warm to room temperature and stirring was continued for a total of 16 hours. Reaction went to completion as monitored by LC-MS. The reaction mixture was quenched by the addition of saturated aqueous solution of NaHCO$_3$ (60 ml) at room temperature and the stirring was continued at room temperature for 4 hours. Most THF was removed in vacuo and the mixture was extracted with EtOAc (~60 ml), two layers were separated, organic layer was washed with brine (~50 ml), repeat the extraction/wash cycle one more time. Organic layers were combined, dried (Na$_2$SO$_4$), filtered, solvent was removed in vacuo. Crude product was purified by silica gel chromatography (Hexane/EtOAc, gradient from 100:0 to 50:50). Compound (S)-tert-butyl 4,4-difluoro-2-(hydroxymethyl)pyrrolidine-1-carboxylate was obtained as a colorless oil: 2.6473 g (74% yield).

$^1$H NMR (300 MHz, CDCl$_3$) δ 4.18 (br s, 1H), 3.88-3.58 (m, 4H), 2.58-2.41 (m, 1H), 2.15 (br s, 1H), 1.59-1.33 (m, 9H, overlapped with water peak); LRMS (M+H–"Boc") m/z 137.96.

Preparation of (R)-tert-Butyl 2-(cyanomethyl)-4,4-difluoropyrrolidine-1-carboxylate

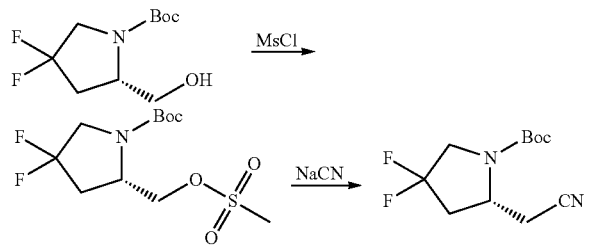

To a CH$_2$Cl$_2$ (22 ml) solution of (S)-tert-butyl 4,4-difluoro-2-(hydroxymethyl)pyrrolidine-1-carboxylate (2.65 g, 11.2 mmol) and Et$_3$N (2.3 ml, 16.8 mmol), at 0° C., methylsulfonyl chloride (0.95 ml, 12.3 mmol) was added dropwise over ~2 minutes, ice bath was removed after 15 minutes, and stirring was continued at room temperature for another 30 minutes. Reaction went to completion as monitored by LC-MS. The reaction mixture was cooled to 0° C. and was quenched by addition of saturated aqueous solution of NaHCO$_3$ (~30 ml), stirring was continued at 0° C. for 5 minutes and at room temperature for 15 minutes. Two layers were separated, aqueous layer was extracted with CH$_2$Cl$_2$ (~30 ml). Organic layers were combined, washed with brine (~25 ml), dried (Na$_2$SO$_4$), filtered, solvent was removed in vacuo. Compound ((S)-1-(tert-butoxycarbonyl)-4,4-difluoropyrrolidin-2-yl)methyl methanesulfonate was obtained as a very light yellow oil: 3.40 g (96% crude yield).

$^1$H NMR (300 MHz, CDCl$_3$) δ 4.42-4.23 (m, 3H), 3.84 (br s, 1H), 3.64 (dddd, J=12.6, 12.6, 12.6, 0.9 Hz, 1H), 3.04 (s, 3H), 2.59-2.43 (m, 2H), 1.49 (s, 9H); LRMS (M+H–"Boc") m/z 215.97. Crude product was used directly in next reaction without further purification.

A DMSO (40 ml) solution of ((S)-1-(tert-butoxycarbonyl)-4,4-difluoropyrrolidin-2-yl)methyl methanesulfonate and NaCN (1.59 g, 3.24 mmol) was stirred at 45° C. for 4 hours and at 50° C. for 2 days, the progress of the reaction was monitored by LC-MS. After cooling to room temperature, the reaction was quenched by the addition of water (~60 ml). Reaction mixture was extracted with EtOAc (~40 ml), two layers were separated, organic layer was washed with brine (~25 ml), the extraction and wash sequence was repeated for two more times. Organic layers were combined, dried (Na$_2$SO$_4$), filtered, solvent was removed in vacuo. Product was purified by silica gel chromatography (Hexane/EtOAc, gradient from 100:0 to 80:20). Compound (R)-tert-butyl 2-(cyanomethyl)-4,4-difluoropyrrolidine-1-carboxylate was obtained as a colorless oil: 2.10 g (76% yield over 2 steps).

$^1$H NMR (300 MHz, CDCl$_3$) δ 4.31-4.22 (m, 1H), 3.86-3.63 (m, 2H), 2.88-2.56 (m, 3H), 2.49-2.34 (m, 1H), 1.48 (s, 9H); LRMS (M+H–"Boc") m/z 146.94.

Preparation of (R)-tert-Butyl 2-((N-methoxy-N-methylcarbamoyl)methyl)-4,4-difluoropyrrolidine-1-carboxylate

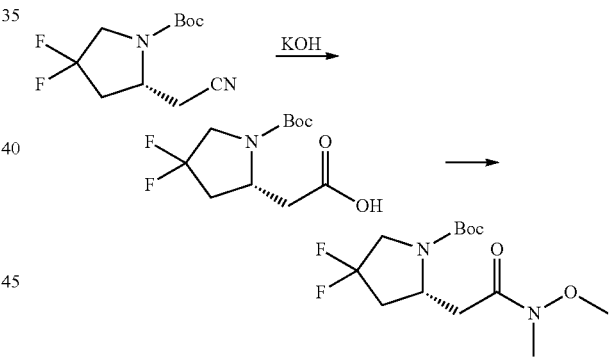

A MeOH (20 ml) solution of (R)-tert-butyl 2-(cyanomethyl)-4,4-difluoropyrrolidine-1-carboxylate (2.10 g, 8.5 mmol) and 0.5 N NaOH aqueous solution (34 ml, 17.0 mmol) was heated at 70° C. for 6 days until desired product became major, as monitored by LC-MS. Significant amount of de-Boc product was also observed. After cooling to room temperature, MeOH was removed in vacuo, aqueous mixture was extracted with Et$_2$O (~30 ml) which was discarded (note: mainly carboxamide intermediate). Aqueous layer was acidified with 6N HCl (aq.) until pH≤2 and was extracted with EtOAc (~25 ml×3). Organic layers were combined, dried (Na$_2$SO$_4$), filtered, solvent was removed in vacuo. A light brown oil was obtained: 1.62 g; LRMS (M+H–"Boc") m/z 166.89.

Additional product was recovered from aqueous layer by adding Boc group onto de-Boc by-product as follows: aqueous layer was basified to pH 8 by the addition of solid NaHCO$_3$, and was concentrated to ~15 ml in volume; to this aqueous mixture, THF (20 ml) was added, followed by Boc₂O (1.2 g, 5 mmol). The mixture was stirred at room temperature for 1 hour, LC-MS indicated the complete formation of the product. The reaction mixture was worked-up as above described and 0.4 g of product was obtained.

To a CH₂Cl₂ (10 ml) solution of 2-((R)-1-(tert-butoxycarbonyl)-4,4-difluoropyrrolidin-2-yl)acetic acid and hydroxylamine hydrogen chloride (713.8 mg, 7.32 mmol), EDCl.HCl (1.64 g, 8.54 mmol) and NMM (1.5 ml, 13.4 mmol) were added, the reaction mixture was stirred at room temperature for 15 hours. The reaction went to completion monitored by LC-MS and was quenched by addition of saturated aqueous NaHCO₃ solution (~25 ml). Two layers were separated, aqueous layer was extracted with CH₂Cl₂ (~20 ml). Organic layers were combined, dried (Na₂SO₄), filtered, solvent was removed in vacuo. Crude product was purified by silica gel chromatography (Hexane/EtOAc, gradient from 100:0 to 70:30). Compound (R)-tert-butyl 2-((N-methoxy-N-methylcarbamoyl)methyl)-4,4-difluoropyrrolidine-1-carboxylate was obtained as a light yellow oil: 1.20 g; additional product was obtained from recovered carboxylic acid: 0.2 g (53% combined overall yield over 2 steps).

$^1$H NMR (300 MHz, CDCl₃) δ 4.46-4.40 (m, 1H), 3.80-3.58 (m, 1H, overlapped), 3.69 (s, 3H, overlapped), 3.17 (s, 3H), 3.10-2.93 (m, 2H), 2.73-2.53 (m, 2H), 2.38-2.26 (m, 1H), 1.47 (s, 9H); LRMS (M+H−"Boc") m/z 208.98.

Preparation of (R)-tert-Butyl 4,4-difluoro-2-(4-methyl-2-oxopent-3-enyl)pyrrolidine-1-carboxylate

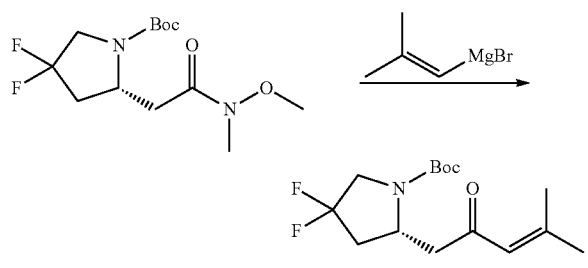

To a THF (23 ml) solution of (R)-tert-butyl 2-((N-methoxy-N-methylcarbamoyl)methyl)-4,4-difluoropyrrolidine-1-carboxylate (1.4 g, 4.54 mmol) over ice bath, 2-methyl-1-propenylmagnesium bromide solution (0.5 M in THF, 45 ml, 22.7 mmol) was added dropwise over 1 hour. Remove ice bath, stirring was continued for another 3 hours. The reaction was quenched with 1N HCl (aq., 30 ml) at 0° C., and was stirred at room temperature for 30 minutes. Two layers were separated, aqueous layer was extracted with EtOAc (25 ml×2), organic layers were combined, dried (Na₂SO₄), filtered, solvent was removed in vacuo. Product was purified by silica gel chromatography (Hexane/EtOAc, linear gradient from 100:0 to 80:20). Compound (R)-tert-butyl 4,4-difluoro-2-(4-methyl-2-oxopent-3-enyl)pyrrolidine-1-carboxylate was obtained as a light yellow oil: 1.10 g (79.5% yield).

$^1$H NMR (300 MHz, CDCl₃) δ 6.04 (s, 1H), 4.41-4.35 (m, 1H), 3.75-3.58 (m, 2H), 2.69-2.51 (m, 2H), 2.27-2.14 (m, 1H), 2.14 (s, 3H), 1.89 (s, 3H), 1.74 (dt, J=19.4, 10.4 Hz, 1H), 1.46 (s, 9H); LRMS (M+H−"Boc") m/z 204.07.

Preparation of (R)-2,2-Difluoro-hexahydro-5,5-dimethylindolizin-7(1H)-one

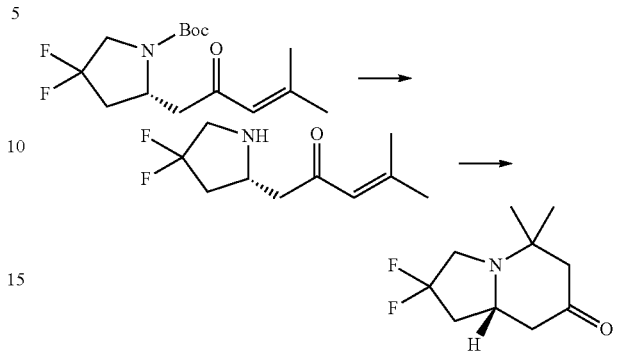

A HCO₂H (20 ml) solution of (R)-tert-butyl 4,4-difluoro-2-(4-methyl-2-oxopent-3-enyl)pyrrolidine-1-carboxylate (1.10 g, 3.6 mmol) was stirred at room temperature for 6 hours until only trace amount of SM was detected by LC-MS. Solvent was removed in vacuo with bath temperature ≤23° C. Compound 1-((R)-4,4-difluoropyrrolidin-2-yl)-4-methylpent-3-en-2-one was obtained as a light brown oil and was used directly in next reaction.

$^1$H NMR (300 MHz, CDCl₃) δ 8.08 (s, >1H, HCO₂H), 7.39 (br s, >2H, H⁺), 6.06-6.05 (m, 1H), 4.14-4.04 (m, 1H), 3.68 (dd, J=24.5, 13.2 Hz, 1H), 3.54 (td, J=13.9, 10.4 Hz, 1H), 3.09 (dd, J=18.2, 7.4 Hz, 1H), 2.91 (dd, J=18.2, 5.2 Hz, 1H), 2.68-2.55 (m, 1H), 2.42-2.23 (m, 1H), 2.16 (d, J=1.0 Hz, 3H), 1.93 (d, J=1.0 Hz, 3H); LRMS (M+H) m/z 204.08.

A MeOH (350 ml) solution of 1-((R)-4,4-difluoropyrrolidin-2-yl)-4-methylpent-3-en-2-one and K₂CO₃ (2.5 g, 18 mmol) was stirred at 40° C. for 15 hours, the reaction went to completion as monitored by LC-MS. Solvent was removed in vacuo, remaining material was suspended in CH₂Cl₂, solid was filtered off, filtrate was collected and solvent was removed in vacuo. Product was purified by silica gel chromatography (Hexane/EtOAc, linear gradient from 100:0 to 80:20). Compound (R)-2,2-difluoro-hexahydro-5,5-dimethylindolizin-7(1H)-one was obtained as a light yellow solid: 637.4 mg (69% yield over 3 steps).

$^1$H NMR (300 MHz, CDCl₃) δ 3.39 (ddd, J=14.2, 10.8, 7.6 Hz, 1H), 3.16-3.06 (m, 1H), 2.87 (ddd, J=19.1, 14.5, 10.8 Hz, 1H), 2.51-2.39 (m, 3H), 2.32 (dd, J=22.4, 11.0 Hz, 1H), 2.20 (dd, J=13.6, 2.1 Hz, 1H), 2.15-1.96 (m, 1H), 1.23 (s, 3H), 0.95 (s, 3H); LRMS (M+H) m/z 204.33.

Preparation of (8aR)-2,2-Difluoro-octahydro-5,5-dimethylindolizin-7-amine

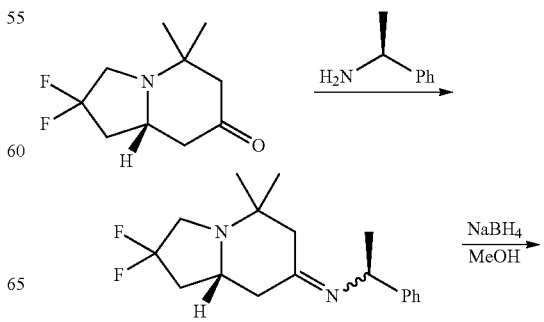

-continued

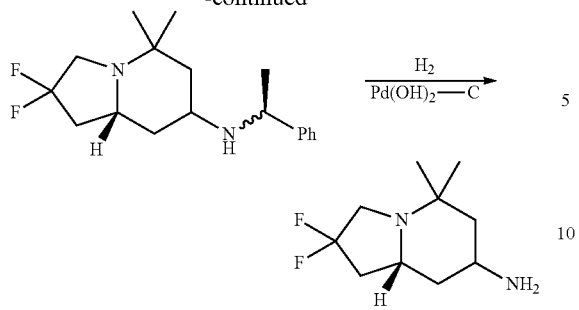

A toluene (12 ml) solution of (R)-2,2-difluoro-hexahydro-5,5-dimethylindolizin-7(1H)-one (487.8 mg, 2.4 mmol) and (S)-1-phenylethylamine (306 μL, 2.4 mmol) was heated under reflux in a flask equipped with a Dean-Stark distillation receiver. After 22 hours, most solvent was distilled off through Dean-Stark distillation receiver, and remaining solvent was removed in vacuo. Compound (1S)-N-((R)-2,2-difluoro-hexahydro-5,5-dimethylindolizin-7(1H)-ylidene)-1-phenylethanamine was obtained as a brown oil and was used directly in next reaction.

Over an ice bath, to a MeOH (10 ml) solution of (1S)-N-((R)-2,2-difluoro-hexahydro-5,5-dimethylindolizin-7(1H)-ylidene)-1-phenylethanamine, NaBH$_4$ (136 mg, 3.6 mmol) was added. After 30 minutes, reaction went to completion monitored by LC-MS. The reaction was quenched by the addition of saturated aqueous NaHCO$_3$ (10 ml), and most MeOH was removed in vacuo. More water (~10 ml) was added and aqueous solution was extracted with EtOAc (15 ml×3). Organic layers were combined, dried (Na$_2$SO$_4$), filtered, solvent was removed in vacuo. A light brown oil was obtained (690 mg: LRMS (M+H) m/z 309.22) and was dissolved in MeOH (5 ml). This MeOH solution was cooled with ice bath, and concentrated HCl aqueous solution (0.3 ml) was added and mixed well. Volatiles was removed in vacuo and provided a brownish-green oil: 869 mg as HCl salt and was used directly in next reaction.

A MeOH (20 ml) solution of (8aR)-2,2-difluoro-octahydro-5,5-dimethyl-N-((S)-1-phenylethyl)indolizin-7-amine hydrogen chloride and Pd(OH)$_2$—C (20% on activated carbon, 50% wet, 0.2 g) was hydrogenated in a Parr flask under 45 psi of hydrogen. Additional Pd(OH)$_2$—C was added (~0.2 g) was added at 16 hours and 24 hours, and the reaction went to completion at 39 hours monitored by LC-MS. Solid was removed by filtration through a short Celite column, washing with MeOH. Filtrate was collected, solvent was removed in vacuo. Compound (8aR)-2,2-difluoro-octahydro-5,5-dimethylindolizin-7-amine hydrogen chloride was obtained as an off-white solid and was used directly in next reaction: 0.56 g; LRMS] (M+H) m/z 204.99.

Preparation of N-(2-Chloro-5-fluoropyrimidin-4-yl)-2,2-difluoro-5,5-dimethyloctahydroindolizin-7-amine

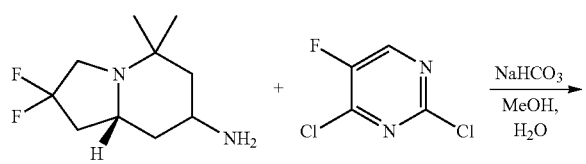

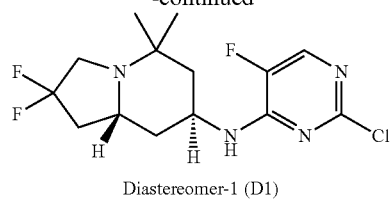

Diastereomer-1 (D1)

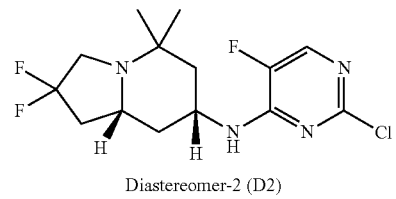

Diastereomer-2 (D2)

To a MeOH—H$_2$O (4:1, 10 ml) solution of (8aR)-2,2-difluoro-octahydro-5,5-dimethylindolizin-7-amine hydrogen chloride (crude product from above reaction, ~2.4 mmol) and 5-fluoro-2,4-dicholopyrimidine (480.9 mg, 2.88 mmol) was stirred at 30° C. for 25 hours until only trace amount of amine starting material was detected by LC-MS. MeOH was removed in vacuo. Additional H$_2$O (~10 ml) was added and the mixture was extracted with EtOAc (10 ml×3). Organic layers were combined, dried (Na$_2$SO$_4$), filtered, solvent was removed in vacuo. Two sets of diastereomers were observed with ratio of 3.1:1 (retention time of 5.6 min and 6.7 min under analytical HPLC conditions used: C18 column, solvents H$_2$O with 0.05% HCOOH and Acetonitrile with 0.05% HCOOH, a linear gradient from 90:10 to 0:100 over 9 minutes with a flow rate of 1.2 ml/min). Some level of diastereomer separation was achieved by prep-TLC (CH$_2$Cl$_2$:7N NH$_3$ in MeOH=97:3) and silica gel chromatography (CH$_2$Cl$_2$/2N NH$_3$ in MeOH, linear gradient from 100:0 to 95:5), pure Diastereomer 1 (7S,8aR)-N-(2-chloro-5-fluoropyrimidin-4-yl)-2,2-difluoro-octahydro-5,5-dimethylindolizin-7-amine was obtained as an off-white solid: ~300 mg; $[\alpha]_D^{20}$ −59.4, c=0.96 in MeOH.

$^1$H NMR (300 MHz, CDCl$_3$) δ 7.90 (d, J=2.7 Hz, 1H), 5.30 (br s, 1H), 4.48-4.36 (m, 1H), 3.35 (ddd, J=13.8, 10.7, 7.4 Hz, 1H), 3.00-2.90 (m, 1H), 2.82 (ddd, J=19.5, 15.1, 10.7 Hz, 1H), 2.43-2.29 (m, 1H), 2.10 (ddd, J=13.7, 4.5, 2.4 Hz, 1H), 2.02-1.77 (m, 3H), 1.66 (ddd, J=13.8, 11.8, 4.3 Hz, 1H), 1.15 (s, 3H), 1.12 (s, 3H); LRMS] (M+H) m/z 335.13.

Diastereomer 2 (7R,8aR)-N-(2-chloro-5-fluoropyrimidin-4-yl)-2,2-difluoro-octahydro-5,5-dimethylindolizin-7-amine was obtained as an off-white solid: 100 mg; $^1$H NMR (300 MHz, CDCl$_3$) δ 7.88 (d, J=2.8 Hz, 1H), 4.93 (br d, J=8.0 Hz, 1H), 4.31-4.18 (m, 1H), 3.30 (ddd, J=14.4, 10.7, 6.6 Hz, 1H), 2.98-2.89 (m, 1H), 2.77 (ddd, J=19.2, 15.3, 10.7 Hz, 1H), 2.43-2.27 (m, 2H), 2.05-1.82 (m, 2H), 1.42 (dd, J=12.2, 12.2 Hz, 1H), 1.22-1.14 (m, 1H, overlapped), 1.16 (s, 3H, overlapped), 1.08 (s, 3H); LRMS (M+H) m/z 335.13.

Relative stereochemistry of Diastereomer-1 and Diastereomer-2 was assigned by using 1D-NOE technique after the assignment of relevant protons via COSY experiment: for Diastereomer-2, positive NOE was observed between H7 and H8a, H7 and CH$_3$ which was absent in Diastereomer-1.

Example 10

Synthesis of N-(2-Chloro-5-fluoropyrimidin-4-yl)-octahydro-5,5,8-trimethylindolizin-7-amine

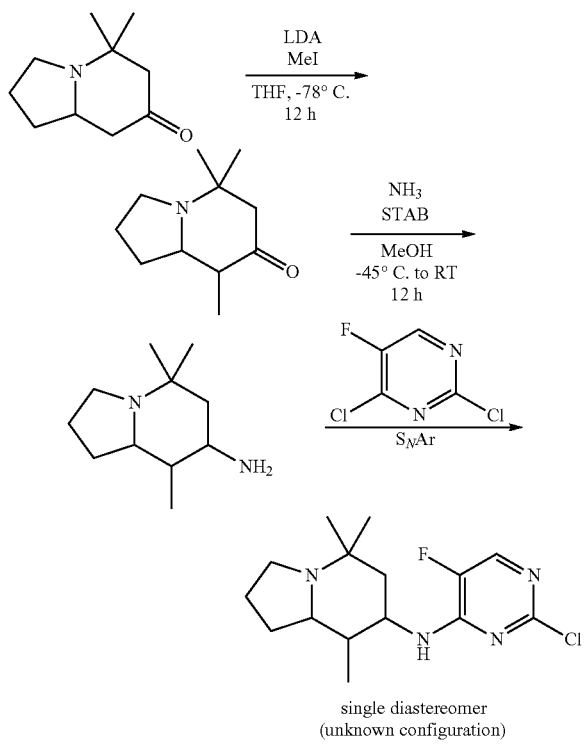

single diastereomer
(unknown configuration)

Preparation of Hexahydro-5,5,8-trimethylindolizin-7(1H)-one

Hexahydro-5,5-dimethylindolizin-7(1H)-one (racemic) (1.41 g, 8.43 mmol) was dissolved in dry THF (50 ml); the flask was flushed with nitrogen and cooled to −78° C. LDA (5.9 ml, 11.8 mmol) was added via syringe and stirred for 30 minutes. Subsequently, neat methyl iodide (1.30 ml, 21.1 mmol) was added via syringe. The clear, pale yellow solution was stirred overnight and allowed to warm to room temperature. The reaction was then quenched with a saturated $NH_4Cl$ solution and extracted with ethyl acetate (3×40 ml). The organic phases were passed through a plug of $MgSO_4$ and solvents were evaporated in vacuo. The crude product (849 mg) was obtained in form of a yellow-brown oil and used without further purification in the next step.

Preparation of Octahydro-5,5,8-trimethylindolizin-7-amine

The crude product from the above reaction was dissolved in a 7M methanolic $NH_3$ (20 ml) solution and stirred for 6 hours at room temperature. $NaBH_4$ (849 mg, 12.6 mmol) was suspended in dry THF in a separate flask and cooled to −45° C. using a dry-ice/MeCN bath. The solution containing the imine was then transferred by cannulation into the flask with the reducing agent. The reaction mixture was stirred for 1 hour at −45° C. and then allowed to warm to room temperature overnight. Water (1 ml) was added to quench remaining hydride then solvents were removed in vacuo. The reaction mixture was passed through a plug of $MgSO_4$ to remove water and salts. After evaporation of solvents the remaining crude product (829 mg) was used without further purification in the next reaction.

Preparation of N-(2-Chloro-5-fluoropyrimidin-4-yl)-octahydro-5,5,8-trimethylindolizin-7-amine The product from the above reaction (829 mg, 4.55 mmol) was combined with 2,4-dichloro-5-fluoro-pyrimidine (911 mg, 5.45 mmol) and $NaHCO_3$ (457 mg, 5.45 mmol). A 4:1 mixture of $MeOH:H_2O$ (50 ml) was added and the ensuing suspension was stirred for 2 days at room temperature. Analysis by HPLC showed that two diastereomers in a ratio of 3:1 had formed. Silica gel was added to the reaction mixture and solvents were evaporated in vacuo. The resulting solid was loaded onto a column and further purified by flash chromatography eluting with DCM/MeOH—$NH_3$ (2M) (gradient 0->5%). Combining the clean product fractions yielded 210 mg of the diastereomerically enriched mono-$S_NAr$ product. MS (ES) 313 (M+H), 311 (M−H).

Example 11

Synthesis of N-(2-Chloro-5-fluoropyrimidin-4-yl)-octahydro-3,3-dimethylindolizin-7(1H)-amine

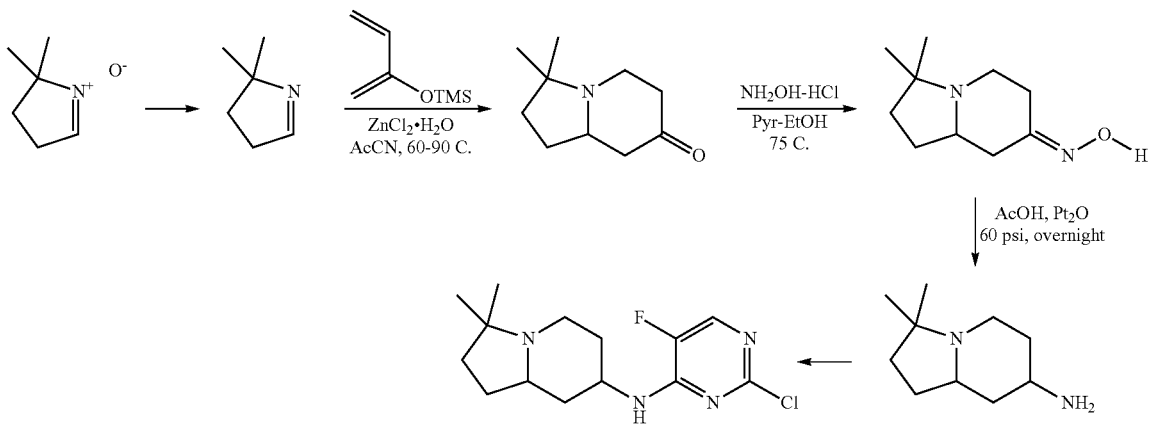

Hexahydro-3,3-Dimethylindolizin-7(1H)-One

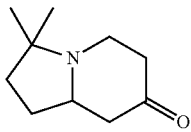

3,4-Dihydro-2,2-diemthyl-2H-pyrrole (900 mg, 9.3 mmol) was added to acetonitrile (90 ml) in a 250 ml round bottom flask, fitted with water condenser. ZnCl$_2$ (0.5M) in THF (23 ml, 11.6 mmol) was added to the solution and warmed to 60° C. 2-(Trimethylsiloxy)-1,3-butadiene (2.6 g, mmol, 18.4 mmol) was added to the mixture and heated at 90° C. overnight. The solution was cooled to room temperature and diluted with dichloromethane (90 ml) and 1N HCl (90 ml). The two layers were separated, the aqueous layer was basified with NH$_3$ (28%) in H$_2$O, and extracted with dichloromethane. The organic layer was washed with brine and dried with Na$_2$SO$_4$. Solid was removed by filtration and mother liquor was concentrated in vacuo to give 250 mg brown color oil. This oil was further purified by column chromatography (100% ethyl acetate to 95% ethyl acetate: 5% methanol) to give a light yellow oil (170 mg, 11% yield).

$^1$H NMR (300 MHz; d$_6$-DMSO) δ 3.05-2.99 (m, 1H), 2.69-2.63 (m, 1H), 2.44-2.11 (m, 5H), 1.87-1.78 (m, 1H), 1.69-1.54 (m, 2H), 1.41-1.31 (m, 1H), 1.13 (s, 3H), 0.87 (s, 3H); $^{13}$C NMR (300 MHz; d$_6$-DMSO) δ 209.7, 60.44, 48.69, 42.63, 41.17, 39.67, 38.60, 28.83, 28.10, 19.87; m/z=168.08 (M+H)$^+$.

Hexahydro-3,3-Dimethylindolizin-7(1H)-Ketoxime

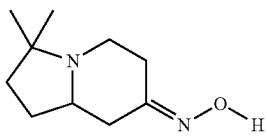

Hexahydro-3,3-dimethylindolizin-7(1H)-one (825 mg, 4.9 mmol) was added to a mixture of pyridine (8 ml) and ethanol (8 ml). Hydroxylamine-HCl salt (412 mg, 5.9 mmol) was added to the solution and the mixture was heated at 75° C. over weekend. The mixture was cooled to room temperature and concentrated under reduced pressure. N-heptane (20 ml) was added to the residue and concentrated in vacuo, this was repeated twice to remove most of the pyridine. Ethanol (10 ml) was added to the residue to form a milky mixture, this was sonicated, filtered and the white color solid collected was dried under reduced pressure to give the product (613 mg, 68% yield).

$^1$H NMR (300 MHz; d$_6$-DMSO) δ 10.85 (s, 1H), 3.46-3.42 (m, 1H), 3.35-3.31 (m, 1H), 2.88-2.78 (m, 2H), 2.67-2.61 (m, 1H), 2.44-2.35 (m, 2H), 2.17-2.1 (m, 1H), 1.99-1.85 (m, 2H), 1.8-1.7 (m, 1H), 1.51 (s, 3H), 1.16 (s, 3H); m/z=184.04 (M+H)$^+$.

Octahydro-3,3-Dimethylindolizin-7(1H)-Amine

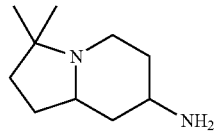

Hexahydro-3,3-diemthylindolizin-7(1H)-ketoxime (613 mg, 3.4 mmol) was added to acetic acid (30 ml) and followed by Pt$_2$O (76 mg) and was shook under 60psi of H$_2$ overnight. Addition 34 mg of Pt$_2$O was added to ensure the completion of the reaction. Methanol (30 ml) was added to the mixture and the catalyst was filtered off through a bed of Celite. The mother liquor was concentrated in vacuo to give a dark brown oil. Ethyl acetate (50 ml) was added to the oil and it was passed through a bed of Celite to remove the residual catalyst. The mother liquor was concentrated in vacuo to give 720 mg of product as an acetate salt and was used for the next step without further purification.

$^1$H NMR (300 MHz; d$_6$-DMSO) δ 2.70-2.67 (m, 1H), 2.34-2.25 (m, 1H), 2.05-1.98 (m, 1H), 1.82-1.66 (m, 2H), 1.53-1.45 (m, 3H), 1.22-1.1 (m, 2H), 1.02 (s, 3H), 0.81 (s, 3H), m/z=169.09 (M+H)$^+$.

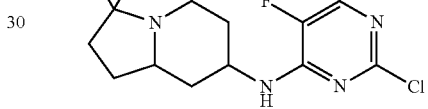

$^1$H NMR (300 MHz; d$_6$-DMSO) δ 8.19 (s, 1H), 8.07 (d, J=7.57 Hz, 1H), 7.68 (bd, J=5.4 Hz, 1H), 4.14 (s, 1H), 2.75-2.72 (m, 1H), 2.61-2.57 (m, 1H), 2.02-1.97 (m, 1H), 1.87-1.82 (m, 1H), 1.71-1.66 (m, 2H), 1.53-1.48 (m, 2H), 1.43-1.33 (m, 1H), 1.22-1.17 (m, 1H), 1.06 (s, 3H), 0.88 (s, 3H); m/z=299.09 (M+H)$^+$; m/z=297.09 (M−H)$^+$.

Example 12

Synthesis of N2-(4,4-dimethyl-4H-benzo[b]tetrazolo[1,5-d][1,4]oxazin-8-yl)-5-fluoro-N4-(octahydro-5,5-dimethylindolizin-7-amine)pyrimidine-2,4-diamine (Compounds 1-4)

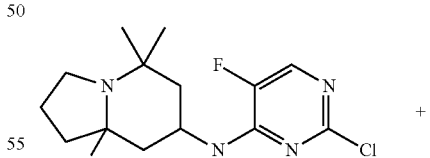

Mixture of both diastereomers (D1:D2 = 1:3)
Each diastereomer is a mixture of two enantiomes

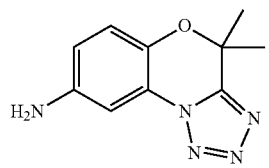

iPrOH, 4N HCl
in dioxane, 100° C.

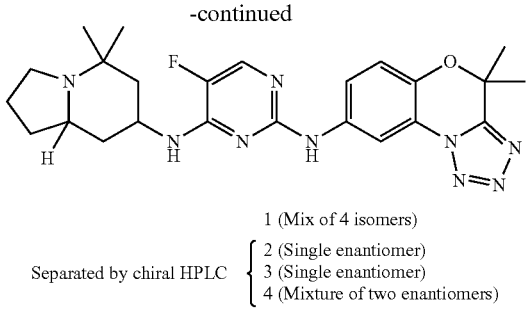

1 (Mix of 4 isomers)

Separated by chiral HPLC {
2 (Single enantiomer)
3 (Single enantiomer)
4 (Mixture of two enantiomers)
}

Compound 1 is a mixture of four isomers. Compound 2 is a single enantiomer separated by chiral HPLC. Compound 3 is a single enantiomer separated by chiral HPLC. Compound 4 is a mixture of two enantiomers (no separation).

The preparation of Compound 1, Compound 2, Compound 3, and Compound 4 is illustrated in accompanying scheme. In the second SNAr reaction the diastereomeric mixture (D1:D2=1:3) of (RS, SR, RR, SS)-N-(2-chloro-5-fluoropyrimidin-4-yl)-octahydro-5, 5-dimethylindolizin-7-amine was used and chiral HPLC was performed on the final product. Absolute stereochemistry of the individual isomers was not established in this series.

A solution of (R/S, S/R, R/R, S/S)-N-(2-chloro-5-fluoro-pyrimidin-4-yl)-octahydro-5, 5-dimethylindolizin-7-amine (0.12 g, 0.4 mmol, mixture of both diastereomers 1:3) in 3 ml of iPrOH, 4,4-dimethyl-4H-benzo[b]tetrazolo[1,5-d][1,4]oxazin-8-amine (0.19 g, 0.5 mmol; prepared according to WO2010/083207 pages 73-74, which is hereby incorporated by reference in its entirety) and 4N HCl in dioxane (0.1 ml) were added. The reaction mixture was heated to 100° C. in a sealed vial for 4 hours. LCMS analysis of the crude reaction mixture indicated the completion of the reaction. The crude product was purified by column chromatography to give 0.18 g (95% yield) of the product as a mixture of four stereoisomers. Two enantiomers (Compounds 2 and 3) were obtained as single enantiomers after chiral HPLC purification. Compound 4 was obtained as a pure diastereomer (mixture of two enantiomers). Absolute stereochemistry of individual isomers was not determined.

Compound 2: (Single Enantiomer)

$^1$H NMR (DMSO d$_6$, 300 MHz) δ: 9.40 (s, 1H), 8.43 (s, 1H), 7.92 (d, J=8.9 Hz, 1H), 7.55-7.63 (m, 2H), 7.19 (d, J=8.9 Hz, 1H), 4.38 (br. m, 1H), 3.08 (m, 1H), 2.18-2.30 (m, 2H), 1.92-1.98 (m, 1H), 1.80-1.90 (m, 3H), 1.74 (s, 6H), 1.38-1.70 (m, 4H), 1.20 (s, 3H), 1.32 (s, 3H); LCMS (m/z): 480 (MH$^+$). Chiral HPLC Pk1 RT=14.91 min. (see protocol-5 in general methods).

Compound 3: (Single Enantiomer)

$^1$H NMR (DMSO d$_6$, 300 MHz) δ: 9.40 (s, 1H), 8.43 (s, 1H), 7.92 (d, J=8.9 Hz, 1H), 7.55-7.63 (m, 2H), 7.19 (d, J=8.9 Hz, 1H), 4.38 (br. m, 1H), 3.08 (m, 1H), 2.18-2.30 (m, 2H), 1.92-1.98 (m, 1H), 1.80-1.90 (m, 3H), 1.74 (s, 6H), 1.38-1.70 (m, 4H), 1.20 (s, 3H), 1.32 (s, 3H); LCMS (m/z): 480 (MH$^+$) (see protocol-1 in general methods). Chiral HPLC Pk1 RT=17.64 min. (see protocol-4 in general methods)

Compound 4: (Mixture of Two Enantiomers)

$^1$H NMR (DMSO d$_6$, 300 MHz) δ: 9.51 (s, 1H), 8.72 (s, 1H), 7.99 (d, J=8.7 Hz, 1H), 7.50-7.65 (m, 2H), 7.15 (d, J=8.7 Hz, 1H), 4.35 (br. s, 1H), 3.18 (m, 1H), 1.92-2.35 (m, 6H), 1.75 (s, 3H), 1.72 (s, 3H), 1.50-1.68 (m, 4H), 1.37 (s, 3H), 1.28 (s, 3H); LCMS (m/z): 480 (MH$^+$) (see protocol-1 in general methods). Chiral HPLC Pk1 RT=19.19 min. (see protocol-4 in general methods).

Example 13

Synthesis of (R/S, S/R, R/R, S/S)-N$^2$-(4-(1-isopropylpiperidin-4-yloxy)-3-(difluoromethoxy)phenyl)-5-fluoro-N$^4$-(octahydro-5,5-dimethylindolizin-7-yl)pyrimidine-2,4-diamine (Compounds 6-10)

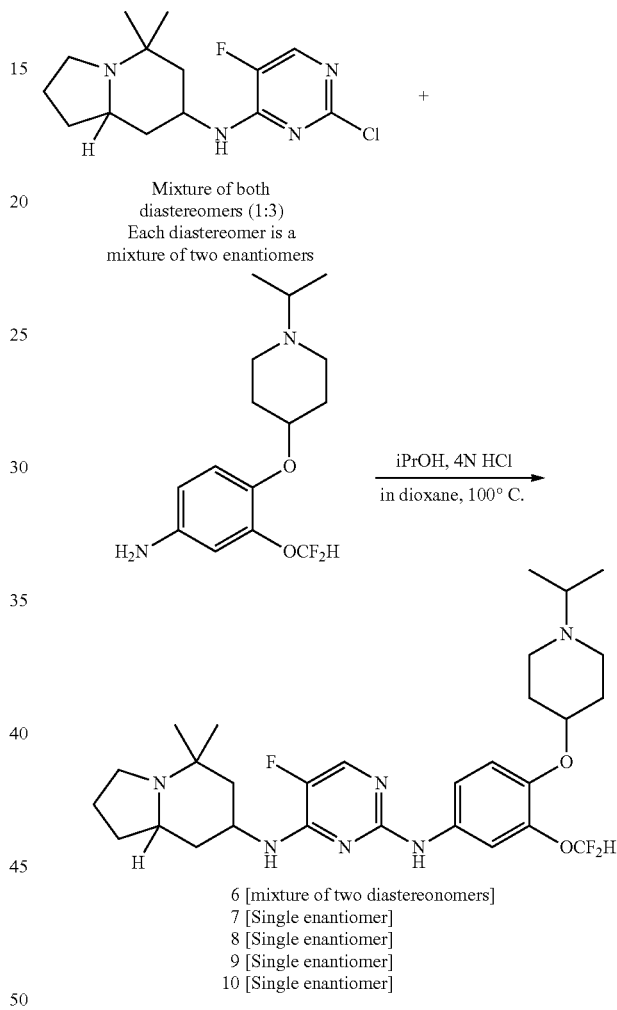

6 [mixture of two diastereonomers]
7 [Single enantiomer]
8 [Single enantiomer]
9 [Single enantiomer]
10 [Single enantiomer]

Synthesis of Compound 6, Compound 7, Compound 8, Compound 9, and Compound 10 is illustrated in the accompanying scheme. In the 2$^{nd}$ SNAr reaction the diastereomeric mixture (D1:D2=1:3) of (R/S, S/R, R/R, S/S)-N-(2-chloro-5-fluoropyrimidin-4-yl)-octahydro-5,5-dimethylindolizin-7-amine was used and chiral HPLC was performed on the final product. Absolute stereochemistry of the individual isomers was not established in this series.

A solution of (R/S, S/R, R/R, S/S)-N-(2-chloro-5-fluoro-pyrimidin-4-yl)-octahydro-5,5-dimethylindolizin-7-amine (0.12 g, 0.40 mmol, mixture of both diastereomers 1:3) in 3 ml of iPrOH, 4-(1-isopropylpiperidin-4yloxy)-3-(difluoromethoxy)benzeneamine (0.144 g, 0.48 mmol) and 4N HCl in dioxane (0.1 ml) were added. The reaction mixture was heated to 100° C. in a sealed vial for overnight. LCMS analysis of the crude reaction mixture indicated the completion of the reaction. The crude product was purified by column chromatography to give 0.15 g (63% yield) of the product as a mixture of four isomers (Compound 6, (two diastereomers and each diastereomer is a mixture of 2 enantiomers). Chiral HPLC purification of the mixture gave all four isomers (Compound 7, Compound 8, Compound 9 and Compound 10). Absolute stereochemistry of the individual isomers was not determined.

Compound 7: (Single Enantiomer)
$^1$H NMR (DMSO d$_6$, 300 MHz): δ 9.39 (s, 1H), 8.47 (s, 1H), 8.11 (s, 1H), 7.94 (d, J=2.8 Hz, 1H), 7.56-7.70 (m, 3H), 7.14 (d, J=8.8 Hz, 1H), 5.74 (s, 1H), 4.32-4.40 (br. m, 1H), 4.11-4.13 (m, 1H), 3.08-3.15 (m, 4H), 2.70-2.81 (m, 2H), 2.44 (s, 3H), 2.21-2.27 (m, 1H), 1.90-1.97 (m, 2H), 1.69-1.75 (m, 1H), 1.51-1.55 (m, 2H), 1.32 (d, J=6.60 Hz, 6H), 1.26-1.41 (m, 2H), 1.13-1.18 (m, 1H), 0.95 (s, 3H), 0.90 (s, 3H); LCMS (m/z): 563 (MH$^+$). Chiral HPLC Pk1 RT=16.22 min. (see protocol-5 in general methods).

Compound 8: (Single Enantiomer)
$^1$H NMR (DMSO d$_6$, 300 MHz): δ 9.42 (s, 1H), 8.66 (s, 1H), 8.11 (s, 1H), 7.92 (d, J=2.9 Hz, 1H), 7.35-7.61 (m, 3H), 7.09 (d, J=8.9 Hz, 1H), 5.68 (s, 1H), 4.32-4.40 (br. s, 1H), 4.05-4.06 (m, 1H), 3.02-3.09 (m, 4H), 2.65-2.78 (m, 2H), 2.35 (s, 3H), 2.19-2.25 (m, 1H), 1.88-1.37 (m, 2H), 1.65-1.70 (m, 1H), 1.50-1.54 (m, 2H), 1.31 (d, J=6.6 Hz, 6H), 1.20-1.35 (m, 2H), 1.10-1.16 (m, 1H), 0.93 (s, 3H), 0.87 (s, 3H); LCMS (m/z): 563 (MH$^+$). Chiral HPLC Pk2 RT=21.28 min. (see protocol-5 in general methods).

Compound 9: (Single Enantiomer)
$^1$H NMR (DMSO d$_6$, 300 MHz): δ 9.45 (s, 1H), 8.40 (s, 1H), 8.25 (s, 1H), 7.90 (d, J=2.7 Hz, 1H), 7.55-7.70 (m, 3H), 7.18 (d, J=8.5 Hz, 1H), 5.72 (s, 1H), 4.30-4.40 (m, 1H), 4.01-4.10 (m, 1H), 3.05-3.16 (m, 4H), 2.75-2.82 (m, 2H), 2.46 (s, 3H), 2.20-2.23 (m, 1H), 1.95-2.15 (m, 2H), 1.69-1.75 (m, 1H), 1.50-1.65 (m, 2H), 1.42 (d, J=6.5 Hz, 6H), 1.26-1.41 (m, 2H), 1.14-1.17 (m, 1H), 1.10 (s, 3H), 0.85 (s, 3H); LCMS (m/z): 563 (MH$^+$). Chiral HPLC Pk3 RT=27.28 min. (see protocol-5 in general methods).

Compound 10: (Single Enantiomer)
$^1$H NMR (DMSO d$_6$, 300 MHz): δ 9.43 (s, 1H), 8.39 (s, 1H), 8.24 (s, 1H), 7.85 (d, J=2.5 Hz, 1H), 7.54-7.64 (m, 3H), 7.20 (d, J=8.5 Hz, 1H), 5.71 (s, 1H), 4.29-4.35 (m, 1H), 4.10-4.15 (m, 1H), 3.05-3.16 (m, 4H), 2.73-2.80 (m, 2H), 2.43 (s, 3H), 2.20-2.23 (m, 1H), 1.95-2.15 (m, 2H), 1.70-1.75 (m, 1H), 1.61-1.65 (m, 2H), 1.45 (d, J=6.50 Hz, 6H), 1.25-1.40 (m, 2H), 1.15-1.18 (m, 1H), 1.09 (s, 3H), 0.89 (s, 3H); LCMS (m/z): 563 (MH$^+$). Chiral HPLC Pk 4 RT=32.53 min. (see protocol-5 in general methods).

Example 14

Synthesis of (R/S, S/R, R/R, S/S)-5-fluoro-N4-(octahydro-5,5-dimethylindolizin-7-yl)N2-(3-methoxy-5-(5-methyl-1H-tetrazol-1-yl)phenyl)pyrimidine-2,4-diamine (Compounds 11-14)

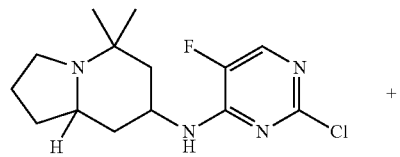

Mixture of both diastereomers (1:3)
Each diastereomer is a mixture of two enantiomers

+

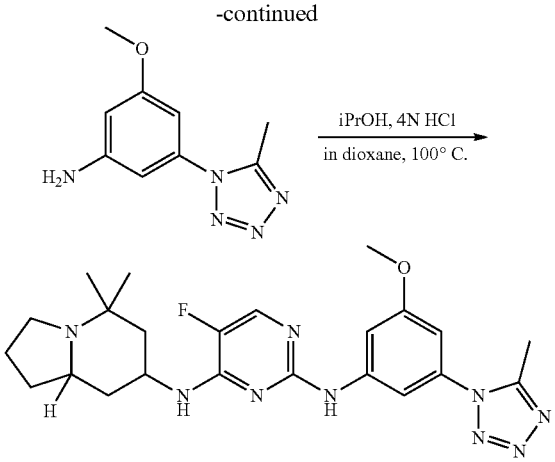

11 [Single enantiomer]
12 [Single enantiomer]
13 [Single enantiomer]
14 [Single enantiomer]

Synthesis of Compound 11, Compound 12, Compound 13 and Compound 14 was described in the accompanying scheme. In the 2$^{nd}$ SNAr reaction the diastereomeric mixture (D1:D2=1:3) of (R/S, S/R, R/R, S/S)-N-(2-chloro-5-fluoropyrimidin-4-yl)-octahydro-5,5-dimethylindolizin-7-amine was used and chiral HPLC was performed on the final product. Absolute stereochemistry of the individual isomers was not established.

A solution of (R/S, S/R, R/R, SS)-N-(2-chloro-5-fluoropyrimidin-4-yl)-octahydro-5,5-dimethylindolizin-7-amine (0.100 g, 0.34 mmol, mixture of two diastereomer (1:3)) in 3 ml of iPrOH, 3-methoxy-5-(5-methyl-1H-tetrazol-1-yl) aniline (0.077 g, 0.4 mmol; ChemBridge Building Blocks) and 4N HCl in dioxane (0.1 ml) were added. The reaction mixture was heated to 100° C. in a sealed vial for 12 hours. LCMS analysis of the crude reaction mixture indicated the completion of the reaction. The crude product was purified by column chromatography to give 0.14 g (Yield=88%) of the product as a mixture of four isomers (two diastereomers and each diastereomer is a mixture of 2 enantiomers). Chiral HPLC purification of the mixture gave all four isomers (Compound 11, Compound 12, Compound 13 and Compound 14). Absolute stereochemistry of the individual isomers was not established.

Compound 11: Single Diastereomer; Single Enantiomer
$^1$H NMR (DMSO d$_6$, 300 MHz) δ: 9.98 (s, 1H), 9.42 (s, 1H), 8.11 (s, 1H), 7.88 (d, J=3.9 Hz, 1H), 7.33 (s, 1H), 6.98 (d, J=5.5 Hz, 1H), 6.94 (s, 1H), 4.19 (br. s, 1H), 3.75 (s, 3H), 2.72-2.82 (m, 2H), 2.45 (s, 3H), 2.21-2.25 (m, 1H), 1.92-1.98 (m, 2H), 1.71-1.75 (m, 1H), 1.49-1.56 (m, 2H), 1.28-1.39 (m, 2H), 1.15-1.20 (m, 1H), 0.92 (s, 3H), 0.90 (s, 3H); LCMS (m/z): 468 (MH$^+$); Chiral HPLC Pk1 RT=17.92 min. (see protocol-5 in general methods).

Compound 12: Single Diastereomer; Single Enantiomer
$^1$H NMR (DMSO d$_6$, 300 MHz) δ: 9.98 (s, 1H), 9.42 (s, 1H), 8.11 (m, 1H), 7.87 (d, J=3.9 Hz, 1H), 7.33 (m, 1H), 6.94 (m, 2H), 4.12 (br. m, 1H), 3.75 (s, 3H), 2.70-2.81 (m, 2H), 2.44 (s, 3H), 2.21-2.27 (m, 1H), 1.90-1.97 (m, 2H), 1.70-1.76 (m, 1H), 1.50-1.57 (m, 2H), 1.26-1.41 (m, 2H), 1.13-1.18 (m, 1H), 0.91 (s, 3H), 0.88 (s, 3H); LCMS (m/z): 468 (MH$^+$); Chiral HPLC Pk2 RT=23.56 min. (see protocol-5 in general methods).

Compound 13: Single Diastereomer; Single Enantiomer

¹H NMR (DMSO d₆, 300 MHz) δ: 9.99 (s, 1H), 9.32 (s, 1H), 7.91 (s, 1H), 7.83 (d, J=3.9 Hz, 1H), 7.40 (s, 1H), 7.25 (d, J=8.5 Hz, 1H), 6.91 (s, 1H), 4.01-4.16 (br. m, 1H), 2.73 (m, 1H), 3.74 (s, 3H), 2.44 (s, 3H), 2.16-2.20 (m, 2H), 1.91-2.03 (m, 1H), 1.49-1.70 (m, 4H), 1.30-1.40 (m, 1H), 1.02-1.19 (m, 2H), 0.99 (s, 3H), 0.73 (s, 3H); LCMS (m/z): 468 (MH⁺); Chiral HPLC Pk3 RT=28.18 min. (see protocol-5 in general methods).

Compound 14: Single Diastereomer; Single Enantiomer

¹H NMR (DMSO d₆, 300 MHz) δ: 9.99 (s, 1H), 9.33 (s, 1H), 7.90 (s, 1H), 7.84 (d, J=3.9 Hz, 1H), 7.39 (s, 1H), 7.26 (d, J=8.5 Hz, 1H), 6.92 (s, 1H), 4.00-4.15 (br. m, 1H), 2.74 (m, 1H), 3.74 (s, 3H), 2.43 (s, 3H), 2.15-2.21 (m, 2H), 1.90-2.00 (m, 1H), 1.49-1.70 (m, 4H), 1.30-1.40 (m, 1H), 1.02-1.19 (m, 2H), 0.98 (s, 3H), 0.72 (s, 3H); LCMS (m/z): 468 (MH⁺); Chiral HPLC Pk4 RT=33.19 min. (see protocol-5 in general methods).

Compounds 11 and 12 appear to be enantiomers of one another.

Compounds 13 and 14 appear to be enantiomers of one another.

Example 15

Synthesis of N2-{4-cyclopropyl-6-fluoro-[3-(4-methyl)-1,2,3,4-tetrazol-5-one-1-yl]}phenyl-5-fluoro-N4(7-amino-hexahydro-3, 3-dimethylindolizin-5 (1H)-one))2,4-pyrimidinediamine (Compound 30)

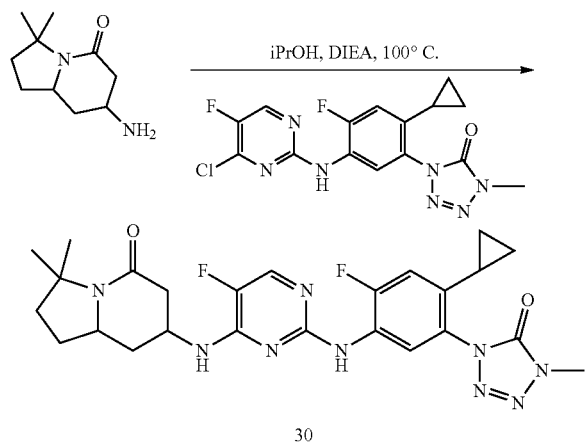

To a solution of 1-(5-(4-chloro-5-fluoropyrimidin-2-ylamino)-2-cyclopropyl-4-fluorophenyl)-4-methyl-1H-tetrazol-5(4H)-one (described in WO 2011/068898, published Jun. 9, 2011, which is hereby incorporated by reference in its entirety; 0.11 g, 0.3 mmol) in iPrOH (10 ml), diisopropyl ethyl amine (0.21 ml, 1.2 mmol) and 7-amino-hexahydro-3,3-dimethylindolizin-5(1H)-one (0.060 g, 0.329 mmol) were added. The reaction mixture was heated at 100° C. for 12 hours. LC-MS analysis indicated the completion of reaction. Volatiles were removed under vacuum and the crude product was adsorbed on silica gel. The crude product was purified by column chromatography to give the product white powder in 75% yield (0.12 g).

¹H NMR (DMSO d₆, 300 MHz) δ: 8.61 (s, 1H), 8.02 (d, J=7.6 Hz, 1H), 7.85 (d, J=3.8 Hz, 1H), 7.78 (d, J=6.7 Hz, 1H), 6.97 (d, J=12.3 Hz, 1H), 4.33 (br. s, 1H), 3.60-3.68 (m, 4H), 2.27 (d, J=17.0 Hz, 1H), 2.16 (d, J=12.0 Hz, 1H), 1.79-1.85 (m, 1H), 1.58-1.72 (m, 3H), 1.46 (s, 3H), 1.35-1.43 (m, 3H), 1.32 (s, 3H), 0.80-0.83 (m, 2H), 0.63-0.65 (m, 2H); ¹⁹F NMR (DMSO) δ: −165.08,-121.69; LCMS (m/z): 526 (MH⁺).

Example 16

Synthesis of 1-(5-(4-((7R,8aS)-octahydro-5,5-dimethylindolizi-7-yl-amino)-5-fluoropyrimidin-2-yl-amino)-2-cyclopropyl-4-fluorophenyl)-4-methyl-1H-tetrazol-5-(4H)-one (Compound 17)

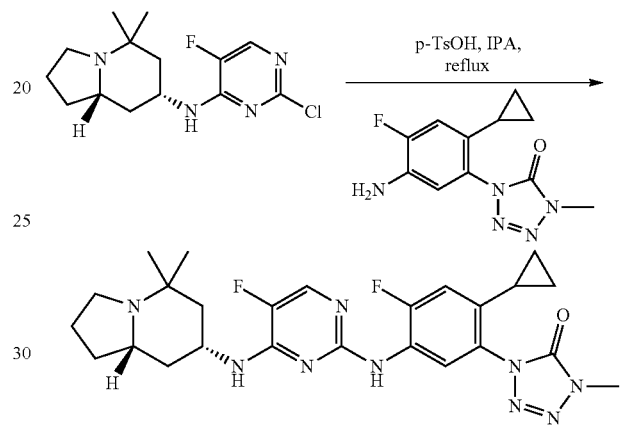

A mixture of (7R,8aS)-N-(2-chloro-5-fluoropyrimidin-4-yl)-octahydro-5,5-dimethylindolizin-7-amine (Compound 3-10 from Example 3) (10.8 g, 36.2 mmol), 1-(5-amino-2-cyclopropyl-4-fluorophenyl)-4-methyl-1H-tetrazol-5(4H)-one (12.6 g, 50.6 mmol) and para-toluenesulfonic acid monohydrate (12.4 g, 65.1 mmol) in ⁱPrOH (120 mL) was heated to reflux and stirred for 16 hours. After allowing the reaction mixture to cool, EtOAc (600 mL) was added and the resulting mixture was washed with 1N NaOH (200 mL). The organic and aqueous layers were partitioned and the aqueous layer extracted with EtOAc (200 mL). The combined organic extracts were dried (MgSO₄), filtered and the solvent removed in vacuo to leave a crude residue. The residue was purified by column chromatography on silica gel using CH₂Cl₂/2N NH₃ in MeOH (95:5) as eluent to give the product (12.7 g) containing a trace of TsOH. The product was dissolved in EtOAc (500 mL) and washed with 1N NaOH (100 mL) and H₂O (100 mL). The organic layer was dried (MgSO₄) and concentrated in vacuo to give the product (12.1 g) as a solid.

[α]$_D$=−7.4 (c=0.25 in MeOH). The absolute stereochemistry of Compound 17 was confirmed by X-ray crystallography of the compound co-crystallized with PKC theta.

¹H NMR (DMSO-d₆, 300 MHz): δ 8.48 (br. s, 1H), 7.96 (d, J=7.8 Hz, 1H), 7.82 (d, J=3.6 Hz, 1H), 7.25 (d, J=8.4 Hz, 1H), 6.98 (d, J=12.3 Hz, 1H), 4.05-3.90 (m, 1H), 3.61 (s, 3H), 2.81 (td, J=8.4, 3.0 Hz, 1H), 2.21 (q, J=8.1 Hz, 1H), 2.20-2.10 (m, 1H), 2.00-1.90 (m, 1H), 1.75-1.48 (m, 5H), 1.38 (t, J=12.3 Hz, 1H), 1.22-1.12 (m, 1H), 1.03 (s, 3H), 1.08-1.00 (m, 1H), 0.83-0.77 (m, 2H), 0.75 (s, 3H), 0.63-0.57 (m, 2H)

$^{19}$F NMR (DMSO-d$_6$, 282 MHz): δ −121.04 (t), −166.01 (s)

m/z=511.0 (M+H)$^+$

The enantiomeric excess of the product is measured by chiral HPLC using the conditions detailed below.

Chiral HPLC Conditions:

Column: Daicel Chemical Industries, Chiralcel OJ, 4.6×250 mm

Mobile phase: 2:2:1 Methanol/Ethanol/Hexane 0.1% triethylamine (isocratic)

Flow rate: 0.5 ml/min

Run time: 15 minutes

Temperature: room temperature

Detection: Water 996 PDA

HPLC: Waters 2690 Separations Module

Large-scale Reaction Avoiding use of Column Chromatography:

1-(5-Amino-2-cyclopropyl-4-fluorophenyl)-4-methyl-1H-tetrazol-5(4H)-one (26.7 g, 107.3 mmol) and para-toluene sulfonic acid monohydrate (30.6 g, 161.0 mmol) were added to a stirred mixture of chloro-pyrimidine (Compound 3-10 from Example 3) (23.0 g, 68.25 mmol) in $^i$PrOH (300 mL). The reaction mixture was heated to reflux and stirred for 16 hours, after which LC-MS analysis indicated completion of the reaction. The reaction mixture was cooled to room temperature and filtered to obtain a tan-colored solid. The filter cake was then washed with $^i$PrOH (1×25 mL). The filtrate was concentrated to ca. half volume in vacuo and the emerging precipitate was filtered. The combined filter cakes from the above procedures were air-dried then dissolved in EtOAc (300 mL) and washed with 1N NaOH (1×200 mL then 3×100 mL). The organic layer was dried over (MgSO$_4$), filtered and solvent removed in vacuo to leave the product (27.2 g, 78%) as a white powder.

Example 17

Synthesis of Octahydro-5,5-dimethylindolizin-7ylamino)-5-fluoropyrimidin-2-yl-amino)-2-cyclopropyl-4-fluorophenyl)-4-methyl-1H-tetrazol-5(4H)-one (Compounds 16-21)

The synthesis of Compounds 16, 17, 18, 19, 20, and 21 is illustrated in the accompanying schemes. First the separation of diastereomers D1 and D2 was accomplished by column chromatography and both the diastereomers were taken to the SNAr reaction separately. The final products were separated by chiral HPLC provide individual enantiomers.

(R/S, S/R)-N-(2-chloro-5-fluoropyrimidin-4-yl)-octahydro-5,5-dimethylindolizin-7-amine (D1) is a racemic mixture of two enantiomers. D1 was taken to 2$^{nd}$ SNAr reaction to form Compound 16. Synthesis of Compound 16 (racemic) was described in the accompanying scheme. Compound 16 was separated by chiral HPLC to give Compound 17 (Single enantiomer) and Compound 18 (Single enantiomer).

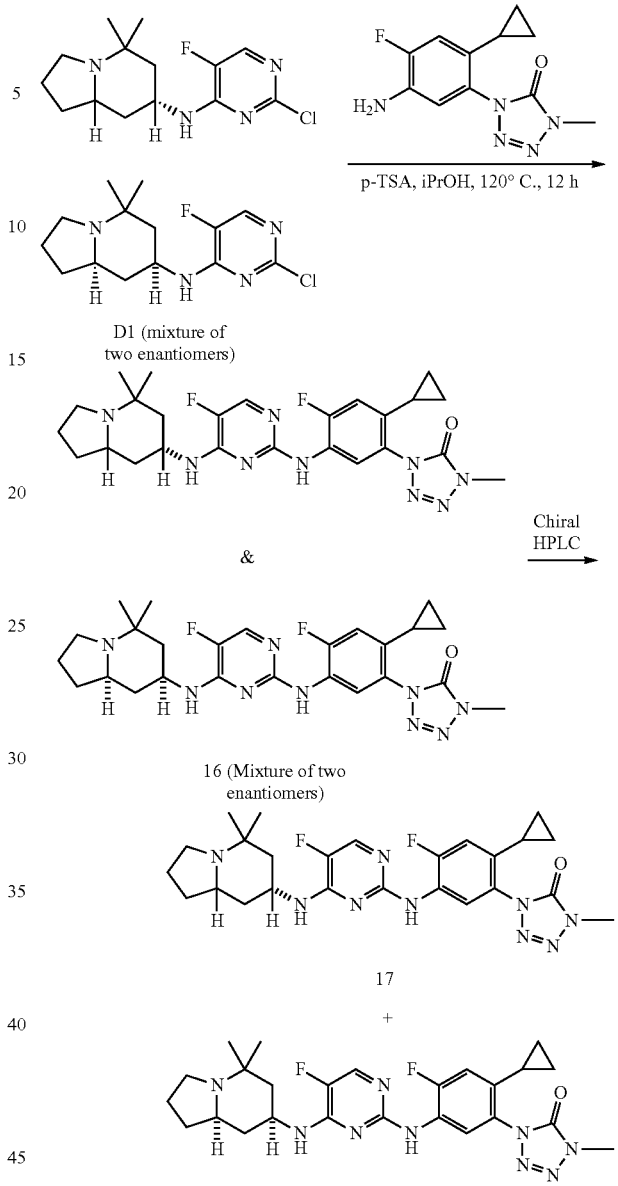

D1 (mixture of two enantiomers)

16 (Mixture of two enantiomers)

17
+
18

To a solution of (R/S, S/R)-N-(2-chloro-5-fluoropyrimidin-4-yl)-octahydro-5,5-dimethylindolizin-7-amine (D1) (0.1 g, 0.3 mmol) in 10 ml of iPrOH, 1-(5-amino-2-cyclopropyl-4-fluorophenyl)-4-methyl-1H-tetrazol-5 (4H)-one (0.092 g, 0.37 mmol) and p-toluene sulfonicacid monohydrate (0.064 g, 0.3 mmol) were added. The reaction mixture was heated at 120° C. (bath temp.) for 16 hours. LC-MS analysis indicated the completion of the reaction. The reaction mixture was cooled to room temperature and filtered off to get tan solid. The filter cake was washed with 5 ml of iPrOH to get white solid. The filtrate was concentrated in vacuo to half the volume and the obtained solids were filtered off. The filtered solids were combined and dried under air. The dried solids were dissolved in 50 ml of EtOAc and partitioned with aqueous 1N NaOH (10 ml). Both the layers were separated and organic layer was washed (×3) with aqueous 1N NaOH (10 ml). Separated organic layer was dried over MgSO$_4$ and concentrated to give 0.12 g (yield=71%) of the product as white powder (Compound 16). Compound 16 was separated by chiral HPLC to give the corresponding enantiomers Compound 17 and Compound 18(see Protocol-3 in general methods).

1-(5-(4-((7R,8aS)-Octahydro-5,5-dimethylindolizin-7ylamino)-5-fluoropyrimidin-2-yl-amino)-2-cyclopropyl-4-fluorophenyl)-4-methyl-1H-tetrazol-5(4H)-one (Compound 17) (single enantiomer)

$^1$H NMR (DMSO d$_6$, 300 MHz) δ: 8.48 (s, 1H), 7.97 (d, J=7.6 Hz, 1H), 7.82 (d, J=3.8 Hz, 1H), 7.25 (d, J=7.9 Hz, 1H), 6.99 (d, J=12.0 Hz, 1H), 3.90-4.10 (br. m, 1H), 3.61 (s, 3H), 2.81 (dt, J=8.2, 2.9 Hz, 1H), 2.10-2.26 (m, 2H), 1.93 (d, J=11.7 Hz, 1H), 1.49-1.75 (m, 5H), 1.39 (t, J=12.3 Hz, 1H), 1.14-1.24 (m, 1H), 1.03 (s, 3H), 0.94-1.01 (m, 1H), 0.77-0.83 (m, 2H), 0.75 (s, 3H), 0.59-0.63 (m, 2H); $^{19}$F NMR (DMSO) δ: −165.99 (d), −121.09 (t); LCMS (m/z): 512 (MH$^+$); Chiral HPLC RT=18.89 min. (see Protocol-4 in general methods).

1-(5-(4-((7S,8aR)-Octahydro-5,5-dimethylindolizin-7ylamino)-5-fluoropyrimidin-2-yl amino)-2-cyclopropyl-4-fluorophenyl)-4-methyl-1H-tetrazol-5(4H)-one (Compound 18) (single enantiomer)

$^1$H NMR (DMSO d$_6$, 300 MHz) δ: 8.48 (s, 1H), 7.97 (d, J=7.6 Hz, 1H), 7.83 (d, J=3.8 Hz, 1H), 7.25 (d, J=8.2 Hz, 1H), 6.99 (d, J=12.3 Hz, 1H), 3.90-4.05 (br. m, 1H), 3.61 (s, 3H), 2.81 (br. m, 1H), 2.10-2.26 (m, 2H), 1.93 (d, J=11.7 Hz, 1H), 1.49-1.75 (m, 5H), 1.39 (t, J=12.0 Hz, 1H), 1.14-1.24 (m, 1H), 1.03 (s, 3H), 0.94-1.01 (m, 1H), 0.77-0.82 (m, 2H), 0.75 (s, 3H), 0.58-0.63 (m, 2H); $^{19}$F NMR (DMSO) δ: −166.00 (d), −121.05 (t); LCMS (m/z): 512 (MH$^+$). Chiral HPLC RT=22.97 (see Protocol-4 in general methods).

(S/S, R/R)-N-(2-chloro-5-fluoropyrimidin-4-yl)-octahydro-5,5-dimethylindolizin-7-amine (D2) is a mixture of two enantiomers. D2 was taken to 2$^{nd}$ SNAr reaction to form Compound 19. Synthesis of Compound 19 (mixture of two enantiomers) was described in the accompanying scheme. Compound 19 was separated by chiral HPLC to give Compound 20 (Single enantiomer) and Compound 21 (Single enantiomer).

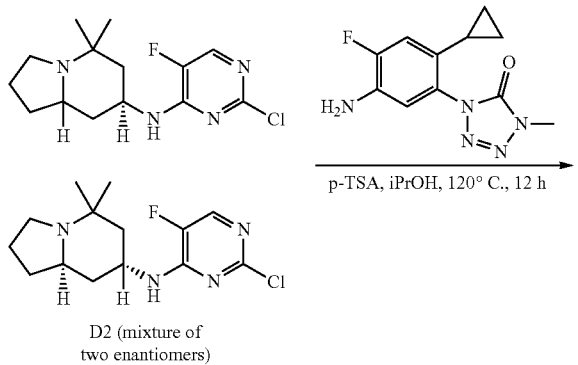

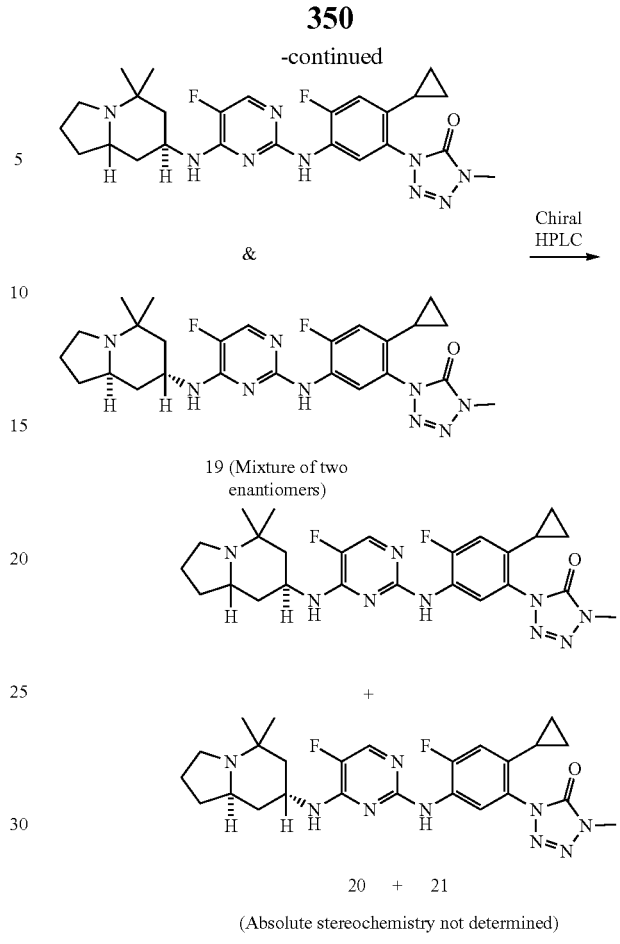

(Absolute stereochemistry not determined)

To a solution of (S/S, R/R)-N-(2-chloro-5-fluoropyrimidin-4-yl)-octahydro-5, 5-dimethylindolizin-7-amine (D2) (0.10 g, 0.34 mmol) in 10 ml of iPrOH, 1-(5-amino-2-cyclopropyl-4-fluorophenyl)-4-methyl-1H-tetrazol-5 (4H)-one (0.092 g, 0.4 mmol) and p-toluene sulfonic acid monohydrate (0.064 g, 0.3 mmol) were added. The reaction mixture was heated at 120° C. (bath temp.) for 16 hours. LC-MS analysis indicated the completion of the reaction. The reaction mixture was cooled to room temperature and filtered off to get tan solid. The filter cake was washed with 1 ml of iPrOH to get white solid. The filtered solids were combined and dried under air. The dried solids were dissolved in 50 ml of EtOAc and partitioned with aqueous 1N NaOH (10 ml). Both the layers were separated and organic layer was washed (×3) with aqueous 1N NaOH (10 ml). Separated organic layer was dried over MgSO$_4$ and concentrated to give 0.13 g (yield=74%) of the product as white powder (Compound 19). Compound 19 was separated by chiral HPLC to give the corresponding enantiomers Compound 20 and Compound 21 (see Protocol-4 in general methods).

Compound 20: (single enantiomer):

$^1$H NMR (DMSO d$_6$, 300 MHz) δ: 8.56 (s, 1H), 8.11 (d, J=7.6 Hz, 1H), 7.84 (d, J=3.8 Hz, 1H), 6.92-6.99 (m, 2H), 4.04 (br. s, 1H), 3.61 (s, 3H), 2.70-2.83 (m, 2H), 2.25-2.35 (m, 1H), 1.75-1.95 (m, 3H), 1.55-1.65 (m, 3H), 1.15-1.36 (m, 3H), 0.94 (s, 3H), 0.92 (s, 3H), 0.78-0.83 (m, 2H), 0.60-0.65 (m, 2H); $^{19}$F NMR (DMSO) δ: −165.78 (d), −122.24 (t); LCMS (m/z): 512 (MH$^+$); Chiral HPLC RT=29.88 min. (see Protocol-4 in general methods).

Compound 21: (Single Enantiomer):

$^1$H NMR (DMSO d$_6$, 300 MHz) δ: 8.57 (s, 1H), 8.11 (d, J=7.6 Hz, 1H), 7.84 (d, J=3.8 Hz, 1H), 6.92-6.99 (m, 2H), 4.04 (br. s, 1H), 3.61 (s, 3H), 2.71-2.83 (m, 2H), 2.25-2.35 (m, 1H), 1.76-1.95 (m, 3H), 1.56-1.68 (m, 3H), 1.15-1.35 (m, 3H), 0.94 (s, 3H), 0.92 (s, 3H), 0.78-0.83 (m, 2H), 0.60-0.65 (m, 2H); $^{19}$F NMR (DMSO) δ: −165.57 (d), −122.24 (t); LCMS (m/z): 512 (MH$^+$); Chiral HPLC RT=34.50 min. (see Protocol-4 in general methods).

Example 18

Synthesis of N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine (Compound 5)

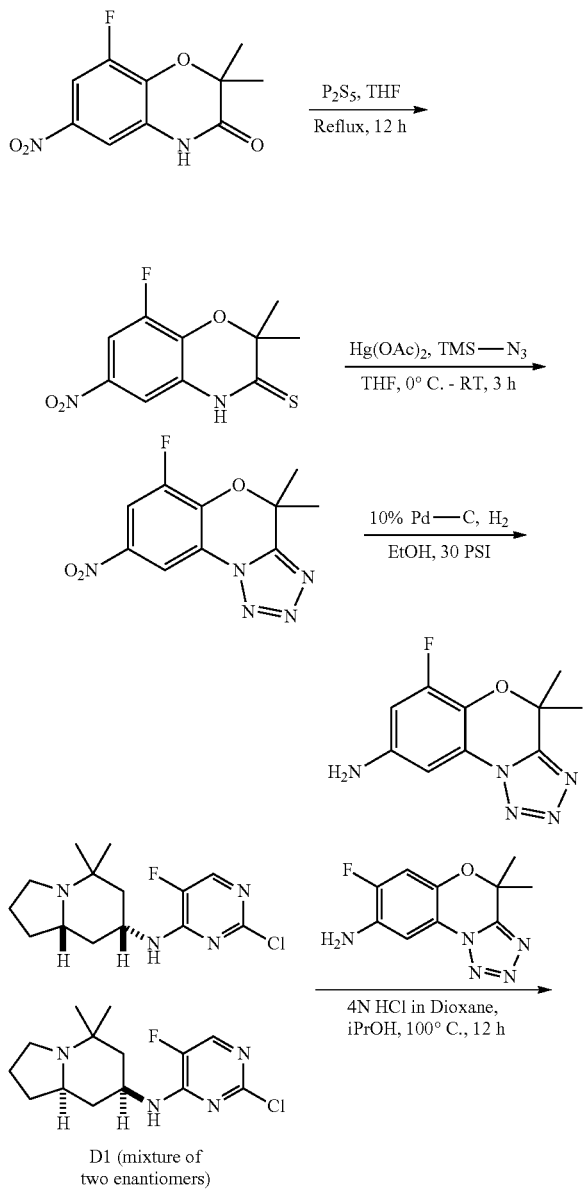

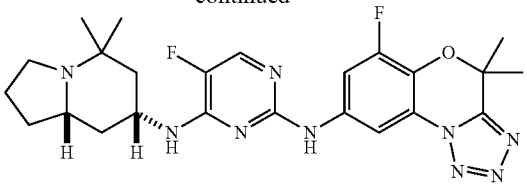

&

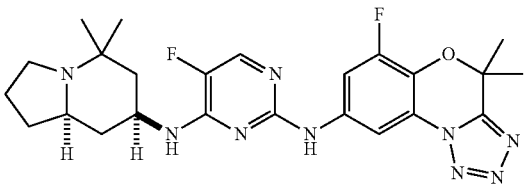

5 (mixture of two enantiomers)

Preparation of 8-Fluoro-2,2-dimethyl-6-nitro-2H-benzo[b][1,4]oxazin-3(4H)-thione To a solution of 8-Fluoro-2,2-dimethyl-6-nitro-2H-benzo[b][1,4]oxazin-3(4H)-one (0.75 g, 3.1 mmol) in 25 ml anhydrous THF, P$_2$S$_5$ (2.8 g, 6.25 mmol) was added and the reaction mixture was heated to reflux for 12 hours. Analysis of LC-MS indicated the completion of the reaction. Volatiles were removed in vacuo and the crude reaction mixture was partitioned in EtOAc (100 ml) and saturated aqueous NH$_4$Cl (100 ml). Layers were separated and the organic layer was washed (×2) with saturated aqueous NH$_4$Cl (50 ml). EtOAc layer was dried over Na$_2$SO$_4$ and concentrated to give the product in 69% yield (0.55 g). LCMS (m/z) 257 (MH$^+$).

Preparation of 4,4-dimethyl-6-fluoro-8-nitro-4H-benzo[b]tetrazolo[1,5-d][1,4]oxazine To a solution of 8-fluoro-2,2-dimethyl-6-nitro-2H-benzo[b][1,4]oxazin-3(4H)-thione (1.0 g, 3.9 mmol) in THF, Hg(OAc)$_2$ was added at 0° C. TMS-N$_3$ was added to the reaction mixture at 0° C. and stirred for 1 hour. Reaction mixture was allowed to warm to room temperature and stirred for 3 hours. LCMS analysis of the reaction mixture indicated completion of the reaction. After 3 hours, the reaction mixture was diluted with 100 ml of EtOAc and partitioned with saturated aqueous NH$_4$Cl (100 ml). Layers were separated and the aqueous layer was washed twice with EtOAc (50 ml). Combined EtOAc layers were dried over Na$_2$SO$_4$ and concentrated. The crude product was purified by column chromatography to give the product in 57% yield (0.57 g). LCMS (m/z) 266 (MH$^+$).

Preparation of 4,4-dimethyl-6-fluoro-4H-benzo[b]tetrazolo[1,5-d][1,4]oxazin-8-amine 4,4-Dimethyl-6-fluoro-8-nitro-4H-benzo[b]tetrazolo[1,5-d][1,4]oxazine (0.82 g, 3.1 mmol) is dissolved in EtOH (20 ml). The clear solution is transferred to a Parr hydrogenation flask and placed under nitrogen. 10% Pd—C (0.25 g) was added to the Parr flask under nitrogen. The mixture was then transferred to a Parr hydrogenation apparatus, evacuated and filled with hydrogen (×3). The mixture was hydrogenated at 30 psi (optionally topping-up hydrogen) until LC/MS and TLC indicated complete reaction to the amine. After complete reaction, the mixture was placed under nitrogen and filtered through a small pad of Celite. The filter cake was washed with EtOH (×1) and the filtrate was concentrated in vacuo to leave the 4,4-dimethyl-6-fluoro-4H-benzo[b]tetrazolo[1,5-d][1,4]oxazin-8-amine in 72% yield (0.53 g). LCMS (m/z): 236 (MH⁺).

Preparation of N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine (Compound 5)

A solution of (R/S, S/R)—N-(2-chloro-5-fluoropyrimidin-4-yl)-octahydro-5,5-dimethylindolizin-7-amine (D1) (0.1 g, 0.3 mmol, single diastereomer) in 3 ml of iPrOH, 4,4-dimethyl-6-fluoro-4H-benzo[b]tetrazolo[1,5-d][1,4]oxazin-8-amine (0.093 g, 0.4 mmol) and 4N HCl in dioxane (0.1 ml) were added. The reaction mixture was heated to 100° C. in a sealed vial for 12 hours. LCMS analysis of the crude reaction mixture indicated the completion of the reaction. The crude product was purified by column chromatography to give 0.12 g (Yield=72%) of the product as a mixture of two enantiomers.

$^1$H NMR (DMSO d$_6$, 300 MHz) δ: 9.58 (s, 1H), 8.40 (s, 1H), 7.90 (d, J=8.5 Hz, 1H), 7.75 (d, J=8.8 Hz, 1H), 7.10 (d, J=5.5 Hz, 1H), 4.25 (br. s, 1H), 2.85 (m, 2H), 2.23-2.335 (m, 1H), 2.15 (m, 2H), 1.88 (s, 6H), 1.40-1.60 (m, 4H), 1.22 (m, 2H), 1.05 (s, 3H), 0.99 (s, 3H); LCMS (m/z): 498 (MH⁺).

Example 19

Synthesis of 4-((R/S,S/R)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile (Compound 66)

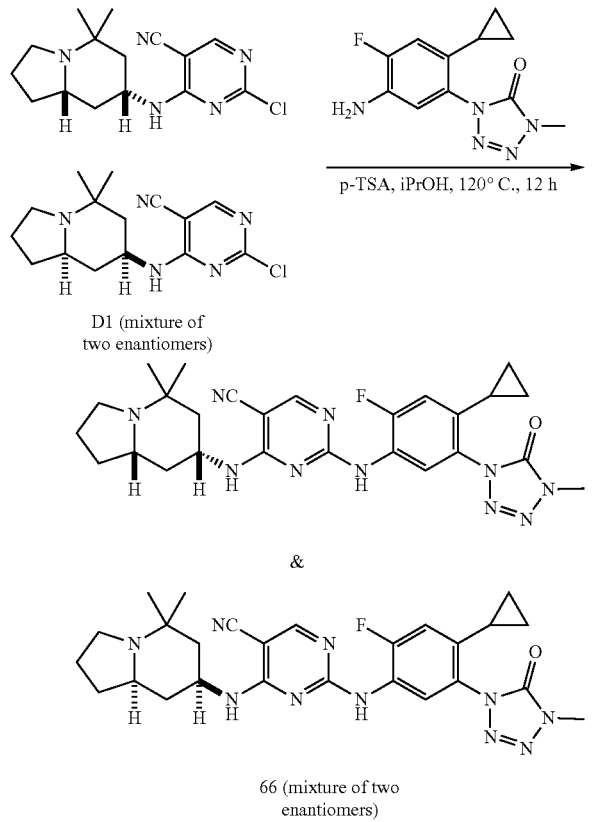

To a solution of (±)-2-chloro-4-(octahydro-5,5-dimethylindolizin-7-ylamino)pyridimine-5-carbonitrile (70% pure, 0.068 g, 0.2 mmol) in iPrOH (10 ml), 1-(5-amino-2-cyclopropyl-4-fluorophenyl)-4-methyl-1H-tetrazol-5 (4H)-one (0.078 g, 0.3 mmol) and p-TSA (0.04 g, 0.2 mmol) were added and the reaction mixture was heated to 82° C. for overnight. LCMS analysis indicated the completion of reaction. Purification of the crude product by column chromatography gave the product as p-toluene sulfonic acid salt. The salt was dissolved in 20 ml EtOAc and partitioned with aqueous 2N NaOH solution. The organic layers were separated and dried over Na$_2$SO$_4$. Removal of the solvents and lyophilization gave the product in 11% yield (0.015 g).

$^1$H NMR (DMSO d$_6$, 300 MHz) δ: 8.43 (s, 1H), 8.29 (s, 1H), 7.65 (d, J=7.3 Hz, 1H), 7.42 (d, J=7.6 Hz, 1H), 7.03 (d, J=11.7 Hz, 1H), 3.99 (br. s, 1H), 3.61 (s, 3H), 2.76-2.80 (m, 1H), 2.10-2.26 (m, 2H), 1.79-1.83 (m, 1H), 1.52-1.70 (m, 4H), 1.34-1.43 (m, 2H), 1.07-1.22 (m, 4H), 1.01 (s, 3H), 0.82-0.86 (m, 2H), 0.63-0.67 (m, 2H); LCMS (m/z): 519 (MH⁺).

Example 20

Synthesis of (±)-N²-(4-cyclopropyl-2-fluoro-5-(1H-tetrazol-1-yl)phenyl)-5-fluoro-n⁴-(octahydroindolizin-7-yl)pyrimidine-2,4-diamine (Compound 24)

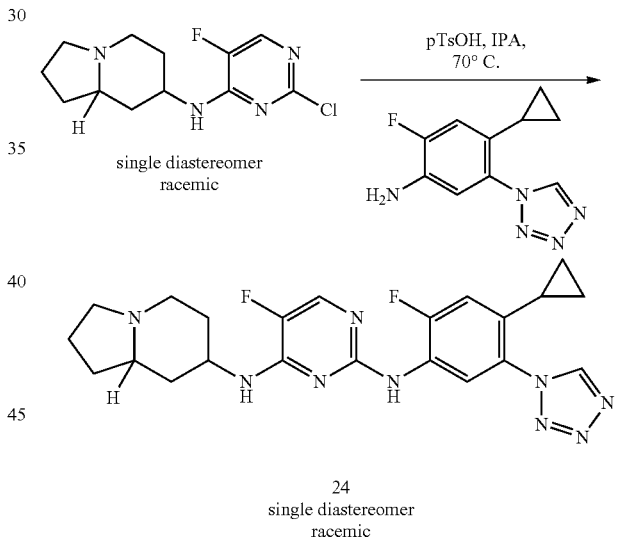

A mixture of N-(2-chloro-5-fluoropyrimidin-4-yl)octahydroindolizin-7-amine (90 mg, 0.34 mmol), 4-cyclopropyl-2-fluoro-5-(1H-tetrazol-1-yl)benzeneamine (87 mg, 0.35 mmol; prepared according to U.S. patent application Ser. No. 13/188,222, filed Jul. 21, 2011, now U.S. patent application publication US2012/0022092, which is hereby incorporated by reference in its entirety) and para-toluenesulfonic acid monohydrate (63 mg, 0.34 mmol) in isopropyl alcohol (3 ml) were combined in a sealed vial, heated to 70° C. and stirred over a couple of days. After cooling, a precipitate emerged which was filtered to give a crude solid (50 mg). The crude solid was purified further by preparative high-performance liquid chromatography to give a solid. The solid was partitioned between EtOAc (20 ml) and 1N NaOH (20 ml). The aqueous layer was extracted with EtOAc (1×20 ml) and the combined organic extracts were dried (MgSO$_4$), filtered and the solvent removed under vacuum to leave the product (10 mg, 7%) as a solid.

$^1$H NMR (300 MHz; $d_6$-DMSO) δ 9.83 (t, J=0.9 Hz, 1H), 8.59 (s, 1H), 8.20 (d, J=7.7 Hz, 1H), 7.80 (d, J=6.5 Hz, 1H), 7.36 (d, J=8.1 Hz, 1H), 7.04 (d, J=12.2 Hz, 1H), 3.73-3.59 (m, 1H), 2.82-2.75 (m, 2H), 1.87 (q, J=8.4 Hz, 1H), 1.82-1.78 (m, 2H), 1.64-1.41 (m, 5H), 1.39-1.28 (m, 2H), 1.20-1.03 (m, 2H), 0.71-0.65 (m, 2H), 0.57-0.52 (m, 2H); $^{19}$F NMR (282 MHz; $d_6$-DMSO) δ −122.1 (t), −165.5 (d); m/z=454.29 (M+H)$^+$; rt=3.37 min (HPLC protocol-1).

Example 21

Synthesis of (±)-1-(5-(5-fluoro-4-(octahydroindolizin-7-ylamino)pyrimidin-2-ylamino)-2-cyclopropyl-4-fluorophenyl)-4-methyl-1H-tetrazol-5(4H)one (Compound 27)

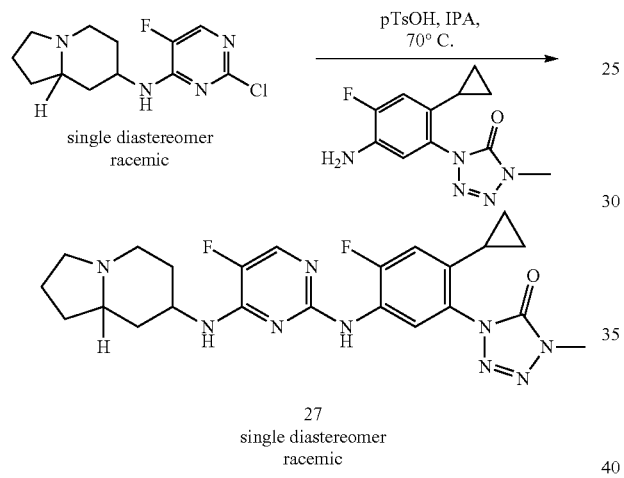

A mixture of N-(2-chloro-5-fluoropyrimidin-4-yl)octahydroindolizin-7-amine (54 mg, 0.2 mmol), 1-(5-amino-2-cyclopropyl-4-fluorophenyl)-4-methyl-1H-tetrazol-5-one (52 mg, 0.21 mmol; prepared according to US20110130415 pages 43-48, which is hereby incorporated by reference in its entirety) and para-toluenesulfonic acid monohydrate (38 mg, 0.2 mmol) in isopropyl alcohol (3 ml) were combined in a sealed vial, heated to 70° C. and stirred for 2 days. After cooling, the mixture was concentrated under vacuum to leave a crude residue. The residue was purified by preparative high-performance liquid chromatography to give a solid. The solid was partitioned between EtOAc (20 ml) and 1N NaOH (20 ml). The aqueous layer was extracted with EtOAc (2×20 ml) and the combined organic extracts were dried (MgSO$_4$), filtered and the solvent removed in vacuo to leave the product (46 mg, 47%) as a solid after freeze-drying from MeCN/H$_2$O.

$^1$H NMR (300 MHz; $d_6$-DMSO) δ 8.52 (br. s, 1H), 8.08 (d, J=7.7 Hz, 1H), 7.83 (dd, J=3.8, 1.2 Hz, 1H), 7.38 (br. d, J=7.7 Hz, 1H), 6.97 (d, J=12.3 Hz, 1H), 3.85-3.71 (m, 1H), 3.62 (app. d, 3H), 2.97-2.87 (m, 2H), 1.93-1.89 (m, 2H), 1.75-1.50 (m, 7H), 1.31-1.15 (m, 3H), 0.83-0.77 (m, 2H), 0.64-0.59 (m, 2H); $^{19}$F NMR (282 MHz; $d_6$-DMSO) δ −122.0 (t), −165.8 (d); m/z=484.27 (M+H)$^+$; rt=3.22 min (HPLC protocol-1).

Example 22

Synthesis of (±)-N$^2$-(4-cyclopropyl-2-fluoro-5-(5-methyl-1H-tetrazol-1-yl)phenyl)-5-fluoro-n$^4$-(octahydroindolizin-7-yl)pyrimidine-2,4-diamine (Compound 28)

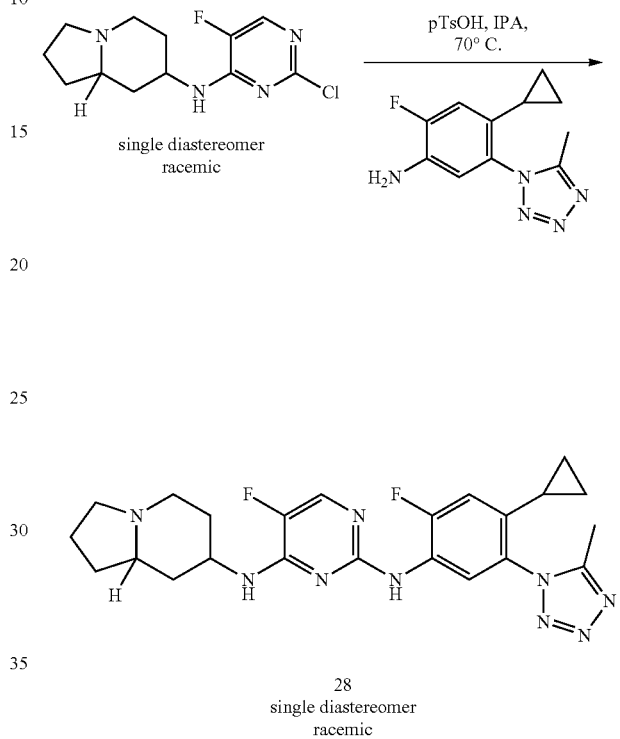

A mixture of N-(2-chloro-5-fluoropyrimidin-4-yl)octahydroindolizin-7-amine (179 mg, 0.66 mmol), 1-(2-Cyclopropyl-4-fluoro-5-nitrophenyl)-5-methyl-1H-tetrazole (140 mg, 0.66 mmol; prepared according to U.S. patent application Ser. No. 13/188,222, now U.S. patent application publication US2012/0022092) and para-toluenesulfonic acid monohydrate (126 mg, 0.66 mol) in isopropyl alcohol (5 ml) were combined in a sealed vial, heated to 70° C. and stirred for 3 days. After cooling, the mixture was concentrated in vacuo and the crude residue partitioned between 1N NaOH (25 ml) and EtOAc (30 ml). The aqueous layer was extracted with EtOAc (1×30 ml) and the combined organic layers were dried (MgSO$_4$), filtered and the solvent removed under vacuum to leave a crude solid. The solid was purified by column chromatography on silica gel (ISCO System) using 2M NH$_3$ in MeOH/CH$_2$Cl$_2$ (gradient system from 0:1 to 1:9) as eluent to give the product (190 mg, 61%) as a solid after freeze-drying from MeCN/H$_2$O.

$^1$H NMR (300 MHz; $d_6$-DMSO) δ 8.61 (br. s, 1H), 8.15 (d, J=7.6 Hz, 1H), 7.86-7.84 (m, 1H), 7.41 (br. d, J=8.1 Hz, 1H), 7.04 (d, J=12.3 Hz, 1H), 3.75-3.64 (m, 1H), 2.92-2.82 (m, 2H), 2.41 (s, 3H), 2.05-2.91 (m, 1H), 1.88-1.85 (m, 2H), 1.71-1.40 (m, 6H), 1.27-1.08 (m, 3H), 0.79-0.70 (m, 2H), 0.68-0.62 (m, 2H); $^{19}$F NMR (282 MHz; $d_6$-DMSO) δ −122.4 (t), −165.6 (d); m/z=468.28 (M+H)$^+$; rt=3.40 min (HPLC protocol-1).

Example 23

Synthesis of (±)-N²-(4-cyclopropyl-2-fluoro-5-(1H-tetrazol-1-yl)phenyl)-5-fluoro-n⁴-(octahydro-5,5-dimethylindolizin-7-yl)pyrimidine-2,4-diamine (Compound 53)

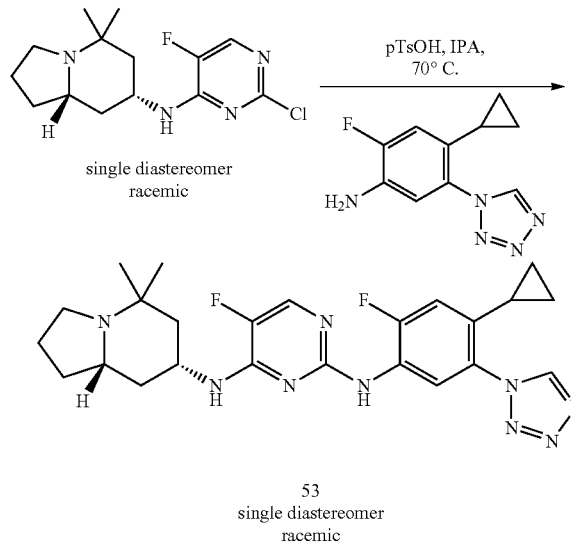

A mixture of N-(2-chloro-5-fluoropyrimidin-4-yl)octahydro-5,5-dimethylindolizin-7-amine hydrochloride (168 mg, 0.5 mmol), 4-cyclopropyl-2-fluoro-5-(1H-tetrazol-1-yl)benzeneamine (153 mg, 0.7 mmol; prepared according to U.S. patent application Ser. No. 13/188,222, filed Jul. 21, 2011, now U.S. patent application publication US2012/0022092) and para-toluenesulfonic acid monohydrate (95 mg, 0.5 mmol) in isopropyl alcohol (3 ml) were combined in a sealed vial, heated to 70° C. and stirred for 4 days. After cooling, the mixture was filtered and the filter cake washed with cold isopropyl alcohol. The filter cake was suspended in EtOAc (50 ml) and 1N NaOH (50 ml) was added. The aqueous and organic layers were partitioned and the aqueous layer was extracted with EtOAc (30 ml). The combined organic extracts were dried (Na₂SO₄), filtered and the solvent removed under vacuum to leave a residue, which was freeze-dried from MeCN/H₂O to give the product (162 mg, 67%) as a solid.

$^1$H NMR (300 MHz; d$_6$-DMSO) δ 9.86 (m, 1H), 8.59 (s, 1H), 8.09 (d, J=7.6 Hz, 1H), 7.83 (d, J=3.8 Hz, 1H), 7.26 (br. d, J=8.0 Hz, 1H), 7.09 (d, J=12.1 Hz, 1H), 4.00-3.88 (m, 1H), 2.81-2.74 (m, 1H), 2.16 (q, J=8.2 Hz, 1H), 1.99-1.83 (m, 2H), 1.72-1.32 (m, 6H), 1.20-0.94 (m, 2H), 1.01 (s, 3H), 0.75-0.71 (m, 2H), 0.69 (s, 3H), 0.63-0.55 (m, 2H); $^{19}$F NMR (282 MHz; d$_6$-DMSO) δ −165.7 (s), −120.9 (t); m/z=482.33 (M+H)⁺; rt=3.44 min (HPLC protocol-1).

Example 24

Resolution of (±)-N²-(4-cyclopropyl-2-fluoro-5-(1H-tetrazol-1-yl)phenyl)-5-fluoro-N⁴-(octahydro-5,5-dimethylindolizin-7-yl)pyrimidine-2,4-diamine (Compounds 54 and 55)

A small quantity of racemic N²-(4-cyclopropyl-2-fluoro-5-(1H-tetrazol-1-yl)phenyl)-5-fluoro-N⁴-(octahydro-5,5-dimethylindolizin-7-yl)pyrimidine-2,4-diamine (40 mg) was purified by chiral high-performance liquid chromatography using the conditions below to give individual enantiomers.

Chiral HPLC Conditions:
Column: Daicel Chemical Industries, Chiracel OJ 4.6×250 mm
Mobile phase: 1:1 MeOH/EtOH containing 0.1% diethylamine
Flow rate: 0.5 ml/min
Run time: 30 minutes
Temperature: room temperature
Detection: Waters 996 PDA
HPLC: Waters 2690 Separations Module Compound 54

Retention time of first eluting isomer=9.30 min (15 mg); Data for first eluting enantiomer from chiral column: $^1$H NMR (300 MHz; d$_6$-DMSO) δ 9.87 (s, 1H), 8.59 (br. s, 1H), 8.08 (d, J=7.5 Hz, 1H), 7.83 (d, J=3.7 Hz, 1H), 7.33-7.24 (br. s, 1H), 7.09 (d, J=12.2 Hz, 1H), 4.03-3.87 (m, 1H), 2.86-2.72 (m, 1H), 2.29-2.14 (m, 1H), 2.00-1.83 (m, 2H), 1.73-1.36 (m, 6H), 1.22-1.03 (m, 5H), 0.78-0.66 (m, 5H), 0.64-0.56 (m, 2H); $^{19}$F NMR (282 MHz; d$_6$-DMSO) δ −165.7, −120.8; m/z=482.44 (M+H)⁺; rt=3.58 min (HPLC protocol-1).

Compound 55

Retention time for second eluting isomer=11.74 min (18 mg); Data same as for 1$^{st}$ eluting isomer.

Example 25

Synthesis of (±)-2-(4-cyclopropyl-2-fluoro-5-(1H-tetrazol-1-yl)phenylamino)-4-(octahydro-5,5-dimethylindolizin-7-ylamino)pyrimidine-5-carbonitrile (Compound 56)

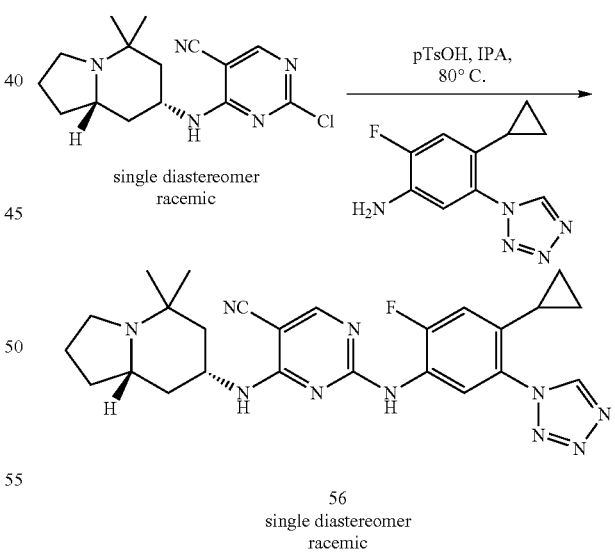

A mixture of (±)-2-chloro-4-(octahydro-5,5-dimethylindolizin-7-ylamino)pyrimidine-5-carbonitrile (60 mg of 70% pure material from previous step), 4-cyclopropyl-2-fluoro-5-(1H-tetrazol-1-yl)benzeneamine (65 mg, 0.3 mmol; prepared according to U.S. patent application Ser. No. 13/188,222, filed Jul. 21, 2011, now U.S. patent application publication US2012/0022092) and para-toluenesulfonic acid monohydrate (37 mg, 0.2 mmol) in isopropyl alcohol (3 ml) were combined in a sealed vial, heated to 80° C. and stirred for 4 hours. After cooling, a precipitate emerged which was filtered. The filter cake was suspended in EtOAc (30 ml) and 1N NaOH (50 ml). The aqueous and organic layers were partitioned and the aqueous layer was extracted with EtOAc (2×25 ml). The combined organic extracts were dried (MgSO$_4$), filtered and the solvent removed under vacuum to leave a solid. The solid was freeze-dried from MeCN/H$_2$O to give the product (26 mg) as a solid.

$^1$H NMR (300 MHz; d$_6$-DMSO) δ 9.85 (m, 1H), 9.51 (br. s, 1H), 8.30 (s, 1H), 7.80 (d, J=7.3 Hz, 1H), 7.44 (d, J=7.3 Hz, 1H), 7.14 (d, J=11.8 Hz, 1H), 4.08-3.89 (m, 1H), 2.83-2.71 (m, 1H), 2.28-2.13 (m, 1H), 2.06-1.88 (m, 1H), 1.84-1.73 (m, 1H), 1.71-1.50 (m, 3H), 1.47-1.34 (m, 2H), 1.21-1.07 (m, 3H), 1.00 (s, 3H), 0.75-0.59 (m, 7H); $^{19}$F NMR (282 MHz; d$_6$-DMSO) δ −117.3 (t); m/z=489.34 (M+H)$^+$; rt=4.01 min (HPLC protocol-1).

Example 26

Synthesis of N2-(4-cyclopropyl-2-fluoro-5-(4,5-dihydro-4-methyl-5-oxotetrazol-yl)phenylamino)-5-fluoro-N4-(Octahydro-5,5-dimethylindolizin-7-ylamino) pyrimidine-2,4-diamine (Compound 26)

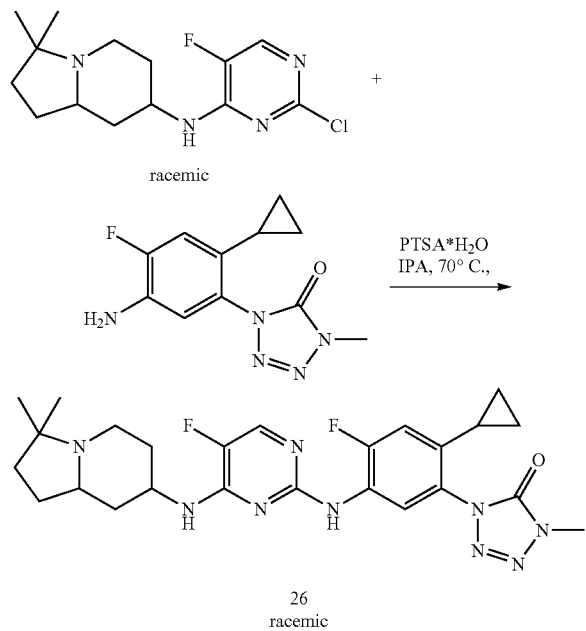

A mixture of N-(2-chloro-5-fluoropyrimidin-4-yl)-octahydro-3,3-dimethylindolizin-7-amine (Diastereomer D1 97% dr; 52 mg, 0.174 mmol, 1 equiv), 1-(5-amino-2-cyclopropyl-4-fluorophenyl)-4-methyl-1H-tetrazol-5(4H)-one (Described in: WO 2011/068898, which is hereby incorporated by reference in its entirety. 43 mg, 0.174 mmol, 1 equiv), and PTSA monohydrate (33 mg, 0.174 mmol, 1 equiv) in IPA (1 ml) were heated to 100° C. for 4 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one (Compound 26) (>90% dr, 53 mg, 60%) as a solid.

$^1$H NMR (300 MHz; d$_6$-DMSO) δ 8.59 (s, 1H), 8.10-8.09 (d, J=8.4 Hz), 7.85-7.86 (d, J=3.6 Hz), 6.95-7.00 (m, 2H), 4.11 (bs, 1H), 3.62 (s, 1H), 2.42-2.71 (m, 2H), 1.49-2.00 (m, 8H), 1.01-1.22 (m, 2H), 1.03-1.06 (m, 3H), 0.823-0.871 (m, 5H), 0.630-0.645 (m, 2H); $^{19}$F NMR (282 MHz; d$_6$-DMSO) δ −122.0 (t), −164.7 (s); m/z=512 (M+H)$^+$.

Example 27

Chiral HPLC resolution of 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one (Compounds 34 and 35)

Chiral HPLC resolution of 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one (Compound 26) (>90% dr, 35 mg) to enantiomers was performed.

Chiral HPLC method: Column: Chiralcel-OJ, 4.6×250 mm, with guard. Mobil phase: 95% Hexane, 2.4% methanol, 2.5% ethanol 0.1% triethylamine. Flow rate: 0.5 ml/min. Injection volume: 3 μL. Concentration: approx 5 mg/ml. Detection: UV at 254 nm.

Compound 34

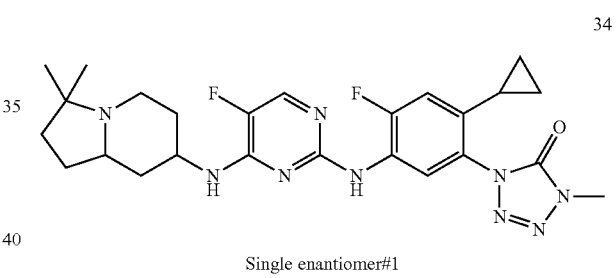

Single enantiomer#1

Compound 34: (>99% ee, 9.5 mg) has Rt=21.86 min.

$^1$H NMR (300 MHz; d$_6$-DMSO) δ 8.59 (s, 1H), 8.10-8.09 (d, J=8.4 Hz), 7.85-7.86 (d, J=3.6 Hz), 6.95-7.00 (m, 2H), 4.11 (bs, 1H), 3.62 (s, 1H), 2.42-2.71 (m, 2H), 1.49-2.00 (m, 8H), 1.01-1.22 (m, 2H), 1.03-1.06 (m, 3H), 0.823-0.871 (m, 5H), 0.630-0.645 (m, 2H); $^{19}$F NMR (282 MHz; d$_6$-DMSO) δ −122.0 (t), −164.7 (s); m/z=512 (M+H)$^+$.

Compound 35

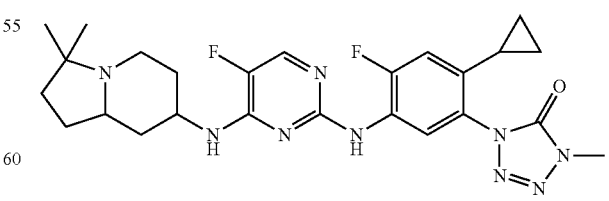

Single enantiomer#2

Compound 35: (>97% ee, 10.7 mg) has Rt=26.56 min.

$^1$H NMR (300 MHz; d$_6$-DMSO) δ 8.59 (s, 1H), 8.10-8.09 (d, 1H, J=8.4 Hz), 7.85-7.86 (d, 1H, J=3.6 Hz), 6.95-7.00

(m, 2H), 4.11 (bs, 1H), 3.62 (s, 1H), 2.42-2.71 (m, 2H), 1.49-2.00 (m, 8H), 1.01-1.22 (m, 2H), 1.03-1.06 (m, 3H), 0.823-0.871 (m, 5H), 0.630-0.645 (m, 2H); $^{19}$F NMR (282 MHz; d$_6$-DMSO) δ −122.0 (t), −164.7 (s); m/z=512 (M+H)$^+$.

Example 28

Synthesis of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one (Compounds 31-33)

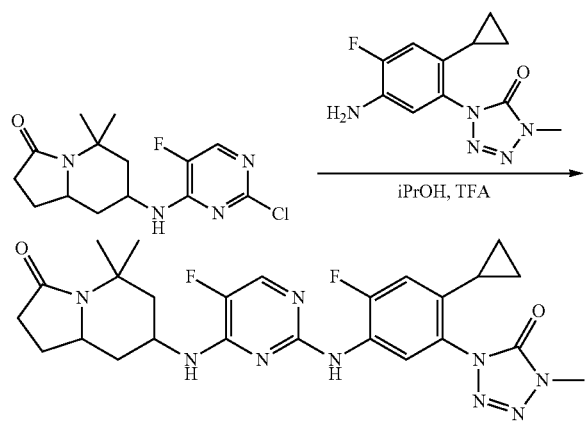

Preparation of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one (Compound 31)

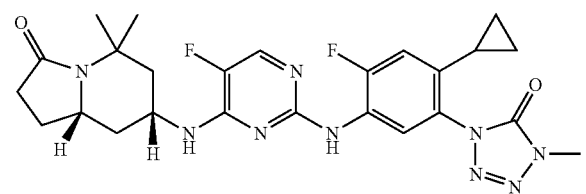 [SMILES: Cn1nnn(-c2cc(Nc3ncc(F)c(N[C@@H]4C[C@@H]5CCC(=O)N5C(C)(C)C4)n3)c(F)cc2C2CC2)c1=O]

A mixture of 7-(2-chloro-5-fluoropyrimidin-4-ylamino)-hexahydro-5,5-dimethylindolizin-3(5H)-one isomer A (cis) (50 mg), 1-(5-amino-2-cyclopropyl-4-fluorophenyl)-4-methyl-1H-tetrazol-5(4H)-one (50 mg) and TFA (5 drops) in isopropanol (1 ml) was heated at 100° C. overnight in a sealed vial. After allowing to cool to room temperature, the solvent was removed in vacuo and the residue was purified by Combiflash chromatography (2.0 M ammonia methanol in dichloromethane=0-30%) to give product as racemic mixture.

$^1$H NMR (300 MHz; d$_6$-DMSO) δ 8.55 (s, 1H), 7.88 (d, J=7.8 Hz, 1H), 7.85 (d, J=3.9 Hz, 1H), 7.34 (d, J=7.8 Hz, 1H), 7.00 (d, J=12.0 Hz, 1H), 4.06-4.04 (m, 1H), 3.59 (s, 3H), 2.14-1.94 (m, 5H), 1.64-1.59 (m, 1H), 1.56 (s, 3H), 1.48-1.12 (m, 4H), 1.02 (s, 3H), 0.81 (dd, J=2.1, 8.7 Hz, 2H), 0.61 (q, J=4.5 Hz, 2H); LC-MS: purity: 97.99%; MS (m/e): 526.39 (M+H)$^+$; m/z=524.33 (M−H)$^+$.

Preparation of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one (Compound 32)

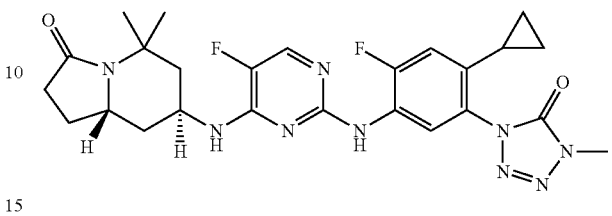

A mixture of 7-(2-chloro-5-fluoropyrimidin-4-ylamino)-hexahydro-5,5-dimethylindolizin-3(5H)-one isomer B (trans) (100 mg), 1-(5-amino-2-cyclopropyl-4-fluorophenyl)-4-methyl-1H-tetrazol-5(4H)-one (100 mg) and TFA (5 drops) in isopropanol (1 ml) was heated at 100° C. overnight in a sealed vial. After allowing to cool to room temperature, the solvent was removed in vacuo and the residue was purified by Combiflash chromatography (2.0 M ammonia methanol in dichloromethane=0-30%) to give product as racemic mixture.

$^1$H NMR (300 MHz; d$_6$-DMSO) δ 8.64 (s, 1H), 8.03 (d, J=7.8 Hz, 1H), 7.88 (d, J=3.9 Hz, 1H), 7.57 (d, J=5.7 Hz, 1H), 6.99 (d, J=12.3 Hz, 1H), 4.22 (m, 1H), 3.89 (m, 1H), 3.59 (s, 3H), 2.26-1.53 (m, 9H), 1.32 (s, 3H), 1.24 (s, 3H), 0.81 (d, J=8.4 Hz, 2H), 0.62 (d, J=3.3 Hz, 2H); LC-MS: purity: 98.22%; MS (m/e): 526.37 (M+H)$^+$; m/z=524.41 (M−H)$^+$.

Preparation of 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one formate (Compound 33)

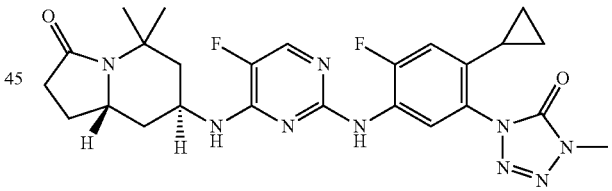

$^1$H NMR (300 MHz; d$_6$-DMSO) δ 8.58 (s, 1H), 8.04 (d, J=7.8 Hz, 1H), 7.86 (d, J=3.9 Hz, 1H), 7.50 (d, J=7.2 Hz, 1H), 6.99 (d, J=12.3 Hz, 1H), 4.21 (m, 1H), 3.90 (m, 1H), 3.59 (s, 3H), 2.26-1.54 (m, 9H), 1.32 (s, 3H), 1.25 (s, 3H), 0.81 (d, J=8.1 Hz, 2H), 0.61 (d, J=3.6 Hz, 2H); LC-MS: purity: 98.65%; MS (m/e): 526.37 (M+H)$^+$; m/z=524.37 (M−H)$^+$.

Example 29

Preparation of Anilines for Synthesis of Compounds

Certain anilines for the synthesis of the present compounds were prepared as illustrated in the scheme below:

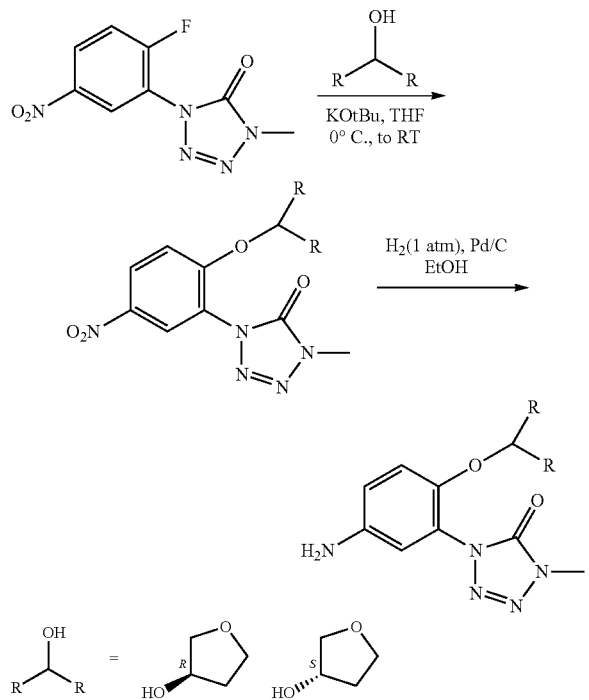

Preparation of 1-(2-((R)-Tetrahydrofuran-3-yloxy)-5-nitrophenyl)-4-methyl-1H-tetrazol-5(4H)-one (R)-(−)-3-Hydroxytetrahydrofuran (440 mg, 5 mmol, 2 equiv) in THF (15 ml) under argon gas, was cooled to 0° C. Potassium tert-butoxide (617 mg, 5.5 mmol, 2.2 equiv) was added in one portion, and the reaction mixture was stirred for 20 minutes at 0° C. Then 1-(2-fluoro-5-nitrophenyl)-4-methyl-1H-tetrazol-5(4H)-one (Described in: WO 2011/068898. 598 mg, 2.5 mmol, 1 equiv) was added in one portion, and the reaction mixture was stirred for 10 minutes at 0° C. and allowed to warm up to ambient temperature over 2 hours. The reaction mixture was concentrated, and the residue was taken in DCM and water. The layers were separated, and the organic layer was washed with water (×2), dried over $Na_2SO_4$, filtered, and concentrated to provide 1-(2-((R)-tetrahydrofuran-3-yloxy)-5-nitrophenyl)-4-methyl-1H-tetrazol-5(4H)-one (723 mg, 94%) as a yellow solid that was used without further purification.

$^1$H NMR (300 MHz; $d_6$-DMSO) δ 8.41-8.47 (m, 2H), 7.51-7.54 (d, 1H, J=9 Hz), 5.31-5.4 (t, 1H, J=3.6 Hz), 3.88-3.93 (dd, 1H, J=4.2 Hz, J=10.5 Hz), 3.70-3.74 (m, 3H), 3.62 (s, 3H), 2.20-2.27 (m, 1H), 1.89-1.93 (m, 1H); m/z=308 $(M+H)^+$.

Preparation of 1-(2-((S)-Tetrahydrofuran-3-yloxy)-5-nitrophenyl)-4-methyl-1H-tetrazol-5(4H)-one (S)-(+)-3-Hydroxytetrahydrofuran (440 mg, 5 mmol, 2 equiv) in THF (15 ml) under argon gas, was cooled to 0° C. Potassium tert-butoxide (617 mg, 5.5 mmol, 2.2 equiv) was added in one portion, and the reaction mixture was stirred for 20 minutes at 0° C. Then, fluoro tetrazole (598 mg, 2.5 mmol, 1 equiv) was added in one portion, and the reaction mixture was stirred for 10 minutes at 0° C. and allowed to warm up to ambient temperature over 2 hours. The reaction mixture was concentrated, and the residue was taken in DCM and water. The layers were separated, and the organic layer was washed with water (×2), dried over $Na_2SO_4$, filtered, and concentrated to provide 1-(2-((S)-tetrahydrofuran-3-yloxy)-5-nitrophenyl)-4-methyl-1H-tetrazol-5(4H)-one (764 mg, 98%) as a yellow solid that was used without further purification.

$^1$H NMR (300 MHz; $d_6$-DMSO) δ 8.41-8.47 (m, 2H), 7.51-7.54 (d, 1H, J=9 Hz), 5.31-5.4 (t, 1H, J=3.6 Hz), 3.88-3.93 (dd, 1H, J=4.2 Hz, J=10.5 Hz), 3.70-3.74 (m, 3H), 3.62 (s, 3H), 2.20-2.27 (m, 1H), 1.89-1.93 (m, 1H); m/z=308 $(M+H)^+$.

Preparation of 1-(2-((R)-Tetrahydrofuran-3-yloxy)-5-aminophenyl)-4-methyl-1H-tetrazol-5(4H)-one A round-bottom flask was charged with 1-(2-((R)-tetrahydrofuran-3-yloxy)-5-nitrophenyl)-4-methyl-1H-tetrazol-5(4H)-one (723 mg, 2.35 mmol), EtOH (25 ml), and 10% Pd/C (50% in water, Degussa type E101; 145 mg, 20 wt % by weight of the starting nitro compound) giving a suspension. The flask was sealed with a rubber septum, degassed, and back-filled with $H_2$ (×3) from a balloon filled with $H_2$. The reaction mixture was stirred for 2 hours using a $H_2$ filled balloon. The reaction mixture was filtered through a pad of Celite, and the pad of Celite was rinsed with MeOH. The filtrate was evaporated to dryness to provide 1-(2-((R)-tetrahydrofuran-3-yloxy)-5-aminophenyl)-4-methyl-1H-tetrazol-5(4H)-one (646 mg, 99%) as a dark-brown solid that was used without further purification.

$^1$H NMR (300 MHz; $d_6$-DMSO) δ 6.96-6.99 (m, 1H), 6.89-6.73 (m, 1H), 6.55-6.60 (m, 1H), 5.06 (bs, 2H), 4.77-4.85 (m, 1H), 3.55-3.77 (m, 7H), 1.94-2.03 (m, 1H), 1.78-1.86 (m, 1H); m/z=278 $(M+H)^+$.

Preparation of 1-(2-((S)-Tetrahydrofuran-3-yloxy)-5-aminophenyl)-4-methyl-1H-tetrazol-5(4H)-one A round-bottom flask was charged with 1-(2-((S)-tetrahydrofuran-3-yloxy)-5-nitrophenyl)-4-methyl-1H-tetrazol-5(4H)-one (764 mg, 2.49 mmol), EtOH (25 ml), and 10% Pd/C (50% in water, Degussa type E101; 153 mg, 20 wt % by weight of the starting nitro compound) giving a suspension. The flask was sealed with a rubber septum, degassed, and back-filled with $H_2$ (×3) from a balloon filled with $H_2$. The reaction mixture was stirred for 2 hours using a $H_2$ filled balloon. The reaction mixture was filtered through a pad of Celite, and the pad of Celite was rinsed with MeOH. The filtrate was evaporated to dryness to provide 1-(2-((S)-tetrahydrofuran-3-yloxy)-5-aminophenyl)-4-methyl-1H-tetrazol-5(4H)-one (677 mg, 98%) as a dark-brown solid that was used without further purification.

$^1$H NMR (300 MHz; $d_6$-DMSO) δ 6.96-6.99 (m, 1H), 6.89-6.73 (m, 1H), 6.55-6.60 (m, 1H), 5.06 (bs, 2H), 4.77-4.85 (m, 1H), 3.55-3.77 (m, 7H), 1.94-2.03 (m, 1H), 1.78-1.86 (m, 1H); m/z=278 $(M+H)^+$.

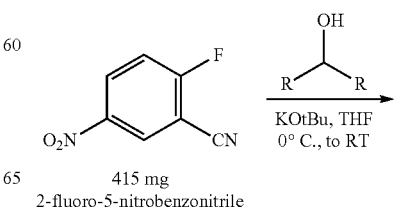

415 mg
2-fluoro-5-nitrobenzonitrile

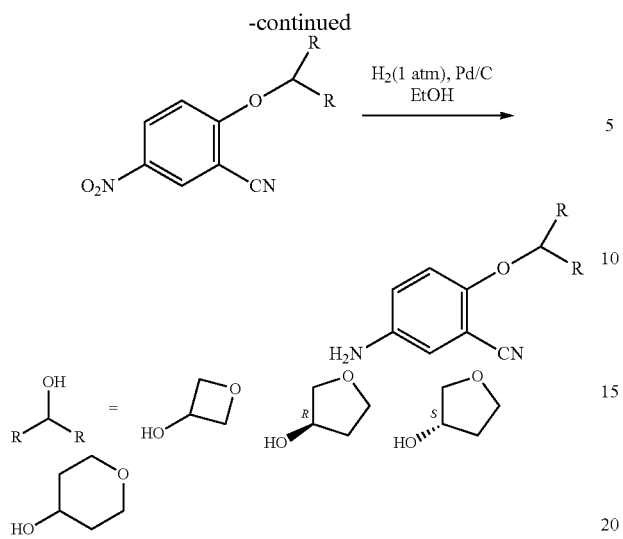

Preparation of 5-Nitro-2-(oxetan-3-yloxy)benzonitrile

General procedure: 3-Hydroxy oxetane (370 mg, 5 mmol, 2 equiv) in THF (15 ml) under argon gas, was cooled to 0° C. Potassium tert-butoxide (617 mg, 5.5 mmol, 2.2 equiv) was added in one portion, and the reaction mixture was stirred for 20 minutes at 0° C. Then 2-fluoro-5-nitrobenzonitrile (415 mg, 2.5 mmol, 1 equiv) was added in one portion, and the reaction mixture was stirred for 10 minutes at 0° C. and allowed to warm up to ambient temperature over 1 hour. The reaction mixture was concentrated, and the residue was taken in DCM and water. The layers were separated, and the organic layer was washed with water (×2), dried over $Na_2SO_4$, filtered, and concentrated to provide 5-nitro-2-(oxetan-3-yloxy)benzonitrile (495 mg, 90%) as a brown-yellow solid that was used without further purification.

$^1$H NMR (300 MHz; $d_6$-DMSO) δ 8.74-8.75 (m, 1H), 8.42-8.47 (m, 1H), 7.09-7.12 (dd, 1H, J=0.9 Hz, J=9.3 Hz), 5.56-5.63 (m, 1H), 4.96-5.00 (m, 2H), 4.59-4.63 (m, 2H); m/z=221 (M+H)$^+$.

Following the general procedure described above, the following compounds were prepared:

Preparation of 2-((R)-tetrahydrofuran-3-yloxy)-5-nitrobenzonitrile (544 mg, 93%) from (R)-(−)-3-hydroxytetrahydrofuran. $^1$H NMR (300 MHz; $d_6$-DMSO) δ 8.67-8.71 (m, 1H), 8.46-8.50 (m, 1H), 7.45-7.48 (d, 1H, J=9.6 Hz), 5.33-5.40 (m, 1H), 3.74-3.95 (m, 4H), 2.27-2.40 (m, 1H), 1.89-2.06 (m, 1H); m/z=235 (M+H)$^+$.

Preparation of 2-((S)-Tetrahydrofuran-3-yloxy)-5-nitrobenzonitrile (544 mg, 93%) from S)-(+)-3-hydroxytetrahydrofuran. $^1$H NMR (300 MHz; $d_6$-DMSO) δ 8.67-8.71 (m, 1H), 8.46-8.50 (m, 1H), 7.45-7.48 (d, 1H, J=9.6 Hz), 5.33-5.40 (m, 1H), 3.74-3.95 (m, 4H), 2.27-2.40 (m, 1H), 1.89-2.06 (m, 1H); m/z=235 (M+H)$^+$.

Preparation of 5-Nitro-2-(tetrahydro-2H-pyran-4-yloxy)benzonitrile (510 mg, 82%) from 4-hydroxytetrahydropyran. $^1$H NMR (300 MHz; $d_6$-DMSO) δ 8.68-8.69 (d, 1H, J=3 Hz), 8.43-8.47 (m, 1H), 7.56-7.59 (d, 1H, J=9.3 Hz), 4.97-5.05 (m, 1H), 3.82-3.87 (m, 2H), 3.50-3.60 (m, 2H), 1.99-2.06 (m, 2H), 1.62-1.72 (m, 2H); m/z=248 (M+H)$^+$.

Preparation of 5-Amino-2-(oxetan-3-yloxy)benzonitrile

General procedure: A round-bottom flask was charged with 5-nitro-2-(oxetan-3-yloxy)benzonitrile (495 mg, 2.25 mmol), EtOH (20 ml), and 10% Pd/C (50% in water, Degussa type E101; 100 mg, 20 wt % by weight of the starting nitro compound) giving a suspension. The flask was sealed with a rubber septum, degassed, and back-filled with $H_2$ (×3) from a balloon filled with $H_2$. The reaction mixture was stirred for 1 hour using a $H_2$ filled balloon. The reaction mixture was filtered through a pad of Celite, and the pad of Celite was rinsed with MeOH. The filtrate was evaporated to dryness to provide 5-amino-2-(oxetan-3-yloxy)benzonitrile (420 mg, 98%) as a pale yellow solid that was used without further purification.

$^1$H NMR (300 MHz; $d_6$-DMSO) δ 6.77-6.81 (m, 2H), 6.53-6.60 (m, 1H), 5.18-5.25 (p, 1H, J=6 Hz), 5.12 (bs, 2H), 4.84-4.89 (t, 2H, J=6.3 Hz), 4.50-4.51 (t, 2H, J=6.2 Hz); m/z=191 (M+H)$^+$.

Following the general procedure described above, the following compounds were prepared:

Preparation of 2-((R)-Tetrahydrofuran-3-yloxy)-5-aminobenzonitrile (465 mg, 98%) from 2-((R)-tetrahydrofuran-3-yloxy)-5-nitrobenzonitrile. $^1$H NMR (300 MHz; $d_6$-DMSO) δ 6.90-6.99 (m, 1H), 6.77-6.85 (m, 2H), 5.10 (bs, 2H), 4.93-4.99 (m, 1H), 3.70-3.87 (m, 4H), 2.07-2.19 (m, 1H), 1.89-1.96 (m, 1H); m/z=205 (M+H)$^+$.

Preparation of 2-((S)-Tetrahydrofuran-3-yloxy)-5-aminobenzonitrile (466 mg, 98%) from 2-((S)-tetrahydrofuran-3-yloxy)-5-nitrobenzonitrile. $^1$H NMR (300 MHz; $d_6$-DMSO) δ 6.90-6.99 (m, 1H), 6.77-6.85 (m, 2H), 5.10 (bs, 2H), 4.93-4.99 (m, 1H), 3.70-3.87 (m, 4H), 2.07-2.19 (m, 1H), 1.89-1.96 (m, 1H); m/z=205 (M+H)$^+$.

Preparation of 5-Amino-2-(tetrahydro-2H-pyran-4-yloxy)benzonitrile (361 mg, 81%) from 5-Nitro-2-(tetrahydro-2H-pyran-4-yloxy)benzonitrile. $^1$H NMR (300 MHz; $d_6$-DMSO) δ 7.00-7.03 (d, 1H, J=8.7 Hz), 6.73-6.84 (m, 2H), 5.11 (bs, 2H), 4.42-4.48 (m, 1H), 3.79-3.85 (m, 2H), 3.40-3.47 (m, 2H), 1.86-1.98 (m, 2H), 1.50-1.61 (m, 2H); m/z=219 (M+H)$^+$.

Preparation of 4-fluoro-2-isopropoxy-1-nitrobenzene

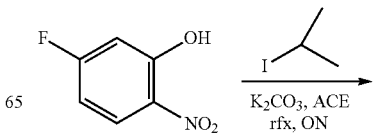

-continued

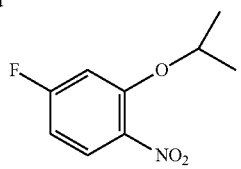

A mixture of 5-fluoro-2-nitrophenol (50.0 g, 318 mmol, 1 equiv), 2-iodopropane (96.0 mL, 955 mmol, 3 equiv), and $K_2CO_3$ (132.0 g, 955 mmol, 3 equiv) in acetone (1 L) was heated to reflux for ON. After cooling to RT, the solid was filtered-off and rinsed with DCM, then the filtrate was concentrated to dryness. The residue was taken in water, EtOAc, and 1N NaOH. The layers were separated, and the organic layer was washed with 1N NaOH 1×. The organic layer was dried over $Na_2SO_4$, filtered, and concentrated to dryness to provide 4-fluoro-2-isopropoxy-1-nitrobenzene (49.3 g, 78%) as a yellow-brown liquid that was used without further purification. $^1$H NMR (300 MHz; $d_6$-DMSO) δ 7.91-7.96 (dd, 1H, J=6.3 Hz, 9.0 Hz), 7.31-7.35 (dd, 1H, J=2.4 Hz, 11 Hz), 6.88-6.95 (m, 1H), 4.77-4.89 (hep, 1H, J=6.0 Hz), 1.27-1.29 (d, 6H, J=6.0 Hz); $^{19}$F NMR (282 MHz; $d_6$-DMSO) δ −102.4 (sextet); m/z=200 (M+H)$^+$.

Preparation of 4-fluoro-2-isopropoxybenzenamine

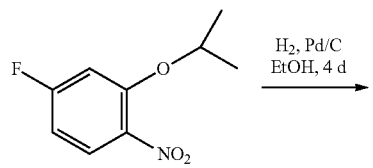

A round-bottom flask was charged with 4-fluoro-2-isopropoxy-1-nitrobenzene (49.3 g, 248 mmol), EtOH (600 mL), and 10% Pd/C (50% in water, Degussa type E101; 10 g, 20 wt % by weight of the starting nitro compound). The flask was sealed with a rubber septum, degassed, and back-filled with $H_2$ (×3) from a balloon filled with $H_2$. The reaction was stirred for 4 d using a $H_2$ filled balloon. The reaction mixture was filtered through a pad of celite, and the pad of celite was rinsed with MeOH. The filtrate was evaporated to dryness to provide 4-fluoro-2-isopropoxybenzenamine (41.0 g, 98%) as a brown liquid that was used without further purification. $^1$H NMR (300 MHz; $d_6$-DMSO) δ 6.67-6.72 (dd, 1H, J=2.7Hz, 11Hz), 6.55-6.60 (dd, 1H, J=6.0Hz, 8.7Hz), 6.43-6.49 (td, 1H, J=2.7Hz, 8.4Hz), 4.47-4.55 (m, 3H), 1.23-1.25 (d, 6H, J=6.0Hz); $^{19}$F NMR (282 MHz; $d_6$-DMSO) δ −127.4 (sextet); m/z=170 (M+H)$^+$.

Preparation of 1-(4-fluoro-2-isopropoxyphenyl)-1H-tetrazol-5(4H)-one

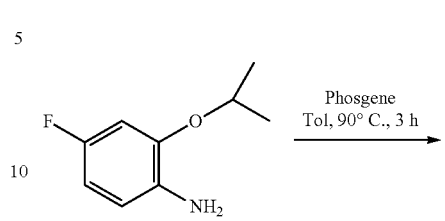

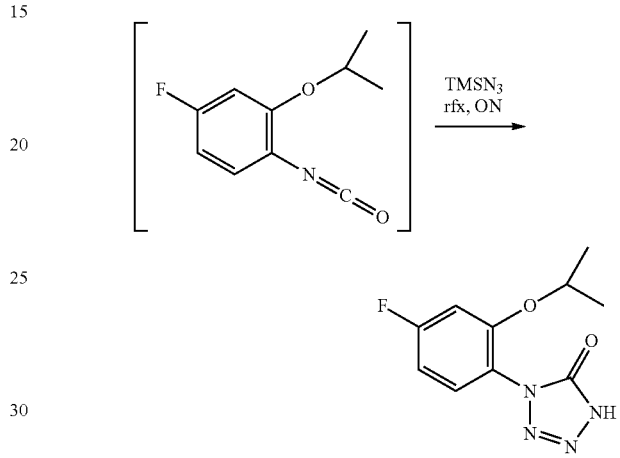

Step 1: Phosgene (20% in toluene; 63 mL, 118.2 mmol, 2 equiv) was cooled to −10° C. (ice/MeOH) under argon. Then 4-fluoro-2-isopropoxybenzenamine (10.0 g, 59.1 mmol, 1 equiv) was added dropwise, and the reaction mixture was stirred at −10° C. for 15 min then heated to 90° C. for 3 h under argon. After cooling, the reaction mixture was evaporated to dryness, and the crude 4-fluoro-1-isocyanato-2-isopropoxybenzene was dried in vacuo.

Step 2: This reaction with TMS-$N_3$ was performed behind a blast shield. The crude 4-fluoro-1-isocyanato-2-isopropoxybenzene was placed under argon and trimethylsilylazide (16 mL, 118.2 mmol, 2 equiv) was added. The reaction mixture was heated to refluxed for ON under argon. After cooling to RT, the reaction mixture was concentrated under vacuum, and the residue was charged with saturated $NaHCO_3$ (100 mL) and stirred vigorously for 5-10 min, then the basic reaction mixture was diluted with EtOAc. The layers were separated, and the organic layer was monitored by TLC to confirm that all the product had been extracted by the saturated $NaHCO_3$ solution. EtOAc was added to the combined basic aqueous extracts, and the pH was adjusted to <3 using 6N HCl. The aqueous and organic layers were partitioned, and the aqueous layer was extracted with EtOAc 3×. The combined organic layers were dried over $Na_2SO_4$, filtered, and the solvent removed under vacuum to provide 1-(4-fluoro-2-isopropoxyphenyl)-1H-tetrazol-5(4H)-one (11.4 g, 81%) as a brown oil that was used without further purification. $^1$H NMR (300 MHz; $d_6$-DMSO) δ 7.47-7.52 (dd, 1H, J=6.0Hz, 8.4Hz), 7.19-7.24 (dd, 1H, J=2.7Hz, 12Hz), 6.87-6.94 (td, 1H, J=2.7Hz, 8.1Hz), 4.63-4.75 (d, 6H, J=6.0Hz), 1.17-1.19 (d, 6H, J=6.0Hz); $^{19}$F NMR (282 MHz; $d_6$-DMSO) δ −107.2 (q); m/z=238 (M+H)$^+$.

Preparation of 1-(4-fluoro-2-isopropoxyphenyl)-4-methyl-1H-tetrazol-5(4H)-one

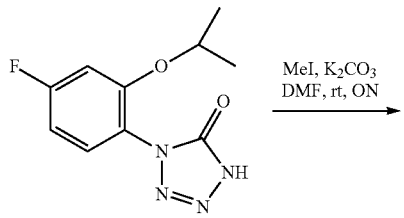

A mixture of 1-(4-fluoro-2-isopropoxyphenyl)-1H-tetrazol-5(4H)-one (4.10 g, 17.2 mmol, 1 equiv), K$_2$CO$_3$ (7.15 g, 52.0 mmol, 3 equiv), and iodomethane (3.25 mL, 52.0 mmol, 3 equiv) in DMF (40 mL) was stirred at RT ON. The reaction mixture was partitioned between water and EtOAc, then the layers were separated. The aqueous layer was extracted with EtOAc 2×, and the combined organic layer was washed with brine 1×. The organic layer was dried over Na$_2$SO$_4$, filtered, and concentrated to dryness to provide 1-(4-fluoro-2-isopropoxyphenyl)-4-methyl-1H-tetrazol-5(4H)-one (3.50 g, 81%) as a brown oil that was used without further purification. $^1$H NMR (300 MHz; d$_6$-DMSO) δ 7.46-7.51 (dd, 1H, J=6.3Hz, 8.4Hz), 7.20-7.25 (dd, 1H, J=2.7Hz, 11Hz), 6.87-6.94 (td, 1H, J=2.7Hz, 8.1Hz), 4.63-4.75 (hept, 1H, J=6.0Hz), 3.59 (s, 3H), 1.16-1.18 (d, 6H, J=6.0Hz); $^{19}$F NMR (282 MHz; d$_6$-DMSO) δ −107.0 (sextet); m/z=253 (M+H)$^+$.

Preparation of 1-(4-fluoro-2-hydroxy-5-nitrophenyl)-4-methyl-1H-tetrazol-5(4H)-one

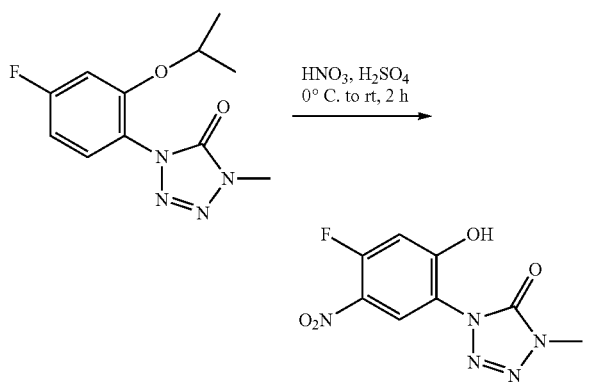

A solution of 1-(4-fluoro-2-isopropoxyphenyl)-4-methyl-1H-tetrazol-5(4H)-one (3.50 g, 13.9 mmol, 1 equiv) in H$_2$SO$_4$ (35 mL) was cooled in ice/water bath. To the cooled solution, was added HNO$_3$ (fuming >90%; 715 uL, 15.3 mmol, 1.1 equiv) dropwise, and the cooled reaction mixture was allowed to warm to RT over 2 h. The reaction mixture was quenched with ice, and extracted with EtOAc 3×. The organic layer was then extracted with saturated NaHCO$_3$ 3×. The basic aqueous layer was acidified to pH<3 with 6N HCl. Then, the acidic layer was extracted with EtOAc 3×, and the organic layer was dried over Na$_2$SO$_4$, filtered, and concentrated to dryness to provide 1-(4-fluoro-2-hydroxy-5-nitrophenyl)-4-methyl-1H-tetrazol-5(4H)-one (2.94 g, 83%) as brown solid that was used without further purification.

$^1$H NMR (300 MHz; d$_6$-DMSO) δ 12.5 (bs, 1H), 8.41-8.44 (d, 1H, J=8.7Hz), 7.04-7.08 (d, 1H, J=13Hz), 3.59 (s, 3H); $^{19}$F NMR (282 MHz; d$_6$-DMSO) δ −111.3 (q); m/z=256 (M+H)$^+$.

Preparation of 1-(5-amino-4-fluoro-2-hydroxyphenyl)-4-methyl-1H-tetrazol-5(4H)-one

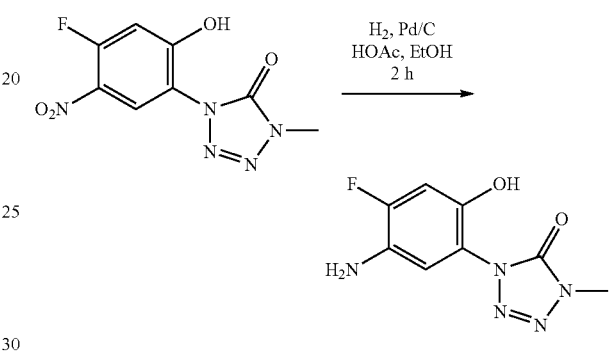

A round-bottom flask was charged with 1-(4-fluoro-2-hydroxy-5-nitrophenyl)-4-methyl-1H-tetrazol-5(4H)-one (500 mg, 1.96 mmol), EtOH (20 mL), HOAc (250 uL), and 10% Pd/C (50% in water, Degussa type E101; 100 mg, 20 wt % by weight of the starting nitro compound). The flask was sealed with a rubber septum, degassed, and back-filled with H$_2$ (×3) from a balloon filled with H$_2$. The reaction was stirred for 2 h using a H$_2$ filled balloon. The reaction mixture was filtered through a pad of celite, and the pad of celite was rinsed with MeOH. The filtrate was evaporated to dryness, and the product dried in vacuo with a water bath at 45° C. to remove any residual HOAc to provide 1-(5-amino-4-fluoro-2-hydroxyphenyl)-4-methyl-1H-tetrazol-5(4H)-one (437 mg, 99%) as a brown solid that was used without further purification. $^1$H NMR (300 MHz; d$_6$-DMSO) δ 9.46 (s, 1H), 6.67-6.72 (m, 2H), 4.80 (bs, 2H), 3.56 (s, 3H); $^{19}$F NMR (282 MHz; d$_6$-DMSO) δ −128.6 (t); m/z=225 (M+H)$^+$.

Example 30

Synthesis of 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compound 38)

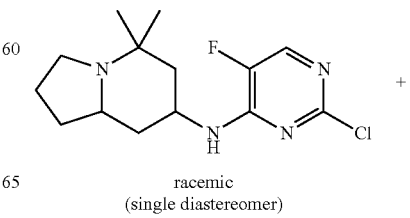

racemic
(single diastereomer)

+

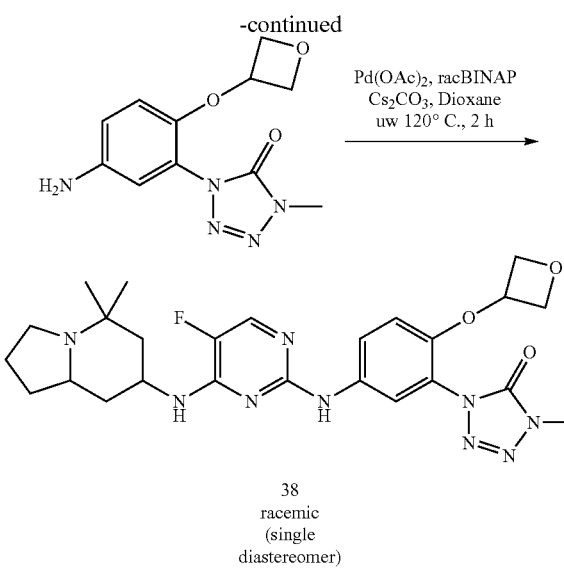

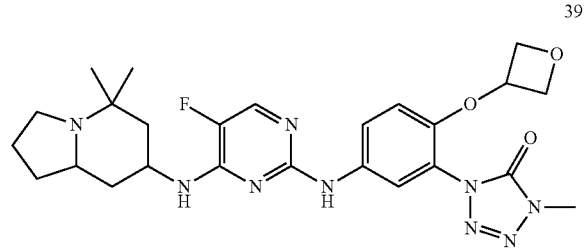

To a microwave vial, was added N-(2-chloro-5-fluoropyrimidin-4-yl)-octahydro-5,5-dimethylindolizin-7-amine (Racemic, single diastereomer; 100 mg, 0.335 mmol, 1 equiv), 1-(5-amino-2-(oxetan-3-yloxy)phenyl)-4-methyl-1H-tetrazol-5(4H)-one (Described in: WO2011/068898 120 mg, 0.455 mmol, 1.36 equiv), rac-BINAP (45 mg, 0.0726 mmol, 0.217 equiv), $Cs_2CO_3$ (327 mg, 1.00 mmol, 3 equiv), $Pd(OAc)_2$ (7 mg, 0.0291 mmol, 0.0870 equiv), and dioxane (4 ml). The microwave vial was capped and sonicated under vacuum for 5 minutes. The reaction mixture was heated in the microwave at 120° C. for 2 hours. The cooled reaction mixture was filtered using a pad of Celite and rinsed with dioxane, and the filtrate was concentrated. The crude product was purified by flash chromatography and eluted with DCM:2M $NH_3$/MeOH=100:0 to 95:5 using 1% 2M $NH_3$/MeOH increments to provide the desired product 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compound 38) (Racemic, single diastereomer; 90 mg, 51%) as a solid.

$^1$H NMR (300 MHz; $d_6$-DMSO) δ 9.21 (s, 1H), 8.06 (s, 1H), 7.83-7.84 (d, 1H, J=3.9Hz), 7.57-7.60 (dd, 1H, J=2.1Hz, J=8.7Hz), 7.23-7.26 (m, 1H), 6.80-6.83 (d, 1H, J=9.3Hz), 5.34-5.27 (p, 1H, J=6.3Hz), 4.79-4.84 (t, 2H, J=6Hz), 4.38-4.42 (t, 2H, J=5.7Hz), 4.04 (bs, 1H), 3.62 (s, 3H), 2.84 (bs, 1H), 1.89-2.42 (m, 4H), 1.13-1.74 (m, 5H), 1.06-1.13 (m, 4H), 0.815 (s, 3H); $^{19}$F NMR (282 MHz; $d_6$-DMSO) δ -166.5 (s); m/z=526 (M+H)$^+$.

Example 31

Chiral HPLC resolution of 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compounds 39-40)

Chiral HPLC resolution of compound 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one (Compound 38) (Racemic, single diastereomer, 55 mg) to enantiomers was performed.

Chiral HPLC method: Column: Chiralcel OJ-H, 4.6×250 mm, with guard. Mobil phase: 90% $CO_2$, 10% methanol w/0.1% triethylamine. Flow rate: 4 ml/min. Injection volume: 10 μL. Concentration: approx 5 mg/ml. Detection: UV at 254 nm.

Compound 39

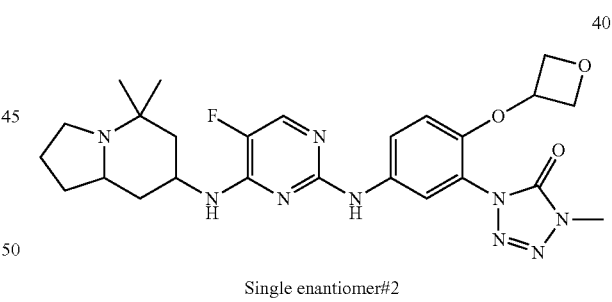

Single enantiomer#1

Compound 39: (>99% ee, 15 mg) has Rt=6.14 min.

$^1$H NMR (300 MHz; $d_6$-DMSO) δ 9.21 (s, 1H), 8.06 (s, 1H), 7.83-7.84 (d, 1H, J=3.9Hz), 7.57-7.60 (dd, 1H, J=2.1Hz, J=8.7Hz), 7.23-7.26 (m, 1H), 6.80-6.83 (d, 1H, J=9.3Hz), 5.34-5.27 (p, 1H, J=6.3Hz), 4.79-4.84 (t, 2H, J=6Hz), 4.38-4.42 (t, 2H, J=5.7Hz), 4.04 (bs, 1H), 3.62 (s, 3H), 2.84 (bs, 1H), 1.89-2.42 (m, 4H), 1.13-1.74 (m, 5H), 1.06-1.13 (m, 4H), 0.815 (s, 3H); $^{19}$F NMR (282 MHz; $d_6$-DMSO) δ -166.5 (s); m/z=526 (M+H)$^+$.

Compound 40

Single enantiomer#2

Compound 40: (>99% ee, 12 mg) has Rt=7.39 min.

$^1$H NMR (300 MHz; $d_6$-DMSO) δ 9.21 (s, 1H), 8.06 (s, 1H), 7.83-7.84 (d, 1H, J=3.9Hz), 7.57-7.60 (dd, 1H, J=2.1Hz, J=8.7Hz), 7.23-7.26 (m, 1H), 6.80-6.83 (d, 1H, J=9.3Hz), 5.34-5.27 (p, 1H, J=6.3Hz), 4.79-4.84 (t, 2H, J=6Hz), 4.38-4.42 (t, 2H, J=5.7Hz), 4.04 (bs, 1H), 3.62 (s, 3H), 2.84 (bs, 1H), 1.89-2.42 (m, 4H), 1.13-1.74 (m, 5H), 1.06-1.13 (m, 4H), 0.815 (s, 3H); $^{19}$F NMR (282 MHz; $d_6$-DMSO) δ -166.5 (s); m/z=526 (M+H)$^+$.

Example 32

Synthesis of 5-(5-fluoro-4-(octahydro-5,5-dimethyl-indolizin-7-ylamino)pyrimidin-2-ylamino)-2-(tetrahydro-2H-pyran-4-yloxy)benzonitrile (Compound 41)

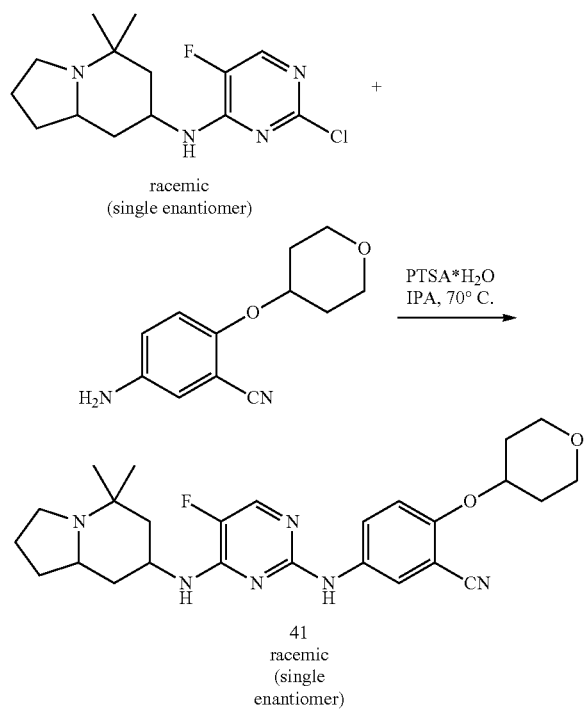

A mixture of N-(2-chloro-5-fluoropyrimidin-4-yl)-octahydro-5,5-dimethylindolizin-7-amine (Racemic, single diastereomer; 150 mg, 0.502 mmol, 1 equiv), 5-amino-2-(tetrahydro-2H-pyran-4-yloxy)benzonitrile (153 mg, 0.703 mmol, 1.4 equiv), and PTSA monohydrate (95 mg, 0.502 mmol, 1 equiv) in IPA (5 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 5-(5-fluoro-4-(octahydro-5,5-dimethylindolizin-7-ylamino)pyrimidin-2-ylamino)-2-(tetrahydro-2H-pyran-4-yloxy)benzonitrile (Compound 41) (Racemic, single diastereomer; 182 mg, 76%) as a solid.

$^1$H NMR (300 MHz; d$_6$-DMSO) δ 9.14 (s, 1H), 8.11-8.12 (d, 1H, J=2.4Hz), 7.84-7.86 (d, 1H, J=3.9Hz), 7.71-7.75 (dd, 2H, J=3Hz, J=9.3Hz), 7.28-7.19 (m, 2H), 4.62-4.67 (m, 1H), 4.14 (bs, 1H), 3.80-3.87 (m, 2H), 3.44-3.52 (m, 2H), 2.86 (bs, 1H), 2.31-2.55 (m, 1H), 1.08-2.06 (m, 15H), 0.985 (s, 3H); $^{19}$F NMR (282 MHz; d$_6$-DMSO) δ −166.3 (s); m/z=481 (M+H)$^+$.

Synthesis of Comnounds with 2,2-Difluoro-5,5-dimethyloctahydroindolizine

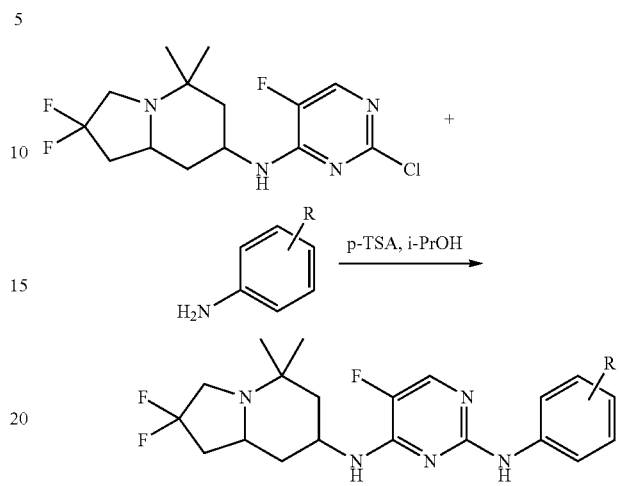

Typical procedures for final compounds synthesis: an i-PrOH (2 ml) solution of N-(2-chloro-5-fluoropyrimidin-4-yl)-2,2-difluoro-octahydro-5,5-dimethylindolizin-7-amine (33.5 mg, 0.1 mmol), aniline (0.14 mmol) and p-TSA-H$_2$O (28.5 mg, 0.15 mmol) was stirred at 90° C. for 15-96 hours until <5% of chloro-SM was detected by LC-MS. Solvent was removed in vacuo and the product was purified by RP-HPLC. Product was obtained as a formate salt and was free-based by following method: a MeOH solution of the salt was passed through a PL-HCO$_3$ column slowly, the column was further washed with MeOH, filtrate was collected and solvent was removed in vacuo to provide final desired products.

Example 33

Synthesis of 1-(5-(4-((7S,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 42)

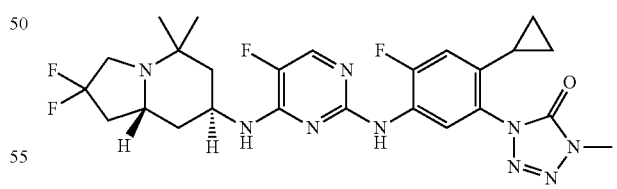

$^1$H NMR (300 MHz, CDCl$_3$) δ 8.57 (d, J=7.8 Hz, 1H), 7.80 (d, J=3.1 Hz, 1H), 7.06 (d, J=3.4 Hz, 1H), 6.87 (d, J=12.2 Hz, 1H), 5.08 (d, J=4.6 Hz, 1H), 4.35-4.29 (m, 1H), 3.74 (s, 3H), 3.34 (ddd, J=14.3, 10.6, 6.9 Hz, 1H), 3.01-2.92 (m, 1H), 2.81 (ddd, J=19.3, 15.3, 10.8 Hz, 1H), 2.42-2.28 (m, 1H), 2.11-2.07 (m, 1H), 2.02-1.79 (m, 3H), 1.70 (dd, J=14.4, 4.5 Hz, 1H), 1.59-1.49 (m, 1H, overlapped with water peak), 1.12 (s, 6H), 0.87-0.81 (m, 2H), 0.60-0.55 (m, 2H); LRMS (M+H) m/z 548.34.

Example 34

Synthesis of N²-(4-cyclopropyl-2-fluoro-5-(1H-tetrazol-1-yl)phenyl)-5-fluoro-N⁴-((7S,8aR)-2,2-difluoro-octahydro-5,5-dimethylindolizin-7-yl)pyrimidine-2,4-diamine (Compound 43)

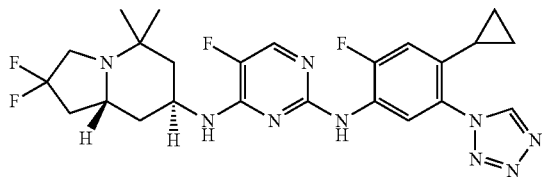 [SMILES: CC1(C)C[C@@H](Nc2nc(Nc3cc(-n4cnnn4)c(C4CC4)cc3F)ncc2F)C[C@@H]2CC(F)(F)CN21]

$^1$H NMR (300 MHz, CDCl$_3$) δ 8.90 (s, 1H), 8.73 (d, J=7.7 Hz, 1H), 7.80 (d, J=3.0 Hz, 1H), 7.10 (d, J=3.4 Hz, 1H), 6.90 (d, J=12.1 Hz, 1H), 5.13 (d, J=5.7 Hz, 1H), 4.31-4.24 (m, 1H), 3.34 (ddd, J=13.8, 10.7, 7.8 Hz, 1H), 3.00-2.88 (m, 1H), 2.81 (ddd, J=19.7, 14.9, 10.8 Hz, 1H), 2.39-2.26 (m, 1H), 2.08-1.80 (m, 4H), 1.69 (dd, J=14.4, 4.5 Hz, 1H), 1.62-1.49 (m, 1H, overlapped with water peak), 1.12 (s, 3H), 1.11 (s, 3H), 0.91-0.84 (m, 2H), 0.64-0.58 (m, 2H); LRMS (M+H) m/z 518.33.

Example 35

5-Synthesis of (4-((7S,8aR)-2,2-difluoro-octahydro-5,5-dimethylindolizin-7-ylamino)-5-fluoropyrimidin-2-ylamino)-2-methylbenzonitrile (Compound 44)

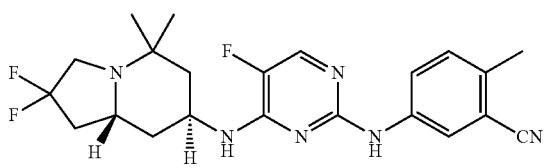 [SMILES: Cc1ccc(Nc2ncc(F)c(N[C@H]3C[C@@H]4CC(F)(F)CN4C(C)(C)C3)n2)cc1C#N]

$^1$H NMR (300 MHz, CDCl$_3$) δ 8.16 (d, J=2.4 Hz, 1H), 7.81 (d, J=3.1 Hz, 1H), 7.41 (dd, J=8.4, 2.4 Hz, 1H), 7.20 (d, J=12.1 Hz, 1H), 6.88-6.86 (m, 1H), 5.10 (d, J=5.6 Hz, 1H), 4.38-4.32 (m, 1H), 3.35 (ddd, J=13.8, 10.7, 7.1 Hz, 1H), 3.04-2.94 (m, 1H), 2.83 (ddd, J=19.6, 15.1, 10.8 Hz, 1H), 2.49 (s, 3H), 2.43-2.29 (m, 1H), 2.15 (br dd, J=13.6, 2.1 Hz, 1H), 2.07-1.82 (m, 3H), 1.70 (ddd, J=13.6, 11.8, 4.3 Hz, 1H), 1.15 (s, 3H), 1.14 (s, 3H); LRMS (M+H) m/z 431.26.

Example 36

Synthesis of 1-(5-(4-((7R,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 45)

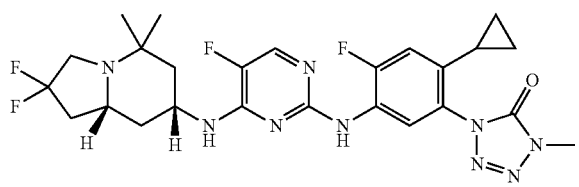 [SMILES: Cn1nnn(-c2cc(Nc3ncc(F)c(N[C@@H]4C[C@@H]5CC(F)(F)CN5C(C)(C)C4)n3)c(F)cc2C2CC2)c1=O]

$^1$H NMR (300 MHz, CDCl$_3$) δ 8.53 (d, J=7.8 Hz, 1H), 7.79 (d, J=3.1 Hz, 1H), 7.05 (d, J=3.1 Hz, 1H), 6.89 (d, J=12.2 Hz, 1H), 4.74 (d, J=6.5 Hz, 1H), 4.17 (tdt, J=11.3, 7.3, 3.8 Hz, 1H), 3.72 (s, 3H), 3.30 (ddd, J=14.3, 10.7, 6.7 Hz, 1H), 2.85-2.68 (m, 2H), 2.40-2.26 (m, 2H), 2.00-1.75 (m, 3H), 1.41 (dd, J=12.3, 12.3 Hz, 1H), 1.12 (s, 3H), 1.17-1.06 (m, 1H), 0.98 (s, 3H), 0.85-0.79 (m, 2H), 0.59-0.53 (m, 2H); LRMS (M+H) m/z 548.35.

Example 37

Synthesis of N²-(4-cyclopropyl-2-fluoro-5-(1H-tetrazol-1-yl)phenyl)-5-fluoro-N⁴-((7R,8aR)-2,2-difluoro-octahydro-5,5-dimethylindolizin-7-yl)pyrimidine-2,4-diamine (Compound 46)

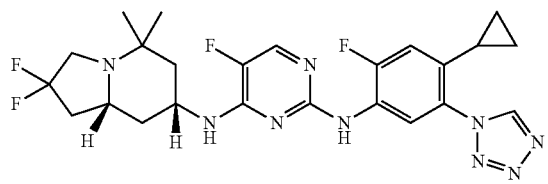 [SMILES: CC1(C)C[C@H](Nc2nc(Nc3cc(-n4cnnn4)c(C4CC4)cc3F)ncc2F)C[C@@H]2CC(F)(F)CN21]

$^1$H NMR (300 MHz, CDCl$_3$) δ 8.89 (s, 1H), 8.67 (d, J=7.7 Hz, 1H), 7.78 (d, J=3.0 Hz, 1H), 7.07 (d, J=3.5 Hz, 1H), 6.90 (d, J=12.1 Hz, 1H), 4.77 (d, J=8.3 Hz, 1H), 4.14 (tdt, J=13.0, 8.8, 4.3 Hz, 1H), 3.28 (ddd, J=14.5, 10.6, 5.8 Hz, 1H), 2.86-2.71 (m, 2H), 2.42-2.25 (m, 2H), 2.00-1.78 (m, 2H), 1.56-1.47 (m, 1H, overlapped with water peak), 1.41 (dd, J=12.3, 12.3 Hz, 1H), 1.14 (s, 3H), 1.18-1.06 (m, 1H), 0.95 (s, 3H), 0.89-0.83 (m, 2H), 0.63-0.57 (m, 2H); LRMS (M+H) m/z 518.34.

Example 38

Synthesis of 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 471

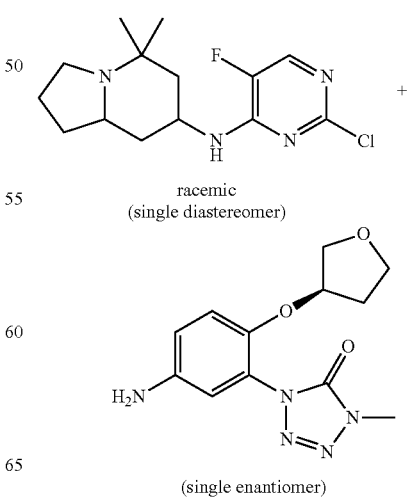

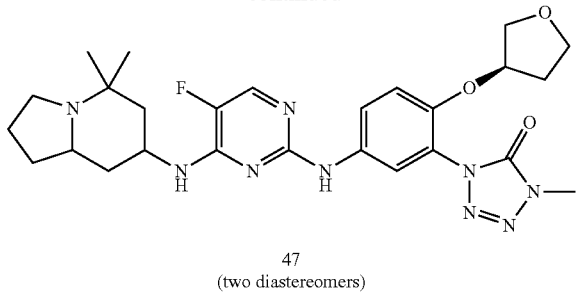

47
(two diastereomers)

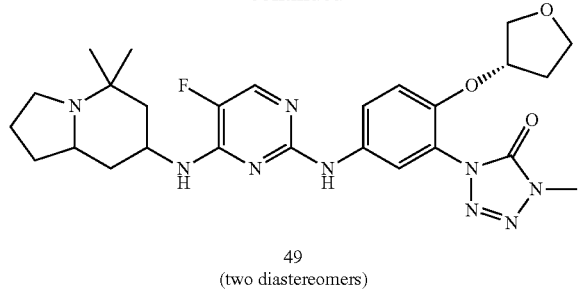

49
(two diastereomers)

A mixture of N-(2-chloro-5-fluoropyrimidin-4-yl)-octahydro-5,5-dimethylindolizin-7-amine (racemic, single diastereomer; 200 mg, 0.669 mmol, 1 equiv), 1-(2-((R)-tetrahydrofuran-3-yloxy)-5-aminophenyl)-4-methyl-1H-tetrazol-5(4H)-one (260 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over $Na_2SO_4$, filtered, and concentrated to dryness. The crude product was purified by flash chromatography and eluted with DCM:2M $NH_3$/MeOH=100:0 to 96:4 using 1% 2M $NH_3$/MeOH increments to give compound 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 47) (Mixture of two diastereomers; 279 mg, 77%) as a solid.

$^1$H NMR (300 MHz; $d_6$-DMSO) δ 9.20 (s, 1H), 8.03 (s, 1H), 7.83-7.84 (d, 1H, J=3.9Hz), 7.60-7.63 (dd, 1H, J=2.1Hz, J=8.7Hz), 7.22-7.25 (d, 1H, J=7.8Hz), 7.14-7.17 (d, 1H, J=9Hz), 4.94-5.07 (m, 1H), 3.99-4.11 (m, 1H), 3.79-3.83 (dd, 1H, J=4.5Hz, J=9.9Hz), 3.59-3.69 (m, 6H), 2.84 (bs, 1H), 1.41-2.24 (m, 11H), 1.06-1.22 (m, 4H), 0.813 (s, 3H); $^{19}$F NMR (282 MHz; $d_6$-DMSO) δ −166.6 (s); m/z=540 (M+H)$^+$.

A mixture of N-(2-chloro-5-fluoropyrimidin-4-yl)-octahydro-5,5-dimethylindolizin-7-amine (Racemic, single diastereomer; 200 mg, 0.669 mmol, 1 equiv), 1-(2-((S)-tetrahydrofuran-3-yloxy)-5-aminophenyl)-4-methyl-1H-tetrazol-5(4H)-one (260 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over $Na_2SO_4$, filtered, and concentrated to dryness. The crude product was purified by flash chromatography and eluted with DCM:2M $NH_3$/MeOH=100:0 to 96:4 using 1% 2M $NH_3$/MeOH increments to give compound 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 49) (Mixture of two diastereomers; 315 mg, 87%) as a solid.

$^1$H NMR (300 MHz; $d_6$-DMSO) δ 9.20 (s, 1H), 8.03 (s, 1H), 7.83-7.84 (d, 1H, J=3.9Hz), 7.60-7.63 (dd, 1H, J=2.1Hz, J=8.7Hz), 7.22-7.25 (d, 1H, J=7.8Hz), 7.14-7.17 (d, 1H, J=9Hz), 4.94-5.07 (m, 1H), 3.99-4.11 (m, 1H), 3.78-3.83 (dd, 1H, J=4.5Hz, J=9.9Hz), 3.59-3.69 (m, 6H), 2.84 (bs, 1H), 1.41-2.24 (m, 11H), 1.06-1.22 (m, 4H), 0.812 (s, 3H); $^{19}$F NMR (282 MHz; $d_6$-DMSO) δ −166.6 (s); m/z=540 (M+H)$^+$.

Example 39

Synthesis of 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 49)

Example 40

Synthesis of 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 51)

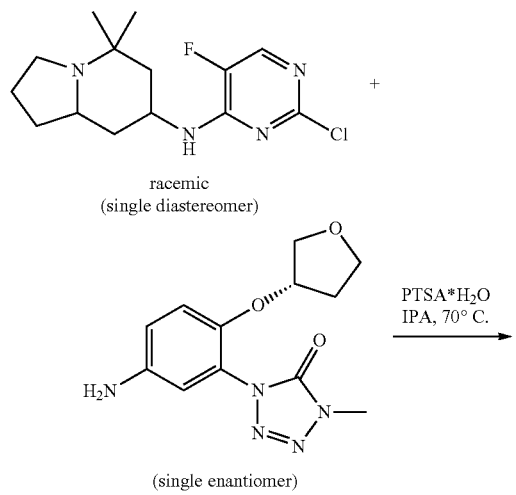

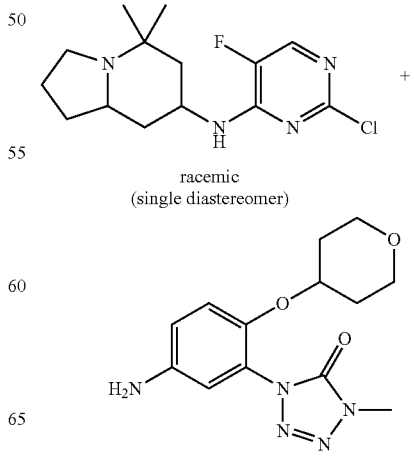

-continued

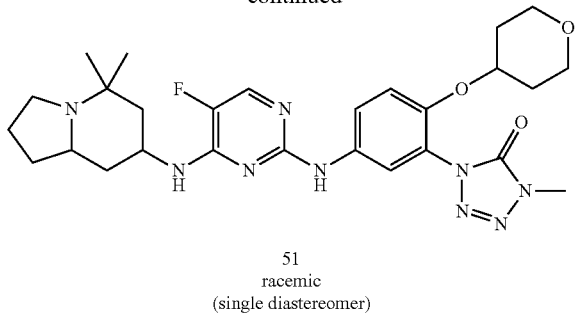

51
racemic
(single diastereomer)

A mixture of N-(2-chloro-5-fluoropyrimidin-4-yl)-octahydro-5,5-dimethylindolizin-7-amine (Racemic, single diastereomer; 200 mg, 0.669 mmol, 1 equiv), 1-(5-amino-2-(tetrahydro-2H-pyran-4-yloxy)phenyl)-4-methyl-1H-tetrazol-5(4H)-one (Described in WO2011068898, 273 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 51) (racemic, single diastereomer; 321 mg, 87%) as a solid.

$^1$H NMR (300 MHz; d$_6$-DMSO) δ 9.19 (s, 1H), 8.06 (s, 1H), 7.83-7.84 (d, 1H, J=3.9Hz), 7.57-7.61 (dd, 1H, J=2.1Hz, J=8.7Hz), 7.22-7.25 (d, 1H, J=7.8Hz), 7.18-7.21 (d, 1H, J=9Hz), 4.44-4.57 (m, 1H), 3.97-4.12 (m, 1H), 3.61-3.67 (m, 7H), 3.37-3.44 (m, 2H), 2.84 (bs, 1H), 1.42-2.24 (m, 11H), 1.06-1.22 (m, 4H), 0.812 (s, 3H); $^{19}$F NMR (282 MHz; d$_6$-DMSO) δ −166.7 (s); m/z=554 (M+H)$^+$.

Example 41

Synthesis of 2-((R)-tetrahydrofuran-3-yloxy)-5-(5-fluoro-4-(octahydro-5,5-dimethylindolizin-7-ylamino)pyrimidin-2-ylamino)benzonitrile (Compound 57)

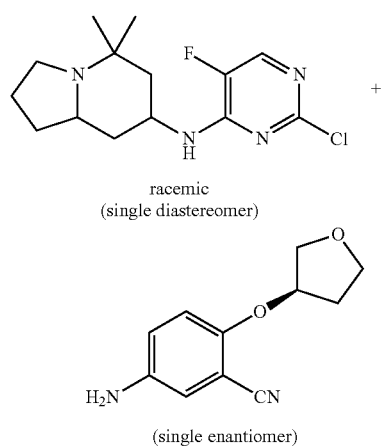

-continued

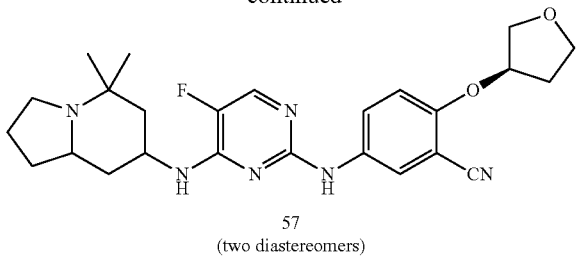

57
(two diastereomers)

A mixture of N-(2-chloro-5-fluoropyrimidin-4-yl)-octahydro-5,5-dimethylindolizin-7-amine (racemic, single diastereomer; 200 mg, 0.669 mmol, 1 equiv), 2-((R)-tetrahydrofuran-3-yloxy)-5-aminobenzonitrile (191 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 2-((R)-tetrahydrofuran-3-yloxy)-5-(5-fluoro-4-(octahydro-5,5-dimethylindolizin-7-ylamino)pyrimidin-2-ylamino)benzonitrile (Compound 57) (two diastereomers; 295 mg, 95%) as a solid.

$^1$H NMR (300 MHz; d$_6$-DMSO) δ 9.14 (s, 1H), 8.10-8.11 (d, 1H, J=2.7Hz), 7.84-7.86 (d, 1H, J=3.9Hz), 7.75-7.78 (dd, 1H, J=2.1Hz, J=8.7Hz), 7.25-7.28 (d, 1H, J=7.8Hz), 7.09-7.12 (d, 1H, J=9Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; d$_6$-DMSO) δ −166.3 (s); m/z=467 (M+H)$^+$.

Example 42

Chiral HPLC separation of 2-((R)-tetrahydrofuran-3-yloxy)-5-(5-fluoro-4-(octahydro-5,5-dimethylindolizin-7-ylamino)pyrimidin-2-ylamino)benzonitrile (Compounds 58-59)

Chiral HPLC separation of compound 2-((R)-tetrahydrofuran-3-yloxy)-5-(5-fluoro-4-(octahydro-5,5-dimethylindolizin-7-ylamino)pyrimidin-2-ylamino)benzonitrile (Compound 57)(two diastereomers 55 mg) to diastereomers (each a single enantiomer) was performed.

Chiral HPLC method: Column: Chiralcel OJ-H, 4.6×250 mm, with guard. Mobil phase: 90% CO$_2$, 10% methanol w/0.1% triethylamine. Flow rate: 4 ml/min. Injection volume: 10 μL. Concentration: approx 5 mg/ml. Detection: UV at 254 nm.

Compound 58

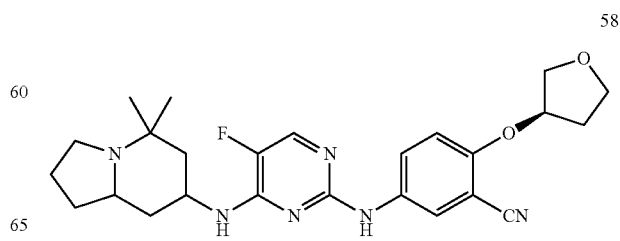

58

Compound 58: (>99% ee, 16 mg) has Rt=3.90 min.

$^1$H NMR (300 MHz; $d_6$-DMSO) δ 9.14 (s, 1H), 8.10-8.11 (d, 1H, J=2.7Hz), 7.84-7.86 (d, 1H, J=3.9Hz), 7.75-7.78 (dd, 1H, J=2.1Hz, J=8.7Hz), 7.25-7.28 (d, 1H, J=7.8Hz), 7.09-7.12 (d, 1H, J=9Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; $d_6$-DMSO) δ −166.3 (s); m/z=467 (M+H)$^+$.

Compound 59

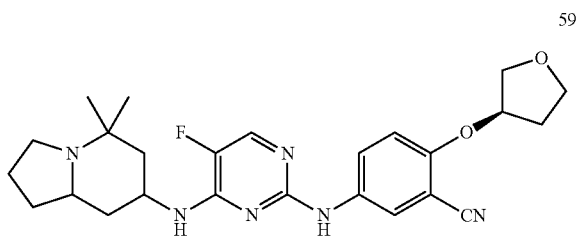 [SMILES: CC1(C)CC(Nc2nc(Nc3ccc(O[C@@H]4CCOC4)c(C#N)c3)ncc2F)CC2CCCN21]

Compound 59: (>99% ee, 16 mg) has Rt=4.95 min.

$^1$H NMR (300 MHz; $d_6$-DMSO) δ 9.14 (s, 1H), 8.10-8.11 (d, 1H, J=2.7Hz), 7.84-7.86 (d, 1H, J=3.9Hz), 7.75-7.78 (dd, 1H, J=2.1Hz, J=8.7Hz), 7.25-7.28 (d, 1H, J=7.8Hz), 7.09-7.12 (d, 1H, J=9Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; $d_6$-DMSO) δ −166.3 (s); m/z=467 (M+H)$^+$.

Example 43

Synthesis of 2-((S-tetrahydrofuran-3-yloxy)-5-(5-fluoro-4-(octahydro-5,5-dimethylindolizin-7-ylamino)pyrimidin-2-ylamino)benzonitrile (Compound 60)

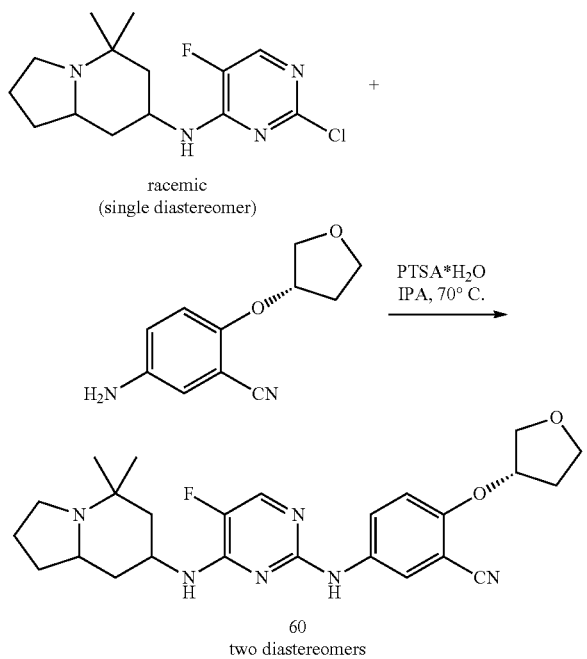

A mixture of N-(2-chloro-5-fluoropyrimidin-4-yl)-octahydro-5,5-dimethylindolizin-7-amine (Racemic, single diastereomer; 200 mg, 0.669 mmol, 1 equiv), 2-((S)-tetrahydrofuran-3-yloxy)-5-aminobenzonitrile (191 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over $Na_2SO_4$, filtered, and concentrated to dryness. The crude product was purified by flash chromatography and eluted with DCM:2M $NH_3$/MeOH=100:0 to 96:4 using 1% 2M $NH_3$/MeOH increments to give compound 2-((S)-tetrahydrofuran-3-yloxy)-5-(5-fluoro-4-(octahydro-5,5-dimethylindolizin-7-ylamino)pyrimidin-2-ylamino)benzonitrile (Compound 60) (two diastereomers; 294 mg, 95%) as a solid.

$^1$H NMR (300 MHz; $d_6$-DMSO) δ 9.14 (s, 1H), 8.10-8.11 (d, 1H, J=2.7Hz), 7.84-7.86 (d, 1H, J=3.9Hz), 7.75-7.78 (dd, 1H, J=2.1Hz, J=8.7Hz), 7.25-7.28 (d, 1H, J=7.8Hz), 7.09-7.12 (d, 1H, J=9Hz), 5.02-5.11 (m, 1H), 4.11-4.21 (m, 1H), 3.72-3.91 (m, 4H), 2.84 (bs, 1H), 1.40-2.42 (m, 11H), 1.08-1.27 (m, 4H), 0.982 (s, 3H); $^{19}$F NMR (282 MHz; $d_6$-DMSO) δ −166.3 (s); m/z=467 (M+H)$^+$.

Example 44

HPLC separation of compound 60 2-((S-tetrahydrofuran-3-yloxy)-5-(5-fluoro-4-(octahydro-5,5-dimethylindolizin-7-ylamino)pyrimidin-2-ylamino)benzonitrile (Compounds 61-62)

HPLC separation of compound 2-((S)-tetrahydrofuran-3-yloxy)-5-(5-fluoro-4-(octahydro-5,5-dimethylindolizin-7-ylamino)pyrimidin-2-ylamino)benzonitrile (Compound 60) (mixture of two diastereomers 55 mg) to constituent single diastereomers was performed.

HPLC method: Column: Chiralcel OJ-H, 4.6×250 mm, with guard. Mobil phase: 90% $CO_2$, 10% methanol w/0.1% triethylamine. Flow rate: 4 ml/min. Injection volume: 10 μL. Concentration: approx 5 mg/ml. Detection: UV at 254 nm.

Compound 61

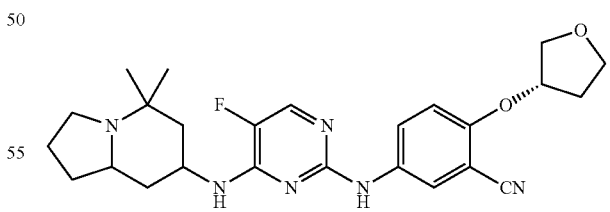

Compound 61: (>96% de, 17 mg) has Rt=6.01 min.

$^1$H NMR (300 MHz; $d_6$-DMSO) δ 9.14 (s, 1H), 8.10-8.11 (d, 1H, J=2.7Hz), 7.84-7.86 (d, 1H, J=3.9Hz), 7.75-7.78 (dd, 1H, J=2.1Hz, J=8.7Hz), 7.25-7.28 (d, 1H, J=7.8Hz), 7.09-7.12 (d, 1H, J=9Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; $d_6$-DMSO) δ −166.3 (s); m/z=467 (M+H)$^+$.

Compound 62

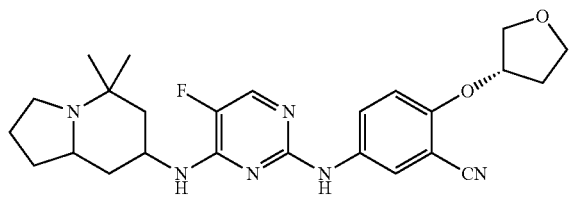 [SMILES: CC1(C)CC(Nc2nc(Nc3ccc(O[C@H]4CCOC4)c(C#N)c3)ncc2F)CC2CCCN21]

Compound 62: (>97% de, 18 mg) has Rt=6.90 min.
$^1$H NMR (300 MHz; $d_6$-DMSO) δ 9.14 (s, 1H), 8.10-8.11 (d, 1H, J=2.7Hz), 7.84-7.86 (d, 1H, J=3.9Hz), 7.75-7.78 (dd, 1H, J=2.1Hz, J=8.7Hz), 7.25-7.28 (d, 1H, J=7.8Hz), 7.09-7.12 (d, 1H, J=9Hz), 5.02-5.11 (m, 1H), 4.11-4.21 (m, 1H), 3.71-3.91 (m, 4H), 2.85 (bs, 1H), 1.41-2.42 (m, 11H), 1.08-1.27 (m, 4H), 0.987 (s, 3H); $^{19}$F NMR (282 MHz; $d_6$-DMSO) δ −166.3 (s); m/z=467 (M+H)$^+$.

Example 45

Synthesis of 5-(5-Fluoro-4-(octahydro-5,5-dimethyl-indolizin-7-ylamino)pyrimidin-2-ylamino)-2-(oxetan-3-yloxy)benzonitrile (Compound 63)

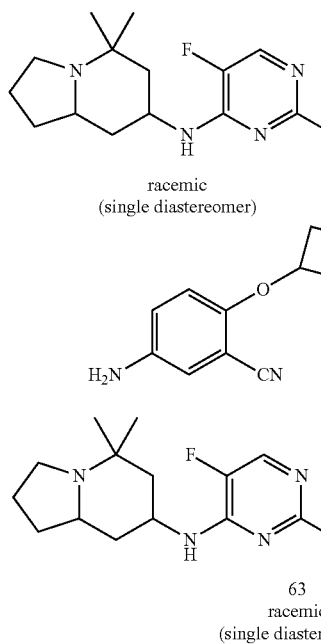

A mixture of N-(2-chloro-5-fluoropyrimidin-4-yl)-octahydro-5,5-dimethylindolizin-7-amine (racemic, single diastereomer; 200 mg, 0.669 mmol, 1 equiv), 5-amino-2-(oxetan-3-yloxy)benzonitrile (178 mg, 0.937 mmol, 1.4 equiv), and PTSA monohydrate (127 mg, 0.669 mmol, 1 equiv) in IPA (7 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 5-(5-fluoro-4-(octahydro-5,5-dimethylindolizin-7-ylamino)pyrimidin-2-ylamino)-2-(oxetan-3-yloxy)benzonitrile (Compound 63)(Racemic, single enantiomer; 163 mg, 54%) as a solid.
$^1$H NMR (300 MHz; $d_6$-DMSO) δ 9.16 (s, 1H), 8.14 (s, 1H), 7.83-7.84 (d, 1H, J=3.9Hz), 7.71-7.74 (dd, 1H, J=2.1Hz, J=8.7Hz), 7.23-7.26 (m, 1H), 6.74-6.77 (d, 1H, J=9.3Hz), 5.24-5.39 (p, 1H, J=6.3Hz), 4.88-4.94 (t, 2H, J=6Hz), 4.49-4.58 (t, 2H, J=5.7Hz), 4.15 (bs, 1H), 2.84 (bs, 1H), 1.42-2.42 (m, 9H), 1.06-1.28 (m, 4H), 0.974 (s, 3H); $^{19}$F NMR (282 MHz; $d_6$-DMSO) δ −166.2 (s); m/z=453 (M+H)$^+$.

Example 46

Synthesis of 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 48)

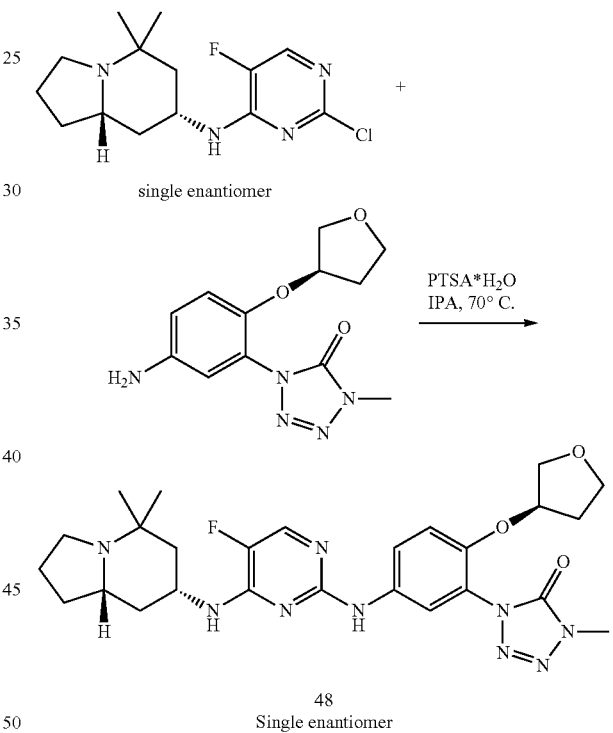

A mixture of N-(2-chloro-5-fluoropyrimidin-4-yl)-octahydro-5,5-dimethylindolizin-7-amine (single enantiomer; 35 mg, 0.116 mmol, 1 equiv), 1-(2-((R)-tetrahydrofuran-3-yloxy)-5-aminophenyl)-4-methyl-1H-tetrazol-5(4H)-one (45 mg, 0.162 mmol, 1.4 equiv), and PTSA monohydrate (22 mg, 0.116 mmol, 1 equiv) in IPA (1.5 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 48) (49 mg, 78%) as a solid.

$^1$H NMR (300 MHz; d$_6$-DMSO) δ 9.20 (s, 1H), 8.03 (s, 1H), 7.83-7.84 (d, 1H, J=3.9Hz), 7.60-7.63 (dd, 1H, J=2.1Hz, J=8.7Hz), 7.22-7.25 (d, 1H, J=7.8Hz), 7.14-7.17 (d, 1H, J=9Hz), 4.94-5.07 (m, 1H), 3.99-4.11 (m, 1H), 3.79-3.83 (dd, 1H, J=4.5Hz, J=9.9Hz), 3.59-3.69 (m, 6H), 2.84 (bs, 1H), 1.41-2.24 (m, 11H), 1.06-1.22 (m, 4H), 0.813 (s, 3H); $^{19}$F NMR (282 MHz; d$_6$-DMSO) δ -166.6 (s); m/z=540 (M+H)$^+$.

Example 47

Synthesis of 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 50)

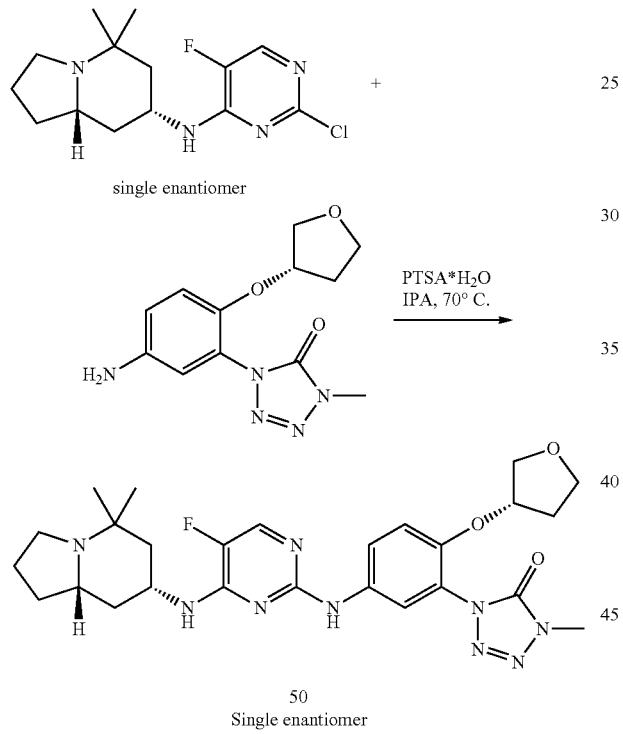

50
Single enantiomer

A mixture of N-(2-chloro-5-fluoropyrimidin-4-yl)-octahydro-5,5-dimethylindolizin-7-amine (Single diastereomer, single enantiomer; 53 mg, 0.178 mmol, 1 equiv), 1-(2-((S)-tetrahydrofuran-3-yloxy)-5-aminophenyl)-4-methyl-1H-tetrazol-5(4H)-one (69 mg, 0.249 mmol, 1.4 equiv), and PTSA monohydrate (34 mg, 0.178 mmol, 1 equiv) in IPA (2 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one (Compound 50) (75 mg, 78%) as a solid.

$^1$H NMR (300 MHz; d$_6$-DMSO) δ 9.20 (s, 1H), 8.03 (s, 1H), 7.83-7.84 (d, 1H, J=3.9Hz), 7.60-7.63 (dd, 1H, J=2.1Hz, J=8.7Hz), 7.22-7.25 (d, 1H, J=7.8Hz), 7.14-7.17 (d, 1H, J=9Hz), 4.94-5.07 (m, 1H), 3.99-4.11 (m, 1H), 3.78-3.83 (dd, 1H, J=4.5Hz, J=9.9Hz), 3.59-3.69 (m, 6H), 2.84 (bs, 1H), 1.41-2.24 (m, 11H), 1.06-1.22 (m, 4H), 0.812 (s, 3H); $^{19}$F NMR (282 MHz; d$_6$-DMSO) δ -166.6 (s); m/z=540 (M+H)$^+$.

Example 48

Synthesis of 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 52)

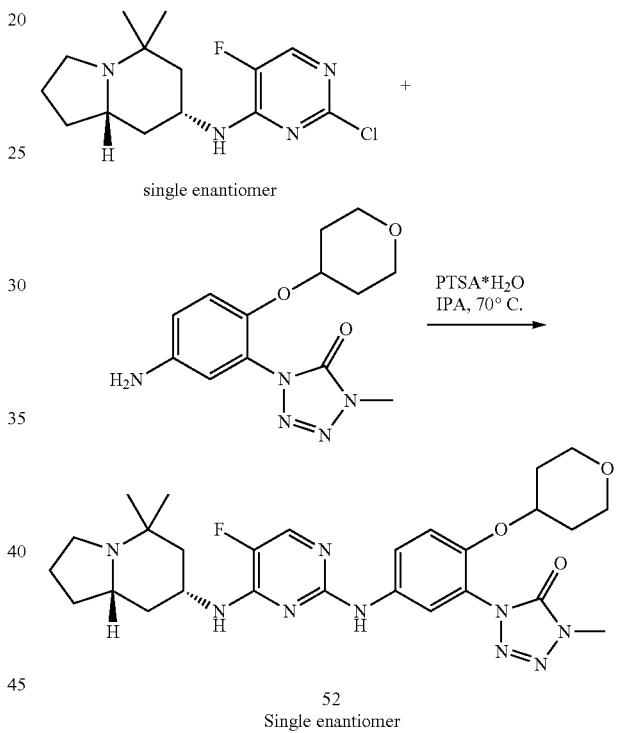

52
Single enantiomer

A mixture of N-(2-chloro-5-fluoropyrimidin-4-yl)-octahydro-5,5-dimethylindolizin-7-amine (Single diastereomer, single enantiomer; 53 mg, 0.178 mmol, 1 equiv), 1-(5-amino-2-(tetrahydro-2H-pyran-4-yloxy)phenyl)-4-methyl-1H-tetrazol-5(4H)-one (Described in: WO 2011/068898, 73 mg, 0.249 mmol, 1.4 equiv), and PTSA monohydrate (34 mg, 0.178 mmol, 1 equiv) in IPA (2 ml) were heated to 70° C. for 3 days. After cooling to ambient temperature, the crude mixture was concentrated to dryness and taken in water, EtOAc, and 1N NaOH. The layers were separated. The organic layer was washed with 1N NaOH (×2), dried over Na$_2$SO$_4$, filtered, and concentrated to dryness. The crude product was purified by flash chromatography and eluted with DCM:2M NH$_3$/MeOH=100:0 to 96:4 using 1% 2M NH$_3$/MeOH increments to give compound 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one (Compound 52) (48 mg, 50%) as a solid.

¹H NMR (300 MHz; d₆-DMSO) δ 9.19 (s, 1H), 8.06 (s, 1H), 7.83-7.84 (d, 1H, J=3.9Hz), 7.57-7.61 (dd, 1H, J=2.1Hz, J=8.7Hz), 7.22-7.25 (d, 1H, J=7.8Hz), 7.18-7.21 (d, 1H, J=9Hz), 4.44-4.57 (m, 1H), 3.97-4.12 (m, 1H), 3.61-3.67 (m, 7H), 3.37-3.44 (m, 2H), 2.84 (bs, 1H), 1.42-2.24 (m, 11H), 1.06-1.22 (m, 4H), 0.812 (s, 3H); ¹⁹F NMR (282 MHz; d₆-DMSO) δ −166.7 (s); m/z=554 (M+H)⁺.

Example 49

Synthesis of 1-(5-(4-((2R,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 64)

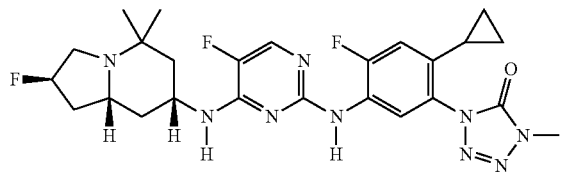 [SMILES: Cn1nnn(-c2cc(Nc3ncc(F)c(N[C@@H]4C[C@@H]5C[C@@H](F)CN5C(C)(C)C4)n3)c(F)cc2C2CC2)c1=O]

¹H NMR (300 MHz, CDCl₃) δ 8.57 (d, J=7.8 Hz, 1H), 7.78 (s, 1H), 7.09 (s, 1H), 6.89 (d, J=12.2 Hz, 1H), 5.18 (dt, J=11.9, 5.7 Hz, 1H), 4.75 (d, J=8.2 Hz, 1H), 4.28-4.12 (m, 1H), 3.73 (s, 3H), 3.52-3.35 (m, 1H), 2.78 (t, J=13.3 Hz, 1H), 2.71-2.52 (m, 1H), 2.33 (d, J=11.8 Hz, 1H), 2.19-1.99 (m, 1H), 1.89-1.75 (m, 2H), 1.74-1.48 (m, 3H), 1.30 (t, J=12.2 Hz, 1H), 1.15 (s, 3H), 1.00 (s, 3H), 0.87-0.78 (m, 2H), 0.61-0.51 (m, 2H). ¹⁹F NMR (282 MHz, CDCl3) δ −129.42 (s), −167.50 (s), −168.35-169.04 (m).

LCMS (m/z): 530.5 (MH⁺).

Example 50

Synthesis of 1-(5-(4-((2R,7S,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 65)

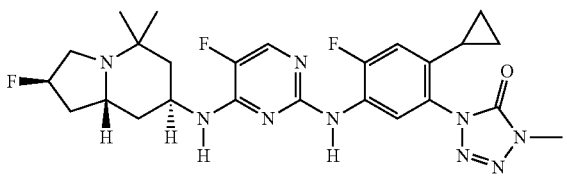 [SMILES: Cn1nnn(-c2cc(Nc3ncc(F)c(N[C@H]4C[C@@H]5C[C@@H](F)CN5C(C)(C)C4)n3)c(F)cc2C2CC2)c1=O]

¹H NMR (300 MHz, CDCl₃) δ 8.59 (d, J=7.8 Hz, 1H), 7.79 (d, J=3.1 Hz, 1H), 7.10 (d, J=3.2 Hz, 1H), 6.86 (d, J=12.2 Hz, 1H), 5.30-5.04 (m, 2H), 4.32 (s, 1H), 3.72 (s, 3H), 3.55-3.37 (m, 1H), 3.01-2.86 (m, 1H), 2.80-2.60 (m, 1H), 2.08 (d, J=13.6 Hz, 2H), 1.92-1.75 (m, 3H), 1.63-1.37 (m, 2H), 1.13 (s, 3H), 1.12 (s, 3H), 0.87-0.79 (m, 2H), 0.60-0.53 (m, 2H).

¹⁹F NMR (282 MHz, CDCl3₃) δ −129.67 (s), −167.84 (s), −168.37-168.79 (m).

LCMS (m/z): 530.5 (MH⁺).

Example 51

Synthesis of 1-(5-(4-((2S,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 67)

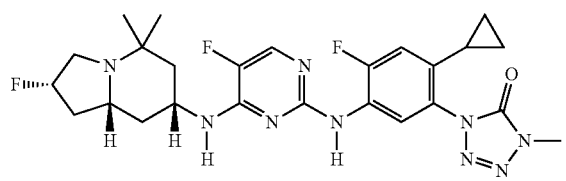 [SMILES: Cn1nnn(-c2cc(Nc3ncc(F)c(N[C@@H]4C[C@@H]5C[C@H](F)CN5C(C)(C)C4)n3)c(F)cc2C2CC2)c1=O]

¹H NMR (300 MHz, CDCl₃) δ 8.54 (d, J=7.8 Hz, 1H), 7.78 (s, 1H), 7.05 (s, 1H), 6.88 (d, J=12.2 Hz, 1H), 5.23-5.00 (m, 1H), 4.77 (d, J=8.0 Hz, 1H), 4.19-4.08 (m, 1H), 3.71 (s, 3H), 3.18 (dd, J=22.9, 11.3 Hz, 1H), 2.46-2.27 (m, 4H), 1.84-1.64 (m, 4H), 1.48 (t, J=12.3 Hz, 1H), 1.26-1.15 (m, 3H), 0.93 (s, 3H), 0.86-0.78 (m, 2H), 0.59-0.53 (m, 2H).

¹⁹F NMR (282 MHz, CDCl₃) δ −129.23 (s), −164.71-165.30 (m), −167.34 (s).

LCMS (m/z): 530.5 (MH⁺).

Example 52

Synthesis of 1-(5-(4-((2R,7R,8aR)-2-hydroxy-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one (Compound 68)

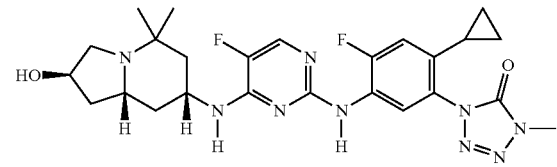 [SMILES: Cn1nnn(-c2cc(Nc3ncc(F)c(N[C@@H]4C[C@@H]5C[C@@H](O)CN5C(C)(C)C4)n3)c(F)cc2C2CC2)c1=O]

¹H NMR (300 MHz, CDCl₃) δ 8.56 (d, J=7.7 Hz, 1H), 7.78 (s, 1H), 7.12 (s, 1H), 6.90 (d, J=12.2 Hz, 1H), 4.79 (d, J=8.0 Hz, 1H), 4.40 (s, 1H), 4.21-4.07 (m, 1H), 3.76 (s, 3H), 3.49 (s, 1H), 3.41 (dd, J=9.9, 6.8 Hz, 1H), 2.70 (dd, J=16.6, 10.3 Hz, 1H), 2.32 (dd, J=9.8, 4.0 Hz, 2H), 2.08 (s, 1H), 1.85-1.63 (m, 4H), 1.35 (t, J=12.3 Hz, 1H), 1.16 (s, 3H), 1.01-0.88 (m, 3H), 0.81 (d, J=8.3 Hz, 2H), 0.57 (d, J=4.0 Hz, 2H).

LCMS (m/z): 528.4 (MH⁺).

Example 53

Synthesis of 5-Fluoro-N2-(4-fluoro-3-(5-methyl-1H-tetrazol-1-yl)phenyl)-N4-(octahydro-5,5,8-trimethyl-indolizin-7-yl)pyrimidine-2,4-diamine (Compounds

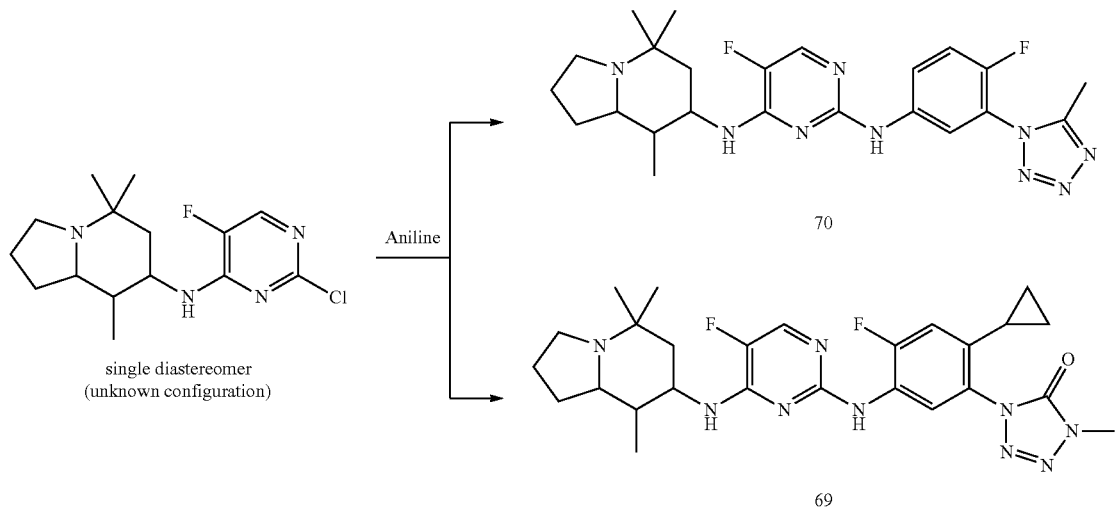 [SMILES: CC1C(Nc2nc(Cl)ncc2F)CC(C)(C)N2CCCC12 ; CC1C(Nc2nc(Nc3cc(-n4nnn(C)c4=O)c(C4CC4)cc3F)ncc2F)CC(C)(C)N2CCCC12 ; Cc1nnnn1-c1cc(Nc2ncc(F)c(NC3CC(C)(C)N4CCCC4C3C)n2)ccc1F]

Synthesis of Compounds 69 and 70

The mono-$S_NAr$ product (50.0 mg, 0.159 mmol) was dissolved in 4 ml of isopropyl alcohol in a 2 dram vial. PTSA-monohydrate (45.3 mg, 0.238 mmol) and the desired aniline (1.5 eq) were added and the vial was sealed. After heating over night at 105° C. using an anodized aluminum heating block the solvent was boiled off by removing the cap. The product was isolated by preparative HPLC eluting with an acetonitrile/water gradient. Analysis by NMR showed that the isolated product is a single diastereomer of unknown configuration.

Synthesis of 5-Fluoro-N2-(4-fluoro-3-(5-methyl-1H-tetrazol-1-yl)phenyl)-N4-(octahydro-5,5,8-trimethyl-indolizin-7-yl)pyrimidine-2,4-diamine (Compound 70)

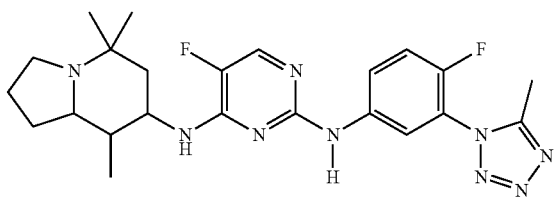 [SMILES: Cc1nnnn1-c1cc(Nc2ncc(F)c(NC3CC(C)(C)N4CCCC4C3C)n2)ccc1F]

$^1$H NMR (300 MHz, d6-DMSO) δ 8.05-7.88 (m, 1H), 7.87-7.71 (m, 1H), 7.70-7.50 (m, 2H), 6.50 (s, 1H), 5.46 (s, 69-70) 1H), 4.17 (s, 1H), 3.70 (s, 1H), 3.02 (s, 1H), 2.61-2.50 (m, 4H), 2.44 (t, J=0.9 Hz, 1H), 2.23 (d, J=20.1 Hz, 2H), 2.14 (d, J=14.0 Hz, 1H), 1.89 (s, 2H), 1.43 (d, J=12.9 Hz, 1H), 1.35 (s, 3H), 1.24 (s, 3H), 1.20 (d, J=23.5 Hz, 3H), 0.97 (d, J=6.8 Hz, 2H); MS (ES) 470 (M+H), 468 (M−H).

Synthesis of 1-(5-(5-Fluoro-4-(octahydro-5,5,8-trimethylindolizin-7-ylamino)pyrimidin-2-ylamino)-2-cyclopropyl-4-fluorophenyl)-4-methyl-1H-tetrazol-5(4H)-one (Compound 69)

$^1$H NMR (300 MHz, CDCl$_3$) δ 8.45 (d, J=7.8 Hz, 1H), 8.36 (s, 1H), 7.78-7.72 (s br, 1H), 7.21 (s, 1H), 6.81 (d, J=12.1 Hz, 1H), 5.95 (s br, 2H), 5.18 (s, 1H), 4.34 (s, 1H), 3.67 (s, 3H), 3.13 (m, 1H), 2.84 (m, 1H), 2.60-2.45 (m, 1H), 2.28 (s, 1H), 2.24-2.03 (m, 4H), 2.05-1.66 (m, 3H), 1.39 (s, 3H), 1.27 (s, 3H), 0.98 (d, J=7.0 Hz, 3H), 0.78 (d, J=8.3 Hz, 1H), 0.56-0.46 (m, 2H); MS (ES) 526 (M+H), 524 (M−H).

Example 54

Synthesis of 1-(5-(4-((7R,8aS)-5,5-dimethyl-octahydroindolizin-7-ylamino)-5-fluoropyrimidin-2-ylamino)-4-fluoro-2-methoxyphenyl)-4-methyl-1H-tetrazol-5(4H)-one (Compound 22)

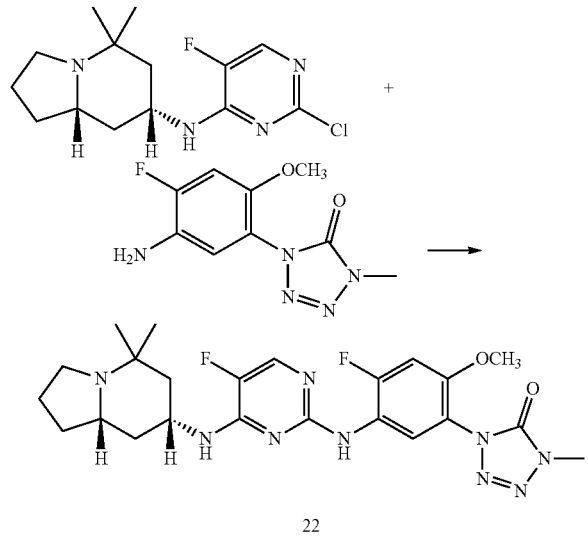

A mixture of (7R,8aS)-N-(2-chloro-5-fluoropyrimidin-4-yl)-octahydro-5,5-dimethylindolizin-7-amine (49 mg, 0.16 mmol, 1 equiv), 1-(5-amino-4-fluoro-2-methoxyphenyl)-4-methyl-1H-tetrazol-5(4H)-one (59 mg, 0.25 mmol, 1.5 equiv) and pTsOH.H$_2$O (25 mg, 0.13 mmol, 0.8 equiv) in isopropanol (1.5 ml) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 8.39 (s, 1H), 7.85 (d, J=8.1 Hz, 1H), 7.78 (d, J=3.9 Hz, 1H), 7.25 (d, J=12.6 Hz, 1H), 7.18 (d, J=8.1 Hz, 1H), 4.05-3.90 (m, 1H), 3.75 (s, 3H), 3.59 (s, 3H), 2.85-2.75 (m, 1H), 2.27-2.15 (m, 2H), 1.93-1.89 (m, 1H), 1.70-1.50 (m, 3H), 1.41-1.32 (m, 1H), 1.24-1.15 (m, 1H), 1.11-0.95 (m, 2H), 1.04 (s, 3H), 0.76 (s, 3H); $^{19}$F NMR (282 MHz; d$_6$-DMSO) δ −115.9 (s), −166.9 (s); m/z=502.1 (M+H)$^+$; m/z=500.4 (M−H)$^+$.

Example 55

Synthesis of 1-(5-(4-((7R,8aS)-5,5-dimethyl-octahydroindolizin-7-ylamino)-5-fluoropyrimidin-2-ylamino)-4-fluoro-2-isopropoxyphenyl)-4-methyl-1H-tetrazol-5(4H)-one (Compound 23)

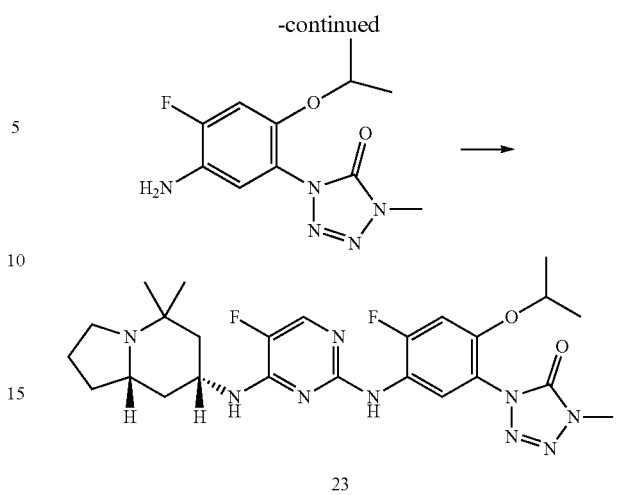

A mixture of (7R,8aS)-N-(2-chloro-5-fluoropyrimidin-4-yl)-octahydro-5,5-dimethylindolizin-7-amine (52 mg, 0.18 mmol, 1 equiv), 1-(5-amino-4-fluoro-2-methoxyphenyl)-4-methyl-1H-tetrazol-5(4H)-one (94 mg, 0.36 mmol, 2 equiv) and pTsOH.H$_2$O (27 mg, 0.14 mmol, 0.8 equiv) in isopropanol (1.5 ml) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 8.38 (s, 1H), 7.82 (d, J=8.4 Hz, 1H), 7.78 (d, J=3.9 Hz, 1H), 7.26 (d, J=12.6 Hz, 1H), 7.20 (d, J=8.1 Hz, 1H), 4.59 (q, J=6.0 Hz, 1H), 4.05-3.90 (m, 1H), 3.59 (s, 3H), 2.90-2.80 (m, 1H), 2.30-2.20 (m, 2H), 1.95-1.91 (m, 1H), 1.72-1.52 (m, 3H), 1.43-1.35 (m, 1H), 1.22-1.00 (m, 3H), 1.55 (d, J=6.0 Hz, 6H), 1.05 (s, 3H), 0.78 (s, 3H); $^{19}$F NMR (282 MHz; d$_6$-DMSO) δ −116.2 (s), −167.0 (s); m/z=530.2 (M+H)$^+$; m/z=528.5 (M−H)$^+$.

Example 56

Synthesis of Compound 71

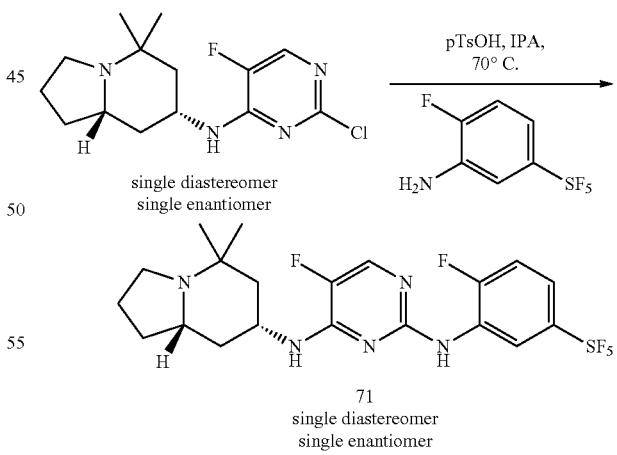

$^1$H NMR (300 MHz; d$_6$-DMSO) δ 8.76 (s, 1H), 8.42-8.39 (m, 1H), 7.86 (d, J=3.6 Hz, 1H), 7.58-7.53 (m, 1H), 7.41 (t, J=6.5 Hz, 1H), 7.27 (br. d, 1H), 4.04 (m, 1H), 2.81 (m, 1H), 2.42-2.20 (m, 2H), 1.98-1.89 (m, 1H), 1.74-1.48 (m, 4H), 1.43-1.35 (m, 1H), 1.30-1.11 (m, 2H), 1.04 (s, 3H), 0.83 (s, 3H); $^{19}$F NMR (282 MHz; d$_6$-DMSO) δ −165.3 (s), −135.6 (s), −135.1 (s), −116.7 (s), −112.5 (m); m/z=500.25 (M+H)$^+$; rt=4.13 min (HPLC conditions-Protocol 1).

Example 57

Synthesis of Compound 72

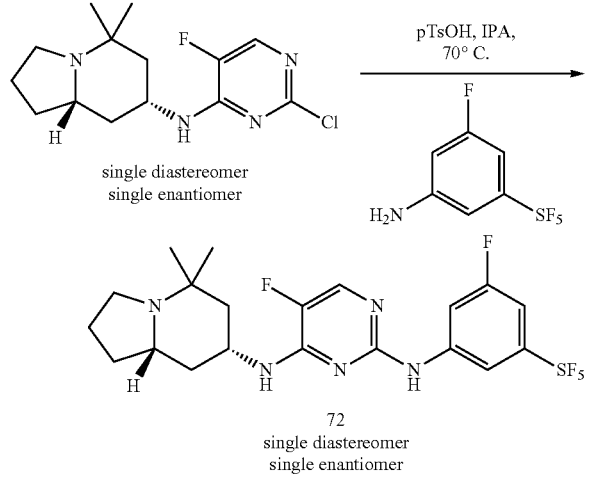

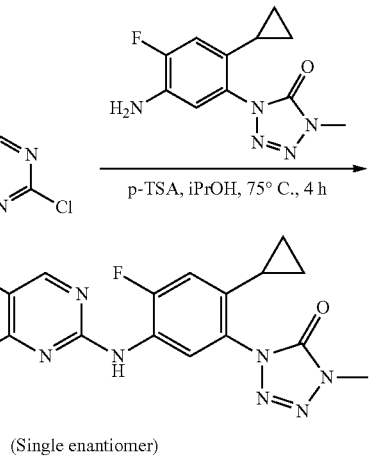

¹H NMR (300 MHz; d₆-DMSO) δ 9.66 (s, 1H), 8.17 (d, J=11.9 Hz, 1H), 7.94-7.92 (m, 2H), 7.43 (br. d, J=7.4 Hz, 1H), 7.27 (d, J=8.8 Hz, 1H), 4.24-4.10 (m, 1H), 2.90-2.79 (m, 1H), 2.36-2.23 (m, 1H), 2.05-2.10 (m, 1H), 1.70-1.44 (m, 4H), 1.30-1.15 (m, 3H), 1.09 (s, 3H), 0.98 (s, 3H); ¹⁹F NMR (282 MHz; d₆-DMSO) δ −164.3 (s), −136.7 (s), −136.1 (s), −113.7 (m), −109.5 (s); m/z=500.37 (M+H)⁺; rt=4.57 min (HPLC conditions-Protocol 1).

Example 58

Synthesis of Compound 76

Synthesis of 4-(R,S)-Octahydro-5,5-dimethylindolizin-7-ylamino)-2-(4-cyclopropyl-2-fluoro-5-(4,5-dihydro-4-methyl-5-oxotetrazol-yl)phenylamino) pyrimidine-5-carbonitrile (Compound 76)

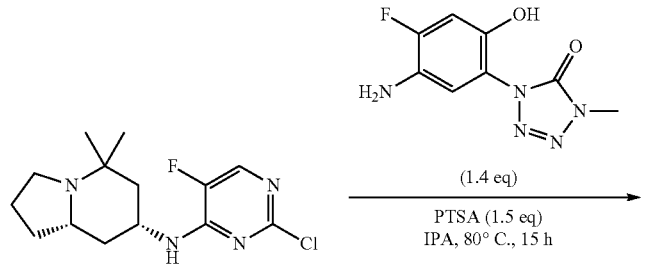

To a solution of (R,S)-2-chloro-4-(octahydro-5,5-dimethylindolizin-7-ylamino)pyridimine-5-carbonitrile (Example 7; 0.300 g, 1.0 mmol) in iPrOH (25 mL), 1-(5-amino-2-cyclopropyl-4-fluorophenyl)-4-methyl-1H-tetrazol-5 (4H)-one (0.34 g, 1.4 mmol) and p-TSA (0.20 g, 1.1 mmol) were added and the reaction mixture was heated to 75° C. for 4 h. LCMS analysis indicated the completion of reaction. Removal of volatiles and purification of the crude by column chromatography gave the desired product as p-toluene sulfonic acid salt. The salt was dissolved in 50 mL EtOAc and partitioned with aq. 2N NaOH solution. The organic layers were separated and dried over Na₂SO₄. Removal of the solvents under vacuum gave the desired product in 78% yield (0.40 g).

¹H NMR (DMSO d₆, 300 MHz) δ: 9.43 (s, 1H), 8.29 (s, 1H), 7.65 (d, J=7.2 Hz, 1H), 7.42 (d, J=8.1 Hz, 1H), 7.02 (d, J=12.0 Hz, 1H), 4.02 (br. s, 1H), 3.60 (s, 3H), 2.76-2.81 (m, 1H), 2.15-2.24 (m, 2H), 1.79-1.83 (m, 1H), 1.50-1.68 (m, 4H), 1.34-1.43 (m, 2H), 1.07-1.22 (m, 5H), 1.01 (s, 3H), 0.82-0.86 (m, 2H), 0.63-0.67 (m, 2H); LCMS (m/z): 519 (MH⁺).

Example 59

Synthesis of 1-(24(S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 81)

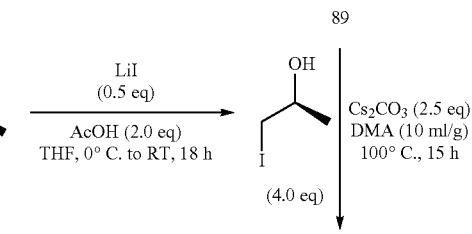

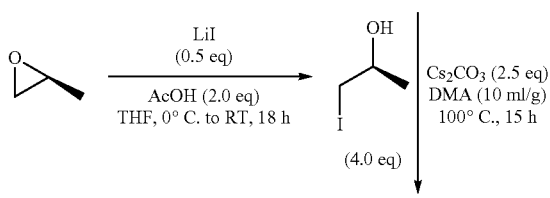

-continued

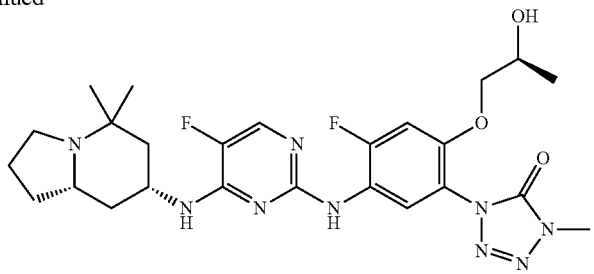

81 other reaction products:

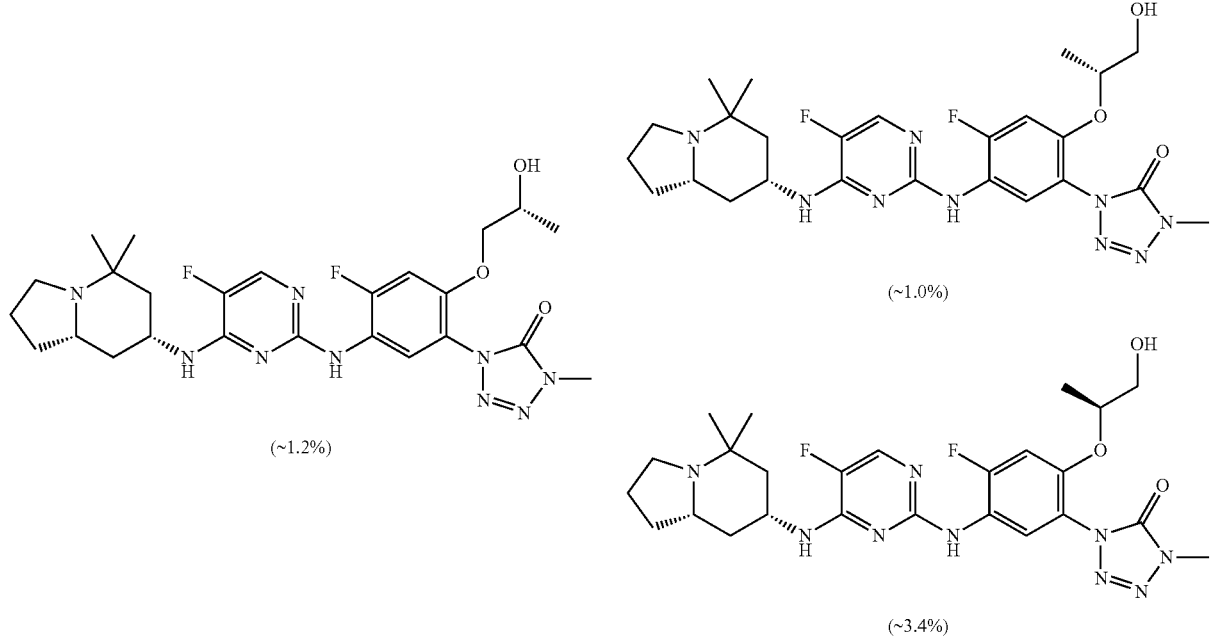

1-(5-amino-4-fluoro-2-hydroxyphenyl)-4-methyl-1H-tetrazol-5(4H)-one was prepared according to Example 29 above. N-(2-chloro-5-fluoropyrimidin-4-yl)-octahydro-5,5-dimethylindolizin-7-amine and 1-(5-amino-4-fluoro-2-hydroxyphenyl)-4-methyl-1H-tetrazol-5(4H)-one were conjugated to form the phenol (compound 89). The phenol (4.61 g, 9.45 mmol), (S)-1-iodopropan-2-ol (7.02 g, 37.7 mmol) (synthesized according to U.S. Application Publication No. 2005/0054701) and $Cs_2CO_3$ (7.68 g, 23.6 mmol) were placed in a pressure vessel. DMA (dimethylacetamide) (50 ml) was added and the vessel was sealed. The pale grey suspension was heated to 100° C. and stirred at this temperature for 15 hours. After cooling down to room temperature, the reaction mixture was analyzed by TLC and HPLC to check for completion. The DMA was distilled off and water (100 ml) was added to the crude reaction mixture. The crude reaction mixture was extracted with DCM (2×100 ml) and EtOAc (1×100 ml), filtered through $Na_2SO_4$ and solvents were evaporated under reduced pressure to yield 6.6 gram of crude product. The crude product was re-dissolved in DCM and absorbed on silica gel. Further purification was carried out with a CombiFlash Gold column (spherical silica, 220 gram) eluted with DCM and MeOH (2M NH$_3$) (gradient 0% to 6%). The clean fractions were combined to yield 3.04 gram (59%, off-white solid) of compound 81. Reverse phase HPLC and $^1$H-NMR indicated a substantially pure product. Analysis by chiral SFC (12 min method) showed that the product also contained ~1.2% of the other diastereomer and two diastereomeric regioisomers (~1.0% and ~3.4%).

$^1$H NMR (300 MHz, d6-DMSO) δ 8.41 (s, 1H), 7.88 (d, J=8.4 Hz, 1H), 7.80 (d, J=3.8 Hz, 1H), 7.27 (d, J=12.5 Hz, 1H), 7.20 (d, J=7.8 Hz, 1H), 4.74 (d, J=4.1 Hz, 1H), 4.08-3.94 (m, 1H), 3.93-3.76 (m, 3H), 3.60 (s, 3H), 3.32 (m, 1H), 2.90-2.75 (m, 1H), 2.30-2.11 (m, 2H), 1.94 (d, J=11.0 Hz, 1H), 1.78-1.47 (m, 4H), 1.47-1.33 (m, 1H), 1.30-1.09 (m, 2H), 1.09-0.99 (m, 6H), 0.77 (s, 3H); MS (ES) m/z 546 (M+H)$^+$.

Example 60

Synthesis of 1-(2-(2-hydroxyethoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 77)

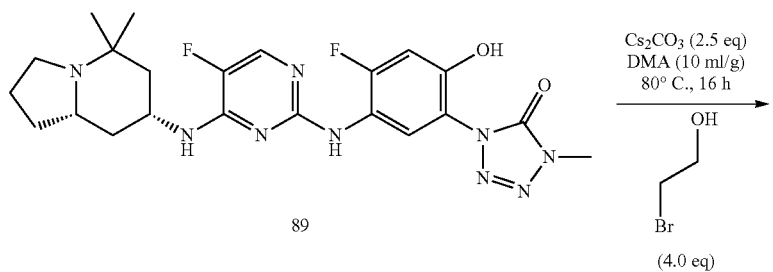

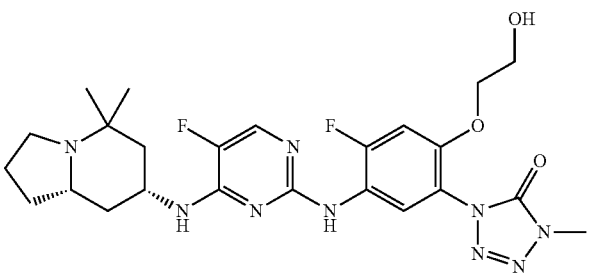

The phenol (compound 89) (9.90 g, 20.3 mmol), 2-bromoethanol (10.2 g, 81.2 mmol) and Cs$_2$CO$_3$ (16.5 g, 50.7 mmol) were placed in a pressure vessel. DMA (dimethylacetamide) (100 ml) was added and the vessel was sealed. The reaction mixture was heated to 80° C. and stirred at this temperature for 16 hours. The reaction was then analyzed by TLC and HPLC to check for completion. The DMA was distilled off, water (150 ml) was added and the crude reaction mixture was extracted with DCM (3×150 ml). The organic layers were combined, filtered through Na$_2$SO$_4$ and solvents were evaporated under reduced pressure. The crude product was further purified using CombiFlash chromatography (regular silica gel, 330 gram) eluted with DCM and MeOH (2M NH$_3$) (gradient 0% to 6%). The clean fractions were combined to yield 6.40 gram (59%) of compound 77 in the form of an off-white solid. Slightly less pure factions were also combined to yield another 3.35 gram (31%) of the product.

$^1$H NMR (300 MHz, d6-DMSO) δ 8.39 (s, 1H), 7.89 (d, J=8.4 Hz, 1H), 7.79 (d, J=3.8 Hz, 1H), 7.28 (d, J=12.5 Hz, 1H), 7.18 (d, J=7.9 Hz, 1H), 4.71 (t, J=5.6 Hz, 1H), 4.03 (t, J=4.9 Hz, 2H), 3.97 (dd, J=7.8, 4.0 Hz, 1H), 3.65-3.53 (m, 5H), 3.34 (m, 1H), 2.80 (dd, J=8.4, 5.4 Hz, 1H), 2.27-2.09 (m, 2H), 2.05 (s, 1H), 1.92 (d, J=11.4 Hz, 1H), 1.68 (dd, J=11.1, 6.6 Hz, 1H), 1.62-1.45 (m, 3H), 1.37 (t, J=12.2 Hz, 1H), 1.27-1.05 (m, 1H), 1.03 (s, 3H), 0.75 (s, 3H); $^{19}$F NMR (300 MHz, d6-DMSO) δ −116.5,−166.8; MS (ES) m/z 532 (M+H)$^+$.

Example 61

Synthesis of Compound 80

Preparation of (7R,8aS)-N-(5-aminocarbonyl-2-chloropyrimidin-4-yl)-octahydro-5,5-dimethylindolizin-7-amine

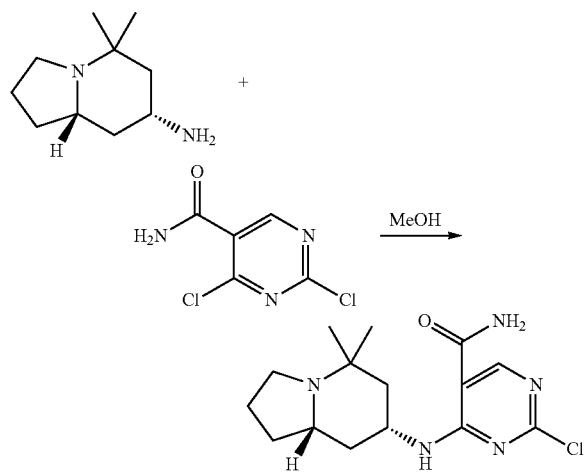

A mixture of (7R,8aS)-octahydro-5,5-dimethylindolizin-7-amine (1.25 g) and 5-aminocarbonyl-2,4-dichloropyrimidine (2.14 g, 1.5 eq.) in iPrOH (50 mL) was stirred at −10° C. to rt for 3 d. The solid was filtered off and washed with methanol (3×10 mL). The filtrate was evaporated under vacuum and the residue was purified by CombiFlash chromatography on silica gel (2N NH$_3$ in MeOH/CH$_2$Cl$_2$=0-30%) to give the desired product (1.3 g, 54% over 3 steps). m/z=324.11 (M+H)$^+$.

Preparation of (7R,8aS)-N-(2-chloro-5-cyanopyrimidin-4-yl)-octahydro-5,5-dimethylindolizin-7-amine

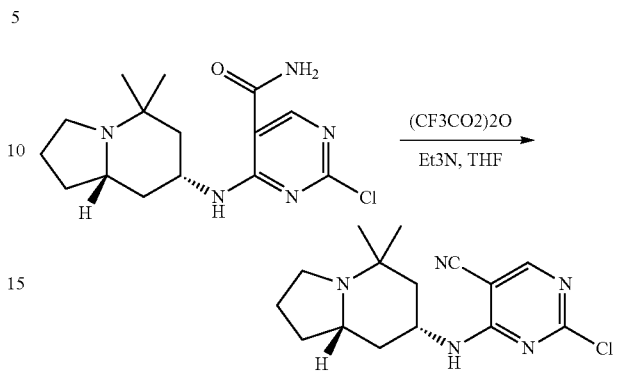

To a mixture of (7R,8aS)-N-(5-aminocarbonyl-2-chloropyrimidin-4-yl)-octahydro-5,5-dimethylindolizin-7-amine (1.3 g) and triethylamine (1.72 mL) in THF (50 mL) was added trifluoroacetic anhydride (1.33 mL) at −78° C. After stirring for 2 h, the reaction was quenched with ice (150 mL). The aqueous solution was extracted with EtOAc (6×150 mL). The organic layers were evaporated under vacuum and the residue was purified by CombiFlash chromatography on silica gel (2N NH$_3$ in MeOH/CH$_2$Cl$_2$=0-20%) to give the desired product (1.1 g, 89%).

$^1$H NMR (CDCl$_3$, 300 MHz): δ 8.29 (s, 1H), 5.41 (d, J=6.0 Hz, 1H), 4.34-4.29 (m, 1H), 3.01-2.94 (m, 1H), 2.57-2.52 (m, 1H), 2.39 (q, J=8.7 Hz, 1H), 2.27-2.20 (m, 1H), 1.94-1.62 (m, 5H), 1.48-1.35 (m, 2H), 1.21 (s, 3H), 1.06 (s, 3H); m/z=306.06 (M+H)$^+$.

Synthesis of 4-((7R,8aS)-octahydro-5,5-dimethylindolizin-7-ylamino)-2-(4-(2-hydroxy-2-methylpropoxy)-2-fluoro-5-(4,5-dihydro-4-methyl-5-oxotetrazol-1-yl)phenylamino)pyrimidine-5-carbonitrile (Compound 80)

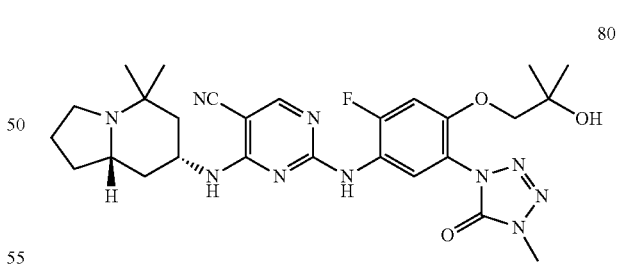

A mixture of 1-(5-amino-2-(2-hydroxy-2-methylpropoxy)-4-fluorophenyl)-4-methyl-1H-tetrazol-5(4H)-one (305 mg), (7R,8aS)-N-(2-chloro-5-cyanopyrimidin-4-yl)-octahydro-5,5-dimethylindolizin-7-amine (262 mg), and benzenesulfonic acid (160 mg) in IPA (2 mL) were heated to 80° C. overnight. After cooling to ambient temperature, the crude mixture was concentrated to dryness. The crude product was absorbed onto silica gel and purified by CombiFlash chromatography (2N NH$_3$ in MeOH/CH$_2$Cl$_2$=0-30%) to give desired product (386 mg, 80%).

$^1$H NMR (300 MHz; $d_6$-DMSO) δ 9.32 (bs, 1H), 8.26 (s, 1H), 7.68 (d, 1H, J=7.8 Hz), 7.38 (d, 1H, J=7.2 Hz), 7.27 (d, 1H, J=12.0 Hz), 4.57 (s, 1H), 3.96 (br, 1H), 3.72 (s, 2H), 3.58 (s, 3H), 2.78 (m, 1H), 2.16 (m, 2H), 1.82-1.42 (m, 6H), 1.22-1.01 (m, 5H), 0.67 (bs, 3H); m/z=567.10 (M+H)$^+$.

Example 62

Synthesis of 4-((7R,8aS)-octahydro-5,5-dimethylindolizin-7-ylamino)-2-(4-((S)-2-hydroxypropoxy)-2-fluoro-5-(4,5-dihydro-4-methyl-5-oxotetrazol-1-yl)phenylamino)pyrimidine-5-carbonitrile (Compound 79)

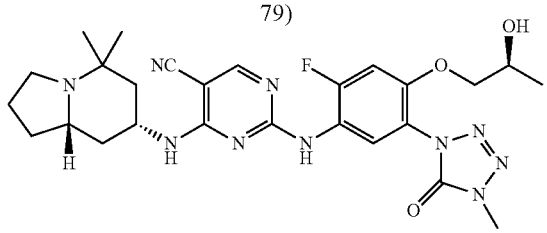

A mixture of 1-(5-amino-4-fluoro-2-hydroxyphenyl)-4-methyl-1H-tetrazol-5(4H)-one (210 mg), (7R,8aS)-N-(2-chloro-5-cyanopyrimidin-4-yl)-octahydro-5,5-dimethylindolizin-7-amine (220 mg), and benzenesulfonic acid (200 mg) in IPA (2 mL) were heated to 80° C. for overnight. After cooling to ambient temperature, the crude mixture was concentrated to dryness. The crude product was absorbed onto silica gel and purified by CombiFlash chromatography (2N NH$_3$ in MeOH/CH$_2$Cl$_2$=0-30%) to give compound 1-(5-(4-((7R,8aS)-octahydro-5,5-dimethylindolizin-7-ylamino)-5-cyanopyrimidin-2-ylamino)-4-fluoro-2-hydroxyphenyl)-4-methyl-1H-tetrazol-5(4H)-one (540 mg with some benzenesulfonic acid).

m/z=495.08 (M+H)$^+$.

A mixture of 1-(5-(4-((7R,8aS)-octahydro-5,5-dimethylindolizin-7-ylamino)-5-cyanopyrimidin-2-ylamino)-4-fluoro-2-hydroxyphenyl)-4-methyl-1H-tetrazol-5(4H)-one (600 mg), (S)-1-iodopropan-2-ol (1.13 g) and cesium carbonate (1.19 g) in DMA (5 mL) were heated to 100° C. for overnight. The reaction mixture was diluted with water (100 mL), and extracted with EtOAc (2×100 mL). The organic layers were evaporated and purified by CombiFlash chromatography (2N NH$_3$ in MeOH/CH$_2$Cl$_2$=0-30%) to give compound 79 (400 mg, 78%).

$^1$H NMR (300 MHz; $d_6$-DMSO) δ 9.32 (bs, 1H), 8.26 (s, 1H), 7.64 (d, 1H, J=8.7 Hz), 7.37 (d, 1H, J=7.8 Hz), 7.30 (d, 1H, J=12.3 Hz), 4.74 (d, 1H, J=4.2 Hz), 3.90-3.81 (m, 5H), 3.58 (s, 3H), 2.78 (m, 1H), 2.17 (m, 2H), 1.82-1.42 (m, 6H), 1.18-1.01 (m, 5H), 0.68 (bs, 3H); m/z=553.06 (M+H)$^+$.

Example 63

Synthesis of 4-((7R,8aS)-octahydro-5,5-dimethylindolizin-7-ylamino)-2-(4-(2-hydroxyethoxy)-2-fluoro-5-(4,5-dihydro-4-methyl-5-oxotetrazol-1-yl)phenylamino)pyrimidine-5-carbonitrile (Compound 78)

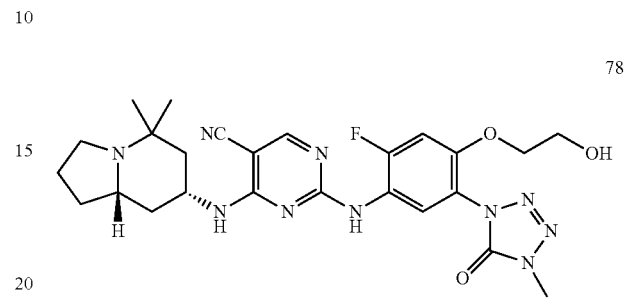

A mixture of 1-(5-amino-2-(2-(tert-butyldimethylsilyl)oxyethoxy)-4-fluorophenyl)-4-methyl-1H-tetrazol-5(4H)-one (200 mg), (7R,8aS)-N-(2-chloro-5-cyanopyrimidin-4-yl)-octahydro-5,5-dimethylindolizin-7-amine (120 mg), and benzenesulfonic acid (120 mg) in IPA (2 mL) was heated to 80° C. overnight. After cooling to ambient temperature, the crude mixture was concentrated to dryness. The crude product was absorbed onto silica gel and purified by CombiFlash chromatography (2N NH$_3$ in MeOH/CH$_2$Cl$_2$=0-20%) to give desired product with benzenesulfonic acid. The methanol solution of the salt was passed through an ion-exchange resin column to remove acid to give the free base of compound 78 (120 mg, 57%).

$^1$H NMR (300 MHz; $d_6$-DMSO) δ 9.33 (bs, 1H), 8.26 (s, 1H), 7.64 (d, 1H, J=7.5 Hz), 7.37 (d, 1H, J=7.5 Hz), 7.32 (d, 1H, J=12.3 Hz), 4.71 (t, 1H, J=5.4 Hz), 4.05 (t, 2H, J=4.8 Hz), 4.01 (br, 1H), 3.58 (m, 5H), 2.78 (m, 1H), 2.17 (m, 2H), 1.79-1.42 (m, 6H), 1.16-1.08 (m, 2H), 1.01 (s, 3H), 0.69 (bs, 3H); m/z=539.11 (M+H)$^+$.

Example 64

Synthesis of 1-(5-(4-((7R,8aS)-5,5-dimethyloctahydroindolizin-7-ylamino)-5-fluoropyrimidin-2-ylamino)-4-fluoro-24(R)-2-hydroxypropoxy)phenyl)-4-methyl-1H-tetrazol-5(4H)-one (Compound 82)

Method 1:

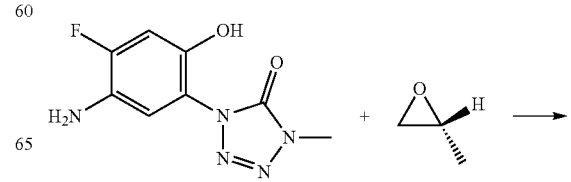

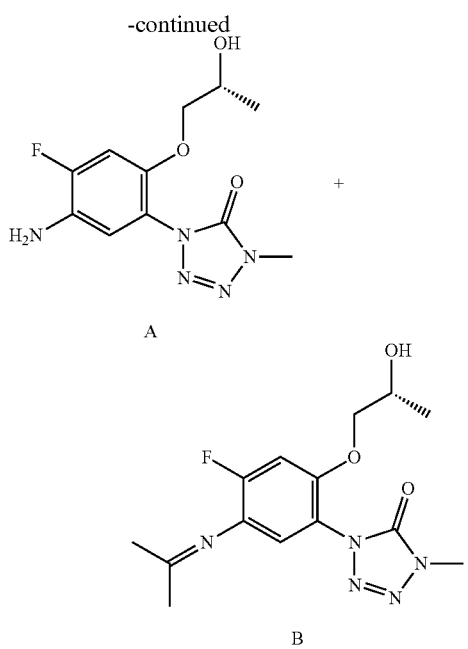

A mixture of anilino-phenol (300 mg, 1.33 mmol, 1 equiv), (R)-propylene oxide (387 mg, 6.66 mmol, 5.0 equiv), K₂CO₃ (221 mg, 1.60 mmol, 1.2 equiv) and ⁿBu₄NBr (43 mg, 0.13 mmol, 0.1 equiv) in 6 mL of acetone was heated in a sealed vessel at 70° C. for 16 h. The mixture was cooled to room temperature, filtered and washed with EtOAc (~50 mL). The filtrate was concentrated and the resulting residue was purified by column chromatography on silica gel using hexane/EtOAc (1:4) as eluent to give 280 mg (Y=74%) of product A and B (~3:1). This mixture was directly used in the next step.

¹H NMR (CDCl₃, 300 MHz) of mixture: δ 6.92 (d, J=8.1 Hz, 1H, compound B), 6.86 (d, J=9.0 Hz, 1H, compound A), 6.80 (d, J=11.1 Hz, 1H, compound B), 6.77 (d, J=12.0 Hz, 1H, compound A), 4.12-4.05 (m, 3H, compound A), 3.85-3.70 (m, 3H, compound B), 3.71 (s, 3H, compound B), 3.70 (s, 3H, compound A), 2.24 (s, 3H, compound B), 2.18 (s, 3H, compound B), 1.21 (d, J=6.3 Hz, 3H, compound B), 1.19 (d, J=6.3 Hz, 3H, compound A); m/z=283.93 (M+H)⁺.

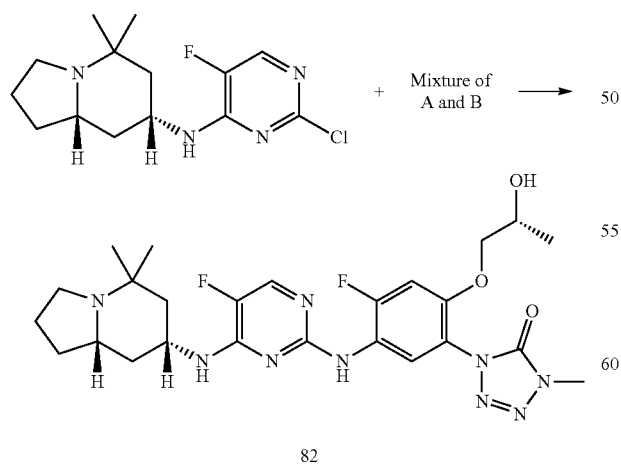

A mixture of above A and B (98 mg, 0.35 mmol, 1.3 equiv), mono-SNAr product (80 mg, 0.27 mmol, 1 equiv), Pd(OAc)₂ (6 mg, 0.03 mmol, 0.1 equiv), (±)BINAP (34 mg, 0.05 mmol, 0.2 equiv) and Cs₂CO₃ (264 mg, 0.81 mmol, 3 equiv) in 2 mL of dioxane was microwaved at 120° C. for 2 hours. The mixture was filtered and washed with EtOAc (10 mL). The filtrate was concentrated and the residue was purified by HPLC to give compound 82.

¹H NMR (DMSO-d₆, 300 MHz): δ 8.39 (s, 1H), 7.86 (d, J=8.1 Hz, 1H), 7.78 (d, J=3.9 Hz, 1H), 7.25 (d, J=12.6 Hz, 1H), 7.18 (d, J=7.2 Hz, 1H), 4.05-3.90 (m, 1H), 3.88-3.78 (m, 3H), 3.59 (s, 3H), 2.80 (td, J=8.4, 3.0 Hz, 1H), 2.26-2.16 (m, 3H), 1.93-1.89 (m, 1H), 1.69-1.50 (m, 4H), 1.37 (t, J=12.6 Hz, 1H), 1.19-1.14 (m, 1H), 1.03 (s, 3H), 1.01 (d, J=5.7 Hz, 3H), 0.75 (s, 3H); ¹⁹F NMR (DMSO-d₆, 282 MHz): δ −116.18 (s), −166.94 (s); m/z=546.05 (M+H)⁺.

Method 2:

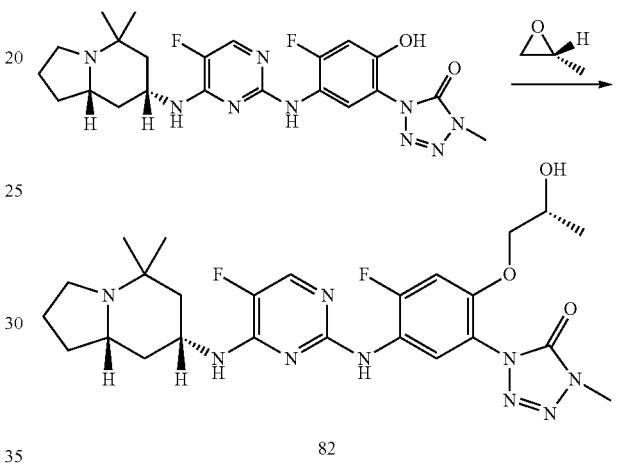

A mixture of the starting phenol (1.8 g, 3.69 mmol, 1 equiv), (R)-propylene oxide (1.1 mL, 14.77 mmol, 4.0 equiv), K₂CO₃ (1.0 g, 7.38 mmol, 2.0 equiv) and ⁿBu₄NBr (0.12 g, 0.37 mmol, 0.1 equiv) in 15 mL of acetone was heated in a sealed vessel at 70° C. for 4 days. The mixture was cooled to room temperature, filtered and washed with EtOAc (~100 mL). The filtrated was washed with brine and concentrated. The resulting residue was purified by column chromatography on silica gel using DCM/2N NH₃ in MeOH (95:5) as eluent to give 1.4 g (Y=71%) of compound 82.

Example 65

Synthesis of Compound 86

Preparation of 1-(tert-butyldimethylsilyloxy)-2-methylpropan-2-ol

2-Methylpropane-1,2-diol (1.08 g, 12.0 mmol, 1.0 equiv) in DCM (40 mL) under argon was cooled to 0° C. TEA (2.50 mL, 18.0 mmol, 1.5 equiv), DMAP (75.0 mg, 0.600 mmol, 0.05 equiv), and TBSCl (2.00 g, 13.2 mmol, 1.1 equiv) were added sequentially, and the reaction was allowed to warm up to ambient temperature overnight. Complete conversion of reactant to product was confirmed by TLC eluted with EtOAc and visualized with KMnO₄. The solvent was removed in vacuo, and the residue was partitioned between water and EtOAc. The aqueous layer was extracted with EtOAc 2×, and the combined organics were dried with Na₂SO₄, filtered, and concentrated to provide 1-(tertbutyldimethylsilyloxy)-2-methylpropan-2-ol (2.05 g, 84%) as a light brown oil that was used without further purification.

¹H NMR (300 MHz; d₆-DMSO) δ 3.46 (s, 1H), 3.31 (s, 2H), 1.08 (s, 6H), 0.920 (s, 9H), 0.0710 (s, 6H).

Preparation of 1-(2-(1-(tert-butyldimethylsilyloxy)-2-methylpropan-2-yloxy)-5-nitrophenyl)-4-methyl-1H-tetrazol-5(4H)-one

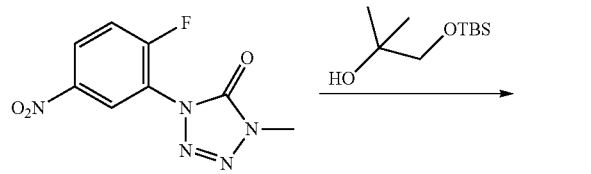

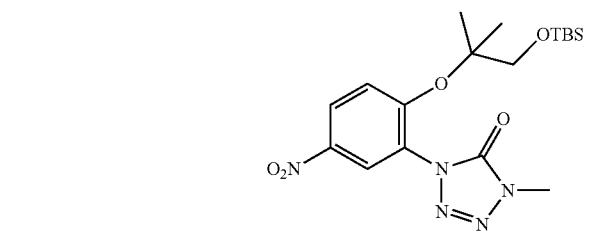

1-(Tertbutyldimethylsilyloxy)-2-methylpropan-2-ol (1.80 g, 8.81 mmol, 1.10 equiv) in THF (30 mL) under argon gas, was cooled to −78° C. Potassium tert-butoxide (1.165 g, 9.61 mmol, 1.20 equiv) was added in one portion, and the reaction mixture was stirred for 15 min at −78° C. Then a solution of 1-(2-fluoro-5-nitrophenyl)-4-methyl-1H-tetrazol-5(4H)-one (prepared according to WO2011068898, which is incorporated herein by reference; 1.915 g, 8.00 mmol, 1.00 equiv) in THF (10 mL) was added slowly, and the reaction mixture was stirred for 30 min at −78° C. and allowed to warm up to ambient temperature over 1 h. The reaction mixture was concentrated, and the residue was taken in EtOAc and water. The layers were separated, and the aqueous layer was extracted with EtOAc 2×. The organic layer was dried over Na₂SO₄, filtered, and concentrated. The crude product was absorbed onto silica gel and purified by flash chromatography and eluted with heptane:EtOAc=100:0 to 30% EtOAc using 10% EtOAc increments to provide 1-(2-(1-(tert-butyldimethylsilyloxy)-2-methylpropan-2-yloxy)-5-nitrophenyl)-4-methyl-1H-tetrazol-5(4H)-one (2.28 g, 67%) as a yellow oil.

¹H NMR (300 MHz; d₆-DMSO) δ 8.44-8.53 (m, 2H), 7.54-7.57 (d, J=9.3 Hz, 1H), 4.04 (s, 2H), 3.63 (s, 3H), 1.23 (s, 6H), 0.770 (s, 9H), 0.00300 (s, 6H); m/z=424 (M+H)⁺.

Preparation of 1-(5-amino-2-(1-(tert-butyldimethylsilyloxy)-2-methylpropan-2-yloxy)phenyl)-4-methyl-1H-tetrazol-5(4H)-one

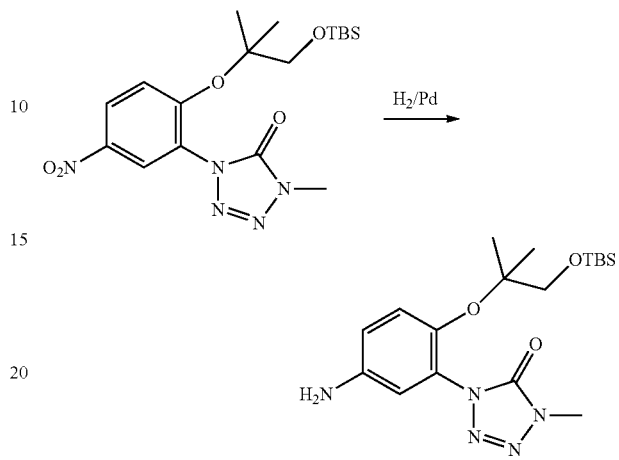

A round-bottom flask was charged with 1-(2-(1-(tert-butyldimethylsilyloxy)-2-methylpropan-2-yloxy)-5-nitrophenyl)-4-methyl-1H-tetrazol-5(4H)-one (2.54 g, 6.00 mmol), EtOH (60 mL), and 10% Pd/C (50% in water, Degussa type E101; 510 mg, 20 wt % by weight of the starting nitro compound). The flask was sealed with a rubber septum, degassed, and back-filled with H₂ (3×) from a balloon filled with H₂. The reaction was stirred for 4 h using a H₂ filled balloon. The reaction mixture was filtered through a pad of celite, and the pad of celite was rinsed with EtOAc/MeOH. The filtrate was evaporated to dryness to provide 1-(5-amino-2-(1-(tert-butyldimethylsilyloxy)-2-methylpropan-2-yloxy)phenyl)-4-methyl-1H-tetrazol-5(4H)-one (2.26 g, 96%) as a light brown solid that was used without further purification.

¹H NMR (300 MHz; d₆-DMSO) δ 6.97-7.00 (d, J=9.0 Hz, 1H), 6.74-6.78 (m, 1H), 6.64-6.68 (m, 1H), 5.04 (bs, 2H), 3.66 (s, 2H), 3.60 (s, 3H), 1.17 (s, 6H), 0.803 (s, 9H), 0.00300 (s, 6H); m/z=394 (M+H)⁺.

Preparation of 1-(2-(1-hydroxy-2-methylpropan-2-yloxy)-5-(44(7R,8aS)-octahydro-5,5-dimethylindolizin-7-ylamino)-5-fluoropyrimidin-2-ylamino)phenyl)-4-methyl-1H-tetrazol-5(4H)-one (Compound 86)

-continued

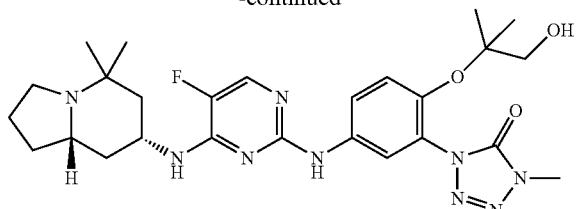

86

A mixture of (7R,8aS)-N-(2-chloro-5-fluoropyrimidin-4-yl)-octahydro-5,5-dimethylindolizin-7-amine hydrochloride (775 mg, 2.31 mmol, 1.00 equiv), 1-(5-amino-2-(1-(tert-butyldimethylsilyloxy)-2-methylpropan-2-yloxy)phenyl)-4-methyl-1H-tetrazol-5(4H)-one (1.00 g, 2.54 mmol, 1.10 equiv), and PTSA monohydrate (880 mg, 4.62 mmol, 2.00 equiv) in IPA (80 mL) was heated to reflux for 3 d as monitored by LCMS. After the first day, in the morning, LCMS indicated a ratio of OTBS-protected product:product=1.5:1. Thus, more PTSA monohydrate (220 mg, 1.16 mmol, 0.50 equiv) was added and refluxing was continued. The reaction was checked by LCMS in the afternoon, which indicated a ratio of OTBS-protected product:product=1:1.2. Thus, more PTSA monohydrate (220 mg, 1.16 mmol, 0.50 equiv) was added and refluxing was continued. On the second day, in the morning, LCMS indicated a ratio of OTBS-protected product:product=1:6.5. Thus, more PTSA monohydrate (220 mg, 1.16 mmol, 0.50 equiv) was added and refluxing was continued. The reaction was checked by LCMS in the afternoon, which indicated a ratio of OTBS-protected product:product =1:9. Thus, more PTSA monohydrate (220 mg, 1.16 mmol, 0.50 equiv) was added and refluxing was continued. On the third day, LCMS indicated the reaction was completed. After cooling to ambient temperature, the crude mixture was concentrated to dryness. The residue was taken in water, EtOAc, and aqueous 1N NaOH. The aqueous and organic layers were partitioned, and the aqueous layer was extracted with EtOAc 2x. The organic layer was dried (Na$_2$SO$_4$), filtered, and the solvent removed under vacuum. The crude product was purified by flash chromatography and eluted with DCM:2M NH$_3$/MeOH=100:0 to 94:6 using 1% 2M NH$_3$/MeOH increments to give compound 1-(2-(1-hydroxy-2-methylpropan-2-yloxy)-5-(4-((7R,8aS)-octahydro-5,5-dimethylindolizin-7-ylamino)-5-fluoropyrimidin-2-ylamino)phenyl)-4-methyl-1H-tetrazol-5(4H)-one (compound 86) (870 mg, 70%) as a solid.

$^1$H NMR (300 MHz; d$_6$-DMSO) δ 9.82 (s, 1H), 8.07 (s, 1H), 7.83-7.84 (d, J=3.6 Hz, 1H), 7.58-7.61 (m, 1H), 7.21-7.24 (m, 1H), 7.09-7.12 (d, J=9.3 Hz, 1H), 4.51 (s, 1H), 4.05 (bs, 1H), 3.65 (s, 2H), 3.59 (s, 3H), 2.83 (m, 1H), 0.803-2.26 (m, 22H); $^{19}$F NMR (282 MHz; d$_6$-DMSO) δ −166.7 (s); m/z=542 (M+H)$^+$.

Example 66

Preparation of 4-((7R,8aS)-octahydro-5,5-dimethyl-indolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile (Compound 83)

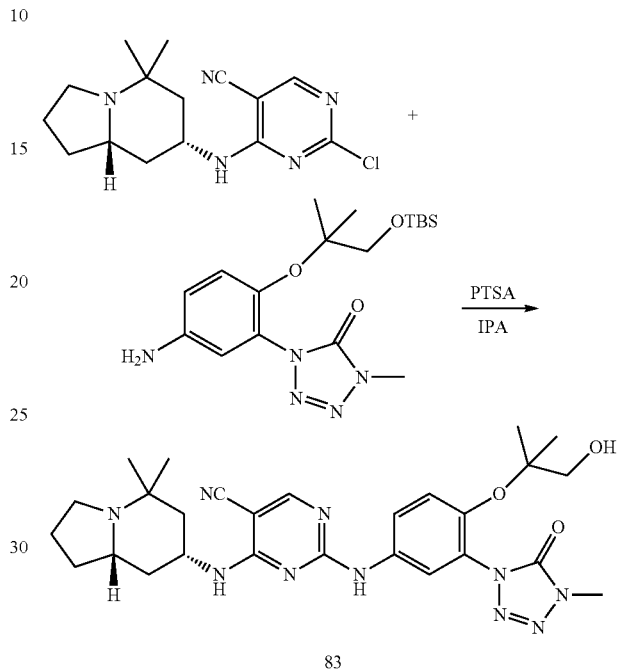

83

A mixture of 4-((7R,8aS)-octahydro-5,5-dimethylindolizin-7-ylamino)-2-chloropyrimidine-5-carbonitrile hydrochloride (200 mg, 0.584 mmol, 1.00 equiv), 1-(5-amino-2-(1-(tert-butyldimethylsilyloxy)-2-methylpropan-2-yloxy)phenyl)-4-methyl-1H-tetrazol-5(4H)-one (255 mg, 0.643 mmol, 1.10 equiv), and PTSA monohydrate (225 mg, 1.17 mmol, 2.00 equiv) in IPA (20 mL) was heated at 70° C. overnight. After the first day, in the morning, LCMS indicated a ratio of OTBS-protected product:product=3:1. Thus, more PTSA monohydrate (56 mg, 0.292 mmol, 0.50 equiv) was added and temperature was raised to reflux. The reaction was checked by LCMS in the afternoon, which indicated a ratio of OTBS-protected product:product=1.5:1. Thus, more PTSA monohydrate (56 mg, 0.292 mmol, 0.50 equiv) was added and refluxing was continued. On the second day, in the morning, LCMS indicated a ratio of OTBS-protected product:product=1:4.5. Thus, more PTSA monohydrate (112 mg, 0.585 mmol, 1.00 equiv) was added and refluxing was continued. The reaction awas checked by LCMS in the afternoon, which indicated a ratio of OTBS-protected product:product =1:8. Thus, more PTSA monohydrate (56 mg, 0.292 mmol, 0.50 equiv) was added and refluxing was continued. On the third day, LCMS indicated the reaction was completed. After cooling to ambient temperature, the crude mixture was concentrated to dryness. The residue was taken in water, EtOAc, and aqueous 1N NaOH. The aqueous and organic layers were partitioned, and the aqueous layer was extracted with EtOAc 2x. The organic layer was dried (Na$_2$SO$_4$), filtered, and the solvent removed under vacuum. The crude product was purified by flash chromatography and eluted with DCM:2M NH$_3$/

MeOH=100:0 to 94:6 using 1% 2M NH₃/MeOH increments to give compound 4-((7R,8aS)-octahydro-5,5-dimethylindolizin-7-ylamino)-2-(4-(1-hydroxy-2-methylpropan-2-yloxy)-3-(4,5-dihydro-4-methyl-5-oxotetrazol-1-yl)phenylamino)pyrimidine-5-carbonitrile (compound 83) (252 mg, 79%) as a solid.

¹H NMR (300 MHz; d₆-DMSO) δ 9.56 (bs, 1H), 8.30 (s, 1H), 8.04 (bs, 1H), 7.63-7.66 (m, 1H), 7.46 (bs, 1H), 7.16-7.19 (d, J=9.3 Hz, 1H), 4.56 (s, 1H), 4.15 (bs, 1H), 3.68 (s, 2H), 3.59 (s, 3H), 2.81 (m, 1H), 0.760-2.26 (m, 22H); m/z=549 (M+H)⁺.

Example 67

Synthesis of Compound 84

Preparation of ethyl 2-(4-amino-5-fluoro-2-(4-methyl-5-oxo-4,5-dihydro-1H-tetrazol-1-yl)phenoxy)-2-methylpropanoate

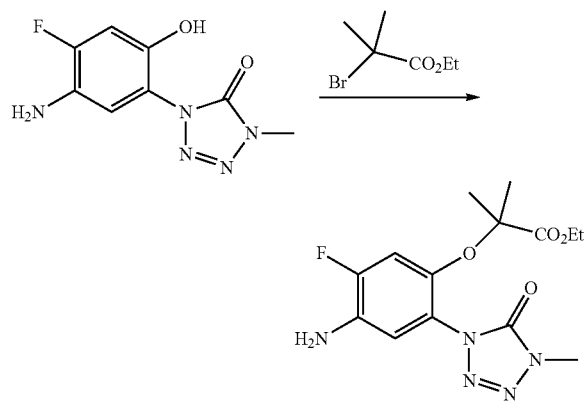

A mixture of 1-(5-amino-4-fluoro-2-hydroxyphenyl)-4-methyl-1H-tetrazol-5(4H)-one (5.00 g, 22.2 mmol, 1.00 equiv), ethyl 2-bromo-2-methylpropanoate (6.50 g, 4.94 mL, 33.3 mmol, 1.50 equiv), K₂CO₃ (6.15 g, 44.4 mmol, 2.00 equiv), and tetra-n-butylammonium bromide (716 mg, 2.22 mmol, 0.10 equiv) in acetone (220 mL) was heated at reflux overnight. After cooling to RT, the reaction mixture was concentrated to dryness. The crude product was taken in excess water and EtOAc. The layers were separated, and the aqueous layer was extracted with EtOAc 2×. The organic layer was dried over Na₂SO₄, filtered, and concentrated to dryness. The crude product was absorbed onto silica gel and purified by flash chromatography and eluted with DCM:MeOH=100:0 to 98% MeOH using 1% MeOH increments to provide ethyl 2-(4-amino-5-fluoro-2-(4-methyl-5-oxo-4,5-dihydro-1H-tetrazol-1-yl)phenoxy)-2-methylpropanoate (5.60 g, 74%) as a clear brown oil.

¹H NMR (300 MHz; d₆-DMSO) δ 6.81-6.82 (d, J=5.7 Hz, 1H), 6.76-6.79 (d, J=8.4 Hz, 1H), 5.26 (bs, 2H), 4.11-4.18 (q, J=7.2 Hz, 2H), 3.58 (s, 3H), 1.31 (s, 6H), 1.16-1.21 (t, J=6.9 Hz, 3H); ¹⁹F NMR (282 MHz; d₆-DMSO) δ −128.5 (q); m/z=340 (M+H)⁺.

Preparation of 1-(5-amino-4-fluoro-2-(1-hydroxy-2-methylpropan-2-yloxy)phenyl)-4-methyl-1H-tetrazol-5(4H)-one

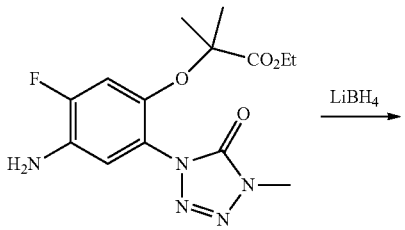

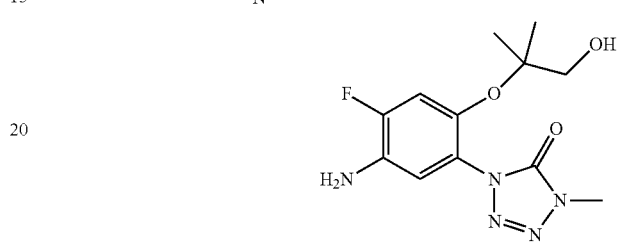

A solution of ethyl 2-(4-amino-5-fluoro-2-(4-methyl-5-oxo-4,5-dihydro-1H-tetrazol-1-yl)phenoxy)-2-methylpropanoate (5.60 g, 16.5 mmol, 1.00 equiv) in Et₂O (155 mL) under argon was cooled to 0° C. The ice-cooled solution was charged with lithium borohydride (791 mg, 36.3 mmol, 2.20 equiv) followed by MeOH (1.540 mL), which resulted in the formation of a free-flowing precipitate. The reaction was stirred at 0° C. for 30 min, then the ice-bath was removed, and the reaction was stirred at ambient temperature for 1 h. At ambient temperature, the reaction was slowly quenched with aqueous 1 N NaOH (100 mL, 100 mmol, 6.00 equiv), which dissolved the free-flowing precipitate. The layers were separated, and the aqueous layer was extracted with DCM 2×. The organic layer was dried over Na₂SO₄, filtered, and concentrated to dryness to give 1-(5-amino-4-fluoro-2-(1-hydroxy-2-methylpropan-2-yloxy)phenyl)-4-methyl-1H-tetrazol-5(4H)-one (4.60 g, 94%) as a white solid that was used without further purification.

¹H NMR (300 MHz; d₆-DMSO) δ 7.05-7.11 (dd, J=3.9 Hz, 12.6 Hz, 1H), 6.73-6.77 (d, J=3.9 Hz, 9.3 Hz, 1H), 5.20 (bs, 2H), 4.81 (bs, 1H), 3.58 (s, 3H), 3.21 (s, 2H), 0.965 (s, 3H); ¹⁹F NMR (282 MHz; d₆-DMSO) δ −129.1 (q); m/z=298 (M+H)⁺.

Preparation of 4-((7R,8aS)-octahydro-5,5-dimethylindolizin-7-ylamino)-2-(4-(1-hydroxy-2-methylpropan-2-yloxy)-2-fluoro-5-(4,5-dihydro-4-methyl-5-oxotetrazol-1-yl)phenylamino)pyrimidine-5-carbonitrile (Compound 84)

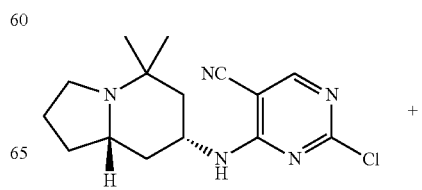

-continued

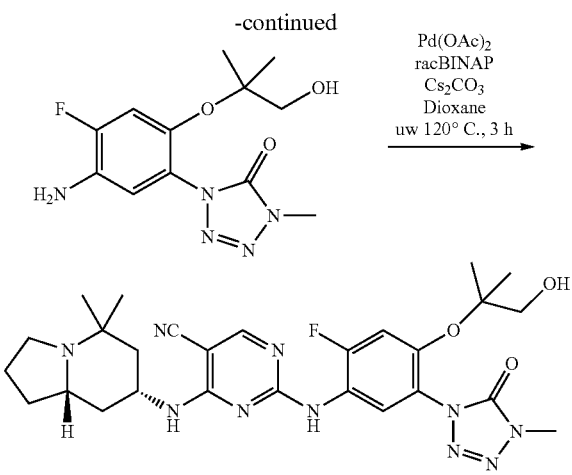

84

To a microwave vial, was added 4-((7R,8aS)-octahydro-5,5-dimethylindolizin-7-ylamino)-2-chloropyrimidine-5-carbonitrile hydrochloride (100 mg, 0.292 mmol, 1.00 equiv), 1-(5-amino-4-fluoro-2-(1-hydroxy-2-methylpropan-2-yloxy)phenyl)-4-methyl-1H-tetrazol-5(4H)-one (130 mg, 0.438 mmol, 1.50 equiv), rac-BINAP (37 mg, 0.0584 mmol, 0.200 equiv), $Cs_2CO_3$ (286 mg, 0.877 mmol, 3.00 equiv), $Pd(OAc)_2$ (7 mg, 0.0292 mmol, 0.100 equiv), and dioxane (3 mL). The microwave vial was capped and sonicated under vacuum for 5 min. The reaction mixture was heated in the microwave at 120° C. for 3 h. The cooled reaction mixture was filtered using a pad of celite and rinsed with dioxane, and the filtrate was concentrated. The crude product was purified by flash chromatography and eluted with DCM:2M $NH_3$/MeOH=100:0 to 95:5 using 1% 2M $NH_3$/MeOH increments to provide 4-((7R,8aS)-octahydro-5,5-dimethylindolizin-7-ylamino)-2-(4-(1-hydroxy-2-methylpropan-2-yloxy)-2-fluoro-5-(4,5-dihydro-4-methyl-5-oxotetrazol-1-yl)phenylamino)pyrimidine-5-carbonitrile (compound 84) (65 mg, 39%) as a solid.

$^1$H NMR (300 MHz; $d_6$-DMSO) δ 9.32 (bs, 1H), 8.27 (s, 1H), 7.66-7.69 (d, J=8.4 Hz, 1H), 7.37-7.41 (m, 1H), 7.25-7.29 (d, J=12 Hz, 1H), 4.57 (s, 1H), 3.98 (bs, 1H), 3.73 (s, 2H), 3.59 (s, 3H), 2.79 (m, 1H), 0.692-2.21 (m, 22H); $^{19}$F NMR (282 MHz; $d_6$-DMSO) δ −113.6 (s); m/z=567 (M+H)$^+$.

The structure of Compound 84 was confirmed by X-ray crystallography:
Empirical formula $C_{28}H_{39}FN_{10}O_4$
Formula weight 598.69
Temperature/K 100
Crystal system triclinic
Space group P1
a/Å 8.0280(2)
b/Å 14.2688(3)
c/Å 14.6295(3)
α/° 62.0220(10)
β/° 88.8670 (10)
γ/° 84.1180(10)
Volume/Å$^3$ 1471.40(6)
Z 2
$ρ_{calc}$mg/mm$^3$ 1.351
m/mm$^{−1}$ 0.814
F(000) 636.0
Crystal size/mm$^3$ 0.229×0.145×0.13
2Θ range for data collection 6.84 to 133.32°

Index ranges −9≤h≤9, −16≤k≤16, −17≤l≤17
Reflections collected 39690
Independent reflections 9819[R(int)=0.0366]
Data/restraints/parameters 9819/3/791
Goodness-of-fit on F$^2$ 1.027
Final R indexes [I>=2σ (I)] R$_1$=0.0380, wR$_2$=0.0982
Final R indexes [all data] R$_1$=0.0405, wR$_2$=0.1008
Largest diff. peak/hole/e Å$^{−3}$ 0.89/−0.29
Flack parameter −0.04(13)

Example 68

Synthesis of 1-(2-(1-hydroxy-2-methylpropan-2-yloxy)-5-(4((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 85)

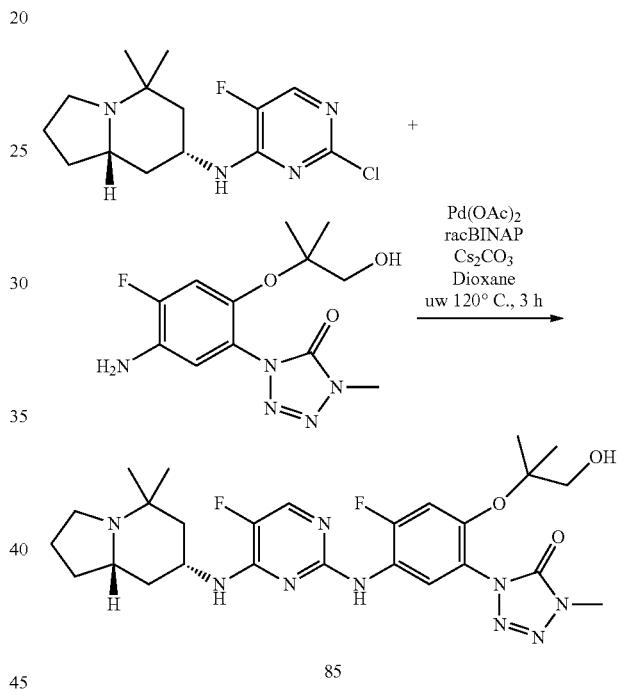

85

To a microwave vial, was added (7R,8aS)-N-(2-chloro-5-fluoropyrimidin-4-yl)-octahydro-5,5-dimethylindolizin-7-amine hydrochloride (100 mg, 0.298 mmol, 1.00 equiv), 1-(5-amino-4-fluoro-2-(1-hydroxy-2-methylpropan-2-yloxy)phenyl)-4-methyl-1H-tetrazol-5(4H)-one (133 mg, 0.447 mmol, 1.50 equiv), rac-BINAP (38 mg, 0.0597 mmol, 0.200 equiv), $Cs_2CO_3$ (292 mg, 0.895 mmol, 3.00 equiv), $Pd(OAc)_2$ (7 mg, 0.0298 mmol, 0.100 equiv), and dioxane (3 mL). The microwave vial was capped and sonicated under vacuum for 5 min. The reaction mixture was heated in the microwave at 120° C. for 3 h. The cooled reaction mixture was filtered using a pad of celite and rinsed with dioxane, and the filtrate was concentrated. The crude product was purified by flash chromatography and eluted with DCM:2M $NH_3$/MeOH=100:0 to 95:5 using 1% 2M $NH_3$/MeOH increments to provide 1-(2-(1-hydroxy-2-methylpropan-2-yloxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (compound 85) (85 mg, 51%) as a solid.

$^1$H NMR (300 MHz; d$_6$-DMSO) δ 8.47 (s, 1H), 7.94-7.97 (d, J=8.7 Hz, 1H), 7.81-7.82 (d, J=3.6 Hz, 1H), 7.31-7.35 (d, J=12.3 Hz, 1H), 7.20-7.25 (m, 1H), 4.91-4.95 (t, J=5.7 Hz, 1H), 3.98 (bs, 1H), 3.58 (s, 3H), 3.29 (s, 2H), 2.81 (m, 1H), 0.767-2.21 (m, 22H); $^{19}$F NMR (282 MHz; d$_6$-DMSO) δ −117.8 (s), −166.4 (s); m/z=560 (M+H)$^+$.

Example 69

Synthesis of 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5(4H)-one (Compound 87)

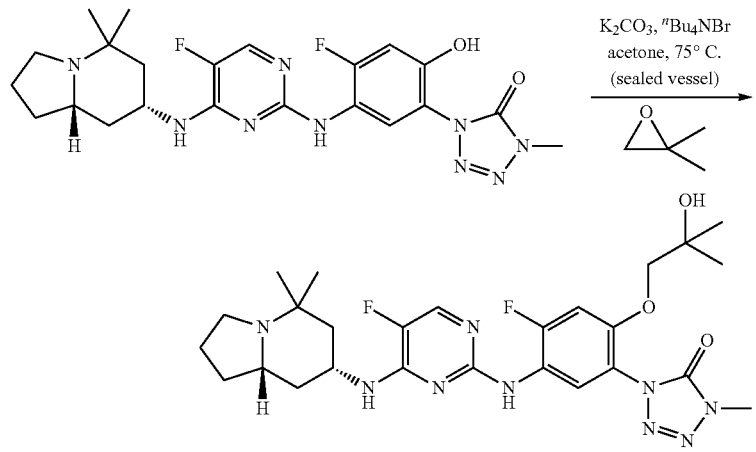

Into a vessel was weighed compound 89 (10.2 g, 20.9 mmol), K$_2$CO$_3$ (3.5 g, 25.1 mmol) and tetra-butylammonium bromide (674 mg, 2.09 mmol). Acetone (100 mL) then isobutylene oxide (5.6 mL, 62.8 mmol) was added and the vessel sealed. The mixture was then heated to a bath temperature of 78° C. for 5 days. The mixture was allowed to cool, then filtered and the filter cake was washed with acetone (2×30 mL). The filtrate was concentrated under vacuum and the residue was partitioned between EtOAc (100 mL) and H$_2$O (100 mL). The aqueous layer was extracted with EtOAc (2×75 mL) and the combined organic extracts were dried (Na$_2$SO$_4$), filtered and the solvent removed under vacuum to leave a crude residue. The residue was dry-loaded on to silica gel and then purified by column chromatography on silica gel using EtOAc/2M NH$_3$ in MeOH (1:0 to 9:1 in increments of 0.02 2M NH$_3$ in MeOH) to give compound 87 (8.0 g, 68%) as a solid. Super-critical fluid chromatography using a chiral stationary phase indicated that the product material contained ~1.2% of an impurity, which may correspond to a regio-isomeric product arising from ring-opening of the epoxide at the more hindered terminus. Also obtained from the column were mixed fractions containing the desired product (~2 g).

$^1$H NMR (300 MHz; d$_6$-DMSO): δ 8.39 (br. s, 1H), 7.91 (d, J=8.4 Hz, 1H), 7.79 (d, J=3. 8Hz, 1H), 7.24 (d, J=12.5 Hz, 1H), 7.18 (br. s, 1H), 4.54 (s, 1H), 4.03-4.90 (m, 1H), 3.71 (s, 2H), 3.58 (s, 3H), 2.83 (br. t, J=8.7 Hz, 1H), 2.24-2.10 (m, 2H), 1.94 (m, 1H), 1.74-1.50 (m, 5H), 1.38 (t, J=12.2 Hz, 1H), 1.24-1.11 (m, 1H), 1.03 (s, 9H), 0.75 (s, 3H); $^{19}$F NMR (287 MHz; d$_6$-DMSO): δ −166.9 (d), −116.2 (s); m/z=560.15 [M+H]$^+$.

Example 70

Synthesis of 1-(5-(4-((7R,8aS)-octahydro-5,5-dimethylindolizin-7-ylamino)-5-fluoropyrimidin-2-ylamino)-4-fluoro-2-(oxetan-3-yloxy)phenyl)-4-methyl-1H-tetrazol-5(4H)-one (Compound 88)

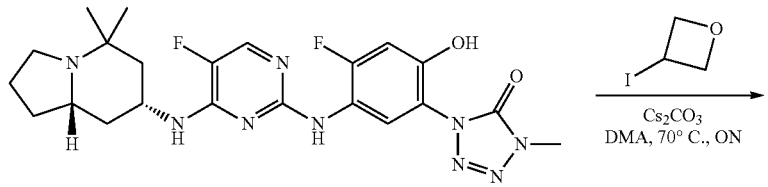

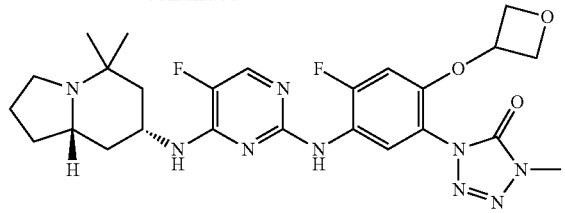

A mixture of 1-(5-(4-(((7R,8aS)-octahydro-5,5-dimethyl-indolizin-7-ylamino)-5-fluoropyrimidin-2-ylamino)-4-fluoro-2-hydroxyphenyl)-4-methyl-1H-tetrazol-5(4H)-one (900 mg, 1.85 mmol, 1 equiv), 3-iodooxetane (1.02 g, 5.54 mmol, 3 equiv), and $Cs_2CO_3$ (665 mg, 2.03 mmol, 1.1 equiv) in DMA was heated to 70° C. overnight. After cooling to RT, the reaction mixture was diluted with excess water (200 mL) and EtOAc (200 mL). The layers were separated, and the aqueous layer extracted with EtOAc 3×. The combined organics were dried over $Na_2SO_4$, filtered, and concentrated to dryness. The crude product was absorbed onto silica gel and purified by flash chromatography and eluted with DCM:2M $NH_3$/MeOH=100:0 to 95:5 using 1% 2M $NH_3$/MeOH increments to give compound 88 as a solid.

$^1$H NMR (300 MHz; $d_6$-DMSO) δ 8.44 (s, 1H), 7.90-7.93 (d, 1H, J=8.7Hz), 7.78-7.79 (d, 1H, J=3.9Hz), 7.19-7.21 (s, 1H, J=8.1Hz), 6.95-6.99 (s, 1H, J=12Hz), 5.28-5.36 (p, 1H, J=5.7Hz), 4.83-4.88 (m, 2H), 4.39-4.43 (m, 2H), 3.91-4.09 (m, 1H), 3.61 (s, 3H), 2.75-2.99 (m, 1H), 0.974-2.25 (m, 13H), 0.750 (bs, 3H); $^{19}$F NMR (282 MHz; $d_6$-DMSO) δ −115.8 (t), −166.8 (s); m/z=544 (M+H)$^+$.

Example 71

Synthesis of 4-((7R,8aS)-octahydro-5,5-dimethylindolizin-7-ylamino)-2-(5-(4,5-dihydro-4-methyl-5-oxotetrazol-1-yl)-2-fluoro-4-hydroxyl-phenylamino)pyrimidine-5-carbonitrile

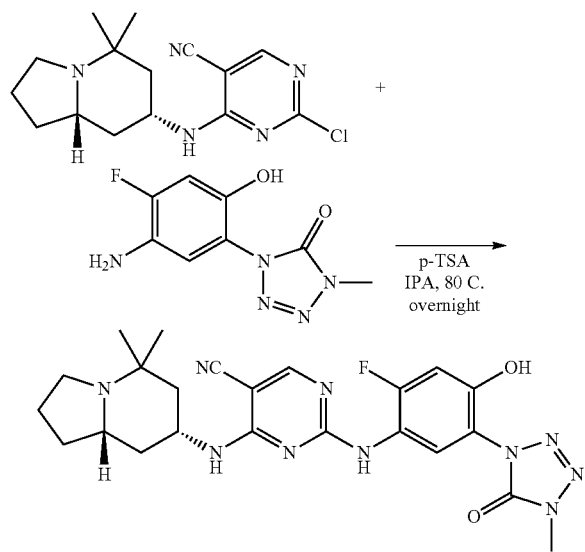

To a mixture of (7R,8aS)-N-(2-chloro-5-cyanopyrimidinal-4-yl)-octahydro-5,5dimethylindolizin-7-amine (150 mg, 1.0 eq.) in isopropyl alcohol (2.45 ml, 0.2M), 5-(4,5-dihydro-4-methyl-5-oxotetrazol-1-yl)-2-fluoro-4-hydroxylphenylamine (144 mg, 1.3 eq.) was added, followed by p-toluenesulfonic acid (112 mg, 1.2 eq.), and was heated at 80° C. overnight under nitrogen. Upon completion of the reaction indicated by LC/MS, the mixture was cooled to room temperature, and concentrated under reduced pressure. The residue was dissolved into ethyl acetate, absorbed into silica gel and purified by Combi-flash chromatography (2N $NH_3$ in MeOH/EtOAc=0-20%), yield 160 mg of desired product as a light yellow solid.

$^1$H NMR (300 MHz; $d_6$-DMSO) δ 9.24 (bs, 1H), 8.25 (s, 1H), 7.5 (d, J=7.5Hz, 1H), 7.33 bs, 1H), 6.87 (d, J=11.7Hz, 1H), 3.57 (s, 3H), 2.82 (bs, 1H), 1.96-1.67 (m, 8H), 1.13 (m, 6H), 0.76 (m, 2H); m/z=495.01 (M+H)$^+$.

Synthesis of 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimidine-5-carbonitrile (Compound 90)

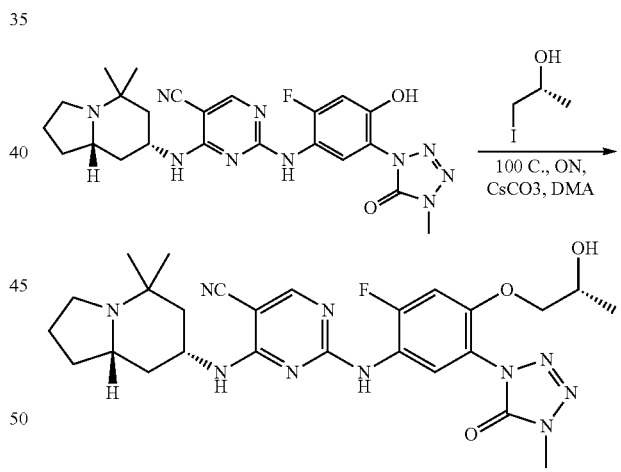

4-((7R,8aS)-octahydro-5,5-dimethylindolizin-7-ylamino)-2-(5-(4,5-dihydro-4-methyl-5-oxotetrazol-1-yl)-2-fluoro-4-hydroxyl-phenylamino)pyrimidine-5-carbonitrile (467 mg, 1.0 eq.) was added to N,N-dimethylacetamide (4.7 ml, 0.2M), followed by $Cs_2CO_3$ (922 mg, 3.0 eq.) and 3-iodo-2-(R)-propanol (0.88 g, 5.0 eq.) and heated at 100° C. under nitrogen overnight. It was cooled to room temperature and concentrated under reduced pressure. The residue was treated with ethyl acetate (10 ml) and treated with saturated $NaHCO_3$ (10 ml). The aqueous layer was extracted with ethyl acetate (2×10 ml), and the combined organic solution was washed with brine (10 ml), and dried with $Na_2SO_4$. Solid was filtered off, and the organic solution was concentrated under reduced pressure. 5 ml of ethyl acetate was added to the residue, silica gel was added to form a thick paste, and was concentrated under reduced pressure. This silica gel mixture was loaded onto the Combiflash chromatography and product was eluted using 2N NH₃ in MeOH (0-20%)/Ethyl Acetate (100%-80%) gradient to yield 124 mg of product as a light beige solid.

¹H NMR (300 MHz; d₆-DMSO) δ 9.33 (s, 1H), 8.26 (s, 1H), 7.65 (d, J=8.1Hz, 1H), 7.37 (d, J=7.5Hz, 1H), 7.3 (d, J=12Hz, 1H), 4.75 (d, J=4.2Hz, 1H), 3.97-3.8 (m, 3H), 3.58 (s, 3H), 2.76 (m, 1H), 2.20 (m, 2H), 1.83-1.4 (m, 8H), 1.22-1.07 (m, 2H), 1.03 (m, 6H), 1.0 (bs, 1H); m/z=553.04 (M+H)⁺.

Example 72

Synthesis of 1-(5-(4-((7R,8aS)-octahydro-5,5-dimethylindolizin-7-ylamino)-5-fluoropyrimidin-2-ylamino)-2-bromo-4-fluorophenyl)-4-methyl-1H-tetrazol-5(4H)-one (Compound 91)

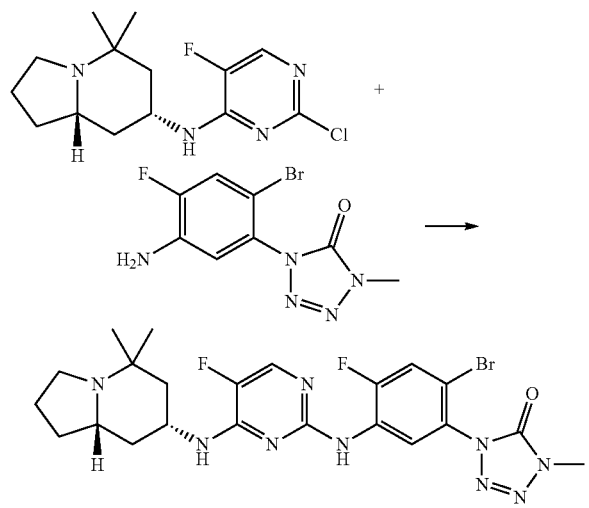

(7R,8aS)-N-(2-chloro-5-fluoropyrimidin-4-yl)-octahydro-5,5-dimethylindolizin-7-amine (1.4525 g, 4.86 mmol) and p-toluenesulfonic acid (1.7288 g, 9.09 mmol) were weighed out and added to a large reaction tube containing 1-(5-amino-2-bromo-4-fluorophenyl)-4-methyl-1H-tetrazol-5(4H)-one (2.10 g, 7.29 mmol). 42 mL isopropyl alcohol was added, and the tube was sealed and heated overnight at 110° C. The reaction was basified with saturated aqueous sodium bicarbonate and extracted three times with ethyl acetate. The combined organic layer was washed with brine and dried over sodium sulfate. Product solution was filtered, concentrated onto a plug of silica, and purified by column chromatography. Pure fractions were combined, concentrated and dried under high vacuum to give 1.4063 g of the title compound (53% yield).

¹H NMR (300 MHz; d₆-DMSO) δ 8.77 (s, 1H), 8.34 (d, J=7.7 Hz, 1H), 7.92-7.80 (m, 2H), 7.35 (d, J=7.8 Hz, 1H), 4.03-3.88 (m, 1H), 3.62 (s, 3H), 2.87-2.76 (m, 1H), 2.27-2.10 (m, 2H), 1.93 (d, J=11.2 Hz, 1H), 1.74-1.49 (m, 4H), 1.41 (t, J=12.2 Hz, 1H), 1.23-1.13 (m, 1H), 1.12-0.94 (m, 4H), 0.76 (s, 3H) m/z=550/552 (bromine) (M+H)⁺.

Example 73

Synthesis of 1-(5-(4-((7R,8aS)-octahydro-5,5-dimethylindolizin-7-ylamino)-5-fluoropyrimidin-2-ylamino)-4-fluoro-2-vinylphenyl)-4-methyl-1H-tetrazol-5(4H)-one (Compound 92)

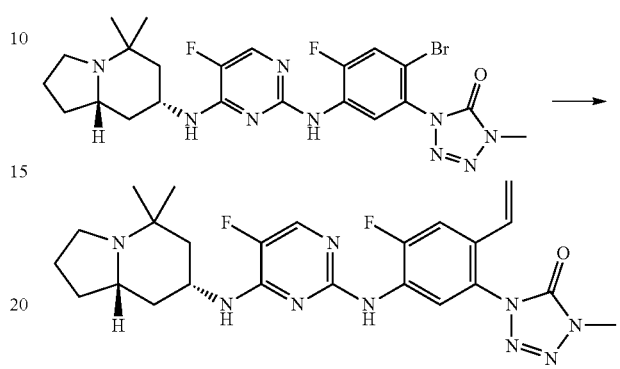

1-(5-(4-((7R,8aS)-octahydro-5,5-dimethylindolizin-7-ylamino)-5-fluoropyrimidin-2-ylamino)-2-bromo-4-fluorophenyl)-4-methyl-1H-tetrazol-5(4H)-one (301.9 mg, 0.55 mmol) was weighed out and added to a reaction tube with magnetic stir bar. It was dissolved in 24 mL of a solution of dimethoxyethane, ethanol, and water in a ratio of 7:3:2, respectively. Sodium carbonate (174.6 mg, 1.65 mmol) was weighed out, and vinylboronic acid pinacol ester (0.205 mL, 1.21 mmol) was then added. The solution was subjected to vigorous sub-surface nitrogen sparging. Bis(triphenylphosphine)palladium(II) dichloride (17.3 mg, 0.025 mmol) was weighed out and added, the tube was sealed under nitrogen, and the reaction was heated overnight at 110° C. The reaction solution was then combined with a 0.162 mmol pilot reaction run under the same conditions. This was concentrated directly onto silica, and purified by column chromatography. Pure fractions were combined, concentrated, and dried under high vacuum to give 256.0 mg of the title compound (72% total).

¹H NMR (300 MHz, CDCl₃) δ 8.53 (d, J=7.7 Hz, 1H), 7.72 (d, J=3.0 Hz, 1H), 7.35 (d, J=12.3 Hz, 1H), 7.09 (d, J=3.9 Hz, 1H), 6.37 (dd, J=17.4, 11.0 Hz, 1H), 5.59 (d, J=17.4 Hz, 1H), 5.23 (d, J=10.9 Hz, 1H), 4.74 (s, 1H), 4.11 (s, 1H), 3.65 (s, 3H), 3.42 (d, J=5.4 Hz, 1H), 2.98 (s, 1H), 2.43-2.31 (m, 1H), 2.25 (d, J=10.8 Hz, 1H), 1.86-1.72 (m, 3H), 1.70-1.47 (m, 3H), 1.17 (s, 3H), 0.94 (s, 3H). m/z=498 (M+H)⁺.

Example 74

Synthesis of 1-(5-(4-((7R,8aS)-octahydro-5,5-dimethylindolizin-7-ylamino)-5-fluoropyrimidin-2-ylamino)-4-fluoro-2-(2-hydroxyethyl)phenyl)-4-methyl-1H-tetrazol-5(4H)-one (Compound 93)

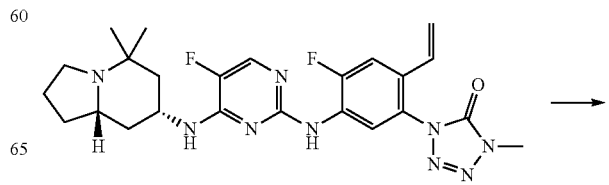

-continued

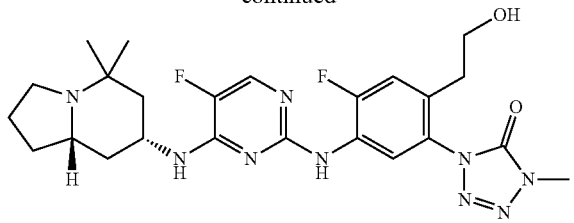

1-(5-(4-((7R,8aS)-octahydro-5,5-dimethylindolizin-7-ylamino)-5-fluoropyrimidin-2-ylamino)-4-fluoro-2-(2-hydroxyethyl)phenyl)-4-methyl-1H-tetrazol-5(4H)-one starting material was dried directly in the reaction flask and weighed by difference (78.0 mg, 0.16 mmol). 2 mL THF was added and the solution was cooled to 0° C. with stirring. BH$_3$.THF (1.0 M solution in THF) was added (0.63 mL, 0.63 mmol) and the reaction was stirred 1 hour at 0° C. and at room temperature overnight. The reaction was cooled back to 0° C. and 1.0 M aqueous NaOH was added (0.73 mL, 0.73 mmol) followed by 30 wt % hydrogen peroxide (0.73 mL, 7.15 mmol). After stirring to room temperature it was heated at reflux for 3 hours. The reaction solution was extracted three times with ethyl acetate, washed with brine, and dried over sodium sulfate. Product solution was filtered, concentrated onto a plug of silica, and purified by column chromatography. Pure fractions were combined, concentrated, and dried under high vacuum to give 19.0 mg of the title compound (23% yield).

$^1$H NMR (300 MHz, CDCl$_3$) δ 8.50 (dd, J=7.7, 1.7 Hz, 1H), 7.69 (dd, J=3.1, 2.0 Hz, 1H), 7.11 (dd, J=11.9, 1.7 Hz, 1H), 7.06-6.99 (m, 1H), 4.84 (d, J=7.6 Hz, 1H), 4.23-3.93 (m, 1H), 3.80-3.72 (m, 2H), 3.65 (s, 3H), 2.93 (t, J=8.5 Hz, 1H), 2.63 (t, J=6.2 Hz, 2H), 2.39-2.26 (m, 2H), 2.20 (d, J=11.8 Hz, 1H), 1.87-1.69 (m, 4H), 1.39-1.34 (m, 1H), 1.13 (s, 3H), 0.91 (s, 3H), 0.82-0.75 (m, 1H). m/z=516 (M+H)$^+$.

Example 75

Preparation of 1-(5-(44(7R,8aS)-octahydro-5,5-dimethylindolizin-7-ylamino)-5-fluoropyrimidin-2-ylamino)-4-fluoro-2-(1-hydroxyethyl)phenyl)-4-methyl-1H-tetrazol-5(4H)-one (Compound 94)

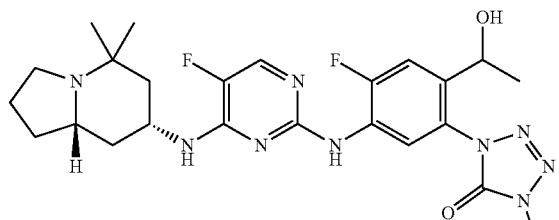

5.8 mg of the title compound (a 1:1 mixture of diastereomers at the benzylic carbon) was isolated from the chromatographic purification of 1-(5-(4-((7R,8aS)-octahydro-5,5-dimethylindolizin-7-ylamino)-5-fluoropyrimidin-2-ylamino)-4-fluoro-2-(2-hydroxyethyl)phenyl)-4-methyl-1H-tetrazol-5(4H)-one.

$^1$H NMR (300 MHz, CDCl$_3$) δ 8.49 (dd, J=9.7, 7.7 Hz, 1H), 7.72 (d, J=2.9 Hz, 1H), 7.34 (d, J=12.1 Hz, 1H), 7.06 (dd, J=6.9, 3.8 Hz, 1H), 4.90-4.69 (m, 1H), 4.64 (q, J=7.0 Hz, 1H), 4.23-4.03 (m, 1H), 3.66 (s, 3H), 3.30-3.14 (m, 1H), 3.08-2.92 (m, 1H), 2.45-2.33 (m, 1H), 2.25 (d, J=11.2 Hz, 1H), 1.92-1.69 (m, 4H), 1.39 (d, J=6.4 Hz, 4H), 1.22-1.16 (m, 3H), 1.03-0.92 (m, 3H), 0.85-0.71 (m, 1H). m/z=516 (M+H)$^+$.

Example 76

Preparation of 1-(5-(4-((7R,8aS)-octahydro-5,5-dimethylindolizin-7-ylamino)-5-fluoropyrimidin-2-ylamino)-2-ethyl-4-fluorophenyl)-4-methyl-1H-tetrazol-5(4H)-one (Compound 95)

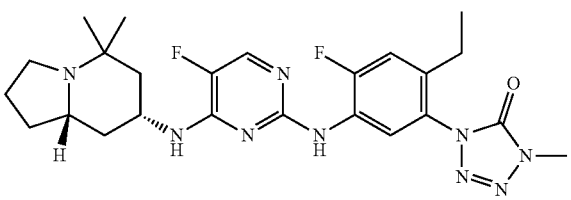 [SMILES: CCc1cc(F)c(Nc2ncc(F)c(N[C@@H]3C[C@@H]4CCCN4C(C)(C)C3)n2)cc1-n1nnn(C)c1=O]

3.4 mg of the title compound was isolated from the chromatographic purification of 1-(5-(4-((7R,8aS)-octahydro-5,5-dimethylindolizin-7-ylamino)-5-fluoropyrimidin-2-ylamino)-4-fluoro-2-(2-hydroxyethyl)phenyl)-4-methyl-1H-tetrazol-5(4H)-one.

$^1$H NMR (300 MHz, DMSO) δ 8.50 (s, 1H), 7.94 (d, J=7.6 Hz, 1H), 7.83 (d, J=3.7 Hz, 1H), 7.31 (d, J=11.9 Hz, 1H), 7.25 (d, J=8.1 Hz, 1H), 4.05-3.92 (m, 1H), 3.61 (s, 3H), 2.81 (td, J=8.7, 3.3 Hz, 1H), 2.38 (q, J=7.5 Hz, 2H), 2.27-2.11 (m, 2H), 1.92 (d, J=11.5 Hz, 1H), 1.75-1.49 (m, 4H), 1.38 (t, J=12.2 Hz, 1H), 1.21-1.12 (m, 1H), 1.04 (t, J=7.4 Hz, 3H), 1.03 (s, 3H), 0.95-0.81 (m, 1H), 0.75 (s, 3H). m/z=500 (M+H)$^+$.

Example 77

Synthesis of 1-(5-(4-((7R,8aS)-octahydro-5,5-dimethylindolizin-7-ylamino)-5-fluoropyrimidin-2-ylamino)-4-fluoro-2-(3-hydroxyprop-1-ynyl)phenyl)-4-methyl-1H-tetrazol-5(4H)-one (Compound 96)

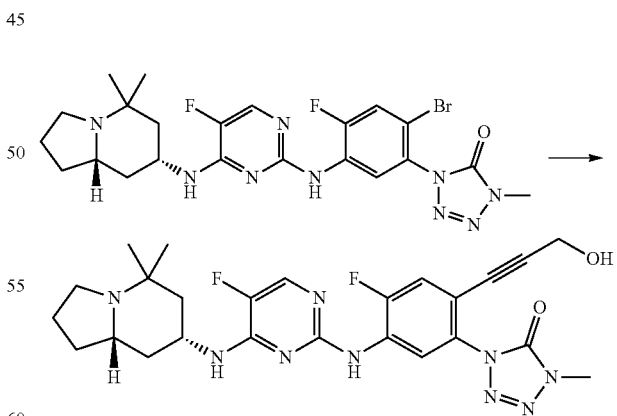

1-(5-(4-((7R,8aS)-octahydro-5,5-dimethylindolizin-7-ylamino)-5-fluoropyrimidin-2-ylamino)-2-bromo-4-fluorophenyl)-4-methyl-1H-tetrazol-5(4H)-one (304.5 mg, 0.55 mmol) was weighed out and added to a reaction tube with magnetic stir bar. Triphenylphosphine (43.5 mg, 0.17 mmol) and copper(I) iodide (12.9 mg, 0.068 mmol) were then weighed out and added. 11 mL dioxane was added, followed by diisopropylethylamine (0.65 mL, 3.73 mmol) and propargyl alcohol (0.054 mL, 0.93 mmol). The reaction was subjected to vigorous sub-surface nitrogen sparge and [1,1'-bis(diphenylphosphino)ferrocene]dichloropalladium (40.5 mg, 0.055 mmol) was weighed out and added, and the reaction was sealed under nitrogen. The reaction was heated overnight at 110° C. The reaction solution was then combined with a 0.186 mmol pilot reaction run under the same conditions, concentrated directly onto silica, and purified by column chromatography. Pure fractions were combined, concentrated, and dried under high vacuum to give 84.0 mg of the title compound (22% total).

$^1$H NMR (300 MHz, $d_6$-DMSO) δ 8.90 (s, 1H), 8.45 (d, J=7.6 Hz, 1H), 7.97 (d, J=3.7 Hz, 1H), 7.60 (d, J=11.4 Hz, 1H), 7.47 (d, J=7.8 Hz, 1H), 5.34 (t, J=6.0 Hz, 1H), 4.23 (d, J=6.0 Hz, 2H), 4.14-4.00 (m, 1H), 3.68 (s, 3H), 2.98-2.83 (m, 1H), 2.33-2.13 (m, 2H), 2.03 (d, J=10.9 Hz, 1H), 1.79-1.46 (m, 5H), 1.31-1.26 (m, 1H), 1.12 (s, 3H), 0.96-0.88 (m, 1H), 0.83 (s, 3H). m/z=526 (M+H)$^+$.

Example 78

Synthesis of 1-(5-(4-((7R,8aS)-octahydro-5,5-dimethylindolizin-7-ylamino)-5-fluoropyrimidin-2-ylamino)-4-fluoro-2-(3-hydroxypropyl)phenyl)-4-methyl-1H-tetrazol-5(4H)-one (Compound 97)

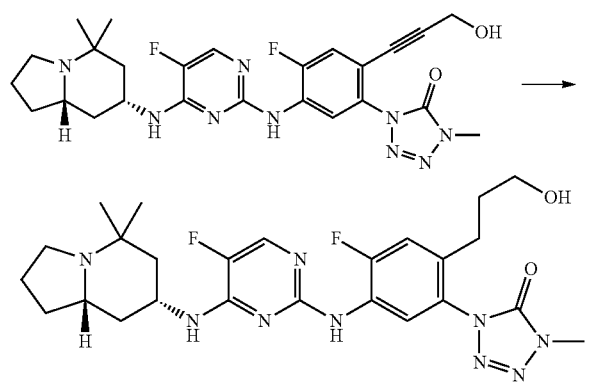

1-(5-(4-((7R,8aS)-octahydro-5,5-dimethylindolizin-7-ylamino)-5-fluoropyrimidin-2-ylamino)-4-fluoro-2-(3-hydroxyprop-1-ynyl)phenyl)-4-methyl-1H-tetrazol-5(4H)-one (77.9 mg, 0.15 mmol) was dissolved in 10 mL methanol. After purging with nitrogen, the flask was charged with 32.7 mg (0.015 mmol) 10% palladium on carbon (50 wt % water for safety). The reaction was then evacuated and back-filled with nitrogen three times before one final evacuation and introduction of a hydrogen balloon. This was stirred overnight at room temperature under one atmosphere of hydrogen. After filtration of the catalyst, the methanol was evaporated to give 72.6 mg (93% crude recovery). 63.0 mg was subjected to column chromatography. After drying, 39.6 mg was obtained of the title compound (63% yield).

$^1$H NMR (300 MHz, $d_6$-DMSO) δ 8.50 (s, 1H), 7.94 (d, J=7.6 Hz, 1H), 7.82 (d, J=3.8 Hz, 1H), 7.29 (d, J=12.0 Hz, 1H), 7.25 (d, 1H), 4.40 (t, J=5.1 Hz, 1H), 4.16-3.82 (m, 1H), 3.60 (s, 3H), 2.81 (td, J=8.7, 3.5 Hz, 1H), 2.44-2.36 (m, 2H), 2.27-2.11 (m, 2H), 1.92 (d, J=11.7 Hz, 1H), 1.74-1.66 (m, 1H), 1.65-1.44 (m, 5H), 1.39 (t, J=12.3 Hz, 1H), 1.31-1.13 (m, 2H), 1.03 (s, 4H), 0.91-0.81 (m, 1H), 0.75 (s, 3H). m/z=530 (M+H)$^+$.

Example 79

Synthesis of 4-(4-((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)benzonitrile (Compound 98)

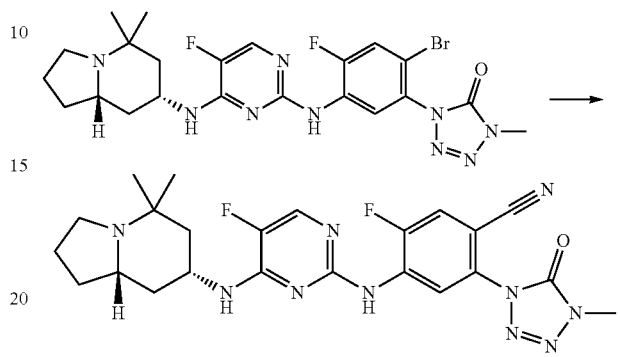

1-(5-(4-((7R,8aS)-octahydro-5,5-dimethylindolizin-7-ylamino)-5-fluoropyrimidin-2-ylamino)-2-bromo-4-fluorophenyl)-4-methyl-1H-tetrazol-5(4H)-one (54.3 mg, 0.10 mmol) was added to a tared reaction vial with magnetic stir bar and weighed. This was dissolved in 2 mL dimethylformamide and copper(I) cyanide (18.0 mg, 0.20 mmol) was weighed out and added. The reaction was heated at 100° C. for three hours, recharged with additional copper cyanide (37.7 mg, 0.42 mmol) and heated overnight at 115° C. The reaction was diluted into ethyl acetate and washed in succession with brine and water to remove DMF. The ethyl acetate layer was dried over sodium sulfate, filtered, and concentrated onto silica. Product was purified by column chromatography. After drying, 21.1 mg was obtained of the title compound (43% yield).

$^1$H NMR (300 MHz, $d_6$-DMSO) δ 9.34 (s, 1H), 8.73 (d, J=7.2 Hz, 1H), 8.16 (d, J=11.0 Hz, 1H), 8.02 (d, J=3.6 Hz, 1H), 7.57 (d, J=8.5 Hz, 1H), 4.19-4.03 (m, 1H), 3.72 (s, 3H), 2.89 (td, J=8.6, 3.3 Hz, 1H), 2.37-2.18 (m, 2H), 2.03 (d, J=12.1 Hz, 1H), 1.86-1.56 (m, 4H), 1.48 (t, J=12.2 Hz, 1H), 1.21-1.13 (m, 1H), 1.11 (s, 3H), 0.98-0.88 (m, 1H), 0.83 (s, 3H). m/z=497 (M+H)$^+$.

Example 80

Preparation of 1-(2-(4(R)-1-hydroxypropan-2-yloxy)-5-(4-(4(7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 99)

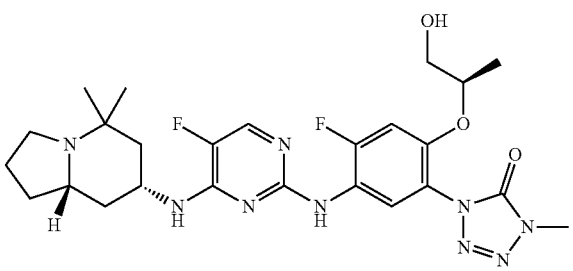 [SMILES: C[C@H](CO)Oc1cc(F)c(Nc2ncc(F)c(N[C@@H]3C[C@@H]4CCCN4C(C)(C)C3)n2)cc1-n1nnn(C)c1=O]

During chromatographic purification of 1-(2-((S)-2-hydroxypropoxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one (Compound 81), supercritical fluid chromatography (SFC) identified a second component present in some fractions. After preparative SFC, 19.0 mg was obtained of the observed second component. This was identified as the title compound.

$^1$H NMR (300 MHz, d$_6$-DMSO) δ 8.38 (s, 1H), 7.84 (d, J=8.5 Hz, 1H), 7.78 (d, J=3.7 Hz, 1H), 7.30 (d, J=12.7 Hz, 1H), 7.19 (d, J=7.6 Hz, 1H), 4.70 (t, J=5.9 Hz, 1H), 4.52-4.29 (m, 1H), 4.09-3.86 (m, 1H), 3.59 (s, 3H), 3.47-3.33 (m, 2H), 2.80 (td, J=8.2, 2.9 Hz, 1H), 2.26-2.11 (m, 2H), 1.92 (d, J=12.1 Hz, 1H), 1.75-1.47 (m, 4H), 1.37 (t, J=12.1 Hz, 1H), 1.24-1.15 (m, 1H), 1.11 (d, J=6.2 Hz, 3H), 1.09-0.95 (m, 4H), 0.75 (s, 3H). m/z=546 (M+H)$^+$.

Example 81

Preparation of 5-nitro-2-(2-oxa-6-azaspiro[3.3]heptan-6-yl)benzonitrile for the Synthesis of Compound 101

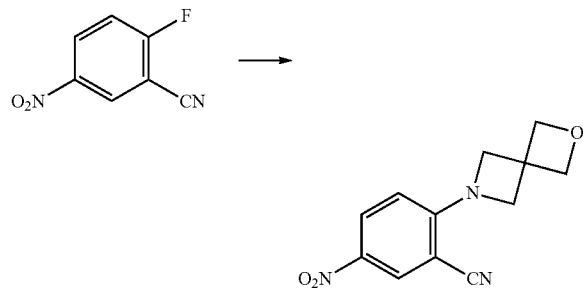

2-Fluoro-5-nitrobenzonitrile (1.0 g, 6.02 mmol, purchased from Combi-Blocks AN1040) was dissolved in dimethylformamide (25 mL) under nitrogen. Potassium carbonate (3.50 g, 25.3 mmol) and 2-oxa-6-azaspiro[3.3]heptane (1.05 g, 7.22 mmol, purchased from Ryan Scientific EN300-89755) were added to the mixture. The resulting mixture was stirred at room temperature overnight. The reaction was then diluted with water (75 mL) and extracted with ethyl acetate (4×75 mL). The organic layer was washed with water (5×75 mL) and dried over anhydrous sodium sulfate, filtered and concentrated under reduced pressure. The crude residue was purified by Combiflash, eluting with hexane and ethyl acetate to provide the desired product as a bright yellow solid (350 mg, 24% yield).

$^1$H NMR (DMSO d$_6$, 300 MHz): δ 8.39 (s, 1H), 8.17 (d, 1H), 6.60 (d, 1H), 4.75 (s, 1H), 4.68 (s, 4H); LCMS (m/z): 246.09 (MH$^+$).

Synthesis of 5-(4-((7R,8aS)-5,5-dimethyloctahydroindolizin-7-ylamino)-5-fluoropyrimidin-2-ylamino)-2-(2-oxa-6-azaspiro[3.3]heptan-6-yl)benzonitrile (Compound 101)

Compound 101 was synthesized from 5-nitro-2-(2-oxa-6-azaspiro[3.3]heptan-6-yl)benzonitrile according to the following scheme:

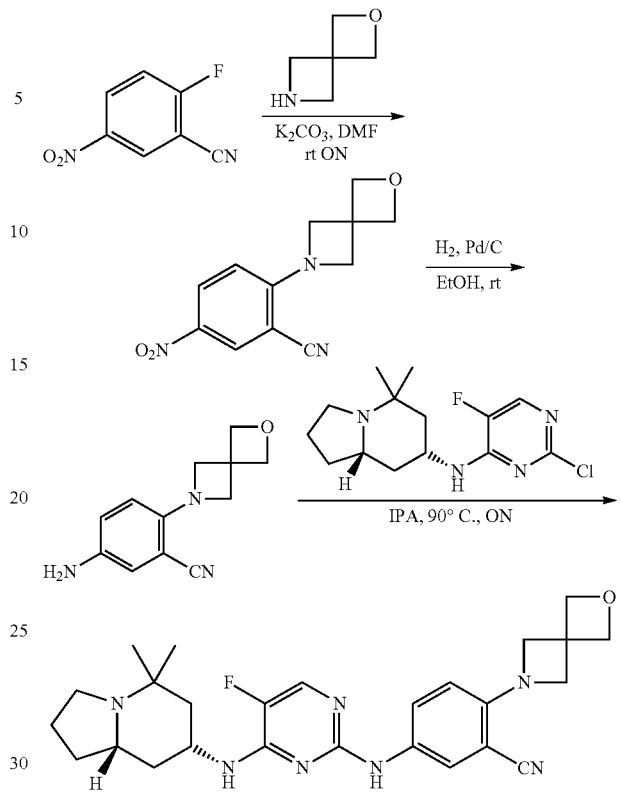

5-(4-((7R,8aS)-5,5-dimethyloctahydroindolizin-7-ylamino)-5-fluoropyrimidin-2-ylamino)-2-(2-oxa-6-azaspiro[3.3]heptan-6-yl)benzonitrile (Compound 101): $^1$H NMR (DMSO d$_6$, 300MHz): δ 8.94 (s, 1H), 7.90 (s, 1H), 7.81 (d, 1H), 7.60 (d, 1H), 7.19 (d, 1H), 6.51 (d, 1H), 4.71 (s, 4H), 4.19 (s, 4H), 2.88-2.75 (m, 1H), 2.35-2.22 (m, 1H), 2.08-1.95 (m, 1H), 1.90-1.75 (m, 1H), 1.66-1.54 (m, 3H) 1.45 (t, 1H), 1.30-1.15 (m, 2H), 1.09 (s, 3H), 0.98 (s, 3H); LCMS (m/z): 477.99 (MH$^+$).

Synthesis of 5-(4-((7R,8aS)-5,5-dimethyloctahydroindolizin-7-ylamino)-5-fluoropyrimidin-2-ylamino)-2-(2-oxa-7-azaspiro[3.5]nonan-7-yl)benzonitrile (Compound 100)

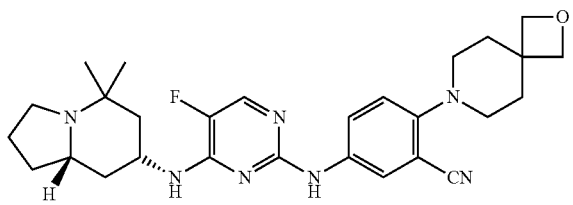

Compound 100 was synthesized using the same general synthetic schemes as presented above for Compound 101.

5-(4-((7R,8aS)-5,5-dimethyloctahydroindolizin-7-ylamino)-5-fluoropyrimidin-2-ylamino)-2-(2-oxa-7-azaspiro[3.5]nonan-7-yl)benzonitrile (Compound 100): $^1$H NMR (DMSO d$_6$, 300MHz): δ 9.16 (s, 1H), 8.10 (d, 1H), 7.85 (d, 1H), 7.71 (d, 1H), 7.28 (d, 1H), 7.02 (d, 1H), 4.35 (s, 4H), 4.24-4.11 (m, 2H), 2.96-2.83 (m, 4H), 2.38-2.24 (m, 1H), 2.05-1.90 (m, 5H), 1.80-1.75 (m, 1H), 1.63-1.56 (m, 3H), 1.45 (t, 1H), 1.27-1.10 (m, 3H), 1.08 (s, 3H), 0.98 (s, 3H); LCMS (m/z): 506.66 (MH+).

Example 82

Preparation of N2-(4,4-dimethyl-4H-benzo[b]tetrazolo[1,5-d][1,4]oxazin-8-yl)-N4-((7S,8aR)-5,5-dimethyloctahydroindolizin-7-yl)-5-fluoropyrimidine-2,4-diamine (Compound 102)

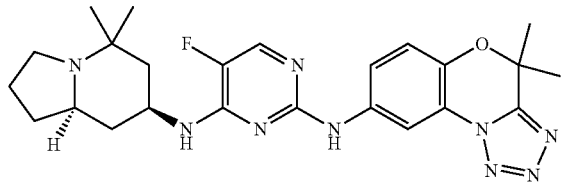 [SMILES: CC1(C)Oc2ccc(Nc3ncc(F)c(N[C@H]4C[C@H]5CCCN5C(C)(C)C4)n3)cc2-n2nnnc21]

Compound 102 is an enantiomer of Compound 136. Compound 102 was isolated from a racemic mixture of Compound 2 by chiral HPLC resolution.

¹H NMR (DMSO d₆, 300MHz): δ 9.30 (s, 1H), 8.47 (d, J=3.3Hz, 1H), 7.88 (d, J=3.3Hz, 1H), 7.63 (dd, J=3.3, 10.0Hz, 1H), 7.25 (d, J=10.0Hz, 1H), 7.11 (d, J=10.0Hz, 1H), 4.21 (bs, 1H), 2.81 (bm, 1H), 2.52 (m, 2H), 2.24 (bm, 1H), 2.03 (bm, 1H), 1.73 (s, 3H), 1.69 (s, 3H), 1.58 (m, 4H), 1.41 (m, 1H), 1.17 (m, 3H), 1.04 (s, 3H), 0.85 (s, 3H); LCMS (m/z): 480.00 (MH+).

Example 83

Synthesis of Compounds 103, 106, 107 and 108

Compounds 103, 106, 107 and 108 were prepared according to the following synthetic scheme:

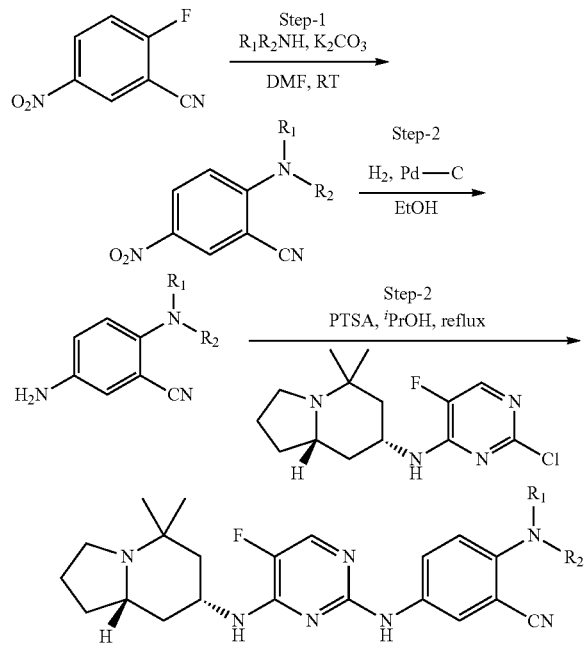

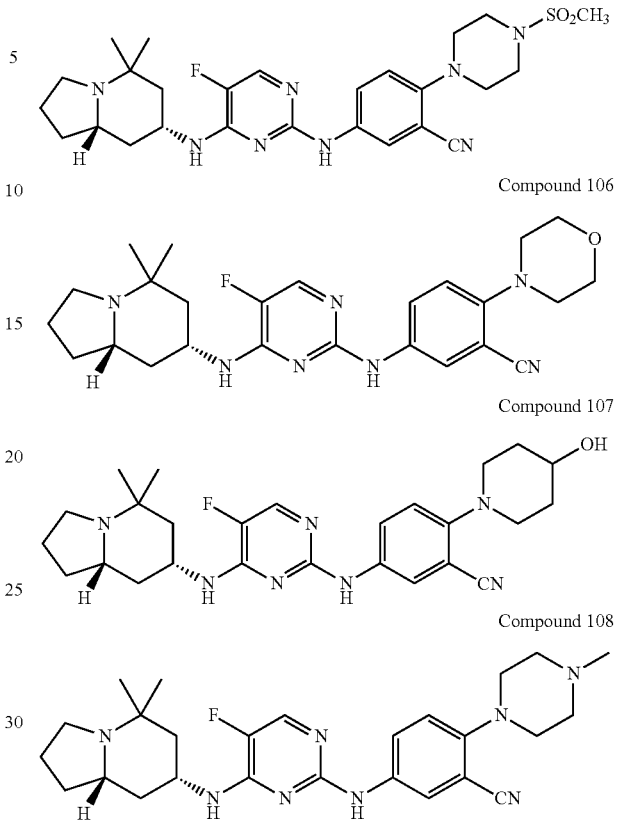

Step-1: 2-Fluoro-5-nitrobenzonitrile (1.4 g, 1.0 eq, 8.4 mmol) was taken in annhydrous DMF (10 mL). Secondary amine (1.2 eq, 10.12 mmol) was added to the above solution followed by the addition of K₂CO₃ (3.5 g, 3.0 eq, 25.3 mmol). The reaction mixture was allowed to stir at room temperature overnight. The reaction mixture was diluted with EtOAc (100 mL) and partitioned with water (100 mL). Organic layers were separated and the aqueous layers were washed with EtOAc (1×50 mL). The combined oragnic layers were washed with aqueous staurated NaHCO₃ solution (100 mL) and dried over Na₂SO₄. Organic layers were concentrated under reduced pressure to leave a crude mixture. The mixture was purified by column chromatography on silica gel (ISCO System) using EtOAc/Hexane (gradient system from 0:1 to 2:8) as eluent to give the product as a solid.

Step-2: A mixture of the nitro compound from Step-1 (1.0 eq) and Pd—C (10%, 1.2 eq) in EtOH (50 mL) was hydrogenated for 3 hours under H₂ balloon pressure. The mixture was filtered through celite and the filter cake was washed with EtOH (2×10 mL). The filtrate was concentrated under vacuum to give the product in quantitative yield. The product was taken to next step with out further purification.

Step-3: A mixture of (7R,8aS)-N-(2-chloro-5fluoropyrimidin-4-yl)-5,5-dimethyloctahydroindolizin-7-amine (0.13 g, 1.0 eq, 0.42 mmol), aniline (1.4 eq) and PTSA (1.0 eq) was taken in ⁱPrOH (10 mL) and heated to reflux overnight. The volatiles were removed under vacuum to leave a crude solid. The solid was purified by column chromatography on silica gel (ISCO System) using 2M NH₃ in MeOH/CH₂Cl₂ (gradient system from 0:1 to 2:8) as eluent to give the product as a solid after freeze-drying from MeCN/H₂O.

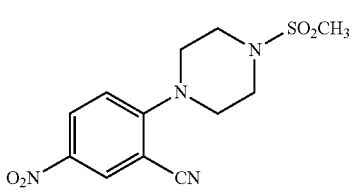

2-(4-(Methylsulfonyl)piperazin-1-yl)-5-nitrobenzonitrile

Synthesized as described in Step-1. Yield=73%, $^1$H NMR (300 MHz, CDCl$_3$) δ 8.43 (d, J=2.7 Hz, 1H), 8.27 (dd, J=9.3, 2.7 Hz, 1H), 6.98 (d, J=9.3 Hz, 1H), 3.59-3.48 (m, 4H), 2.68-2.57 (m, 4H), 2.38 (s, 3H); LCMS (m/z): 311 (M+H)$^+$.

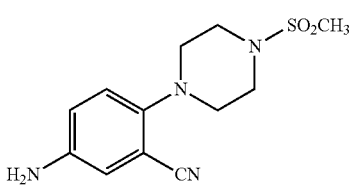

5-Amino-2-(4-(methylsulfonyl)piperazin-1-yl)benzonitrile

Synthesized as described in Step-2. Yield=90% $^1$H NMR (300 MHz, d$_6$-DMSO) δ 7.00 (d, J=9.5 Hz, 1H), 6.89-6.73 (m, 2H), 5.26 (s, 2H), 3.26-3.17 (m, 4H), 3.02-2.94 (m, 4H), 2.91 (d, J=5.0 Hz, 3H); LCMS (m/z): 282 (M+H)$^+$.

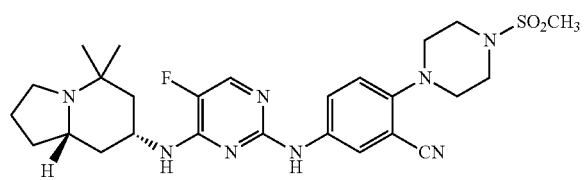 [SMILES: CC1(C)C[C@H](Nc2nc(Nc3ccc(N4CCN(S(C)(=O)=O)CC4)c(C#N)c3)ncc2F)C[C@@H]2CCCN21]

5-((4-(((7R,8aS)-5,5-Dimethyloctahydroindolizin-7-yl)amino)-5-fluoropyrimidin-2-yl)amino)-2-(4-(methylsulfonyl)piperazin-1-yl)benzonitrile (Compound 103)

Synthesized as described in Step-3. Yield=77%, $^1$H NMR (300 MHz, d$_6$-DMSO) δ 9.21 (s, 1H), 8.16 (d, J=2.2 Hz, 1H), 7.85 (d, J=3.2 Hz, 1H), 7.77 (dd, J=8.9, 2.2 Hz, 1H), 7.28 (d, J=7.8 Hz, 1H), 7.12 (d, J=9.0 Hz, 1H), 4.17 (s, 1H), 3.10 (d, J=4.7 Hz, 4H), 2.94 (s, 3H), 2.84 (s, 1H), 2.29 (d, J=8.1 Hz, 1H), 2.02 (d, J=11.7 Hz, 1H), 1.78 (s, 1H), 1.60 (d, J=8.6 Hz, 3H), 1.44 (t, J=12.3 Hz, 1H), 1.21 (d, J=11.6 Hz, 2H), 1.13-1.02 (m, 8H), 0.98 (s, 3H); $^{19}$F NMR (282 MHz; d$_6$-DMSO) δ −166.1 (s); LCMS (m/z): 543 (M+H)$^+$.

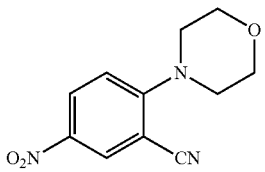

2-morpholino-5-nitrobenzonitrile

Synthesized as described in Step-1. Yield=59%, $^1$H NMR (300 MHz, CDCl$_3$) δ 8.45 (d, J=2.7 Hz, 1H), 8.34-8.24 (m, 1H), 7.00 (d, J=9.3 Hz, 1H), 3.97-3.85 (m, 4H), 3.55-3.43 (m, 4H); LCMS (m/z): 234 (M+H)$^+$.

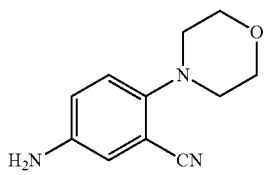

5-amino-2-morpholinobenzonitrile

Synthesized as described in Step-2. Yield=90%, $^1$H NMR (300 MHz, d$_6$-DMSO) δ 6.95 (d, J=9.5 Hz, 1H), 6.88-6.73 (m, 2H), 5.30 (s, 2H), 3.77-3.64 (m, 4H), 2.95-2.79 (m, 4H); LCMS (m/z): 204 (M+H)$^+$.

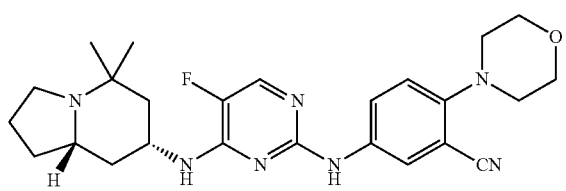 [SMILES: CC1(C)C[C@H](Nc2nc(Nc3ccc(N4CCOCC4)c(C#N)c3)ncc2F)C[C@@H]2CCCN21]

5-((4-(((7R,8aS)-5,5-dimethyloctahydroindolizin-7-yl)amino)-5-fluoropyrimidin-2-yl)amino)-2-morpholinobenzonitrile (Compound 106)

Synthesized as described in Step-3. Yield=77%, $^1$H NMR (300 MHz, d$_6$-DMSO) δ 9.18 (s, 1H), 8.13 (d, J=2.0 Hz, 1H), 7.85 (d, J=2.9 Hz, 1H), 7.79-7.66 (m, 1H), 7.26 (d, J=8.0 Hz, 1H), 7.07 (d, J=8.9 Hz, 1H), 4.17 (s, 1H), 3.78-3.64 (m, 4H), 3.04-2.91 (m, 4H), 2.83 (s, 1H), 2.29 (d, J=8.2 Hz, 1H), 1.99 (s, 1H), 1.78 (s, 1H), 1.58 (s, 3H), 1.44 (t, J=11.9 Hz, 1H), 1.17 (dd, J=21.7, 10.5 Hz, 3H), 1.07 (s, 3H), 0.98 (s, 3H); $^{19}$F NMR (282 MHz; d$_6$-DMSO) δ −166.2 (s); LCMS (m/z): 466 (M+H)$^+$.

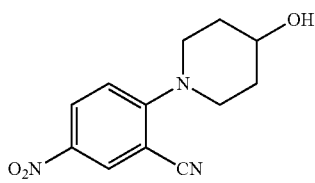 [SMILES: N#Cc1cc([N+](=O)[O-])ccc1N1CCC(O)CC1]

2-(4-hydroxypiperidin-1-yl)-5-nitrobenzonitrile

Synthesized as described in Step-1. Yield=36%, $^1$H NMR (300 MHz, CDCl$_3$) δ 8.43 (d, J=2.8 Hz, 1H), 8.25 (dd, J=9.4, 2.7 Hz, 1H), 6.98 (d, J=9.4 Hz, 1H), 4.12-3.98 (m, 1H), 3.85-3.68 (m, 2H), 3.44-3.31 (m, 2H), 2.20-1.98 (m, 2H), 1.93-1.70 (m, 2H), 1.52 (d, J=4.1 Hz, 1H); LCMS (m/z): 248 (M+H)$^+$.

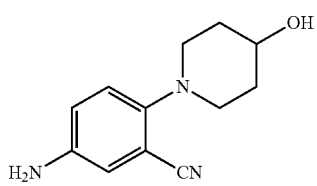

5-amino-2-(4-hydroxypiperidin-1-yl)benzonitrile

Synthesized as described in Step-2. Yield=91%, ¹H NMR (300 MHz, d₆-DMSO) δ 7.00-6.85 (m, 1H), 6.83-6.70 (m, 2H), 5.15 (s, 2H), 4.62 (d, J=4.2 Hz, 1H), 3.64-3.45 (m, 1H), 3.14-2.93 (m, 2H), 2.74-2.58 (m, 2H), 1.81 (d, J=9.6 Hz, 2H), 1.63-1.37 (m, 2H); LCMS (m/z): 218 (M+H)⁺.

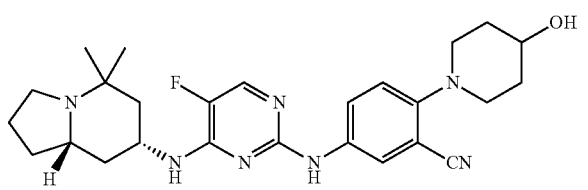 [SMILES: CC1(C)C[C@H](Nc2nc(Nc3ccc(N4CCC(O)CC4)c(C#N)c3)ncc2F)C[C@@H]2CCCN21]

5-((4-(((7R,8aS)-5,5-dimethyloctahydroindolizin-7-yl)amino)-5-fluoropyrimidin-2-yl)amino)-2-(4-hydroxypiperidin-1-yl)benzonitrile (Compound 107)

Synthesized as described in Step-3. Yield=76%, ¹H NMR (300 MHz, d₆-DMSO) δ 9.13 (s, 1H), 8.08 (d, J=2.4 Hz, 1H), 7.84 (d, J=3.8 Hz, 1H), 7.73 (d, J=9.2 Hz, 1H), 7.24 (d, J=7.3 Hz, 1H), 7.04 (d, J=8.9 Hz, 1H), 4.66 (d, J=4.2 Hz, 1H), 4.17 (s, 1H), 3.59 (s, 1H), 3.20 (d, J=14.4 Hz, 2H), 2.89-2.65 (m, 3H), 2.29 (d, J=8.3 Hz, 1H), 1.99 (s, 1H), 1.82 (s, 3H), 1.71-1.32 (m, 7H), 1.16 (dd, J=22.8, 11.1 Hz, 2H), 1.09 (d, J=11.8 Hz, 3H), 0.98 (s, 3H); ¹⁹F NMR (282 MHz; d₆-DMSO) δ −166.4 (s); LCMS (m/z): 480 (M+H)⁺.

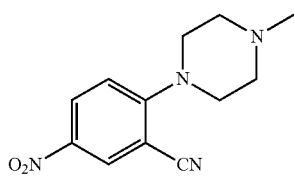 [SMILES: CN1CCN(c2ccc([N+](=O)[O-])cc2C#N)CC1]

2-(4-methylpiperazin-1-yl)-5-nitrobenzonitrile

Synthesized as described in Step-1. Yield=64%, ¹H NMR (300 MHz, CDCl₃) δ 8.45 (d, J=2.7 Hz, 1H), 8.34-8.24 (m, 1H), 7.00 (d, J=9.3 Hz, 1H), 3.97-3.85 (m, 5H), 3.55-3.43 (m, 6H); LCMS (m/z): 247 (M+H)⁺.

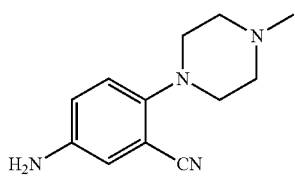

5-amino-2-(4-methylpiperazin-1-yl)benzonitrile

Synthesized as described in Step-2. Yield=95%, ¹H NMR (300 MHz, d₆-DMSO) δ 6.93 (d, J=9.6 Hz, 1H), 6.85-6.71 (m, 2H), 5.32 (s, 2H), 2.96-2.81 (m, 4H), 2.43 (s, 4H), 2.18 (d, J=8.4 Hz, 3H); LCMS (m/z): 217 (M+H)⁺.

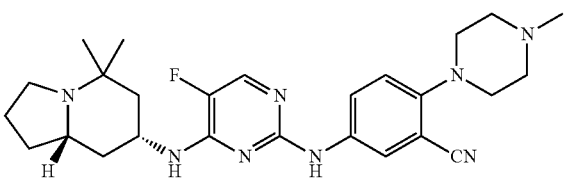 [SMILES: CN1CCN(c2ccc(Nc3ncc(F)c(N[C@@H]4C[C@@H]5CCCN5C(C)(C)C4)n3)cc2C#N)CC1]

5-((4-(((7R,8aS)-5,5-dimethyloctahydroindolizin-7-yl)amino)-5-fluoropyrimidin-2-yl)amino)-2-(4-methylpiperazin-1-yl)benzonitrile, formate salt (Compound 108)

Synthesized as described in Step-3. Yield=32%, ¹H NMR (300 MHz, d₆-DMSO) δ 9.15 (s, 1H), 8.10 (d, J=2.2 Hz, 1H), 7.84 (d, J=3.2 Hz, 1H), 7.73 (dd, J=9.0, 2.0 Hz, 1H), 7.25 (d, J=8.1 Hz, 1H), 7.05 (d, J=9.1 Hz, 1H), 4.14 (s, 1H), 3.09-2.92 (m, 4H), 2.83 (dd, J=8.4, 5.4 Hz, 1H), 2.34-2.24 (m, 2H), 2.21 (s, 3H), 2.00 (d, J=11.6 Hz, 1H), 1.89-1.70 (m, 3H), 1.59 (d, J=8.1 Hz, 3H), 1.43 (t, J=12.1 Hz, 1H), 1.31-1.11 (m, 2H), 1.08 (d, J=12.4 Hz, 5H), 0.97 (s, 3H); ¹⁹F NMR (282 MHz; d₆-DMSO) δ −166.3 (s); LCMS (m/z): 479 (M+H)⁺.

Example 84

Synthesis of Compounds 104 and 105

Compounds 104 and 105 were prepared according to the following synthetic scheme:

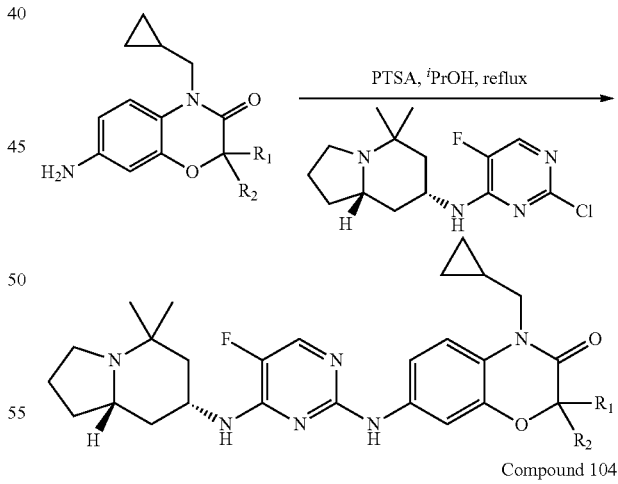

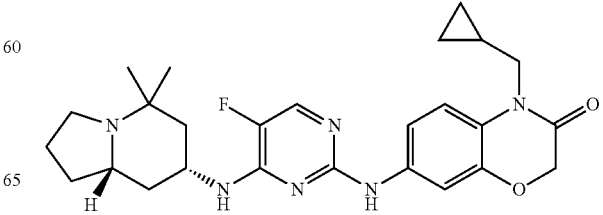

-continued

Compound 105

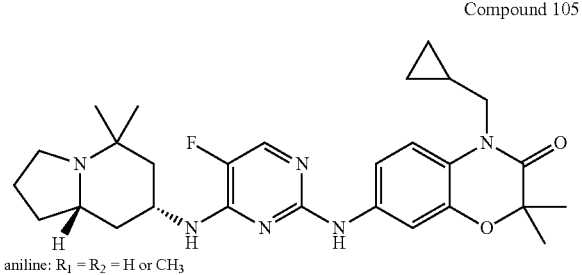

aniline: R₁ = R₂ = H or CH₃

A mixture of (7R,8aS)-N-(2-chloro-5fluoropyrimidin-4-yl)-5,5-dimethyloctahydroindolizin-7-amine (0.13 g, 1.0 eq, 0.42 mmol), aniline (1.4 eq) (see, e.g., EP 296416; WO 2009/012421), PTSA (1.0 eq) were taken in ⁱPrOH (10 mL) and heated to reflux for over night. The volatiles were removed under vacuum to leave a crude solid. The solid was purified by column chromatography on silica gel (ISCO System) using 2M $NH_3$ in $MeOH/CH_2Cl_2$ (gradient system from 0:1 to 1:9) as eluent to give the product as a solid after freeze-drying from $MeCN/H_2O$.

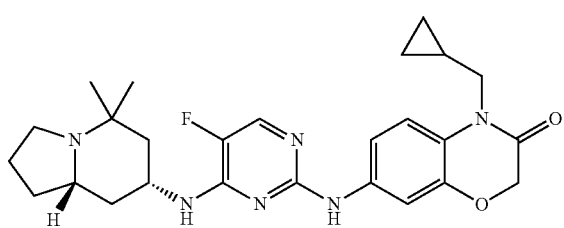 [SMILES: CC1(C)C[C@H](Nc2nc(Nc3ccc4c(c3)OCC(=O)N4CC3CC3)ncc2F)C[C@@H]2CCCN21]

4-(cyclopropylmethyl)-7-((4-(((7R,8aS)-5,5-dimethyloctahydroindolizin-7-yl)amino)-5-fluoropyrimidin-2-yl)amino)-2H-benzo[b][1,4]oxazin-3(4H)-one (Compound 104)

Yield=66%, $^1$H NMR (300 MHz, d$_6$-DMSO) δ 8.73 (s, 1H), 7.51 (d, J=3.8 Hz, 1H), 7.24 (d, J=2.2 Hz, 1H), 7.06-6.81 (m, 2H), 6.77 (d, J=8.9 Hz, 1H), 4.22 (s, 2H), 3.87 (s, 1H), 3.45 (d, J=6.8 Hz, 2H), 2.52 (s, 1H), 2.37-1.79 (m, 1H), 1.69 (d, J=11.3 Hz, 1H), 1.52-1.10 (m, 5H), 1.10-0.91 (m, 4H), 0.89 (s, 3H), 0.68 (s, 3H), 0.20-0.06 (m, 4H); $^{19}$F NMR (282 MHz; d$_6$-DMSO) δ −166.8 (s); LCMS (m/z): 481 (M+H)$^+$.

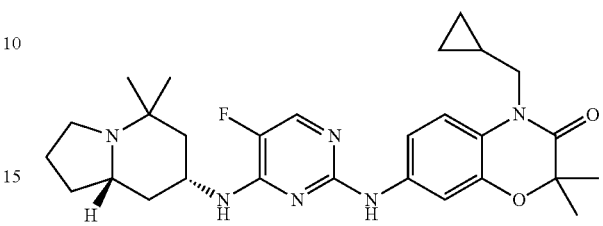

4-(cyclopropylmethyl)-7-((4-(((7R,8aS)-5,5-dimethyloctahydroindolizin-7-yl)amino)-5-fluoropyrimidin-2-yl)amino)-2,2-dimethyl-2H-benzo[b][1,4]oxazin-3(4H)-one (Compound 105)

Yield=75%, $^1$H NMR (300 MHz, d$_6$-DMSO) δ 8.81 (s, 1H), 7.52 (dd, J=10.5, 2.6 Hz, 2H), 6.98 (d, J=8.4 Hz, 1H), 6.89-6.67 (m, 2H), 3.92 (s, 1H), 3.47 (d, J=6.6 Hz, 2H), 2.56 (s, 1H), 2.25 (s, 1H), 2.08-1.89 (m, 1H), 1.76 (d, J=11.8 Hz, 1H), 1.44 (s, 1H), 1.25 (dt, J=24.7, 12.2 Hz, 5H), 1.06 (d, J=2.2 Hz, 4H), 0.97 (d, J=20.5 Hz, 3H), 0.87-0.67 (m, 6H), 0.53 (d, J=7.3 Hz, 1H), 0.12 (d, J=7.9 Hz, 2H), 0.01 (t, J=4.1 Hz, 2H); $^{19}$F NMR (282 MHz; d$_6$-DMSO) δ −166.9 (s); LCMS (m/z): 509 (M+H)$^+$.

Example 85

Synthesis of Compounds 109-115

Compounds 109-115 were prepared according to the following synthetic scheme:

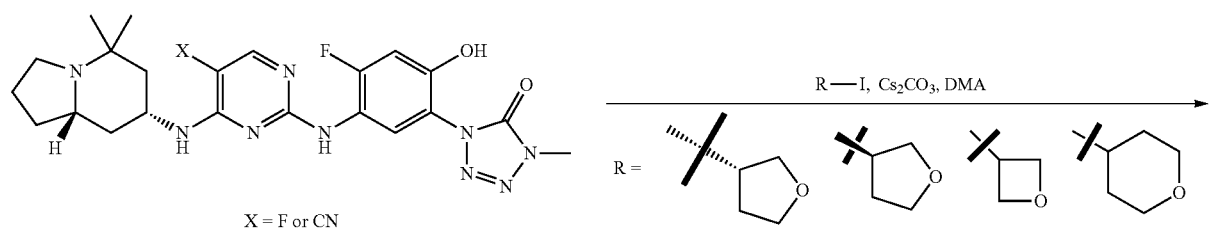

X = F or CN

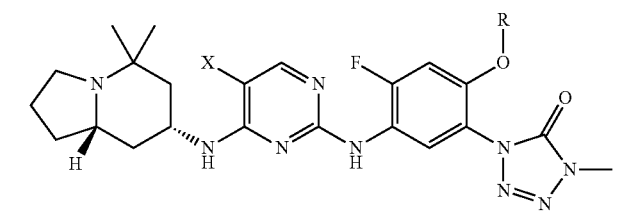

-continued
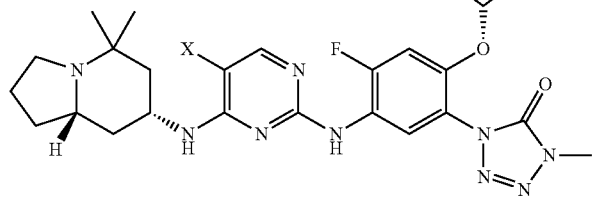
X = F; Compound 109
X = CN; Compound 111
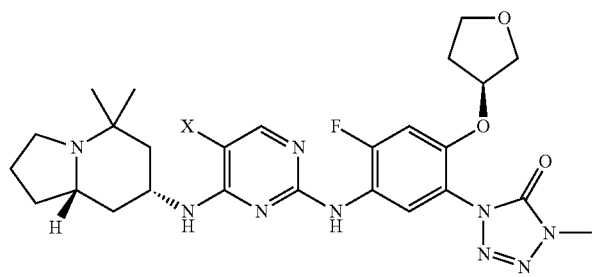
X = F; Compound 110
X = CN; Compound 112
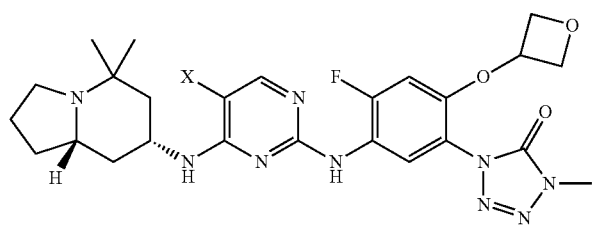
X = CN; Compound 113
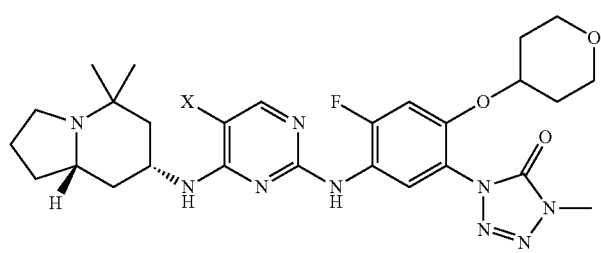
X = F; Compound 114
X = CN; Compound 115

A mixture of 1-(5-((4-(((7R,8aS)-5,5-dimethyloctahydroindolizin-7-yl)amino)-5-fluoropyrimidin-2-yl)amino)-4-fluoro-2-hydroxyphenyl)-4-methyl-1,4-dihydro-5H-tetrazol-5-one (0.16 g, 1.0 eq, 0.35 mmol), iodooxetane (0.2 g, 3.0 eq, 1.00 mmol) and $Cs_2CO_3$ (0.12 g, 1.1 eq, 0.36 mmol) was taken in DMA (10 mL). The reaction mixture was heated at 70° C. and stirred overnight. After the completion of the reaction the crude mixture was diluted with EtOAc (50 mL) and partitioned with $H_2O$ (50 mL). The layers were seperated and the aqueous layer was washed with EtOAc (2×50 mL). The combined organic layers were dried over $Na_2SO_4$ and concentrated under reduced pressure to leave a crude oil. The crude mixture was purified by column chromatography on silica gel (ISCO System) using 2M $NH_3$ in MeOH/$CH_2Cl_2$ (gradient system from 0:1 to 1:9) as eluent to give the product as a solid.

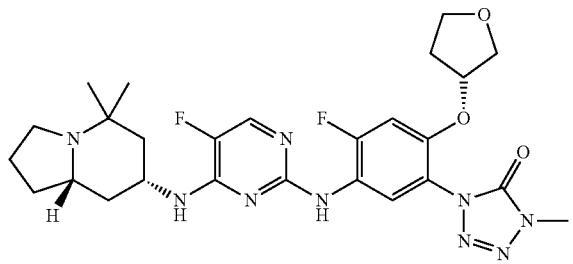

1-(5-((4-(((7R,8aS)-5,5-dimethyloctahydroindolizin-7-yl)amino)-5-fluoropyrimidin-2-yl)amino)-4-fluoro-2-(((R)-tetrahydrofuran-3-yl)oxy)phenyl)-4-methyl-1,4-dihydro-5H-tetrazol-5-one (Compound 109)

Yield=66%, $^1$H NMR (300 MHz, $d_6$-DMSO) δ 8.41 (s, 1H), 7.88 (d, J=8.5 Hz, 1H), 7.79 (d, J=3.8 Hz, 1H), 7.24 (dd, J=27.0, 9.9 Hz, 2H), 5.07 (s, 1H), 3.96 (s, 1H), 3.83 (dd, J=10.2, 4.5 Hz, 1H), 3.67 (ddd, J=18.9, 9.7, 4.4 Hz, 3H), 3.30 (d, J=0.6 Hz, 3H), 2.81 (s, 1H), 2.30-1.99 (m, 3H), 2.02-1.76 (m, 2H), 1.76-1.45 (m, 5H), 1.38 (t, J=12.1 Hz, 1H), 1.17 (s, 1H), 1.03 (s, 3H), 0.76 (s, 3H); $^{19}$F NMR (282 MHz; $d_6$-DMSO) δ −116.0 (s), −166.9 (d); LCMS (m/z): 558 (M+H)$^+$.

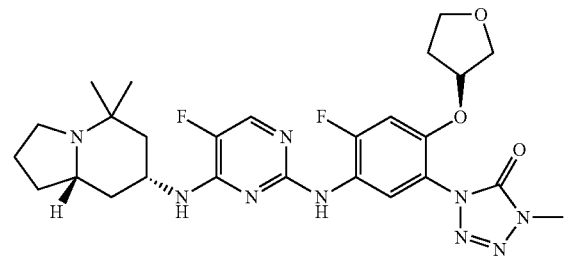

1-(5-((4-(((7R,8aS)-5,5-dimethyloctahydroindolizin-7-yl)amino)-5-fluoropyrimidin-2-yl)amino)-4-fluoro-2-(((S)-tetrahydrofuran-3-yl)oxy)phenyl)-4-methyl-1,4-dihydro-5H-tetrazol-5-one (Compound 110)

Yield=68%, $^1$H NMR (300 MHz, $d_6$-DMSO) δ 8.41 (s, 1H), 7.88 (d, J=8.4 Hz, 1H), 7.79 (d, J=3.8 Hz, 1H), 7.24 (dd, J=26.6, 10.1 Hz, 2H), 5.07 (s, 1H), 3.96 (s, 1H), 3.83 (dd, J=10.2, 4.6 Hz, 1H), 3.74-3.60 (m, 3H), 3.58 (s, 3H), 2.81 (s, 1H), 2.31-2.00 (m, 3H), 2.00-1.76 (m, 2H), 1.76-1.44 (m, 4H), 1.38 (t, J=12.3 Hz, 1H), 1.20 (d, J=17.3 Hz, 2H), 1.03 (s, 3H), 0.76 (s, 3H); $^{19}$F NMR (282 MHz; $d_6$-DMSO) δ −116.0 (s), −166.9 (d); LCMS (m/z): 558 (M+H)$^+$.

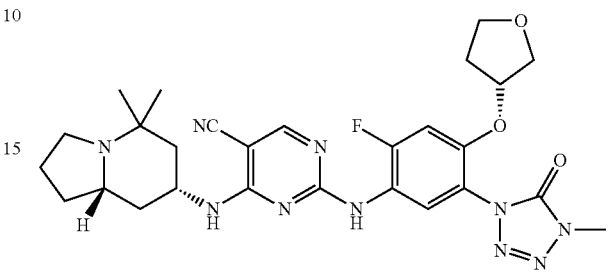

4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-4(R)-tetrahydrofuran-3-yl)oxy)phenyl)amino)pyrimidine-5-carbonitrile (Compound 111)

Yield=80%, $^1$H NMR (300 MHz, $d_6$-DMSO) δ 9.34 (s, 1H), 8.27 (s, 1H), 7.66 (d, J=8.2 Hz, 1H), 7.36 (dd, J=17.7, 9.7 Hz, 2H), 5.10 (s, 1H), 4.01 (s, 1H), 3.85 (dd, J=10.5, 4.4 Hz, 1H), 3.77-3.62 (m, 3H), 3.58 (s, 3H), 3.43-3.32 (m, 1H), 2.78 (s, 1H), 2.26-2.01 (m, 2H), 1.83 (s, 2H), 1.58 (s, 2H), 1.43 (s, 2H), 1.27-1.05 (m, 3H), 1.03 (d, J=11.0 Hz, 3H), 0.69 (s, 3H); $^{19}$F NMR (282 MHz; $d_6$-DMSO) δ −113.3 (s); LCMS (m/z): 565 (M+H)$^+$.

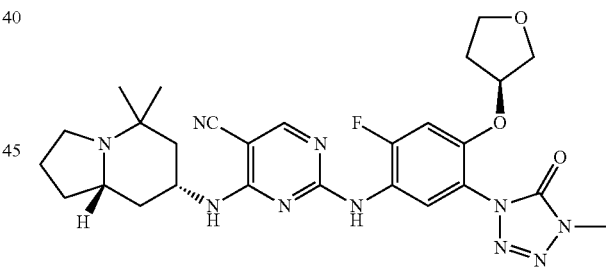

4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-4(S)-tetrahydrofuran-3-yl)oxy)phenyl)amino)pyrimidine-5-carbonitrile (Compound 112)

Yield=75%, $^1$H NMR (300 MHz, $d_6$-DMSO) δ 9.34 (s, 1H), 8.27 (s, 1H), 7.66 (d, J=8.4 Hz, 1H), 7.36 (dd, J=17.8, 10.0 Hz, 2H), 5.10 (s, 1H), 4.01 (s, 1H), 3.85 (dd, J=10.3, 4.5 Hz, 1H), 3.77-3.61 (m, 3H), 3.49-3.33 (m, 1H), 2.78 (s, 1H), 2.14 (dd, J=13.8, 5.5 Hz, 4H), 1.85 (d, J=13.1 Hz, 3H), 1.51 (d, J=43.7 Hz, 4H), 1.27-0.88 (m, 6H), 0.70 (s, 3H); $^{19}$F NMR (282 MHz; $d_6$-DMSO) δ −113.3 (s); LCMS (m/z): 565 (M+H)$^+$.

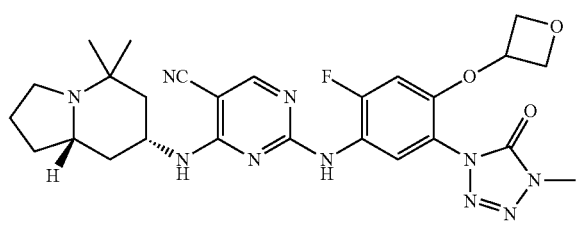 [SMILES: Cn1nnn(-c2cc(Nc3ncc(C#N)c(N[C@@H]4C[C@@H]5CCCN5C(C)(C)C4)n3)c(F)cc2OC2COC2)c1=O]

4-(((7R,8aS)-5,5-dimethyloctahydroindolizin-7-yl)
amino)-2-((2-fluoro-5-(4-methyl-5-oxo-4,5-dihydro-
1H-tetrazol-1-yl)-4-(oxetan-3-yloxy)phenyl)amino)
pyrimidine-5-carbonitrile (Compound 113)

Yield=82%, $^{1}$H NMR (300 MHz, d$_6$-DMSO) δ 9.36 (s, 1H), 8.27 (s, 1H), 7.70 (d, J=8.2 Hz, 1H), 7.39 (d, J=8.0 Hz, 1H), 7.01 (d, J=11.9 Hz, 1H), 5.34 (s, 1H), 4.87 (t, J=6.6 Hz, 2H), 4.50-4.25 (m, 2H), 4.20-3.83 (m, 1H), 3.61 (s, 2H), 2.78 (s, 1H), 2.17 (s, 2H), 1.69 (d, J=62.9 Hz, 4H), 1.41 (s, 2H), 1.14 (d, J=12.8 Hz, 3H), 1.01 (s, 3H), 0.67 (s, 3H); $^{19}$F NMR (282 MHz; d$_6$-DMSO) δ −113.2 (s); LCMS (m/z): 551 (M+H)$^+$.

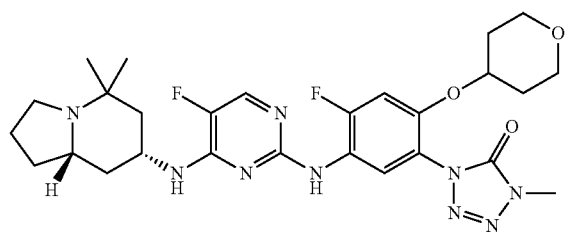 [SMILES: Cn1nnn(-c2cc(Nc3ncc(F)c(N[C@@H]4C[C@@H]5CCCN5C(C)(C)C4)n3)c(F)cc2OC2CCOCC2)c1=O]

1-(5-((4-(((7R,8aS)-5,5-dimethyloctahydroindolizin-
7-yl)amino)-5-fluoropyrimidin-2-yl)amino)-4-
fluoro-2-((tetrahydro-2H-pyran-4-yl)oxy)phenyl)-4-
methyl-1,4-dihydro-5H-tetrazol-5-one (Compound 114)

Yield=77%, $^{1}$H NMR (300 MHz, d$_6$-DMSO) δ 8.39 (s, 1H), 7.89 (d, J=8.5 Hz, 1H), 7.79 (d, J=3.8 Hz, 1H), 7.34 (d, J=12.5 Hz, 1H), 7.19 (d, J=7.6 Hz, 1H), 4.64 (s, 1H), 3.96 (s, 1H), 3.80-3.61 (m, 1H), 3.61 (d, J=8.2 Hz, 4H), 3.50-3.32 (m, 2H), 2.80 (s, 1H), 2.19 (d, J=8.0 Hz, 2H), 1.88 (d, J=33.9 Hz, 3H), 1.76-1.28 (m, 7H), 1.14 (dd, J=34.9, 13.0 Hz, 2H), 1.02 (d, J=9.9 Hz, 3H), 0.75 (s, 3H); $^{19}$F NMR (282 MHz; d$_6$-DMSO) δ −116.4 (s), −166.9 (d); LCMS (m/z): 572 (M+H)$^+$.

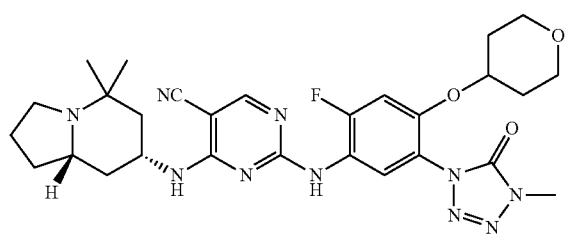 [SMILES: Cn1nnn(-c2cc(Nc3ncc(C#N)c(N[C@@H]4C[C@@H]5CCCN5C(C)(C)C4)n3)c(F)cc2OC2CCOCC2)c1=O]

4-(((7R,8aS)-5,5-dimethyloctahydroindolizin-7-yl)
amino)-2-((2-fluoro-5-(4-methyl-5-oxo-4,5-dihydro-
1H-tetrazol-1-yl)-4-((tetrahydro-2H-pyran-4-yl)oxy)
phenyl)amino)pyrimidine-5-carbonitrile (Compound 115)

Yield=68%, $^{1}$H NMR (300 MHz, d$_6$-DMSO) δ 9.33 (s, 1H), 8.27 (s, 1H), 7.67 (d, J=8.2 Hz, 1H), 7.47-7.29 (m, 2H), 4.68 (d, J=3.5 Hz, 1H), 3.99 (s, 1H), 3.78-3.62 (m, 1H), 3.61 (d, J=7.5 Hz, 3H), 3.51-3.32 (m, 2H), 2.75 (d, J=23.1 Hz, 1H), 2.20 (d, J=30.7 Hz, 2H), 1.91 (d, J=39.4 Hz, 3H), 1.75-1.30 (m, 7H), 1.15 (dd, J=24.3, 16.0 Hz, 3H), 1.01 (s, 3H), 0.83 (d, J=7.3 Hz, 1H), 0.67 (s, 2H); $^{19}$F NMR (282 MHz; d$_6$-DMSO) δ −113.7 (s); LCMS (m/z): 579 (M+H)$^+$.

Example 86

Synthesis of Compound 116

Compound 116 was prepared according to the following synthetic scheme:

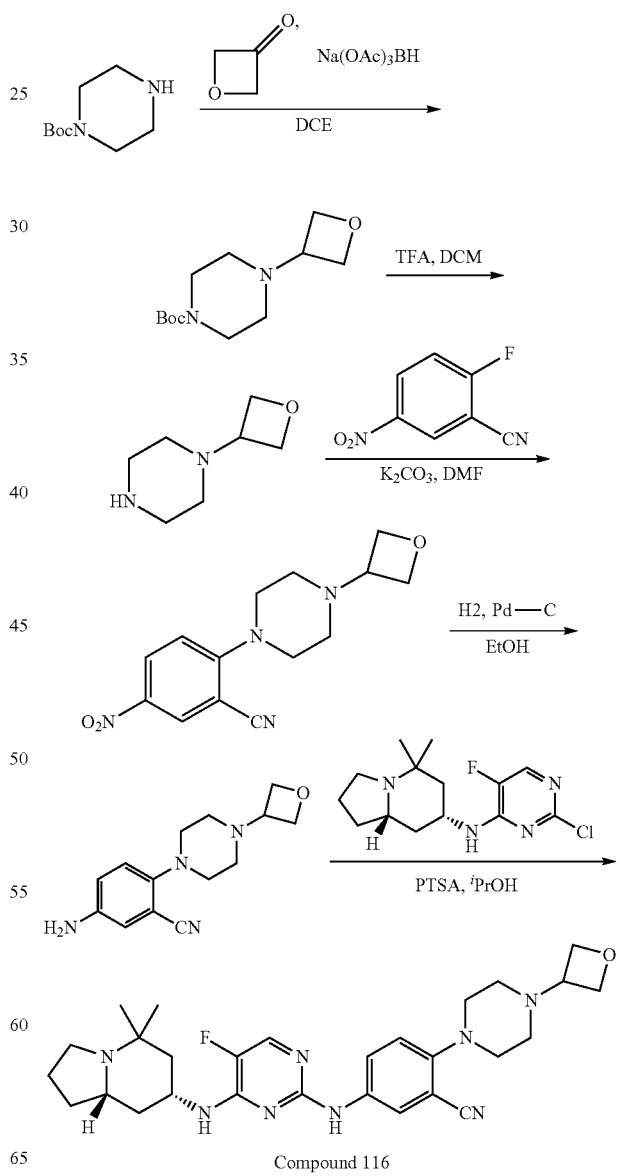

Compound 116

Synthesis of tert-butyl 4-(oxetan-3-yl)piperazine-1-carboxylate

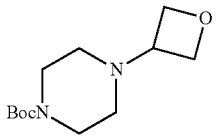

A solution of tert-butyl piperazine-1-carboxylate (10.8 g, 1.2 eq, 58.0 mmol) and oxetan-3-one (3.5 g, 1.0 eq, 14 mmol) in 1,2-dichloroethane (100 mL) was stirred at room temperature. Sodium triacetoxyborohydride (16.4 g, 1.6 eq, 77.3 mmol) was added in portions to the above solution and the heterogeneous mixture was stirred at room temperature overnight. The reaction mixture was diluted with $CH_2Cl_2$ (200 mL) and partioned with aqueous saturated $NaHCO_3$ solution (100 mL). The layers were seperated and the organic layer was washed with brine solution (2×50 mL). The combined organic layers were dried over $Na_2SO_4$. Removal of the solvents and purification of the crude mixture by column chromatography on silica gel (ISCO System) using 20% MeOH in $CH_2Cl_2/CH_2Cl_2$ (gradient system from 0:1 to 1:9) as eluent gave tert-butyl 4-(oxetan-3-yl)piperazine-1-carboxylate in 84% yield.

$^1$H NMR (300 MHz, CDCl$_3$) δ 4.63 (dd, J=9.9, 6.4 Hz, 4H), 3.54-3.36 (m, 5H), 2.35-2.14 (m, 4H), 1.45 (s, 9H).

Synthesis of 1-(oxetan-3-yl)piperazine

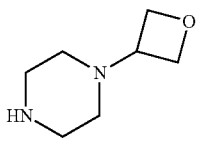

Trifluoroacetic acid (100 mL, 33.0 eq, 1327.9 mmol) was added to a solution of tert-butyl 4-(oxetan-3-yl)piperazine-1-carboxylate (9.8 g, 1.0 eq, 40.2 mmol) in $CH_2Cl_2$ (500 mL). Reaction mixture was allowed to stir at room temperature. Progress of the reaction was monitered by TLC analysis. After 30 minutes the reaction mixture was concentrated on a rotovap (bath temperature was maintained at 20° C.) to remove the volatiles. The crude solution was loaded on to SCX-2 (100 g, obtained from Sillicycle) and eluted with $CH_2Cl_2$/MeOH [1:1 $CH_2Cl_2$/MeOH (100 mL) & then with neat MeOH (100 mL)]. Then the product was eluted with 2M $NH_3$ in MeOH (200 mL). Fractions eluted with 2M $NH_3$ in MeOH were combined and concentrated under reduced pressure to leave 1-(oxetan-3-yl)piperazine as a colourless oil in 98% yield.

$^1$H NMR (300 MHz, CDCl$_3$) δ 4.68 (t, J=6.6 Hz, 2H), 4.56 (t, J=6.1 Hz, 2H), 3.66-3.56 (m, 1H), 3.48 (d, J=1.3 Hz, 1H), 3.22 (s, 4H), 2.60 (s, 4H).

Synthesis of 5-nitro-2-(4-(oxetan-3-yl)piperazin-1-yl)benzonitrile

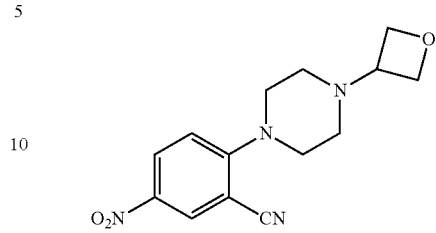

A mixture of 2-fluoro-5-nitrobenzonitrile (7 g, 1.2 eq, 41.2 mmol), 1-(oxetan-3-yl)piperazine (5.0 g, 1.0 eq, 35.2 mmol) was dissolved in annhydrous DMF (100 mL). $K_2CO_3$ (12.2 g, 2.5 eq, 87.9 mmol) was added to the above solution and the reaction mixture was stirred at room temperature for over night. The reaction mixture was diluted with of EtOAc (100 mL) and partitioned with $H_2O$ (100 mL). Layers were seperated and the aqueous layer was washed once with of EtOAc (100 mL). Combined organic layers were dried over $Na_2SO_4$ and concentrated under reduced pressure to leave a crude oil. Purification of the crude mixture by column chromatography on silica gel (ISCO System) using 20% MeOH in $CH_2Cl_2/CH_2Cl_2$ (gradient system from 1:9 to 4:6) as eluent gave 5-nitro-2-(4-(oxetan-3-yl)piperazin-1-yl)benzonitrile in 97% yield.

$^1$H NMR (300 MHz, CDCl$_3$) δ 8.47-8.36 (m, 1H), 8.28 (ddd, J=9.3, 2.7, 1.1 Hz, 1H), 6.99 (d, J=9.3 Hz, 1H), 4.67 (dt, J=20.0, 6.1 Hz, 4H), 3.67-3.49 (m, 5H), 2.65-2.48 (m, 4H). LCMS (m/z): 289 (M+H)$^+$.

Synthesis of 5-amino-2-(4-(oxetan-3-yl)piperazin-1-yl)benzonitrile

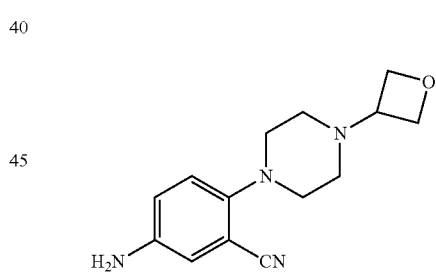

A mixture of 5-nitro-2-(4-(oxetan-3-yl)piperazin-1-yl)benzonitrile (9.8 g, 1.0 eq, 34.0 mmol) and Pd—C (10% loading, 3.6 g) in EtOH (300 mL) was stirred in a 500 mL round bottom flask. The reaction flask was evacuated under house vacuum and subsequently filled with hydrogen while stirring. This procedure was repeated three times and the reaction mixture was hydrogenated for 3 hours under an $H_2$ balloon. The mixture was filtered through celite and the filter cake was washed with EtOH (2×50 mL). The filtrate was concentrated under vacuum to leave a white solid, which upon high vacuum drying gave 5-amino-2-(4-(oxetan-3-yl)piperazin-1-yl)benzonitrile in 93% yield.

$^1$H NMR (300 MHz, d$_6$-DMSO) δ 6.95 (d, J=9.7 Hz, 1H), 6.80 (d, J=7.2 Hz, 2H), 5.19 (s, 2H), 4.53 (t, J=6.5 Hz, 2H), 4.43 (t, J=6.0 Hz, 2H), 3.53-3.38 (m, 1H), 2.99-2.86 (m, 4H), 2.38 (s, 4H). LCMS (m/z): 259 (M+H)$^+$.

Synthesis of 5-44-4(7R,8aS)-5,5-dimethyloctahydroindolizin-7-yl)amino)-5-fluoropyrimidin-2-yl)amino)-2-(4-(oxetan-3-yl)piperazin-1-yl)benzonitrile (Compound 116)

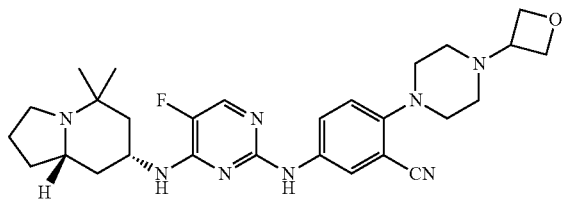 [SMILES: CC1(C)C[C@H](Nc2nc(Nc3ccc(N4CCN(C5COC5)CC4)c(C#N)c3)ncc2F)C[C@@H]2CCCN21]

A mixture of (7R,8aS)-N-(2-chloro-5fluoropyrimidin-4-yl)-5,5-dimethyloctahydroindolizin-7-amine (1.0 g, 1.0 eq, 3.4 mmol), 5-amino-2-(4-(oxetan-3-yl)piperazin-1-yl)benzonitrile (1.2 g, 1.4 eq, 4.7 mmol), PTSA (0.77 g, 1.2 eq, 4.0 mmol) were taken in $^i$PrOH (10 mL) and heated at 100° C. overnight. The volatiles were removed under vacuum to leave a crude solid. The solid was purified by column chromatography on silica gel (ISCO System) using 2M $NH_3$ in MeOH/$CH_2Cl_2$ (gradient system from 0:1 to 1:9) as eluent to give the product as a solid in 63% yield.

$^1$H NMR (300 MHz, $d_6$-DMSO) δ 9.16 (s, 1H), 8.09 (d, J=2.2 Hz, 1H), 7.85 (d, J=3.2 Hz, 1H), 7.78-7.68 (m, 1H), 7.26 (d, J=8.2 Hz, 1H), 7.07 (d, J=8.9 Hz, 1H), 4.54 (t, J=6.4 Hz, 2H), 4.44 (t, J=6.1 Hz, 2H), 4.14 (s, 1H), 3.53-3.32 (m, 1H), 3.03 (s, 4H), 2.83 (s, 1H), 2.42 (s, 3H), 2.29 (d, J=8.7 Hz, 2H), 2.01 (d, J=10.7 Hz, 1H), 1.78 (s, 1H), 1.58 (s, 3H), 1.43 (t, J=12.2 Hz, 1H), 1.17 (dd, J=22.0, 10.7 Hz, 2H), 1.08 (d, J=7.2 Hz, 4H), 0.98 (s, 3H); $^{19}$F NMR (282 MHz; $d_6$-DMSO) δ −166.3 (s); LCMS (m/z): 521 (M+H)$^+$.

Example 87

Synthesis of Compound 117

Compound 117 was prepared according to the following synthetic scheme:

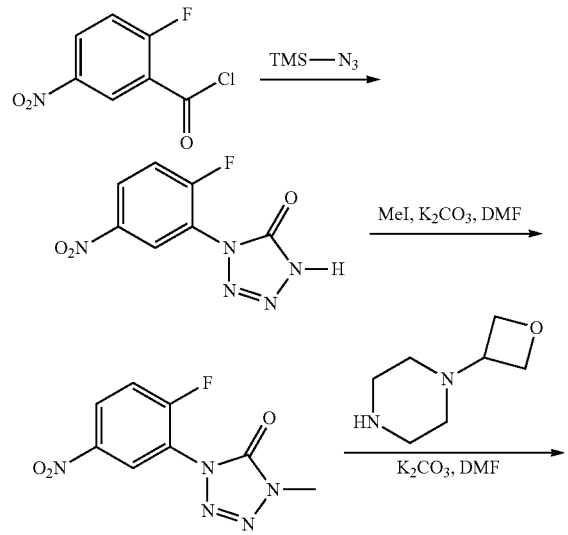

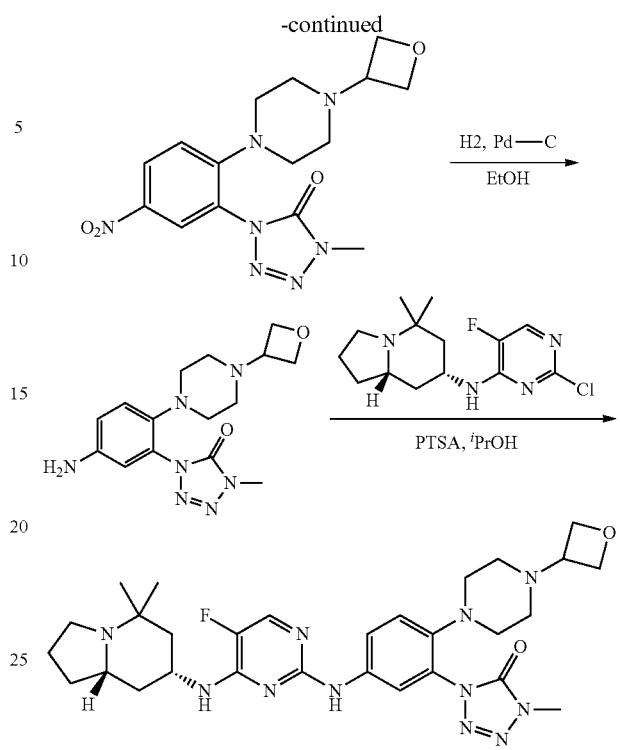

Synthesis of 1-methyl-4-(5-nitro-2-(4-(oxetan-3-yl)piperazin-1-yl)phenyl)-1,4-dihydro-5H-tetrazol-5-one

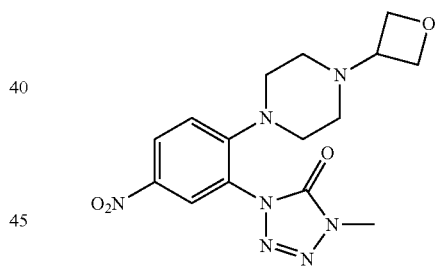

A mixture of 1-(2-fluoro-5-nitrophenyl)-4-methyl-1,4-dihydro-5H-tetrazol-5-one (1.1 g, 1.0 eq, 4.5 mmol) (see, e.g., WO 2011/068898), 1-(oxetan-3-yl)piperazine (0.64 g, 1.0 eq, 4.5 mmol) was dissolved in annhydrous DMF (100 mL) and stirred at room temperature. $K_2CO_3$ (1.9 g, 3.0 eq, 13.5 mmol) was added to the above solution and the heterogeneous mixture was stirred at room temperature overnight. The reaction mixture was diluted with EtOAc (50 mL) and partitioned with $H_2O$ (50 mL). The layers were seperated and the aqueous layer was washed with EtOAc (50 mL). The combined organic layers were dried over $Na_2SO_4$ and concentrated under reduced pressure to leave a crude solid. Purification of the crude solid by column chromatography on silica gel (ISCO System) using 20% MeOH in $CH_2Cl_2$/$CH_2Cl_2$ (gradient system from 1:9 to 1:1) as eluent gave the product in 50% yield.

$^1$H NMR (300 MHz, CDCl$_3$) δ 8.29 (ddd, J=9.1, 4.3, 2.7 Hz, 1H), 8.20 (dd, J=4.3, 2.7 Hz, 1H), 7.17 (dd, J=9.1, 4.2 Hz, 1H), 4.74-4.48 (m, 4H), 3.73 (d, J=4.3 Hz, 3H), 3.52

(dd, J=10.3, 6.1 Hz, 1H), 3.20-3.02 (m, 4H), 2.44-2.28 (m, 4H). LCMS (m/z): 362 (M+H)+.

Synthesis of 1-(5-amino-2-(4-(oxetan-3-yl)piperazin-1-yl)phenyl)-4-methyl-1,4-dihydro-5H-tetrazol-5-one

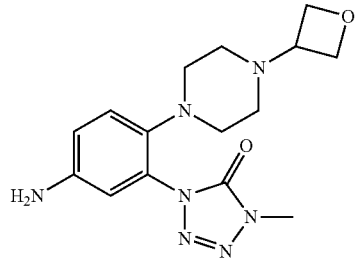 [SMILES: Cn1nnn(-c2cc([N+](=O)[O-])ccc2N2CCN(C3COC3)CC2)c1=O]

1-methyl-4-(5-nitro-2-(4-(oxetan-3-yl)piperazin-1-yl)phenyl)-1,4-dihydro-5H-tetrazol-5-one (0.75 g, 1.0 eq, 2.1 mmol) was suspended in a mixture of EtOH/MeOH (1:1, 100 mL) in a 250 mL round bottom flask and the reaction flask was charged with Pd-C (10% loading, 0.25 g). The reaction flask was evacuated under house vacuum and subsequently filled with hydrogen while stirring. This procedure was repeated three times and the reaction mixture was stirred for 3 hours under an H₂ balloon. The mixture was filtered through celite and the filter cake was washed with MeOH (2×10 mL). The filtrate was concentrated on a rotovap to leave a white solid which upon high vacuum drying gave the product in 78% yield.

$^1$H NMR (300 MHz, d$_6$-DMSO) δ 7.11 (d, J=8.6 Hz, 1H), 6.71 (dd, J=8.6, 2.7 Hz, 1H), 6.54 (d, J=2.6 Hz, 1H), 5.24 (s, 2H), 4.47 (t, J=6.5 Hz, 2H), 4.36 (t, J=6.1 Hz, 2H), 3.58 (d, J=4.0 Hz, 3H), 3.34 (s, 3H), 2.66 (t, J=4.6 Hz, 3H), 2.12 (s, 3H). LCMS (m/z): 332 (M+H)+.

Synthesis of 1-(5-((4-(((7R,8aS)-5,5-dimethyloctahydroindolizin-7-yl)amino)-5-fluoropyrimidin-2-yl)amino)-2-(4-(oxetan-3-yl)piperazin-1-yl)phenyl)-4-methyl-1,4-dihydro-5H-tetrazol-5-one (Compound 117)

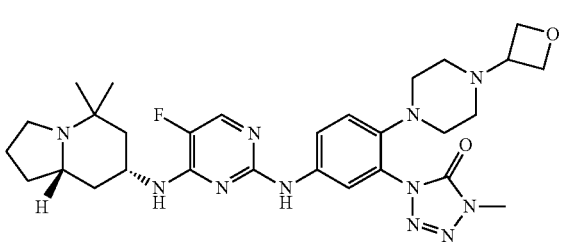 [SMILES: Cn1nnn(-c2cc(Nc3ncc(F)c(N[C@@H]4C[C@@H]5CCCN5C(C)(C)C4)n3)ccc2N2CCN(C3COC3)CC2)c1=O]

A mixture of (7R,8aS)-N-(2-chloro-5fluoropyrimidin-4-yl)-5,5-dimethyloctahydroindolizin-7-amine (0.2 g, 1.0 eq, 0.7 mmol), 1-(5-amino-2-(4-(oxetan-3-yl)piperazin-1-yl)phenyl)-4-methyl-1,4-dihydro-5H-tetrazol-5-one (0.3 g, 1.4 eq, 0.9 mmol), PTSA (0.4 g, 2.0 eq, 1.9 mmol) was taken in $^i$PrOH (50 mL) and heated at 120° C. overnight. The volatiles were removed under vacuum to leave a crude solid. The solid was purified by column chromatography on silica gel (ISCO System) using 2M NH₃ in MeOH/CH₂Cl₂ (gradient system from 0:1 to 2:8) as eluent to give the product as a solid in 55% yield.

$^1$H NMR (300 MHz, d$_6$-DMSO) δ 9.28 (s, 1H), 8.01 (s, 1H), 7.85 (d, J=3.6 Hz, 1H), 7.65 (d, J=7.3 Hz, 1H), 7.28 (d, J=8.7 Hz, 2H), 4.48 (t, J=6.4 Hz, 2H), 4.37 (t, J=6.1 Hz, 2H), 4.07 (d, J=4.8 Hz, 1H), 3.60 (s, 3H), 3.34 (d, J=6.2 Hz, 1H), 3.15 (d, J=5.1 Hz, 1H), 2.82 (s, 1H), 2.70 (d, J=4.0 Hz, 4H), 2.14 (s, 6H), 1.96 (s, 2H), 1.76-1.28 (m, 3H), 1.18 (s, 2H), 1.06 (s, 3H), 0.82 (s, 3H). $^{19}$F NMR (282 MHz; d$_6$-DMSO) δ −166.3 (s); LCMS (m/z): 594 (M+H)+.

Example 88

Synthesis of Compound 118 and Compound 120

Compounds 118 and 120 were prepared according to the following synthetic scheme:

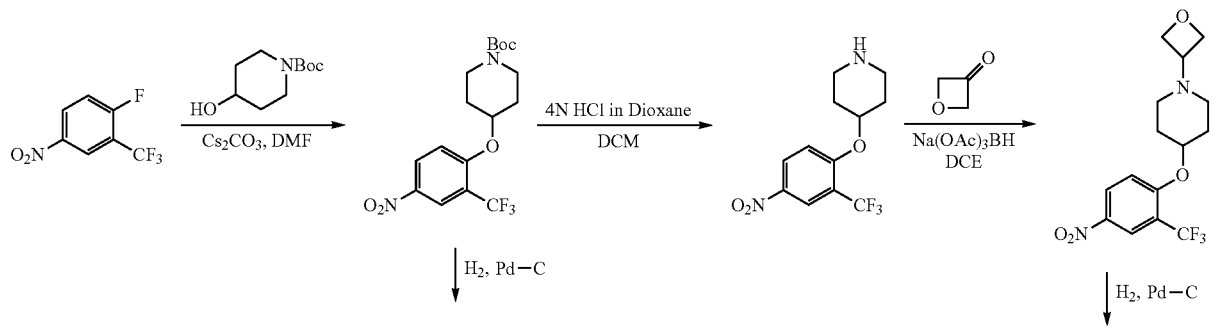

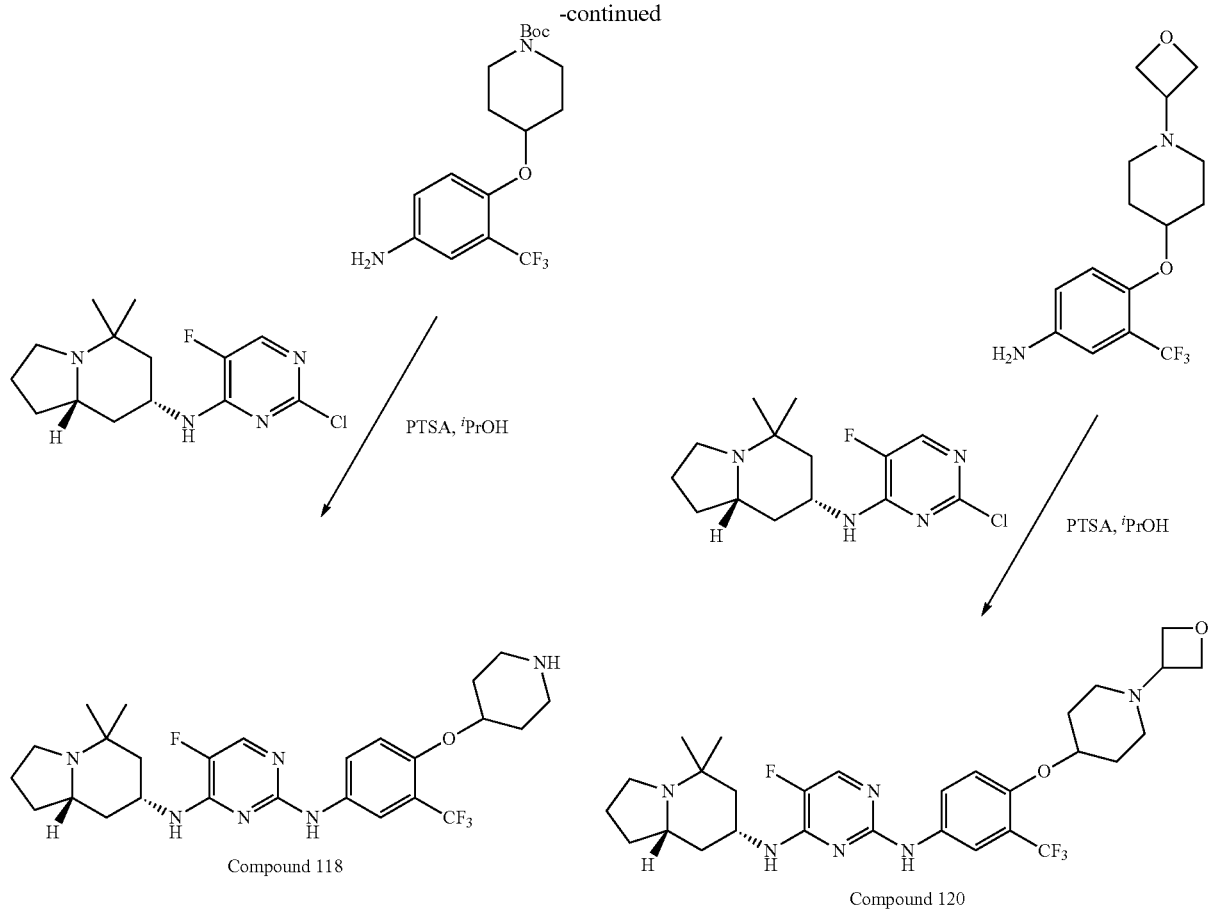

Compound 118

Compound 120

Synthesis of tert-butyl 4-(4-nitro-2-(trifluoromethyl)phenoxy)piperidine-1-carboxylate

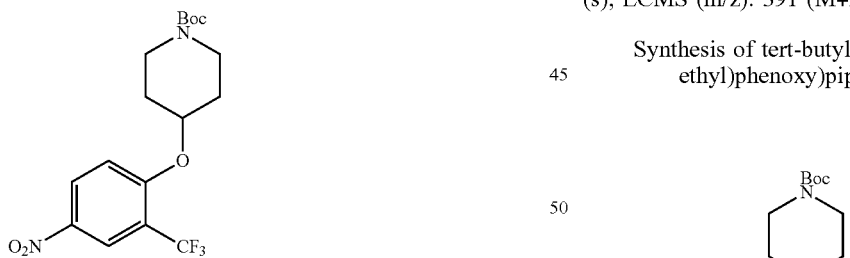

A mixture of 1-fluoro-4-nitro-2-(trifluoromethyl)benzene (2.0 g, 1.0 eq, 9.6 mmol) and tert-butyl 4-hydroxypiperidine-1-carboxylate (2.1 g, 1.1 eq, 10.5 mmol) was taken in annhydrous DMF (100 mL) and stirred at room temerature. $Cs_2CO_3$ (7.2 g, 2.3 eq, 22.1 mmol) was added to the above solution and the heterogeneous mixture was heated at 100° C. overnight. The reaction mixture was diluted with $CH_2Cl_2$ (100 mL) and partioned with $H_2O$ (50 mL). The layers were seperated and the aqueous layer was washed with $CH_2Cl_2$ (2×50 mL). The combined organic layers were dried over $Na_2SO_4$ and concentrated to leave a crude solid. Purification of the crude mixture by column chromatography on silica gel (ISCO System) using EtOAc/hexane (gradient system from 0:10 to 2:8) as eluent gave the product in 60% yield.

$^1$H NMR (300 MHz, CDCl$_3$) δ 8.51 (d, J=2.6 Hz, 1H), 8.39 (dd, J=9.2, 2.7 Hz, 1H), 7.08 (d, J=9.2 Hz, 1H), 4.81 (s, 1H), 3.70-3.56 (m, 2H), 3.54-3.36 (m, 2H), 1.98-1.83 (m, 4H), 1.47 (s, 9H). $^{19}$F NMR (282 MHz; d$_6$-DMSO) δ −63.3 (s); LCMS (m/z): 391 (M+H)$^+$.

Synthesis of tert-butyl 4-(4-amino-2-(trifluoromethyl)phenoxy)piperidine-1-carboxylate A mixture of tert-butyl 4-(4-nitro-2-(trifluoromethyl)phenoxy)piperidine-1-carboxylate (0.75 g, 1.0 eq, 1.9 mmol) and Pd—C (10%, 0.3 g) in EtOH (50 mL) was hydrogenated at 30 psi for 2 hours. The mixture was filtered through celite and the filter cake washed with EtOH (2×10 mL). The filtrate was concentrated under vacuum to give the desired product in 90% yield. This product was taken to next step with out further purification.

¹H NMR (300 MHz, CDCl₃) δ 6.91 (d, J=2.5 Hz, 1H), 6.80 (dd, J=12.0, 5.6 Hz, 2H), 4.45 (s, 1H), 3.68-3.49 (m, 4H), 3.42 (dd, J=11.7, 6.1 Hz, 3H), 1.81 (dd, J=10.5, 5.5 Hz, 5H), 1.46 (s, 10H); ¹⁹F NMR (282 MHz; d₆-DMSO) δ −61.9 (s); LCMS (m/z): 361 (M+H)⁺.

Synthesis of N⁴-((7R,8aS)-5,5-dimethyloctahydroindolizin-7-yl)-5-fluoro-N²-(4-(piperidin-4-yloxy)-3-(trifluoromethyl)phenyl)pyrimidine-2,4-diamine (Compound 118)

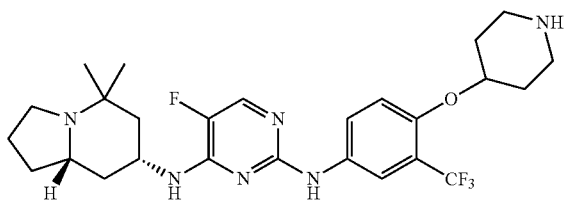 [SMILES: CC1(C)C[C@H](Nc2nc(Nc3ccc(OC4CCNCC4)c(C(F)(F)F)c3)ncc2F)C[C@@H]2CCCN21]

A mixture of (7R,8aS)-N-(2-chloro-5-fluoropyrimidin-4-yl)-5,5-dimethyloctahydroindolizin-7-amine (0.2 g, 0.95 eq, 0.7 mmol), tert-butyl 4-(4-amino-2-(trifluoromethyl)phenoxy)piperidine-1-carboxylate (0.25 g, 1.0 eq, 0.7 mmol) and PTSA (0.24 g, 1.8 eq, 1.3 mmol) was taken in ⁱPrOH (50 mL) and heated at 110° C. overnight. After 18 hours of heating, reaction mixture was cooled to room temperature and PTSA (1.0 eq) was added to complete the deprotection of the Boc group. Next, the reaction mixture was heated at 110° C. for 2 hours while stirring and cooled to room temperature. The volatiles were removed under vacuum to leave a crude solid. The crude mixture was dissolved in EtOAc (100 mL) and partitioned with 1N aqueous NaOH solution (50 mL). Organic layers were separated and the aqueous layer was washed with EtOAc (50 mL). The combined organic layers were dried over Na₂SO₄ and concentrated under vacuum to leave a crude solid. The solid was purified by column chromatography on silica gel (ISCO System) using 2M NH₃ in MeOH/CH₂Cl₂ (gradient system from 0:1 to 2:8) as eluent to give the product as a solid in 36% yield.

¹H NMR (300 MHz, d₆-DMSO) δ 9.08 (s, 1H), 7.99 (s, 1H), 7.89 (d, J=3.9 Hz, 2H), 7.35-7.09 (m, 2H), 4.60 (s, 1H), 4.20 (s, 2H), 2.71 (t, J=9.1 Hz, 2H), 2.48-2.40 (m, 1H), 2.35 (d, J=8.3 Hz, 2H), 2.15-1.88 (m, 3H), 1.83 (s, 1H), 1.63 (s, 5H), 1.48 (t, J=12.2 Hz, 2H), 1.36-1.17 (m, 3H), 1.13 (s, 3H), 1.00 (s, 3H); ¹⁹F NMR (282 MHz; d₆-DMSO) δ −60.3 (s), −166.7 (s); LCMS (m/z): 523 (M+H)⁺.

Synthesis of 4-(4-nitro-2-(trifluoromethyl)phenoxy)piperidine

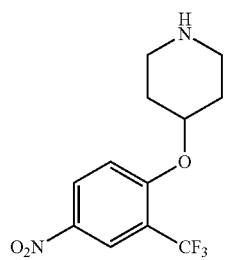 [SMILES: O=[N+]([O-])c1ccc(OC2CCNCC2)c(C(F)(F)F)c1]

A solution of tert-butyl 4-(4-nitro-2-(trifluoromethyl)phenoxy)piperidine-1-carboxylate (1.4 g, 1.0 eq, 3.6 mmol) in CH₂Cl₂ (25 mL) was cooled to 0° C. while stirring. 4N HCl in dioxane (15 mL) was added to the above solution and stirred at 0° C. for 30 minutes and brought to room temperature for 2 hours. The volatiles were removed under vacuum to leave a crude solid. The crude mixture was dissolved in EtOAc (100 mL) and partitioned with 1N aqueous NaOH solution (50 mL). Organic layers were separated and the aqueous layer was washed with EtOAc (50 mL). The combined organic layers were dried over Na₂SO₄ and concentrated under vacuum to give the desired product in 90% yield.

¹H NMR (300 MHz, CDCl₃) δ 8.44 (d, J=2.6 Hz, 1H), 8.32 (dd, J=9.2, 2.7 Hz, 1H), 7.01 (d, J=9.2 Hz, 1H), 4.78-4.55 (m, 1H), 3.08 (ddd, J=11.9, 8.2, 3.4 Hz, 1H), 2.94-2.68 (m, 1H), 2.35 (s, 2H), 2.10-1.89 (m, 2H), 1.89-1.69 (m, 2H); ¹⁹F NMR (282 MHz; d₆-DMSO) δ −63.3 (s); LCMS (m/z): 291 (M+H)⁺.

Synthesis of 4-(4-nitro-2-(trifluoromethyl)phenoxy)-1-(oxetan-3-yl)piperidine

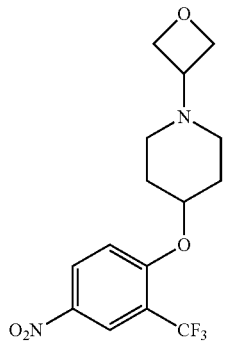

A solution of 4-(4-nitro-2-(trifluoromethyl)phenoxy)piperidine (1.0 g, 1.0 eq, 3.5 mmol) and oxetan-3-one (0.35 g, 1.4 eq, 4.8 mmol) in 1,2-dichloroethane (50 mL) was stirred at room temperature for 30 minutes. Sodium triacetoxyborohydride (1.3 g, 1.8 eq, 6.2 mmol) was added in portions to the above solution and the heterogeneous mixture was stirred at room temperature overnight. The reaction mixture was diluted with CH₂Cl₂ (50 mL) and partioned with aqueous saturated NaHCO₃ solution (100 mL). The layers were seperated and the organic layer was washed with brine solution (2×50 mL). The combined organic layers were dried over Na₂SO₄. Removal of the solvents and purification of the crude mixture by column chromatography on silica gel (ISCO System) using 20% MeOH in CH₂Cl₂/CH₂Cl₂ (gradient system from 0:1 to 1:9) as eluent gave the product in 77% yield.

¹H NMR (300 MHz, CDCl₃) δ 8.45 (s, 1H), 8.34 (d, J=9.1 Hz, 1H), 7.01 (d, J=9.1 Hz, 1H), 4.70 (s, 1H), 4.62 (d, J=6.5 Hz, 4H), 3.62-3.45 (m, 1H), 2.43 (s, 4H), 2.07 (s, 2H), 1.98 (d, J=3.9 Hz, 2H); ¹⁹F NMR (282 MHz; d₆-DMSO) δ −63.2 (s); LCMS (m/z): 347 (M+H)⁺.

449
Synthesis of 4-41-(oxetan-3-yl)piperidin-4-yl)oxy)-3-(trifluoromethyl)aniline

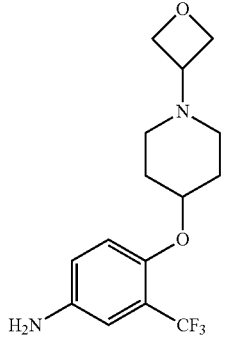 [SMILES: O=[N+]([O-])c1ccc(OC2CCN(C3COC3)CC2)c(C(F)(F)F)c1]

A mixture of 4-(4-nitro-2-(trifluoromethyl)phenoxy)-1-(oxetan-3-yl)piperidine (0.9 g, 1.0 eq, 2.6 mmol) and Pd—C (10%, 0.3 g) in EtOH (50 mL) was hydrogenated at 30 psi for 1 hour. The mixture was filtered through celite and the filter cake washed with EtOH (2×10 mL). The filtrate was concentrated under vacuum to give the desired product in 90% yield. This product was taken to next step with out further purification.

$^1$H NMR (300 MHz, CDCl$_3$) δ 6.90 (d, J=2.5 Hz, 1H), 6.79 (dd, J=10.2, 5.7 Hz, 2H), 4.75-4.57 (m, 4H), 4.38 (s, 1H), 3.53 (dd, J=13.1, 6.5 Hz, 2H), 3.47 (s, 1H), 2.50 (dd, J=13.5, 5.8 Hz, 2H), 2.28 (d, J=5.0 Hz, 2H), 2.10-1.82 (m, 2H); $^{19}$F NMR (282 MHz; d$_6$-DMSO) δ −61.8 (s); LCMS (m/z): 317 (M+H)$^+$.

450
Synthesis of N$^4$-((7R,8aS)-5,5-dimethyloctahydroindolizin-7-yl)-5-fluoro-N$^2$-(4-41-(oxetan-3-yl)piperidin-4-yl)oxy)-3-(trifluoromethyl)phenyl)pyrimidine-2,4-diamine (Compound 120)

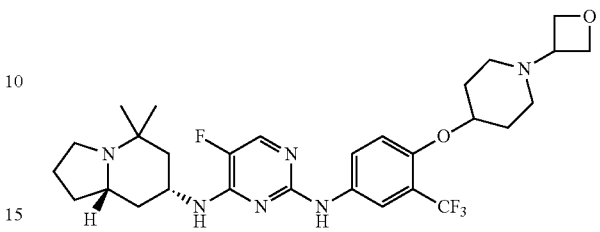

A mixture of (7R,8aS)-N-(2-chloro-5-fluoropyrimidin-4-yl)-5,5-dimethyloctahydroindolizin-7-amine (0.25 g, 1.0 eq, 0.8 mmol), 4-((1-(oxetan-3-yl)piperidin-4-yl)oxy)-3-(trifluoromethyl)aniline (0.3 g, 1.2 eq, 1.0 mmol), PTSA (0.14 g, 0.9 eq, 0.8 mmol) was taken in $^i$PrOH (20 mL) and heated at 100° C. overnight. The volatiles were removed under vacuum to leave a crude solid. The crude mixture was dissolved in EtOAc (50 mL) and partitioned with 1N aqueous NaOH solution (25 mL). Organic layers were separated and the aqueous layer was washed with EtOAc (2×20 mL). The combined organic layers were dried over Na$_2$SO$_4$ and concentrated under vacuum to leave a crude solid. The solid was purified by column chromatography on silica gel (ISCO System) using 2M NH$_3$ in MeOH/CH$_2$Cl$_2$ (gradient system from 0:1 to 2:8) as eluent to give the product in 70% yield.

$^1$H NMR (300 MHz, d$_6$-DMSO) δ 9.00 (s, 1H), 7.91 (s, 1H), 7.82 (dd, J=3.8, 1.5 Hz, 2H), 7.14 (dd, J=14.0, 8.7 Hz, 2H), 4.50 (t, J=6.4 Hz, 3H), 4.39 (t, J=6.1 Hz, 2H), 4.12 (s, 1H), 3.46-3.31 (m, 1H), 2.82 (s, 1H), 2.40 (s, 3H), 2.27 (d, J=8.5 Hz, 1H), 2.12 (s, 2H), 1.93 (d, J=33.3 Hz, 3H), 1.80-1.48 (m, 5H), 1.40 (t, J=12.0 Hz, 1H), 1.16 (dd, J=21.2, 9.8 Hz, 3H), 1.05 (s, 3H), 0.92 (s, 3H); $^{19}$F NMR (282 MHz; d$_6$-DMSO) δ −60.2 (s)-166.8 (s); LCMS (m/z): 579 (M+H)$^+$.

Example 89

Synthesis of Compound 119 and Compound 122

Compounds 119 and 122 were prepared according to the following synthetic scheme:

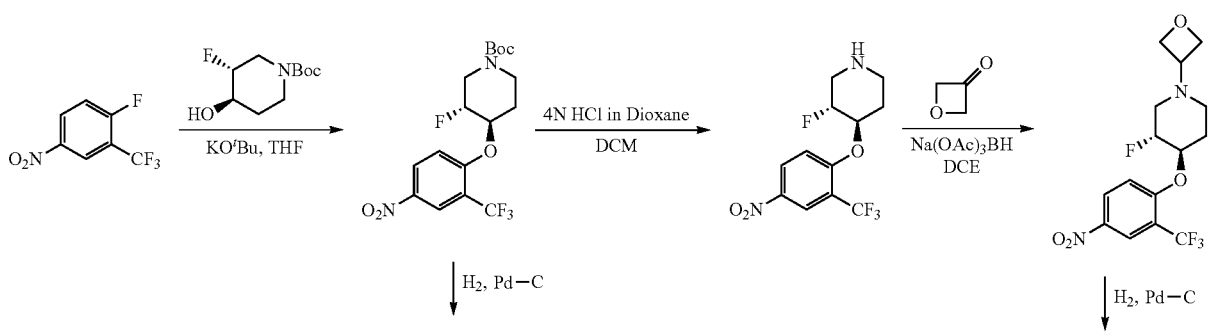

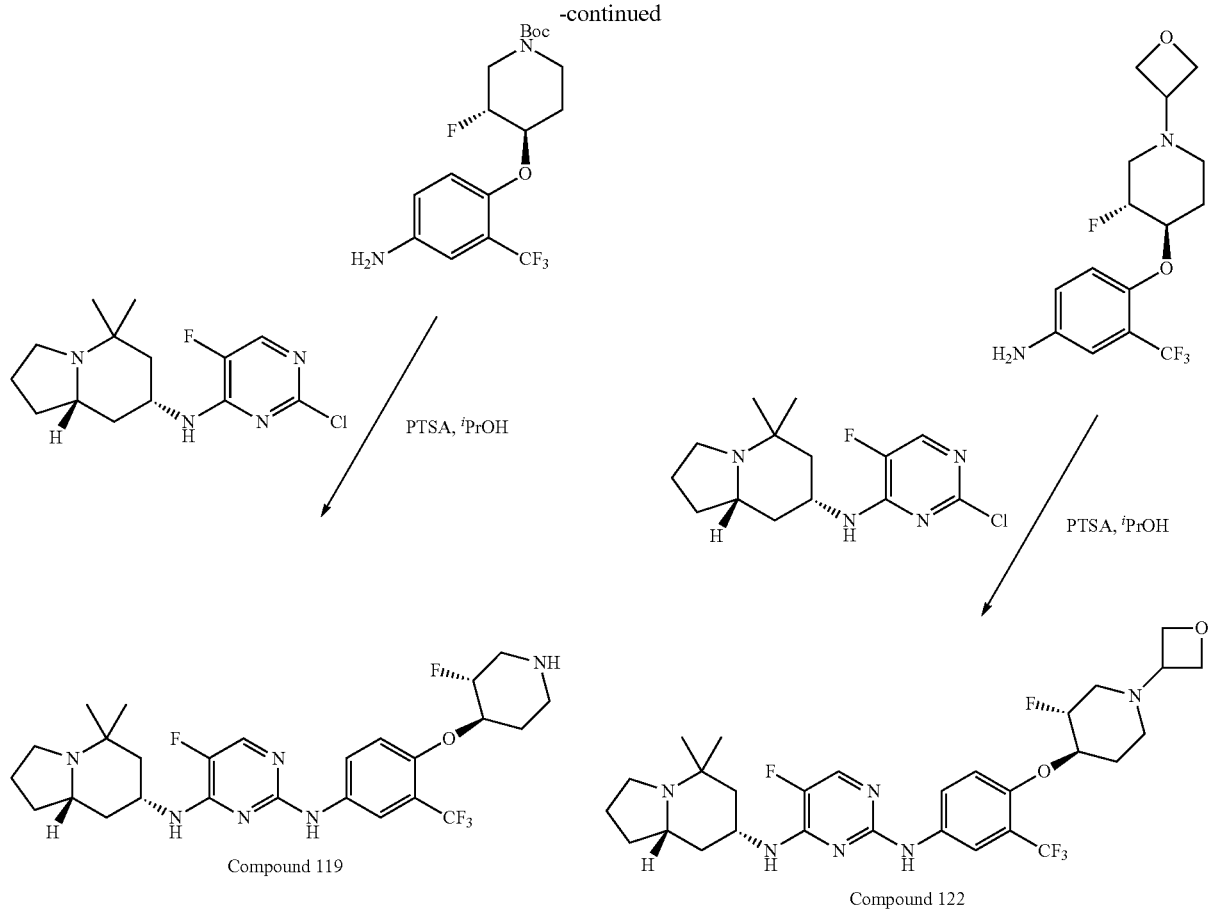

Compound 119

Compound 122

Synthesis of tert-butyl(3R,4R)-3-fluoro-4-(4-nitro-2-(trifluoromethyl)phenoxy)piperidine-1-carboxylate

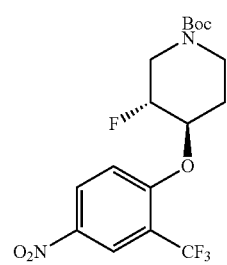

A mixture of 1-fluoro-4-nitro-2-(trifluoromethyl)benzene (2.1 g, 1.0 eq, 10.1 mmol) and tert-butyl (3R,4R)-3-fluoro-4-hydroxypiperidine-1-carboxylate (2.1 g, 1.0 eq, 9.6 mmol) (see, e.g., WO 2012/016217) was taken in annhydrous THF (50 mL) and stirred at 0° C. KO$^t$Bu (1.9 g, 1.8 eq, 17.3 mmol) was added to the above solution at 0° C. and the heterogeneous mixture was warmed to room temperature. Then the reaction mixture was refluxed overnight. After completion of the reaction, the mixture was concentrated under reduced pressure. EtOAc (100 mL) was added to the crude mixture and partioned with aqueous saturated NaHCO$_3$ (50 mL) solution. The layers were seperated and the organic layer was washed with aqueous saturated NaHCO$_3$ (50 mL) solution and brine (1×50 mL). The organic layers were dried over Na$_2$SO$_4$ and concentrated to leave a crude solid. Purification of the crude mixture by column chromatography on silica gel (ISCO System) using EtOAc/hexane (gradient system from 0:1 to 3:7) as eluent gave the product in 72% yield.

$^1$H NMR (300 MHz, CDCl$_3$) δ 8.45 (d, J=2.7 Hz, 1H), 8.35 (dd, J=9.2, 2.8 Hz, 1H), 7.12 (d, J=9.2 Hz, 1H), 4.68 (s, 2H), 4.51 (d, J=4.7 Hz, 1H), 3.74 (d, J=25.3 Hz, 2H), 3.47 (s, 1H), 2.08 (s, 1H), 1.81 (dd, J=14.0, 6.1 Hz, 1H), 1.40 (d, J=8.9 Hz, 9H); $^{19}$F NMR (282 MHz; d$_6$-DMSO) δ −62.8 (s)-63.2 (d); LCMS (m/z): 409 (M+H)$^+$.

Synthesis of tert-butyl(3R,4R)-4-(4-amino-2-(trifluoromethyl)phenoxy)-3-fluoropiperidine-1-carboxylate

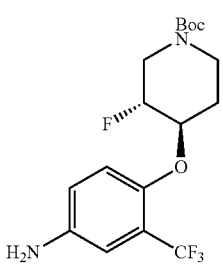 [SMILES: CC(C)(C)OC(=O)N1CC[C@@H](Oc2ccc([N+](=O)[O-])cc2C(F)(F)F)[C@H](F)C1]

A mixture of tert-butyl (3R,4R)-3-fluoro-4-(4-nitro-2-(trifluoromethyl)phenoxy)piperidine-1-carboxylate (1.2 g, 1.0 eq, 2.9 mmol) and Pd-C (10%, 0.3 g) in EtOH (50 mL) was hydrogenated at 30 psi for 1 hour. The mixture was filtered through celite and the filter cake washed with EtOH (2×10 mL). The filtrate was concentrated under vacuum to give the desired product in 82% yield. This product was taken to next step with out further purification.

$^1$H NMR (300 MHz, CDCl$_3$) δ 7.06 (s, 1H), 6.95 (dd, J=15.5, 8.9 Hz, 2H), 4.69 (s, 1H), 4.50 (s, 2H), 3.91-3.62 (m, 2H), 3.55 (d, J=40.9 Hz, 1H), 2.06 (s, 1H), 1.84 (s, 1H), 1.47 (d, J=2.2 Hz, 9H); $^{19}$F NMR (282 MHz; d$_6$-DMSO) δ −62.3 (s)-62.5 (s); LCMS (m/z): 379 (M+H)$^+$.

Synthesis of N$^4$-((7R,8aS)-5,5-dimethyloctahydroindolizin-7-yl)-5-fluoro-N$^2$-(4-(3R,4R)-3-fluoropiperidin-4-yl)oxy)-3-(trifluoromethyl)phenyl)pyrimidine-2,4-diamine (Compound 119)

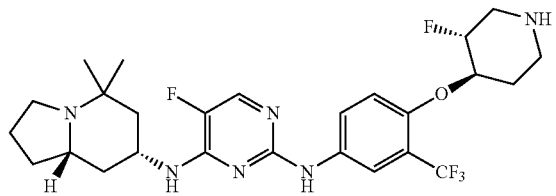 [SMILES: CC1(C)C[C@H](Nc2nc(Nc3ccc(O[C@@H]4CCNC[C@H]4F)c(C(F)(F)F)c3)ncc2F)C[C@@H]2CCCN21]

A mixture of (7R,8aS)-N-(2-chloro-5-fluoropyrimidin-4-yl)-5,5-dimethyloctahydroindolizin-7-amine (0.3 g, 1.0 eq, 1.0 mmol), tert-butyl (3R,4R)-4-(4-amino-2-(trifluoromethyl)phenoxy)-3-fluoropiperidine-1-carboxylate (0.42 g, 1.1 eq, 1.1 mmol) and PTSA (0.2 g, 0.9 eq, 0.9 mmol) was taken in $^i$PrOH (25 mL) and heated at 90° C. overnight. After 18 hours of heating, reaction mixture was cooled to room temperature and PTSA (1.0 eq) was added to complete the deprotection of the Boc group. Then the reaction mixture was heated at 120° C. for 3 hours while stirring and cooled to room temperature. The volatiles were removed under vacuum to leave a crude solid. 4N HCl in dioxane (5 mL) was added to the crude mixture to ensure complete deprotection of the Boc group and the mixture was concentrated to dryness. The crude mixture was dissolved in EtOAc (50 mL) and partitioned with 1N aqueous NaOH solution (25 mL). Organic layers were separated and the aqueous layer was washed with EtOAc (25 mL). The combined organic layers were dried over Na$_2$SO$_4$ and concentrated under vacuum to leave a crude solid. The solid was purified by column chromatography on silica gel (ISCO System) using 2M NH$_3$ in MeOH/CH$_2$Cl$_2$ (gradient system from 0:1 to 2:8) as eluent to give the product as a solid in 43% yield.

$^1$H NMR (300 MHz, d$_6$-DMSO) δ 9.03 (s, 1H), 7.93 (d, J=2.6 Hz, 1H), 7.87-7.71 (m, 2H), 7.19 (t, J=9.3 Hz, 2H), 4.53 (d, J=4.5 Hz, 1H), 4.36 (d, J=4.3 Hz, 1H), 4.13 (s, 1H), 3.13 (d, J=8.1 Hz, 1H), 2.81 (d, J=8.8 Hz, 2H), 2.64-2.52 (m, 2H), 2.27 (d, J=8.2 Hz, 2H), 1.97 (s, 2H), 1.76 (s, 1H), 1.58 (d, J=9.4 Hz, 3H), 1.41 (t, J=12.1 Hz, 2H), 1.29-1.10 (m, 3H), 1.05 (s, 3H), 0.92 (s, 3H); $^{19}$F NMR (282 MHz; d$_6$-DMSO) δ −60.2 (d), −166.6 (s); LCMS (m/z): 541 (M+H)$^+$.

Synthesis of (3R,4R)-3-fluoro-4-(4-nitro-2-(trifluoromethyl)phenoxy)piperidine

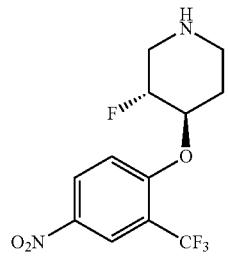 [SMILES: O=[N+]([O-])c1ccc(O[C@@H]2CCNC[C@H]2F)c(C(F)(F)F)c1]

A solution of tert-butyl (3R,4R)-3-fluoro-4-(4-nitro-2-(trifluoromethyl)phenoxy)piperidine-1-carboxylate (1.6 g, 1.0 eq, 3.9 mmol) in CH$_2$Cl$_2$ (10 mL) was cooled to 0° C. while stirring. 4N HCl in dioxane (10 mL) was added to the above solution and stirred at 0° C. for 30 minutes and brought to room temperature for 3 hours. The volatiles were removed under vacuum to leave a crude solid. The crude mixture was dissolved in EtOAc (100 mL) and partitioned with 1N aqueous NaOH solution (50 mL). Organic layers were separated and the aqueous layer was washed with EtOAc (50 mL). The combined organic layers were dried over Na$_2$SO$_4$ and concentrated under vacuum to give the desired product in 95% yield.

$^1$H NMR (300 MHz, CDCl$_3$) δ 8.45 (t, J=5.0 Hz, 1H), 8.34 (dt, J=9.1, 2.4 Hz, 1H), 7.13 (d, J=9.2 Hz, 1H), 4.65 (d, J=3.0 Hz, 1H), 4.54-4.40 (m, 1H), 3.77-3.17 (m, 1H), 3.14-2.81 (m, 1H), 2.81-2.61 (m, 1H), 2.28-2.04 (m, 1H), 1.98 (d, J=2.4 Hz, 1H), 1.90-1.65 (m, 1H); $^{19}$F NMR (282 MHz; d$_6$-DMSO) δ −62.8 (s), −63.2 (s); LCMS (m/z): 309 (M+H)$^+$.

Synthesis of (3R,4R)-3-fluoro-4-(4-nitro-2-(trifluoromethyl)phenoxy)-1-(oxetan-3-yl)piperidine

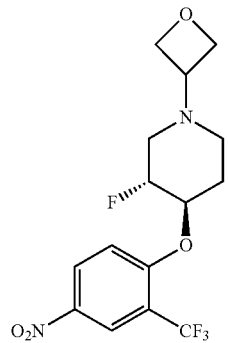

A solution of (3R,4R)-3-fluoro-4-(4-nitro-2-(trifluoromethyl)phenoxy)piperidine (1.3 g, 1.0 eq, 4.3 mmol) and oxetan-3-one (0.43 g, 1.4 eq, 6.0 mmol) in 1,2-dichloroethane (50 mL) was stirred at room temperature for 30 minutes. Sodium triacetoxyborohydride (1.6 g, 1.8 eq, 7.7 mmol) was added in portions to the above solution and the heterogeneous mixture was stirred at room temperature overnight. Work-up and purification of the crude mixture used the same conditions as Example 88 above for Compound 120, and gave the product in 66% yield.

$^1$H NMR (300 MHz, CDCl$_3$) δ 8.45 (d, J=2.5 Hz, 1H), 8.34 (d, J=9.2 Hz, 1H), 7.14 (d, J=9.1 Hz, 1H), 4.81 (d, J=4.3 Hz, 1H), 4.77-4.45 (m, 5H), 3.72-3.47 (m, 1H), 3.02-2.77 (m, 1H), 2.60 (s, 1H), 2.42 (s, 1H), 2.22 (s, 2H), 1.93 (d, J=8.8 Hz, 1H); $^{19}$F NMR (282 MHz; d$_6$-DMSO) δ −62.8 (s), −63.1 (s); LCMS (m/z): 365 (M+H)$^+$.

Synthesis of 4-(((3R,4R)-3-fluoro-1-(oxetan-3-yl) piperidin-4-yl)oxy)-3-(trifluoromethyl)aniline

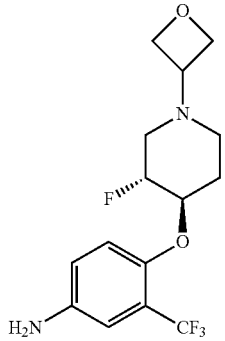 [SMILES: O=[N+]([O-])c1ccc(O[C@@H]2CCN(C3COC3)C[C@H]2F)c(C(F)(F)F)c1]

A mixture of (3R,4R)-3-fluoro-4-(4-nitro-2-(trifluoromethyl)phenoxy)-1-(oxetan-3-yl)piperidine (0.9 g, 1.0 eq, 2.6 mmol) and Pd—C (10%, 0.3 g) in EtOH (50 mL) was hydrogenated at 30 psi for 1 hour. The mixture was filtered through celite and the filter cake washed with EtOH (2×10 mL). The filtrate was concentrated under vacuum to give the desired product in 90% yield. This product was taken to next step with out further purification.

$^1$H NMR (300 MHz, d$_6$-DMSO) δ 7.04 (d, J=8.7 Hz, 2H), 6.81-6.65 (m, 2H), 5.06 (s, 2H), 4.76-4.58 (m, 1H), 4.51 (t, J=6.5 Hz, 2H), 4.40 (dt, J=12.0, 6.1 Hz, 3H), 3.47 (J=6.3 Hz, 1H), 2.87 (t, J=10.5 Hz, 1H), 2.15 (dd, J=18.0, 8.4 Hz, 1H), 2.02 (t, J=9.6 Hz, 2H), 1.66-1.42 (m, 1H); $^{19}$F NMR (282 MHz; d$_6$-DMSO) δ −60.0 (s), −59.9 (s); LCMS (m/z): 335 (M+H)$^+$.

Synthesis of N$^4$-((7R,8aS)-5,5-dimethyloctahydroindolizin-7-yl)-5-fluoro-N$^2$-(4-4(3R,4R)-3-fluoro-1-(oxetan-3-yl)piperidin-4-yl)oxy)-3-(trifluoromethyl) phenyl)pyrimidine-2,4-diamine (Compound 122)

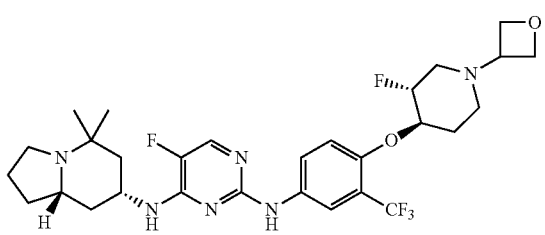 [SMILES: CC1(C)C[C@H](Nc2nc(Nc3ccc(O[C@@H]4CCN(C5COC5)C[C@H]4F)c(C(F)(F)F)c3)ncc2F)C[C@@H]2CCCN21]

(7R,8aS)-N-(2-chloro-5-fluoropyrimidin-4-yl)-5,5-dimethyloctahydroindolizin-7-amine (0.25 g, 1.0 eq, 0.8 mmol) was coupled to 4-(((3R,4R)-3-fluoro-1-(oxetan-3-yl)piperidin-4-yl)oxy)-3-(trifluoromethyl)aniline (0.3 g, 1.2 eq, 1.0 mmol) using the same reaction conditions, work-up and purification conditions as in Example 88 above for Compound 120, and gave the product in 70% yield.

$^1$H NMR (300 MHz, d$_6$-DMSO) δ 9.13 (s, 1H), 8.02 (s, 1H), 7.91 (d, J=3.8 Hz, 2H), 7.38-7.13 (m, 2H), 4.60 (t, J=6.4 Hz, 3H), 4.49 (dt, J=12.1, 6.0 Hz, 2H), 4.22 (s, 1H), 3.65-3.50 (m, 1H), 2.92 (s, 2H), 2.49 (s, 1H), 2.32 (dd, J=18.0, 9.4 Hz, 3H), 2.21-1.97 (m, 2H), 1.82 (s, 1H), 1.66 (d, J=9.1 Hz, 4H), 1.49 (t, J=12.0 Hz, 2H), 1.36-1.17 (m, 3H), 1.14 (s, 3H), 1.01 (s, 3H). $^{19}$F NMR (282 MHz; d$_6$-DMSO) δ −60.17 (s), −60.15 (s), −166.6 (s); LCMS (m/z): 597 (M+H)$^+$.

Example 90

Synthesis of Compound 121 and Compound 123

Compounds 121 and 123 were prepared according to the following synthetic scheme:

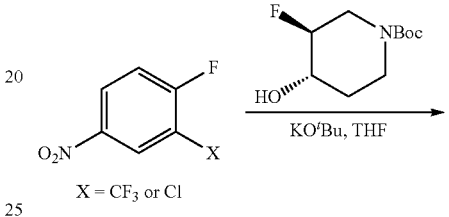

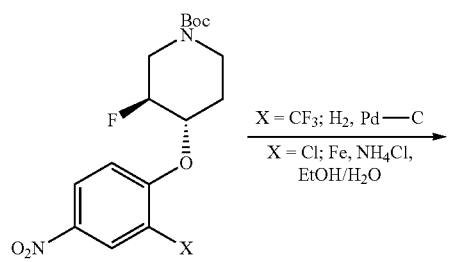

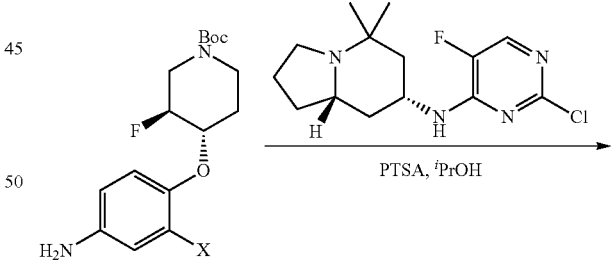

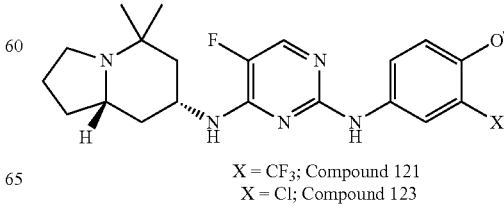

X = CF$_3$; Compound 121
X = Cl; Compound 123

Synthesis of tert-butyl (3S,4S)-3-fluoro-4-(4-nitro-2-(trifluoromethyl)phenoxy)piperidine-1-carboxylate

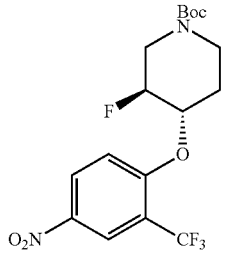 [SMILES: CC(C)(C)OC(=O)N1CC[C@H](Oc2ccc([N+](=O)[O-])cc2C(F)(F)F)[C@@H](F)C1]

Tert-butyl (3S,4S)-3-fluoro-4-(4-nitro-2-(trifluoromethyl)phenoxy)piperidine-1-carboxylate was produced from tert-butyl (3S,4S)-3-fluoro-4-hydroxypiperidine-1-carboxylate (2.1 g, 1.0 eq, 9.6 mmol) using the same reaction conditions, work-up and purification conditions as in Example 89 above for Compound 119, and gave the desired product in 75% yield.

$^1$H NMR (300 MHz, CDCl$_3$) δ 8.49 (dd, J=14.0, 2.7 Hz, 1H), 8.42 (dd, J=9.2, 2.7 Hz, 1H), 7.18 (d, J=9.3 Hz, 1H), 4.75 (d, J=3.1 Hz, 1H), 4.58 (d, J=4.9 Hz, 1H), 3.79 (d, J=23.6 Hz, 1H), 3.53 (s, 2H), 2.15 (s, 1H), 1.88 (dd, J=14.0, 5.5 Hz, 1H), 1.69 (s, 1H), 1.42 (s, 9H); $^{19}$F NMR (282 MHz; d$_6$-DMSO) δ −62.8 (d)-63.1 (s); LCMS (m/z): 409 (M+H)$^+$.

Synthesis of tert-butyl (3S,4S)-4-(4-amino-2-(trifluoromethyl)phenoxy)-3-fluoropiperidine-1-carboxylate

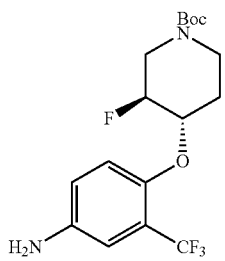

A mixture of tert-butyl (3S,4S)-3-fluoro-4-(4-nitro-2-(trifluoromethyl)phenoxy)piperidine-1-carboxylate (0.6 g, 1.0 eq, 1.5 mmol) and Pd—C (10%, 0.15 g) in EtOH (20 mL) was hydrogenated at 30 psi for 1 hour. The mixture was filtered through celite and the filter cake washed with EtOH (2×10 mL). The filtrate was concentrated under vacuum to give the desired product in 64% yield. This product was taken to next step with out further purification.

$^1$H NMR (300 MHz, CDCl$_3$) δ 7.29 (s, 1H), 7.23 (d, J=8.6 Hz, 1H), 6.99 (d, J=8.7 Hz, 1H), 4.69 (s, 1H), 4.53 (s, 1H), 3.73 (d, J=24.5 Hz, 2H), 3.48 (s, 2H), 2.04 (s, 1H), 1.84 (s, 1H), 1.50 (s, 9H). $^{19}$F NMR (282 MHz; d$_6$-DMSO) δ −62.3 (s)-62.5 (s); LCMS (m/z): 379 (M+H)$^+$.

Synthesis of N$^4$-((7R,8aS)-5,5-dimethyloctahydroindolizin-7-yl)-5-fluoro-N$^2$-(4-4(3S,4S)-3-fluoropiperidin-4-yl)oxy)-3-(trifluoromethyl)phenyl)pyrimidine-2,4-diamine (Compound 121)

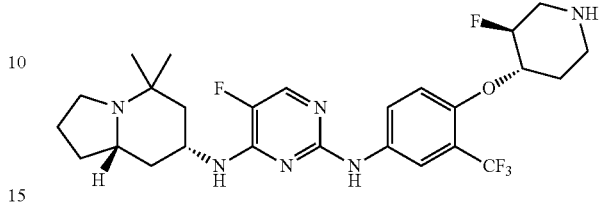

A mixture of (7R,8aS)-N-(2-chloro-5fluoropyrimidin-4-yl)-5,5-dimethyloctahydroindolizin-7-amine (0.23 g, 1.1 eq, 0.8 mmol), tert-butyl (3S,4S)-4-(4-amino-2-(trifluoromethyl)phenoxy)-3-fluoropiperidine-1-carboxylate (0.28 g, 1.0 eq, 0.74 mmol) and PTSA (0.13 g, 0.9 eq, 0.7 mmol) was taken in $^i$PrOH (10 mL) and heated at 100° C. overnight. After 18 hours of heating, reaction mixture was cooled to room temperature and PTSA (1.0 eq) was added to complete the deprotection of the Boc group. Later the reaction mixture was heated at 100° C. for 3 hours while stirring and cooled to room temperature. The volatiles were removed under vacuum to leave a crude solid. 4N HCl in dioxane (5 mL) was added to the crude mixture to ensure complete deprotection of the Boc group and the mixture was concentrated to dryness. Work-up and purification conditions were the same as in Example 89 above for Compound 119, and gave the product as a solid in 48% yield.

$^1$H NMR (300 MHz, d$_6$-DMSO) δ 9.11 (s, 1H), 8.01 (s, 1H), 7.90 (d, J=3.8 Hz, 2H), 7.27 (t, J=9.0 Hz, 2H), 4.61 (s, 1H), 4.45 (s, 1H), 4.21 (s, 1H), 3.24 (s, 2H), 2.91 (s, 2H), 2.51 (s, 1H), 2.35 (s, 1H), 2.05 (s, 2H), 1.83 (s, 1H), 1.66 (s, 3H), 1.51 (d, J=12.0 Hz, 2H), 1.38-1.17 (m, 4H), 1.14 (s, 3H), 1.01 (s, 3H). $^{19}$F NMR (282 MHz; d$_6$-DMSO) δ −60.16 (s), −60.18 (s), −166.6 (s); LCMS (m/z): 541 (M+H)$^+$.

Synthesis of tert-butyl (3S,4S)-4-(2-chloro-4-nitrophenoxy)-3-fluoropiperidine-1-carboxylate

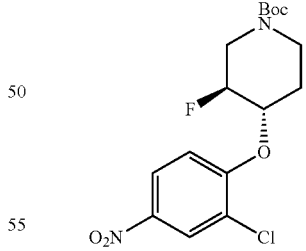

A mixture of 2-chloro-1-fluoro-4-nitrobenzene (2.0 g, 1.1 eq, 11.5 mmol) and tert-butyl (3S,4S)-3-fluoro-4-hydroxypiperidine-1-carboxylate (2.3 g, 1.0 eq, 10.5 mmol) was taken in annhydrous THF (50 mL) and stirred at 0° C. KO$^t$Bu (2.1 g, 1.8 eq, 18.9 mmol) was added to the above solution at 0° C. and the heterogeneous mixture was warmed to room temperature. Then the reaction mixture was refluxed overnight. After completion of the reaction, the mixture was concentrated under reduced pressure. EtOAc (100 mL) was added to the crude mixture and partioned with aqueous saturated NaHCO₃ (50 mL) solution. The layers were seperated and the organic layer was washed with aqueous saturated NaHCO₃ (50 mL) solution and brine (1×50 mL). The organic layers were dried over Na₂SO₄ and concentrated to leave cude solid. Purification of the crude mixture by column chromatography on silica gel (ISCO System) using EtOAc/hexane (gradient system from 0:1 to 2:8) as eluent gave the desired product in 63% yield.

¹H NMR (300 MHz, CDCl₃) δ 8.40-8.24 (m, 1H), 8.14 (dd, J=9.1, 2.6 Hz, 1H), 7.09 (d, J=9.2 Hz, 1H), 4.63 (d, J=22.7 Hz, 2H), 3.91 (s, 1H), 3.60 (s, 2H), 3.48 (s, 1H), 2.15 (s, 1H), 1.87 (s, 1H), 1.48 (s, 9H). LCMS (m/z): 375 (M+H)⁺.

Synthesis of tert-butyl (3S,4S)-4-(4-amino-2-chlorophenoxy)-3-fluoropiperidine-1-carboxylate

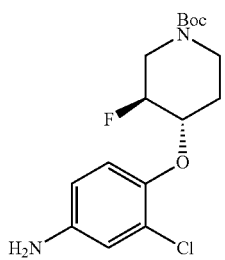 [SMILES: CC(C)(C)OC(=O)N1CC[C@H](Oc2ccc([N+](=O)[O-])cc2Cl)[C@@H](F)C1]

A mixture of tert-butyl (3S,4S)-4-(2-chloro-4-nitrophenoxy)-3-fluoropiperidine-1-carboxylate (0.8 g, 1.0 eq, 2.2 mmol), Fe (0.6 g, 5.0 eq, 10.8 mmol) and NH₄Cl (0.6 g, 5.0 eq, 10.8 mmol) in EtOH/H₂O (1:1, 50 mL) was stirred at 90° C. for 1 hour. The mixture was cooled to room temperature and concentrated under reduced pressure to leave a crude solid. The crude mixture was dissolved in EtOAc (50 mL) and partitioned with H₂O (50 mL). Organic layers were separated and the aqueous layer was washed with EtOAc (50 mL). The combined organic layers were dried over Na₂SO₄ and concentrated under vacuum to give the desired product in 45% yield. This product was taken to next step with out further purification.

¹H NMR (300 MHz, CDCl₃) δ 6.91 (t, J=11.1 Hz, 2H), 6.73 (d, J=8.7 Hz, 1H), 4.72 (s, 1H), 4.55 (s, 1H), 4.34 (s, 1H), 3.83 (s, 1H), 3.75 (s, 1H), 3.51 (s, 1H), 2.04 (s, 1H), 1.81 (s, 1H), 1.47 (s, 9H). LCMS (m/z): 345 (M+H)⁺.

Synthesis of N²-(3-chloro-4-(((3S,4S)-3-fluoropiperidin-4-yl)oxy)phenyl)-N⁴7R,8aS)-5,5-dimethyloctahydroindolizin-7-yl)-5-fluoropyrimidine-2,4-diamine (Compound 123)

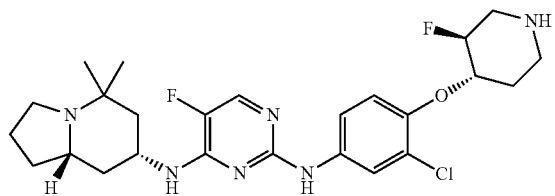 [SMILES: CC1(C)C[C@H](Nc2nc(Nc3ccc(O[C@H]4CCNC[C@@H]4F)c(Cl)c3)ncc2F)C[C@@H]2CCCN21]

A mixture of (7R,8aS)-N-(2-chloro-5-fluoropyrimidin-4-yl)-5,5-dimethyloctahydroindolizin-7-amine (0.2 g, 1.0 eq, 0.6 mmol), tert-butyl (3S,4S)-4-(4-amino-2-chlorophenoxy)-3-fluoropiperidine-1-carboxylate (0.2 g, 1.0 eq, 0.64 mmol) and PTSA (0.1 g, 0.9 eq, 0.6 mmol) was taken in ⁱPrOH (10 mL) and heated at 100° C. for over night. After 18 hours of heating, reaction mixture was cooled to room temperature and PTSA (1.0 eq) was added to complete the deprotection of the Boc group. Then the reaction mixture was heated at 100° C. for 3 hours while stirring and cooled to room temperature. The volatiles were removed under vacuum to leave a crude solid. 4N HCl in dioxane (5 mL) was added to the crude mixture to ensure complete dprotection of the Boc group and the mixture was concentrated to dryness. Work-up and purification conditions used were the same as in Example 89 above for Compound 119, and gave the product as a solid in 50% yield.

¹H NMR (300 MHz, d₆-DMSO) δ 9.01 (s, 1H), 7.92 (d, J=2.5 Hz, 1H), 7.83 (d, J=3.8 Hz, 1H), 7.43 (dd, J=9.0, 2.4 Hz, 1H), 7.22 (d, J=7.4 Hz, 1H), 7.08 (d, J=9.0 Hz, 1H), 4.57 (s, 1H), 4.32 (s, 1H), 4.18 (s, 1H), 3.15 (d, J=5.1 Hz, 1H), 2.85 (s, 2H), 2.54 (s, 1H), 2.31 (s, 2H), 2.00 (s, 2H), 1.76 (s, 1H), 1.58 (s, 4H), 1.48 (d, J=11.8 Hz, 2H), 1.23 (s, 3H), 1.08 (s, 3H), 0.99 (s, 3H). LCMS (m/z): 507 (M+H)⁺.

Example 91

Synthesis of Compound 124

Compound 124 was prepared according to the following synthetic scheme:

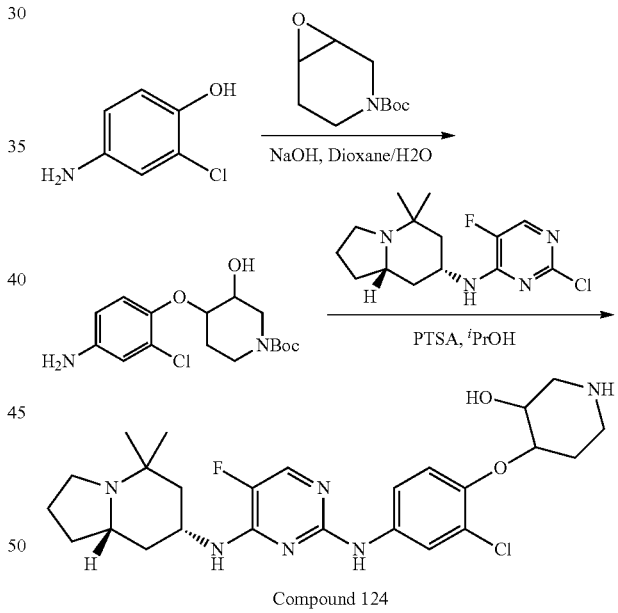

Compound 124

Synthesis of tert-butyl-4-(4-amino-2-chlorophenoxy)-3-hydroxypiperidine-1-carboxylate

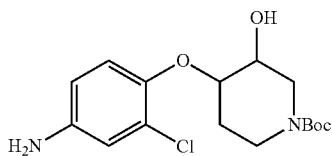

A mixture of 4-amino-2-chlorophenol (0.5 g, 1.0 eq, 3.3 mmol) tert-butyl 7-oxa-3-azabicyclo[4.1.0]heptane-3-carboxylate (0.7 g, 1.0 eq, 3.3 mmol) was taken in dioxane (10 mL) and stirred at room temperature. NaOH (0.14 g, 1.0 eq, 3.3 mmol) was added to the above solution and the mixture was heated to 120° C. overnight. After completion of the reaction, the mixture was cooled to room temperature and concentrated under reduced pressure. EtOAc (25 mL) was added to the crude mixture and partioned with $H_2O$ (50 mL). Layers were seperated and the organic layer was washed with $H_2O$ (2×25 mL) and brine (1×25 mL). The organic layers were dried over $Na_2SO_4$ and concentrated to leave a crude solid. Purification of the crude mixture by column chromatography on silica gel (ISCO System) using EtOAc/hexane (gradient system from 0:1 to 4:6) as eluent gave the desired product in 30% yield.

$^1$H NMR (300 MHz, $d_6$-DMSO) δ 6.92 (d, J=8.7 Hz, 1H), 6.58 (d, J=2.6 Hz, 1H), 6.44 (dd, J=8.7, 2.6 Hz, 1H), 5.21 (d, J=4.5 Hz, 1H), 4.94 (s, 2H), 3.95 (s, 1H), 3.62 (d, J=12.9 Hz, 1H), 3.50 (s, 2H), 3.13 (dd, J=10.1, 7.3 Hz, 2H), 1.86 (s, 1H), 1.45 (s, 1H), 1.38 (s, 9H). LCMS (m/z): 343 (M+H)$^+$.

Synthesis of 4-(2-chloro-4-44-4(7R,8aS)-5,5-dimethyloctahydroindolizin-7-yl)amino)-5-fluoropyrimidin-2-yl)amino)phenoxy)piperidin-3-ol (Compound 124)

A mixture of (7R,8aS)-N-(2-chloro-5-fluoropyrimidin-4-yl)-5,5-dimethyloctahydroindolizin-7-amine (0.14 g, 1.0 eq, 0.5 mmol), tert-butyl-4-(4-amino-2-chlorophenoxy)-3-hydroxypiperidine-1-carboxylate (0.16 g, 1.0 eq, 0.5 mmol) and PTSA (0.1 g, 0.9 eq, 0.4 mmol) was taken in $^i$PrOH (10 mL) and heated at 100° C. for over night. After 18 hours of heating, reaction mixture was cooled to room temperature and PTSA (1.0 eq) was added to complete the deprotection of the Boc group. Then the reaction mixture was heated at 100° C. for 3 hours while stirring and cooled to room temperature. The volatiles were removed under vacuum to leave a crude solid. 4N HCl in dioxane (5 mL) was added to the crude mixture to ensure complete dprotection of the Boc group and the mixture was concentrated to dryness. Work-up and purification conditions used were the same as in Example 89 above for Compound 119, and gave the required product as a solid in 33% yield.

$^1$H NMR (300 MHz, $d_6$-DMSO) δ 8.97 (s, 1H), 7.95-7.73 (m, 2H), 7.41 (dd, J=9.1, 2.6 Hz, 1H), 7.20 (d, J=8.1 Hz, 1H), 7.07 (d, J=9.1 Hz, 1H), 4.96 (d, J=4.8 Hz, 1H), 4.15 (s, 1H), 4.00 (s, 1H), 3.44 (s, 1H), 3.36 (q, J=7.0 Hz, 2H), 2.98 (d, J=8.3 Hz, 1H), 2.80 (d, J=16.1 Hz, 2H), 2.41-2.15 (m, 4H), 2.01 (d, J=12.5 Hz, 1H), 1.85 (s, 1H), 1.76 (s, 1H), 1.57 (s, 2H), 1.43 (dd, J=22.5, 10.6 Hz, 2H), 1.23 (s, 2H), 1.16-1.01 (m, 3H), 0.98 (s, 3H). LCMS (m/z): 505 (M+H)$^+$.

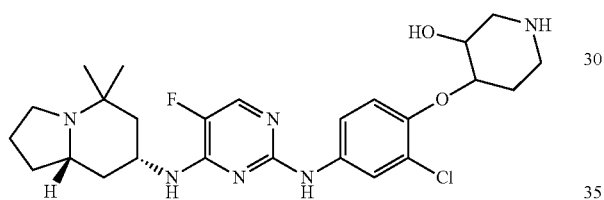

Example 92

Synthesis of 8-((4-(((7R,8aS)-5,5-dimethyloctahydroindolizin-7-yl)amino)-5-fluoropyrimidin-2-yl)amino)-4H-benzo[b]tetrazolo[1,5-d][1,4]oxazine-4,4-diyl)dimethanol (Compound 125)

Compound 125 was prepared according to the following synthetic scheme:

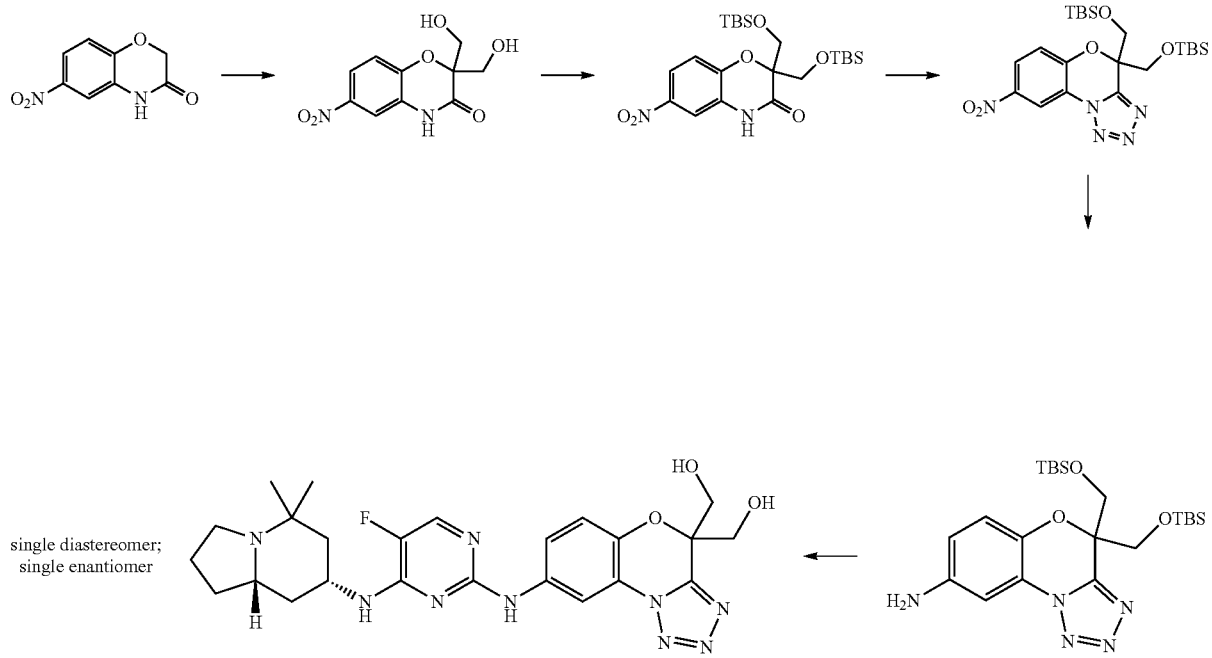

Step 1: preparation of 2,2-bis(hydroxymethyl)-6-nitro-2H-benzo[b][1,4]oxazin-3(4H)-one A mixture of 6-nitro-2H-benzo[b][1,4]oxazin-3(4H)-one (17.0 g, 87.6 mmol), 3N NaOH (30 mL, 90 mmol) and formaldehyde (37% solution in $H_2O$; 60 mL) was stirred in a sealed tube at between 135-150° C. for 4 days, then allowed to cool to room temperature. The mixture was then transferred to a round-bottom flask and dry-loaded on to silica gel (using MeOH to assist solubility). The residue was purified by column chromatography on silica gel using DCM/MeOH (1:0 to 9:1) as eluent to give the product (4.4 g, 19% yield) as a solid. Also obtained from the column was recovered stating material (4.6 g).

$^1$H NMR ($d_6$-DMSO, 300 MHz): δ 10.98 (br. s, 1H), 7.77 (dd, J=8.9, 2.7 Hz, 1H), 7.65 (d, J=2.7 Hz, 1H), 7.05 (d, J=8.9 Hz, 1H), 5.23 (br. s, 2H), 3.82 (d, J=11.5 Hz, 2H), 3.55 (d, J=11.5 Hz, 2H); m/z=254.94 [M+H]$^+$.

Step 2: preparation of 2,2-bis(((tert-butyldimethylsilyl)oxy)methyl)-6-nitro-2H-benzo[b][1,4]oxazin-3(4H)-one Tert-butyldimethylsilyl chloride (7.6 g, 50.4 mmol) was added to a stirred mixture of 2,2-bis(hydroxymethyl)-6-nitro-2H-benzo[b][1,4]oxazin-3(4H)-one (3.2 g, 12.6 mmol), $Et_3N$ (7.9 mL, 56.6 mmol) and N,N-dimethylaminopyridine (catalytic quantity) in DCM (60 mL) at 0° C. under nitrogen. The mixture was allowed to warm to room temperature and stirred over a weekend. The solvent was removed under vacuum and the residue was partitioned between EtOAc (150 mL) and $H_2O$ (100 mL). The organic layer was washed with brine (1×100 mL) and the combined aqueous layers were extracted with EtOAc (1×100 mL). The combined organic layers were dried ($Na_2SO_4$), filtered and the solvent removed under vacuum to leave a crude residue. The residue was dry-loaded on to silica gel then purified by column chromatography on silica gel using hexane/DCM (3:1 to 1:0) then DCM/EtOAc (1:0 to 9:1) as eluent to give the product (7 g) with ca. 50 mol % of TBS-Cl.

Another experiment using 3 equiv. of TBS-Cl with 1.02 g of 2,2-bis(hydroxymethyl)-6-nitro-2H-benzo[b][1,4]oxazin-3(4H)-one, gave the pure product (0.62 g, 32% yield), followed by the product with TBS-Cl (0.8 g), followed by mono-silylated material-2-(((tert-butyldimethylsilyl)oxy)methyl)-2-(hydroxymethyl)-6-nitro-2H-benzo[b][1,4]oxazin-3(4H)-one (0.56 g, 38%)

$^1$H NMR (CDCl$_3$, 300 MHz): δ 9.64 (br. s, 1H), 7.90 (dd, J=8.9, 2.9 Hz, 1H), 7.68 (d, J=2.9 Hz, 1H), 6.99 (d, J=8.9 Hz, 1H), 4.17 (d, J=10.6 Hz, 2H), 3.85 (d, J=10.6 Hz, 2H), 0.74 (s, 94), 0.01 (s, 3H), −0.05 (s, 3H); m/z=481.02 [M−H]$^+$.

Step 3: preparation of 4,4-bis(((tert-butyldimethylsilyl)oxy)methyl)-8-nitro-4H-benzo[b]tetrazolo[1,5-d][1,4]oxazine Trifluoromethanesulfonic anhydride (650 μL, 3.9 mmol) was added dropwise over 5 min to a stirred solution of 2,2-bis(((tert-butyldimethylsilyl)oxy)methyl)-6-nitro-2H-benzo[b][1,4]oxazin-3(4H)-one (0.62 g, 1.3 mmol) and NaN$_3$ (0.50 g, 7.7 mmol) in MeCN (15 mL) at −10° C. (ice/MeOH bath) under nitrogen. The mixture was allowed to warm to room temperature slowly, then stirred at room temperature overnight. The mixture was then re-cooled to −10° C. and quenched by the addition of cold EtOAc (30 mL) followed by cold saturated NaHCO$_3$ (30 mL) [note: saturated NaHCO$_3$ solution was added over ca. 5 min]. Further EtOAc (50 mL) and H$_2$O (30 mL) was added and the aqueous and organic layers were partitioned. The organic layer was dried (Na$_2$SO$_4$), filtered and the solvent removed under vacuum to leave a crude residue. The residue was dry-loaded on to silica gel and then purified by column chromatography on silica gel using hexane/DCM as eluent (1:0 to 0:1) to give the product (320 mg, 49% yield).

$^1$H NMR (CDCl$_3$, 300 MHz): δ 8.89 (d, J=2.6 Hz, 1H), 8.30 (dd, J=9.0, 2.6 Hz, 1H), 7.32 (d, J=0.8 Hz, 1H), 4.31 (d, J=11.2 Hz, 2H), 4.26 (d, J=11.2 Hz, 2H), 0.72 (s, 9H), −0.01 (s, 3H), −0.02 (s, 3H); m/z=507.91 [M+H]$^+$.

Step 4: preparation of 4,4-bis(((tert-butyldimethylsilyl)oxy)methyl)-4H-benzo[b]tetrazolo[1,5-d][1,4]oxazin-8-amine A mixture of 4,4-bis(((tert-butyldimethylsilyl)oxy)methyl)-8-nitro-4H-benzo[b]tetrazolo[1,5-d][1,4]oxazine (127 mg, 0.3 mmol), palladium(II) hydroxide on carbon (Aldrich cat. number 212911) (25 mg) and EtOH (10 mL) was hydrogenated at 30 psi for 6 hr. The mixture was then filtered through a short plug of celite, and the filter cake washed with EtOH (3×10 mL). The filtrate was concentrated under vacuum to give the product (yield assumed quantitative=119 mg).

$^1$H NMR (CDCl$_3$, 300 MHz): δ 7.36-7.32 (m, 1H), 7.02-6.97 (m, 1H), 6.71-6.66 (m, 1H), 4.29-4.17 (m, 4H), 3.75 (br. s, 2H), 0.89 (s, 9H), 0.04 (s, 3H), 0.02 (s, 3H).

Step 5: preparation of (8-((4-(((7R,8aS)-5,5-dimethyloctahydroindolizin-7-yl)amino)-5-fluoropyrimidin-2-yl)amino)-4H-benzo[b]tetrazolo[1,5-d][1,4]oxazine-4,4-diyl)dimethanol (Compound 125)

The general displacement procedure described herein was used with 4,4-bis(((tert-butyldimethylsilyl)oxy)methyl)-4H-benzo[b]tetrazolo[1,5-d][1,4]oxazin-8-amine (119 mg, 0.3 mmol), (7R,8aS)-N-(2-chloro-5-fluoropyrimidin-4-yl)-octahydro-5,5-dimethylindolizin-7-amine (112 mg, 0.4 mmol) and pTsOH.H$_2$O (95 mg, 0.5 mmol) in IPA (3 mL) at reflux. The crude mixture was dry-loaded straight to silica and purification was by column chromatography on silica gel using DCM/2M NH$_3$ in MeOH as eluent (1:0 to 8:2) to give the product (presumed tosylate salt). The product was partitioned between EtOAc (30 mL) and 0.5 N NaOH (30 mL). The aqueous layer was saturated with NaCl and then extracted with EtOAc (2×40 mL). The combined organic layers were dried (Na$_2$SO$_4$), filtered and the solvent removed under vacuum to leave the product (63 mg, 49% yield) as a solid.

$^1$H NMR ($d_6$-DMSO, 300 MHz): δ 9.19 (s, 1H), 8.35 (s, 1H), 7.85 (s, 1H), 7.57 (d, J=8.4 Hz, 1H), 7.19 (br. s, 1H), 7.03 (d, J=8.9 Hz, 1H), 5.28 (t, J=5.7 Hz, 2H), 4.34-4.14 (m, 1H), 3.85-3.77 (m, 4H), 2.89-2.70 (m, 1H), 2.18-1.11 (m, 10 h), 1.04 (s, 3H), 0.89 (s, 3H); $^{19}$F NMR ($d_6$-DMSO, 282 MHz): δ −166.3 (s); m/z=511.98 [M+H]$^+$ & 510.04 [M−H]$^+$.

Example 93

Preparation of Compound 126

Compound 126 was prepared according to the following synthetic scheme:

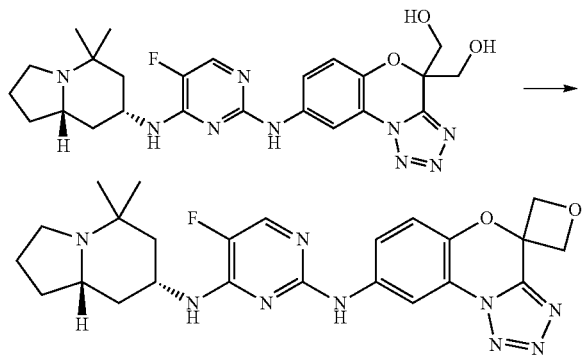

Step 1: Synthesis of (8-44-4(7R,8aS)-5,5-dimethyl-octahydroindolizin-7-yl)amino)-5-fluoropyrimidin-2-yl)amino)-4-(hydroxymethyl)-4H-benzo[b]tetrazolo[1,5-d][1,4]oxazin-4-yl)methyl 2,4,6-trimethylbenzenesulfonate A mixture of (8-((4-(((7R,8aS)-5,5-dimethyloctahydroindolizin-7-yl)amino)-5-fluoropyrimidin-2-yl)amino)-4H-benzo[b]tetrazolo[1,5-d][1,4]oxazine-4,4-diyl)dimethanol (30 mg, 0.06 mmol), 2,4,6-trimethylbenzenesulfonyl chloride (26 mg, 0.12 mmol), pyridine (0.2 mL) and DCM (3 mL) was stirred at 40° C. overnight. A further aliquot of 2,4,6-trimethylbenzenesulfonyl chloride (26 mg, 0.12 mmol) was added, and the mixture stirred at 40° C. for a further 4 days. After allowing to cool, the mixture was concentrated under vacuum and the residue partitioned between EtOAc (40 mL) and H$_2$O (15 mL). The organic layer was washed with brine (1×15 mL), dried (Na$_2$SO$_4$), filtered and the solvent removed under vacuum to leave a crude residue. The residue was purified by preparative thin-layer chromatography using DCM/2M NH$_3$ in MeOH as eluent (6 preparative TLC plates used) to give the product (15 mg, 37% yield).

m/z=693.99 [M+H]$^+$ & 692.06 [M−H]$^+$.

Also isolated from the preparative TLC plates was di-sulfonylated material (30 mg, 59%)—(8-((4(4-(((7R,8aS)-5,5-dimethyloctahydroindolizin-7-yl)amino)-5-fluoropyrimidin-2-yl)amino)-4H-benzo[b]tetrazolo[1,5-d][1,4]oxazine-4,4-diyl)bis(methylene) bis(2,4,6-trimethylbenzenesulfonate).

Step 2: Synthesis of N$^4$-((7R,8aS)-5,5-dimethyloctahydroindolizin-7-yl)-5-fluoro-N$^2$-(spiro[benzo[b]tetrazolo[1,5-d][1,4]oxazine-4,3'-oxetan]-8-yl)pyrimidine-2,4-diamine, TFA salt (Compound 126)

$^n$BuLi (1.6 M in hexanes, 45 μL, 0.07 mmol) was added dropwise over 2 min to a stirred solution of (8-((4-(((7R,8aS)-5,5-dimethyloctahydroindolizin-7-yl)amino)-5-fluoropyrimidin-2-yl)amino)-4-(hydroxymethyl)-4H-benzo[b]tetrazolo[1,5-d][1,4]oxazin-4-yl)methyl 2,4,6-trimethylbenzenesulfonate (15 mg, 0.02 mmol) in THF (5 mL) at 0° C. under nitrogen. After complete addition, the mixture was stirred at 0° C. for 30 min, then heated to reflux and stirred for 2 hr. TLC indicated some starting material. The mixture was re-cooled to 0° C. and additional $^n$BuLi (1.6 M in hexanes; 50 μL, 0.07 mmol) was added. The mixture was stirred at 0° C. for 10 min then heated to reflux and stirred for 1 hr. TLC indicated complete reaction. The mixture was allowed to cool to room temperature, then MeOH (2 mL) was added and the mixture was concentrated under vacuum to leave a crude residue. The residue was purified by preparative thin-layer chromatography using DCM/2M NH$_3$ in MeOH (9:1) as eluent, then purified further by preparative high-performance liquid chromatography to give the product (3 mg, 28% yield) as a solid and as a trifluoroacetic acid (TFA) salt.

$^1$H NMR (d$_6$-DMSO, 300 MHz): δ −166.0 (s), −73.5 (s, TFA)

$^{19}$F NMR (d$_6$-DMSO, 282 MHz): δ 9.31 (d, J=4.3 Hz, 1H), 8.44-8.42 (m, 1H), 8.24 (d, J=3.7 Hz, 1H), 7.90 (t, J=3.7 Hz, 1H), 7.71-7.66 (m, 1H), 7.29-7.18 (m, 1H), 5.07 (dd, J=7.5, 4.1 Hz, 2H), 4.96 (app. t, J=6.2 Hz, 2H), 4.35-4.14 (m, 1H), 2.88-2.79 (m, 1H), 2.39-2.23 (m, 1H), 2.10-1.98 (m, 1H), 1.90-1.73 (m, 1H), 1.70-1.37 (m, 4H), 1.36-1.13 (m, 3H), 1.08 (s, 3H), 0.97 (s, 3H)

m/z=494.45 [M+H]$^+$

Example 94

Preparation of 9-44-4(7R,8aS)-5,5-dimethyloctahydroindolizin-7-yl)amino)-5-fluoropyrimidin-2-yl)amino)-4-methyl-4,5-dihydrobenzo[b]tetrazolo[1,5-d][1,4]oxazepin-4-ol (Compound 127)

Compound 127 was prepared according to the following synthetic scheme:

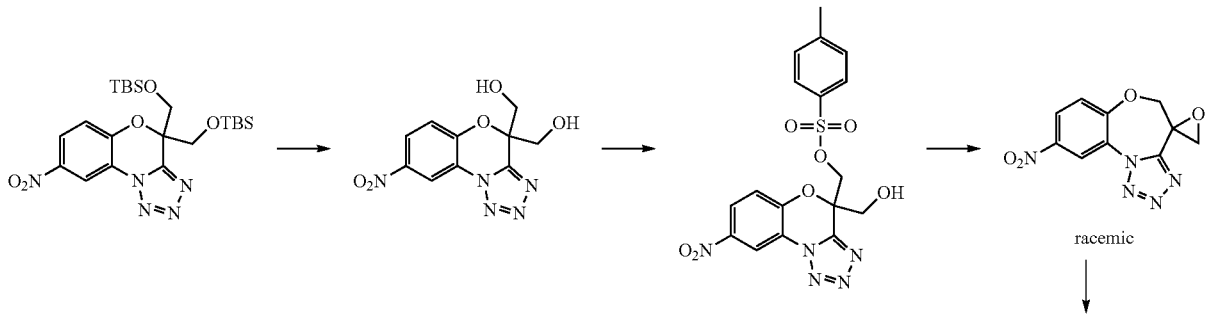

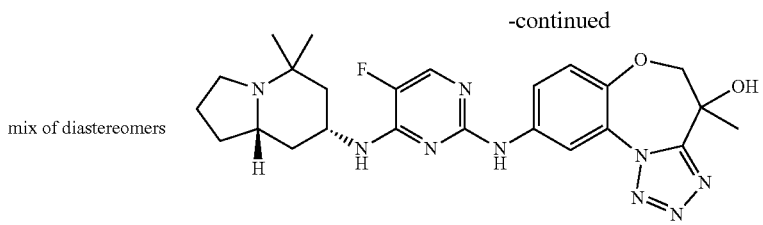 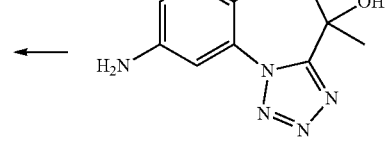

mix of diastereomers

Step 1: preparation of (8-nitro-4H-benzo[b]tetrazolo[1,5-d][1,4]oxazine-4,4-diyl)dimethanol Tetra-butylammonium fluoride (1M solution in THF; 37.2 mL, 37.2 mmol) was added to a stirred solution of 4,4-bis(((tert-butyldimethylsilyl)oxy)methyl)-8-nitro-4H-benzo[b]tetrazolo[1,5-d][1,4]oxazine (6.3 g, 12.4 mmol) and AcOH (2.1 mL, 37.2 mmol) in THF (200 mL). The mixture was stirred at room temperature for 2 hr then concentrated under vacuum. The residue was partitioned between EtOAc (200 mL) and H$_2$O (150 mL) and the organic layer was washed with brine (1×100 mL), dried (Na$_2$SO$_4$), filtered and the solvent removed under vacuum to leave a crude residue. The residue was dry-loaded on to silica gel then purified by column chromatography on silica gel using DCM/MeOH (1:0 to 92:8) as eluent to provide the desired compound (1.6 g). The desired compound was dissolved in EtOAc (150 mL) and washed with H$_2$O (12×100 mL). The organic layer was dried (Na$_2$SO$_4$), filtered and the solvent removed under vacuum to leave the product (0.9 g) as a solid.

$^1$H NMR (d$_6$-DMSO, 300 MHz): δ 8.59 (d, J=2.6 Hz, 1H), 8.28 (ddd, J=9.2, 2.6, 0.6 Hz, 1H), 7.45 (d, J=9.2 Hz, 1H), 5.52 (br. s, 2H), 3.98 (s, 2H), 3.97 (s, 2H); m/z=279.92 [M+H]$^+$.

Step 2: preparation of (4-(hydroxymethyl)-8-nitro-4H-benzo[b]tetrazolo[1,5-d][1,4]oxazin-4-yl)methyl 4-methylbenzenesulfonate A mixture of (8-nitro-4H-benzo[b]tetrazolo[1,5-d][1,4]oxazine-4,4-diyl)dimethanol (279 mg, 1.0 mmol), para-toluenesulfonyl chloride (381 mg, 2.0 mmol), pyridine (0.1 mL) and DCM (10 mL) was stirred at 40° C. overnight. After allowing to cool, the mixture was concentrated under vacuum and the residue partitioned between EtOAc (50 mL) and H$_2$O (50 mL). The organic layer was dried (Na2SO4), filtered and the solvent removed under vacuum to leave a crude residue. The residue was dry-loaded on to silica gel and then purified by column chromatography on silica gel using DCM/EtOAc (1:0 to 0:1) then EtOAc/MeOH (9:1) as eluent to give the desired product (177 mg, 41% yield) as a solid.

$^1$H NMR (d$_6$-DMSO, 300 MHz): δ 8.55 (d, J=2.7 Hz, 1H), 8.27 (dd, J=9.2, 2.7, 0.7 Hz), 7.64 (d, J=8.1 Hz, 2H), 7.41 (d, J=8.1 Hz, 2H), 7.30 (d, J=9.2 Hz, 1H), 5.72 (t, J=5.8 Hz, 1H), 4.83 (d, J=11.6 Hz, 1H), 4.74 (d, J=11.6 Hz, 1H), 3.95 (dd, J=5.8, 1.4 Hz, 2H), 2.38 (s, 3H); m/z=433.76 [M+H]$^+$ and 431.86 [M−H]$^+$.

Step 3: preparation of (R/S) 9-nitro-5H-spiro[benzo[b]tetrazolo[1,5-d][1,4]oxazepine-4,2'-oxirane]

"BuLi (1.6 M in hexanes, 110 μL, 0.18 mmol) was added dropwise over 5 min to a stirred solution of (4-(hydroxymethyl)-8-nitro-4H-benzo[b]tetrazolo[1,5-d][1,4]oxazin-4-yl)methyl 4-methylbenzenesulfonate (70 mg, 0.16 mmol) in THF (10 mL) at 0° C. under nitrogen. The mixture was stirred at 0° C. for 1 hr, then heated to reflux and stirred for 2 hr. After allowing to cool, the mixture was concentrated under vacuum to leave a crude residue. The residue was purified by preparative thin-layer chromatography using DCM/EtOAc (9:1) as eluent to give the product (16 mg, 38% yield) as a solid.

$^1$H NMR (CDCl$_3$, 300 MHz): δ 9.33 (dd, J=2.6, 0.7 Hz, 1H), 8.34 (ddd, J=9.0, 2.6, 1.0 Hz, 1H), 7.50 (dd, J=9.0, 0.7 Hz, 1H), 4.58 (dd, J=13.5, 1.0 Hz, 1H), 4.48 (d, J=13.5 Hz, 1H), 4.07 (dd, J=5.1, 0.7 Hz, 1H), 3.43 (dd, J=5.1, 0.9 Hz, 1H); m/z=261.94 [M+H]$^+$.

The structure of the product was confirmed by obtaining an X-ray structure of a crystal from EtOAc/hexane in a separate experiment:
Crystal Data and Structure Refinement:
Empirical formula C$_{10}$H$_7$N$_5$O$_4$
Formula weight 261.21
Temperature/K 100
Crystal system monoclinic
Space group C2/c
a/Å 21.3599(4)
b/Å 5.67930(10)
c/Å 18.7387(3)
α/° 90.00
β/° 109.5830 (10)
γ/° 90.00
Volume/Å$^3$ 2141.69 (6)
Z 8
ρ$_{calc}$mg/mm$^3$ 1.620
m/mm$^{-1}$ 1.115
F(000) 1072.0
Crystal size/mm$^3$ 0.271×0.25×0.201
2Θ range for data collection 8.78 to 147.62°
Index ranges −25≤h≤26, −6≤k≤7, −20≤l≤23
Reflections collected 11452
Independent reflections 2112[R(int)=0.0221]
Data/restraints/parameters 2112/0/172
Goodness-of-fit on F$^2$ 1.058
Final R indexes [I>=2σ (I)] R$_1$=0.0348, wR$_2$=0.0906
Final R indexes [all data] R$_1$=0.0363, wR$_2$=0.0918
Largest diff. peak/hole/e Å$^{-3}$ 0.29/−0.29

Step 4: preparation of (R/S) 9-amino-4-methyl-4,5-dihydrobenzo[b]tetrazolo[1,5-d][1,4]oxazepin-4-ol The general hydrogenation procedure described herein was used with 9-nitro-5H-spiro[benzo[b]tetrazolo[1,5-d][1,4]oxazepine-4,2'-oxirane] (16 mg, 0.06 mmol) and Pd(OH)$_2$ on carbon (3 mg), at 1 atm H$_2$ (Balloon) in EtOH (15 mL) to give the product (yield assumed quantitative=14 mg).

$^1$H NMR (CD$_3$OD, 300 MHz): δ 7.58 (d, J=2.6 Hz, 1H), 7.03 (d, J=8.7 Hz, 1H), 6.76 (ddd, J=8.7, 2.6, 0.6 Hz, 1H), 4.25 (d, J=12.5 Hz, 1H), 4.14 (dd, J=12.5, 0.5 Hz, 1H), 3.31-329 (m, 2H), 1.72 (s, 3H); m/z=234.17 [M+H]$^+$.

Step 5: preparation of 9-((4-((((7R,8aS)-5,5-dimethyloctahydroindolizin-7-yl)amino)-5-fluoropyrimidin-2-yl)amino)-4-methyl-4,5-dihydrobenzo[b]tetrazolo[1,5-d][1,4]oxazepin-4-ol (Compound 127)

The general displacement procedure described herein was used with 9-amino-4-methyl-4,5-dihydrobenzo[b]tetrazolo[1,5-d][1,4]oxazepin-4-ol (14 mg, 0.06 mmol), (7R,8aS)-N-(2-chloro-5-fluoropyrimidin-4-yl)-octahydro-5,5-dimethyl-indolizin-7-amine hydrochloride (31 mg, 0.09 mmol) and pTsOH.H$_2$O (46 mg, 0.24 mmol) in IPA (3 mL) at 70° C. to give the product. Purification was by preparative thin-layer chromatography using DCM/2M NH$_3$ in MeOH (9:1) as eluent. The product from the preparative TLC plates was then partitioned between EtOAc (30 mL) and saturated NaHCO$_3$ (20 mL). The organic layer was dried (Na$_2$SO$_4$), filtered and the solvent removed under vacuum to leave the product (18 mg, 61% yield) as a solid.

$^1$H NMR (d$_6$-DMSO, 300 MHz): δ 9.35 (s, 1H), 8.67 (t, J=2.8 Hz, 1H), 7.95 (d, J=3.3 Hz, 1H), 7.87-7.82 (m, 1H), 7.34 (d, J=8.0 Hz, 1H), 7.22 (d, J=8.9 Hz, 1H), 6.41 (s, 1H), 4.33-4.22 (m, 3H), 2.99-2.83 (m, 1H), 2.42-2.66 (m, 1H), 2.13-2.06 (m, 1H), 1.93-1.15 (m, 5H), 1.71 (d, J=3.5 Hz, 3H), 1.13 (s. 3H), 0.96 (d, J=10.0 Hz, 3H); $^{19}$F NMR (d$_6$-DMSO, 282 MHz): δ −166.0 (s); m/z=496.43 [M+H]$^+$.

Example 95

Preparation of N$^2$-(3-(difluoromethoxy)-4-(piperidin-4-yloxy)phenyl)-N$^4$-((7R,8aS)-5,5-dimethyloctahydroindolizin-7-yl)-5-fluoropyrimidine-2,4-diamine (Compound 128)

Compound 128 was prepared according to the following synthetic scheme:

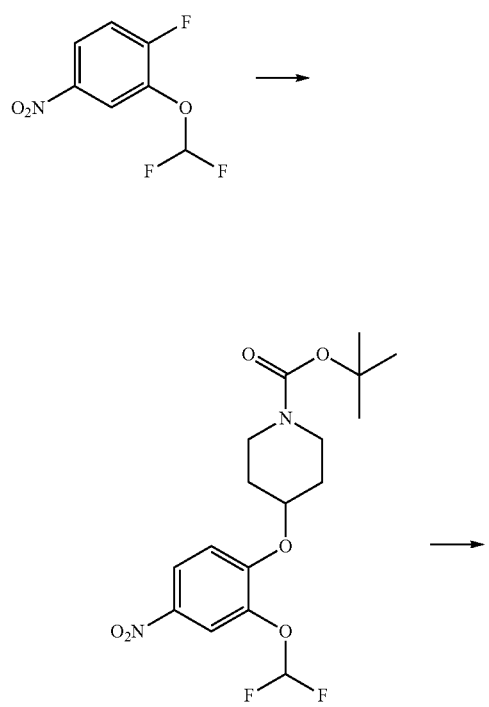

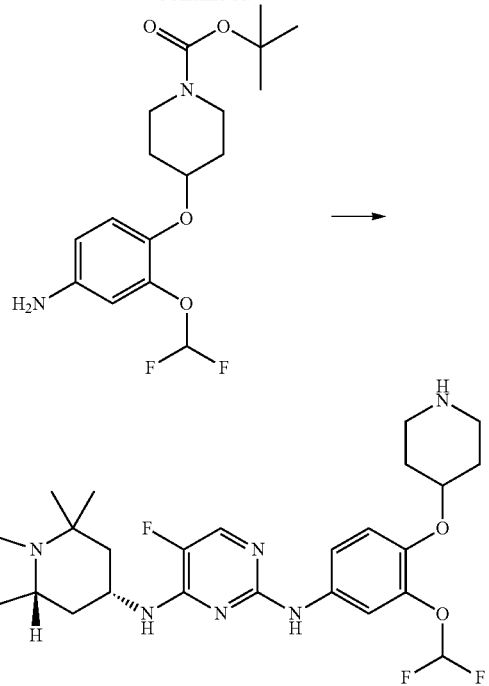

single diastereomer; single enantiomer

Step 1: preparation of tert-butyl 4-(2-(difluoromethoxy)-4-nitrophenoxy)piperidine-1-carboxylate Using similar procedure detailed below for Compound 133, but using 1-chloro-2-(difluoromethoxy)-4-nitrobenzene (prepared according to US patent application no. 2010/090875) (1.12 g, 5.0 mmol), potassium tert-butoxide (1.18 g, 10.0 mmol) and N-Boc-4-hydroxypiperidine (2.0 g, 10.0 mmol) in THF (30 mL) was stirred for a weekend at room temperature to give the product (406 mg, 28% yield) after workup and purification by column chromatography on silica gel using EtOAc/heptane (1:9 to 1:1) as eluent. The product was about 70% purity by LC/MS and $^1$H NMR.

$^1$H NMR (CDCl$_3$, 300 MHz): δ 8.16-8.10 (m, 1H), 7.18 (dd, J=8.6, 1.6 Hz, 1H), 6.83 (dt, J=73.5, 1.6 Hz, 1H), 6.55-6.46 (m, 1H), 4.73-4.63 (m, 1H), 3.70-3.62 (m, 2H), 3.49-3.41 (m, 2H), 2.01-1.94 (m, 2H), 1.89-1.79 (m, 2H), 1.48 (m, 9H).

Step 2: preparation of tert-butyl 4-(4-amino-2-(difluoromethoxy)phenoxy)piperidine-1-carboxylate The general hydrogenation procedure as described herein was used with tert-butyl 4-(2-(difluoromethoxy)-4-nitrophenoxy)piperidine-1-carboxylate (193 mg, 0.5 mmol), palladium on charcoal (39 mg) and MeOH (5 mL) under atmospheric pressure (H$_2$ balloon) to give the product (113 mg, 63% yield) after purification by column chromatography on silica gel using EtOAc/heptane (2:8 to 6:4) as eluent.

$^1$H NMR (CDCl$_3$, 300 MHz): δ 6.84-6.77 (m, 1H), 6.78 (t, J=75.3 Hz, 1H), 6.52-6.45 (m, 2H), 4.24-4.18 (m, 1H), 3.75-3.68 (m, 2H), 3.57 (br. s, 2H), 3.30-3.22 (m, 2H), 1.90-1.80 (m, 2H), 1.75-1.63 (m, 2H). 1.47 (m, 9H).

Step 3: preparation of N²-(3-(difluoromethoxy)-4-(piperidin-4-yloxy)phenyl)-N⁴-((7R,8aS)-5,5-dimethyloctahydroindolizin-7-yl)-5-fluoropyrimidine-2,4-diamine (Compound 128)

The general displacement procedure described herein was used with tert-butyl 4-(4-amino-2-(difluoromethoxy)phenoxy)piperidine-1-carboxylate (113 mg, 0.3 mmol), (7R,8aS)-N-(2-chloro-5-fluoropyrimidin-4-yl)-octahydro-5,5-dimethylindolizin-7-amine hydrochloride (106 mg, 0.3 mmol) and pTsOH.H₂O (42 mg, 0.2 mmol) in IPA (3 mL) at reflux to give the product (91 mg, 55% yield) as a solid, after workup and purification by column chromatography on silica gel using DCM/2M NH₃ in MeOH (1:0 to 85:15) as eluent.

¹H NMR (d₆-DMSO, 300 MHz): δ 8.97 (s, 1H), 7.82 (dd, J=3.9, 1.4 Hz, 1H), 7.63 (br. s, 1H), 7.46-7.42 (m, 1H), 7.20-7.17 (m, 1H), 7.00 (dd, J=9.1, 1.2 Hz, 1H), 6.93 (dt, J=75.1, 1.4 Hz, 1H), 4.30-4.08 (m, 2H), 3.00-2.78 (m, 3H), 2.59-2.51 (m, 2H), 2.32 (app. q, J=8.4 Hz, 1H), 2.04-1.94 (m, 2H), 1.91-1.69 (m, 3H), 1.64-1.34 (m, 3H), 1.28-1.10 (m, 6H), 1.06 (s, 3H), 0.96 (s, 3H); ¹⁹F NMR (d₆-DMSO, 282 MHz): δ −80.1 (s), 166.8 (s); m/z=521.55 [M+H]⁺.

Example 96

Preparation of 2-(2-(5-cyclopropyl-1H-tetrazol-1-yl)-4-((4-(((7R,8aS)-5,5-dimethyloctahydroindolizin-7-yl)amino)-5-fluoropyrimidin-2-yl)amino)phenoxy)ethan-1-ol (Compound 129)

Compound 129 was prepared according to the following synthetic scheme:

with DCM (50 mL) and H₂O (100 mL) and stirred for 30 min. The aqueous and organic layers were partitioned and the aqueous layer extracted with DCM (2×50 mL). The combined organic layers were dried (Na₂SO₄), filtered and the solvent removed under vacuum to leave a crude residue. The residue was dry-loaded onto silica gel and purified by column chromatography on silica gel using EtOAc/heptane (1:9 to 4:6) as eluent to give the product (2.2 g, 98% yield) as a solid.

¹H NMR (d₆-DMSO, 300 MHz): δ 10.39 (br. s, 1H), 9.02-8.97 (m, 1H), 8.01-7.95 (m, 1H), 7.57-7.48 (m, 1H), 2.13-2.06 (m, 1H), 0.86-0.74 (m, 4H); ¹⁹F NMR (d₆-DMSO, 282 MHz): −115.2 (s).

Step 2: preparation of 5-cyclopropyl-1-(2-fluoro-5-nitrophenyl)-1H-tetrazole

A stirred solution of N-(2-fluoro-5-nitrophenyl)cyclopropanecarboxamide (210 mg, 1.0 mmol) in MeCN (6 mL) under nitrogen was cooled to −10 to −20° C. (ice/MeOH bath) and a precipitate developed. Tf₂O (0.34 mL, 2.0 mmol) was added dropwise over 3-5 min (a solution developed). The mixture was stirred in the cold bath for a further 2 min then TMS-N₃ (0.53 mL, 4.0 mmol) was added dropwise over 2 min (bath temp ca. −10° C.). After complete addition, the mixture was stirred for 90 min (bath temperature ca. 15° C.). The mixture was worked-up by addition of EtOAc (30 mL) and saturated NaHCO₃ (15 mL). After stirring for 2 min, the mixture was placed in a separating funnel and H₂O (30 mL) added. The aqueous and organic layers were partitioned and the aqueous layer extracted with EtOAc (2×20 mL). The combined organic layers were dried (Na₂SO₄), filtered and the solvent removed under vacuum to leave a crude residue.

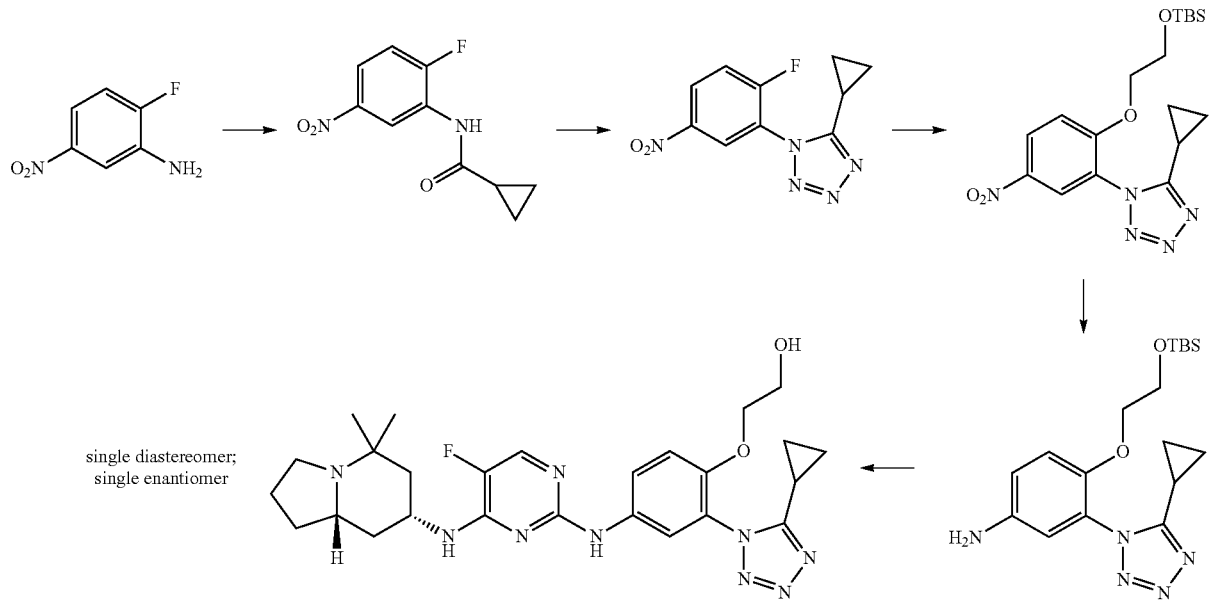

Step 1: preparation of N-(2-fluoro-5-nitrophenyl)cyclopropanecarboxamide

Cyclopropanecarbonyl chloride (5.4 mL, 60 mmol) was added dropwise over 5 min to a stirred solution of 2-fluoro-5-nitroaniline (1.56 g, 10.0 mmol) and solid NaHCO₃ (7.65 g, 90 mmol) in DCM (50 mL) at room temperature under nitrogen. The mixture was stirred overnight then diluted The residue was dry-loaded on to silica gel then purified by column chromatography on silica gel using EtOAc/heptane (2:8 to 4:6) as eluent to give the desired product (112 mg, 45% yield).

¹H NMR (CDCl₃, 300 MHz): δ 8.51 (m, 2H), 7.63-7.57 (m, 1H), 1.81-1.72 (m, 1H), 1.40-1.37 (m, 2H), 1.28-1.21

(m, 2H)]; $^{19}$F NMR (CDCl$_3$, 282 MHz): −108.7 (s); m/z=292.54 [M+MeCN+H]$^+$ & 247.54 [M−H]$^+$.

Step 3: preparation 1-(2-(2-((tert-butyldimethylsilyl)oxy)ethoxy)-5-nitrophenyl)-5-cyclopropyl-1H-tetrazole A mixture of 5-cyclopropyl-1-(2-fluoro-5-nitrophenyl)-1H-tetrazole (112 mg, 0.45 mmol), 2-((tert-butyldimethylsilyl)oxy)ethan-1-ol (159 mg, 0.9 mmol) and Cs$_2$CO$_3$ (325 mg, 1.0 mmol) in DMF (3 mL) was heated to 50° C. and stirred for 4 hr. The reaction was cooled and then poured in to EtOAc (30 mL) and H$_2$O (20 mL). The aqueous and organic layers were partitioned and the aqueous was extracted with EtOAc (2×20 mL). The combined organic layers were dried (Na$_2$SO$_4$), filtered and the solvent removed under vacuum to leave a crude residue. The residue was dry-loaded on to silica gel and purified by column chromatography on silica gel using EtOAc/heptane (4:6 to 1:0) to give the desired product (23 mg, 13% yield), followed by the desired product as de-silylated material, 2-(2-(5-cyclopropyl-1H-tetrazol-1-yl)-4-nitrophenoxy)ethan-1-ol (82 mg, 63%). Both products were taken to the final desired compound.

$^1$H NMR (CDCl$_3$, 300 MHz): δ 8.49 (dd, J=9.2, 2.7 Hz, 1H), 8.37 (d, J=2.7 Hz, 1H), 7.36 (d, J=9.2 Hz, 1H), 4.28 (t, J=4.8 Hz, 2H), 3.91 (t, J=4.8 Hz, 2H), 1.76-1.68 (m, 1H), 1.35-1.31 (m, 2H), 1.18-1.11 (m, 2H), 0.84 (s, 9H), −0.02 (s, 3H), −0.02 (s, 3H); m/z=407.64 [M+H]$^+$.

Data for 2-(2-(5-cyclopropyl-1H-tetrazol-1-yl)-4-nitrophenoxy)ethan-1-ol: $^1$H NMR (CDCl$_3$, 300 MHz): δ 8.51 (dd, J=9.3, 2.7 Hz, 1H), 8.39 (d, J=2.7 Hz, 1H), 7.34 (d, J=9.3 Hz, 1H), 4.33 (t, J=4.5 Hz, 2H), 3.94 (t, J=4.5 Hz, 2H), 1.80-1.72 (m, 1H), 1.34-1.31 (m, 2H), 1.21-1.15 (m, 2H).

Step 4: preparation 4-(2-((tert-butyldimethylsilyl)oxy)ethoxy)-3-(5-cyclopropyl-1H-tetrazol-1-yl)aniline A mixture of 1-(2-(2-((tert-butyldimethylsilyl)oxy)ethoxy)-5-nitrophenyl)-5-cylopropyl-1H-tetrazole (23 mg, 0.06 mmol), palladium on charcoal (Degussa type E101; 5 mg) and MeOH (5 mL) was hydrogenated at atmospheric pressure (H$_2$ balloon) for 3 hr. The mixture was then filtered through a short plug of celite, and the filter cake washed with MeOH (3×5 mL). The filtrate was concentrated under vacuum to leave the product (yield assumed quantitative=21 mg).

$^1$H NMR (CDCl$_3$, 300 MHz): δ 7.03 (d, J=8.7 Hz, 1H), 6.91 (dd, J=8.7, 2.5 Hz, 1H), 6.78 (d, J=2.5 Hz, 1H), 3.99 (t, J=5.2 Hz, 2H), 3.80 (t, J=5.2 Hz, 2H), 1.86-1.77 (m, 1H), 1.28-1.23 (m, 2H), 1.12-1.05 (m, 2H), 0.84 (s, 9H), −0.02 (s, 6H).

Similarly, 2-(2-(5-cyclopropyl-1H-tetrazol-1-yl)-4-nitrophenoxy)ethan-1-ol (82 mg, 0.3 mmol), palladium on charcoal (16 mg) and MeOH (7 mL) was hydrogenated to give 2-(4-amino-2-(5-cyclopropyl-1H-tetrazol-1-yl)phenoxy)ethan-1-ol (67 mg, 91%) after workup.

$^1$H NMR (CDCl$_3$, 300 MHz): δ 6.99 (d, J=8.8 Hz, 1H), 6.87 (dd, J=8.8, 2.8 Hz, 1H), 6.73 (d, J=2.8 Hz, 1H), 4.04 (t, J=4.5 Hz, 2H), 3.77 (t, J=4.5 Hz, 2H), 3.10 (br. s, 2H), 1.87-1.75 (m, 1H), 1.29-1.24 (m, 2H), 1.15-1.09 (m, 2H).

Step 5: preparation of 2-(2-(5-cyclopropyl-1H-tetrazol-1-yl)-4-((4-(((7R,8aS)-5,5-dimethyloctahydroindolizin-7-yl)amino)-5-fluoropyrimidin-2-yl)amino)phenoxy)ethan-1-ol (Compound 129)

A mixture of (7R,8aS)-N-(2-chloro-5-fluoropyrimidin-4-yl)-octahydro-5,5-dimethylindolizin-7-amine hydrochloride (20 mg, 0.06 mmol), 4-(2-(tert-butyldimethylsilyl)oxy)ethoxy)-3-(5-cylopropyl-1H-tetrazol-1-yl)aniline (21 mg, 0.06 mmol) and pTsOH.H$_2$O (22 mg, 0.12 mmol) in IPA (5 mL) was heated to reflux and stirred overnight. After allowing to cool, the mixture was concentrated under vacuum and the residue partitioned between EtOAc (30 mL) and 1N NaOH (15 mL). The aqueous layer was extracted with EtOAc (2×10 mL) and the combined organic layers dried (Na$_2$SO$_4$), filtered and the solvent removed under vacuum to leave a crude residue. The residue was purified by preparative thin-layer chromatography using DCM/2M NH$_3$ in MeOH (9:1) as eluent (5 prep TLC plates used) to give the product (17 mg, 56% yield) as a solid.

$^1$H NMR (d$_6$-DMSO, 300 MHz): δ 9.24 (s, 1H), 8.09 (m, 1H), 7.82 (dd, J=3.7, 1.8 Hz, 1H), 7.71 (dd, J=12.0, 2.6 Hz, 1H), 7.29-7.22 (m, 2H), 4.74 (t, J=5.2 Hz, 1H), 4.10-4.02 (m, 1H), 4.01 (t, J=5.1 Hz, 2H), 3.58-3.53 (m, 2H), 2.92-2.71 (m, 1H), 2.33-2.14 (m, 1H), 2.06-1.36 (m, 9H), 1.35-0.96 (m, 9H), 0.89-0.69 (m, 2H); $^{19}$F NMR (d$_6$-DMSO, 282 MHz): δ-166.5 (s); m/z=524.29 [M+H]$^+$.

Similarly, 2-(4-amino-2-(5-cyclopropyl-1H-tetrazol-1-yl)phenoxy)ethan-1-ol (67 mg, 0.26 mmol) was used in a similar displacement reaction using (7R,8aS)-N-(2-chloro-5-fluoropyrimidin-4-yl)-octahydro-5,5-dimethylindolizin-7-amine hydrochloride (95 mg, 0.28 mmol) and pTsOH.H$_2$O (98 mg, 0.51 mmol) in IPA (5 mL) at reflux to give the product (88 mg, 66% yield) after workup and purification by column chromatography on silica gel using DCM/2M NH$_3$ in MeOH (1:0 to 9:1).

Example 97

Preparation of 2-(4-((4-(((7R,8aS)-5,5-dimethyloctahydroindolizin-7-yl)amino)-5-fluoropyrimidin-2-yl)amino)-2-fluorophenoxy)ethan-1-ol (Compound 130)

Compound 130 was prepared according to the following synthetic scheme:

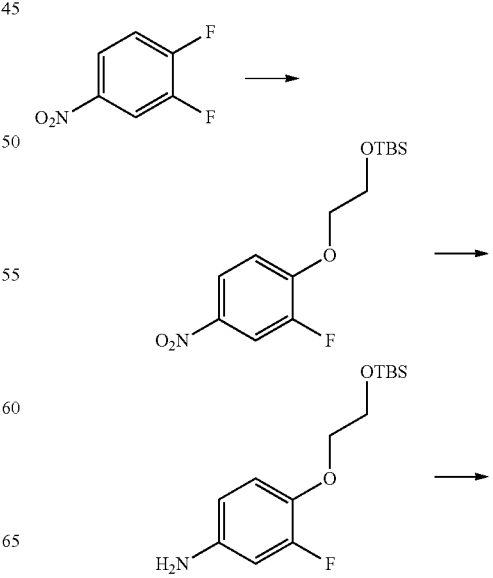

475

-continued

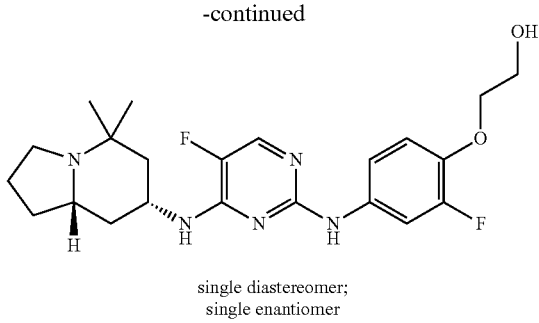

single diastereomer;
single enantiomer

Step 1: preparation of tert-butyl-(2-(2-fluoro-4-nitrophenoxy)ethoxy)dimethylsilane The same procedure detailed below for Compound 133 was used, but using 3,4-difluoronitrobenzene (225 mg, 1.4 mmol), potassium tert-butoxide (354 mg, 3.2 mmol) and 2-((tert-butyldimethylsilyl)oxy)ethan-1-ol (506 mg, 2.9 mmol) in THF (3 mL) to give the product (451 mg) after workup (yield assumed quantitative). The product was used in the next step without further purification.

Step 2: preparation of 4-(2-((tert-butyldimethyl)silyl)oxy)ethoxy)-3-fluoroaniline A mixture of tert-butyl-(2-(2-fluoro-4-nitrophenoxy)ethoxy)dimethylsilane (451 mg, 1.4 mmol), palladium on charcoal (90 mg) and MeOH (5 mL) was hydrogenated at atmospheric pressure ($H_2$ balloon) for 3 hr. The mixture was filtered through celite and the filter cake washed with MeOH (3×10 mL). The filtrate was concentrated under vacuum and dry-loaded on to silica gel, then purified by column chromatography on silica gel using EtOAc/heptane (0:1 to 4:6) as eluent to give the product (291 mg, 71% yield over 2 steps).
$^1$H NMR (CDCl$_3$, 300 MHz): δ 6.88 (dt, J=8.9, 2.9 Hz, 1H), 6.49 (dt, J=12.6, 5.6 Hz, 1H), 6.39-6.35 (m, 1H), 4.04-4.01 (m, 2H), 3.96-3.92 (m, 2H), 3.50 (br. s, 2H), 0.92 (m, 9H), 0.11-0.10 (m, 6H); $^{19}$F NMR (CDCl$_3$, 282 MHz): δ −132.3 (dd).

Step 3: preparation of 2-(44(4-4(7R,8aS)-5,5-dimethyloctahydroindolizin-7-yl)amino)-5-fluoropyrimidin-2-yl)amino)-2-fluorophenoxy)ethan-1-ol (Compound 130)

The general displacement procedure described herein was used with 4-(2-(((tert-butyldimethyl)silyl)oxy)ethoxy)-3-fluoroaniline (285 mg, 1.0 mmol), (7R,8aS)-N-(2-chloro-5-fluoropyrimidin-4-yl)-octahydro-5,5-dimethylindolizin-7-amine hydrochloride (336 mg, 1.0 mmol) and pTsOH.H$_2$O (381 mg, 2.0 mmol) in IPA (10 mL) at reflux to give the product (143 mg, 33% yield) as a solid, after workup and purification by column chromatography on silica gel using DCM/2M NH$_3$ in MeOH (1:0 to 9:1) as eluent.
$^1$H NMR (d$_6$-DMSO, 300 MHz): δ 9.03 (d, J=4.0 Hz, 1H), 7.84-7.75 (m, 2H), 7.25-7.21 (m, 2H), 7.02-6.94 (m, 1H), 4.89-4.74 (m, 1H), 4.40-4.09 (m, 1H), 4.00-3.90 (m, 2H), 3.75-3.57 (m, 2H), 2.92-2.77 (m, 1H), 2.39-2.22 (m, 1H), 2.12-1.93 (m, 1H), 1.87-1.52 (m, 1H), 1.70-1.52 (m, 3H), 1.51-1.35 (m, 1H), 1.32-1.12 (m, 3H), 1.09 (s, 3H), 0.99 (s, 3H); $^{19}$F NMR (d$_6$-DMSO, 282 MHz): δ −166.9 (s), −133.2 (m); m/z=434.23 [M+H]$^+$.

476

Example 98

Preparation of 2-(4-44-4(7R,8aS)-5,5-dimethyloctahydroindolizin-7-yl)amino)-5-fluoropyrimidin-2-yl)amino)-2-(trifluoromethyl)phenoxy)ethan-1-ol (Compound 131)

Compound 131 was prepared according to the following synthetic scheme:

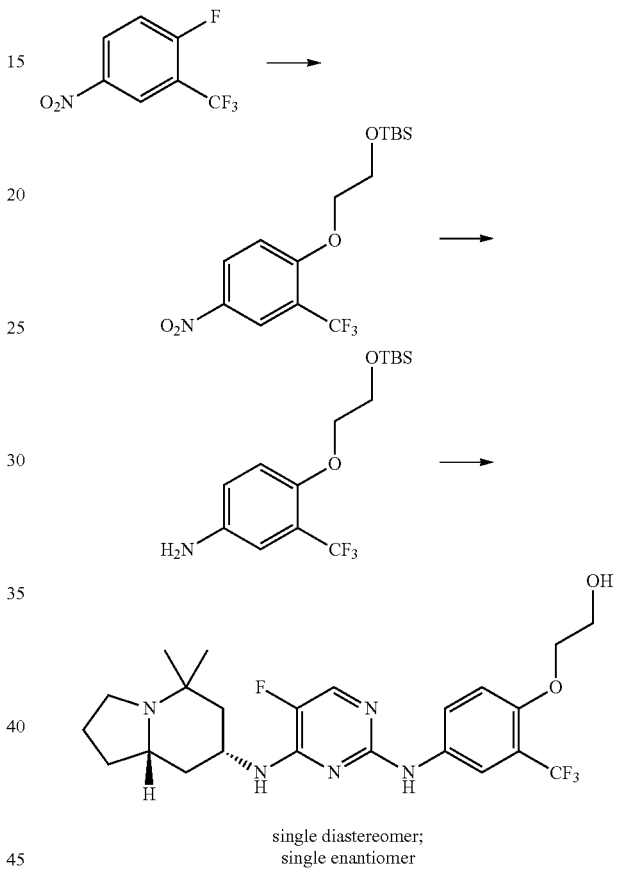

single diastereomer;
single enantiomer

Step 1: preparation of tert-butyl-(2-(2-fluoro-4-nitrophenoxy)ethoxy)dimethylsilane The same procedure detailed below for Compound 133 was used, but using 1-fluoro-4-nitro-2-(trifluoromethyl)benzene (299 mg, 1.4 mmol), potassium tert-butoxide (354 mg, 3.2 mmol) and 2-((tert-butyldimethylsilyl)oxy)ethan-1-ol (506 mg, 2.9 mmol) in THF (3 mL) to give the product (451 mg) after workup (yield assumed quantitative). The product was used in the next step without further purification.

Step 2: preparation of 4-(2-((tert-butyldimethylsilyl)oxy)ethoxy)-3-(trifluoromethyl)aniline The general hydrogenation procedure as described herein was used to give the product (481 mg). The product was used in the next step without further purification.

Step 3: preparation of 2-(4-((4-(((7R,8aS)-5,5-dimethyloctahydroindolizin-7-yl)amino)-5-fluoropyrimidin-2-yl)amino)-2-(trifluoromethyl)phenoxy)ethan-1-ol (Compound 131)

The general displacement procedure described herein was used with 4-(2-((tert-butyldimethylsilyl)oxy)ethoxy)-3-(trifluoromethyl)aniline (481 mg, 1.4 mmol), (7R,8aS)-N-(2-chloro-5-fluoropyrimidin-4-yl)-octahydro-5,5-dimethylindolizin-7-amine hydrochloride (480 mg, 1.4 mmol) and pTsOH.H$_2$O (546 mg, 2.9 mmol) in IPA (10 mL) at reflux to give the product (387 mg, 56% yield) as a solid, after workup and purification by column chromatography on silica gel using DCM/2M NH$_3$ in MeOH (1:0 to 9:1) as eluent.

$^1$H NMR (d$_6$-DMSO, 300 MHz): δ 9.04 (d, J=4.0 Hz, 1H), 7.90-7.82 (m, 3H), 7.18 (br. s, 1H), 7.13 (dd, J=9.2, 4.0 Hz, 1H), 4.82 (q, J=4.7 Hz, 1H), 4.28-4.08 (m, 1H), 4.05-4.00 (m, 2H), 3.72-3.65 (m, 2H), 2.95-2.74 (m, 1H), 2.37-2.17 (m, 1H), 2.08-1.90 (m, 1H), 1.86-1.34 (m, 5H), 1.32-1.16 (m, 3H), 1.08 (s, 3H), 0.96 (s, 3H); $^{19}$F NMR (d$_6$-DMSO, 282 MHz): δ −60.3 (d), −166.6 (s); m/z=484.30 [M+H]$^+$.

Example 99

Preparation of 1-(5-((4-(((7R,8aS)-5,5-dimethyloctahydroindolizin-7-yl)amino)-5-fluoropyrimidin-2-yl)amino)-2-(2-hydroxyethoxy)phenyl)-4-methyl-1,4-dihydro-5H-tetrazol-5-one (Compound 132)

Compound 132 was prepared according to the following synthetic scheme:

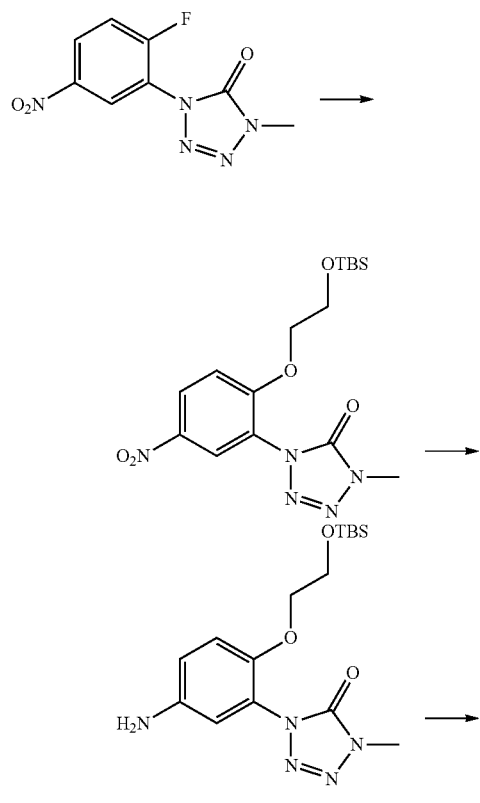

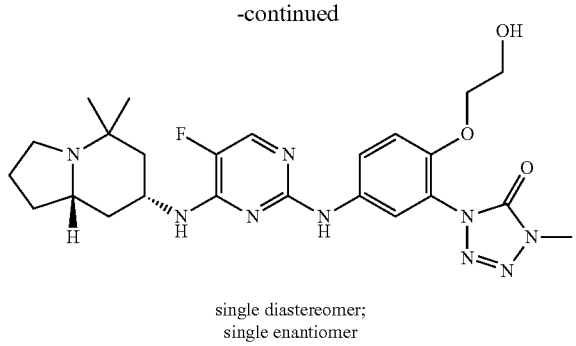

single diastereomer;
single enantiomer

Step 1: preparation of 1-(2-(2-((tert-butyldimethylsilyl)oxy)ethoxy)-5-nitrophenyl)-4-methyl-1,4-dihydro-5H-tetrazol-5-one A similar procedure as detailed below for Compound 133 was used. 1-(2-fluoro-5-nitrophenyl)-4-methyl-1,4-dihydro-5H-tetrazol-5-one (prepared according to US patent application no. 2011/0130415) (250 mg, 1.1 mmol), potassium tert-butoxide (258 mg, 2.3 mmol) and 2-((tert-butyldimethylsilyl)oxy)ethan-1-ol (369 mg, 2.1 mmol) in THF (2 mL) was stirred for 1 hr at room temperature to give the product after workup (yield assumed quantitative=413 mg). The product was used in the next step without further purification.

Step 2: preparation of 1-(5-amino-2-(2-((tert-butyldimethylsilyl)oxy)ethoxy)phenyl)-4-methyl-1,4-dihydro-5H-tetrazol-5-one The general hydrogenation procedure described herein was used to give the product after workup (yield assumed quantitative=382 mg). The product was used in the next step without further purification.

Step 3: preparation of 1-(5-((4-(((7R,8aS)-5,5-dimethyloctahydroindolizin-7-yl)amino)-5-fluoropyrimidin-2-yl)amino)-2-(2-hydroxyethoxy)phenyl)-4-methyl-1,4-dihydro-5H-tetrazol-5-one (Compound 132)

The general displacement procedure was described herein was used with 1-(5-amino-2-(2-((tert-butyldimethylsilyl)oxy)ethoxy)phenyl)-4-methyl-1,4-dihydro-5H-tetrazol-5-one (382 mg, 1.1 mmol), (7R,8aS)-N-(2-chloro-5-fluoropyrimidin-4-yl)-octahydro-5,5-dimethylindolizin-7-amine hydrochloride (350 mg, 1.1 mmol) and pTsOH.H$_2$O (398 mg, 2.1 mmol) in IPA (10 mL) at reflux to give the product (113 mg, 21% yield) as a solid, after workup and purification by column chromatography on silica gel using DCM/2M NH$_3$ in MeOH (1:0 to 95:5) as eluent.

$^1$H NMR (d$_6$-DMSO, 300 MHz): δ 9.25 (s, 1H), 8.10 (d, J=2.4 Hz, 1H), 7.92-7.91 (m, 1H), 7.71 (dd, J=9.0, 2.4 Hz, 1H), 7.31 (d, J=8.1 Hz, 1H), 7.21 (d, J=9.0 Hz, 1H), 4.74 (t, J=5.2 Hz, 2H), 4.16-4.13 (m, 1H), 4.07 (t, J=5.2 Hz, 2H), 3.67 (s, 3H), 3.64 (m, 2H), 2.93 (t, J=8.1 Hz, 1H), 2.32-2.26 (m, 2H), 2.08-2.04 (m, 1H), 1.79-1.62 (m, 4H), 1.56 (t, J=12.2 Hz, 1H), 1.32-1.19 (m, 2H), 1.13 (s, 3H), 0.89 (s, 3H); $^{19}$F NMR (d$_6$-DMSO, 282 MHz): δ −166.6 (s); m/z=514.36 [M+H]$^+$.

Example 100

Preparation of 2-(2-chloro-4-((4-(((7R,8aS)-5,5-dimethyloctahydroindolizin-7-yl)amino)-5-fluoropyrimidin-2-yl)amino)phenoxy)ethan-1-ol (Compound 133)

Compound 133 was prepared according to the following synthetic scheme:

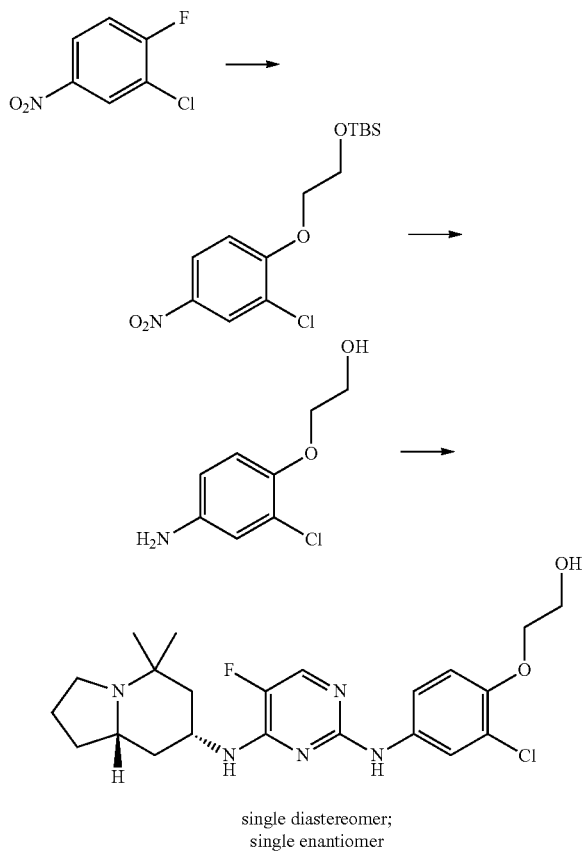

single diastereomer; single enantiomer

Step 1: preparation of tert-butyl-(2-(2-chloro-4-nitrophenoxy)ethoxy)dimethylsilane Potassium tert-butoxide (354 mg, 3.2 mmol) was added in one portion to a stirred solution of 2-((tert-butyldimethylsilyl)oxy)ethan-1-ol (506 mg, 2.9 mmol) in THF (3 mL) at 0° C. under nitrogen. The mixture was stirred at 0° C. for 30 min then 3-chloro-4-fluoronitrobenzene (251 mg, 1.4 mmol) was added in one portion (reaction turned dark color). The mixture was stirred at 0° C. for 10 min then the ice-bath removed, the reaction was allowed to warm to room temperature (10 min) and stirred for 1 hr. The solvent was removed under vacuum and the residue partitioned between EtOAc (50 mL) and H₂O (50 mL). The aqueous layer was extracted with EtOAc (2×50 mL) and the combined organic layers dried (Na₂SO₄), filtered and the solvent removed under vacuum to leave the product as an oil (yield assumed quantitative=475 mg). The product was used in the next step without further purification.

Step 2: preparation of 2-(4-amino-2-chlorophenoxy)ethan-1-ol

A mixture of tert-butyl-(2-(2-chloro-4-nitrophenoxy)ethoxy)dimethylsilane (475 mg, 1.4 mmol) and SnCl₂.2H₂O (1.07 g, 5.7 mmol) in EtOH (40 mL) was heated to reflux and stirred for 4 hr. After allowing to cool, the mixture was poured into EtOAc (50 mL) and saturated NaHCO₃ (50 mL), then filtered through celite. The filtrate was partitioned and the aqueous layer extracted with EtOAc (2×50 mL). The combined organic layers were dried (Na₂SO₄), filtered and concentrated under vacuum to leave a crude residue. The residue was dry-loaded on to silica gel and purified by column chromatography on silica gel using EtOAc/heptane (2:8 to 1:0) as eluent to give the product (9 mg, 3% yield).

$^1$H NMR (CDCl₃, 300 MHz): δ 6.83 (d, J=8.6 Hz, 1H), 6.75 (d, J=2.7 Hz, 1H), 6.56 (dd, J=8.6, 2.7 Hz, 1H), 4.08-4.05 (m, 2H), 3.93-3.91 (m, 2H), 3.52 (br. s, 2H), 2.33 (br. s, 1H); m/z=188.0 [M+H]⁺.

Step 3: preparation of 2-(2-chloro-4-((4-(((7R,8aS)-5,5-dimethyloctahydroindolizin-7-yl)amino)-5-fluoropyrimidin-2-yl)amino)phenoxy)ethan-1-ol (Compound 133)

The general displacement procedure described herein was used with 2-(4-amino-2-chlorophenoxy)ethan-1-ol (9 mg, 0.05 mmol), (7R,8aS)-N-(2-chloro-5-fluoropyrimidin-4-yl)-octahydro-5,5-dimethylindolizin-7-amine hydrochloride (16 mg, 0.05 mmol) and pTsOH.H₂O (18 mg, 0.1 mmol) in IPA (5 mL) at reflux to give the product (16 mg, 74% yield) as a solid after workup and purification by preparative thin-layer chromatography using DCM/2M NH₃ in MeOH as eluent (9:1; 5 preparative TLC plates).

$^1$H NMR (d₆-DMSO, 300 MHz): δ 8.98 (s, 1H), 7.91-7.90 (m, 1H), 7.83-7.81 (m, 1H), 7.47-7.44 (m, 1H), 7.21-7.18 (m, 1H), 7.01 (dd, J=9.0, 3.1 Hz, 1H), 4.94-4.78 (br. s, 1H), 4.25-4.10 (m, 1H), 3.97-3.94 (m, 2H), 3.71-3.67 (m, 2H), 2.88-2.81 (m, 1H), 2.33-2.24 (m, 1H), 2.03-1.99 (m, 1H), 1.84-1.70 (m, 1H), 1.67-1.52 (m, 3H), 1.50-1.39 (m, 1H), 1.31-1.12 (m, 3H), 1.07 (s, 3H), 0.98 (s, 3H); $^{19}$F NMR (d₆-DMSO, 282 MHz): δ -166.8 (s); m/z=450.27 [M+H]⁺.

Example 101

Preparation of 2-(4-((4-(((7R,8aS)-5,5-dimethyloctahydroindolizin-7-yl)amino)-5-fluoropyrimidin-2-yl)amino)-2-(methyl)phenoxy)ethan-1-ol (Compound 134)

Compound 134 was prepared according to the following synthetic scheme:

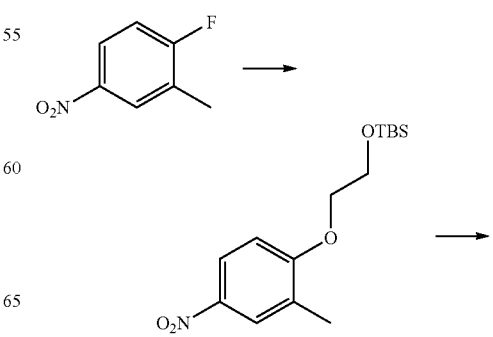

-continued

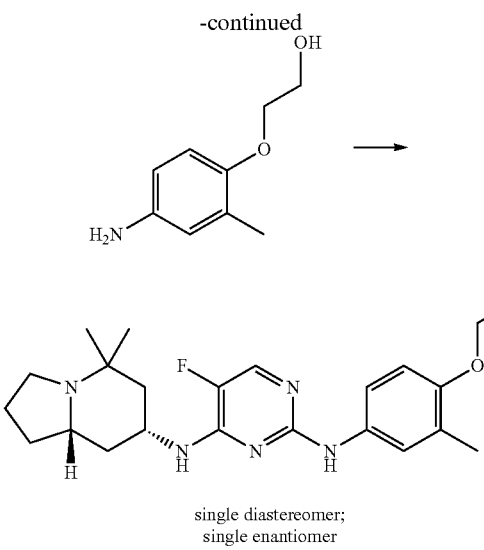

single diastereomer;
single enantiomer

Step 1: preparation of tert-butyldimethyl(2-(2-methyl-4-nitrophenoxy)ethoxy) silane A similar procedure as detailed above for Compound 133 was used. 2-fluoro-5-nitrotoluene (310 mg, 2.0 mmol), potassium tert-butoxide (494 mg, 4.4 mmol) and 2-((tert-butyldimethylsilyl)oxy)ethan-1-ol (705 mg, 4.0 mmol) in THF (6 mL) was stirred for 3 hr at room temperature to give the product after workup (yield assumed quantitative=623 mg). The product was used in the next step without further purification.

Step 2: preparation of 4-(2-((tert-butyldimethylsilyl)oxy)ethoxy)-3-methylaniline The general hydrogenation procedure was described herein was used to give the product after workup (yield assumed quantitative=563 mg). The product was used in the next step without further purification.

Step 3: preparation of 2-(4-((4-(((7R,8aS)-5,5-dimethyloctahydroindolizin-7-yl)amino)-5-fluoropyrimidin-2-yl)amino)-2-(methyl)phenoxy)ethan-1-ol (Compound 134)

The general displacement procedure described herein was used with 4-(2-((tert-butyldimethylsilyl)oxy)ethoxy)-3-methylaniline (563 mg, 2.0 mmol), (7R,8aS)-N-(2-chloro-5-fluoropyrimidin-4-yl)-octahydro-5,5-dimethylindolizin-7-amine hydrochloride (478 mg, 1.4 mmol) and pTsOH.H$_2$O (544 mg, 2.9 mmol) in IPA (10 mL) at reflux to give the product (360 mg, 59% yield) as a solid, after workup and purification by column chromatography on silica gel using DCM/2M NH$_3$ in MeOH (1:0 to 9:1) as eluent.

$^1$H NMR (d$_6$-DMSO, 300 MHz): δ 8.68 (s, 1H), 7.79 (d, J=3.8 Hz, 1H), 7.47 (d, J=8.8 Hz, 1H), 7.35 (s, 1H), 7.10 (br. s, 1H), 6.75 (d, J=8.8 Hz, 1H), 4.78 (t, J=5.4 Hz, 1H), 4.27-4.11 (m, 1H), 3.90-3.84 (m, 2H), 3.71-3.63 (m, 2H), 2.95-2.78 (m, 1H), 2.45-2.20 (m, 1H), 2.11 (s, 3H), 2.06-1.92 (m, 1H), 1.90-1.35 (m, 6H), 1.32-1.15 (m, 2H), 1.09 (s, 3H), 1.00 (s, 3H); $^{19}$F NMR (d$_6$-DMSO, 282 MHz): δ −167.9 (s); m/z=484.30 [M+H]$^+$.

Example 102

Preparation of 1-(5-((4-(((7R,8aS)-5,5-dimethyloctahydroindolizin-7-yl)amino)-5-fluoropyrimidin-2-yl)amino)-2-(((S)-1-hydroxypropan-2-yl) oxy)phenyl)-4-methyl-1,4-dihydro-5H-tetrazol-5-one (Compound 135)

Compound 135 was prepared according to the following synthetic scheme:

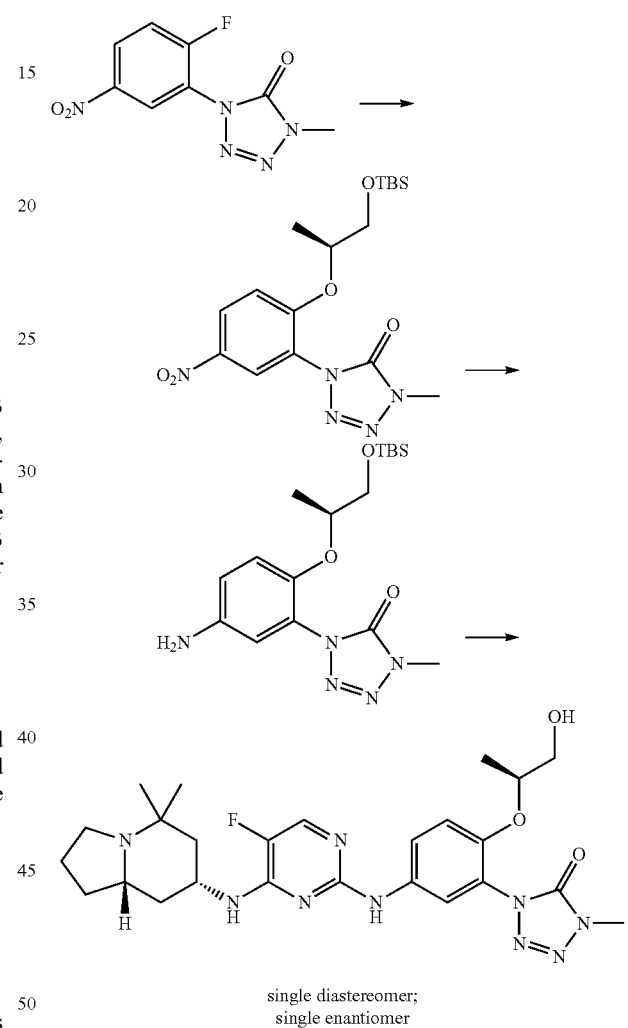

single diastereomer;
single enantiomer

Step 1: preparation of (S)-1-(2-41-((tert-butyldimethylsilyl)oxy)propan-2-yl)oxy)-5-nitrophenyl)-4-methyl-1,4-dihydro-5H-tetrazol-5-one A similar procedure as detailed above for Compound 133 was used. 1-(2-fluoro-5-nitrophenyl)-4-methyl-1,4-dihydro-5H-tetrazol-5-one (prepared according to US patent application 20110130415) (239 mg, 1.0 mmol), potassium tert-butoxide (146 mg, 1.2 mmol) and (S)-1-((tert-butyldimethylsilyl)oxy)propan-2-ol (Milestone PharmaTech) (209 mg, 1.1 mmol) in THF (10 mL) was stirred for 2 hr at room temperature to give the product after workup (yield assumed quantitative=410 mg). The product was used in the next step without further purification.

Step 2: preparation of (S)-1-(5-amino-2-41-((tert-butyldimethylsilyl)oxy)propan-2-yl)oxy)phenyl)-4-methyl-1,4-dihydro-5H-tetrazol-5-one The general hydrogenation procedure as described herein was used with 410 mg of starting material, palladium on charcoal (80 mg) and MeOH (10 mL) at 1 atm H$_2$ pressure (balloon) to give the product after workup (yield assumed quantitative=380 mg). The product was used in the next step without further purification.

Step 3: preparation of 1-(5-((4-(((7R,8aS)-5,5-dimethyloctahydroindolizin-7-yl)amino)-5-fluoropyrimidin-2-yl)amino)-2-4(S)-1-hydroxypropan-2-yl) oxy) phenyl)-4-methyl-1,4-dihydro-5H-tetrazol-5-one (Compound 135)

The general displacement procedure as described herein was used with (S)-1-(5-amino-2-((1-((tert-butyldimethylsilyl)oxy)phenyl)-4-methyl-1m4-dihydro-5H-tetrazol-5-one (380 mg, 1.0 mmol), (7R,8aS)-N-(2-chloro-5-fluoropyrimidin-4-yl)-octahydro-5,5-dimethylindolizin-7-amine hydrochloride (240 mg, 0.7 mmol) and pTsOH.H$_2$O (272 mg, 1.4 mmol) in IPA (10 mL) at reflux to give the product (120 mg, 32% yield) as a solid, after workup and purification by column chromatography on silica gel using DCM/2M NH$_3$ in MeOH (1:0 to 9:1) as eluent.

$^1$H NMR (CDCl$_3$, 300 MHz): δ 9.17 (s, 1H), 8.00 (br. s, 1H), 7.85 (d, J=3.5 Hz, 1H), 7.61 (br. s, 1H), 7.21-7.13 (m, 2H), 4.69-4.64 (m, 1H), 4.25-4.00 (m, 1H), 3.86-3.67 (m, 3H), 3.60 (s, 3H), 2.90-2.77 (m, 1H), 2.35-1.36 (m, 8H), 1.30-1.11 (m, 2H), 1.09 (d, J=6.2 Hz, 3H), 1.01 (d, J=5.7 Hz, 3H), 0.83 (d, J=7.7 Hz, 3H); $^{19}$F NMR (CDCl$_3$, 282 MHz): δ −166.6 (s); m/z=528.14 [M+H]$^+$ & 526.10 [M−H]$^+$.

Example 103

Preparation of Compound 136

Synthesis of 4,4-dimethyl-4H-benzo[b]tetrazolo[1,5-d][1,4]oxazin-8-amine

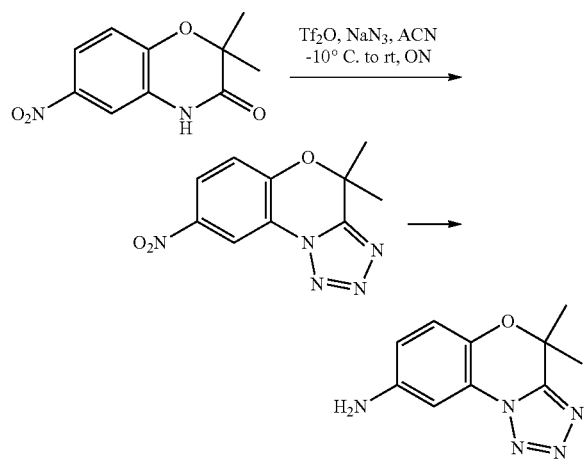

To a solution of nitro bicyclic amide (100 mg, 0.450 mmol, 1 equiv) in ACN (5 mL) under argon gas was added NaN$_3$ (117 mg, 1.80 mmol, 4 equiv) in one portion. The suspension was cooled to −10° C. (brine and ice), and Tf$_2$O (152 μL, 254 mg, 0.900 mmol, 2 equiv) was slowly added dropwise. The reaction mixture was allowed to warm up to ambient temperature overnight. LCMS indicated a ratio of reactant:product=30:70. The reaction mixture was cooled back to −10° C. and quenched by the slow dropwise addition of ice-cold saturated sodium bicarbonate and diluted with ice-cold EtOAc. The layers were separated, and the organic layer was washed with water 1×, dried over Na$_2$SO$_4$, filtered, and concentrated. The crude product was purified by flash chromatography and eluted with DCM to give the nitro tricyclic tetrazole intermediate (88 mg, 79%) as a white solid.

$^1$H NMR (300 MHz; d$_6$-DMSO) δ 8.60-8.61 (d, 1H, J=2.4Hz), 8.28-8.31 (dd, 1H, J=1.2Hz, 9.0Hz), 7.46-7.49 (d, J=9.0Hz), 1.83 (s, 6H); m/z=248 (M+H)$^+$. Synthesis of N2-(4,4-dimethyl-4H-benzo[b]tetrazolo[1,5-d][1,4]oxazin-8-yl)-N4-((7R,8aS)-5,5-dimethyloctahydroindolizin-7-yl)-5-fluoropyrimidine-2,4-diamine (Compound 136)

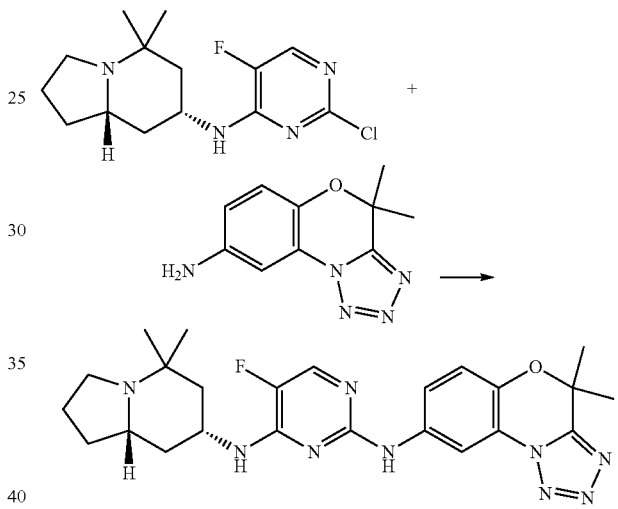

A mixture of tricyclic aniline (232 mg, 1.07 mmol, 1.2 equiv), (7R,8aS)-N-(2-chloro-5-fluoropyrimidin-4-yl)-octahydro-5,5-dimethylindolizin-7-amine (266 mg, 0.890 mmol, 1.0 equiv), and PTSA monohydrate (170 mg, 0.890 mmol, 1.0 equiv) in IPA (9 mL) was heated to 70° C. for 3 days. LCMS indicated 7% unreacted (7R,8aS)-N-(2-chloro-5-fluoropyrimidin-4-yl)-octahydro-5,5-dimethylindolizin-7-amine. 3-amino benzoic acid (366 mg, 2.67 mmol, 3 equiv) was added and heated to 70° C. overnight to scavenge the unreacted pyrimidine. After cooling to ambient temperature, the crude mixture was concentrated to dryness and taken in water, EtOAc, and 1N NaOH. The layers were separated. The organic layer was washed with 1N NaOH 1×, dried over Na$_2$SO$_4$, filtered, and concentrated to dryness. The crude product was purified by flash chromatography and eluted with DCM:2M NH$_3$/MeOH=100:0 to 95:5 using 1% 2M NH$_3$/MeOH increments to give Compound 136 (350 mg, 82% yield) as a solid.

$^1$H NMR (300 MHz; d$_6$-DMSO) δ 9.30 (s, 1H), 8.46-8.47 (d, 1H, J=2.1Hz), 7.88-7.89 (d, 1H, J=3.6Hz), 7.61-7.64 (dd, 1H, J=2.1Hz, 9.0Hz), 7.23-7.26 (d, J=6.6Hz), 7.10-7.13 (d, 1H, J=8.7Hz), 4.21 (bs, 1H), 2.80 (bs, 1H), 0.85-2.26 (m, 22H); $^{19}$F NMR (282 MHz; d$_6$-DMSO) δ −166.0 (s); m/z=480 (M+H)$^+$.

Example 104

Preparation of Compound 137

Synthesis of pyran spirocyclic amide

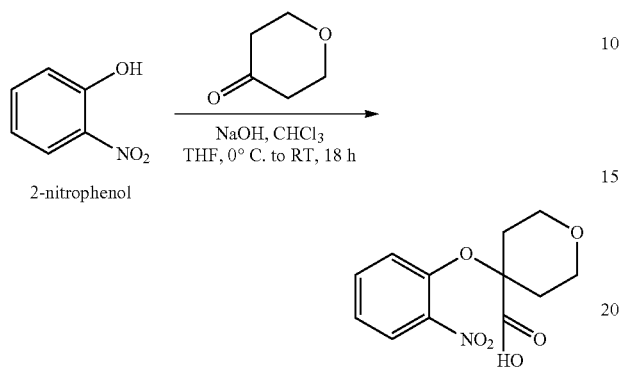

To a solution of 2-nitrophenol (2.0 g, 14.38 mmol, 1 equiv) in 50 mL of THF was added powdered NaOH (4.89 g, 122.23 mmol, 8.5 equiv), and the reaction mixture was stirred at room temperature for 15 min. Tetrahydro-4H-pyran-4-one (12.95 g, 129.39 mmol, 9.0 equiv) was added and the mixture was cooled to 0° C. Chloroform was then added dropwise and the reaction mixture was stirred at 0° C. for 1 h, then at room temperature for 18 h. The reaction mixture was partitioned between water (~100 mL) and DCM (~100 mL). The aqueous layer was separated, washed with ~60 mL of DCM and acidified with 3N HCl (~20 mL) to pH 3, then extracted with DCM (100 mL×3). The organic layers were combined, dried (MgSO$_4$) and concentrated to give the crude product as a yellow oil which was used in the next step without further purification.

$^1$H NMR (CDCl$_3$, 300 MHz): δ 10.60 (br. s, 1H), 8.13 (dm, J=8.4 Hz, 1H), 7.60 (tm, J=8.7 Hz, 1H), 7.18 (dm, J=8.4 Hz, 1H), 7.01 (tm, J=8.7 Hz, 1H), 3.90-3.71 (m, 4H), 2.41-1.74 (m, 4H). m/z=266.0 (M−H)$^+$.

Synthesis of 2',3',5',6'-tetrahydrospiro[benzo[b][1,4]oxazine-2,4'-pyran]-3(4H)-one

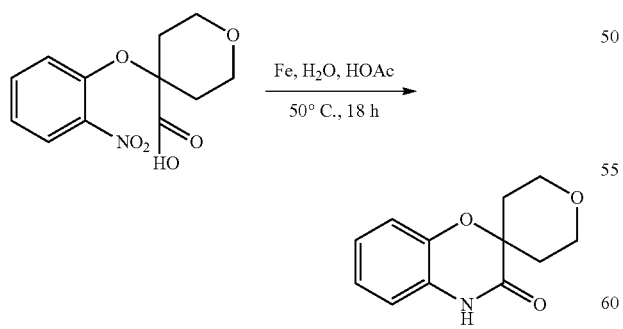

A solution of the above crude acid (14.38 mmol, 1 equiv) in HOAc (45 mL) and H$_2$O (4.5 mL) at 50° C. was treated with iron powder. The reaction mixture was then stirred at this temperature for 18 h. The reaction mixture was cooled to room temperature and filtered through celite. The filter cake was washed with DCM and water. The phases were separated and the aqueous phase was extracted with DCM (100 mL×3). The combined organic extracts were washed 1N NaOH (~150 mL), dried over MgSO$_4$ and concentrated. The residue was purified by column chromatography on silica gel using EtOAc/hexanes (1:1) as eluent to give 0.98 g of product (33% yield for the two steps above).

$^1$H NMR (CDCl$_3$, 300 MHz): δ 8.94 (br. s, 1H), 7.08-6.97 (m, 3H), 6.84-6.81 (m, 1H), 3.98-3.81 (m, 4H), 2.27-2.20 (m, 2H), 1.87-1.78 (m, 2H). m/z=218.1 (M−H)$^+$.

Synthesis of Nitro Pyran Spirocyclic Amide

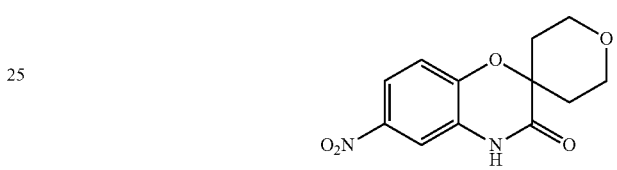

The pyran spirocyclic amide (155 mg, 0.707 mmol, 1 equiv) was vigorously stirred at ambient temperature in H$_2$SO$_4$ (7 mL) until homogeneous. The solution was cooled to −25° C. (external temperature) and HNO$_3$ (fuming >90%; 32 uL, 0.707 mmol, 1 equiv) was slowly added dropwise and stirred for 15 min at −25° C. The reaction mixture was quenched with ice, diluted with EtOAc, and the layers were separated. The organic layer was washed with water 1×, dried over Na$_2$SO$_4$, filtered, and concentrated to dryness. The crude product was absorbed onto silica gel and purified by flash chromatography and eluted with Hex:EtOAc=100:0 to 70:30 using 10% EtOAc increments to provide the nitro pyran spirocyclic amide (110 mg, 59% yield) as yellow-brown solid.

$^1$H NMR (300 MHz; d$_6$-DMSO) δ 11.1 (s, 1H), 7.85-7.89 (m, 1H), 7.73-7.74 (m, 1H), 7.27-7.30 (d, 1H, J=9.0Hz), 3.66-3.75 (m, 4H), 1.97-2.07 (m, 2H), 1.68-1.72 (m, 1H); m/z=265 (M+H)$^+$.

Synthesis of Nitro Pyran Spirocyclic Tetrazole

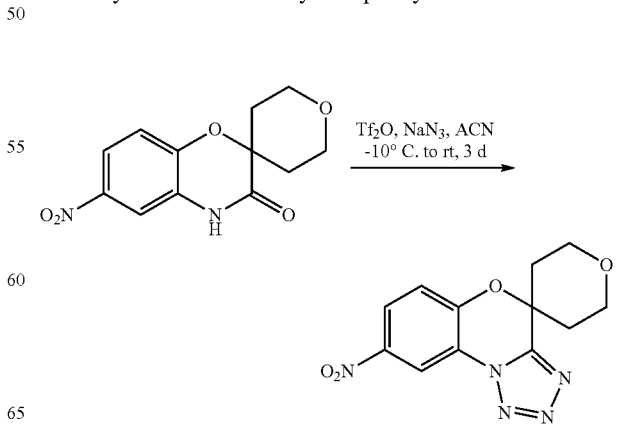

To a solution of nitro pyran spirocyclic amide (50 mg, 0.189 mmol, 1 equiv) in ACN (1 mL) under argon gas was added NaN₃ (50 mg, 0.757 mmol, 4 equiv) in one portion. The suspension was cooled to −10° C. (brine and ice), and Tf₂O (64 uL, 107 mg, 0.378 mmol, 2 equiv) was slowly added dropwise. The reaction mixture was allowed to warm up to ambient temperature and stirred for 3 days. The reaction mixture was cooled back to −10° C. and quenched by the slow dropwise addition of ice-cold saturated sodium bicarbonate and diluted with ice-cold EtOAc. The layers were separated, and the organic layer was washed with water 1×, dried over Na₂SO₄, filtered, and concentrated. The crude product was purified by preparative TLC and eluted with Hex:EtOAc=1:1 to give the nitro pyran spirocyclic tetrazole (7 mg, 13% yield) as a pale white solid.

¹H NMR (300 MHz; d₆-DMSO) δ 8.61-8.62 (d, 1H, J=2.7Hz), 8.31-8.35 (dd, 1H, J=2.7 Hz, 9.0Hz), 7.58-7.61 (d, 1H, J=9.0 Hz), 3.82-3.90 (m, 4H), 2.12-2.30 (m, 4H); m/z=290 (M+H)⁺.

Synthesis of Pyran Spirocyclic Aniline

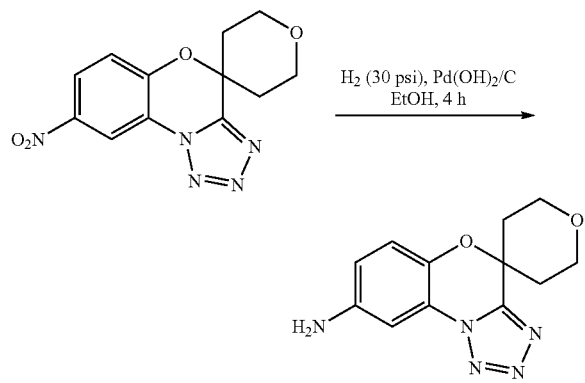

A Parr vessel was charged with nitro pyran spirocyclic tetrazole (14 mg, 0.0484 mmol), EtOH (3 mL) and 20% Pd(OH)₂/C (2.8 mg, 20 wt % by weight of the starting nitro compound) giving a suspension. The vessel was sealed, degassed, and back-filled with H₂ (×3). The vessel was then charged with 30 psi H₂ and allowed to shake for 4 h. The reaction mixture was filtered through a pad of celite, and the pad of celite was rinsed with MeOH. The filtrate was evaporated to dryness to provide pyran spirocyclic aniline (13 mg, 99% yield) as a brown solid that was used without further purification.

¹H NMR (300 MHz; d₆-DMSO) δ 7.12-7.15 (m, 1H), 7.01-7.05 (dd, 1H, J=0.9Hz, 8.7Hz), 5.35 (bs, 2H), 3.79-3.90 (m, 4H), 1.97-2.20 (m, 4H); m/z=260 (M+H)⁺.

Synthesis of N4-((7R,8aS)-5,5-dimethyloctahydroindolizin-7-yl)-5-fluoro-N2-(2',3',5',6'-tetrahydrospiro[benzo[b]tetrazolo[1,5-d][1,4] oxazine-4,4'-pyran]-8-yl)pyrimidine-2,4-diamine, formate salt (Compound 137)

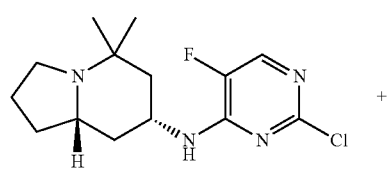

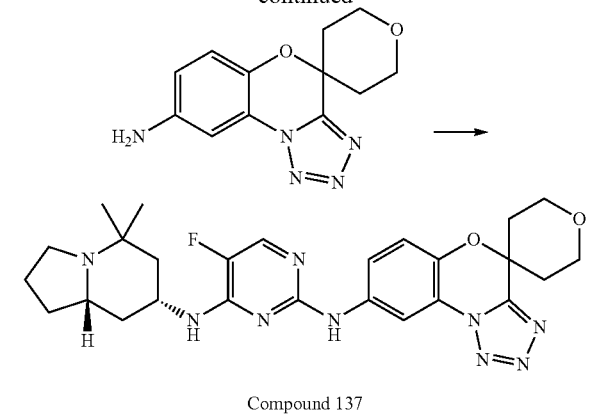

Compound 137

A mixture of pyran spirocyclic aniline (13 mg, 0.0501 mmol, 1.0 equiv), (7R,8aS)-N-(2-chloro-5-fluoropyrimidin-4-yl)-octahydro-5,5-dimethylindolizin-7-amine (20 mg, 0.0652 mmol, 1.3 equiv), and PTSA monohydrate (20 mg, 0.100 mmol, 2.0 equiv) in IPA (1 mL) was heated to reflux overnight. After cooling to ambient temperature, the crude mixture was concentrated to dryness and taken in water, EtOAc, and 1N NaOH. The layers were separated. The organic layer was washed with 1N NaOH 1×, dried over Na₂SO₄, filtered, and concentrated to dryness. The crude product was purified by reverse-phase HPLC using formic acid as the modifier to provide the semi-formate salt of Compound 137 (8.2 mg, 29% yield) as a solid.

¹H NMR (300 MHz; d₆-DMSO) δ 9.27 (s, 1H), 8.42-8.43 (d, 1H, J=1.8Hz), 8.11 (s, 0.5H, formic acid-H), 7.83-7.84 (d, 1H, J=3.0Hz), 7.58-7.62 (dd, 1H, J=1.8Hz, 9.0Hz), 7.21-7.23 (d, 1H, J=8.1Hz), 7.15-7.18 (d, 1H, J=9.0Hz), 6.49 (s, 0.5H, formic acid-OH), 4.15-4.20 (m, 1H), 3.73-3.84 (m, 4H), 2.76-2.81 (m, 1H), 0.83-2.26 (m, 20H); ¹⁹F NMR (282 MHz; d₆-DMSO) δ −166.0 (s); m/z=522 (M+H)⁺.

Example 105

Preparation of Compound 138

Synthesis of 2-(4-isopropylpiperazin-1-yl)-5-nitrobenzonitrile

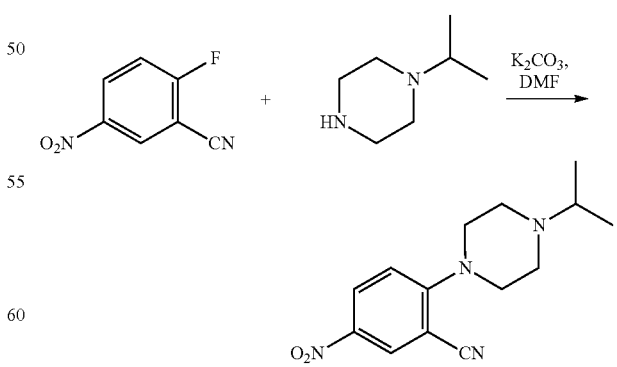

A mixture of 2-fluoro-5-nitrobenzonitrile (1.08 g, 6.50 mmol, 1 equiv), 1-isopropylpiperazine (1.0 g, 7.80 mmol, 1.2 equiv), and K₂CO₃ (2.69 g, 19.50 mmol, 3 equiv) in DMF (20 mL) was stirred at room temperature overnight.

The reaction mixture was partitioned between excess water and EtOAc, and then the layers were separated. The aqueous layer was extracted with EtOAc 2×, and the combined organic layer was washed with brine 1×. The organic layer was dried over Na$_2$SO$_4$, filtered, and concentrated to dryness to provide 2-(4-isopropylpiperazin-1-yl)-5-nitrobenzonitrile (1.76 g, 99% yield) as a brown oil that was used without further purification.

$^1$H NMR (300 MHz; d$_6$-DMSO) δ 8.49-8.50 (m, 1H), 8.24-8.29 (m, 1H), 7.20-7.24 (d, 1H, J=9.3Hz), 3.47-3.49 (m, 4H), 2.60-2.78 (m, 1H), 2.55-2.65 (m, 4H), 0.98-1.00 (d, 6H, J=6.9Hz); m/z=275 (M+H)$^+$.

Synthesis of
5-amino-2-(4-isopropylpiperazin-1-yl)benzonitrile

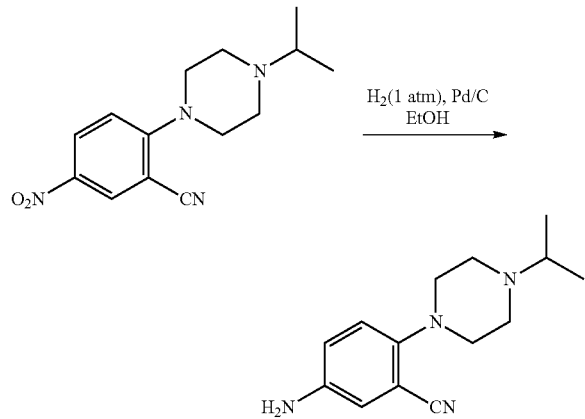

A round-bottom flask was charged with 2-(4-isopropylpiperazin-1-yl)-5-nitrobenzonitrile (1.76 g, 6.42 mmol), EtOH (65 mL), and 10% Pd/C (50% in water, Degussa type E101; 355 mg, 20 wt % by weight of the starting nitro compound). The flask was sealed with a rubber septum, degassed, and back-filled with H$_2$ (×3) from a balloon filled with H$_2$. The reaction was stirred for 2 h using a H$_2$ filled balloon. The reaction mixture was filtered through a pad of celite, and the pad of celite was rinsed with MeOH. The filtrate was evaporated to dryness, and the product dried in vacuo to provide 5-amino-2-(4-isopropylpiperazin-1-yl) benzonitrile (1.49 g, 95% yield) as a yellow solid that was used without further purification.

$^1$H NMR (300 MHz; d$_6$-DMSO) δ 6.91-6.94 (m, 1H), 6.78-6.80 (m, 2H), 5.16 (bs, 1H), 2.87 (bs, 4H), 2.60-2.78 (m, 1H), 2.55 (bs, 4H), 0.96-0.99 (m, 6H); m/z=245 (M+H)$^+$.

Synthesis of 5-(4-((7R,8aS)-octahydro-5,5-dimethylindolizin-7-ylamino)-5-fluoropyrimidin-2-ylamino)-2-(4-isopropylpiperazin-1-yl)benzonitrile (Compound 138)

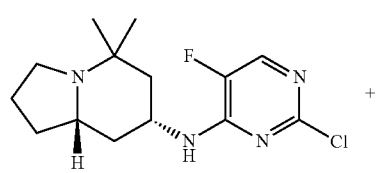

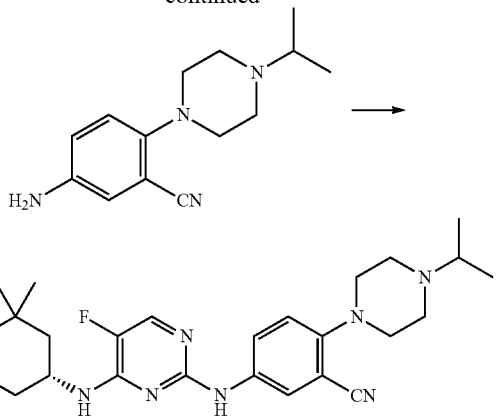

A mixture of (7R,8aS)-N-(2-chloro-5-fluoropyrimidin-4-yl)-octahydro-5,5-dimethylindolizin-7-amine (163 mg, 0.546 mmol, 1.0 equiv), 5-amino-2-(4-isopropylpiperazin-1-yl)benzonitrile (200 mg, 0.819 mmol, 1.5 equiv), and PTSA monohydrate (208 mg, 1.09 mmol, 2.0 equiv) in IPA (5 mL) was heated to reflux for 2 days. After cooling to ambient temperature, the crude mixture was concentrated to dryness and taken in water, EtOAc, and 1N NaOH. The layers were separated. The organic layer was washed with 1N NaOH 1×, dried over Na$_2$SO$_4$, filtered, and concentrated to dryness. The crude product was purified by flash chromatography and eluted with DCM:2M NH$_3$/MeOH=100:0 to 95:5 using 1% 2M NH$_3$/MeOH increments to give Compound 138 (195 mg, 71% yield) as a solid.

$^1$H NMR (300 MHz; d$_6$-DMSO) δ 9.15 (s, 1H), 8.08-8.09 (d, 1H, J=2.4Hz), 7.83-7.84 (d, 1H, J=3.6Hz), 7.72-7.76 (dd, 1H, J=2.4Hz, 9.0Hz), 7.24-7.27 (d, 1H, J=8.1Hz), 7.03-7.06 (d, 1H, J=9.3Hz), 4.15-4.20 (m, 1H), 2.93-3.08 (m, 4H), 2.80-2.86 (m, 1H), 2.52-2.72 (m, 5H), 0.98-2.32 (m, 23H); $^{19}$F NMR (282 MHz; d$_6$-DMSO) δ −166.3 (s); m/z=507 (M+H)$^+$.

Example 106

Preparation of 1-(5-(4-(((7R,8aS)-5,5-dimethyloctahydroindolizin-7-yl)(2-hydroxy-2-methylpropyl)amino)-5-fluoropyrimidin-2-ylamino)-4-fluoro-2-(2-hydroxy-2-methylpropoxy)phenyl)-4-methyl-1H-tetrazol-5(4H)-one (Compound 139)

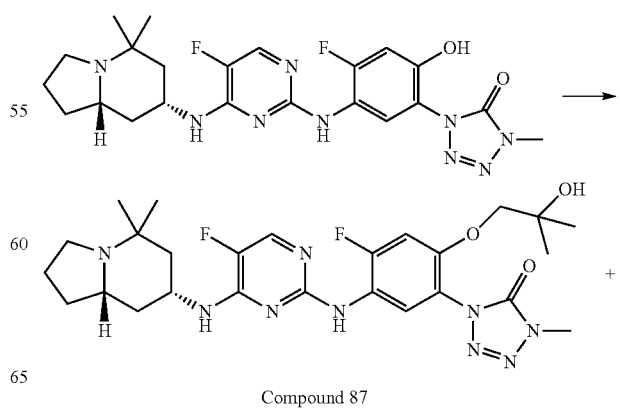

Compound 87

-continued

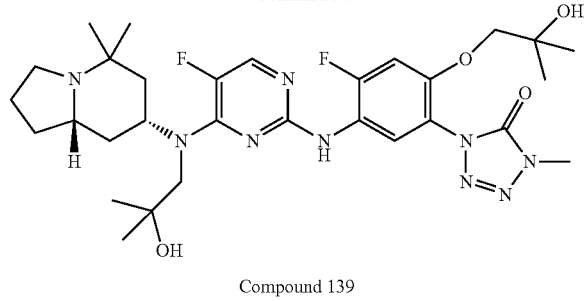

Compound 139

Compound 139 was isolated as a byproduct from mixed fractions from the synthesis of 1-(5-(4-((7R,8aS)-5,5-dimethyloctahydroindolizin-7-ylamino)-5-fluoropyrimidin-2-ylamino)-4-fluoro-2-(2-hydroxy-2-methylpropoxy)phenyl)-4-methyl-1H-tetrazol-5(4H)-one (Compound 87).

$^1$H NMR (300 MHz; d$_6$-DMSO) δ 7.77-7.79 (d, 2H, J=7.2Hz), 7.53-7.56 (d, 1H, J=9.0Hz), 6.98-7.02 (d, 1H, J=12.6Hz), 5.90 (bs, 1H), 4.49 (s, 1H), 3.83-3.94 (m, 3H), 3.63 (s, 2H), 3.56 (s, 3H), 2.71-2.89 (m, 1H), 0.62-2.16 (m, 28H); $^{19}$F NMR (282 MHz; d$_6$-DMSO) δ −116.8 (s), −170.9 (s); m/z=632 (M+H)$^+$.

Example 107

Preparation of Compounds 140-240

General Procedure for the Synthesis of Compounds Via 2$^{nd}$ S$_N$Ar

The mono-S$_N$Ar product (50.0 mg, 1.0 eq) was dissolved in 4 ml of isopropyl alcohol in a 2 dram vial. p-Toluenesulfonic acid monohydrate (1.2 eq) and the desired aniline (1.5 eq) were added and the vial was sealed. After heating overnight at 80° C. using an anodized aluminum heating block the solvent was boiled off by removing the cap. The product was isolated by preparative HPLC eluting with an acetonitrile/water gradient.

General Scheme and Procedure for Synthesis of Compound via Late-stage Alkylation

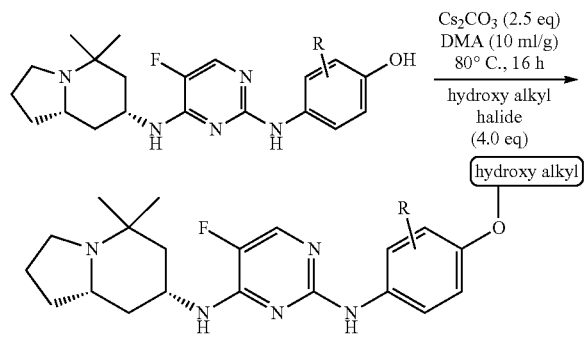

The phenol (1 mmol), the hydroxy alkyl halide (4 mmol) and Cs$_2$CO$_3$ (2.5 mmol) were placed in a pressure vessel. DMA (dimethylacetamide) (5 ml) was added and the vessel was sealed. The suspension was heated to 100° C. and stirred at this temperature for 16 hours. After cooling to room temperature, the reaction mixture was analyzed by TLC and HPLC to check for completion. The DMA was distilled off and water (10 ml) was added to the crude reaction mixture. Extraction with DCM (2×10 ml), EtOAc (1×10 ml), filtering through Na$_2$SO$_4$ and evaporation of solvents under reduced pressure yielded the crude product. This crude mixture was re-dissolved in DCM and absorbed on silica gel. Further purification was carried out with a CombiFlash Gold column (spherical silica) eluting with DCM and MeOH (2M NH$_3$) (gradient 0% to 10%).

Synthesis of N4-((7R,8aS)-5,5-dimethyloctahydroindolizin-7-yl)-5-fluoro-N2-(4-methoxy-3-(5-methyl-1H-tetrazol-1-yl)phenyl)pyrimidine-2,4-diamine, bis-formate salt (Compound 140)

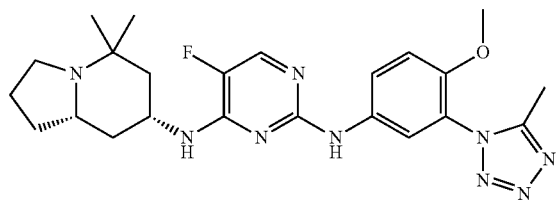 [SMILES: COc1ccc(Nc2ncc(F)c(N[C@@H]3C[C@@H]4CCCN4C(C)(C)C3)n2)cc1-n1nnnc1C]

$^1$H NMR (300 MHz, DMSO-d$_6$) δ 9.84 (s, 1H), 9.13 (s, 1H), 8.61 (s, 1H), 8.09 (d, J=4.8 Hz, 1H), 7.80-7.69 (m, 1H), 7.32 (d, J=9.0 Hz, 1H), 4.26 (s, OH), 3.45-3.28 (m, 1H), 3.22 (s, 1H), 3.04 (dd, J=10.6, 7.8 Hz, 1H), 2.38 (d, J=0.6 Hz, 3H), 2.27 (s, 3H), 2.18-1.80 (m, 3H), 1.65 (m, 2H); MS (ES) 468 (M+H).

Synthesis of N4-((7R,8aS)-5,5-dimethyloctahydroindolizin-7-yl)-5-fluoro-N2-(4-fluoro-3-(5-methyl-1H-tetrazol-1-yl)phenyl)pyrimidine-2,4-diamine, bis-formate salt (Compound 141)

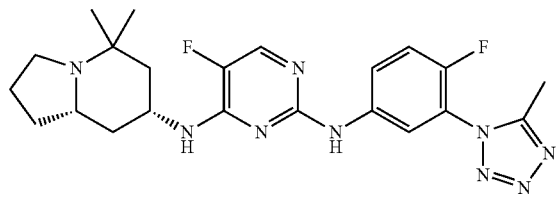 [SMILES: Cc1nnnn1-c1cc(Nc2ncc(F)c(N[C@@H]3C[C@@H]4CCCN4C(C)(C)C3)n2)ccc1F]

$^1$H NMR (300 MHz, DMSO-d$_6$) δ 9.27-9.04 (m, 1H), 8.42-8.19 (m, 1H), 8.07 (d, J=4.4 Hz, 1H), 8.01-7.83 (m, 2H), 7.56 (d, J=9.5 Hz, 1H), 4.40-4.18 (m, 1H), 3.45-3.31 (m, 1H), 3.24 (s, 1H), 3.04 (dd, J=10.7, 8.0 Hz, 1H), 2.34-2.29 (m, 1H), 2.46 (s, 3H), 2.16-1.83 (m, 4H), 1.81-1.66 (m, 1H), 1.66-1.51 (m, 2H), 1.33 (s, 3H), 1.19 (s, 3H); MS (ES) 456 (M+H).

Synthesis of N4-((7R,8aS)-5,5-dimethyloctahydroindolizin-7-yl)-5-fluoro-N2-(2-fluoro-5-(5-methyl-1H-tetrazol-1-yl)phenyl)pyrimidine-2,4-diamine, formate salt (Compound 142)

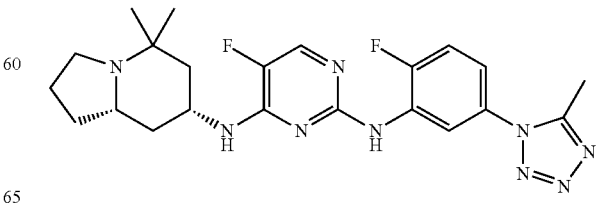

MS (ES) 456 (M+H).

Synthesis of N2-(3-(5-cyclopropyl-1H-tetrazol-1-yl)-4-fluorophenyl)-N4-((7R,8aS)-5,5-dimethyloctahydroindolizin-7-yl)-5-fluoropyrimidine-2,4-diamine, bis-formate salt (Compound 143)

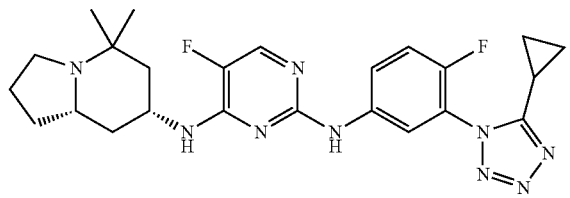 [SMILES: CC1(C)C[C@H](Nc2nc(Nc3ccc(F)c(-n4nnnc4C4CC4)c3)ncc2F)C[C@@H]2CCCN21]

¹H NMR (300 MHz, DMSO-d₆) δ 9.71 (s, 1H), 9.12 (s, 1H), 8.13-7.96 (m, 2H), 7.96-7.83 (m, 1H), 7.55 (d, J=9.4 Hz, 1H), 4.35-4.16 (m, 1H), 3.95 (m, 1H), 3.45-3.30 (m, 1H), 3.19 (d, J=10.8 Hz, 1H), 3.12-2.94 (m, 1H), 2.37-2.30 (m, 1H), 2.18-1.84 (m, 4H), 1.84-1.67 (m, 1H), 1.67-1.49 (m, 2H), 1.33 (s, 3H), 1.21 (s, 3H), 1.19-1.11 (m, 2H), 1.12-1.04 (m, 2H); MS (ES) 482 (M+H).

Synthesis of N2-(5-(5-cyclopropyl-1H-tetrazol-1-yl)-2-fluorophenyl)-N4-((7R,8aS)-5,5-dimethyloctahydroindolizin-7-yl)-5-fluoropyrimidine-2,4-diamine, bis-formate salt (Compound 144)

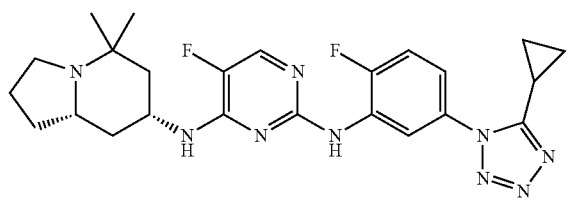

¹H NMR (300 MHz, DMSO-d₆) δ 9.18-9.02 (m, 1H), 8.82 (s, 1H), 8.30 (dd, J=7.0, 2.6 Hz, 1H), 7.95 (d, J=3.7 Hz, 1H), 7.71 (d, J=7.4 Hz, 1H), 7.36 (ddd, J=8.7, 4.1, 2.6 Hz, 1H), 4.33-4.13 (m, 1H), 3.28-3.10 (m, 3H), 3.12-2.92 (m, 1H), 2.18-1.82 (m, 5H), 1.84-1.63 (m, 1H), 1.63-1.47 (m, 2H), 1.31 (s, 3H), 1.24-1.13 (m, 5H), 1.10 (ddd, J=5.0, 3.0, 2.2 Hz, 2H); MS (ES) 482 (M+H).

Synthesis of N2-(4-chloro-3-(5-cyclopropyl-1H-tetrazol-1-yl)phenyl)-N4-((7R,8aS)-5,5-dimethyloctahydroindolizin-7-yl)-5-fluoropyrimidine-2,4-diamine, bis-formate salt (Compound 145)

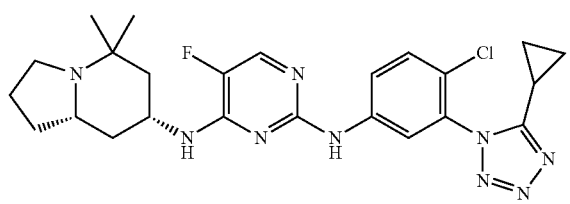 [SMILES: CC1(C)C[C@H](Nc2nc(Nc3ccc(Cl)c(-n4nnnc4C4CC4)c3)ncc2F)C[C@@H]2CCCN21]

¹H NMR (300 MHz, DMSO-d₆) δ 9.67 (s, 1H), 8.11 (d, J=5.3 Hz, 1H), 8.03-7.92 (m, 2H), 7.70-7.57 (m, 2H), 4.24 (m, 1H), 3.33 (dd, J=11.9, 5.1 Hz, 1H), 3.30-3.14 (m, 2H), 3.06 (d, J=9.6 Hz, 2H), 2.14-1.87 (m, 4H), 1.88-1.69 (m, 2H), 1.57 (q, J=12.6 Hz, 2H), 1.32 (s, 3H), 1.25 (s, 3H), 1.14 (dt, J=8.1, 2.9 Hz, 2H), 1.11-1.02 (m, 2H); MS (ES) 498 (M+H).

Synthesis of 5-chloro-N2-(4-cyclopropyl-2-fluoro-5-(1H-tetrazol-1-yl)phenyl)-N4-((7R,8aS)-5,5-dimethyloctahydroindolizin-7-yl)pyrimidine-2,4-diamine, bis-formate salt (Compound 146)

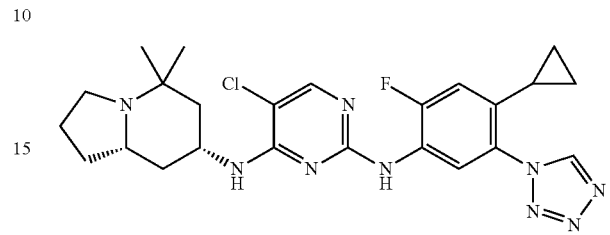

¹H NMR (300 MHz, DMSO-d₆) δ 9.87 (d, J=1.0 Hz, 1H), 9.15-8.97 (m, 1H), 8.90 (s, 1H), 8.02-7.87 (m, 2H), 7.24-7.13 (m, 1H), 4.38-4.08 (m, 1H), 3.16-2.93 (m, 3H), 2.24-1.85 (m, 5H), 1.88-1.51 (m, 2H), 1.52-1.36 (m, 1H), 1.30 (s, 3H), 1.24 (d, J=7.2 Hz, 1H), 1.08 (s, 3H), 0.76 (dd, J=8.5, 2.2 Hz, 2H), 0.63 (dd, J=5.3, 2.1 Hz, 2H); MS (ES) 498 (M+H).

Synthesis of 5-chloro-N4-((7R,8aS)-5,5-dimethyloctahydroindolizin-7-yl)-N2-(4-methyl-3-(1H-tetrazol-1-yl)phenyl)pyrimidine-2,4-diamine, bis-formate salt (Compound 147)

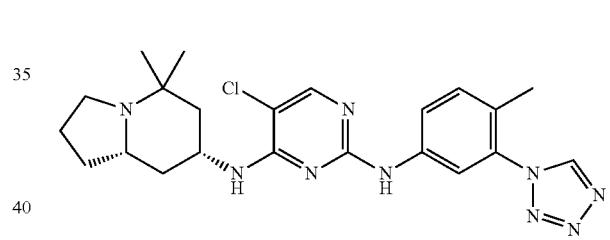

¹H NMR (300 MHz, DMSO-d₆) δ 9.88 (d, J=0.8 Hz, 1H), 9.71 (d, J=4.5 Hz, 1H), 9.19-9.04 (m, 1H), 8.16-8.02 (m, 1H), 7.87-7.73 (m, 2H), 7.46-7.30 (m, 1H), 4.52-4.21 (m, 1H), 3.90 (s, 1H), 3.47-3.25 (m, 1H), 3.03 (q, J=9.2 Hz, 1H), 2.22 (dd, J=9.5, 4.1 Hz, 1H), 2.03 (s, 3H), 2.01-1.75 (m, 4H), 1.75-1.49 (m, 2H), 1.34-1.20 (m, 5H), 1.16 (s, 3H); MS (ES) 454 (M+H).

Synthesis of 1-(5-((5-chloro-4-(((7R,8aS)-5,5-dimethyloctahydroindolizin-7-yl)amino)pyrimidin-2-yl)amino)-2-cyclopropyl-4-fluorophenyl)-4-methyl-1,4-dihydro-5H-tetrazol-5-one, formate salt (Compound 148)

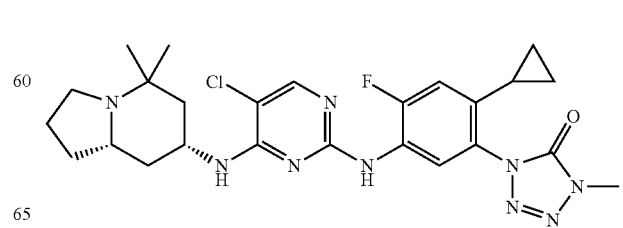

¹H NMR (300 MHz, DMSO-d₆) δ 9.17-8.93 (m, 1H), 8.82 (s, 1H), 7.93 (s, 1H), 7.66 (d, J=7.5 Hz, 1H), 7.02 (d, J=11.9 Hz, 1H), 4.37-4.07 (m, 1H), 3.61 (s, 3H), 3.27 (m, 2H), 3.14-2.90 (m, 1H), 2.25-2.03 (m, 2H), 2.04-1.83 (m, 2H), 1.84-1.48 (m, 4H), 1.29 (s, 3H), 1.09 (s, 3H), 0.84 (dd, J=8.3, 2.2 Hz, 2H), 0.75-0.56 (m, 2H); MS (ES) 528 (M+H).

Synthesis of 5-chloro-N4-((7R,8aS)-5,5-dimethyloctahydroindolizin-7-yl)-N2-(4-fluoro-3-(5-methyl-1H-tetrazol-1-yl)phenyl)pyrimidine-2,4-diamine, bis-formate salt (Compound 149)

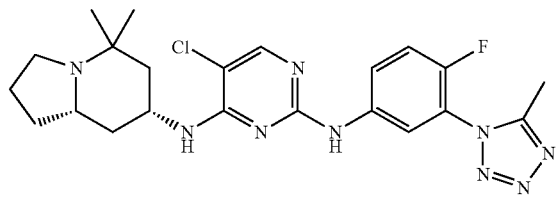 [SMILES: Cc1nnnn1-c1cc(Nc2ncc(Cl)c(N[C@@H]3C[C@@H]4CCCN4C(C)(C)C3)n2)ccc1F]

¹H NMR (300 MHz, DMSO-d₆) δ 9.64 (d, J=8.5 Hz, 1H), 9.18-8.96 (m, 1H), 8.01-7.84 (m, 2H), 7.65-7.49 (m, 1H), 7.20 (d, J=8.0 Hz, 1H), 4.33 (dt, J=12.0, 5.1 Hz, 1H), 3.27-2.95 (m, 3H), 2.42-2.28 (m, 1H), 2.27 (s, 3H), 2.17-1.90 (m, 3H), 1.92-1.72 (m, 2H), 1.73-1.51 (m, 2H), 1.34 (s, 3H), 1.22 (s, 3H); MS (ES) 472 (M+H).

Synthesis of 5-chloro-N4-((7R,8aS)-5,5-dimethyloctahydroindolizin-7-yl)-N2-(2-fluoro-5-(5-methyl-1H-tetrazol-1-yl)phenyl)pyrimidine-2,4-diamine, bis-formate salt (Compound 150)

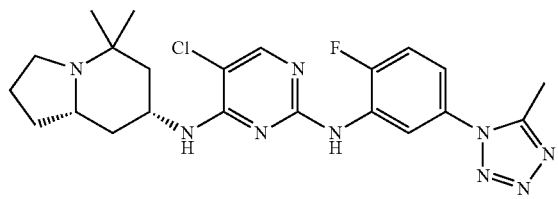 [SMILES: Cc1nnnn1-c1ccc(F)c(Nc2ncc(Cl)c(N[C@@H]3C[C@@H]4CCCN4C(C)(C)C3)n2)c1]

¹H NMR (300 MHz, DMSO-d₆) δ 9.59 (s, 1H), 9.15-8.91 (m, 1H), 8.03-7.88 (m, 2H), 7.62-7.41 (m, 1H), 7.21 (d, J=8.2 Hz, 1H), 4.30 (m, 1H), 3.25-2.92 (m, 3H), 2.39-2.20 (m, 1H), 2.21 (s, 3H), 2.15-1.94 (m, 3H), 1.91-1.68 (m, 2H), 1.71-1.55 (m, 2H), 1.31 (s, 3H), 1.25 (s, 3H); MS (ES) 472 (M+H).

Synthesis of 5-chloro-N4-((7R,8aS)-5,5-dimethyloctahydroindolizin-7-yl)-N2-(4-methoxy-3-(5-methyl-1H-tetrazol-1-yl)phenyl)pyrimidine-2,4-diamine, bis-formate salt (Compound 151)

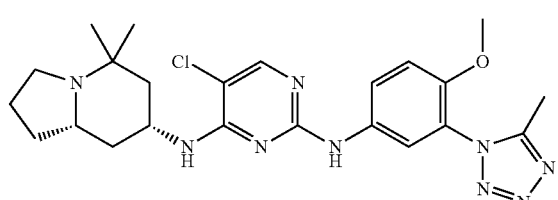

¹H NMR (300 MHz, DMSO-d₆) δ 9.38 (s, 1H), 8.06-7.95 (m, 1H), 7.92 (s, 1H), 7.75 (dd, J=9.1, 2.7 Hz, 1H), 7.24 (d, J=9.2 Hz, 1H), 6.90-6.64 (m, 1H), 4.23-4.01 (m, 1H), 3.74 (s, 3H), 3.28-3.19 (m, 2H), 2.84 (t, J=40.0 Hz, 1H), 2.36 (s, 3H), 2.13-1.82 (m, 2H), 1.82-1.38 (m, 4H), 1.25-0.98 (m, 4H), 0.79 (s, 3H); MS (ES) 484 (M+H).

Synthesis of 5-chloro-N4-((7R,8aS)-5,5-dimethyloctahydroindolizin-7-yl)-N2-(3-methoxy-5-(5-methyl-1H-tetrazol-1-yl)phenyl)pyrimidine-2,4-diamine, bis-formate salt (Compound 152)

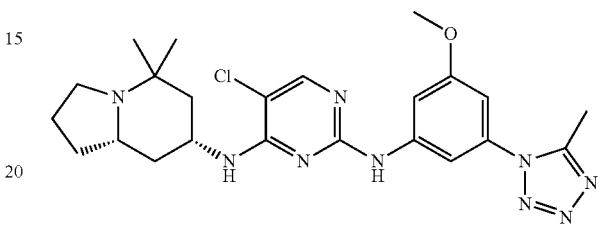

¹H NMR (300 MHz, DMSO-d₆) δ 9.61 (s, 1H), 9.31-9.04 (m, 1H), 8.03 (d, J=0.8 Hz, 1H), 7.62-7.52 (m, 1H), 7.24 (d, J=7.3 Hz, 1H), 6.84 (s, 1H), 4.50-4.18 (m, 1H), 3.78 (d, J=0.8 Hz, 3H), 3.26-2.93 (m, 3H), 2.61-2.53 (m, 1H), 2.34 (dd, J=10.3, 4.2 Hz, 1H), 2.31-2.24 (m, 4H), 2.17-1.84 (m, 2H), 1.84-1.49 (m, 3H), 1.34 (s, 3H), 1.21 (s, 3H); MS (ES) 484 (M+H).

Synthesis of 3-((5-chloro-4-(((7R,8aS)-5,5-dimethyloctahydroindolizin-7-yl)amino)pyrimidin-2-yl)amino)benzonitrile (Compound 153)

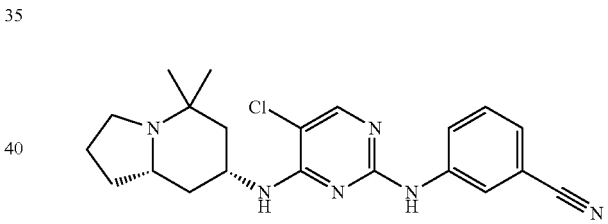

¹H NMR (300 MHz, DMSO-d₆) δ 9.57 (s, 1H), 8.23-8.14 (m, 1H), 7.96 (d, J=0.5 Hz, 1H), 7.91 (d, J=9.4 Hz, 1H), 7.39 (dd, J=8.3, 7.6 Hz, 1H), 7.30 (d, J=7.6 Hz, 1H), 6.81 (d, J=8.2 Hz, 1H), 4.36-4.13 (m, 1H), 2.82 (td, J=8.4, 3.3 Hz, 1H), 2.55 (ddd, J=11.4, 5.9, 2.8 Hz, 1H), 2.51-2.44 (m, 1H), 2.28 (q, J=8.5 Hz, 1H), 2.00 (d, J=11.7 Hz, 1H), 1.86-1.70 (m, 1H), 1.70-1.46 (m, 4H), 1.32-1.11 (m, 2H), 1.06 (s, 3H), 0.98 (s, 3H); MS (ES) 397 (M+H).

Synthesis of 5-((5-chloro-4-(((7R,8aS)-5,5-dimethyloctahydroindolizin-7-yl)amino)pyrimidin-2-yl)amino)-2-methylbenzonitrile (Compound 154)

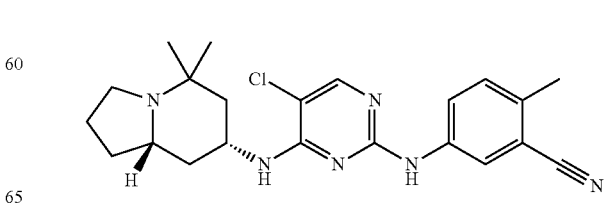

MS (ES) 411 (M+H).

Synthesis of 5-((5-chloro-4-(((7R,8aS)-5,5-dimethyloctahydroindolizin-7-yl)amino)pyrimidin-2-yl)amino)-2-cyclopropylbenzonitrile (Compound 155)

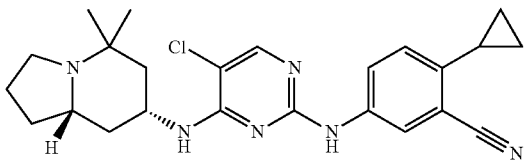 [SMILES: CC1(C)C[C@H](Nc2nc(Nc3ccc(C4CC4)c(C#N)c3)ncc2Cl)C[C@@H]2CCCN21]

MS (ES) 437 (M+H).

Synthesis of N4-((7R,8aS)-5,5-dimethyloctahydroindolizin-7-yl)-5-fluoro-N2-(3,4,5-trimethoxyphenyl)pyrimidine-2,4-diamine (Compound 156)

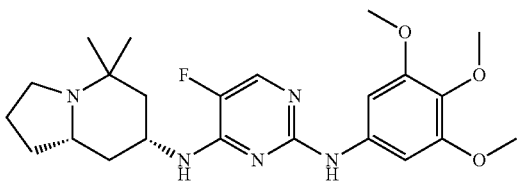 [SMILES: COc1cc(Nc2ncc(F)c(N[C@@H]3C[C@@H]4CCCN4C(C)(C)C3)n2)cc(OC)c1OC]

MS (ES) 446 (M+H).

Synthesis of N2-(2,2-dimethylbenzo[d][1,3]dioxol-5-yl)-N4-((7R,8aS)-5,5-dimethyloctahydroindolizin-7-yl)-5-fluoropyrimidine-2,4-diamine (Compound 157)

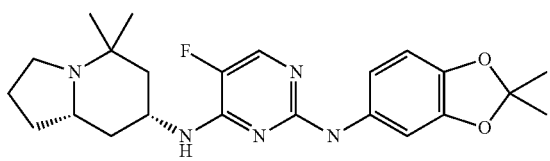 [SMILES: CC1(C)Oc2ccc(Nc3ncc(F)c(N[C@@H]4C[C@@H]5CCCN5C(C)(C)C4)n3)cc2O1]

MS (ES) 428 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(2-methoxyethoxy)phenyl)-4-methyl-1,4-dihydro-5H-tetrazol-5-one (Compound 158)

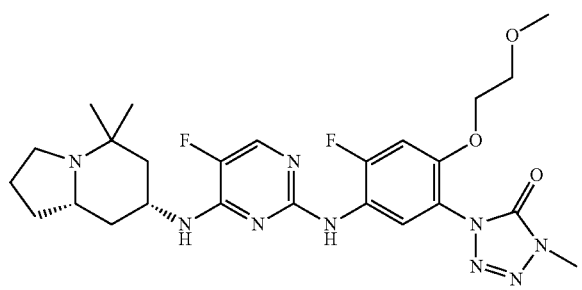 [SMILES: COCCOc1cc(F)c(Nc2ncc(F)c(N[C@@H]3C[C@@H]4CCCN4C(C)(C)C3)n2)cc1-n1nnn(C)c1=O]

¹H NMR (300 MHz, DMSO-d₆) δ 8.40 (s, 1H), 7.89 (d, J=8.4 Hz, 1H), 7.79 (d, J=3.8 Hz, 1H), 7.28 (d, J=12.5 Hz, 1H), 7.24-7.15 (m, 1H), 4.17-4.07 (m, 2H), 4.07-3.89 (m, 2H), 3.58 (s, 3H), 3.57-3.47 (m, 2H), 3.19 (s, 3H), 2.81 (dt, J=9.7, 4.9 Hz, 1H), 2.20 (q, J=9.0 Hz, 2H), 1.92 (d, J=11.2 Hz, 1H), 1.78-1.45 (m, 5H), 1.44-1.30 (m, 2H), 1.27-1.07 (m, 1H), 1.03 (s, 3H), 0.76 (s, 3H); MS (ES) 546 (M+H).

Synthesis of 1-(5-((4-(((7R,8aS)-5,5-dimethyloctahydroindolizin-7-yl)amino)-5-fluoropyrimidin-2-yl)amino)-4-fluoro-2-((3-methyloxetan-3-yl)methoxy)phenyl)-4-methyl-1,4-dihydro-5H-tetrazol-5-one (Compound 159)

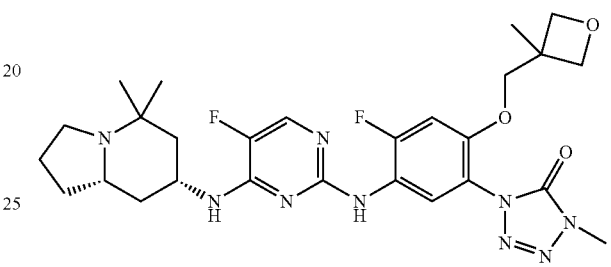

¹H NMR (300 MHz, DMSO-d₆) δ 8.41 (s, 1H), 7.98 (d, J=8.4 Hz, 1H), 7.80 (d, J=3.8 Hz, 1H), 7.30 (d, J=12.4 Hz, 1H), 7.21 (d, J=8.2 Hz, 1H), 4.31 (d, J=5.8 Hz, 2H), 4.17 (d, J=5.8 Hz, 2H), 4.07-3.89 (m, 2H), 3.55 (d, J=2.8 Hz, 2H), 3.30 (s, 3H), 2.80 (td, J=8.5, 3.1 Hz, 1H), 2.27-2.08 (m, 2H), 1.93 (d, J=11.4 Hz, 1H), 1.77-1.45 (m, 5H), 1.46-1.29 (m, 1H), 1.23-1.14 (m, 4H), 1.03 (s, 3H), 0.75 (s, 3H); MS (ES) 572 (M+H).

Synthesis of N4-((7R,8aS)-5,5-dimethyloctahydroindolizin-7-yl)-5-fluoro-N2-(2-fluoro-3,4-bis(2-methoxyethoxy)phenyl)pyrimidine-2,4-diamine, bis-TFA salt (Compound 160)

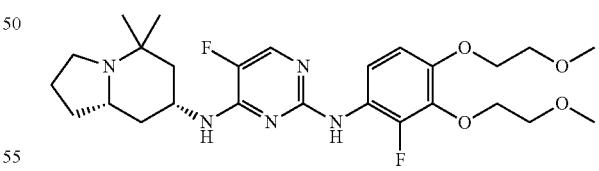

¹H NMR (300 MHz, DMSO-d₆) δ 9.72 (s, 1H), 9.23-8.98 (m, 2H), 8.13 (d, J=5.5 Hz, 1H), 7.20 (t, J=8.7 Hz, 1H), 6.90 (dd, J=9.1, 1.9 Hz, 1H), 4.19-4.01 (m, 4H), 3.72-3.62 (m, 2H), 3.62-3.53 (m, 2H), 3.31 (s, 3H), 3.27 (s, 3H), 3.02 (dd, J=10.8, 8.0 Hz, 1H), 2.23-2.03 (m, 2H), 2.03-1.82 (m, 4H), 1.73 (t, J=12.7 Hz, 2H), 1.67-1.47 (m, 2H), 1.30 (s, 2H), 1.09 (s, 2H); MS (ES) 520 (M+H).

Synthesis of N2-(3,5-dimethoxyphenyl)-N4-((7R, 8aS)-5,5-dimethyloctahydroindolizin-7-yl)-5-fluoro-pyrimidine-2,4-diamine, bis-TFA salt (Compound 161)

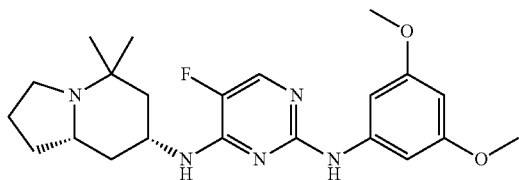 [SMILES: COc1cc(Nc2ncc(F)c(N[C@@H]3C[C@@H]4CCCN4C(C)(C)C3)n2)cc(OC)c1]

MS (ES) 416 (M+H).

Synthesis of 5-chloro-N2-(3,5-dimethoxyphenyl)-N4-((7R,8aS)-5,5-dimethyloctahydroindolizin-7-yl)pyrimidine-2,4-diamine, bis-TFA salt (Compound 162)

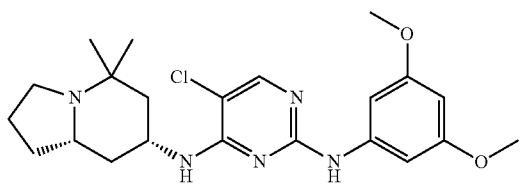 [SMILES: COc1cc(Nc2ncc(Cl)c(N[C@@H]3C[C@@H]4CCCN4C(C)(C)C3)n2)cc(OC)c1]

MS (ES) 432 (M+H).

Synthesis of 5-chloro-N2-(3-(5-cyclopropyl-1H-tetrazol-1-yl)-4-fluorophenyl)-N4-((7R,8aS)-5,5-dimethyloctahydroindolizin-7-yl)pyrimidine-2,4-diamine, bis-TFA salt (Compound 163)

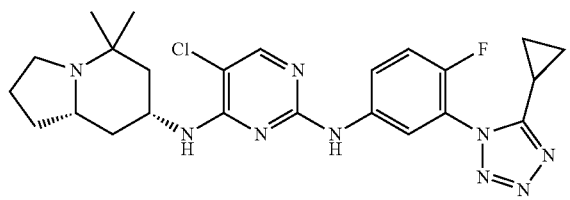

MS (ES) 498 (M+H).

Synthesis of 5-chloro-N2-(5-(5-cyclopropyl-1H-tetrazol-1-yl)-2-fluorophenyl)-N4-((7R,8aS)-5,5-dimethyloctahydroindolizin-7-yl)pyrimidine-2,4-diamine, bis-formate salt (Compound 164)

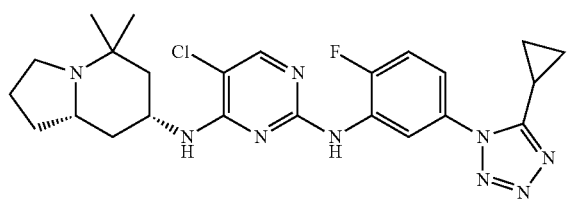 [SMILES: CC1(C)C[C@H](Nc2nc(Nc3cc(-n4nnnc4C4CC4)ccc3F)ncc2Cl)C[C@@H]2CCCN21]

MS (ES) 498 (M+H).

Synthesis of 1-(5-((4-(((7R,8aS)-5,5-dimethyloctahydroindolizin-7-yl)amino)-5-fluoropyrimidin-2-yl)amino)-4-fluoro-2-43-(hydroxymethyl)oxetan-3-yl)methoxy)phenyl)-4-methyl-1,4-dihydro-5H-tetrazol-5-one, bis-formate salt (Compound 165)

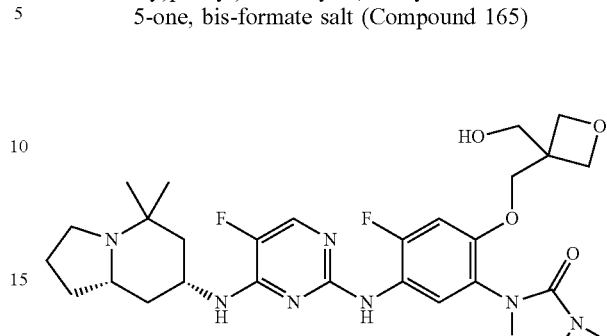

MS (ES) 588 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(oxetan-3-ylmethoxy)phenyl)-4-methyl-1,4-dihydro-5H-tetrazol-5-one, bis-formate salt (Compound 166)

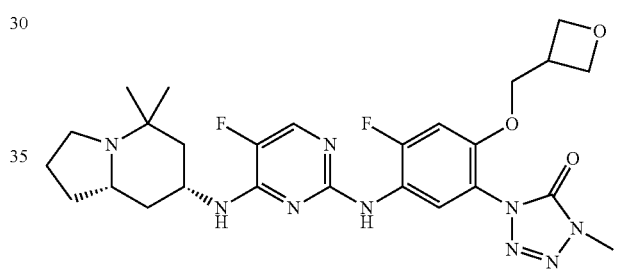

$^1$H NMR (300 MHz, DMSO-$d_6$) δ 8.42 (s, 1H), 8.21 (s, 1H), 7.96-7.84 (m, 1H), 7.79 (td, J=2.9, 1.5 Hz, 1H), 7.30 (d, J=12.3 Hz, 1H), 7.26-7.17 (m, 1H), 4.57 (dd, J=8.0, 6.0 Hz, 1H), 4.27 (t, J=6.0 Hz, 1H), 4.18 (d, J=6.0 Hz, 1H), 4.08-3.85 (m, 3H), 3.56 (s, 3H), 2.95-2.77 (m, 1H), 2.37-2.15 (m, 3H), 1.94 (d, J=11.6 Hz, 1H), 1.79-1.49 (m, 4H), 1.49-1.34 (m, 1H), 1.31-1.13 (m, 2H), 1.06 (s, 3H), 0.79 (s, 3H); MS (ES) 558 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(oxetan-2-ylmethoxy)phenyl)-4-methyl-1,4-dihydro-5H-tetrazol-5-one, bis-formate salt (Compound 167)

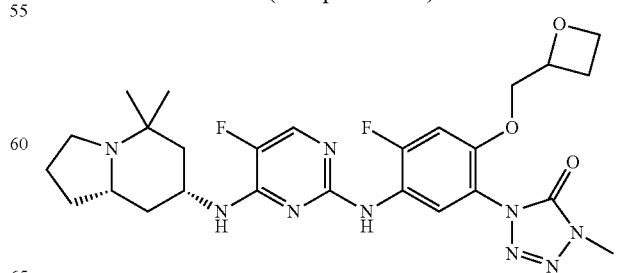

MS (ES) 558 (M+H).

Synthesis of 5-44-4(7R,8aS)-5,5-dimethyloctahydroindolizin-7-yl)amino)-5-fluoropyrimidin-2-yl)amino)-2-hydroxybenzonitrile (Compound 168)

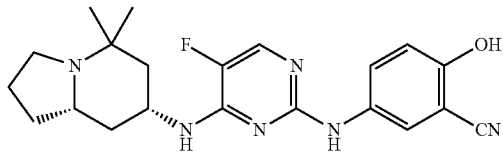

¹H NMR (300 MHz, DMSO-d₆) δ 11.01-10.10 (m, 1H), 8.99 (s, 1H), 7.91 (d, J=2.5 Hz, 1H), 7.82 (s, 1H), 7.65 (dd, J=9.1, 2.5 Hz, 1H), 7.31-7.16 (m, 1H), 6.88 (dd, J=9.0, 1.9 Hz, 1H), 4.26-4.06 (m, 1H), 2.88 (d, J=11.7 Hz, 1H), 2.55 (s, 1H), 2.45-2.19 (m, 1H), 2.02 (d, J=11.7 Hz, 1H), 1.91-1.72 (m, 2H), 1.72-1.53 (m, 3H), 1.46 (t, J=11.9 Hz, 1H), 1.35-1.14 (m, 2H), 1.09 (s, 3H), 1.00 (s, 3H); MS (ES) 397 (M+H).

Synthesis of 1-(2-((1,4-dioxan-2-yl)methoxy)-5-44-4(7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, bis-TFA salt (Compound 169)

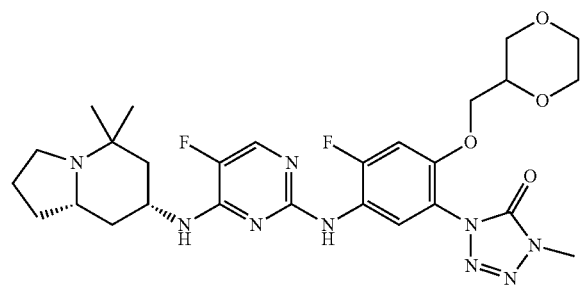 [SMILES: Cn1nnn(-c2cc(Nc3ncc(F)c(N[C@@H]4C[C@@H]5CCCN5C(C)(C)C4)n3)c(F)cc2OCC2COCCO2)c1=O]

MS (ES) 588 (M+H).

Synthesis of 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)methoxy)phenyl)-4-methyl-1,4-dihydro-5H-tetrazol-5-one, bis-TFA salt (Compound 170)

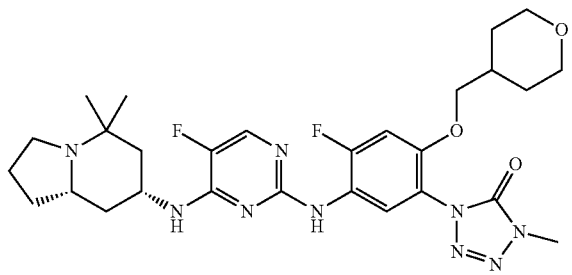 [SMILES: Cn1nnn(-c2cc(Nc3ncc(F)c(N[C@@H]4C[C@@H]5CCCN5C(C)(C)C4)n3)c(F)cc2OCC2CCOCC2)c1=O]

MS (ES) 586 (M+H).

Synthesis of 3-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)-2-oxopropanoic acid, bis-TFA salt (Compound 171)

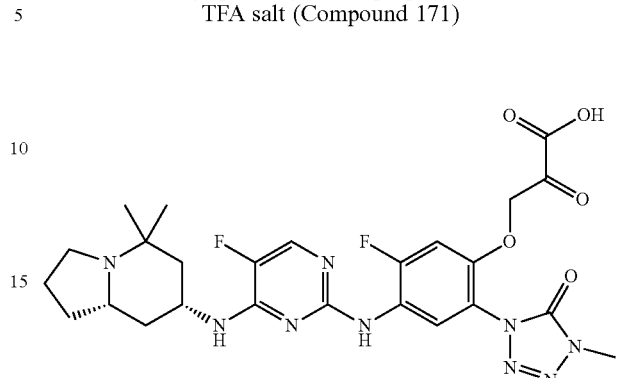

MS (ES) 574 (M+H).

Synthesis of 5-44-4(7R,8aS)-5,5-dimethyloctahydroindolizin-7-yl)amino)-5-fluoropyrimidin-2-yl)amino)-2-(2-methoxyethoxy)benzonitrile (Compound 172)

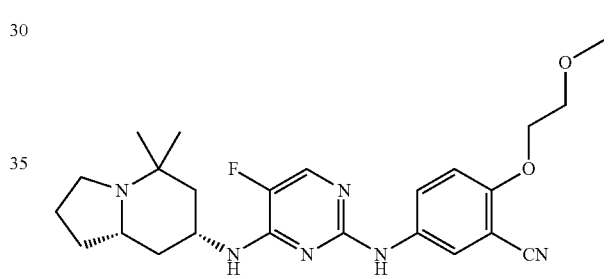

¹H NMR (300 MHz, DMSO-d₆) δ 9.12 (s, 1H), 8.09 (d, J=2.7 Hz, 1H), 7.88-7.70 (m, 2H), 7.24 (d, J=7.8 Hz, 1H), 7.11 (d, J=9.3 Hz, 1H), 4.22-4.12 (m, 2H), 3.70-3.61 (m, 2H), 3.31 (d, J=0.9 Hz, 3H), 2.83 (td, J=8.4, 3.3 Hz, 1H), 2.59-2.49 (m, 1H), 2.35-2.20 (m, 1H), 2.07-1.95 (m, 1H), 1.83-1.69 (m, 1H), 1.66-1.53 (m, 2H), 1.51-1.30 (m, 2H), 1.27-1.03 (m, 3H), 0.97 (s, 3H); MS (ES) 455 (M+H).

Synthesis of 5-(4-((7R,8aS)-5,5-dimethyloctahydroindolizin-7-ylamino)-5-fluoropyrimidin-2-ylamino)-2-((3-methyloxetan-3-yl)methoxy)benzonitrile (Compound 173)

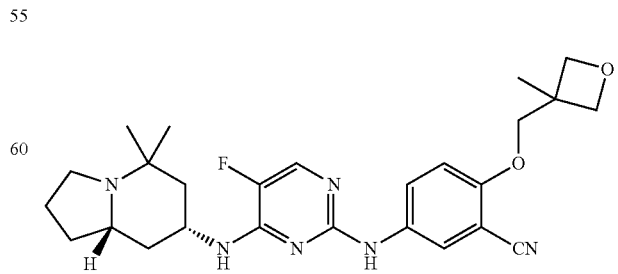

MS (ES) 481 (M+H).

503

Synthesis of 5-(4-((7R,8aS)-5,5-dimethyloctahydroindolizin-7-ylamino)-5-fluoropyrimidin-2-ylamino)-2-((3-(hydroxymethyl)oxetan-3-yl)methoxy)benzonitrile (Compound 174)

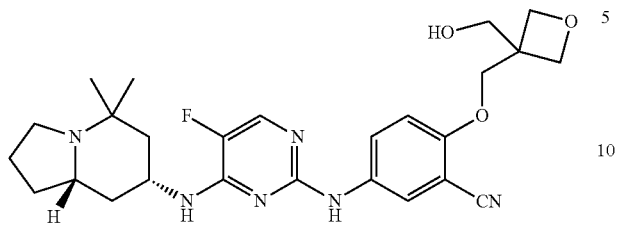

MS (ES) 497 (M+H).

Synthesis of 5-(4-((7R,8aS)-5,5-dimethyloctahydroindolizin-7-ylamino)-5-fluoropyrimidin-2-ylamino)-2-(oxetan-3-ylmethoxy)benzonitrile (Compound 175)

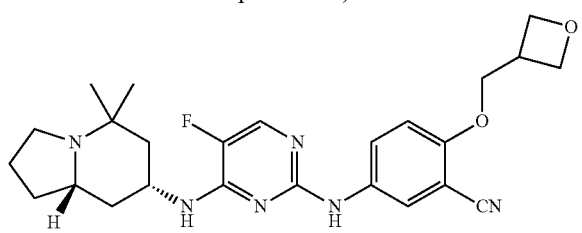

MS (ES) 467 (M+H).

Synthesis of 5-(4-((7R,8aS)-5,5-dimethyloctahydroindolizin-7-ylamino)-5-fluoropyrimidin-2-ylamino)-2-(oxetan-2-ylmethoxy)benzonitrile (Compound 176)

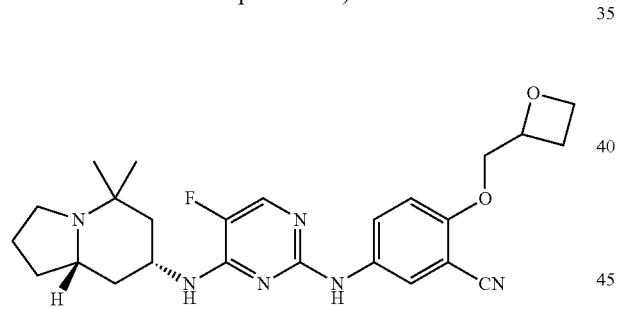

MS (ES) 467 (M+H).

Synthesis of 2-((1,4-dioxan-2-yl)methoxy)-5-(4-((7R,8aS)-5,5-dimethyloctahydroindolizin-7-ylamino)-5-fluoropyrimidin-2-ylamino)benzonitrile (Compound 177)

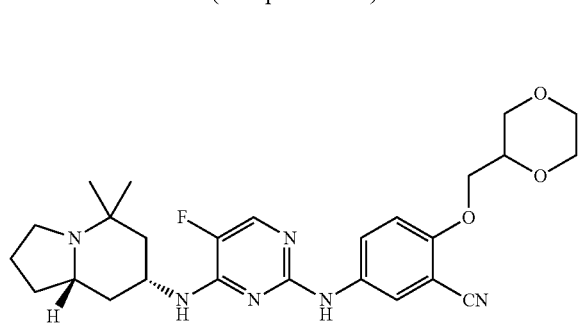

MS (ES) 497 (M+H).

504

Synthesis of 5-(4-((7R,8aS)-5,5-dimethyloctahydroindolizin-7-ylamino)-5-fluoropyrimidin-2-ylamino)-2-((tetrahydro-2H-pyran-4-yl)methoxy)benzonitrile (Compound 178)

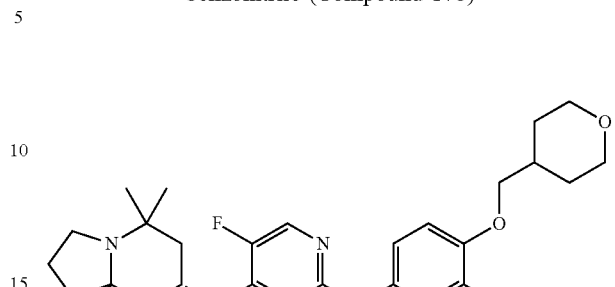

MS (ES) 495 (M+H).

Synthesis of 5-(4-((7R,8aS)-5,5-dimethyloctahydroindolizin-7-ylamino)-5-fluoropyrimidin-2-ylamino)-2-(oxetan-3-yloxy)benzonitrile, formate salt (Compound 179)

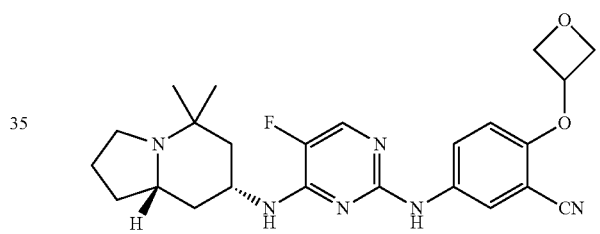

MS (ES) 453 (M+H).

Synthesis of 2-bromo-5-((4-(((7R,8aS)-5,5-dimethyloctahydroindolizin-7-yl)amino)-5-fluoropyrimidin-2-yl)amino)benzonitrile (Compound 180)

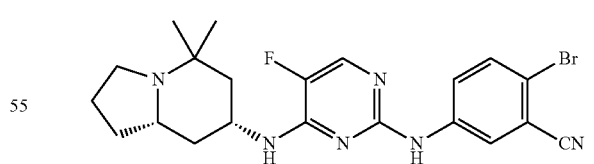

$^1$H NMR (300 MHz, DMSO-d$_6$) δ 9.53 (s, 1H), 8.32 (d, J=2.6 Hz, 1H), 7.90 (d, J=3.8 Hz, 1H), 7.80 (dd, J=9.0, 2.7 Hz, 1H), 7.63 (d, J=9.0 Hz, 1H), 7.37 (d, J=8.8 Hz, 1H), 4.15 (tdt, J=12.2, 8.3, 4.3 Hz, 1H), 2.83 (td, J=8.3, 3.2 Hz, 1H), 2.60-2.47 (m, 1H), 2.28 (q, J=8.7 Hz, 2H), 2.08-1.96 (m, 1H), 1.77 (td, J=10.8, 10.3, 4.9 Hz, 1H), 1.70-1.52 (m, 3H), 1.45 (t, J=12.1 Hz, 1H), 1.31-1.09 (m, 2H), 1.07 (s, 3H), 0.98 (s, 3H); MS (ES) 459 (M+H).

Synthesis of 5-((5-chloro-4-(((7R,8aS)-5,5-dimethyloctahydroindolizin-7-yl)amino)pyrimidin-2-yl)amino)-2-cyclopropyl-4-fluorobenzonitrile (Compound 181)

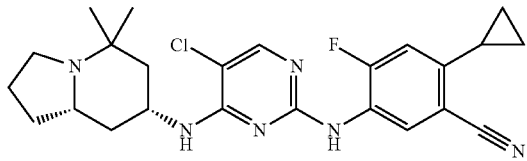 [SMILES: CC1(C)C[C@H](Nc2nc(Nc3cc(C#N)c(C4CC4)cc3F)ncc2Cl)C[C@@H]2CCCN21]

¹H NMR (300 MHz, DMSO-d₆) δ 8.77 (s, 1H), 8.10 (d, J=7.9 Hz, 1H), 7.90 (s, 1H), 6.96 (d, J=12.2 Hz, 1H), 6.74 (d, J=8.0 Hz, 1H), 4.15-3.96 (m, 1H), 2.89-2.74 (m, 1H), 2.46-2.33 (m, 1H), 2.34-2.18 (m, 1H), 2.17-2.03 (m, 1H), 1.98-1.84 (m, 1H), 1.84-1.68 (m, 1H), 1.59 (ddt, J=14.0, 10.0, 7.2 Hz, 2H), 1.51-1.36 (m, 2H), 1.29-1.06 (m, 4H), 1.04 (s, 3H), 0.83 (s, 3H), 0.81-0.77 (m, 2H); MS (ES) 455 (M+H).

Synthesis of 5-chloro-N2-(4-chloro-3-(5-cyclopropyl-1H-tetrazol-1-yl)phenyl)-N4-((7R,8aS)-5,5-dimethyloctahydroindolizin-7-yl)pyrimidine-2,4-diamine (Compound 182)

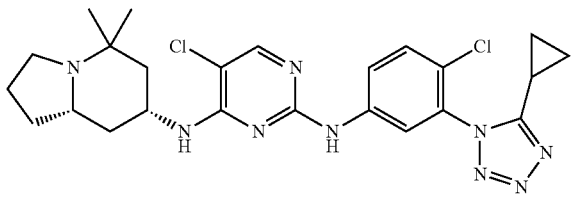 [SMILES: CC1(C)C[C@H](Nc2nc(Nc3ccc(Cl)c(-n4nnnc4C4CC4)c3)ncc2Cl)C[C@@H]2CCCN21]

¹H NMR (300 MHz, DMSO-d₆) δ 9.81 (s, 1H), 8.28 (d, J=2.5 Hz, 1H), 7.98 (s, 1H), 7.83 (dd, J=9.0, 2.6 Hz, 1H), 7.65 (d, J=9.0 Hz, 1H), 6.86 (d, J=8.2 Hz, 1H), 4.19-3.97 (m, 1H), 2.79 (d, J=6.2 Hz, 1H), 2.22 (d, J=8.6 Hz, 1H), 1.98-1.86 (m, 2H), 1.81 (tt, J=8.1, 4.8 Hz, 1H), 1.75-1.43 (m, 5H), 1.25-1.10 (m, 3H), 1.10-1.05 (m, 2H), 1.04 (s, 3H), 0.79-0.70 (m, 3H); MS (ES) 514 (M+H).

Synthesis of 5-chloro-N4-((7R,8aS)-5,5-dimethyloctahydroindolizin-7-yl)-N2-(3,4,5-trimethoxyphenyl)pyrimidine-2,4-diamine (Compound 183)

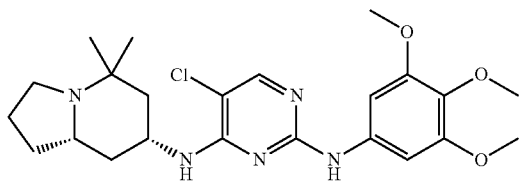 [SMILES: COc1cc(Nc2ncc(Cl)c(N[C@@H]3C[C@@H]4CCCN4C(C)(C)C3)n2)cc(OC)c1OC]

¹H NMR (300 MHz, DMSO-d₆) δ 8.88 (s, 1H), 7.90 (s, 1H), 7.01 (s, 2H), 6.59 (d, J=8.2 Hz, 1H), 4.36-4.14 (m, 1H), 3.72 (s, 6H), 3.59 (s, 3H), 2.93-2.77 (m, 1H), 2.46-2.20 (m, 2H), 2.07-1.91 (m, 1H), 1.88-1.70 (m, 1H), 1.71-1.42 (m, 3H), 1.36-1.13 (m, 3H), 1.07 (s, 3H), 0.91 (s, 3H); MS (ES) 462 (M+H).

Synthesis of ethyl 2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)propanoate (Compound 184)

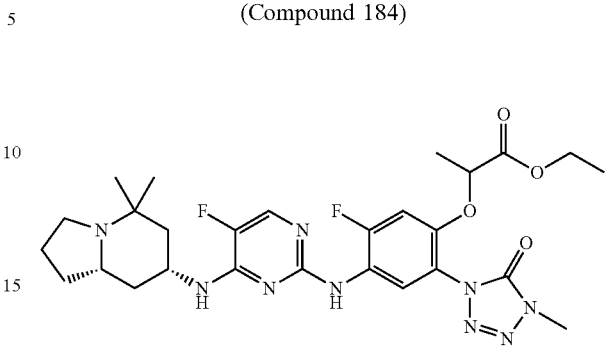

¹H NMR (300 MHz, DMSO-d₆) δ 8.45 (s, 1H), 7.92 (t, J=8.4 Hz, 1H), 7.80 (d, J=3.7 Hz, 1H), 7.24 (s, 1H), 7.17 (dd, J=12.4, 2.7 Hz, 1H), 5.08-4.93 (m, 1H), 4.10 (q, J=7.1 Hz, 3H), 4.06-3.93 (m, 1H), 3.59 (s, 3H), 2.99-2.75 (m, 1H), 2.54-2.51 (m, 1H), 2.44-2.08 (m, 1H), 2.07-1.87 (m, 1H), 1.86-1.50 (m, 8H), 1.38 (d, J=6.7 Hz, 3H), 1.15 (td, J=7.1, 0.8 Hz, 3H), 1.07 (s, 3H), 0.81 (s, 3H); MS (ES) 588 (M+H).

Synthesis of 1-(5-((4-(((7R,8aS)-5,5-dimethyloctahydroindolizin-7-yl)amino)-5-fluoropyrimidin-2-yl)amino)-4-fluoro-2-((2-oxotetrahydrofuran-3-yl)oxy)phenyl)-4-methyl-1,4-dihydro-5H-tetrazol-5-one, formate salt (Compound 185)

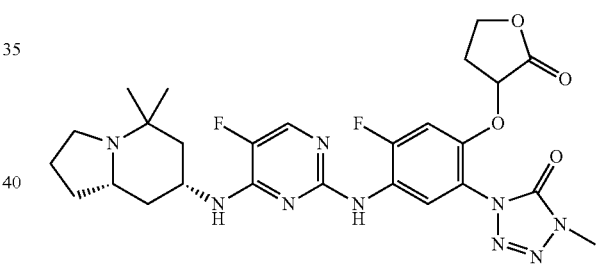

¹H NMR (300 MHz, DMSO-d₆) δ 8.40 (d, J=6.1 Hz, 1H), 8.19 (s, 1H), 7.84-7.70 (m, 2H), 7.27 (dd, J=7.6, 3.9 Hz, 1H), 6.91 (dd, J=12.6, 3.5 Hz, 1H), 4.64-4.53 (m, 1H), 4.07 (d, J=15.2 Hz, 1H), 3.59 (s, 3H), 3.42 (dt, J=7.7, 5.1 Hz, 2H), 3.20-3.02 (m, 1H), 2.96-2.77 (m, 1H), 2.78-2.61 (m, 1H), 2.52 (s, 1H), 2.10-1.97 (m, 2H), 1.91 (ddt, J=11.0, 7.2, 3.9 Hz, 1H), 1.84-1.65 (m, 3H), 1.56 (m, 1H), 1.50-1.21 (m, 2H), 1.17 (s, 3H), 1.01 (s, 3H); MS (ES) 572 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(2-hydroxyethoxy)phenyl)-4-methyl-1,4-dihydro-5H-tetrazol-5-one, formate salt (Compound 186)

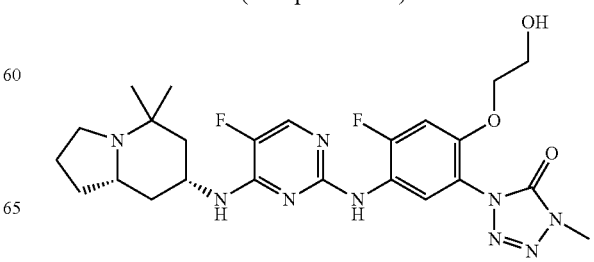

Compound 186 is the formate salt of Compound 77: ¹H NMR (300 MHz, d6-DMSO) δ 8.39 (s, 1H), 7.89 (d, J=8.4 Hz, 1H), 7.79 (d, J=3.8 Hz, 1H), 7.28 (d, J=12.5 Hz, 1H), 7.18 (d, J=7.9 Hz, 1H), 4.71 (t, J=5.6 Hz, 1H), 4.03 (t, J=4.9 Hz, 2H), 3.97 (dd, J=7.8, 4.0 Hz, 1H), 3.65-3.53 (m, 5H), 3.34 (m, 1H), 2.80 (dd, J=8.4, 5.4 Hz, 1H), 2.27-2.09 (m, 2H), 2.05 (s, 1H), 1.92 (d, J=11.4 Hz, 1H), 1.68 (dd, J=11.1, 6.6 Hz, 1H), 1.62-1.45 (m, 3H), 1.37 (t, J=12.2 Hz, 1H), 1.27-1.05 (m, 1H), 1.03 (s, 3H), 0.75 (s, 3H); ¹⁹F NMR (300 MHz, d6-DMSO) δ −116.5,−166.8; MS (ES) 532 (M+H).

Synthesis of 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)methoxy)phenyl)-4-methyl-1,4-dihydro-5H-tetrazol-5-one, TFA salt (Compound 187)

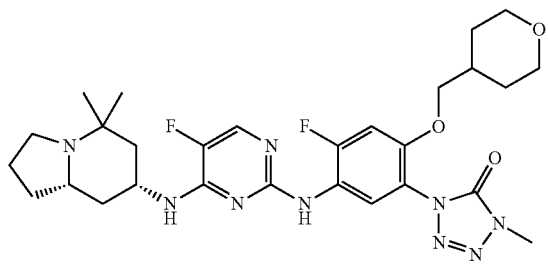 [SMILES: Cn1nnn(-c2cc(Nc3ncc(F)c(N[C@@H]4C[C@@H]5CCCN5C(C)(C)C4)n3)c(F)cc2OCC2CCOCC2)c1=O]

Compound 187 is the mono-TFA salt of Compound 170; MS (ES) 586 (M+H).

Synthesis of 1-(2-((R)-2,3-dihydroxypropoxy)-5-44-4(7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, TFA salt (Compound 188)

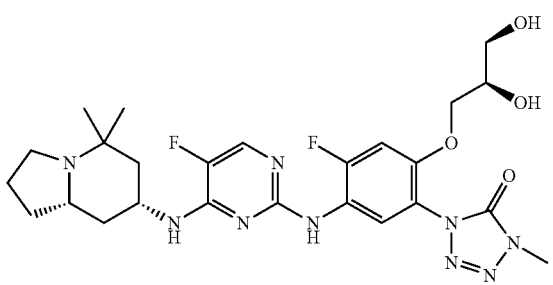

MS (ES) 562 (M+H).

Synthesis of 5-44-4(7R,8aS)-5,5-dimethyloctahydroindolizin-7-yl)amino)-5-fluoropyrimidin-2-yl)amino)-2-(2-hydroxyethoxy)benzonitrile, formate salt (Compound 189)

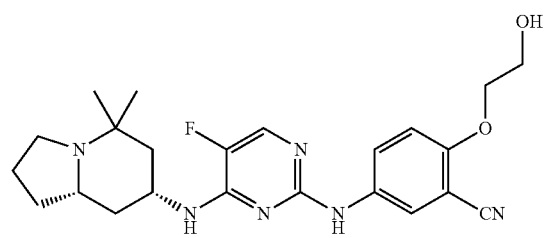 [SMILES: CC1(C)C[C@H](Nc2nc(Nc3ccc(OCCO)c(C#N)c3)ncc2F)C[C@@H]2CCCN21]

¹H NMR (300 MHz, DMSO-d₆) δ 9.19 (s, 1H), 8.16 (d, J=2.7 Hz, 1H), 7.92 (d, J=3.8 Hz, 1H), 7.83 (dd, J=9.2, 2.7 Hz, 1H), 7.33 (d, J=8.1 Hz, 1H), 7.20 (d, J=9.3 Hz, 1H), 4.24 (qd, J=7.4, 3.8 Hz, 1H), 4.15 (t, J=5.0 Hz, 2H), 3.79 (t, J=5.0 Hz, 2H), 2.92 (td, J=8.5, 3.4 Hz, 1H), 2.70-2.58 (m, 2H), 2.38 (q, J=8.5 Hz, 1H), 2.09 (d, J=12.0 Hz, 1H), 1.96-1.79 (m, 1H), 1.79-1.59 (m, 3H), 1.52 (t, J=12.2 Hz, 1H), 1.44-1.18 (m, 2H), 1.15 (s, 3H), 1.06 (s, 3H); MS (ES) 441 (M+H).

Synthesis of 5-44-4(7R,8aS)-5,5-dimethyloctahydroindolizin-7-yl)amino)-5-fluoropyrimidin-2-yl)amino)-2-(2-(2-methoxyethoxy)ethoxy)benzonitrile, formate salt (Compound 190)

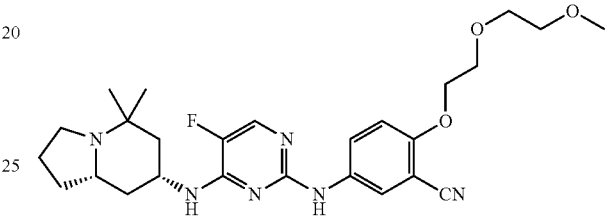

¹H NMR (300 MHz, DMSO-d₆) δ 9.13 (s, 1H), 8.12-8.05 (m, 1H), 7.85 (dd, J=3.8, 0.8 Hz, 1H), 7.75 (dd, J=9.2, 2.7 Hz, 1H), 7.29 (d, J=8.4 Hz, 1H), 7.12 (d, J=9.2 Hz, 1H), 4.17 (dd, J=5.5, 3.8 Hz, 2H), 3.79-3.69 (m, 2H), 3.64-3.54 (m, 2H), 3.48-3.40 (m, 2H), 3.23 (s, 3H), 2.92 (td, J=8.7, 3.6 Hz, 1H), 2.76-2.61 (m, 1H), 2.46-2.33 (m, 1H), 2.05 (d, J=11.9 Hz, 1H), 1.83 (td, J=11.2, 10.5, 4.3 Hz, 1H), 1.65 (dd, J=12.2, 5.4 Hz, 4H), 1.50 (t, J=12.3 Hz, 1H), 1.38-1.14 (m, 2H), 1.11 (s, 3H), 1.04 (s, 3H); MS (ES) 499 (M+H).

Synthesis of (3S,4R,5R)-2-((4(4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)tetrahydro-2H-pyran-3,4,5-triyl triacetate (Compound 191)

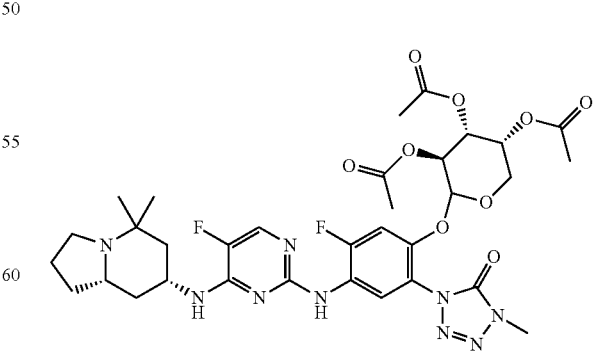

MS (ES) 746 (M+H).

Synthesis of 1-(2-(2-(dimethylamino)ethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one (Compound 192)

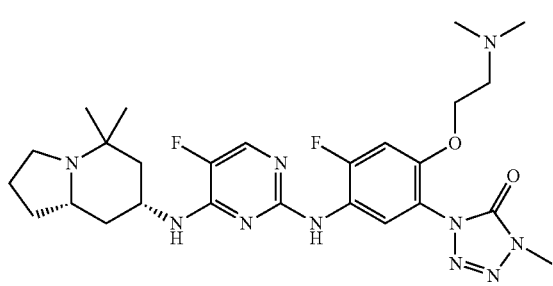 [SMILES: CN(C)CCOc1cc(F)c(Nc2ncc(F)c(N[C@@H]3C[C@@H]4CCCN4C(C)(C)C3)n2)cc1-n1nnn(C)c1=O]

MS (ES) 559 (M+H).

Synthesis of 1-(2-(2-(dimethylamino)ethoxy)-5-((2-(dimethylamino)ethyl)(4-(7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one (Compound 193)

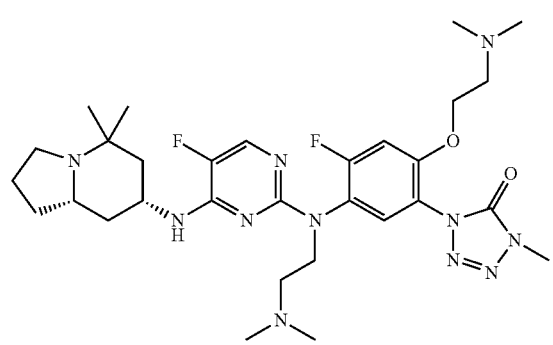 [SMILES: CN(C)CCOc1cc(F)c(N(CCN(C)C)c2ncc(F)c(N[C@@H]3C[C@@H]4CCCN4C(C)(C)C3)n2)cc1-n1nnn(C)c1=O]

MS (ES) 630 (M+H).

Synthesis of 1-(2-(2-(diethylamino)ethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, TFA salt (Compound 194)

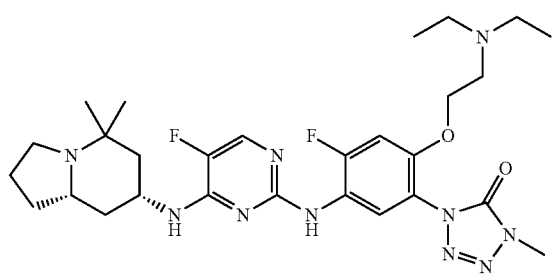 [SMILES: CCN(CC)CCOc1cc(F)c(Nc2ncc(F)c(N[C@@H]3C[C@@H]4CCCN4C(C)(C)C3)n2)cc1-n1nnn(C)c1=O]

$^1$H NMR (300 MHz, DMSO-$d_6$) δ 8.99 (s, 1H), 8.03-7.90 (m, 2H), 7.82 (d, J=8.3 Hz, 1H), 7.39 (d, J=12.1 Hz, 1H), 4.46-4.32 (m, 2H), 4.18 (s, 1H), 3.60 (s, 3H), 3.47 (d, J=4.6 Hz, 2H), 3.43-3.24 (m, 2H), 3.13 (dt, J=11.3, 5.8 Hz, 2H), 3.07-2.93 (m, 1H), 2.27 (s, 1H), 2.19-2.04 (m, 1H), 2.05-1.81 (m, 3H), 1.80-1.49 (m, 3H), 1.32 (s, 3H), 1.24-1.06 (m, 9H); MS (ES) 587 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(2-morpholinoethoxy)phenyl)-4-methyl-1,4-dihydro-5H-tetrazol-5-one (Compound 195)

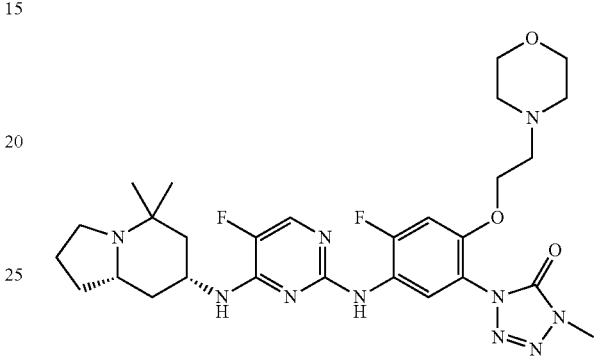

$^1$H NMR (300 MHz, DMSO-$d_6$) δ 8.39 (s, 1H), 7.88 (d, J=8.4 Hz, 1H), 7.79 (d, J=3.8 Hz, 1H), 7.28 (d, J=12.5 Hz, 1H), 7.20 (d, J=7.9 Hz, 1H), 4.10 (t, J=5.5 Hz, 2H), 4.06-3.86 (m, 2H), 3.58 (d, J=0.8 Hz, 3H), 3.54-3.44 (m, 4H), 3.42-3.22 (m, 3H), 2.93-2.76 (m, 1H), 2.56 (t, J=5.4 Hz, 2H), 2.41-2.30 (m, 4H), 2.30-2.17 (m, 2H), 1.93 (d, J=11.4 Hz, 1H), 1.79-1.47 (m, 4H), 1.38 (t, J=12.3 Hz, 1H), 1.31-1.11 (m, 1H), 1.04 (s, 3H), 0.77 (s, 3H); MS (ES) 601 (M+H).

Synthesis of 4-44-4(7R,8aS)-5,5-dimethyloctahydroindolizin-7-yl)amino)-5-fluoropyrimidin-2-yl)amino)-2-(1H-tetrazol-1-yl)phenol (Compound 196)

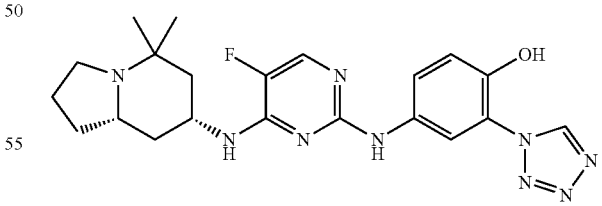

$^1$H NMR (300 MHz, DMSO-$d_6$) δ 9.75 (s, 1H), 9.06 (s, 1H), 8.05 (d, J=2.6 Hz, 1H), 7.82 (d, J=3.8 Hz, 1H), 7.61 (dd, J=9.0, 2.6 Hz, 1H), 7.17 (dd, J=8.0, 1.4 Hz, 1H), 6.99 (d, J=8.9 Hz, 1H), 4.07 (dp, J=12.1, 4.0 Hz, 1H), 2.79 (td, J=8.2, 3.7 Hz, 1H), 2.22 (q, J=8.6 Hz, 1H), 2.16-2.05 (m, 1H), 2.01-1.88 (m, 1H), 1.77-1.63 (m, 1H), 1.64-1.49 (m, 3H), 1.39 (t, J=12.3 Hz, 1H), 1.25-1.05 (m, 2H), 1.02 (s, 3H), 0.76 (s, 3H); MS (ES) 440 (M+H).

511

Synthesis of (3S,4R,5R)-2-(2-cyano-44(4-(((7R,8aS)-5,5-dimethyloctahydroindolizin-7-yl)amino)-5-fluoropyrimidin-2-yl)amino)phenoxy)tetrahydro-2H-pyran-3,4,5-triyl triacetate (Compound 197)

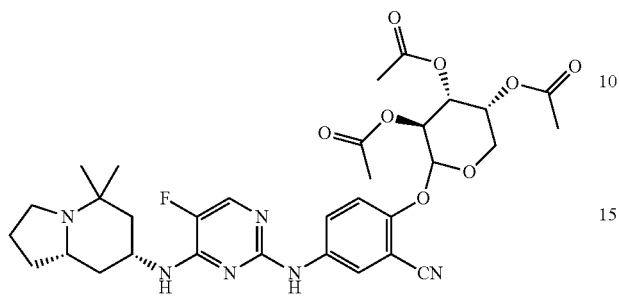

MS (ES) 655 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(2-(2-methoxyethoxy)ethoxy)phenyl)-4-methyl-1,4-dihydro-5H-tetrazol-5-one, TFA salt (Compound 198)

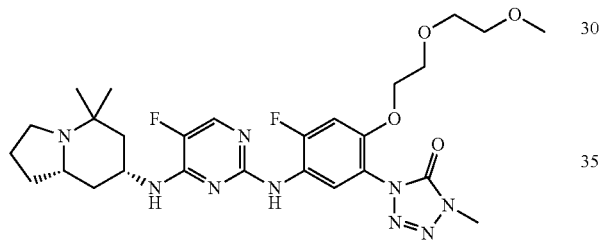

$^1$H NMR (300 MHz, DMSO-d$_6$) δ 8.92 (s, 1H), 7.94 (d, J=4.2 Hz, 2H), 7.69 (d, J=8.4 Hz, 1H), 7.33 (d, J=12.2 Hz, 1H), 4.20-4.09 (m, 2H), 3.63 (dd, J=5.7, 3.5 Hz, 2H), 3.58 (s, 3H), 3.52-3.43 (m, 2H), 3.43-3.34 (m, 2H), 3.20 (s, 3H), 3.09-2.90 (m, 1H), 2.30-2.17 (m, 2H), 2.17-2.04 (m, 1H), 2.03-1.77 (m, 4H), 1.76-1.48 (m, 4H), 1.30 (s, 3H), 1.11 (s, 3H); MS (ES) 590 (M+H).

Synthesis of 1-(2-(2,3-dihydroxypropoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, bis-TFA salt (Compound 199)

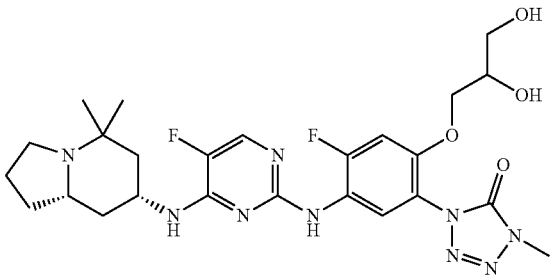 [SMILES: Cn1nnn(-c2cc(Nc3ncc(F)c(N[C@@H]4C[C@@H]5CCCN5C(C)(C)C4)n3)c(F)cc2OCC(O)CO)c1=O]

MS (ES) 562 (M+H).

512

Synthesis of 1-(5-((4-(((7R,8aS)-5,5-dimethyloctahydroindolizin-7-yl)amino)-5-fluoropyrimidin-2-yl)amino)-4-fluoro-2-(2-hydroxypropoxy)phenyl)-4-methyl-1,4-dihydro-5H-tetrazol-5-one, TFA salt (Compound 200)

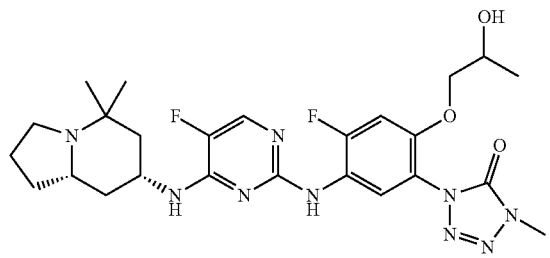 [SMILES: CC(O)COc1cc(F)c(Nc2ncc(F)c(N[C@@H]3C[C@@H]4CCCN4C(C)(C)C3)n2)cc1-n1nnn(C)c1=O]

MS (ES) 546 (M+H).

Synthesis of 5-44-4(7R,8aS)-5,5-dimethyloctahydroindolizin-7-yl)amino)-5-fluoropyrimidin-2-yl)amino)-2-(2-hydroxypropoxy)benzonitrile, formate salt (Compound 201)

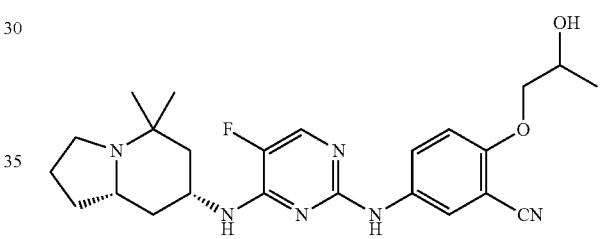

MS (ES) 455 (M+H).

Synthesis of N4-((7R,8aS)-5,5-dimethyloctahydroindolizin-7-yl)-5-fluoro-N2-(4-(2-methoxyethoxy)-3-(1H-tetrazol-1-yl)phenyl)pyrimidine-2,4-diamine, formate salt (Compound 202)

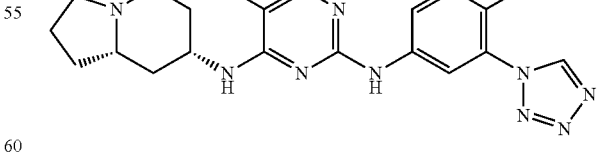

$^1$H NMR (300 MHz, DMSO-d$_6$) δ 9.72 (d, J=0.7 Hz, 1H), 9.21 (s, 1H), 8.21 (d, J=2.6 Hz, 1H), 7.84 (d, J=3.8 Hz, OH), 7.70 (dd, J=9.1, 2.6 Hz, 1H), 7.24 (dd, J=8.6, 3.7 Hz, 2H), 4.20-4.13 (m, 2H), 4.13-4.00 (m, 1H), 3.61-3.53 (m, 2H), 3.20 (s, 3H), 2.82 (td, J=8.3, 3.7 Hz, 1H), 2.23 (dq, J=20.1, 9.7, 9.1 Hz, 2H), 2.02-1.90 (m, 1H), 1.80-1.65 (m, 1H), 1.66-1.51 (m, 3H), 1.41 (t, J=12.2 Hz, 1H), 1.30-1.06 (m, 2H), 1.04 (s, 3H), 0.78 (s, 3H); MS (ES) 498 (M+H).

Synthesis of N4-((7R,8aS)-5,5-dimethyloctahydroindolizin-7-yl)-5-fluoro-N2-(4-((3-methyloxetan-3-yl)methoxy)-3-(1H-tetrazol-1-yl)phenyl)pyrimidine-2,4-diamine, formate salt (Compound 203)

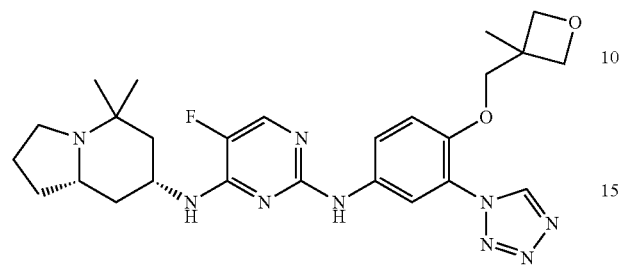

¹H NMR (300 MHz, DMSO-d₆) δ 9.74 (s, 1H), 9.22 (s, 1H), 8.23 (d, J=2.6 Hz, 1H), 7.85 (d, J=3.8 Hz, 1H), 7.71 (dd, J=9.1, 2.7 Hz, 1H), 7.28 (d, J=9.2 Hz, 1H), 7.23 (d, J=7.8 Hz, 1H), 4.33 (d, J=5.8 Hz, 2H), 4.19 (d, J=5.9 Hz, 2H), 4.06 (d, J=1.1 Hz, 2H), 2.79 (td, J=8.1, 3.7 Hz, 1H), 2.22 (q, J=8.4 Hz, 1H), 2.15-2.01 (m, 1H), 2.01-1.87 (m, 1H), 1.78-1.63 (m, 1H), 1.63-1.47 (m, 4H), 1.47-1.30 (m, 1H), 1.26-1.17 (m, 1H), 1.15 (s, 3H), 1.07 (d, J=11.7 Hz, 1H), 1.03 (s, 3H), 0.75 (s, 3H); MS (ES) 524 (M+H).

Synthesis of (3-44-((4-(((7R,8aS)-5,5-dimethyloctahydroindolizin-7-yl)amino)-5-fluoropyrimidin-2-yl)amino)-2-(1H-tetrazol-1-yl)phenoxy)methyl)oxetan-3-yl)methanol, formate salt (Compound 204)

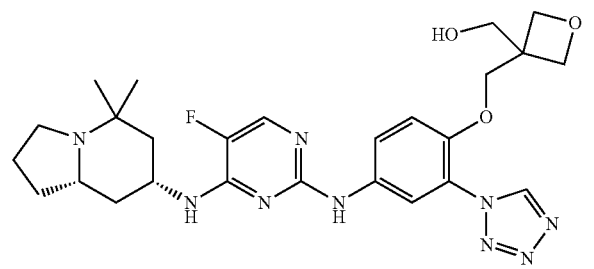 [SMILES: CC1(C)C[C@H](Nc2nc(Nc3ccc(OCC4(CO)COC4)c(-n4cnnn4)c3)ncc2F)C[C@@H]2CCCN21]

¹H NMR (300 MHz, DMSO-d₆) δ 9.72 (s, 1H), 9.23 (s, 1H), 8.21 (d, J=2.6 Hz, 1H), 8.18 (s, 1H), 7.86 (d, J=3.8 Hz, 1H), 7.72 (dd, J=9.1, 2.7 Hz, 1H), 7.28 (d, J=9.2 Hz, 1H), 4.31-4.23 (m, 4H), 4.17 (s, 2H), 3.49 (s, 2H), 2.89 (td, J=8.3, 4.3 Hz, 1H), 2.45-2.21 (m, 2H), 2.07-1.92 (m, 1H), 1.84-1.55 (m, 5H), 1.47 (t, J=12.3 Hz, 1H), 1.35-1.10 (m, 2H), 1.08 (s, 3H), 0.83 (s, 3H); MS (ES) 540 (M+H).

Synthesis of 2-(44(4-(((7R,8aS)-5,5-dimethyloctahydroindolizin-7-yl)amino)-5-fluoropyrimidin-2-yl)amino)-2-(1H-tetrazol-1-yl)phenoxy)ethan-1-ol (Compound 205)

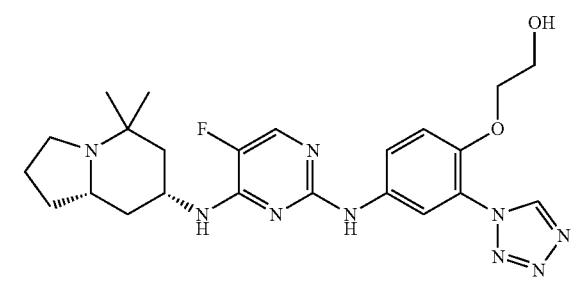 [SMILES: CC1(C)C[C@H](Nc2nc(Nc3ccc(OCCO)c(-n4cnnn4)c3)ncc2F)C[C@@H]2CCCN21]

¹H NMR (300 MHz, DMSO-d₆) δ 9.84 (s, 1H), 9.19 (s, 1H), 8.23 (d, J=2.6 Hz, 1H), 7.84 (d, J=3.8 Hz, 1H), 7.70 (dd, J=9.1, 2.7 Hz, 1H), 7.24 (d, J=9.2 Hz, 1H), 4.08 (t, J=4.8 Hz, 2H), 3.72-3.58 (m, 2H), 2.86-2.74 (m, 1H), 2.41 (q, J=1.9 Hz, 1H), 2.29-2.10 (m, 2H), 1.93 (s, 1H), 1.79-1.48 (m, 4H), 1.38 (t, J=12.2 Hz, 1H), 1.27-1.05 (m, 2H), 1.02 (s, 3H), 0.76 (s, 3H); MS (ES) 484 (M+H).

Synthesis of 1-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-2-ol, formate salt (Compound 206)

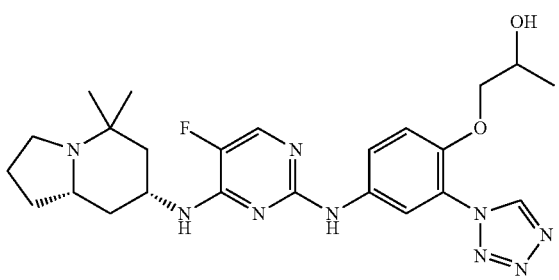 [SMILES: CC(O)COc1ccc(Nc2ncc(F)c(N[C@@H]3C[C@@H]4CCCN4C(C)(C)C3)n2)cc1-n1cnnn1]

¹H NMR (300 MHz, DMSO-d₆) δ 9.92 (s, 1H), 9.27 (s, 1H), 8.35 (s, 1H), 8.31 (dd, J=2.7, 1.1 Hz, 1H), 7.92 (d, J=3.8 Hz, 1H), 7.77 (dd, J=9.1, 2.7 Hz, 1H), 7.30 (d, J=9.2 Hz, 1H), 4.25-4.07 (m, 1H), 4.01-3.91 (m, 2H), 2.95-2.82 (m, 1H), 2.63 (p, J=1.8 Hz, 1H), 2.52-2.48 (m, 1H), 2.38-2.15 (m, 2H), 2.10-1.97 (m, 1H), 1.86-1.71 (m, 1H), 1.73-1.56 (m, 2H), 1.54-1.38 (m, 1H), 1.35-1.15 (m, 2H), 1.14-1.07 (m, 6H), 0.83 (s, 2H); MS (ES) 498 (M+H).

Synthesis of N4-((7R,8aS)-5,5-dimethyloctahydroindolizin-7-yl)-5-fluoro-N2-(4-(2-(2-methoxyethoxy)ethoxy)-3-(1H-tetrazol-1-yl)phenyl)pyrimidine-2,4-diamine (Compound 207)

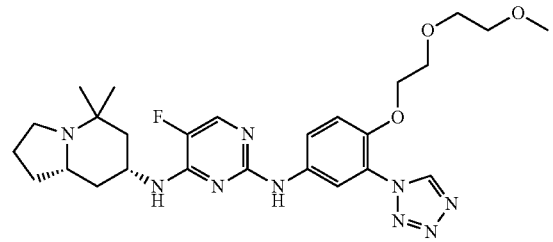 [SMILES: COCCOCCOc1ccc(Nc2ncc(F)c(N[C@@H]3C[C@@H]4CCCN4C(C)(C)C3)n2)cc1-n1cnnn1]

¹H NMR (300 MHz, DMSO-d₆) δ 9.74 (d, J=0.5 Hz, 1H), 9.20 (s, 1H), 8.23 (d, J=2.6 Hz, 1H), 7.88-7.80 (m, 1H), 7.70 (dd, J=9.1, 2.6 Hz, 1H), 7.28-7.16 (m, 2H), 4.23-4.14 (m, 2H), 4.07 (dp, J=12.0, 3.9 Hz, 1H), 3.70-3.62 (m, 2H), 3.53-3.44 (m, 2H), 3.43-3.37 (m, 2H), 3.37-3.29 (m, 1H), 3.20 (d, J=0.4 Hz, 3H), 2.79 (td, J=8.2, 3.5 Hz, 1H), 2.28-2.06 (m, 2H), 2.02-1.89 (m, 1H), 1.78-1.63 (m, 1H), 1.63-1.49 (m, 2H), 1.47-1.29 (m, 1H), 1.26-1.04 (m, 2H), 1.02 (s, 3H), 0.75 (s, 3H); MS (ES) 542 (M+H).

Synthesis of 4-44-4(7R,8aS)-5,5-dimethyloctahy-droindolizin-7-yl)amino)-5-fluoropyrimidin-2-yl)amino)-2-methoxyphenol (Compound 208)

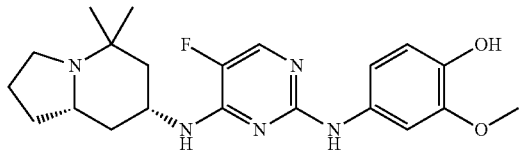 [SMILES: COc1cc(Nc2ncc(F)c(N[C@@H]3C[C@@H]4CCCN4C(C)(C)C3)n2)ccc1O]

MS (ES) 402 (M+H).

Synthesis of 5-((4-(((7R,8aS)-5,5-dimethyloctahy-droindolizin-7-yl)amino)-5-fluoropyrimidin-2-yl)amino)-2-(3,3,3-trifluoro-2-hydroxy-2-(trifluoromethyl)propoxy)benzonitrile, formate salt (Compound 209)

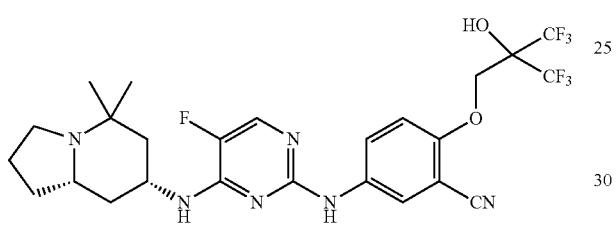

$^1$H NMR (300 MHz, DMSO-d$_6$) δ 9.21 (d, J=3.5 Hz, 1H), 8.14 (d, J=2.7 Hz, 1H), 7.87 (d, J=3.7 Hz, 1H), 7.77 (dd, J=9.2, 2.8 Hz, 1H), 7.38 (d, J=7.9 Hz, 1H), 7.23 (d, J=9.3 Hz, 1H), 4.49 (d, J=8.1 Hz, 2H), 4.32-4.11 (m, 2H), 3.76 (s, 1H), 3.03 (td, J=9.2, 8.7, 4.6 Hz, 1H), 2.98-2.83 (m, 2H), 2.70-2.51 (m, 2H), 2.23-2.05 (m, 1H), 1.91 (t, J=7.2 Hz, 1H), 1.84-1.65 (m, 3H), 1.66-1.51 (m, 1H), 1.51-1.24 (m, 2H), 1.17 (s, 3H), 1.12 (s, 3H); MS (ES) 577 (M+H).

Synthesis of 5-44-4(7R,8aS)-5,5-dimethyloctahy-droindolizin-7-yl)amino)-5-fluoropyrimidin-2-yl)amino)-2-(2-hydroxyethoxy-1,1,2,2-d4)benzonitrile, formate salt (Compound 210)

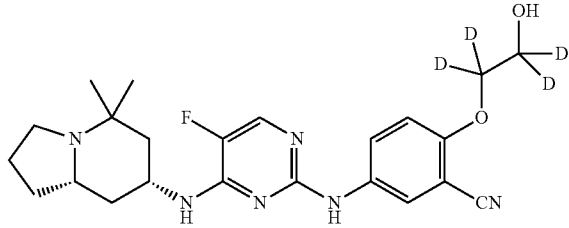 [SMILES: [2H]C([2H])(O)C([2H])([2H])Oc1ccc(Nc2ncc(F)c(N[C@@H]3C[C@@H]4CCCN4C(C)(C)C3)n2)cc1C#N]

$^1$H NMR (300 MHz, DMSO-d$_6$) δ 9.11 (s, 1H), 8.08 (d, J=2.7 Hz, 1H), 7.84 (d, J=3.9 Hz, 1H), 7.74 (dd, J=9.3, 2.8 Hz, 1H), 7.29-7.20 (m, 1H), 7.11 (d, J=9.2 Hz, 1H), 4.83 (s, 1H), 4.25-4.06 (m, 1H), 2.84 (td, J=8.3, 3.1 Hz, 1H), 2.55 (dt, J=3.8, 2.1 Hz, OH), 2.39-2.22 (m, 1H), 2.09-1.95 (m, 1H), 1.78 (dq, J=10.7, 5.3, 4.1 Hz, 1H), 1.71-1.51 (m, 3H), 1.44 (t, J=12.2 Hz, 1H), 1.32-1.11 (m, 2H), 1.07 (s, 3H), 0.98 (s, 3H); MS (ES) 445 (M+H).

Synthesis of 2-(2,3-dihydroxypropoxy)-5-((4-((2,3-dihydroxypropyl)((7R,8aS)-5,5-dimethyloctahy-droindolizin-7-yl)amino)-5-fluoropyrimidin-2-yl)amino)benzonitrile, TFA salt (Compound 211)

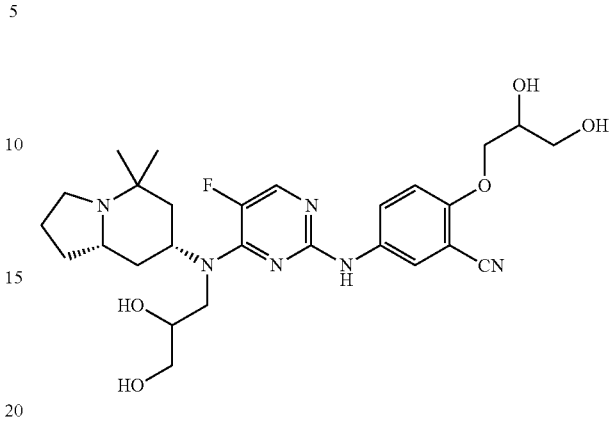

MS (ES) 545 (M+H).

Synthesis of 2-(2,3-dihydroxypropoxy)-5-44-4(7R,8aS)-5,5-dimethyloctahydroindolizin-7-yl)amino)-5-fluoropyrimidin-2-yl)amino)benzonitrile, TFA salt (Compound 212)

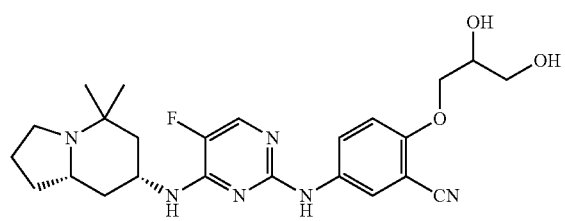 [SMILES: CC1(C)C[C@H](Nc2nc(Nc3ccc(OCC(O)CO)c(C#N)c3)ncc2F)C[C@@H]2CCCN21]

MS (ES) 471 (M+H).

Synthesis of 5-44-4(7R,8aS)-5,5-dimethyloctahy-droindolizin-7-yl)amino)-5-fluoropyrimidin-2-yl)amino)-2-(3-hydroxypropoxy)benzonitrile, TFA salt (Compound 213)

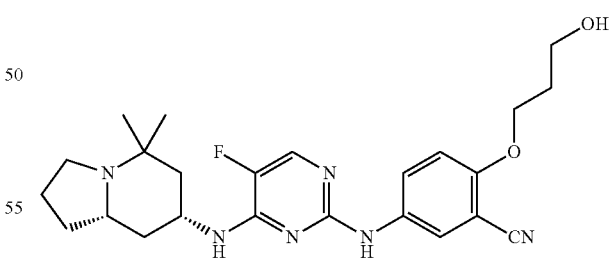

$^1$H NMR (300 MHz, DMSO-d$_6$) δ 9.64 (s, 1H), 9.44 (d, J=12.9 Hz, 1H), 8.11 (d, J=7.4 Hz, 1H), 8.02 (dd, J=3.6, 1.8 Hz, 1H), 7.98 (d, J=2.7 Hz, 1H), 7.76 (dd, J=9.2, 2.7 Hz, 1H), 7.17 (d, J=9.3 Hz, 1H), 4.28 (ddd, J=12.3, 8.1, 4.4 Hz, 1H), 4.13 (t, J=6.2 Hz, 2H), 3.56 (t, J=6.2 Hz, 2H), 3.50-3.28 (m, 2H), 3.05 (tt, J=17.2, 7.9 Hz, 1H), 2.33 (dd, J=12.8, 3.5 Hz, 1H), 2.15 (dt, J=12.0, 5.6 Hz, 1H), 2.10-1.78 (m, 7H), 1.78-1.55 (m, 4H), 1.35 (s, 3H), 1.31 (s, 3H); MS (ES) 455 (M+H).

517

Synthesis of 3-(4-((4-(((7R,8aS)-5,5-dimethylocta-hydroindolizin-7-yl)amino)-5-fluoropyrimidin-2-yl)amino)-2-(1H-tetrazol-1-yl)phenoxy)propane-1,2-diol, TFA salt (Compound 214)

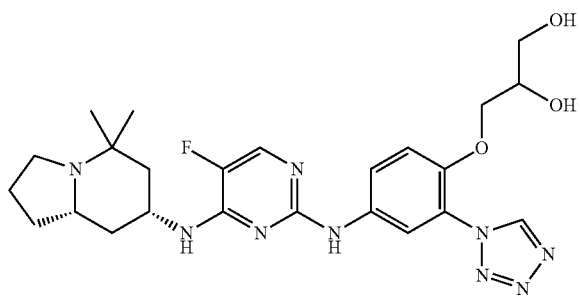 [SMILES: CC1(C)C[C@H](Nc2nc(Nc3ccc(OCC(O)CO)c(-n4cnnn4)c3)ncc2F)C[C@@H]2CCCN21]

MS (ES) 514 (M+H).

Synthesis of 3-(4-((4-(((7R,8aS)-5,5-dimethylocta-hydroindolizin-7-yl)amino)-5-fluoropyrimidin-2-yl)amino)-2-(1H-tetrazol-1-yl)phenoxy)propan-1-ol, TFA salt (Compound 215)

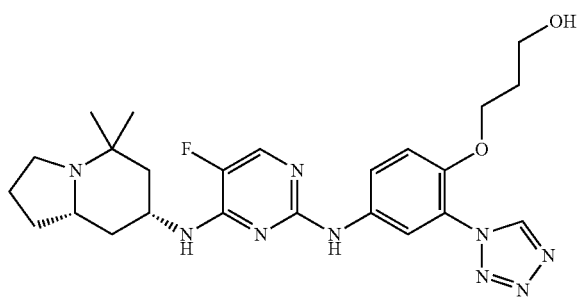 [SMILES: CC1(C)C[C@H](Nc2nc(Nc3ccc(OCCCO)c(-n4cnnn4)c3)ncc2F)C[C@@H]2CCCN21]

MS (ES) 498 (M+H).

Synthesis of 2-(4-((4-(((7R,8aS)-5,5-dimethylocta-hydroindolizin-7-yl)amino)-5-fluoropyrimidin-2-yl)amino)-2-methoxyphenoxy)ethan-1-ol (Compound 216)

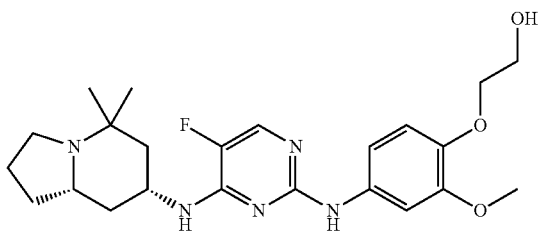 [SMILES: COc1cc(Nc2ncc(F)c(N[C@@H]3C[C@@H]4CCCN4C(C)(C)C3)n2)ccc1OCCO]

MS (ES) 446 (M+H).

518

Synthesis of 2-(4-((4-(((7R,8aS)-5,5-dimethylocta-hydroindolizin-7-yl)amino)-5-fluoropyrimidin-2-yl)amino)-2-methoxyphenoxy)ethan-1,1,2,2-d4-1-ol (Compound 217)

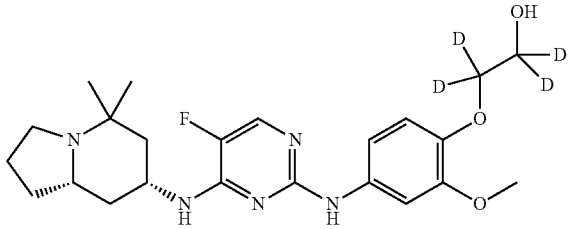 [SMILES: [2H]C([2H])(O)C([2H])([2H])Oc1ccc(Nc2ncc(F)c(N[C@@H]3C[C@@H]4CCCN4C(C)(C)C3)n2)cc1OC]

MS (ES) 450 (M+H).

Synthesis of 3-(4-((4-(((7R,8aS)-5,5-dimethylocta-hydroindolizin-7-yl)amino)-5-fluoropyrimidin-2-yl)amino)-2-(1H-tetrazol-1-yl)phenoxy)propan-1-ol (Compound 218)

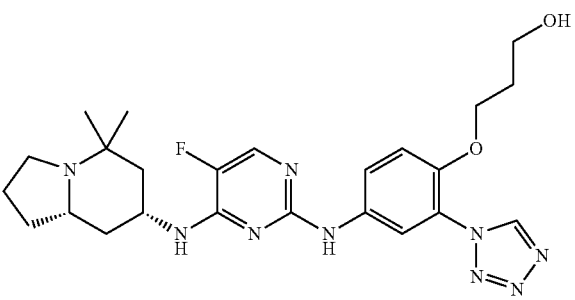 [SMILES: CC1(C)C[C@H](Nc2nc(Nc3ccc(OCCCO)c(-n4cnnn4)c3)ncc2F)C[C@@H]2CCCN21]

Compound 218 is the freebase of Compound 215.

Synthesis of 5-44-4(7R,8aS)-5,5-dimethyloctahy-droindolizin-7-yl)amino)-5-fluoropyrimidin-2-yl)amino)-2-(2-hydroxyethoxy-1,1,2,2-d4)benzonitrile (Compound 219)

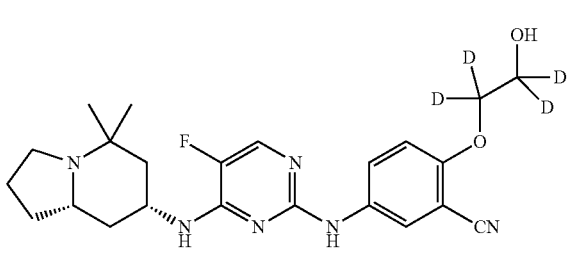 [SMILES: [2H]C([2H])(O)C([2H])([2H])Oc1ccc(Nc2ncc(F)c(N[C@@H]3C[C@@H]4CCCN4C(C)(C)C3)n2)cc1C#N]

Compound 219 is the freebase of Compound 210); MS (ES) 445 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(2-hydroxypropoxy)phenyl)-4-methyl-1,4-dihydro-5H-tetrazol-5-one (Compound 220)

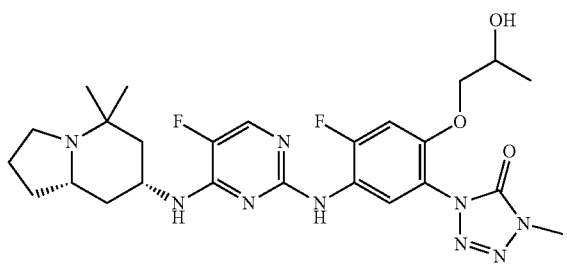 [SMILES: CC(O)COc1cc(F)c(Nc2ncc(F)c(N[C@@H]3C[C@@H]4CCCN4C(C)(C)C3)n2)cc1-n1nnn(C)c1=O]

Compound 220 is the freebase of Compound 200; MS (ES) 546 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(2-hydroxyethoxy-1,1,2,2-d4)phenyl)-4-methyl-1,4-dihydro-5H-tetrazol-5-one (Compound 221)

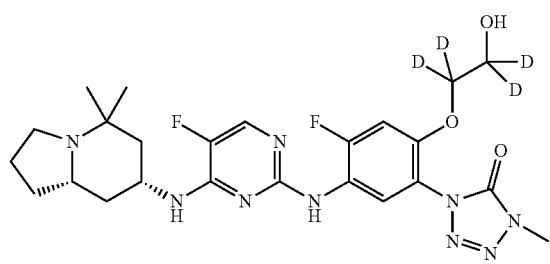 [SMILES: [2H]C([2H])(O)C([2H])([2H])Oc1cc(F)c(Nc2ncc(F)c(N[C@@H]3C[C@@H]4CCCN4C(C)(C)C3)n2)cc1-n1nnn(C)c1=O]

MS (ES) 536 (M+H).

Synthesis of 1-(5-((4-(((7R,8aS)-5,5-dimethyloctahydroindolizin-7-yl)amino)-5-fluoropyrimidin-2-yl)amino)-4-fluoro-2-((R)-3-hydroxy-2-methylpropoxy)phenyl)-4-methyl-1,4-dihydro-5H-tetrazol-5-one (Compound 222)

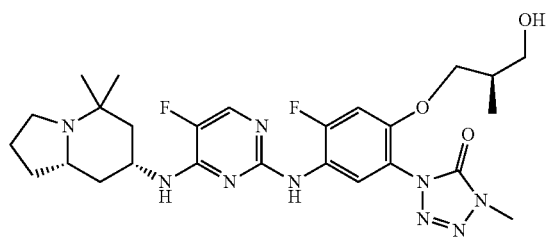 [SMILES: C[C@H](CO)COc1cc(F)c(Nc2ncc(F)c(N[C@@H]3C[C@@H]4CCCN4C(C)(C)C3)n2)cc1-n1nnn(C)c1=O]

$^1$H NMR (300 MHz, DMSO-$d_6$) δ 8.38 (s, 2H), 7.88 (d, J=8.3 Hz, 1H), 7.78 (d, J=3.8 Hz, 1H), 7.27-7.14 (m, 3H), 4.07-3.78 (m, 2H), 3.58 (s, 3H), 3.34-3.16 (m, 2H), 2.82 (dt, J=9.6, 4.8 Hz, 2H), 2.21 (dt, J=14.3, 7.2 Hz, 2H), 2.02-1.75 (m, 1H), 1.76-1.46 (m, 4H), 1.45-1.29 (m, 1H), 1.28-1.08 (m, 2H), 1.04 (s, 3H), 0.92-0.83 (m, 1H), 0.80 (d, J=6.8 Hz, 3H), 0.76 (s, 3H); MS (ES) 560 (M+H).

Synthesis of 2-(4-((5-chloro-4-(((7R,8aS)-5,5-dimethyloctahydroindolizin-7-yl)amino)pyrimidin-2-yl)amino)-2-(1H-tetrazol-1-yl)phenoxy)ethan-1-ol (Compound 223)

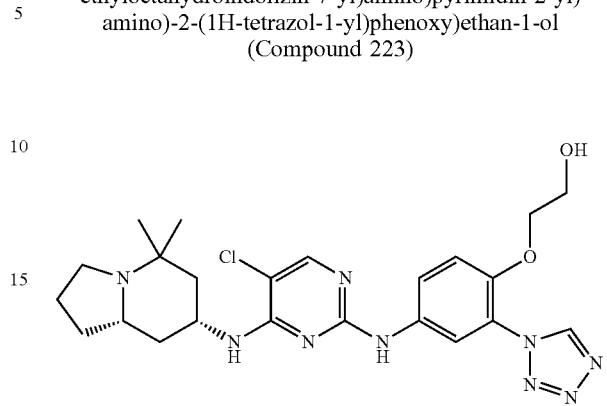

$^1$H NMR (300 MHz, DMSO-$d_6$) δ 9.89 (s, 1H), 9.50 (s, 1H), 9.09 (s, 1H), 8.15-8.09 (m, 1H), 7.72 (dd, J=9.1, 2.7 Hz, 1H), 7.30 (dd, J=9.2, 0.9 Hz, 1H), 7.22 (d, J=7.7 Hz, 1H), 4.11 (ddd, J=5.1, 4.1, 2.0 Hz, 2H), 3.73-3.64 (m, 2H), 3.12-2.94 (m, 1H), 2.56-2.50 (m, 1H), 2.37-2.27 (m, 2H), 2.19-1.87 (m, 4H), 1.82 (d, J=13.0 Hz, 1H), 1.77-1.51 (m, 3H), 1.32 (s, 3H), 1.18 (s, 3H); MS (ES) 500 (M+H).

Synthesis of 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol, formate salt (Compound 224)

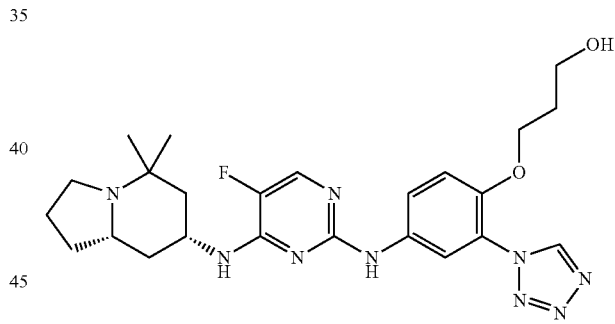

MS (ES) 498 (M+H).

Synthesis of 1-(2-(3-(benzyloxy)cyclobutoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one (Compound 225)

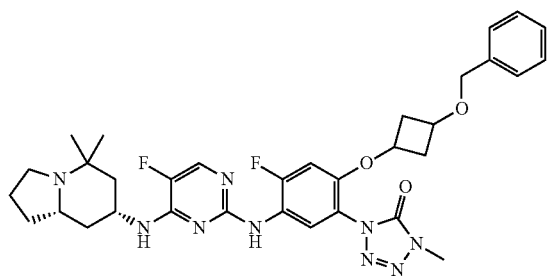 [SMILES: Cn1nnn(-c2cc(Nc3ncc(F)c(N[C@@H]4C[C@@H]5CCCN5C(C)(C)C4)n3)c(F)cc2OC2CC(OCc3ccccc3)C2)c1=O]

MS (ES) 648 (M+H).

521

Synthesis of tert-butyl (2-(4-44-4(7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)ethyl)carbamate (Compound 226)

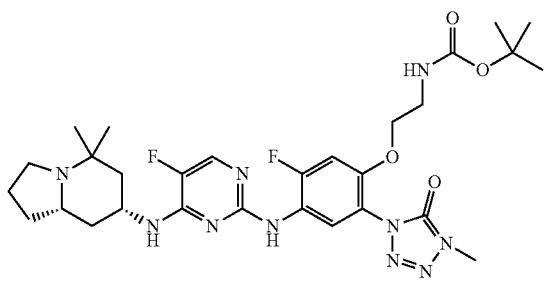

MS (ES) 631 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(3-hydroxycyclobutoxy)phenyl)-4-methyl-1,4-dihydro-5H-tetrazol-5-one (Compound 227)

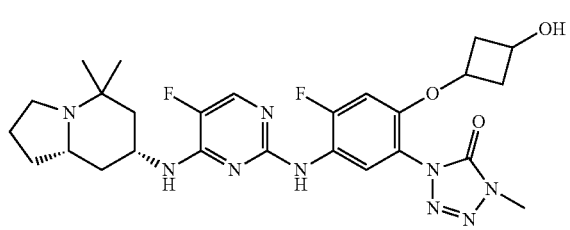 [SMILES: Cn1nnn(-c2cc(Nc3ncc(F)c(N[C@@H]4C[C@@H]5CCCN5C(C)(C)C4)n3)c(F)cc2OC2CC(O)C2)c1=O]

$^1$H NMR (300 MHz, Chloroform-d) δ 8.43 (d, J=8.6 Hz, 1H), 7.68 (d, J=3.2 Hz, 1H), 7.19 (s, 1H), 6.85 (d, J=3.2 Hz, 1H), 6.58 (d, J=12.4 Hz, 1H), 4.93-4.82 (m, 1H), 4.77 (tq, J=9.4, 3.4, 2.8 Hz, 1H), 4.51 (tt, J=6.9, 4.8 Hz, 1H), 4.11 (dtd, J=12.1, 7.9, 4.2 Hz, 1H), 3.63 (d, J=2.7 Hz, 5H), 2.99 (td, J=8.7, 3.1 Hz, 1H), 2.56-2.17 (m, 4H), 1.92-1.57 (m, 5H), 1.54-1.34 (m, 3H), 1.16 (s, 3H), 1.14-1.04 (m, 1H), 0.92 (s, 3H), 0.88-0.71 (m, 1H); MS (ES) 558 (M+H).

Synthesis of 1-(2-(2-aminoethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one (Compound 228)

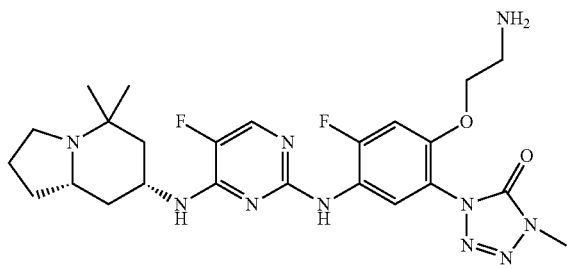 [SMILES: Cn1nnn(-c2cc(Nc3ncc(F)c(N[C@@H]4C[C@@H]5CCCN5C(C)(C)C4)n3)c(F)cc2OCCN)c1=O]

522

$^1$H NMR (300 MHz, DMSO-d$_6$) δ 8.40 (s, 1H), 7.88 (d, J=8.4 Hz, 1H), 7.79 (d, J=3.7 Hz, 1H), 7.27 (d, J=12.5 Hz, 1H), 7.23-7.14 (m, 1H), 4.09-3.88 (m, 4H), 3.59 (s, 3H), 2.81 (t, J=5.4 Hz, 3H), 2.20 (p, J=7.2, 6.2 Hz, 2H), 1.99-1.85 (m, 1H), 1.78-1.47 (m, 4H), 1.45-1.31 (m, 1H), 1.28-1.08 (m, 1H), 1.03 (s, 3H), 0.75 (s, 3H); MS (ES) 531 (M+H).

Synthesis of 5-((5-chloro-4-(((7R,8aS)-5,5-dimethyloctahydroindolizin-7-yl)amino)pyrimidin-2-yl)amino)-2-(2-hydroxypropoxy)benzonitrile, formate salt (Compound 229)

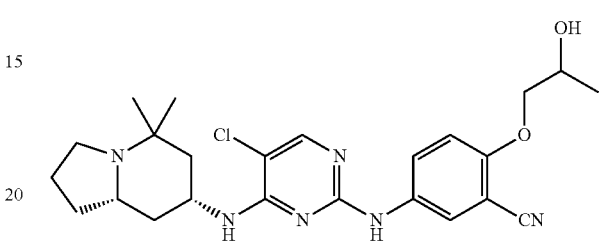

MS (ES) 471 (M+H).

Synthesis of 1-(5-((4-(((7R,8aS)-5,5-dimethyloctahydroindolizin-7-yl)amino)-5-fluoropyrimidin-2-yl)amino)-4-fluoro-2-(3,3,3-trifluoro-2-hydroxypropoxy)phenyl)-4-methyl-1,4-dihydro-5H-tetrazol-5-one, formate salt (Compound 230)

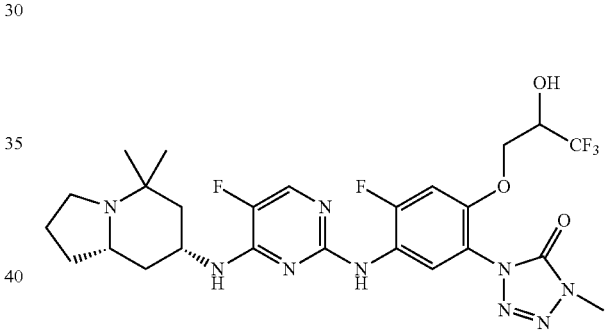

$^1$H NMR (300 MHz, DMSO-d$_6$) δ 8.44 (s, 1H), 8.19 (s, 1H), 7.91 (dd, J=8.4, 1.9 Hz, 1H), 7.80 (d, J=3.8 Hz, 1H), 7.37 (d, J=12.3 Hz, 1H), 7.30-7.19 (m, 1H), 4.31-4.17 (m, 1H), 4.15 (d, J=4.1 Hz, 2H), 4.08-3.89 (m, 1H), 3.57 (s, 3H), 2.86 (td, J=8.4, 3.3 Hz, 1H), 2.29 (q, J=8.6 Hz, 2H), 1.93 (dd, J=8.9, 5.5 Hz, 1H), 1.81-1.50 (m, 4H), 1.41 (t, J=12.3 Hz, 1H), 1.22 (qd, J=12.2, 11.6, 8.0 Hz, 1H), 1.06 (s, 3H), 0.80 (s, 3H); MS (ES) 600 (M+H).

Synthesis of 1-(2-(2-aminoethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, formate salt (Compound 231)

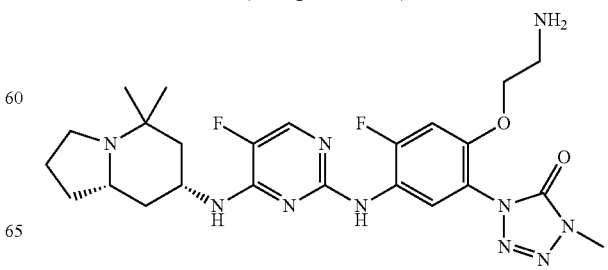

Compound 231 is the formate salt of Compound 228.

Synthesis of 1-(5-((5-chloro-4-(((7R,8aS)-5,5-dimethyloctahydroindolizin-7-yl)amino)pyrimidin-2-yl)amino)-4-fluoro-2-hydroxyphenyl)-4-methyl-1,4-dihydro-5H-tetrazol-5-one (Compound 232)

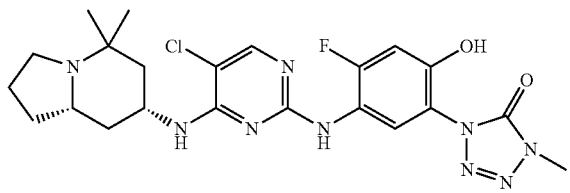 [SMILES: Cn1nnn(-c2cc(Nc3ncc(Cl)c(N[C@@H]4C[C@@H]5CCCN5C(C)(C)C4)n3)c(F)cc2O)c1=O]

MS (ES) 504 (M+H).

Synthesis of 1-(5-((4-(((7R,8aS)-5,5-dimethyloctahydroindolizin-7-yl)amino)-5-fluoropyrimidin-2-yl)amino)-4-fluoro-2-((S)-2-methoxypropoxy)phenyl)-4-methyl-1,4-dihydro-5H-tetrazol-5-one (Compound 233)

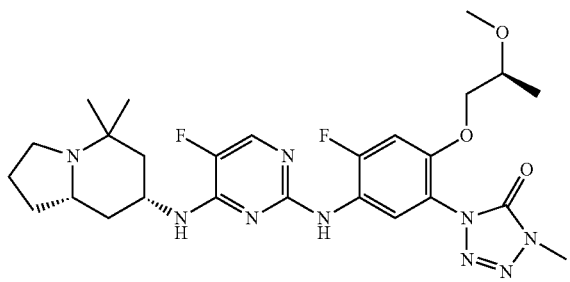 [SMILES: CO[C@@H](C)COc1cc(F)c(Nc2ncc(F)c(N[C@@H]3C[C@@H]4CCCN4C(C)(C)C3)n2)cc1-n1nnn(C)c1=O]

$^1$H NMR (300 MHz, DMSO-d$_6$) δ 8.39 (d, J=1.4 Hz, 1H), 7.91 (d, J=8.4 Hz, 1H), 7.79 (d, J=3.8 Hz, 1H), 7.27 (d, J=12.5 Hz, 1H), 7.23-7.16 (m, 1H), 4.07-3.85 (m, 2H), 3.58 (s, 3H), 3.55-3.39 (m, 3H), 2.80 (td, J=8.4, 3.1 Hz, 1H), 2.27-2.09 (m, 2H), 1.91 (d, J=11.7 Hz, 1H), 1.76-1.45 (m, 4H), 1.38 (t, J=12.2 Hz, 1H), 1.28-1.07 (m, 1H), 1.03 (d, J=2.1 Hz, 3H), 1.02 (s, 3H), 0.75 (s, 3H).

Synthesis of 1-(5-((4-(((7R,8aS)-5,5-dimethyloctahydroindolizin-7-yl)((S)-2-methoxypropyl)amino)-5-fluoropyrimidin-2-yl)amino)-4-fluoro-2-((S)-2-methoxypropoxy)phenyl)-4-methyl-1,4-dihydro-5H-tetrazol-5-one (Compound 234)

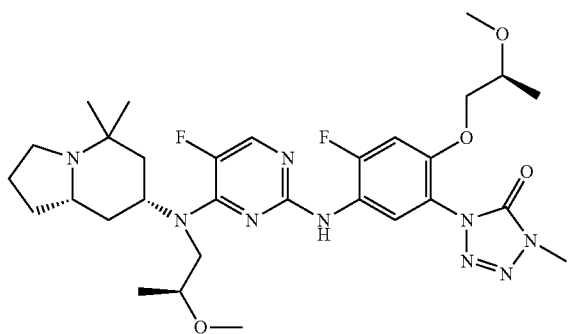 [SMILES: CO[C@@H](C)COc1cc(F)c(Nc2ncc(F)c(N(C[C@H](C)OC)[C@@H]3C[C@@H]4CCCN4C(C)(C)C3)n2)cc1-n1nnn(C)c1=O]

MS (ES) 632 (M+H).

Synthesis of 1-(5-((5-chloro-4-(((7R,8aS)-5,5-dimethyloctahydroindolizin-7-yl)amino)pyrimidin-2-yl)amino)-4-fluoro-2-((S)-2-hydroxypropoxy)phenyl)-4-methyl-1,4-dihydro-5H-tetrazol-5-one, formate salt (Compound 235)

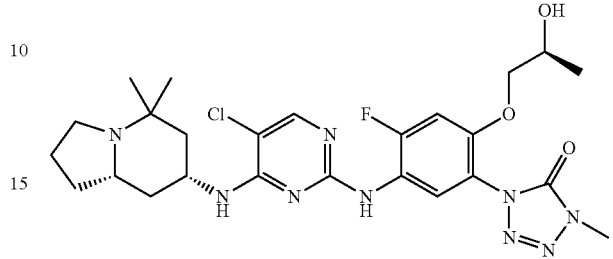

$^1$H NMR (300 MHz, DMSO-d$_6$) δ 8.65 (s, 1H), 8.15 (s, 1H), 7.88 (s, 1H), 7.71 (d, J=8.3 Hz, 1H), 7.28 (d, J=12.3 Hz, 1H), 6.77 (d, J=7.9 Hz, 1H), 4.07 (s, 1H), 3.95-3.74 (m, 3H), 3.59 (s, 3H), 3.01 (td, J=8.8, 4.3 Hz, 1H), 2.68 (s, 1H), 2.56 (q, J=8.2, 7.4 Hz, 1H), 1.95 (d, J=12.3 Hz, 1H), 1.90-1.63 (m, 4H), 1.63-1.47 (m, 2H), 1.45-1.23 (m, 2H), 1.13 (s, 3H), 1.02 (d, J=5.7 Hz, 3H), 0.90 (s, 3H); MS (ES) 562 (M+H).

Synthesis of 1-(5-((5-chloro-4-(((7R,8aS)-5,5-dimethyloctahydroindolizin-7-yl)amino)pyrimidin-2-yl)amino)-4-fluoro-2-(2-hydroxypropoxy)phenyl)-4-methyl-1,4-dihydro-5H-tetrazol-5-one, formate salt, mixture of diastereomers (Compound 236)

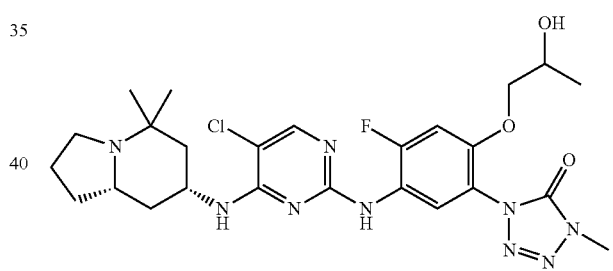

Compound 236 is a racemic mixture of diastereomers of Compound 235.

Synthesis of 1-(5-((5-chloro-4-(((7R,8aS)-5,5-dimethyloctahydroindolizin-7-yl)amino)pyrimidin-2-yl)amino)-4-fluoro-2-(2-hydroxyethoxy)phenyl)-4-methyl-1,4-dihydro-5H-tetrazol-5-one, formate salt (Compound 237)

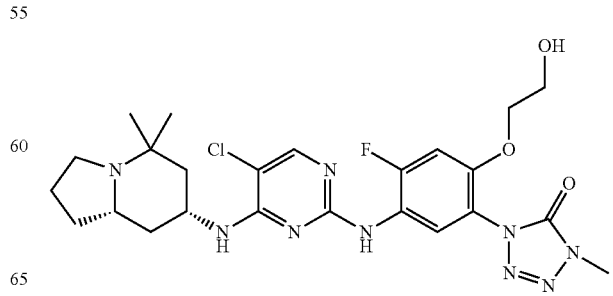

525

¹H NMR (300 MHz, DMSO-d₆) δ 8.62 (s, 1H), 8.27 (s, 1H), 7.86 (s, 1H), 7.75 (d, J=8.3 Hz, 1H), 7.29 (d, J=12.3 Hz, 1H), 6.66 (d, J=8.1 Hz, 1H), 4.52-3.89 (m, 4H), 3.59 (s, 3H), 2.81 (td, J=8.6, 3.3 Hz, 1H), 2.32-2.12 (m, 3H), 2.05-1.79 (m, 2H), 1.78-1.40 (m, 4H), 1.40-1.07 (m, 2H), 1.03 (s, 3H), 0.75 (s, 3H); MS (ES) 548 (M+H).

Synthesis of 1-(5-((5-chloro-4-(((7R,8aS)-5,5-dimethyloctahydroindolizin-7-yl)amino)pyrimidin-2-yl)amino)-4-fluoro-2-((S)-2-methoxypropoxy)phenyl)-4-methyl-1,4-dihydro-5H-tetrazol-5-one, formate salt (Compound 238)

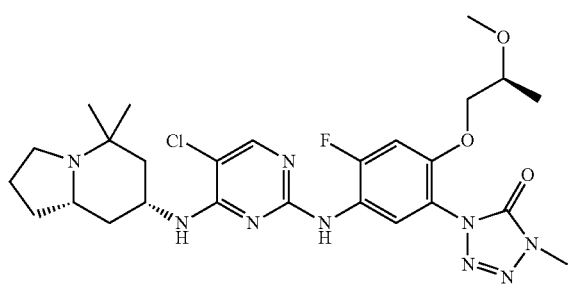 [SMILES: CO[C@@H](C)COc1cc(F)c(Nc2ncc(Cl)c(N[C@@H]3C[C@@H]4CCCN4C(C)(C)C3)n2)cc1-n1nnn(C)c1=O]

MS (ES) 576 (M+H).

Synthesis of 1-(5-((5-chloro-4-(((7R,8aS)-5,5-dimethyloctahydroindolizin-7-yl)((S)-2-methoxypropyl)amino)pyrimidin-2-yl)amino)-4-fluoro-2-((S)-2-methoxypropoxy)phenyl)-4-methyl-1,4-dihydro-5H-tetrazol-5-one, formate salt (Compound 239)

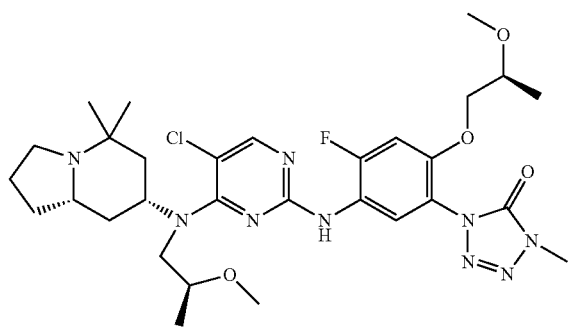 [SMILES: CO[C@@H](C)COc1cc(F)c(Nc2ncc(Cl)c(N(C[C@H](C)OC)[C@@H]3C[C@@H]4CCCN4C(C)(C)C3)n2)cc1-n1nnn(C)c1=O]

MS (ES) 648 (M+H).

Synthesis of 1-(5-((5-chloro-4-(((7R,8aS)-5,5-dimethyloctahydroindolizin-7-yl)amino)pyrimidin-2-yl)amino)-4-fluoro-2-(2-hydroxy-2-methylpropoxy)phenyl)-4-methyl-1,4-dihydro-5H-tetrazol-5-one (Compound 240)

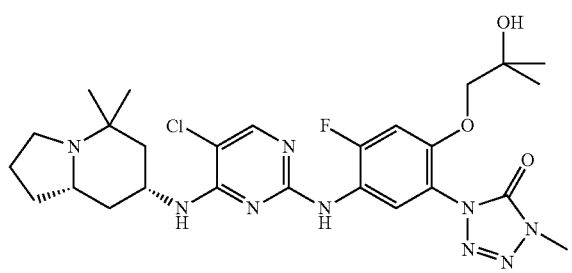 [SMILES: Cn1nnn(-c2cc(Nc3ncc(Cl)c(N[C@@H]4C[C@@H]5CCCN5C(C)(C)C4)n3)c(F)cc2OCC(C)(C)O)c1=O]

526

¹H NMR (300 MHz, DMSO-d₆) δ 8.56 (s, 1H), 7.81 (s, 1H), 7.75 (d, J=8.3 Hz, 1H), 7.19 (d, J=12.3 Hz, 1H), 6.61 (d, J=8.1 Hz, 1H), 4.51 (s, 1H), 3.92 (d, J=14.0 Hz, 1H), 3.66 (s, 2H), 3.53 (s, 3H), 2.75 (td, J=8.4, 3.1 Hz, 1H), 2.22-2.03 (m, 2H), 1.90-1.76 (m, 1H), 1.73-1.35 (m, 5H), 1.05 (d, J=2.6 Hz, 2H), 0.99 (s, 6H), 0.97 (s, 3H), 0.68 (s, 3H); MS (ES) 576 (M+H).

Example 108

Preparation of Compounds 241-314

The synthesis of representative building blocks for the preparation of Compounds 241-314 is described below.

Synthesis of 8-amino-2,4,4-trimethyl-2,4-dihydro-1H-benzo[b][1,2,4]triazolo[4,3-d][1,4]oxazin-1-one

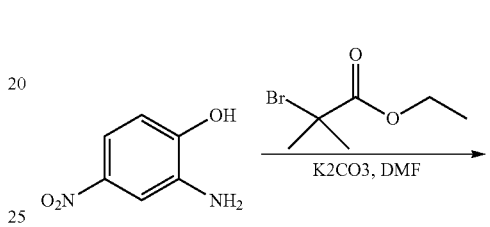

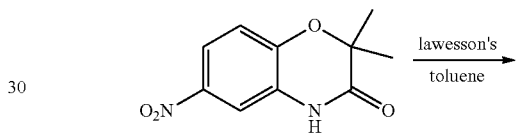

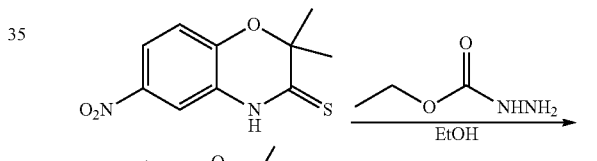

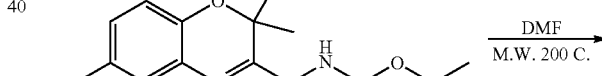

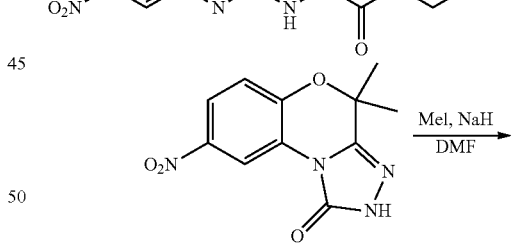

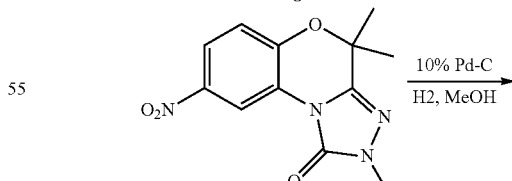

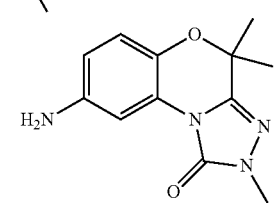

2-Amino-4-nitrophenol (5 g), ethyl 2-bromo-2-methylpropanoate (5.77 mL, 1.2 eq.), and $K_2CO_3$ (6.7 g, 1.5 eq.) were suspended in DMF (50 ml). The reaction mixture was heated at 70° C. overnight. The mixture was then diluted with water (200 mL) and EtOAc (150 mL). The EtOAc layer was washed with water (2×150 mL) and evaporated. The residue was purified by Combiflash chromatography (EtOAc in hexanes=10-100%) to give 2,2-dimethyl-6-nitro-2H-benzo[b][1,4]oxazin-3(4H)-one (3.45 g).

$^1$H NMR (300 MHz; $d_6$-DMSO) δ 11.00 (s, 1H), 7.84 (dd, J=2.4, 8.7 Hz, 1H), 7.74 (d, J=2.4 Hz, 1H), 7.14 (d, J=8.7 Hz, 1H), 1.45 (s, 6H).

2,2-Dimethyl-6-nitro-2H-benzo[b][1,4]oxazin-3(4H)-one (3.4 g) and Lawesson's reagent (6.19 g, 1.0 eq.) were suspended in toluene (100 ml). The reaction mixture was refluxed for one hour. The mixture was then evaporated. The residue was purified by Combiflash chromatography (EtOAc in hexanes=0-100%) to give 2,2-dimethyl-6-nitro-2H-benzo[b][1,4]oxazine-3(4H)-thione (3 g, 82% yield).

$^1$H NMR (300 MHz; $d_6$-DMSO) δ 12.92 (s, 1H), 7.93 (m, 2H), 7.19 (d, J=9.9 Hz, 1H), 1.59 (s, 6H).

2,2-Dimethyl-6-nitro-2H-benzo[b][1,4]oxazine-3(4H)-thione (3 g) and ethyl hydrazinecarboxylate (3.94 g, 3.0 eq.) were suspended in ethanol (50 ml). The reaction mixture was refluxed for 6 hours. The yellow precipitation was filtered and washed with ether to give ethyl 2-(2,2-dimethyl-6-nitro-2H-benzo[b][1,4]oxazin-3-yl)hydrazine-1-carboxylate (3.37 g, 87% yield).

$^1$H NMR (300 MHz; $d_6$-DMSO) δ 9.76 (s, 1H), 9.25 (s, 1H), 7.78-7.71 (m, 2H), 7.07 (d, J=8.7 Hz, 1H), 4.08 (q, J=7.2 Hz, 2H), 1.44 (s, 6H), 1.20 (t, J=6.9 Hz, 3H).

Ethyl 2-(2,2-dimethyl-6-nitro-2H-benzo[b][1,4]oxazin-3-yl)hydrazine-1-carboxylate (300 mg) was dissolved in DMF (3 ml). The reaction mixture was microwaved at 200° C. for 10 min. The reaction solution was evaporated to give 4,4-dimethyl-8-nitro-2,4-dihydro-1H-benzo[b][1,2,4]triazolo[4,3-d][1,4]oxazin-1-one.

$^1$H NMR (300 MHz; $d_6$-DMSO) δ 12.32 (s, 1H), 8.98 (d, J=3.0 Hz, 1H), 8.96 (dd, J=2.7, 9.0 Hz, 1H), 7.32 (d, J=8.7 Hz, 1H), 1.62 (s, 6H).

4,4-Dimethyl-8-nitro-2,4-dihydro-1H-benzo[b][1,2,4]triazolo[4,3-d][1,4]oxazin-1-one, iodomethane (73 μL, 1.2 eq.) were dissolved in DMF (4 mL). Sodium hydride (58 mg, 60% suspension in oil, 1.5 eq.) was added to the solution in an ice bath. The reaction mixture was stirred at room temperature for two hours. Water (15 mL) was added to the reaction. White precipitation was filtered and washed with water to give 2,4,4-trimethyl-8-nitro-2,4-dihydro-1H-benzo[b][1,2,4]triazolo[4,3-d][1,4]oxazin-1-one (249 mg, 92% yield in two steps).

$^1$H NMR (300 MHz; $d_6$-DMSO) δ 8.95 (d, J=2.7 Hz, 1H), 8.10 (dd, J=2.7, 8.7 Hz, 1H), 7.32 (d, J=8.7 Hz, 1H), 3.40 (s, 3H), 1.63 (s, 6H).

2,4,4-Trimethyl-8-nitro-2,4-dihydro-1H-benzo[b][1,2,4]triazolo[4,3-d][1,4]oxazin-1-one (249 mg) and 10% Pd—C were suspended in methanol (5 mL). The reaction mixture was stirred at room temperature under $H_2$ atmosphere (1 atm) overnight. The catalyst was filtered off over celite and washed with methanol (5×20 mL). The filtrate was evaporated to give 8-amino-2,4,4-trimethyl-2,4-dihydro-1H-benzo[b][1,2,4]triazolo[4,3-d][1,4]oxazin-1-one (245 mg, quant).

$^1$H NMR (300 MHz; $d_6$-DMSO) δ 7.41 (d, J=1.8 Hz, 1H), 6.75 (dd, J=9.9 Hz, 1H), 6.36 (dd, J=1.5, 8.4 Hz, 1H), 5.08 (s, 2H), 3.36 (s, 3H), 1.49 (s, 6H).

Synthesis of 8-amino-2-methylspiro[benzo[b][1,2,4]triazolo[4,3-d][1,4]oxazine-4,3'-oxetan]-1(2H)-one and 9-amino-4-hydroxy-2,4-dimethyl-4,5-dihydrobenzo[b][1,2,4]triazolo[4,3-d][1,4]oxazepin-1(2H)-one

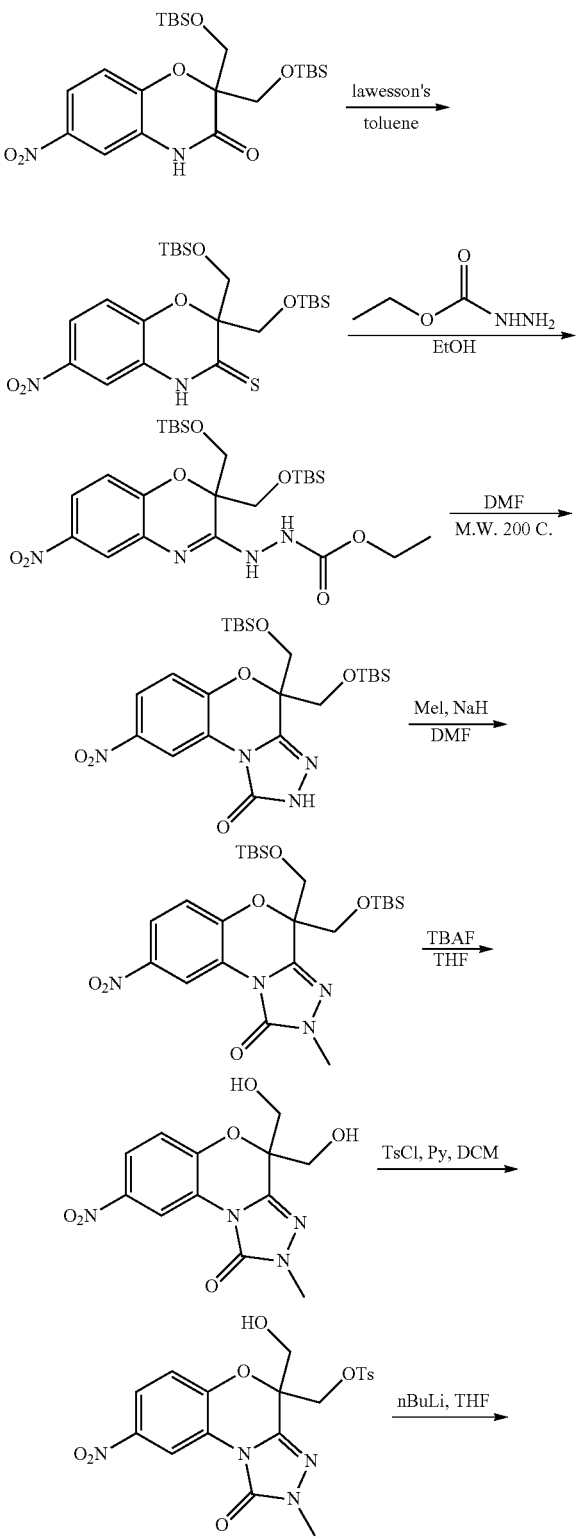

-continued

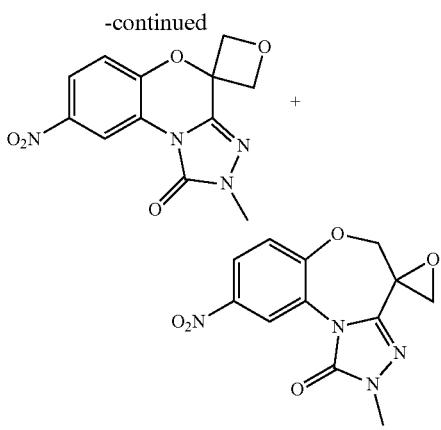

2,2-Bis(((tert-butyldimethylsilyl)oxy)methyl)-6-nitro-2H-benzo[b][1,4]oxazin-3(4H)-one (7.8 g) and Lawesson's reagent (7.8 g, 1.2 eq.) were suspended in toluene (100 ml). The reaction mixture was refluxed for four hours. The mixture was then evaporated. The residue was purified by Combiflash chromatography (EtOAc in hexanes=0-80%) to give 2,2-bis(((tert-butyldimethylsilyl)oxy)methyl)-6-nitro-2H-benzo[b][1,4]oxazine-3(4H)-thione (4.6 g).

$^1$H NMR (300 MHz; $d_6$-DMSO) δ 13.07 (s, 1H), 7.97 (dd, J=2.7, 9.0 Hz, 1H), 7.92 (d, J=2.4 Hz, 1H), 7.15 (d, J=9.0 Hz, 1H), 4.36 (d, J=10.8 Hz, 2H), 4.03 (d, J=10.8 Hz, 2H), 0.78 (s, 18H), 0.08 (s, 6H), 0.00 (s, 6H).

2,2-Bis(((tert-butyldimethylsilyl)oxy)methyl)-6-nitro-2H-benzo[b][1,4]oxazine-3(4H)-thione (4.6 g) and ethyl hydrazinecarboxylate (2.88 g, 3.0 eq.) were suspended in ethanol (50 ml). The reaction mixture was refluxed for three days. The mixture was then evaporated. The residue was purified by Combiflash chromatography (EtOAc in hexanes=0-80%) to give ethyl 2-(2,2-bis(((tert-butyldimethylsilyl)oxy)methyl)-6-nitro-2H-benzo[b][1,4]oxazin-3-yl)hydrazine-1-carboxylate (4 g).

$^1$H NMR (300 MHz; $d_6$-DMSO) δ 9.85 (s, 1H), 9.35 (s, 1H), 7.78 (dd, J=2.7, 8.7 Hz, 1H), 7.72 (d, J=3.3 Hz, 1H), 7.07 (d, J=8.4 Hz, 1H), 4.18 (q, J=6.9 Hz, 2H), 4.01 (s, 4H), 1.29 (t, J=6.9 Hz, 3H), 0.80 (s, 18H), 0.04 (s, 6H), 0.00 (s, 6H).

Ethyl 2-(2,2-bis(((tert-butyldimethylsilyl)oxy)methyl)-6-nitro-2H-benzo[b][1,4]oxazin-3-yl)hydrazine-1-carboxylate (4 g) was dissolved in DMF (34 ml). The reaction mixture was microwaved at 200° C. for 10 min. The reaction solution was evaporated to give 4,4-bis(((tert-butyldimethylsilyl)oxy)methyl)-8-nitro-2,4-dihydro-1H-benzo[b][1,2,4]triazolo[4,3-d][1,4]oxazin-1-one.

4,4-Bis(((tert-butyldimethylsilyl)oxy)methyl)-8-nitro-2,4-dihydro-1H-benzo[b][1,2,4]triazolo[4,3-d][1,4]oxazin-1-one and iodomethane (0.626 mL) were dissolved in DMF. Cesium carbonate (4.13 g) was added to the solution. The reaction mixture was stirred at room temperature overnight. Water (250 mL) was added to the reaction. The aqueous solution was extracted with EtOAc (2×200 mL). The organic layers were evaporated to give 4,4-bis(((tert-butyldimethylsilyl)oxy)methyl)-2-methyl-8-nitro-2,4-dihydro-1H-benzo[b][1,2,4]triazolo[4,3-d][1,4]oxazin-1-one.

$^1$H NMR (300 MHz; $d_6$-DMSO) δ 9.09 (d, J=2.7 Hz, 1H), 8.18 (dd, J=2.7, 9.0 Hz, 1H), 7.37 (d, J=8.4 Hz, 1H), 4.15 (s, 4H), 3.52 (s, 3H), 0.76 (s, 18H), 0.04 (s, 6H0, 0.00 (s, 6H).

4,4-Bis(((tert-butyldimethylsilyl)oxy)methyl)-2-methyl-8-nitro-2,4-dihydro-1H-benzo[b][1,2,4]triazolo[4,3-d][1,4]oxazin-1-one (3 g) was dissolved in THF (15 mL). 1.0 M TBAF in THF solution was added (14 mL, 2.5 eq.). The reaction solution was stirred at room temperature for one hour and then evaporated. The residue was purified by Combiflash chromatography (methanol in dichloromethane=0-20%) to give 4,4-bis(hydroxymethyl)-2-methyl-8-nitro-2,4-dihydro-1H-benzo[b][1,2,4]triazolo[4,3-d][1,4]oxazin-1-one (1.6 g).

$^1$H NMR (300 MHz; $d_6$-DMSO) δ 9.01 (d, J=3.0 Hz, 1H), 8.06 (dd, J=2.7, 8.7 Hz, 1H), 7.27 (d, J=9.0 Hz, 1H), 5.34 (t, J=5.7 Hz, 2H), 4.81 (d, J=6.0 Hz, 4H), 3.42 (s, 3H).

4,4-Bis(hydroxymethyl)-2-methyl-8-nitro-2,4-dihydro-1H-benzo[b][1,2,4]triazolo[4,3-d][1,4]oxazin-1-one (1.6 g) and pyridine (0.84 mL, 2 eq.) were dissolved in anhydrous dichloromethane (100 mL). In an ice bath, tosyl chloride (1.2 g, 1.2 eq.) was added to the reaction solution in portions. The reaction was stirred in an ice bath to room temperature overnight. Then triethylamine (1.5 mL, 2 eq.) and more of tosyl chloride (500 mg, 0.5 eq.) were added and stirred at room temperature overnight. LCMS showed mixtures of starting material, mono-tosylated product and bis-tosylated product. The reaction solution was evaporated. The residue was purified by Combiflash chromatography (EtOAc in hexanes=20-100%) to give (4-(hydroxymethyl)-2-methyl-8-nitro-1-oxo-2,4-dihydro-1H-benzo[b][1,2,4]triazolo[4,3-d][1,4]oxazin-4-yl)methyl 4-methylbenzenesulfonate. m/z=462.83 (M+H)$^+$.

(4-(Hydroxymethyl)-2-methyl-8-nitro-1-oxo-2,4-dihydro-1H-benzo[b][1,2,4]triazolo[4,3-d][1,4]oxazin-4-yl)methyl 4-methylbenzenesulfonate (1.1 g) was dissolved in anhydrous THF (100 mL). In an ice bath, 2.5 M n-butyl lithium in hexanes (1.05 mL, 1.1 eq.) was added to the reaction. The solution was reacted at 0° C. to room temperature, and then refluxed for three hours. The solvent was removed in vacuo. The residue was partitioned between EtOAc (100 mL) and 5% aqueous sodium bicarbonate (100 mL). The aqueous layer was extracted with EtOAc (2×100 mL). The organic layers were evaporated and purified by Combiflash chromatography (EtOAc in hexanes=20-100%) to give 2-methyl-8-nitrospiro[benzo[b][1,2,4]triazolo[4,3-d][1,4]oxazine-4,3'-oxetan]-1(2H)-one (150 mg, isomer a, m/z=290.92 (M+H)$^+$) and 2-methyl-9-nitro-5H-spiro[benzo[b][1,2,4]triazolo[4,3-d][1,4]oxazepine-4,2'-oxiran]-1(2H)-one (250 mg, isomer b, m/z=290.92 (M+H)$^+$).

Synthesis of 8-amino-2-methylspiro[benzo[b][1,2,4]triazolo[4,3-d][1,4]oxazine-4,3'-oxetan]-1(2H)-one

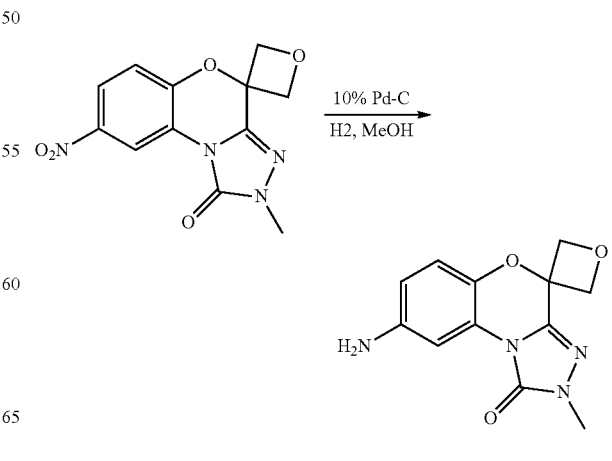

2-Methyl-8-nitrospiro[benzo[b][1,2,4]triazolo[4,3-d][1,4]oxazine-4,3'-oxetan]-1(2H)-one (150 mg) and 10% Pd—C were suspended in methanol (10 mL). The reaction mixture was shaken at room temperature under H2 atmosphere (30 psi) for one hour. The catalyst was filtered off over celite and washed with methanol (5×50 mL). The filtrate was evaporated to give 8-amino-2-methylspiro[benzo[b][1,2,4]triazolo[4,3-d][1,4]oxazine-4,3'-oxetan]-1(2H)-one (120 mg). m/z=261.16 (M+H)$^+$.

Synthesis of 9-amino-4-hydroxy-2,4-dimethyl-4,5-dihydrobenzo[b][1,2,4]triazolo[4,3-d][1,4]oxazepin-1(2H)-one

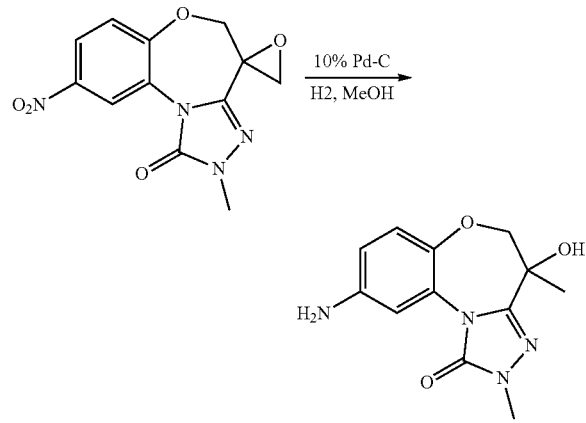

2-Methyl-9-nitro-5H-spiro[benzo[b][1,2,4]triazolo[4,3-d][1,4]oxazepine-4,2'-oxiran]-1(2H)-one (250 mg) and 10% Pd—C were suspended in methanol (10 mL). The reaction mixture was shaken at room temperature under H$_2$ atmosphere (30 psi) for one hour. The catalyst was filtered off over celite and washed with methanol (5×50 mL). The filtrate was evaporated to give 9-amino-4-hydroxy-2,4-dimethyl-4,5-dihydrobenzo[b][1,2,4]triazolo[4,3-d][1,4]oxazepin-1(2H)-one (200 mg). m/z=263.12 (M+H)$^+$.

Additional building blocks and coupling reactions that may be used to prepare Compounds 241-314 are described in the Examples herein.

Synthesis of 5-fluoro-N2-(2-fluoro-5-methoxy-3-(5-methyl-1H-tetrazol-1-yl)phenyl)-N4-((7R,8aS)-octahydro-5,5-dimethylindolizin-7-yl)pyrimidine-2,4-diamine, TFA salt (Compound 241)

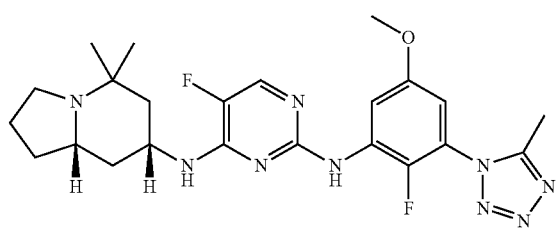 [SMILES: COc1cc(Nc2ncc(F)c(N[C@@H]3C[C@@H]4CCCN4C(C)(C)C3)n2)c(F)c(-n2nnnc2C)c1]

$^1$H NMR (300 MHz, d$_6$-DMSO) δ 9.12 (br, 1H), 8.90 (s, 1H), 7.96 (d, J=3.6 Hz, 1H), 7.76 (m, 2H), 7.01 (m, 1H), 4.26 (br, 1H), 3.76 (s, 3H), 3.37 (m, 2H), 3.07 (m, 1H), 2.33-2.29 (m, 1H), 2.08-1.94 (m, 4H), 1.71-1.55 (m, 3H), 1.33 (s, 3H), 1.25 (s, 3H); m/z=486.41 (M+H)$^+$.

Synthesis of 5-fluoro-N2-(2-fluoro-3-methoxy-5-(5-methyl-1H-tetrazol-1-yl)phenyl)-N4-((7R,8aS)-octahydro-5,5-dimethylindolizin-7-yl)pyrimidine-2,4-diamine, TFA salt (Compound 242)

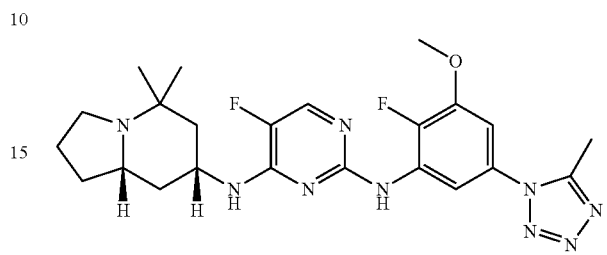

$^1$H NMR (300 MHz, d$_6$-DMSO) δ 9.14 (br, 1H), 8.85 (s, 1H), 7.94 (d, J=3.3 Hz, 1H), 7.71 (m, 2H), 7.20 (dd, J=2.7, 6.6 Hz, 1H), 4.20 (br, 1H), 3.87 (s, 3H), 3.36 (m, 2H), 3.02 (m, 1H), 2.55 (s, 3H), 2.25 (m, 1H), 1.97 (m, 4H), 1.59 (m, 3H), 1.31 (s, 3H), 1.14 (s, 3H); m/z=486.41 (M+H)$^+$.

Synthesis of 5-fluoro-N2-(2,6-difluoro-3-methoxy-5-(5-methyl-1H-tetrazol-1-yl)phenyl)-N4-((7R,8aS)-octahydro-5,5-dimethylindolizin-7-yl)pyrimidine-2,4-diamine, TFA salt (Compound 243)

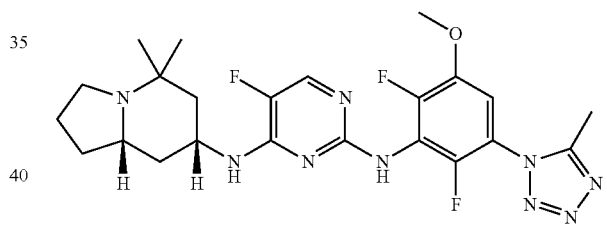

$^1$H NMR (300 MHz, d$_6$-DMSO) δ 9.13 (br, 1H), 8.90 (s, 1H), 7.91 (d, J=3.9 Hz, 1H), 7.77 (m, 1H), 7.68 (m, 1H), 4.14 (br, 1H), 3.90 (s, 3H), 3.35 (m, 2H), 3.07 (m, 1H), 2.51 (s, 3H), 2.25 (m, 1H), 1.98 (m, 4H), 1.60-1.55 (m, 3H), 1.31 (s, 3H), 1.17 (s, 3H); m/z=504.43 (M+H)$^+$.

Synthesis of 5-fluoro-N2-(1H-2,4-dihydron-2,4,4-trimethyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine (Compound 248)

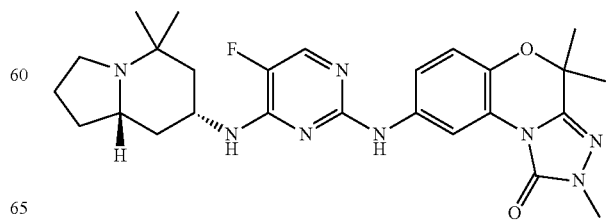

¹H NMR (300 MHz, d₆-DMSO) δ 9.10 (s, 1H), 8.57 (d, J=2.1 Hz, 1H), 7.81 (d, J=4.2 Hz, 1H), 7.33 (dd, J=2.7, 9.0 Hz, 1H), 7.15 (d, J=7.8 Hz, 1H), 6.93 (d, J=8.7 Hz, 1H), 4.24 (s, 1H), 3.37 (s, 3H), 2.79 (t, 1H), 2.38 (m, 1H), 2.18 (q, J=8.4 Hz, 1H), 1.96 (d, J=12.9 Hz, 1H), 1.70 (m, 1H), 1.56 (s, 5H), 1.48 (s, 3H), 1.35-1.08 (m, 4H), 1.00 (s, 3H), 0.78 (s, 3H); m/z=509.04 (M+H)⁺.

Synthesis of 5-fluoro-N2-(2-fluoro-5-(5-methyl-1H-tetrazol-1-yl)-4-(oxetan-3-yloxy)phenyl)-N4-((7R,8aS)-octahydro-5,5-dimethylindolizin-7-yl)pyrimidine-2,4-diamine (Compound 249)

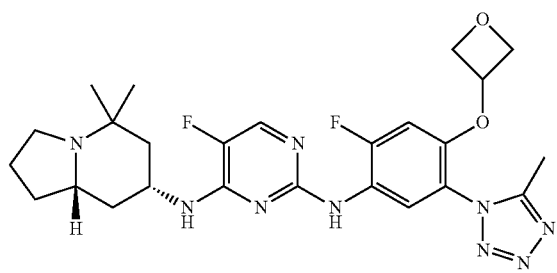 [SMILES: Cc1nnnn1-c1cc(Nc2ncc(F)c(N[C@@H]3C[C@@H]4CCCN4C(C)(C)C3)n2)c(F)cc1OC1COC1]

¹H NMR (300 MHz, d₆-DMSO) δ 8.50 (s, 1H), 7.98 (d, J=8.4 Hz, 1H), 7.79 (d, J=3.9 Hz, 1H), 7.21 (d, J=8.7 Hz, 1H), 7.03 (d, J=12.0 Hz, 1H), 5.32 (p, J=5.1 Hz, 1H), 4.86 (t, J=6.6 Hz, 2H), 4.35 (t, J=5.7 Hz, 2H), 3.94 (m, 1H), 2.77 (m, 1H), 2.43 (s, 3H), 2.21 (q, J=8.4 Hz, 1H), 2.04 (m, 1H), 1.87 (d, J=12.6 Hz, 1H), 1.68-1.47 (m, 4H), 1.34 (t, J=12.0 Hz, 1H), 1.22-1.04 (m, 2H), 1.01 (s, 3H), 0.70 (s, 3H); m/z=528.38 (M+H)⁺.

Synthesis of 5-fluoro-N2-(1H-2,4-dihydron-4,4-dimethyl-2-(3-chloropropanol-2-yl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine, two diastereomers (Compound 250)

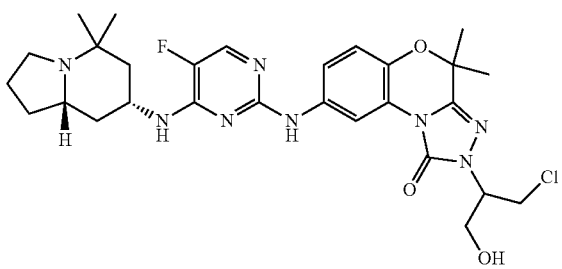 [SMILES: CC1(C)Oc2ccc(Nc3ncc(F)c(N[C@@H]4C[C@@H]5CCCN5C(C)(C)C4)n3)cc2-n2c1nn(C(CO)CCl)c2=O]

¹H NMR (300 MHz, d₆-DMSO) δ 9.11 (s, 2H), 8.64 (d, J=2.4 Hz, 1H), 8.55 (d, J=2.4 Hz, 1H), 7.82 (d, J=3.9 Hz, 2H), 7.43 (d, J=6.0 Hz, 1H), 7.34 (d, J=11.4 Hz, 1H), 7.14 (d, J=6.9 Hz, 2H), 6.94 (d, J=8.7 Hz, 2H), 5.08 (q, J=6.6 Hz, 2H), 4.33 (m, 2H), 4.24 (br, 2H), 3.95 (m, 2H), 3.83 (m, 2H), 3.63 (m, 4H), 2.78 (m, 2H), 2.22 (m, 2H), 1.92 (m, 2H), 1.76 (m, 2H), 1.59 (s, 7H), 1.57 (s, 7H), 1.51 (s, 3H), 1.48 (s, 3H), 1.29-1.15 (m, 6H), 1.01 (s, 3H), 0.98 (s, 3H), 0.85 (s, 3H), 0.81 (s, 3H); m/z=586.95 (M+H)⁺.

Synthesis of 5-fluoro-N2-(1H-2,4-dihydron-4,4-dimethyl-2-(oxetan-3-yl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine (Compound 251)

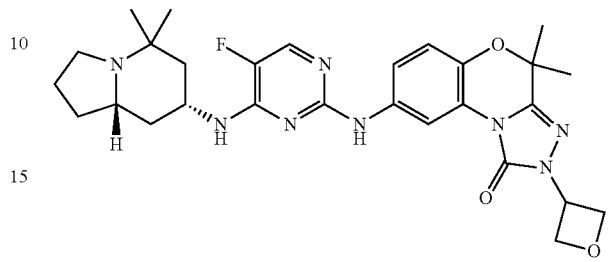

¹H NMR (300 MHz, d₆-DMSO) δ 9.11 (s, 1H), 8.58 (d, J=1.8 Hz, 1H), 7.81 (d, J=3.9 Hz, 1H), 7.32 (d, J=8.7 Hz, 1H), 7.14 (d, J=8.1 Hz, 1H), 6.95 (d, J=9.0 Hz, 1H), 5.39 (p, J=6.9 Hz, 1H), 4.83 (t, J=6.9 Hz, 4H), 4.20 (br, 1H), 2.78 (t, 1H), 2.30 (m, 1H), 2.13 (q, J=8.4 Hz, 1H), 1.94 (d, J=9.3 Hz, 1H), 1.76 (m, 1H), 1.62 (s, 6H), 1.53 (s, 3H), 1.33-1.09 (m, 3H), 0.97-0.99 (s, 3H), 0.75 (s, 3H); m/z=551.50 (M+H)⁺.

Synthesis of 4-(44(7R,8aS)-octahydro-5,5-dimethylindolizin-7-ylamino)-5-fluoropyrimidin-2-ylamino)-5-fluoro-2-(5-methyl-1H-tetrazol-1-yl)phenol, besylate salt (Compound 252)

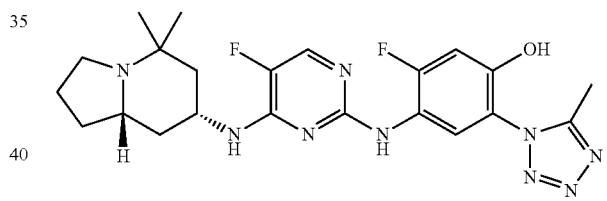

¹H NMR (300 MHz, d₆-DMSO) δ 10.95 (s, 1H), 9.03 (br, 1H), 8.77 (br, 1H), 7.93 (d, J=4.5 Hz, 1H), 7.71 (d, J=8.4 Hz, 1H), 6.96 (d, J=11.4 Hz, 1H), 4.15 (br, 1H), 3.04 (m, 1H), 2.39 (s, 3H), 2.24 (d, J=11.1 Hz, 1H), 2.11 (m, 1H), 1.96 (m, 4H), 1.83-1.48 (m, 4H), 1.31 (s, 3H), 1.12 (s, 3H); m/z=472.49 (M+H)⁺.

Synthesis of N5-(4-((7R,8aS)-octahydro-5,5-dimethylindolizin-7-ylamino)-5-fluoropyrimidin-2-yl)-6-fluoro-N2-methylbenzo[d]oxazole-2,5-diamine, formate salt (Compound 253)

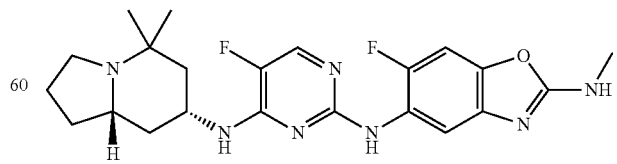

¹H NMR (300 MHz, d₆-DMSO) δ 8.18 (s, 1H), 7.78 (d, J=3.6 Hz, 1H), 7.71 (d, J=5.1 Hz, 1H), 7.51 (d, J=7.5 Hz, 1H), 7.31 (d, J=9.9 Hz, 1H), 7.21 (m, 1H), 4.06 (br, 1H), 2.96 (br, 1H), 2.85 (d, J=4.5 Hz, 3H), 1.99 (m, 1H), 1.85 (m, 1H), 1.68 (m, 4H), 1.45-1.21 (m, 4H), 1.12 (s, 3H), 0.92 (s, 3H); m/z=444.43 (M+H)⁺.

Synthesis of N5-(4-((7R,8aS)-octahydro-5,5-dimethylindolizin-7-ylamino)-5-fluoropyrimidin-2-yl)-6-fluoro-N2-methylbenzo[d]oxazole-2,5-diamine, besylate salt (Compound 254)

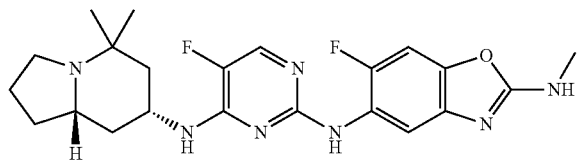 [SMILES: CNc1nc2cc(Nc3ncc(F)c(N[C@@H]4C[C@@H]5CCCN5C(C)(C)C4)n3)c(F)cc2o1]

$^1$H NMR (300 MHz, d$_6$-DMSO) δ 7.92 (m, 1H), 7.80 (m, 1H), 7.57 (d, J=7.8 Hz, 2H), 7.49 (d, J=6.6 Hz, 1H), 7.40 (d, J=9.9 Hz, 1H), 7.28 (m, 3H), 4.12 (br, 1H), 3.02 (br, 1H), 2.86 (d, J=4.2 Hz, 3H), 2.25 (m, 1H), 2.07 (m, 1H), 1.92 (m, 4H), 1.57 (m, 4H), 1.31 (s, 3H), 1.10 (s, 3H); m/z=444.42 (M+H)⁺.

Synthesis of N2-(5-(5-cyclopropyl-1H-tetrazol-1-yl)-2-fluoro-4-(oxetan-3-yloxy)phenyl)-5-fluoro-N4-((7R,8aS)-octahydro-5,5-dimethylindolizin-7-yl)pyrimidine-2,4-diamine (Compound 255)

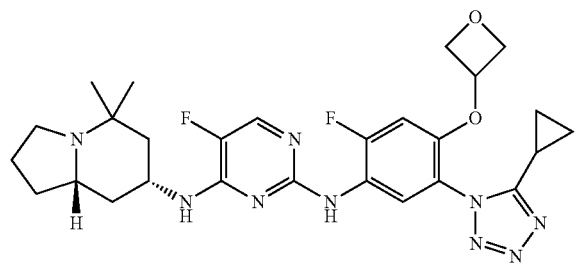 [SMILES: CC1(C)C[C@H](Nc2nc(Nc3cc(-n4nnnc4C4CC4)c(OC4COC4)cc3F)ncc2F)C[C@@H]2CCCN21]

$^1$H NMR (300 MHz, d$_6$-DMSO) δ 8.51 (s, 1H), 8.10 (d, J=8.4 Hz, 1H), 7.81 (d, J=3.9 Hz, 1H), 7.23 (d, J=7.8 Hz, 1H), 7.04 (d, J=12.0 Hz, 1H), 5.33 (p, J=5.1 Hz, 1H), 4.88 (t, J=6.9 Hz, 2H), 4.40 (d, J=5.7 Hz, 2H), 3.96 (m, 1H), 2.77 (m, 1H), 2.19 (q, J=8.1 Hz, 1H), 1.99 (m, 1H), 1.87 (m, 2H), 1.67-1.32 (m, 5H), 1.16-1.07 (m, 6H), 1.01 (s, 3H), 0.68 (s, 3H); m/z=554.52 (M+H)⁺.

Synthesis of 4-(4-((7R,8aS)-octahydro-5,5-dimethylindolizin-7-ylamino)-5-fluoropyrimidin-2-ylamino)-2-(5-cyclopropyl-1H-tetrazol-1-yl)-5-fluorophenol, TFA salt (Compound 256)

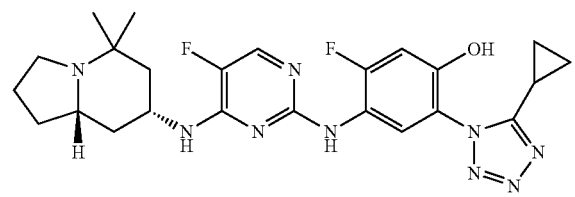 [SMILES: CC1(C)C[C@H](Nc2nc(Nc3cc(-n4nnnc4C4CC4)c(O)cc3F)ncc2F)C[C@@H]2CCCN21]

$^1$H NMR (300 MHz, d$_6$-DMSO) δ 10.88 (s, 1H), 9.30 (br, 1H), 8.60 (br, 1H), 7.89 (d, J=4.2 Hz, 1H), 7.75 (d, J=7.8 Hz, 1H), 6.96 (d, J=11.7 Hz, 1H), 4.14 (m, 1H), 3.01 (m, 1H), 2.25 (m, 1H), 1.97-1.46 (m, 8H), 1.32 (m, 5H), 1.13-1.02 (m, 7H); m/z=498.42 (M+H)⁺.

Synthesis of N2-(5-(5-cyclopropyl-1H-tetrazol-1-yl)-2-fluoro-4-isopropoxyphenyl)-5-fluoro-N4-((7R,8aS)-octahydro-5,5-dimethylindolizin-7-yl)pyrimidine-2,4-diamine, TFA salt (Compound 257)

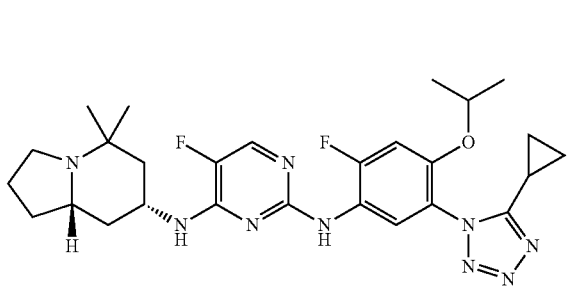 [SMILES: CC(C)Oc1cc(F)c(Nc2ncc(F)c(N[C@@H]3C[C@@H]4CCCN4C(C)(C)C3)n2)cc1-n1nnnc1C1CC1]

$^1$H NMR (300 MHz, d$_6$-DMSO) δ 11.79 (s, 1H), 10.54 (br, 1H), 8.65 (s, 1H), 7.88 (d, J=8.4 Hz, 1H), 7.82 (d, J=3.6 Hz, 1H), 5.35 (p, J=6.4 Hz, 1H), 4.06 (m, 1H), 3.00 (m, 1H), 2.25-1.86 (m, 9H), 1.66 (d, J=6.6 Hz, 6H), 1.38-1.02 (m, 12H); m/z=540.65 (M+H)⁺.

Synthesis of 5-fluoro-N2-(2-fluoro-5-(5-(methylamino)-1H-tetrazol-1-yl)-4-(oxetan-3-yloxy)phenyl)-N4-((7R,8aS)-octahydro-5,5-dimethylindolizin-7-yl)pyrimidine-2,4-diamine (Compound 258)

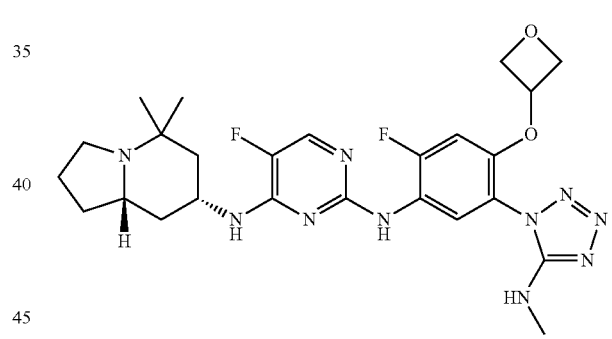

$^1$H NMR (300 MHz, d$_6$-DMSO) δ 8.45 (s, 1H), 8.04 (d, J=8.4 Hz, 1H), 7.81 (d, J=3.9 Hz, 1H), 7.23 (d, J=8.7 Hz, 1H), 6.95 (d, J=12.3 Hz, 1H), 6.67 (m, 1H), 5.28 (m, 1H), 4.83 (t, J=6.6 Hz, 2H), 4.39 (m, 2H), 4.00 (m, 1H), 2.84 (d, J=4.5 Hz, 3H), 2.78 (m, 1H), 2.25-1.88 (m, 4H), 1.57-1.22 (m, 6H), 1.02 (s, 3H), 0.73 (s, 3H); m/z=543.65 (M+H)⁺.

Synthesis of 1-(3-(4-((7R,8aS)-octahydro-5,5-dimethylindolizin-7-ylamino)-5-fluoropyrimidin-2-ylamino)phenyl)-1H-tetrazole-5-thiol, formate salt (Compound 259)

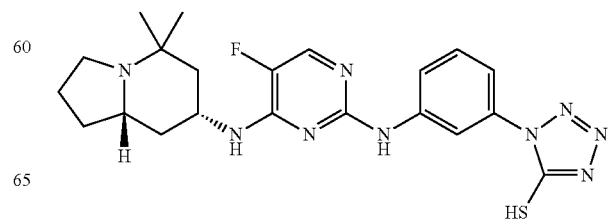

¹H NMR (300 MHz, d₆-DMSO) δ 9.30 (s, 1H), 8.85 (br, 1H), 8.49 (s, 1H), 7.88 (d, J=3.6 Hz, 1H), 7.50 (d, J=6.0 Hz, 1H), 7.24 (m, 3H), 4.29 (m, 1H), 3.00 (m, 3H), 2.86 (t, 1H), 2.30-1.35 (m, 8H), 1.17 (s, 3H), 1.15 (d, J=14.1 Hz, 1H), 1.00 (s, 3H); m/z=455.95 (M+H)⁺.

Synthesis of 1-(3-(4-((7R,8aS)-octahydro-5,5-dimethylindolizin-7-ylamino)-5-fluoropyrimidin-2-ylamino)phenyl)-1H-tetrazol-5(4H)-one (Compound 260)

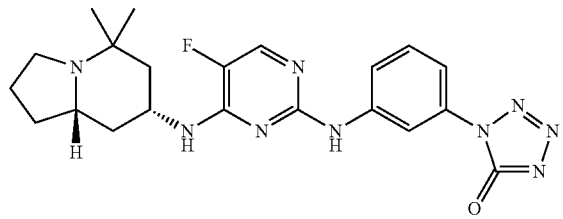

¹H NMR (300 MHz, d₆-DMSO) δ 9.33 (s, 1H), 8.26 (s, 1H), 7.92 (d, J=3.9 Hz, 1H), 7.56 (m, 1H), 7.34 (m, 4H), 4.36 (m, 1H), 2.99 (br, 1H), 2.25-1.60 (m, 10H), 1.29 (s, 3H), 1.23 (s, 3H); m/z=439.96 (M+H)⁺.

Synthesis of 5-fluoro-N4-((7R,8aS)-octahydro-5,5-dimethylindolizin-7-yl)-N2-(3-(5-(methylthio)-1H-tetrazol-1-yl)phenyl)pyrimidine-2,4-diamine (Compound 261)

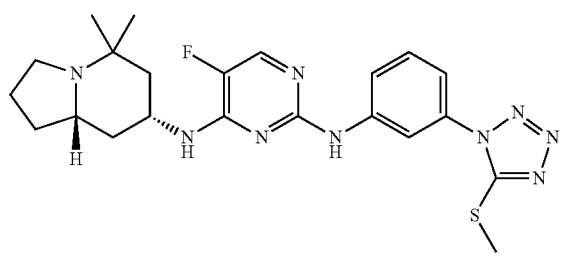 [SMILES: CSc1nnnn1-c1cccc(Nc2ncc(F)c(N[C@@H]3C[C@@H]4CCCN4C(C)(C)C3)n2)c1]

¹H NMR (300 MHz, cdcl₃) δ 8.41 (s, 1H), 7.93 (m, 1H), 7.81 (d, J=3.0 Hz, 1H), 7.43 (t, J=8.1 Hz, 1H), 7.38 (d, J=3.0 Hz, 1H), 7.19 (m, 1H), 7.14 (d, J=7.8 Hz, 1H), 5.19 (br, 1H), 4.40 (br, 1H), 3.41 (br, 1H), 2.83 (s, 3H), 2.40 (d, J=12.6 Hz, 1H), 2.00 (m, 3H), 1.89 (d, J=9.3 Hz, 1H), 1.61 (br, 4H), 1.46 (s, 3H), 1.20 (s, 3H); m/z=469.95 (M+H)⁺.

Synthesis of 5-fluoro-N4-((7R,8aS)-octahydro-5,5-dimethylindolizin-7-yl)-N2-(3-(5-(oxetan-3-ylthio)-1H-tetrazol-1-yl)phenyl)pyrimidine-2,4-diamine (Compound 262)

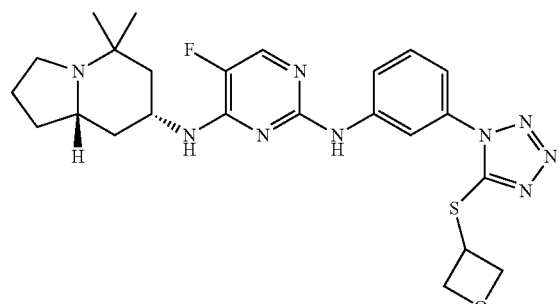

¹H NMR (300 MHz, d₆-DMSO) δ 9.54 (s, 1H), 8.20 (s, 1H), 7.89 (d, J=3.6 Hz, 1H), 7.76 (d, J=8.4 Hz, 1H), 7.46 (t, J=8.1 Hz, 1H), 7.33 (d, J=8.7 Hz, 1H), 7.09 (d, J=7.8 Hz, 1H), 5.03 (m, 2H), 4.90 (p, J=6.3 Hz, 1H), 4.57 (q, J=5.7 Hz, 2H), 4.06 (br, 1H), 2.79 (m, 1H), 2.21-1.98 (m, 3H), 1.56 (m, 4H), 1.40 (t, J=12.3 Hz, 1H), 1.18-1.07 (m, 2H), 1.02 (s, 3H), 0.72 (s, 3H); m/z=511.96 (M+H)⁺.

Synthesis of 2-(1-(3-(4-((7R,8aS)-octahydro-5,5-dimethylindolizin-7-ylamino)-5-fluoropyrimidin-2-ylamino)phenyl)-1H-tetrazol-5-ylthio)propane-1,3-diol (Compound 263)

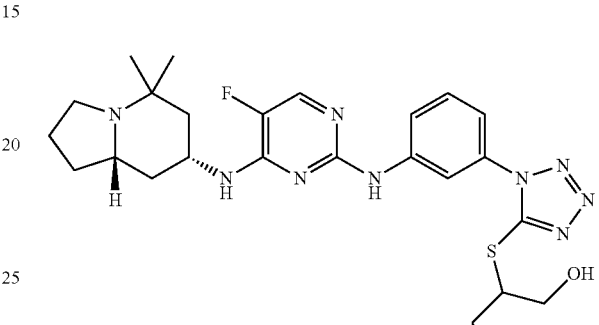

¹H NMR (300 MHz, d₆-DMSO) δ 9.33 (s, 1H), 8.24 (s, 1H), 7.87 (d, J=3.9 Hz, 1H), 7.73 (m, 1H), 7.34 (m, 2H), 7.25 (d, J=7.2 Hz, 1H), 5.18 (m, 1H), 4.28 (dd, J=5.7, 15.3 Hz, 1H), 4.19 (br, 1H), 4.01 (m, 1H), 3.64 (m, 2H), 3.52 (m, 1H), 2.82 (m, 1H), 2.24 (m, 1H), 1.98 (m, 1H), 1.77 (m, 1H), 1.59 (m, 3H), 1.38 (t, J=11.4 Hz, 1H), 1.19 (m, 2H), 1.04 (s, 3H), 0.87 (s, 3H); m/z=530.27 (M+H)⁺.

Synthesis of 2-(1-(3-(4-((7R,8aS)-octahydro-5,5-dimethylindolizin-7-ylamino)-5-fluoropyrimidin-2-ylamino)phenyl)-1H-tetrazol-5-ylthio)-3-aminopropan-1-ol, besylate salt (Compound 264)

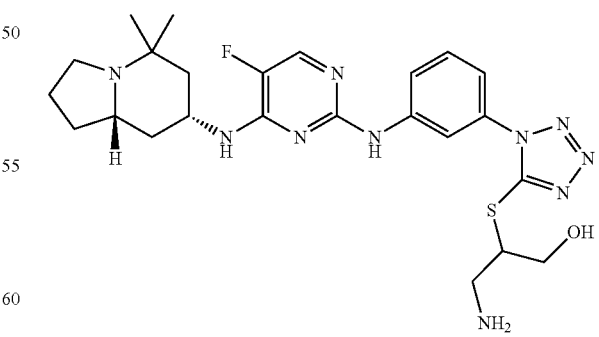

¹H NMR (300 MHz, d₆-DMSO) δ 9.38 (s, 1H), 9.13 (br, 1H), 8.18 (s, 1H), 7.94 (s, 1H), 7.74 (s, 1H), 7.36 (d, 1H), 5.24 (br, 1H), 4.33 (br, 5H), 3.68 (br, 2H), 2.04 (m, 5H), 1.62 (m, 4H), 1.32 (s, 3H), 1.29 (s, 3H); m/z=529.44 (M+H)⁺.

Synthesis of 1-(3-(4-((7R,8aS)-octahydro-5,5-dimethylindolizin-7-ylamino)-5-fluoropyrimidin-2-ylamino)phenyl)-4-(oxetan-3-yl)-1H-tetrazol-5(4H)-one, formate salt (Compound 265)

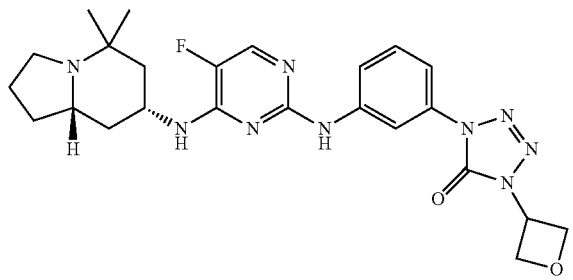 [SMILES: CC1(C)C[C@H](Nc2nc(Nc3cccc(-n4nnn(C5COC5)c4=O)c3)ncc2F)C[C@@H]2CCCN21]

¹H NMR (300 MHz, d₆-DMSO) δ 9.36 (s, 1H), 8.24 (t, J=2.1 Hz, 1H), 7.87 (d, J=3.9 Hz, 1H), 7.73 (d, J=8.1 Hz, 1H), 7.39-7.25 (m, 3H), 5.47 (p, J=6.9 Hz, 1H), 4.93 (d, J=6.9 Hz, 4H), 4.17 (m, 1H), 2.83 (m, 1H), 2.41 (m, 1H), 2.24 (q, J=8.4 Hz, 1H), 1.99 (d, J=12.3 Hz, 1H), 1.75 (m, 1H), 1.59 (m, 3H), 1.39 (t, J=12.3 Hz, 1H), 1.19 (m, 2H), 1.05 (s, 3H), 0.86 (s, 3H); m/z=495.98 (M+H)⁺.

Synthesis of 2-(1-(3-(4-((7R,8aS)-octahydro-5,5-dimethylindolizin-7-ylamino)-5-fluoropyrimidin-2-ylamino)phenyl)-1H-tetrazol-5-ylthio)ethanol, besylate salt (Compound 266)

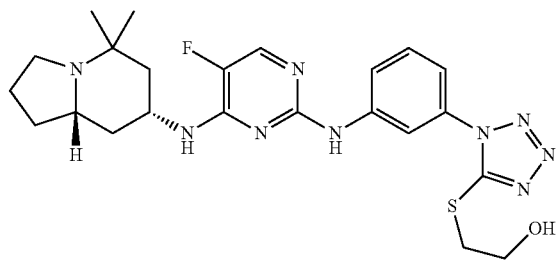 [SMILES: CC1(C)C[C@H](Nc2nc(Nc3cccc(-n4nnnc4SCCO)c3)ncc2F)C[C@@H]2CCCN21]

¹H NMR (300 MHz, d₆-DMSO) δ 9.55 (s, 1H), 9.07 (br, 1H), 8.04 (s, 1H), 7.97 (d, 1H), 7.83 (d, 1H), 7.65 (d, 1H), 7.48 (t, J=8.1 Hz, 1H), 7.12 (d, J=8.1 Hz, 1H), 5.10 (t, 1H), 4.28 (br, 1H), 3.71 (q, J=6.3 Hz, 2H), 3.43 (t, J=6.0 Hz, 2H), 3.07 (br, 1H), 2.03 (m, 6H), 1.60 (m, 4H), 1.33 (s, 3H), 1.22 (s, 3H); m/z=500.31 (M+H)⁺.

Synthesis of 1-(3-(4-((7R,8aS)-octahydro-5,5-dimethylindolizin-7-ylamino)-5-fluoropyrimidin-2-ylamino)phenyl)-4-(2-hydroxyethyl)-1H-tetrazol-5(4H)-one, formate salt (Compound 267)

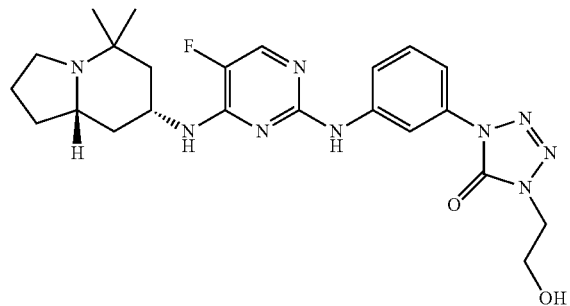 [SMILES: CC1(C)C[C@H](Nc2nc(Nc3cccc(-n4nnn(CCO)c4=O)c3)ncc2F)C[C@@H]2CCCN21]

¹H NMR (300 MHz, d₆-DMSO) δ 9.34 (s, 1H), 8.22 (s, 1H), 7.88 (d, J=3.6 Hz, 1H), 7.74 (d, J=6.0 Hz, 1H), 7.33 (m, 3H), 5.00 (br, 1H), 4.19 (br, 1H), 4.01 (t, J=5.1 Hz, 2H), 3.74 (t, 2H), 2.87 (m, 1H), 2.32 (m, 1H), 2.02 (m, 1H), 1.79 (1H), 1.63 (m, 3H), 1.41 (t, J=13.8 Hz, 1H), 1.21 (m, 2H), 1.07 (s, 3H), 0.91 (s, 3H); m/z=484.34 (M+H)⁺.

Synthesis of 5-fluoro-N2-(1H-2,4-dihydron-2-(2-hydroxyethyl)-4,4-dimethyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine (Compound 268)

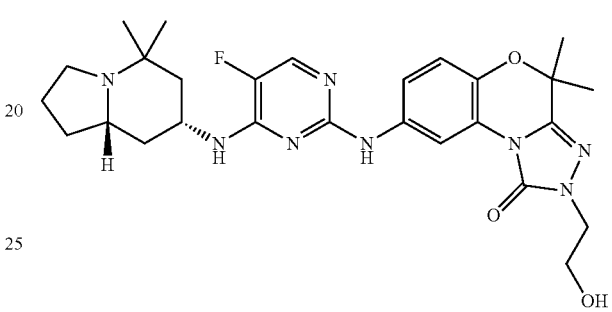

¹H NMR (300 MHz, d₆-DMSO) δ 9.10 (s, 1H), 8.56 (d, J=2.4 Hz, 1H), 7.81 (d, J=3.6 Hz, 1H), 7.37 (dd, J=2.7, 9.3 Hz, 1H), 7.15 (d, J=7.8 Hz, 1H), 6.93 (d, J=8.7 Hz, 1H), 4.82 (t, J=5.7 Hz, 1H), 4.22 (br, 1H), 3.75 (q, J=5.4 Hz, 2H), 3.64 (q, J=5.4 Hz, 2H), 2.79 (t, 1H), 2.38 (m, 1H), 2.20 (q, J=8.7 Hz, 1H), 1.95 (d, J=11.1 Hz, 1H), 1.74 (m, 1H), 1.56 (s, 6H), 1.49 (s, 3H), 1.35-1.13 (m, 3H), 1.01 (s, 3H), 0.81 (s, 3H); m/z=539.37 (M+H)⁺.

Synthesis of 5-fluoro-N4-((7R,8aS)-octahydro-5,5-dimethylindolizin-7-yl)-N2-(3-(5-(methylsulfonyl)-1H-tetrazol-1-yl)phenyl)pyrimidine-2,4-diamine, TFA salt (Compound 269)

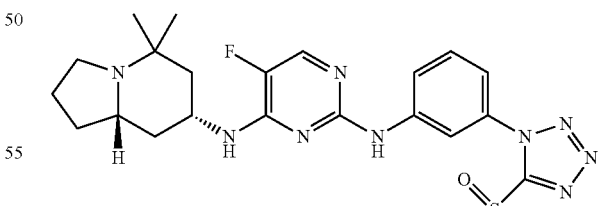

¹H NMR (300 MHz, d₆-DMSO) δ 11.47 (s, 1H), 9.59 (s, 1H), 8.13 (d, 1H), 7.96 (d, J=3.6 Hz, 1H), 7.52 (m, 2H), 7.28 (d, 1H), 4.34 (br, 1H), 3.72 (br, 2H), 3.28 (d, J=3.9 Hz, 3H), 2.13 (m, 5H), 1.88 (m, 4H), 1.50 (s, 3H), 1.44 (s, 3H); m/z=501.93 (M+H)⁺.

Synthesis of 5-fluoro-N4-((7R,8aS)-octahydro-5,5-dimethylindolizin-7-yl)-N2-(3-(5-(methylsulfinyl)-1H-tetrazol-1-yl)phenyl)pyrimidine-2,4-diamine, TFA salt (Compound 270)

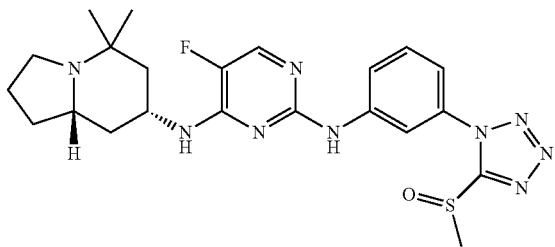 [SMILES: CS(=O)c1nnnn1-c1cccc(Nc2ncc(F)c(N[C@@H]3C[C@@H]4CCCN4C(C)(C)C3)n2)c1]

¹H NMR (300 MHz, d₆-DMSO) δ 11.69 (s, 1H), 10.42 (s, 1H), 8.84 (d, J=5.7 Hz, 1H), 8.74 (br, 1H), 7.96 (s, 1H), 7.86 (d, J=9.0 Hz, 1H), 7.58 (t, J=8.1 Hz, 1H), 7.50 (d, J=8.4 Hz, 1H), 4.34 (br, 1H), 4.24 (s, 3H), 4.05 (m, 1H), 3.71 (m, 2H), 2.07 (m, 6H), 1.81 (m, 2H), 1.40 (s, 3H), 1.37 (s, 3H); m/z=486.31 (M+H)⁺.

Synthesis of 2-(1-(3-(44(7R,8aS)-octahydro-5,5-dimethylindolizin-7-ylamino)-5-fluoropyrimidin-2-ylamino)phenyl)-1H-tetrazol-5-ylthio)ethanol (Compound 271)

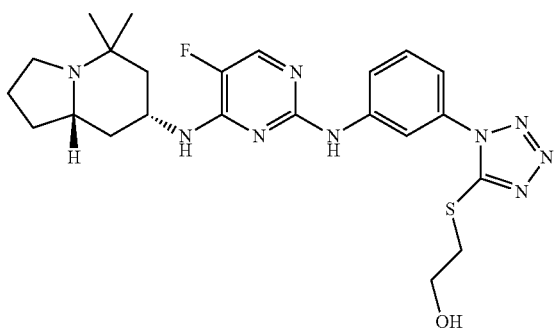 [SMILES: CC1(C)C[C@H](Nc2nc(Nc3cccc(-n4nnnc4SCCO)c3)ncc2F)C[C@@H]2CCCN21]

¹H NMR (300 MHz, d₆-DMSO) δ 9.53 (s, 1H), 8.22 (s, 1H), 7.89 (d, J=3.6 Hz, 1H), 7.71 (d, J=8.4 Hz, 1H), 7.44 (t, J=8.1 Hz, 1H), 7.32 (d, J=8.1 Hz, 1H), 7.06 (d, J=7.5 Hz, 1H), 5.10 (t, J=5.4 Hz, 1H), 4.08 (br, 1H), 3.70 (q, J=5.7 Hz, 2H), 3.39 (q, J=6.3 Hz, 2H), 2.79 (m, 1H), 2.21 (m, 1H), 1.98 (m, 2H), 1.56 (m, 4H), 1.40 (t, J=12.6 Hz, 1H), 1.17 (m, 2H), 1.02 (s, 3H), 0.70 (s, 3H); m/z=500.27 (M+H)⁺.

Synthesis of 1-(5-(4-((7R,8aS)-octahydro-5,5-dimethylindolizin-7-ylamino)-5-fluoropyrimidin-2-ylamino)-2-methylphenyl)-1H-tetrazol-5(4H)-one, besylate salt (Compound 272)

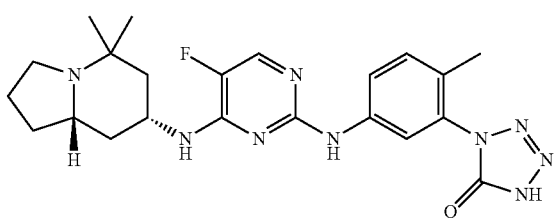 [SMILES: Cc1ccc(Nc2ncc(F)c(N[C@@H]3C[C@@H]4CCCN4C(C)(C)C3)n2)cc1-n1nn[nH]c1=O]

¹H NMR (300 MHz, d₆-DMSO) δ 9.26 (s, 1H), 7.88 (d, J=3.9 Hz, 1H), 7.84 (s, 1H), 7.42 (d, 1H), 7.21 (d, J=8.7 Hz, 1H), 4.18 (br, 1H), 3.15 (m, 1H), 2.78 (m, 2H), 2.12 (d, 1H), 2.05 (s, 3H), 1.92 (m, 5H), 1.46 (m, 2H), 1.24 (s, 3H), 1.12 (s, 3H); m/z=454.31 (M+H)⁺.

Synthesis of 1-(5-(4-((7R,8aS)-octahydro-5,5-dimethylindolizin-7-ylamino)-5-fluoropyrimidin-2-ylamino)-2-methylphenyl)-4-methyl-1H-tetrazol-5(4H)-one, HCl salt (Compound 273)

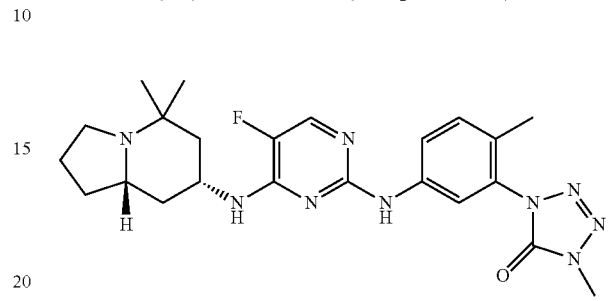

¹H NMR (300 MHz, d₆-DMSO) δ 9.26 (s, 1H), 9.06 (br, 1H), 7.92 (d, J=3.6 Hz, 1H), 7.78 (d, J=8.4 Hz, 1H), 7.66 (s, 1H), 7.58 (d, J=7.5 Hz, 1H), 7.26 (d, J=8.1 Hz, 1H), 4.33 (m, 1H), 3.62 (s, 3H), 3.36 (s, 2H), 3.08 (p, J=9.0 Hz, 1H), 2.33 (d, J=14.1 Hz, 1H), 2.08 (s, 3H), 1.96 (m, 5H), 1.61 (m, 2H), 1.34 (s, 3H), 1.31 (m, 3H); m/z=468.01 (M+H)⁺.

Synthesis of 1-(5-(4-((7R,8aS)-octahydro-5,5-dimethylindolizin-7-ylamino)-5-fluoropyrimidin-2-ylamino)-2-methylphenyl)-4-methyl-1H-tetrazol-5(4H)-one (Compound 274)

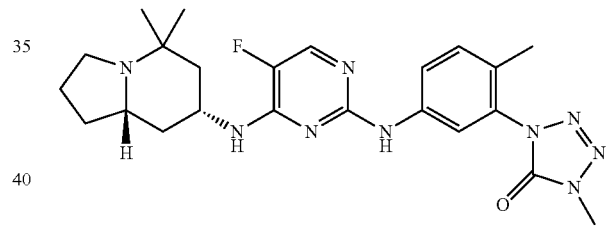

¹H NMR (300 MHz, d₆-DMSO) δ 9.29 (s, 1H), 7.94 (s, 1H), 7.85 (d, J=3.6 Hz, 1H), 7.62 (d, J=8.7 Hz, 1H), 7.24 (d, J=9.3 Hz, 2H), 4.06 (m, 1H), 3.61 (s, 3H), 2.83 (t, 1H), 2.22 (m, 2H), 2.05 (s, 3H), 1.98 (d, J=8.4 Hz, 1H), 1.58 (m, 4H), 1.43 (t, J=12.3 Hz, 1H), 1.21 (m, 2H), 1.05 (s, 3H), 0.83 (s, 3H); m/z=468.01 (M+H)⁺.

Synthesis of 1-(5-(4-((7R,8aS)-octahydro-5,5-dimethylindolizin-7-ylamino)-5-fluoropyrimidin-2-ylamino)-2-methylphenyl)-4-(2-hydroxyethyl)-1H-tetrazol-5(4H)-one (Compound 275)

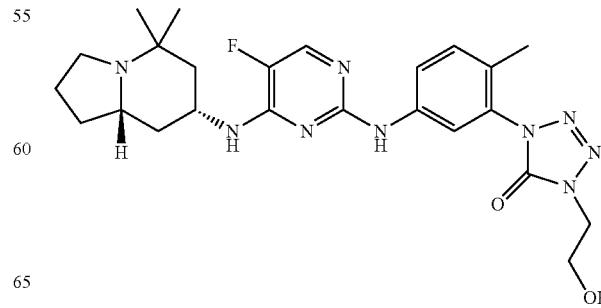

543

¹H NMR (300 MHz, d₆-DMSO) δ 9.26 (s, 1H), 7.87-7.84 (m, 2H), 7.70 (dd, J=1.8, 8.4 Hz, 1H), 7.23 (d, J=8.1 Hz, 2H), 5.03 (t, J=5.4 Hz, 1H), 4.10 (m, 1H), 4.01 (t, J=5.4 Hz, 2H), 3.75 (q, J=5.4 Hz, 2H), 2.83 (dt, J=3.3, 8.7 Hz, 1H), 2.25 (q, J=8.1 Hz, 2H), 2.05 (s, 3H), 1.96 (d, 1H), 1.72 (m, 1H), 1.59 (m, 3H), 1.42 (t, J=12.6 Hz, 1H), 1.19 (m, 2H), 1.05 (s, 3H), 0.87 (s, 3H); m/z=497.99 (M+H)⁺.

Synthesis of 1-(5-(4-((7R,8aS)-octahydro-5,5-dimethylindolizin-7-ylamino)-5-fluoropyrimidin-2-ylamino)-2-methylphenyl)-4-(oxetan-3-yl)-1H-tetrazol-5(4H)-one, formate salt (Compound 276)

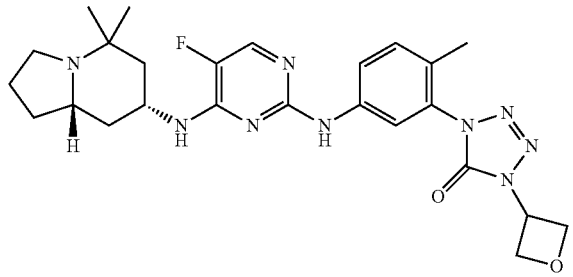 [SMILES: Cc1ccc(Nc2ncc(F)c(N[C@@H]3C[C@@H]4CCCN4C(C)(C)C3)n2)cc1-n1nnn(C2COC2)c1=O]

¹H NMR (300 MHz, d₆-DMSO) δ 9.26 (s, 1H), 7.84 (d, J=3.6 Hz, 2H), 7.71 (d, J=10.5 Hz, 1H), 7.23 (d, J=8.4 Hz, 2H), 5.48 (t, J=6.9 Hz, 2H), 4.95 (d, J=6.6 Hz, 4H), 4.09 (m, 1H), 2.83 (m, 1H), 2.25 (m, 2H), 2.07 (s, 3H), 1.95 (m, 1H), 1.71 (m, 1H), 1.57 (m, 3H), 1.42 (m, 1H), 1.17 (m, 2H), 1.05 (s, 3H), 0.85 (s, 3H); m/z=509.97 (M+H)⁺.

Synthesis of 1-(5-(4-((7R,8aS)-octahydro-5,5-dimethylindolizin-7-ylamino)-5-fluoropyrimidin-2-ylamino)-2-methoxyphenyl)-1H-tetrazol-5(4H)-one (Compound 277)

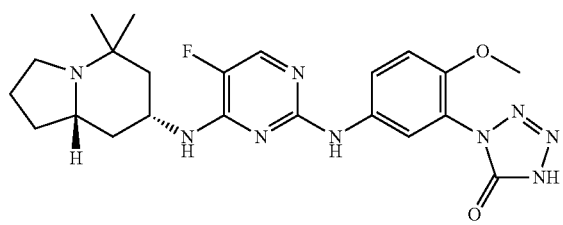 [SMILES: COc1ccc(Nc2ncc(F)c(N[C@@H]3C[C@@H]4CCCN4C(C)(C)C3)n2)cc1-n1nn[nH]c1=O]

¹H NMR (300 MHz, d₆-DMSO) δ 9.22 (s, 1H), 7.99 (d, J=2.4 Hz, 1H), 7.94 (d, J=3.9 Hz, 1H), 7.71 (dd, J=2.7, 9.0 Hz, 1H), 7.45 (d, 1H), 7.20 (d, J=9.0 Hz, 1H), 4.25 (m, 1H), 3.79 (s, 3H), 3.18 (m, 1H), 2.79 (m, 2H), 2.22 (d, 1H), 1.87 (m, 5H), 1.48 (m, 2H), 1.30 (s, 3H), 1.15 (s, 3H); m/z=470.30 (M+H)⁺.

544

Synthesis of 1-(5-(4-((7R,8aS)-octahydro-5,5-dimethylindolizin-7-ylamino)-5-fluoropyrimidin-2-ylamino)-2-methoxyphenyl)-4-methyl-1H-tetrazol-5(4H)-one, HCl salt (Compound 278)

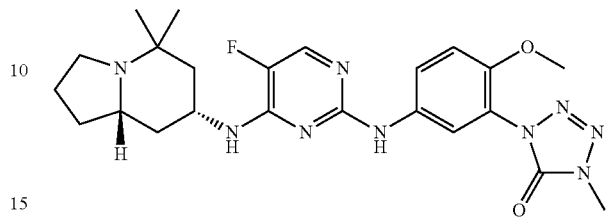

¹H NMR (300 MHz, d₆-DMSO) δ 9.11 (s, 1H), 9.06 (br, 1H), 7.90 (d, J=3.6 Hz, 1H), 7.77 (dd, J=2.7, 8.7 Hz, 1H), 7.71 (d, J=3.0 Hz, 1H), 7.53 (d, J=8.7 Hz, 1H), 7.14 (d, J=9.0 Hz, 1H), 4.31 (m, 1H), 3.73 (s, 3H), 3.60 (s, 3H), 3.36 (m, 2H), 3.06 (t, J=9.9 Hz, 1H), 2.32 (d, J=13.8 Hz, 1H), 2.08-1.95 (m, 5H), 1.68-1.56 (m, 2H), 1.33 (s, 3H), 1.28 (s, 3H); m/z=483.95 (M+H)⁺.

Synthesis of 1-(5-(4-((7R,8aS)-octahydro-5,5-dimethylindolizin-7-ylamino)-5-fluoropyrimidin-2-ylamino)-2-methoxyphenyl)-4-methyl-1H-tetrazol-5(4H)-one (Compound 279)

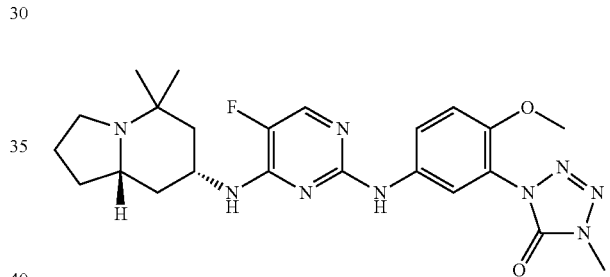

¹H NMR (300 MHz, d₆-DMSO) δ 9.17 (s, 1H), 8.03 (s, 1H), 7.83 (d, J=4.2 Hz, 1H), 7.63 (d, J=8.4 Hz, 1H), 7.22 (d, J=8.7 Hz, 1H), 7.14 (d, J=9.0 Hz, 1H), 4.05 (m, 1H), 3.71 (s, 3H), 3.60 (s, 3H), 2.82 (t, 1H), 2.21 (m, 2H), 1.96 (d, 1H), 1.57 (m, 5H), 1.18 (m, 2H), 1.05 (s, 3H), 0.81 (s, 3H); m/z=483.97 (M+H)⁺.

Synthesis of 1-(5-(4-((7R,8aS)-octahydro-5,5-dimethylindolizin-7-ylamino)-5-fluoropyrimidin-2-ylamino)-2-methoxyphenyl)-4-(2-hydroxyethyl)-1H-tetrazol-5(4H)-one (Compound 280)

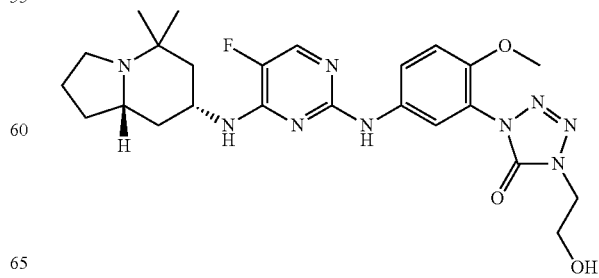

¹H NMR (300 MHz, d₆-DMSO) δ 9.11 (s, 1H), 7.93 (s, 1H), 7.90 (s, 1H), 7.83 (d, J=3.6 Hz, 1H), 7.72 (d, J=7.2 Hz, 1H), 7.19 (brd, 1H), 7.13 (d, J=9.3 Hz, 1H), 5.04 (t, J=5.4 Hz, 1H), 4.11 (m, 1H), 3.98 (d, J=5.4 Hz, 2H), 3.75 (q, J=5.4 Hz, 2H), 3.71 (s, 3H), 2.82 (m, 1H), 2.26 (m, 2H), 1.99 (d, 1H), 1.59 (m, 4H), 1.42 (t, J=13.5 Hz, 1H), 1.20 (m, 2H), 1.06 (s, 3H), 0.86 (s, 3H); m/z=514.33 (M+H)⁺.

Synthesis of 5-fluoro-N4-((7R,8aS)-octahydro-5,5-dimethylindolizin-7-yl)-N2-(4-methyl-3-(5-(methylthio)-1H-tetrazol-1-yl)phenyl)pyrimidine-2,4-diamine (Compound 281)

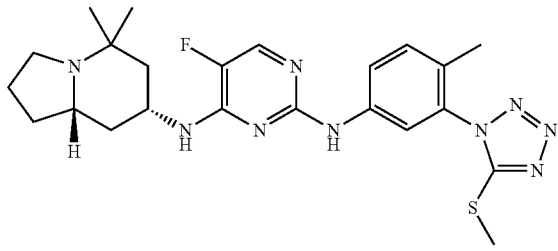 [SMILES: CSc1nnnn1-c1cc(Nc2ncc(F)c(N[C@@H]3C[C@@H]4CCCN4C(C)(C)C3)n2)ccc1C]

¹H NMR (300 MHz, d₆-DMSO) δ 9.43 (s, 1H), 8.06 (m, 1H), 7.86 (m, 1H), 7.61 (m 1H), 7.35 (m, 2H), 3.29 (s, 3H), 2.73 (s, 3H), 1.86 (m, 6H), 1.56 (m, 5H), 1.22 (s, 3H), 1.04 (s, 3H); m/z=484.36 (M+H)⁺.

Synthesis of 2-(1-(5-(44(7R,8aS)-octahydro-5,5-dimethylindolizin-7-ylamino)-5-fluoropyrimidin-2-ylamino)-2-methylphenyl)-1H-tetrazol-5-ylthio)ethanol (Compound 282)

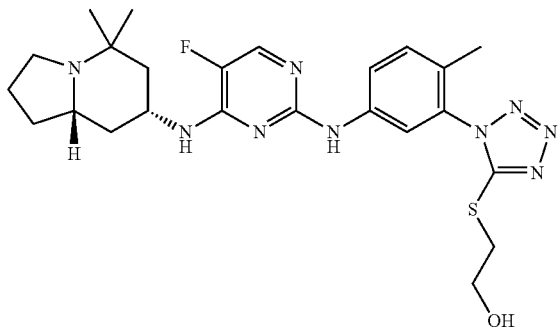 [SMILES: Cc1ccc(Nc2ncc(F)c(N[C@@H]3C[C@@H]4CCCN4C(C)(C)C3)n2)cc1-n1nnnc1SCCO]

¹H NMR (300 MHz, d₆-DMSO) δ 9.42 (s, 1H), 8.02 (s, 1H), 7.86 (d, J=3.9 Hz, 1H), 7.64 (d, J=8.1 Hz, 1H), 7.31 (m, 2H), 5.10 (t, J=5.4 Hz, 1H), 4.02 (m, 1H), 3.68 (q, J=6.0 Hz, 2H), 3.38 (t, J=6.9 Hz, 2H), 2.79 (m, 1H), 2.25 (m, 1H), 1.92 (m, 2H), 1.85 (s, 3H), 1.60 (m, 3H), 1.49 (m, 2H), 1.22 (m, 2H), 1.04 (s, 3H), 0.74 (s, 3H); m/z=514.35 (M+H)⁺.

Synthesis of 5-fluoro-N2-(1H-2,4-dihydron-spiro (2H-1,4-benzoxazine-4,4'-[4H]pyran)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, TFA salt (Compound 283)

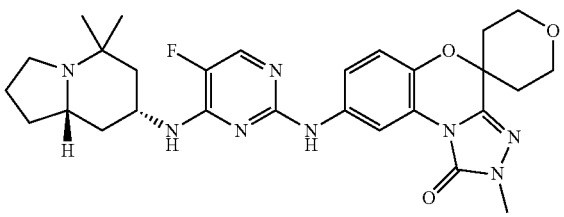 [SMILES: Cn1nc2n(c1=O)-c1cc(Nc3ncc(F)c(N[C@@H]4C[C@@H]5CCCN5C(C)(C)C4)n3)ccc1OC21CCOCC1]

¹H NMR (300 MHz, d₆-DMSO) δ 9.47 (s, 1H), 9.10 (br, 1H), 8.50 (d, J=2.7 Hz, 1H), 7.96 (d, J=4.2 Hz, 1H), 7.85 (br, 1H), 7.38 (dd, J=2.4, 9.0 Hz, 1H), 7.11 (d, J=8.7 Hz, 1H), 4.48 (m, 1H), 3.77 (m, 4H), 3.40 (s, 3H), 3.06 (p, J=8.1 Hz, 1H), 2.29 (d, 1H), 2.15 (m, 1H), 2.05-1.55 (m, 12H), 1.29 (s, 3H), 1.18 (s, 3H); m/z=551.38 (M+H)⁺.

Synthesis of 5-fluoro-N4-((7R,8aS)-octahydro-5,5-dimethylindolizin-7-yl)-N2-(4-methoxy-3-(5-(oxetan-3-yloxy)-1H-tetrazol-1-yl)phenyl)pyrimidine-2,4-diamine, formate salt (Compound 284)

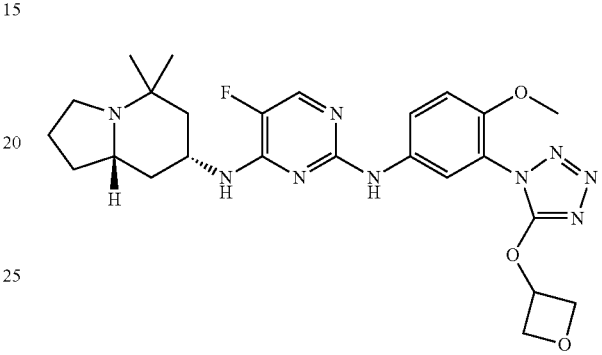

¹H NMR (300 MHz, d₆-DMSO) δ 9.20 (s, 1H), 8.06 (d, J=2.4 Hz, 1H), 7.83 (d, J=3.9 Hz, 1H), 7.70 (dd, J=1.8, 10.2 Hz, 1H), 7.23 (m, 2H), 5.69 (p, J=10.8 Hz, 1H), 4.89 (t, J=6.9 Hz, 2H), 4.55 (dd, J=4.8, 8.1 Hz, 2H), 4.07 (m, 1H), 3.75 (s, 3H), 2.80 (t, 1H), 2.25 (d, J=9.3 Hz, 1H), 2.08 (m, 1H), 1.95 (d, J=12.0 Hz, 1H), 1.63-1.38 (m, 5H), 1.15 (m, 2H), 1.04 (s, 3H), 0.78 (s, 3H); m/z=525.98 (M+H)⁺.

Synthesis of 1-(5-(44(7R,8aS)-octahydro-5,5-dimethylindolizin-7-ylamino)-5-fluoropyrimidin-2-ylamino)-2-methoxyphenyl)-4-(oxetan-3-yl)-1H-tetrazol-5(4H)-one, formate salt (Compound 285)

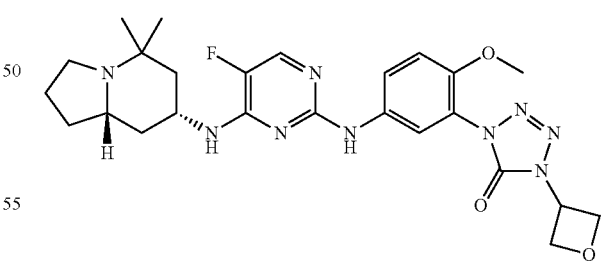

¹H NMR (300 MHz, d₆-DMSO) δ 9.13 (s, 1H), 7.93 (d, J=2.4 Hz, 1H), 7.82 (d, J=3.6 Hz, 1H), 7.71 (dd, J=2.4, 9.3 Hz, 1H), 7.20 (d, J=7.2 Hz, 1H), 7.14 (d, J=9.3 Hz, 1H), 5.47 (p, J=6.9 Hz, 1H), 4.94 (d, J=7.2 Hz, 4H), 4.11 (m, 1H), 3.71 (s, 3H), 2.82 (t, J=5.1 Hz, 1H), 2.24 (m, 2H), 1.97 (d, J=9.0 Hz, 1H), 1.72 (m, 1H), 1.58 (m, 3H), 1.40 (t, J=11.7 Hz, 1H), 1.17 (m, 2H), 1.05 (s, 3H), 0.84 (s, 3H); m/z=525.98 (M+H)⁺.

Synthesis of 5-fluoro-N4-((7R,8aS)-octahydro-5,5-dimethylindolizin-7-yl)-N2-(4-methyl-3-(5-(methylsulfonyl)-1H-tetrazol-1-yl)phenyl)pyrimidine-2,4-diamine, TFA salt (Compound 286)

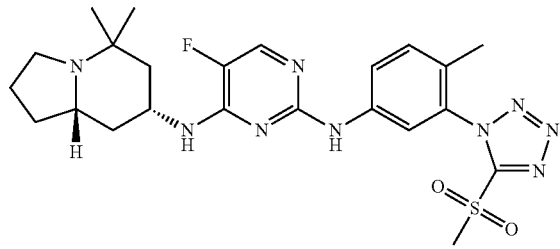 [SMILES: Cc1ccc(Nc2ncc(F)c(N[C@@H]3C[C@@H]4CCCN4C(C)(C)C3)n2)cc1-n1nnnc1S(C)(=O)=O]

m/z=516.63 (M+H)+.

Synthesis of 5-fluoro-N2-(1H-2,4-dihydron-4-(hydroxymethyl)-4-(((1,1-dimethylethyl)dimethylsilyl)oxymethyl)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, besylate salt (Compound 287)

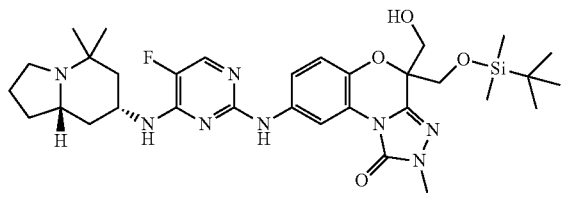 [SMILES: Cn1nc2n(c1=O)-c1cc(Nc3ncc(F)c(N[C@@H]4C[C@@H]5CCCN5C(C)(C)C4)n3)ccc1OC2(CO)CO[Si](C)(C)C(C)(C)C]

¹H NMR (300 MHz, d₆-DMSO) δ 9.23 (s, 1H), 8.69 (s, 1H), 8.03 (s, 1H), 7.60 (d, 1H), 7.50 (d, 1H), 7.06 (d, J=9.3 Hz, 1H), 5.36 (t, 1H), 5.18 (m, 2H), 4.05 (s, 2H), 3.91 (m, 1H), 3.53 (s, 3H), 2.39-1.77 (m, 10H), 1.44 (s, 3H), 1.39 (s, 3H), 0.83 (d, J=5.4 Hz, 9H), 0.06 (d, J=4.2 Hz, 3H), 0.00 (s, 3H); m/z=655.09 (M+H)+.

Synthesis of 5-fluoro-N2-(1H-2,4-dihydron-4,4-di(hydroxymethyl)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, besylate salt (Compound 288)

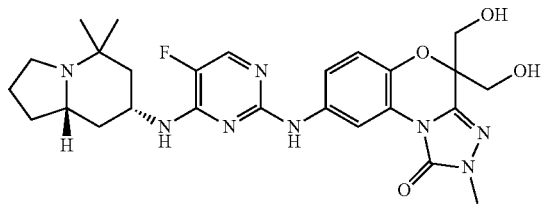 [SMILES: Cn1nc2n(c1=O)-c1cc(Nc3ncc(F)c(N[C@@H]4C[C@@H]5CCCN5C(C)(C)C4)n3)ccc1OC2(CO)CO]

¹H NMR (300 MHz, d₆-DMSO) δ 9.07 (s, 1H), 8.51 (br, 1H), 7.85 (br, 1H), 7.41 (m, 2H), 6.90 (m, 1H), 5.12 (t, J=5.7 Hz, 2H), 4.44 (br, 1H), 3.72 (m, 4H), 3.39 (s, 3H), 1.93 (br, 3H), 1.62 (br, 3H), 1.22 (m, 5H) 1.03 (br, 3H), 0.86 (br, 3H); m/z=541.00 (M+H)+.

Synthesis of 1-(5-(4-((7R,8aS)-octahydro-5,5-dimethylindolizin-7-ylamino)-5-fluoropyrimidin-2-ylamino)-2-methylphenyl)-4-(2-hydroxy-2-methylpropyl)-1H-tetrazol-5(4H)-one, formate salt (Compound 289)

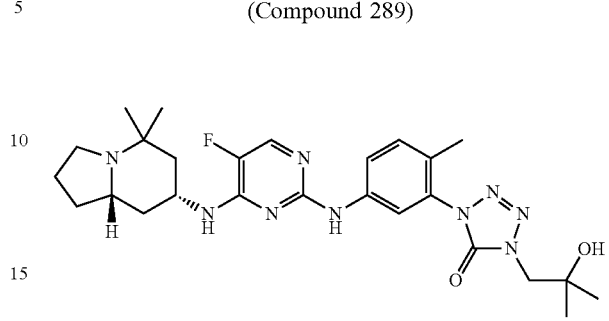

¹H NMR (300 MHz, d₆-DMSO) δ 9.22 (s, 1H), 8.27 (s, 1H), 7.86 (s, 1H), 7.79 (s, 1H), 7.23 (m, 2H), 6.55 (t, J=9.9 Hz, 1H), 4.16 (s, 1H), 3.69 (s, 2H), 2.03 (s, 3H), 1.60 (br, 6H), 1.55 (s, 6H), 1.20 (br, 4H), 1.06 (s, 3H), 0.90 (s, 3H); m/z=526.22 (M+H)+.

Synthesis of 1-(5-(4-((7R,8aS)-octahydro-5,5-dimethylindolizin-7-ylamino)-5-fluoropyrimidin-2-ylamino)-2-methoxyphenyl)-4-(2-hydroxy-2-methylpropyl)-1H-tetrazol-5(4H)-one (Compound 290)

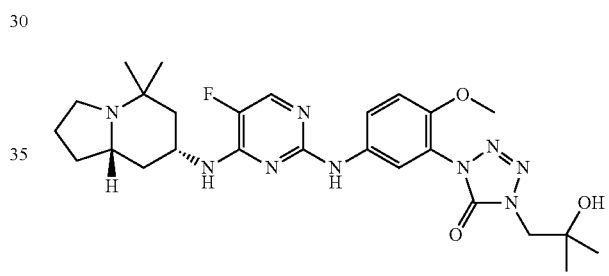

¹H NMR (300 MHz, d₆-DMSO) δ 9.07 (s, 1H), 7.82 (m, 2H), 7.75 (d, J=9.6 Hz, 1H), 7.18 (d, J=7.5 Hz, 1H), 7.10 (d, J=8.7 Hz, 1H), 5.11 (t, J=6.3 Hz, 1H), 4.14 (m, 1H), 3.70 (s, 5H), 2.82 (m, 1H), 2.26 (m, 2H), 1.98 (m, 1H), 1.60 (m, 5H), 1.53 (s, 6H), 1.21 (m, 2H), 1.05 (s, 3H), 0.89 (s, 3H); m/z=542.22 (M+H)+.

Synthesis of 5-fluoro-N2-(1H-2,4-dihydron-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine (Compound 291)

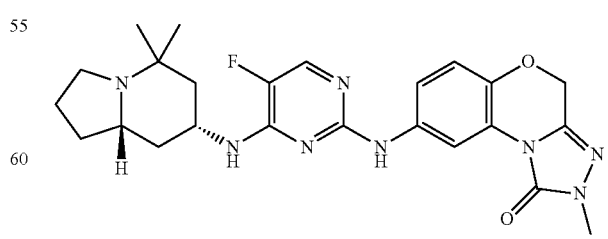

¹H NMR (300 MHz, d₆-DMSO) δ 9.10 (s, 1H), 8.46 (d, J=2.4 Hz, 1H), 7.81 (d, J=3.9 Hz, 1H), 7.44 (dd, J=2.7, 8.4 Hz, 1H), 7.14 (d, J=8.4 Hz, 1H), 6.96 (d, J=8.7 Hz, 1H), 5.04

(ABq, J=14.1, 19.2 Hz, 2H), 4.23 (m, 1H), 3.37 (s, 3H), 2.82 (t, J=9.0 Hz, 1H), 2.22 (m, 1H), 1.97 (d, J=8.7 Hz, 1H), 1.72 (m, 1H), 1.5 m (m, 3H), 1.34 (t, J=12.3 Hz, 1H), 1.24-1.06 (m, 3H), 1.03 (s, 3H), 0.85 (s, 3H); m/z=481.09 (M+H)+.

Synthesis of 5-fluoro-N2-(1H-2,3,4,5-tetrahydron-2, 4-dimethyl-4-hydroxy-[1,2,4]triazolo[4,5-c][1,5] benzoxazepin-1-one-9-yl)-N4-((7R,8aS)-octahydro-5,5-dimethylindolizin-7-yl)pyrimidine-2,4-diamine, two diastereomers (Compound 292)

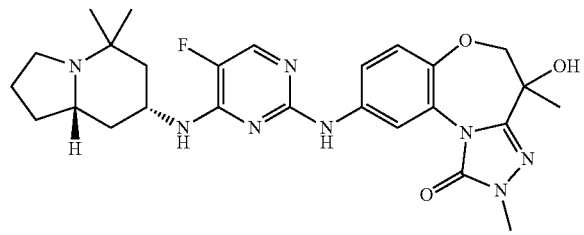 [SMILES: Cn1nc2n(c1=O)-c1cc(Nc3ncc(F)c(N[C@@H]4C[C@@H]5CCCN5C(C)(C)C4)n3)ccc1OCC2(C)O]

$^1$H NMR (300 MHz, d$_6$-DMSO) δ 9.16 (s, 1H), 9.15 (s, 1H), 8.02 (d, 1H), 7.98 (d, 1H), 7.83 (d, J=3.9 Hz, 2H), 7.56 (d, J=8.4 Hz, 2H), 7.18 (m, 2H), 6.99 (d, J=8.4 Hz, 2H), 5.54 (s, 1H), 5.50 (s, 1H), 4.21 (ABq, J=12.0, 49.2 Hz, 4H), 4.20 (br, 2H), 3.39 (s, 6H), 2.82 (t, 2H), 2.26 (m, 2H), 1.99 (m, 2H), 1.75 (m, 2H), 1.58 (m, 8H), 1.38 (s, 3H), 1.37 (s, 3H), 1.20 (m, 6H), 1.07 (s, 3H), 1.03 (s, 3H), 0.94 (s, 3H), 0.85 (s, 3H); m/z=525.13 (M+H)+.

Synthesis of 5-fluoro-N2-(1H-2,4-dihydron-spiro (2H-1,4-benzoxazine-4,3'-[3H]oxetan)-2-methyl-[1, 2,4]triazolo[3,4-c][1,4]benzoxazin-1-one-8-yl)-N4-((7R,8aS)-octahydro-5,5-dimethylindolizin-7-yl) pyrimidine-2,4-diamine (Compound 293)

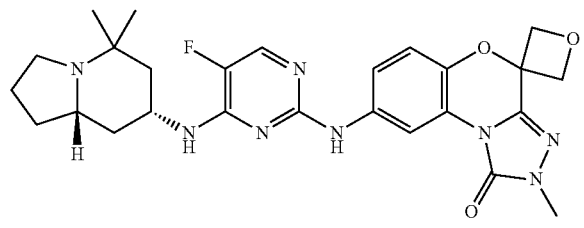 [SMILES: Cn1nc2n(c1=O)-c1cc(Nc3ncc(F)c(N[C@@H]4C[C@@H]5CCCN5C(C)(C)C4)n3)ccc1OC21COC1]

$^1$H NMR (300 MHz, d$_6$-DMSO) δ 9.15 (s, 1H), 8.46 (s, 1H), 7.81 (d, 1H), 7.49 (d, J=7.2 Hz, 1H), 7.16 (d, J=7.8 Hz, 1H), 7.10 (d, J=9.0 Hz, 1H), 4.94 (d, J=7.8 Hz, 1H), 4.86 (d, J=8.4 Hz, 1H), 4.78 (t, J=6.6 Hz, 2H), 4.18 (m, 1H), 3.43 (s, 3H), 2.82 (t, 1H), 2.24 (q, J=9.3 Hz, 1H), 1.96 (d, J=12.6 Hz, 1H), 1.73 (m, 1H), 1.56 (m, 4H), 1.23 (m, 3H), 1.03 (s, 3H), 0.84 (s, 3H); m/z=523.06 (M+H)+.

Preparation of 5-fluoro-N2-(1H-2,3,4,5-tetrahydron-2,4-dimethyl-4-hydroxy-[1,2,4]triazolo[4,5-c][1,5] benzoxazepin-1-one-9-yl)-N4-((7R,8aS)-octahydro-5,5-dimethylindolizin-7-yl)pyrimidine-2,4-diamine, one isomer of Compound 292, peak 1, one diastereomer (Compound 294) and 5-fluoro-N2-(1H-2,3, 4,5-tetrahydron-2,4-dimethyl-4-hydroxy-[1,2,4]triazolo[4,5-c][1,5]benzoxazepin-1-one-9-yl)-N4-((7R, 8aS)-octahydro-5,5-dimethylindolizin-7-yl) pyrimidine-2,4-diamine, one isomer of Compound 292, peak 2, one diastereomer (Compound 295)

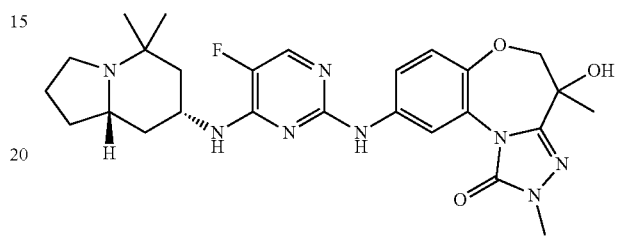

Compound 292 was subjected to chiral HPLC separation to give Compound 294 (peak 1, Rt=3.75) and Compound 295 (peak 2, Rt=6.32).

Compound 294: $^1$H NMR (300 MHz, d$_6$-DMSO) δ 9.16 (s, 1H), 8.03 (d, J=2.1 Hz, 1H), 7.83 (d, J=3.9 Hz, 1H), 7.55 (d, J=9.0 Hz, 1H), 7.19 (d, J=9.3 Hz, 1H), 6.99 (d, J=8.7 Hz, 1H), 5.50 (s, 1H), 4.22 (ABq, J=12.6, 50.4 Hz, 2H), 4.20 (br, 1H), 3.39 (s, 3H), 2.82 (t, J=8.1 Hz, 1H), 2.25 (q, J=7.2 Hz, 1H), 1.96 (d, J=13.8 Hz, 1H), 1.76 (m, 1H), 1.60 (m, 4H), 1.38 (s, 3H), 1.22 (m, 3H), 1.04 (s, 3H), 0.85 (s, 3H); m/z=525.06 (M+H)+.

Compound 295: $^1$H NMR (300 MHz, d$_6$-DMSO) δ 9.15 (s, 1H), 7.99 (d, J=2.1 Hz, 1H), 7.83 (d, J=3.9 Hz, 1H), 7.56 (d, J=11.4 Hz, 1H), 7.17 (d, J=7.2 Hz, 1H), 6.99 (d, J=8.7 Hz, 1H), 5.54 (s, 1H), 4.22 (ABq, J=12.3, 46.5 Hz, 2H), 4.16 (br, 1H), 3.39 (s, 3H), 2.82 (t, 1H), 2.26 (m, 2H), 2.02 (d, J=11.4 Hz, 1H), 1.72 (m, 1H), 1.58 (m, 4H), 1.37 (s, 3H), 1.22 (m, 3H), 1.07 (s, 3H), 0.94 (s, 3H); m/z=525.06 (M+H)+.

Synthesis of 5-fluoro-N2-(1H-2,4-dihydron-2-methyl-4,4-di(methoxymethyl)[1,2,4]triazolo[3,4-c] [1,4]benzoxazin-1-one-8-yl)-N4-((7R,8aS)-octahydro-5,5-dimethylindolizin-7-yl)pyrimidine-2,4-diamine (Compound 296)

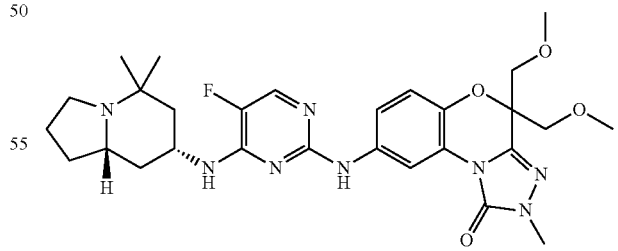

$^1$H NMR (300 MHz, d$_6$-DMSO) δ 9.07 (s, 1H), 8.55 (d, J=2.7 Hz, 1H), 7.80 (d, J=3.9 Hz, 1H), 7.36 (dd, J=2.7, 9.0 Hz, 1H), 7.13 (d, J=8.1 Hz, 1H), 6.92 (d, J=9.0 Hz, 1H), 4.24 (m, 1H), 3.74 (s, 2H), 3.68 (d, J=3.6 Hz, 2H), 3.38 (s, 3H), 3.25 (s, 3H), 3.21 (s, 3H), 2.79 (t, 1H), 2.21 (q, J=7.8 Hz, 1H), 1.95 (d, 1H), 1.72 (m, 1H), 1.57 (m, 4H), 1.36-1.07 (m, 3H), 1.02 (s, 3H), 0.82 (s, 3H); m/z=569.11 (M+H)+.

Synthesis of N2-(3-(Difluoromethoxy)-4-morpholinophenyl)-N44(7S,8aS)-3,3-dimethyloctahydroindolizin-7-yl)-5-fluoropyrimidine-2,4-diamine (Compound 297)

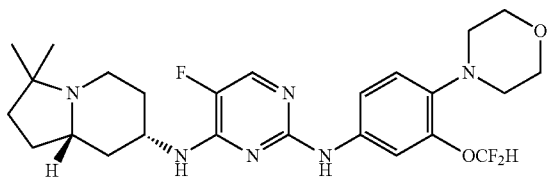

$^1$H NMR (300 MHz; d$_6$-DMSO) δ 9.02 (s, 1H), 7.83 (s, 1H), 7.59 (s, 1H), 7.50 (d, J=7.8Hz, 1H), 7.19 (d, J=6.9Hz, 1H), 7.03 (t, J=75.3Hz, 1H), 6.95 (d, J=8.4Hz, 1H), 4.2 (bs, 1H), 3.68 (s, 4H), 2.85 (s, 4H), 2.30 (m, 2H), 1.97 (m, 2H), 1.73 (m, 2H), 1.58 (m, 3H), 1.35 (m, 2H), 1.07 (s, 3H), 0.98 (s, 3H); m/z=506.99 (M+H)$^+$; m/z=505.02 (M−H)$^+$.

Synthesis of N2-(3-(Difluoromethoxy)-4-(oxetan-3-yloxy)phenyl)-N4-((7S,8aS)-3,3-dimethyloctahydroindolizin-7-yl)-5-fluoropyrimidine-2,4-diamine, formate salt (Compound 298)

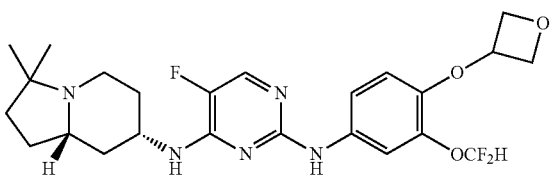

$^1$H NMR (300 MHz; d$_6$-DMSO) δ 8.99 (s, 1H), 7.82 (d, J=3.6Hz, 1H), 7.69 (d, J=2.1Hz, 1H), 7.44 (dd, J=9.0Hz, 1H), 7.19 (d, J=8.1HZ, 1H), 7.02 (t, J=74.7Hz, 1H), 6.64 (d, J=9.0Hz, 1H), 5.21 (m, 1H), 4.85 (t, J=6.6Hz, 2H), 4.54 (t, J=5.7Hz, 2H), 4.16 (m, 1H), 2.84 (m, 1H), 2.34-2.25 (m, 2H), 2.01-1.97 (m, 1H), 1.77 (m, 1H), 1.61-1.57 (m, 2H), 1.46-1.38 (m, 1H), 1.22-1.15 (m, 1H), 1.07 (s, 3H), 0.97 (s, 3H); m/z=493.91 (M+H)$^+$; m/z=492.02 (M−H)$^+$.

Synthesis of N2-(3-(Difluoromethoxy)-4-methoxyphenyl)-N4-((7S,8aS)-3,3-dimethyloctahydroindolizin-7-yl)-5-fluoropyrimidine-2,4-diamine (Compound 299)

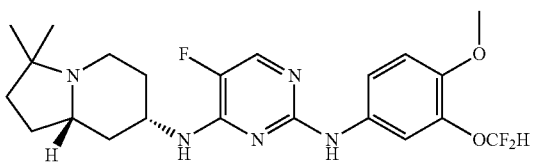

$^1$H NMR (300 MHz; d$_6$-DMSO) δ 8.95 (s, 1H), 7.82 (m, 1H), 7.65 (s, 1H), 7.48 (d, J=8.7Hz, 1H), 7.19-6.69 (m, 3H), 4.18 (bs, 1H), 3.74 (s, 3H), 2.85 (m, 1H), 2.32 (m, 1H), 2.01-1.98 (m, 1H), 1.78-1.6 (m, 3H), 1.47-1.44 (m, 1H), 1.22 (m, 1H), 1.08 (s, 3H), 0.99 (s, 3H); m/z=451.96 (M+H)$^+$; m/z=450.06 (M−H)$^+$.

Synthesis of N2-(3-(Difluoromethoxy)-4-(2,6-dimethylmorpholino)phenyl)-N4-((7S,8aS)-3,3-dimethyloctahydroindolizin-7-yl)-5-fluoropyrimidine-2,4-diamine (Compound 300)

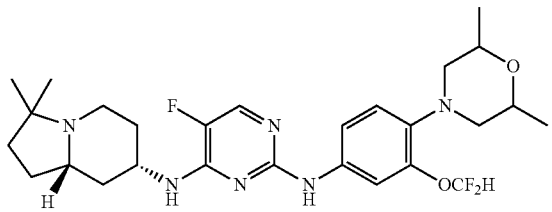

$^1$H NMR (300 MHz; d$_6$-DMSO) δ 9.01 (s, 1H), 7.83 (s, 1H), 7.58 (s, 1H), 7.49 (d, J=8.1Hz, 1H), 7.2 (s, 1H), 7.25-6.76 (m, 2H), 4.1-4.04 (m, 1H), 3.71-3.66 (m, 1H), 3.15 (d, J=5.1Hz, 2H), 3.02 (d, J=11.7Hz, 2H), 2.29-2.24 (m, 4H), 1.97 (m, 1H), 1.61 (m, 4H), 1.09 (s, 3H), 1.07 (s, 3H), 0.98 (m, 2H); m/z=535.00 (M+H)$^+$; m/z=533.10 (M−H)$^+$.

Synthesis of N2-(4-Cyclopropyl-2-fluoro-5-(5-(oxetan-3-yl)-1H-tetrazol-1-yl)phenyl)-N4-((7S,8aS)-3,3-dimethyloctahydroindolizin-7-yl)-5-fluoropyrimidine-2,4-diamine, formate salt (Compound 301)

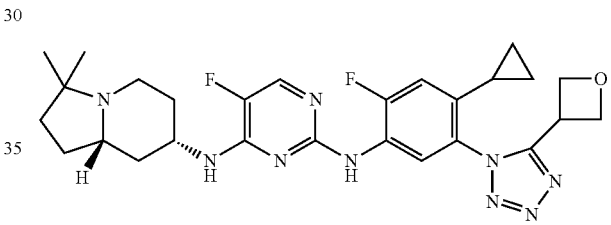

$^1$H NMR (300 MHz; d$_6$-DMSO) δ 8.57 (s, 1H), 8.23 (s, 1H), 7.90 (d, J=7.2Hz, 1H), 7.81 (d, J=4.2Hz, 1H), 7.25 (d, J=8.1Hz, 1H), 7.01 (d, J=12.6Hz, 1H), 6.57 (bs, 1H), 4.8 (s, 2H), 4.77 (s, 2H), 4.35-4.30 (m, 1H), 3.91 (m 1H), 2.81 (bs, 1H), 2.71 (s, 1H), 2.25-2.23 (m, 2H), 2.04 (bs, 1H), 1.85 (bs, 1H), 1.59 (m, 2H), 1.47-1.37 (m, 1H), 1.16 (m, 1H), 1.04 (s, 4H), 0.74 (s, 3H), 0.64 (s, 2H); m/z=538.29 (M+H)$^+$.

Synthesis of N2-(3-(Difluoromethoxy)-4-(2-oxa-6-azaspiro[3.3]heptan-6-yl)phenyl)-N4-((7S,8aS)-3,3-dimethyloctahydroindolizin-7-yl)-5-fluoropyrimidine-2,4-diamine, formate salt (Compound 302'

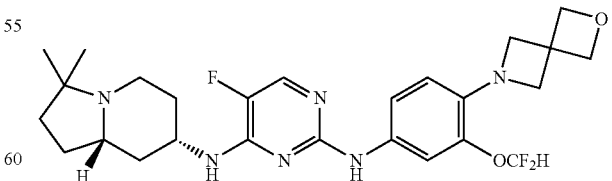

$^1$H NMR (300 MHz; d$_6$-DMSO) δ 8.79 (s, 1H), 8.23 (s, 1H), 7.78 (d, J=3.9Hz, 1H), 7.45 (m, 1H), 7.45 (s, 1H), 7.12 (s, 2H), 6.87 (t, J=75Hz, 1H), 6.4 (d, J=8.1Hz, 1H), 4.67 (s, 4H), 4.13 (m, 1H), 3.93 (s, 4H), 2.82 (m, 1H), 2.34-2.25 (m, 1H), 1.96 (d, J=12.3Hz, 1H), 1.77 (m, 1H), 1.62-1.58 (m,

2H), 1.39 (t, J=12.6Hz, 1H), 1.25-1.13 (m, 1H), 1.07 (s, 3H), 0.97 (s, 3H); 19F NMR (300 MHz; d₆-DMSO) δ −79.4, −167.4; m/z=519.27 (M+H)⁺.

Synthesis of 2-(2-(Difluoromethoxy)-4-((4-(((7S, 8aS)-3,3-dimethyloctahydroindolizin-7-yl)amino)-5-fluoropyrimidin-2-yl)amino)phenoxy)ethan-1-ol, formate salt (Compound 303)

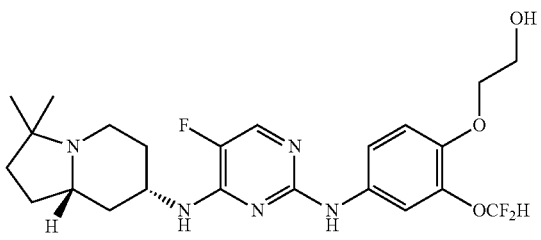

¹H NMR (300 MHz; d₆-DMSO) δ 8.98 (s, 1H), 8.19 (s, 1H), 7.82 (d, J=3.9Hz, 1H), 7.67 (d, J=2.7Hz, 1H), 7.44 (d, J=9.3Hz, 1H), 7.19 (d, J=8.1Hz, 1H), 7.04 (t, J=75.9Hz, 1H), 6.99 (d, J=9.3Hz, 1H), 4.17 (m, 1H), 3.98 (t, J=4.8Hz, 1H), 3.67 (t, J=5.1Hz, 3H), 2.84 (m, 1H), 2.35-2.26 (m, 1H), 2.02-1.98 (m, 2H), 1.76 (m, 1H), 1.62-1.58 (m, 2H), 1.44 (t, J=12Hz, 2H), 1.25-1.12 (m, 2H), 1.08 (s, 3H), 0.99 (s, 3H); m/z=481.00 (M+H)⁺.

Synthesis of 5-44-4(7S,8aS)-3,3-Dimethyloctahydroindolizin-7-yl)amino)-5-fluoropyrimidin-2-yl)amino)-2-(3-hydroxycyclobutoxy)benzonitrile, formate salt (Compound 304)

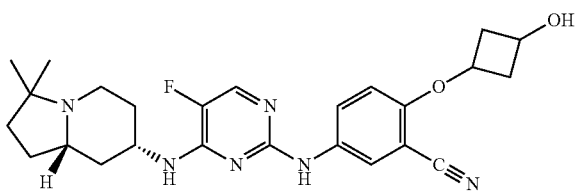 [SMILES: CC1(C)CC[C@H]2C[C@@H](Nc3nc(Nc4ccc(OC5CC(O)C5)c(C#N)c4)ncc3F)CCN21]

¹H NMR (300 MHz; d₆-DMSO) δ 9.11 (s, 1H), 8.18 (s, 1H), 8.05 (d, J=2.4Hz, 1H), 7.84 (d, J=3.9Hz, 1H), 7.75 (d, J=8.4Hz, 1H), 7.25 (d, J=8.4Hz, 1H), 6.92 (d, J=9.3Hz, 1H), 4.31 (m, 1H), 4.15 (m, 1H), 3.81 (m, 1H), 2.84-2.79 (m, 2H), 2.34-2.29 (m, 2H), 2.03-1.98 (m, 2H), 1.88 (m, 1H), 1.78 (m, 1H), 1.61-1.57 (m, 2H), 1.43 (m, 2H), 1.22-1.11 (m, 1H), 1.07 (s, 3H), 0.97 (s, 3H); m/z=467.26 (M+H)⁺.

Synthesis of 3-(4-((4-(((7S,8aS)-3,3-Dimethyloctahydroindolizin-7-yl)amino)-5-fluoropyrimidin-2-yl)amino)-2-(trifluoromethyl)phenoxy)cyclobutan-1-ol, formate salt (Compound 305)

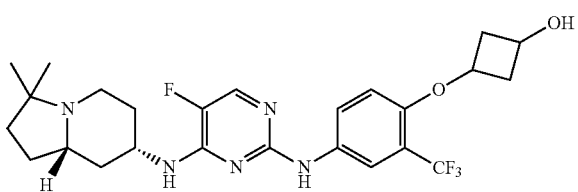 [SMILES: CC1(C)CC[C@H]2C[C@@H](Nc3nc(Nc4ccc(OC5CC(O)C5)c(C(F)(F)F)c4)ncc3F)CCN21]

¹H NMR (300 MHz; d₆-DMSO) δ 9.02 (s, 1H), 8.15 (s, 2H), 7.82 (d, J=3.6Hz, 1H), 7.27 (d, J=8.1Hz, 1H), 7.18 (d, J=8.1Hz, 1H), 6.90 (d, J=8.7Hz, 1H), 4.28 (t, J=6.3Hz, 1H), 4.13 (m, 1H), 3.8 (t, J=6.6Hz, 1H), 2.8-2.75 (m, 2H), 2.35-2.29 (m, 1H), 2.0-1.99 (m, 1H), 1.95-1.72 (m, 2H), 1.62-1.58 (m, 2H), 1.4 (m, 1H), 1.26-1.14 (m, 1H), 1.07 (s, 3H), 0.95 (s, 3H); m/z=510.25 (M+H)⁺.

Synthesis of 3-(2-(Difluoromethoxy)-4-((4-(((7S, 8aS)-3,3-dimethyloctahydroindolizin-7-yl)amino)-5-fluoropyrimidin-2-yl)amino)phenoxy)cyclobutan-1-ol, formate salt (Compound 306)

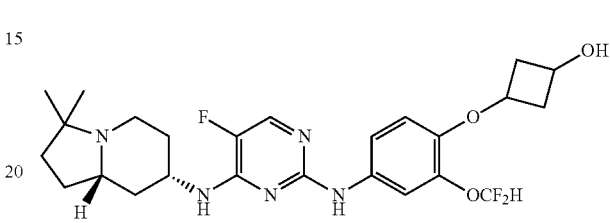

m/z=507.97 (M+H)⁺; m/z=506.04 (M−H)⁺.

Synthesis of 3-(2-(Difluoromethoxy)-4-((4-(((7S, 8aS)-3,3-dimethyloctahydroindolizin-7-yl)amino)-5-fluoropyrimidin-2-yl)amino)phenoxy)propan-1-ol, formate salt (Compound 307)

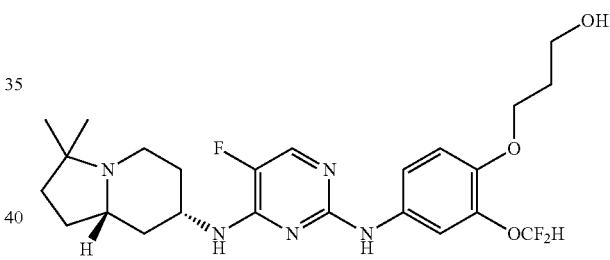

¹H NMR (300 MHz; d₆-DMSO) δ 8.96 (s, 1H), 8.16 (s, 1H), 7.82 (d, J=3.9Hz, 1H), 7.64 (d, J=2.7Hz, 1H), 7.47 (d, J=9.0Hz, 1H), 7.21-6.68 (m, 3H), 4.24-4.17 (m, 1H), 4.00 (t, J=6.3Hz, 2H), 3.53 (t, J=6.3Hz, 2H), 2.88-2.84 (m, 1H), 2.37-2.28 (m, 1H), 2.03-1.99 (m, 1H), 1.87-1.8 (m, 2H), 1.63-1.61 (m, 2H), 1.44 (t, J=12.6Hz, 1H), 1.26-1.13 (m, 1H), 1.08 (s, 3H), 0.99 (s, 3H); m/z=496.25 (M+H)⁺.

Synthesis of 1-(2-(Difluoromethoxy)-4-((4-(((7S, 8aS)-3,3-dimethyloctahydroindolizin-7-yl)amino)-5-fluoropyrimidin-2-yl)amino)phenyl)azetidin-3-ol, formate salt (Compound 308)

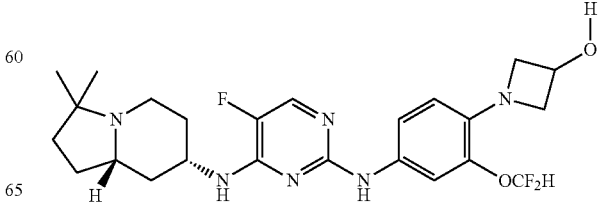

¹H NMR (300 MHz; d₆-DMSO) δ 8.79 (s, 1H), 8.37 (s, 1H), 7.78 (d, J=4.2Hz, 1H), 7.63 (s, 1H), 7.12-6.39 (m, 3H), 4.46 (m, 1H), 4.15 (m, 1H), 2.83 (s, 1H), 1.99 (m, 2H), 1.77 (m, 1H), 1.59 (m, 1H), 1.38-1.1 (m, 1H), 1.06 (s, 3H), 0.96 (s, 3H); m/z=492.91 (M+H)⁺; m/z=490.98 (M−H)⁺.

Synthesis of 1-(5-((4-(((7S,8aS)-3,3-Dimethyloctahydroindolizin-7-yl)amino)-5-fluoropyrimidin-2-yl)amino)-2-(3-hydroxycyclobutoxy-1-d)phenyl)-4-methyl-1,4-dihydro-5H-tetrazol-5-one, formate salt (Compound 309)

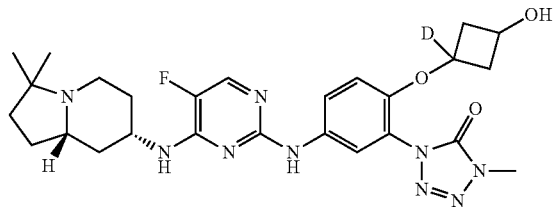 [SMILES: [2H]C1(Oc2ccc(Nc3ncc(F)c(N[C@H]4CCN5[C@@H](CCC5(C)C)C4)n3)cc2-n2nnn(C)c2=O)CC(O)C1]

¹H NMR (300 MHz; d₆-DMSO) δ 8.39 (s, 1H), 8.19 (s, 1H), 7.83 (d, J=8.4Hz, 1H), 7.78 (d, J=3.6Hz, 1H), 7.18 (d, J=7.8Hz, 1H), 6.98 (d, J=12.0Hz, 1H), 4.25 (t, J=5.7Hz, 1H), 3.97 (m, 1H), 3.59 (s, 3H), 2.84-2.79 (m, 1H), 2.25-2.15 (m, 4H), 1.94-1.89 (m, 1H), 1.66-1.5 (m, 2H), 1.37 (m, 1H), 1.21-1.09 (m, 1H), 1.03 (s, 3H), 0.76 (s, 3H); m/z=559.3 (M+H)⁺.

Synthesis of N2-(4-(3-(Benzyloxy)cyclobutoxy)-3-chlorophenyl)-N4-((7S,8aS)-3,3-dimethyloctahydroindolizin-7-yl)-5-fluoropyrimidine-2,4-diamine (Compound 310)

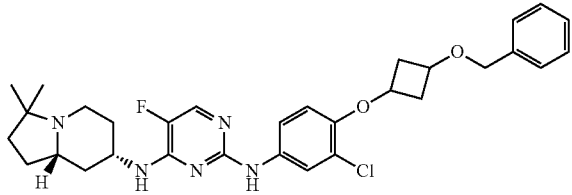 [SMILES: CC1(C)CC[C@H]2C[C@@H](Nc3nc(Nc4ccc(OC5CC(OCc6ccccc6)C5)c(Cl)c4)ncc3F)CCN21]

¹H NMR (300 MHz; d₆-DMSO) δ 8.98 (s, 1H), 7.88 (d, J=2.1Hz, 1H), 7.82 (d, J=3.6Hz, 1H), 7.45 (d, J=8.7Hz, 1H), 7.36-7.25 (m, 5H), 7.2 (d, J=8.4Hz, 1H), 6.82 (d, J=9.3Hz, 1H), 4.38 (s, 2H), 4.33 (t, J=6.9Hz, 1H), 4.15 9 m, 1H), 3.77 (t, J=6.9Hz, 1H), 2.82-2.78 (m, 2H), 2.44-2.27 (m, 1H), 2.07-1.97 (m, 3H), 1.76 (m, 1H), 1.61-1.57 (m, 2H), 1.44 (t, J=12.0Hz, 1H), 1.25-1.1 (m, 1H) 1.07 (s, 3H), 0.97 (s, 3H); m/z=566.00 (M+H)⁺; m/z=564.09 (M−H)⁺.

Synthesis of N2-(4-(3-(benzyloxy)cyclobutoxy-1-d)-3-chlorophenyl)-N4-((7S,8aS)-3,3-dimethyloctahydroindolizin-7-yl)-5-fluoropyrimidine-2,4-diamine (Compound 311)

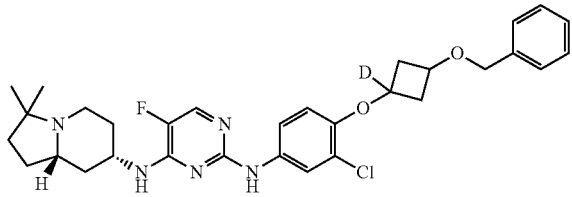 [SMILES: [2H]C1(Oc2ccc(Nc3ncc(F)c(N[C@H]4CCN5[C@@H](CCC5(C)C)C4)n3)cc2Cl)CC(OCc2ccccc2)C1]

¹H NMR (300 MHz; d₆-DMSO) δ 8.98 (s, 1H), 7.88 (d, J=2.4Hz, 1H), 7.82 (d, J=3.9Hz, 1H), 7.45 (d, J=9.0Hz, 1H), 7.33-7.25 (m, 5H), 7.2 (d, J=8.4Hz, 1H), 6.82 (d, J=9.3Hz, 1H), 4.38 (s, 2H), 4.18 (m, 1H), 3.78-3.74 (m, 1H), 2.83-2.77 (m, 2H), 2.32-2.27 (m, 2H), 2.03-1.94 (m, 3H), 1.75 (m, 1H), 1.61-1.58 (m, 2H), 1.48-1.39 (m, 1H), 1.25-1.1 (m, 2H), 1.07 (s, 3H), 0.97 (s, 3H); m/z=567.03 (M+H)+; m/z=565.13 (M−H)+.

Synthesis of 3-(2-Chloro-4-((4-(((7S,8aS)-3,3-dimethyloctahydroindolizin-7-yl)amino)-5-fluoropyrimidin-2-yl)amino)phenoxy)cyclobutan-1-ol, formate salt (Compound 312)

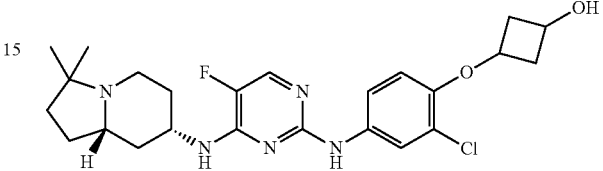

¹H NMR (300 MHz; d₆-DMSO) δ 8.96 (s, 1H), 8.22 (s, 1H), 7.86 (d, J=2.7Hz, 1H), 7.81 (d, J=3.9Hz, 1H), 7.45 (d, J=9.3Hz, 1H), 7.19 (d, J=7.2Hz, 1H), 6.8 (d, J=9.0Hz, 1H), 4.22-4.15 (m, 2H), 3.82-3.77 (m, 1H), 2.87-2.71 (m, 3H), 2.34-2.28 (m, 2H), 2.03-1.99 (m, 1H), 1.90-1.89 (m, 2H), 1.75 (m, 1H), 1.61-1.59 (m, 2H), 1.48-1.39 (m, 1H), 1.25-1.1 (m, 2H), 1.07 (s, 3H), 0.98 (s, 3H); m/z=476.12 (M+H)⁺; m/z=473.98 (M−H)⁺.

Synthesis of 3-(2-Chloro-4-((4-(((7S,8aS)-3,3-dimethyloctahydroindolizin-7-yl)amino)-5-fluoropyrimidin-2-yl)amino)phenoxy)cyclobutan-3-d-1-ol, formate salt (Compound 313)

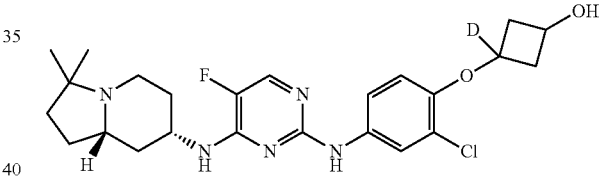

¹H NMR (300 MHz; d₆-DMSO) δ 8.96 (s, 1H), 8.21 (s, 1H), 7.86 (d, J=2.7Hz, 1H), 7.81 (d, J=3.6Hz, 1H), 7.45 (d, J=8.7Hz, 1H), 7.19 (d, J=8.1Hz, 1H), 6.80 (d, J=9.0Hz, 1H), 4.17 (m, 1H) 3.81-3.77 (m, 1H), 2.86-2.82 (m, 1H), 2.78-2.72 (m, 1H), 2.34-2.25 (m, 1H), 2.03-1.98 (m, 1H), 1.91-1.85 (m, 1H), 1.77-1.75 (m, 1H), 1.61-1.57 (m, 2H), 1.48-1.39 (m 1H), 1.25-1.1 (m, 1H), 1.07 (s, 3H), 0.98 (s, 3H); in/z=477.07 (M+H)⁺; in/z=475.02 (M−H)⁺.

Preparation of 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimidine-5-carbonitrile, formate salt (Compound 314)

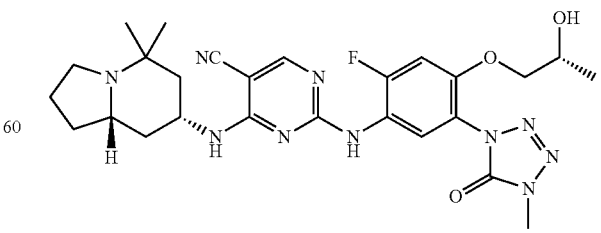

See Compound 90 in Example 71 above. Compound 314 was prepared as the formate salt of Compound 90.

Example 109

Synthesis of 4-methyl-N-(5-(4-((7R,8aS)-octahydro-5,5-dimethylindolizin-7-ylamino)-5-fluoropyrimidin-2-ylamino)-2H-1,4-benzoxazine-3(4H)-one, formate salt (Compound 315)

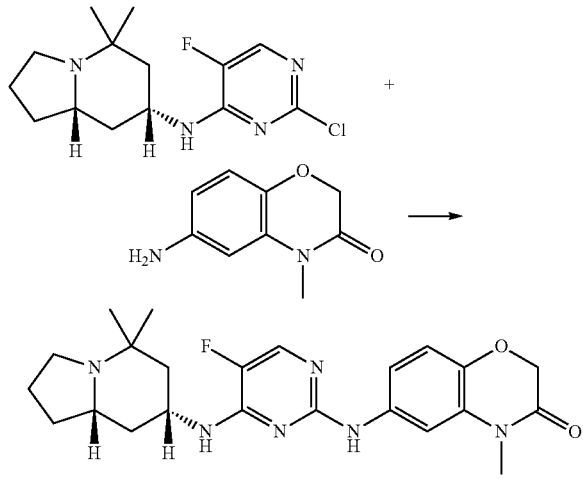

A mixture of (7R,8aS)-N-(2-chloro-5-fluoropyrimidin-4-yl)-octahydro-5,5-dimethylindolizin-7-amine (100 mg, 0.34 mmol, 1 equiv), 6-amino-4-methyl-2H-1,4-benzoxazin-3(4H)-one (89 mg, 0.50 mmol, 1.5 equiv) and pTsOH.H₂O (102 mg, 0.27 mmol, 1.6 equiv) in isopropanol (1.5 mL) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 8.87 (br. s, 1H), 7.82 (d, J=3.6 Hz, 1H), 7.54 (dd, J=9.0, 2.4 Hz, 1H), 7.39 (d, J=2.1 Hz, 1H), 7.19 (d, J=7.8 Hz, 1H), 6.80 (d, J=8.4 Hz, 1H), 4.54 (s, 2H), 4.25-4.10 (m, 1H), 3.22 (s, 3H), 2.93-2.83 (m, 1H), 2.55-2.32 (m, 3H), 2.01-1.97 (m, 1H), 1.85-1.75 (m, 1H), 1.70-1.55 (m, 2H), 1.41 (t, J=12.3 Hz, 1H), 1.30-1.15 (m, 2H), 1.09 (s, 3H), 0.99 (s, 3H); m/z=441.3 (M+H)$^+$; m/z=439.3 (M−H)$^+$.

Example 110

Preparation of Compound 316

Synthesis of 4,4-bis(methoxymethyl)-8-nitro-4h-tetrazolo[5,1-c][1,4]-benzoxazine

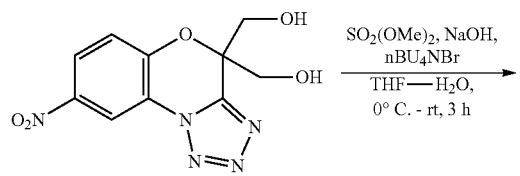

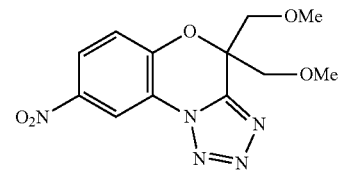

An aqueous solution of NaOH (25 mg, 0.625 mmol, 5 equiv. in 0.1 mL of water) was added dropwise to a mixture of diol (See Compound 125 synthesis above) (35 mg, 0.125 mmol, 1 equiv), nBu₄NBr (4 mg, 0.0125 mmol, 0.1 equiv.) and dimethyl sulfate (0.12 mL, 1.25 mmol, 10 equiv.) in 1 mL of THF at 0° C. The reaction was left at room temperature for 3 h. Then the reaction mixture was partitioned between 50 mL of EtOAc and 50 mL of water. The organic layer was separated, dried (MgSO₄) and concentrated. The residue was purified by column chromatography using a mixture of hexane/EtOAc (1:1) as eluent to give 34 mg (Yield=88%) of product as a white solid.

$^1$H NMR (300 MHz; CDCl₃) δ 8.80 (d, J=2.7 Hz, 1H), 8.22 (dd, J=9.3, 2.7 Hz, 1H), 7.26 (dm, J=9.0 Hz, 1H), 3.98 (q-like, J=11.4 Hz, 4H), 3.275 (s, 3H), 3.272 (s, 3H); m/z=307.9 (M+H)$^+$; m/z=306.0 (M−H)$^+$.

Synthesis of 8-amino-4,4-bis(methoxymethyl)-4h-tetrazolo[5,1-c][1,4]-benzoxazine

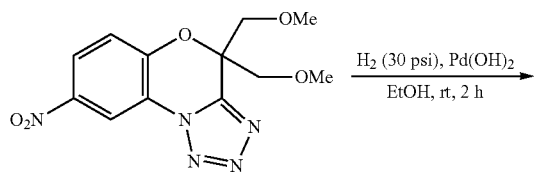

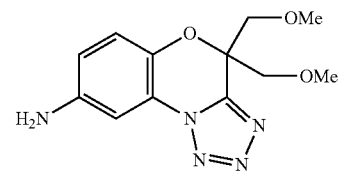

A mixture of starting material (60 mg, 0.195 mmol, 1 equiv.) in 10 mL of EtOH in the presence of 12 mg of Pd(OH)₂ was hydrogenated at room temperature for 2 h. The reaction mixture was then filtered through a pad of celite and the filtrate was concentrated. The residue was purified by column chromatography using a mixture of hexane/EtOAc (2:3) as eluent to give 40 mg (Yield=74%) of product as a white solid.

$^1$H NMR (300 MHz; CDCl₃) δ 7.27-7.25 (m, 1H), 6.98 (d, J=9.0 Hz, 1H), 6.62 (dd, J=8.7, 2.7 Hz, 1H), 3.95 (s, 2H), 3.94 (s, 2H), 3.35 (s, 3H), 3.34 (s, 3H); m/z=278.2 (M+H)$^+$.

559

Synthesis of N²-(4,5-dihydro-4,4-bis(methoxymethyl)tetrazolo[5,1-c][1,4]benzoxazin-8-yl)-N⁴-((7R,8aS)-octahydro-5,5-dimethylindolizin-7-yl)-5-fluoropyrimidin-2,4-diamine (Compound 316)

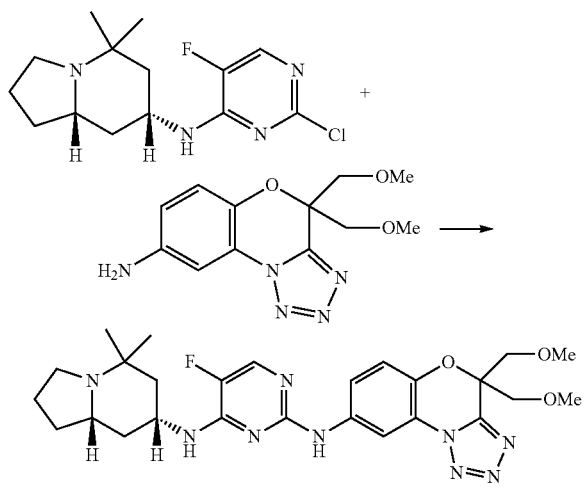

A mixture of (7R,8aS)-N-(2-chloro-5-fluoropyrimidin-4-yl)-octahydro-5,5-dimethylindolizin-7-amine (36 mg, 0.12 mmol, 1 equiv), 8-amino-4,4-bis(methoxymethyl)-4H-tetrazolo[5,1-c]-[1,4]-benzoxazine (40 mg, 0.14 mmol, 1.2 equiv) and pTsOH.H₂O (46 mg, 0.24 mmol, 2.0 equiv) in isopropanol (1.0 mL) was heated at 100° C. overnight in a sealed vial. After allowing to cool to room temperature, the solvent was removed and the residue was purified by column chromatography using a mixture of DCM/2N NH₃ in MeOH (95:5) to give the product as a solid.

¹H NMR (300 MHz; d₆-DMSO) δ 9.43 (br. s, 1H), 8.41 (d, J=2.4 Hz, 1H), 7.96 (d, J=3.6 Hz, 1H), 7.74(br. s, 1H), 7.56 (dd, J=8.7, 2.7 Hz, 1H), 7.14 (d, J=9.0 Hz, 1H), 4.45-4.35 (m, 1H), 3.90 (s, 2H), 3.89 (s, 2H), 3.19 (s, 6H), 3.10-3.00 (m, 1H), 2.60-2.40 (m, 1H), 2.33-2.24 (m, 1H), 2.06-2.02 (m, 1H), 1.70-1.60 (m, 1H), 1.64-1.60 (m, 2H), 1.60-1.55 (m, 2H), 1.50-1.45 (m, 1H), 1.36 (s, 3H), 1.28 (s, 3H); m/z=540.5 (M+H)⁺.

Example 111

Preparation of N²-(4,5-dihydro-4,4-bis(methoxymethyl)tetrazolo[5,1-c][1,4]benzoxazin-8-yl)-N⁴-((7R,8aS)-octahydro-5,5-dimethylindolizin-7-yl)-5-fluoropyrimidin-2,4-diamine, formate salt (Compound 317)

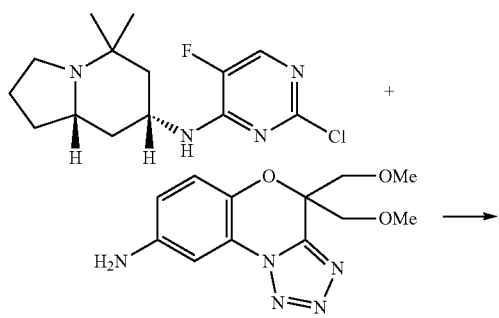

560

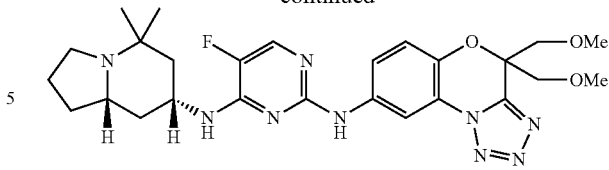

Compound 317 was prepared as the formic acid salt of Compound 316. See the preparation of Compound 316 above. The product was purified by HPLC.

¹H NMR (300 MHz; d₆-DMSO) δ 9.24 (br. s, 1H), 8.42 (d, J=2.4 Hz, 1H), 8.17 (s, 1H), 7.88 (d, J=3.9 Hz, 1H), 7.58 (dd, J=9.0, 2.7 Hz, 1H), 7.25 (d, J=8.1 Hz, 1H), 7.09 (d, J=9.3 Hz, 1H), 4.25-4.15 (m, 1H), 3.90 (s, 2H), 3.89 (s, 2H), 3.21 (s, 3H), 3.18 (s, 3H), 2.88-2.81 (m, 1H), 2.55-2.45 (m, 1H), 2.33-2.24 (m, 1H), 2.06-2.02 (m, 1H), 1.70-1.60 (m, 1H), 1.64-1.60 (m, 2H), 1.43-1.39 (m, 1H), 1.25-1.15 (m, 2H), 1.11 (s, 3H), 0.90 (s, 3H); m/z=540.3 (M+H)⁺; 538.2 (M−H)⁺.

Example 112

Preparation of Compound 318

Synthesis of 2,2,4-trimethyl-6-nitro-2H-1,4-benzoxazine-3(4H)-one

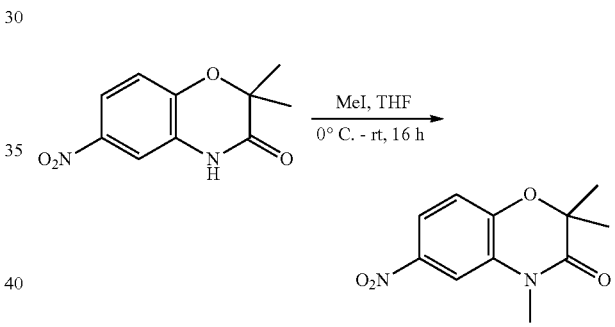

A solution of 2,2-dimethyl-6-nitro-2H-1,4-benzoxazin-3 (4H)-one (300 mg, 1.35 mmol, 1 equiv) in 5 mL of THF was added dropwise to mixture of NaH (81 mg, 2.03 mmol, 1.5 equiv., 60%) in 3 mL of THF at 0° C. The mixture was stirred at this temperature for 10 min. Then MeI (0.25 mL, 4.05 mmol, 3 equiv.) was added and the reaction was left at room temperature overnight. The reaction mixture was partitioned between EtOAc and water. The organic layer was separated and concentrated. The residue was purified by column chromatography using a mixture of EtOAC/hexane (1:4) as eluent to give 290 mg (Yield=91%) of product as a pale yellow solid.

Synthesis of 6-amino-2,2,4-trimethyl-2H-1,4-benzoxazine-3(4H)-one

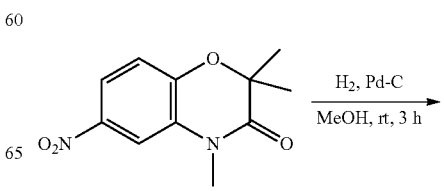

-continued

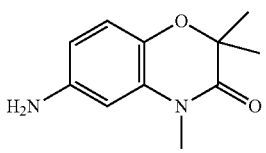

A mixture of 2,2,4-trimethyl-6-nitro-2H-1,4-benzoxazin-3(4H)-one (290 mg, 1.23 mmol, 1 equiv.) in 10 mL of MeOH in the presence of 29 mg of Pd/C was hydrogenated at room temperature for 3 h. The reaction mixture was then filtered through a pad of celite and the filtrate was concentrated to give 240 mg (Yield=95%) of product as a pale brown solid which was used in the next step without further purification.

Synthesis of 2,2,4-trimethyl-N-(5-(4-((7R,8aS)-octahydro-5,5-dimethylindolizin-7-ylamino)-5-fluoropyrimidin-2-ylamino)-2H-1,4-benzoxazine-3(4H)-one, p-toluene sulfonic salt (Compound 318)

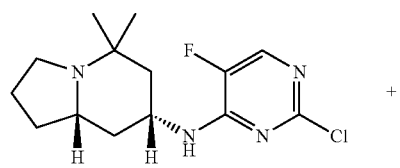

A mixture of (7R,8aS)-N-(2-chloro-5-fluoropyrimidin-4-yl)-octahydro-5,5-dimethylindolizin-7-amine (50 mg, 0.17 mmol, 1 equiv), 6-amino-2,2,4-trimethyl-2H-1,4-benzoxazin-3(4H)-one (52 mg, 0.25 mmol, 1.5 equiv) and pTsOH.H₂O (65 mg, 0.34 mmol, 2.0 equiv) in isopropanol (1.5 mL) was heated at 100° C. overnight in a sealed vial. After allowing to cool to room temperature, the solvent was removed and the residue was purified by HPLC to give the product as a solid.

¹H NMR (300 MHz; d₆-DMSO) δ 9.10 (br. s, 1H), 7.99 (d, J=3.6 Hz, 1H), 7.45 (dd, J=9.0, 2.4 Hz, 1H), 7.13 (d, J=2.1 Hz, 1H), 7.10 (d, J=7.8 Hz, 1H), 6.89 (d, J=8.4 Hz, 1H), 4.40-4.20 (m, 1H), 3.23 (s, 3H), 3.15-3.00 (m, 1H), 2.20-1.80 (m, 4H), 1.74-1.56 (m, 2H), 1.42-1.32 (m, 2H), 1.37 (s, 6H), 1.30-1.25 (m, 2H), 1.32 (s, 3H), 1.25 (s, 3H); m/z=469.3 (M+H)⁺; 466.9 (M–H)⁺.

Example 113

Preparation of Compound 319

Synthesis of 4N-(1-methoxyethyl)-2,2-dimethyl-6-nitro-2H-1,4-benzoxazine-3(4H)-one

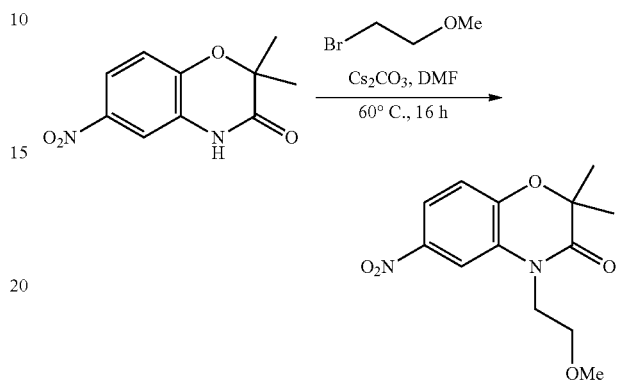

A mixture of 2,2-dimethyl-6-nitro-2H-1,4-benzoxazin-3(4H)-one (300 mg, 1.35 mmol, 1 equiv), 1-bromo-2-methoxyethane (0.32 mL, 3.38 mmol, 2.5 equiv.) and Cs₂CO₃ (880 mg, 2.70 mmol, 2.0 equiv.) in 6 mL of DMF was heated to 60° C. and stirred at this temperature overnight. The reaction mixture was then partitioned between EtOAc and water. The organic layer was separated and concentrated. The residue was purified by column chromatography using a mixture of EtOAC/hexane (1:4) as eluent to give the product as a clear oil (quantitative yield).

Synthesis of 6-amino-4N-(1-methoxyethyl)-2,2-dimethyl-2H-1,4-benzoxazine-3(4H)-one

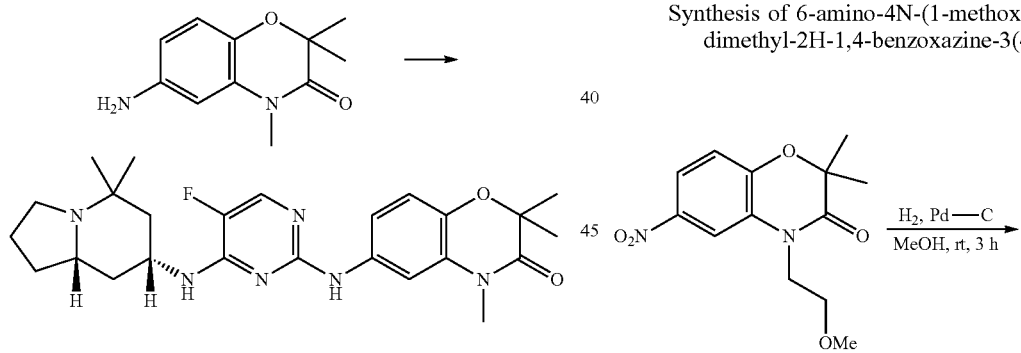

A mixture of 4N-(1-methoxyethyl)-2,2-dimethyl-6-nitro-2H-1,4-benzoxazin-3(4H)-one (378 mg, 1.35 mmol, 1 equiv.) in 10 mL of MeOH in the presence of 38 mg of Pd/C was hydrogenated at room temperature for 3 h. The reaction mixture was then filtered through a pad of celite and the filtrate was concentrated to give the product in quantitative yield. Synthesis of 4N-(1-methoxyethyl)-2,2-dimethyl-N-(5-(44(7R,8aS)-octahydro-5,5-dimethylindolizin-7- ylamino)-5-fluoropyrimidin-2-ylamino)-2H-1,4-benzoxazine-3(4H)-one, p-toluene sulfonic salt (Compound 319)

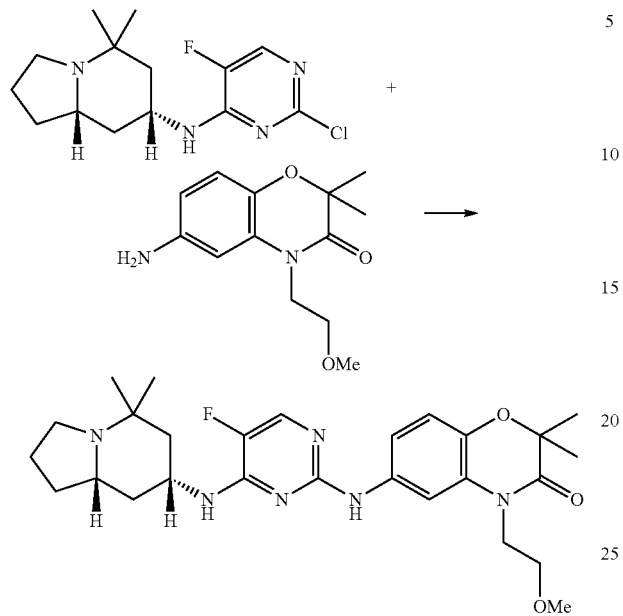

A mixture of (7R,8aS)-N-(2-chloro-5-fluoropyrimidin-4-yl)-octahydro-5,5-dimethylindolizin-7-amine (70 mg, 0.234 mmol, 1 equiv), 6-amino-4N-(1-methoxyethyl)-2,2-dimethyl-6-nitro-2H-1,4-benzoxazin-3(4H)-one (88 mg, 0.351 mmol, 1.5 equiv) and pTsOH.H$_2$O (89 mg, 0.468 mmol, 2.0 equiv) in isopropanol (1.5 mL) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 9.10 (br. s, 1H), 7.96 (d, J=4.2 Hz, 1H), 7.44 (dd, J=9.0, 2.4 Hz, 1H), 7.21 (d, J=2.1 Hz, 1H), 7.08 (d, J=7.8 Hz, 1H), 6.88 (d, J=9.0 Hz, 1H), 4.35-4.25 (m, 1H), 3.99-3.97 (m, 2H), 3.24 (s, 2H), 3.15-3.05 (m, 1H), 2.20-1.80 (m, 4H), 1.74-1.56 (m, 2H), 1.42-1.32 (m, 2H), 1.36 (s, 6H), 1.33 (s, 3H), 1.30-1.25 (m, 2H), 1.28 (s, 3H); m/z=513.9 (M+H)$^+$.

Example 114

Preparation of Compound 320

Synthesis of Methyl 4-amino-2-trifluoromethylbenzoate

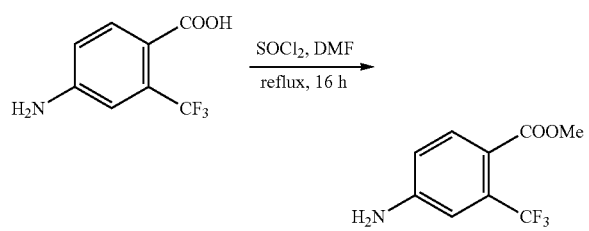

SOCl$_2$ (1.1 mL, 14.62 mmol, 1 equiv.) was added to a solution of 4-amino-2-trifluoromethylbenzoic acid (3 g, 14.62 mmol, 1 equiv.) in 40 mL of MeOH and the reaction mixture was refluxed overnight. Solvent was removed in vacuo and the residue was taken into EtOAc and washed with sat. NaHCO$_3$ (×2), brine and dried over MgSO$_4$, and concentrated to give 2.06 g (Yield=64%) of product as a clear oil.

$^1$H NMR (300 MHz; CDCl$_3$) δ 7.77 (d, J=8.7 Hz, 1H), 6.99 (d, J=2.4 Hz, 1H), 6.77 (dd, J=8.4, 2.1 Hz, 1H), 4.17 (br. s, 2H), 3.88 (s, 3H); m/z=219.97 (M+H)$^+$; 218.0 (M−H)$^+$.

Synthesis of methyl 2-trifluoromethyl-N-(5-(4-((7R,8aS)-octahydro-5,5-dimethylindolizin-7-ylamino)-5-fluoropyrimidin-2-ylamino)benzoate, formate salt (Compound 320)

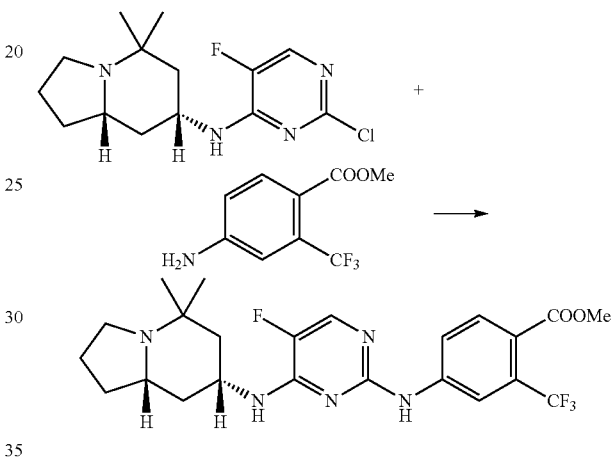

A mixture of (7R,8aS)-N-(2-chloro-5-fluoropyrimidin-4-yl)-octahydro-5,5-dimethylindolizin-7-amine (150 mg, 0.5 mmol, 1 equiv), methyl 4-amino-2-trifluoromethylbenzoate (165 mg, 0.75 mmol, 1.5 equiv) and pTsOH.H$_2$O (171 mg, 0.9 mmol, 1.8 equiv) in isopropanol (1.5 mL) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 9.78 (br. s, 1H), 9.15 (m, 1H), 8.25 (d, J=9.0 Hz, 1H), 8.01 (d, J=3.9 Hz, 1H), 7.80 (d, J=9.0 Hz, 1H), 7.75 (d, J=9.0 Hz, 1H), 4.40-4.30 (m, 1H), 3.80 (s, 3H), 3.20-3.10 (m, 1H), 2.40-2.25 (m, 2H), 2.20-2.05 (m, 2H), 2.05-1.85 (m, 3H), 1.69-1.53 (m, 3H), 1.37 (s, 3H), 1.34 (s, 3H); m/z=482.3 (M+H)$^+$.

Example 115

Preparation of Compound 321

Synthesis of 1-(2-trifluoromethyl-4-nitrophenyl)azetidin-3-ol

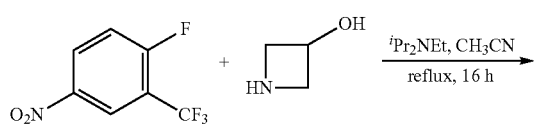

-continued

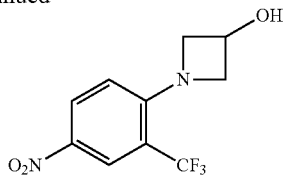

A mixture of 2-fluoro-5-nitrobenzyltrifluoride (0.2 mL, 1.44 mmol, 1 equiv.), 3-hydroxyazetidine hydrochloride (157 mg, 1.44 mmol, 1 equiv.) and (Pr$_2$NEt (0.625 mL, 3.59 mmol, 2.5 equiv.) in 5 mL of CH$_3$CN was refluxed for 2 days. Solvent was removed in vacuo and the residue was taken into EtOAc and washed with water. The organic layer was separated and concentrated. The residue was purified by column chromatography using a mixture of hexane/EtOAc (3:2) as eluent to give 300 mg (Yield=80%) of product as a yellow solid.

$^1$H NMR (300 MHz; CDCl$_3$) δ 8.43 (d, J=2.4 Hz, 1H), 8.15 (dd, J=9.3, 2.7 Hz, 1H), 6.38 (d, J=9.0 Hz, 1H), 4.85-4.75 (m, 1H), 4.49 (t, J=7.5 Hz, 1H), 4.12 (t, J=7.5 Hz, 1H), 2.91 (br. s, 1H); m/z=262.93 (M+H)$^+$; 261.0 (M−H)$^+$.

Synthesis of
1-(4-amino-2-trifluoromethylphenyl)azetidin-3-ol

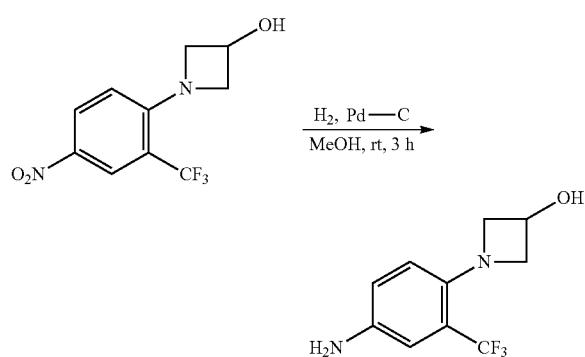

A mixture of starting material (100 mg, 0.38 mmol, 1 equiv.) in 10 mL of MeOH in the presence of 10 mg of Pd/C was hydrogenated at room temperature for 3 h. The reaction mixture was then filtered through a pad of celite and the filtrate was concentrated to give 86 mg (Yield=98%) of product.

m/z=232.99 (M+H)$^+$; 231.0 (M−H)$^+$.

Synthesis of 1-(4-(4-((7R,8aS)-octahydro-5,5-dimethylindolizin-7-ylamino)-5-fluoropyrimidin-2-ylamino)-2-(trifluoromethyl)phenylamino)-3-chloropropa-2-ol, formate salt (Compound 321)

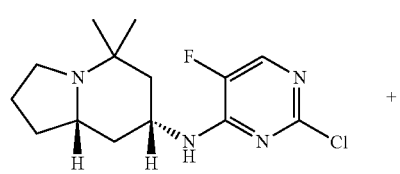

+

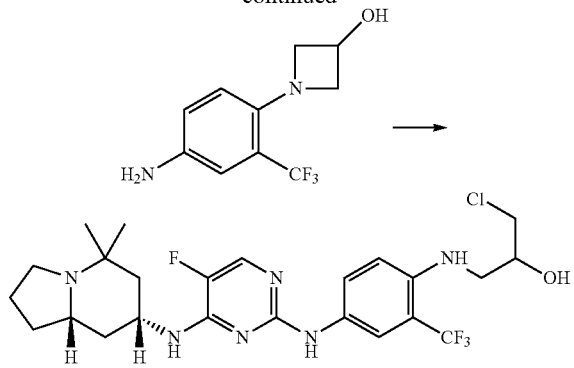

A mixture of (7R,8aS)-N-(2-chloro-5-fluoropyrimidin-4-yl)-octahydro-5,5-dimethylindolizin-7-amine (70 mg, 0.24 mmol, 1 equiv), aniline (82 mg, 0.35 mmol, 1.5 equiv) and pTsOH.H$_2$O (36 mg, 0.19 mmol, 0.8 equiv) in isopropanol (1.5 mL) was heated at 100° C. overnight in a sealed vial. After allowing to cool to room temperature, the solvent was removed and the residue was purified by HPLC to give the product as a solid.

$^1$H NMR (300 MHz; d$_6$-DMSO) δ 8.79 (br. s, 1H), 8.25 (d, J=2.1 Hz, 1H), 7.78-7.60 (m, 2H), 7.10 (d, J=8.1 Hz, 1H), 6.74 (d, J=9.6 Hz, 1H), 5.55-5.45 (m, 1H), 4.88 (br. s, 1H), 4.20-4.10 (m, 1H), 3.80-3.70 (m, 1H), 3.62-3.52 (m, 2H), 3.15-3.05 (m, 2H), 2.88-2.78 (m, 1H), 2.30-2.20 (m, 2H), 2.00-1.90 (m, 1H), 1.80-1.70 (m, 1H), 1.65-1.55 (m, 2H), 1.44-1.36 (m, 1H), 1.25-1.15 (m, 2H), 1.06 (s, 3H), 0.93 (s, 3H); m/z=531.3 (M+H)$^+$.

Example 116

Synthesis of Compound 322 and Compound 323

Synthesis of 2-(4-amino-5-fluoro-2-(4,5-dihydro-4-methyl-5-oxotetrazol-1-yl)phenoxy)acetamide

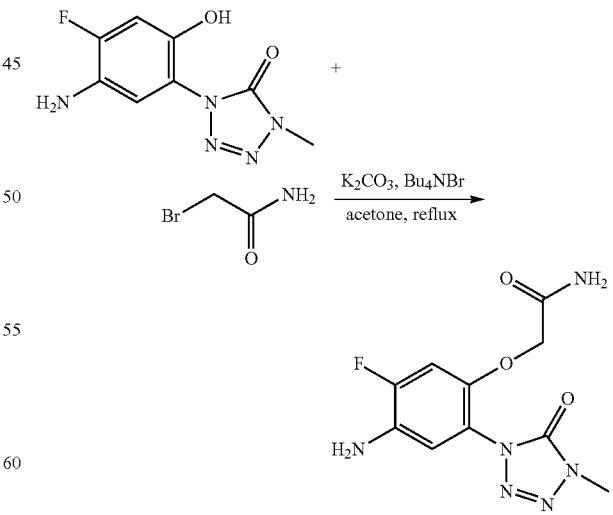

A mixture of anilinophenol (300 mg, 1.33 mmol, 1 equiv.), 2-bromoacetamide (220 mg, 1.60 mmol, 1.2 equiv.), K$_2$CO$_3$ (221 mg, 1.60 mmol, 1.2 equiv.) and Bu$_4$NBr (43 mg, 0.13, 0.1 equiv.) in 6 mL of acetone was refluxed overnight. The reaction mixture was filtered and washed with acetone. The filtrate was concentrated in vacuo and the residue was purified by column chromatography using a mixture of DCM/2N NH₃ in MeOH (95:5) as eluent to give 220 mg (Yield=59%) of product as a pale white solid.

¹H NMR (300 MHz; d-DMSO) δ 7.39 (br. s, 1H), 7.32 (br. s, 1H), 7.04 (d, J=12.6 Hz, 1H), 6.85 (d, J=9.3 Hz, 1H), 5.11 (br. s, 2H), 4.41 (s, 2H), 3.58 (s, 3H), 2.91 (br. s, 1H); m/z=282.9 (M+H)⁺.

Synthesis of 2-(4-(4-((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)phenoxy)acetamide, formate salt (Compound 322) and isopropyl 2-(4-(4-((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)phenoxy)acetate, p-toluene sulfonic salt (Compound 323)

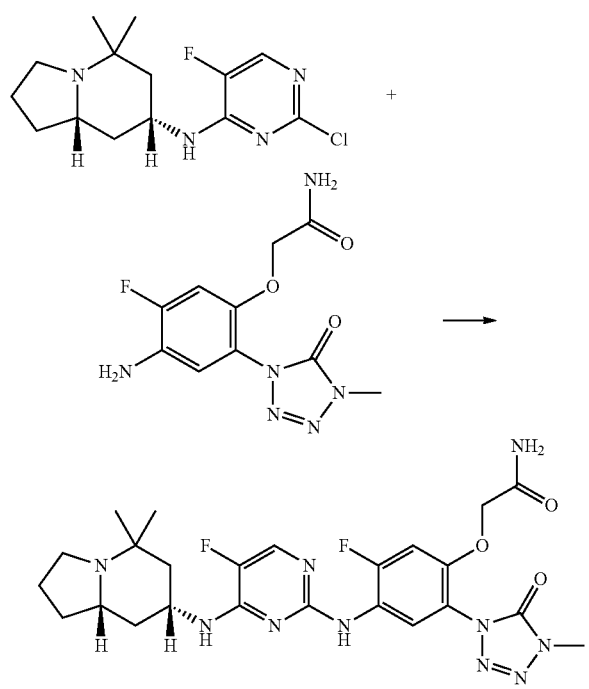

A mixture of (7R,8aS)-N-(2-chloro-5-fluoropyrimidin-4-yl)-octahydro-5,5-dimethylindolizin-7-amine (58 mg, 0.19 mmol, 1 equiv), aniline (76 mg, 0.24 mmol, 1.4 equiv) and pTsOH.H₂O (28 mg, 0.14 mmol, 0.8 equiv) in isopropanol (1.0 mL) was heated at 80° C. overnight in a sealed vial. After allowing to cool to room temperature, the solvent was removed and the residue was purified by HPLC to give 14 mg of Compound 322 and 22 mg of Compound 323.

¹H NMR (300 MHz; d₆-DMSO) of Compound 322: δ 8.45 (br. s, 1H), 7.92 (d, J=8.4 Hz, 1H), 7.79 (d, J=3.9 Hz, 1H), 7.44 (br. s, 1H), 7.34 (br. s, 1H), 7.22 (d, J=12.0 Hz, 1H), 7.18 (br. s, 1H), 4.55 (s, 2H), 4.05-3.95 (m, 1H), 3.61 (s, 2H), 2.85-2.75 (m, 1H), 2.26-2.18 (m, 3H), 1.93-1.90 (m, 1H), 1.69-1.51 (m, 3H), 1.41-1.33 (m, 1H), 1.20-1.10 (m, 2H), 1.03 (s, 3H), 0.76 (s, 3H); m/z=545.3 (M+H)⁺; 544.2 (M−H)⁺.

¹H NMR (300 MHz; d₆-DMSO) of Compound 323: δ 8.78 (br. s, 1H), 7.92 (d, J=3.3 Hz, 1H), 7.72 (d, J=8.1 Hz, 1H), 7.24 (d, J=12.3 Hz, 1H), 4.94 (sept, J=6.6 Hz, 1H), 4.80 (s, 2H), 4.20-4.10 (m, 1H), 3.59 (s, 3H), 3.35-3.25 (m, 2H), 3.05-2.95 (m, 1H), 2.55-2.45 (m, 2H), 2.00-1.90 (m, 2H), 1.65-1.50 (m, 2H), 1.30 (s, 3H), 1.35-1.25 (m, 2H), 1.19 (s, 3H), 1.17 (s, 3H), 1.13 (s, 3H); m/z=588.4 (M+H)⁺.

Example 117

Preparation of Compound 324

Synthesis of 1-(2-trifluoromethyl-4-nitrophenyl)azetidin-3-carboxamide

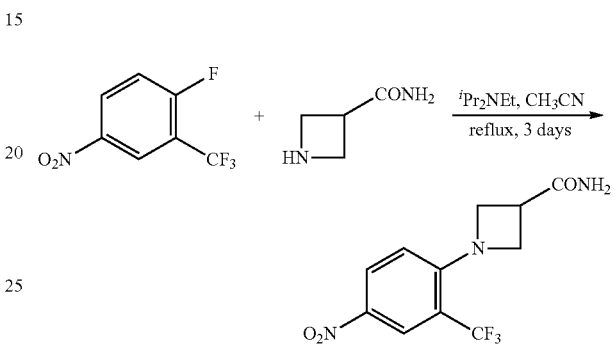

A mixture of 2-fluoro-5-nitrobenzyltrifluoride (0.2 mL, 1.44 mmol, 1 equiv.), 3-azetidinocarboxyamide (144 mg, 1.44 mmol, 1 equiv.) and (Pr₂NEt (0.375 mL, 2.15 mmol, 1.5 equiv.) in 5 mL of CH₃CN was refluxed for 3 days. Solvent was removed in vacuo and the residue was taken into EtOAc and washed with water. The organic layer was separated and concentrated. The residue was triturated with hexane/Et₂O to give 240 mg (Yield=58%) of product as a yellow solid.

¹H NMR (300 MHz; CDCl₃) δ 8.29-8.28 (m, 1H), 8.18 (dm, J=10.5 Hz, 1H), 7.56 (br. s, 1H), 7.12 (br. s, 1H), 6.65 (d, J=9.3 Hz, 1H), 4.34 (t-like, J=9.0 Hz, 2H), 4.24 (t-like, J=6.3 Hz, 2H), 3.47-3.42 (m, 1H); m/z=289.9 (M+H)⁺; 288.0 (M−H)⁺.

Synthesis of 1-(4-amino-2-trifluoromethylphenyl)azetidin-3-carboxamide

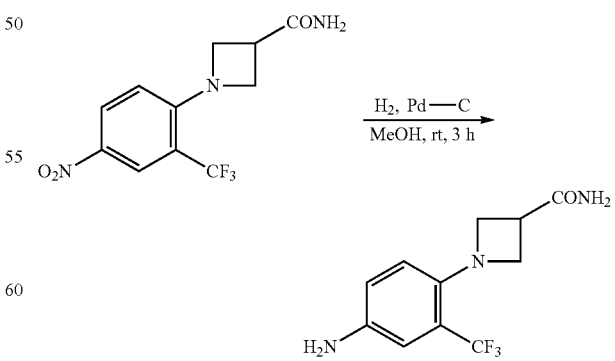

A mixture of nitro starting material (240 mg, 0.83 mmol, 1 equiv.) in 10 mL of MeOH in the presence of 24 mg of Pd/C was hydrogenated at rt for 4 h. The reaction mixture was then filtered through a pad of celite and the filtrate was concentrated to give 220 mg (quantitative yield) of product. m/z=259.95 (M+H)$^+$; 258.1 (M−H)$^+$.

Synthesis of 1-(4-(4-((7R,8aS)-octahydro-5,5-dimethylindolizin-7-ylamino)-5-fluoropyrimidin-2-ylamino)-2-(trifluoromethyl)phenyl)azetidine-3-carboxamide, formate salt (Compound 324)

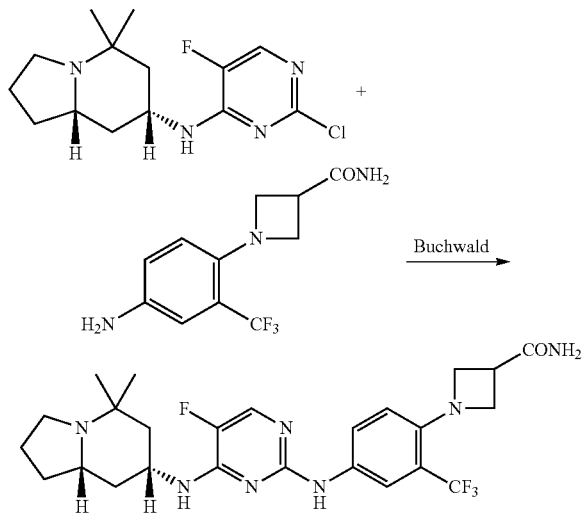

A mixture of (7R,8aS)-N-(2-chloro-5-fluoropyrimidin-4-yl)-octahydro-5,5-dimethylindolizin-7-amine (53 mg, 0.18 mmol, 1 equiv), aniline (60 mg, 0.23 mmol, 1.3 equiv), Pd(OAc)$_2$ (4 mg, 0.02 mmol, 0.1 equiv.), rac. BINAP (22 mg, 0.04 mmol, 0.2 equiv.) and Cs$_2$CO$_3$ (176 mg, 0.54 mmol, 3.0 equiv) in dioxane (1.5 mL) was heated under microwave at 120° C. for 2 h. The reaction mixture was filtered and washed with EtOAc. The filtrate was concentrated and purified by HPLC to give the product as a solid.

$^1$H NMR (300 MHz; d$_6$-DMSO) δ 8.88 (br. s, 1H), 7.83 (d, J=2.4 Hz, 1H), 7.80 (d, J=3.9 Hz, 1H), 7.75 (dd, J=9.0, 2.4 Hz, 1H), 7.44 (br. s, 1H), 7.12 (d, J=8.4 Hz, 1H), 6.98 (br. s, 1H), 6.54 (d, J=9.3 Hz, 1H), 4.20-4.10 (m, 1H), 3.98 (t, J=7.5 Hz, 2H), 3.88 (t, J=6.6 Hz, 2H), 2.88-2.82 (m, 1H), 2.50-2.40 (m, 1H), 2.35-2.25 (m, 1H), 2.00-1.95 (m, 1H), 1.70-1.60 (m, 1H), 1.65-1.55 (m, 3H), 1.37 (t, J=11.7 Hz, 1H), 1.30-1.10 (m, 2H), 1.07 (s, 3H), 0.96 (s, 3H); m/z=522.1 (M+H)$^+$; 520.1 (M−H)$^+$.

Example 118

Synthesis of 1-(4-(4-((7R,8aS)-octahydro-5,5-dimethylindolizin-7-ylamino)-5-fluoropyrimidin-2-ylamino)-24(2-trifluoromethylphenylamino)methyl)-3-chloropropanamide, p-toluene sulfonic salt (Compound 325)

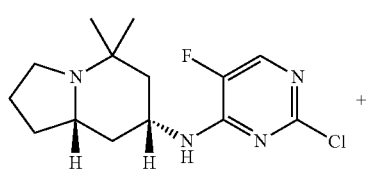

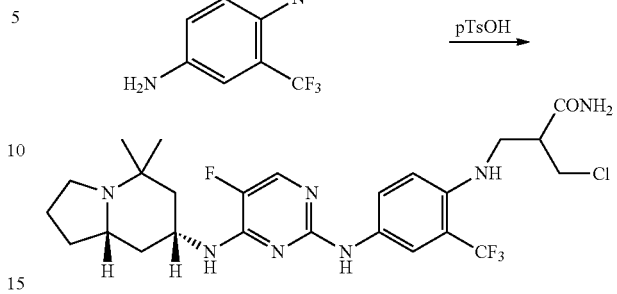

A mixture of (7R,8aS)-N-(2-chloro-5-fluoropyrimidin-4-yl)-octahydro-5,5-dimethylindolizin-7-amine (66 mg, 0.22 mmol, 1 equiv), aniline (60 mg, 0.31 mmol, 1.4 equiv) and pTsOH.H$_2$O (47 mg, 0.25 mmol, 0.8 equiv) in isopropanol (1.5 mL) was heated at 80° C. overnight in a sealed vial. After allowing to cool to room temperature, the solvent was removed and the residue was purified by HPLC to give the product as a solid.

$^1$H NMR (300 MHz; d$_6$-DMSO) δ 9.12 (br. s, 1H), 7.95 (d, J=4.5 Hz, 1H), 7.66 (m, 2H), 7.54 (br. s, 1H), 7.21 (br.s, 1H), 6.82 (d, J=9.3 Hz, 1H), 5.20-5.10 (m, 1H), 4.18-4.08 (m, 1H), 3.84-3.77 (m, 1H), 3.73-3.68 (m, 1H), 3.30-3.20 (m, 2H), 3.09-3.02 (m, 1H), 2.98-2.90 (m, 1H), 2.55-2.52 (m, 2H), 2.18-2.10 (m, 1H), 2.05-1.95 (m, 2H), 1.68-1.58 (m, 2H), 1.41-1.29 (m, 2H), 1.32 (s, 3H), 1.24 (s, 3H); m/z=558.1 (M+H)$^+$; 556.1 (M−H)$^+$.

Example 119

Synthesis of 1-(4-(4-((7R,8aS)-octahydro-5,5-dimethylindolizin-7-ylamino)-5-fluoropyrimidin-2-ylamino)-2-(trifluoromethyl)phenyl)azetidin-3-ol, formate salt (Compound 326)

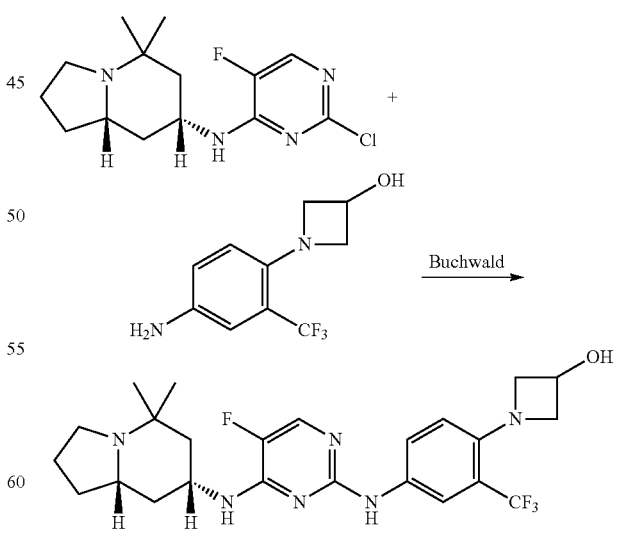

A mixture of (7R,8aS)-N-(2-chloro-5-fluoropyrimidin-4-yl)-octahydro-5,5-dimethylindolizin-7-amine (79 mg, 0.27 mmol, 1 equiv), aniline (86 mg, 0.37 mmol, 1.4 equiv), Pd(OAc)$_2$ (6 mg, 0.03 mmol, 0.1 equiv.), rac. BINAP (33 mg, 0.06 mmol, 0.2 equiv.) and Cs₂CO₃ (259 mg, 0.79 mmol, 3.0 equiv) in dioxane (2.0 mL) was heated under microwave at 120° C. for 2 h. The reaction mixture was filtered and washed with EtOAc. The filtrate was concentrated and purified by HPLC to give the product as a solid.

¹H NMR (300 MHz; d₆-DMSO) δ 8.86 (br. s, 1H), 7.83 (d, J=2.1 Hz, 1H), 7.79 (d, J=3.9 Hz, 1H), 7.74 (dd, J=8.7, 2.1 Hz, 1H), 7.13 (d, J=8.1 Hz, 1H), 6.52 (d, J=8.7 Hz, 1H), 4.46 (quint, J=5.1 Hz, 1H), 4.20-4.10 (m, 1H), 4.08 (t, J=6.6 Hz, 2H), 3.57 (t, J=6.3 Hz, 2H), 2.87-2.82 (m, 1H), 2.50-2.40 (m, 1H), 2.35-2.26 (m, 1H), 1.99-1.95 (m, 1H), 1.80-1.72 (m, 1H), 1.64-1.58 (m, 3H), 1.41 (t, J=12.0 Hz, 1H), 1.26-1.13 (m, 2H), 1.07 (s, 3H), 0.95 (s, 3H); m/z=495.1 (M+H)⁺; 493.1 (M−H)⁺.

Example 120

Synthesis of 4-(4-((7R,8aS)-octahydro-5,5-dimethylindolizin-7-ylamino)-5-fluoropyrimidin-2-ylamino)-2-chloro-N-methylbenzamide, p-toluene sulfonic salt (Compound 327)

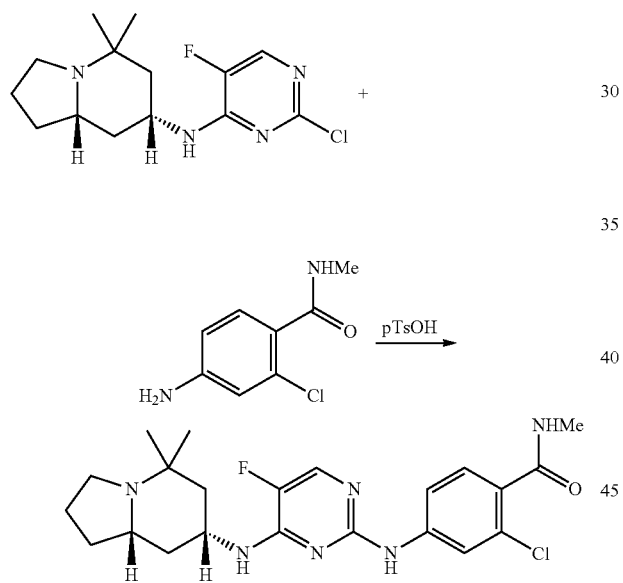

A mixture of (7R,8aS)-N-(2-chloro-5-fluoropyrimidin-4-yl)-octahydro-5,5-dimethylindolizin-7-amine (60 mg, 0.20 mmol, 1 equiv), aniline (52 mg, 0.28 mmol, 1.4 equiv) and pTsOH.H₂O (30 mg, 0.16 mmol, 0.8 equiv) in isopropanol (1.0 mL) was heated at 80° C. overnight in a sealed vial. After allowing to cool to room temperature, the solvent was removed and the residue was purified by HPLC to give the product as a solid.

¹H NMR (300 MHz; d₆-DMSO) δ 9.47 (br. s, 1H), 8.12 (q. J=4.8 Hz, 1H), 7.98 (d, J=3.6 Hz, 1H), 7.86 (d, J=1.8 Hz, 1H), 7.72 (d, J=7.5 Hz, 1H), 7.64 (dd, J=8.4, 1.8 Hz, 1H), 7.30 (d, J=8.4 Hz, 1H), 4.40-4.30 (m, 1H), 3.40-3.30 (m, 1H), 3.15-3.05 (m, 1H), 2.71 (d, J=4.8 Hz, 3H), 2.55-2.45 (m, 1H), 2.20-2.11 (m, 2H), 2.05-1.85 (m, 3H), 1.76-1.54 (m, 3H), 1.37 (s, 3H), 1.35 (s, 3H); m/z=447.1 (M+H)⁺; 445.1 (M−H)⁺.

Example 121

Preparation of Compound 328

Synthesis of 1-(2-(3-hydroxyazetidin-1-yl)-5-nitrophenyl)-4-methyl-1H-tetrazol-5(4H)-one

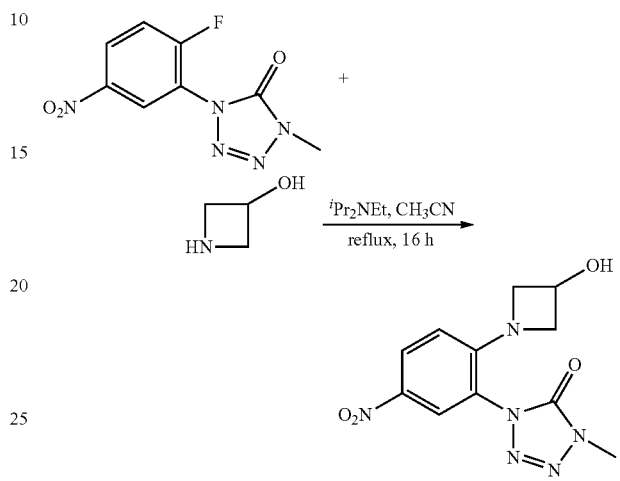

A mixture of 1-(2-fluoro-5-nitrophenyl)-1H-tetrazol-5 (4H)-one (100 mg, 0.42 mmol, 1 equiv.), 3-hydroxyazetidine hydrochloride (55 mg, 0.5 mmol, 1.2 equiv.) and (Pr₂NEt (0.18 mL, 1.05 mmol, 2.5 equiv.) in 2 mL of CH₃CN was refluxed for 3 days. Solvent was removed in vacuo and the residue was taken into EtOAc and washed with water. The organic layer was separated and concentrated. The residue was purified by column chromatography using a mixture of hexane/EtOAc (1:4) as eluent to give 108 mg (Yield=88%) of product as a yellow solid.

m/z=292.9 (M+H)⁺.

Synthesis of 1-(5-amino-2-(3-hydroxyazetidin-1-yl) phenyl)-4-methyl-1H-tetrazol-5(4H)-one

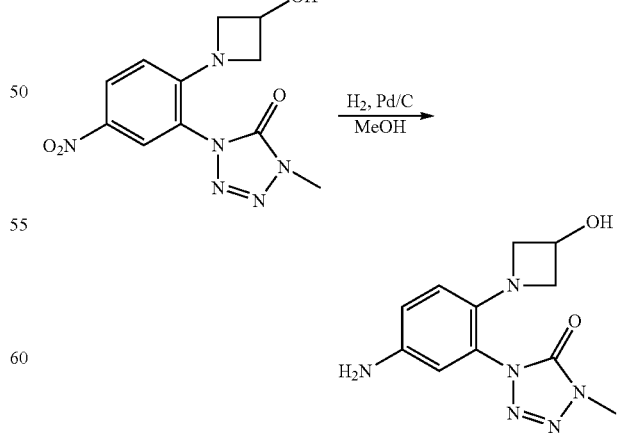

A mixture of starting material (108 mg, 1 equiv.) in 10 mL of MeOH in the presence of 10 mg of Pd/C was hydrogenated at room temperature for 3 h. The reaction mixture was Synthesis of 1-(5-(4-(((7R,8aS)-octahydro-5,5-dimethylindolizin-7-ylamino)-5-fluoropyrimidin-2-ylamino)-2-(3-hydroxyazetidin-1-yl)phenyl)-4-methyl-1H-tetrazol-5(4H)-one (Compound 328)

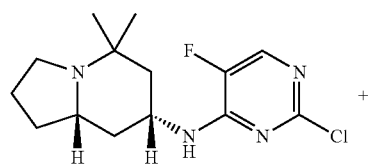

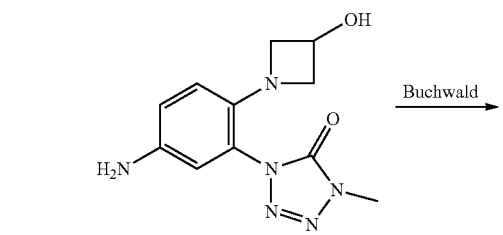

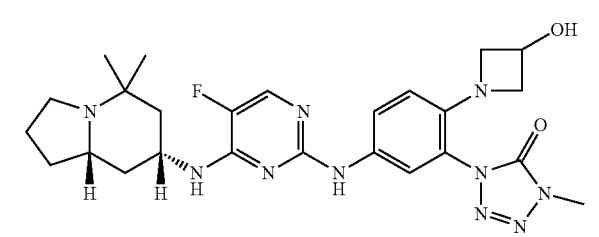

A mixture of (7R,8aS)-N-(2-chloro-5-fluoropyrimidin-4-yl)-octahydro-5,5-dimethylindolizin-7-amine (72 mg, 0.24 mmol, 1 equiv), aniline (88 mg, 0.34 mmol, 1.4 equiv), Pd(OAC)$_2$ (5 mg, 0.02 mmol, 0.1 equiv.), rac. BINAP (30 mg, 0.04 mmol, 0.2 equiv.) and Cs$_2$CO$_3$ (235 mg, 0.72 mmol, 3.0 equiv) in dioxane (2.0 mL) was heated under microwave at 120° C. for 2 h. The reaction mixture was filtered and washed with EtOAc. The filtrate was concentrated and purified by HPLC to give the product as a solid.

$^1$H NMR (300 MHz; d$_6$-DMSO) δ 8.96 (br. s, 1H), 7.79 (d, J=3.9 Hz, 1H), 7.68 (d, J=2.1 Hz, 1H), 7.54 (dd, J=9.0, 2.4 Hz, 1H), 7.14 (d, J=7.5 Hz, 1H), 6.55 (d, J=9.0 Hz, 1H), 5.30-5.20 (m, 1H), 4.37 (quint, J=6.3 Hz, 1H), 4.10-4.00 (m, 1H), 3.64 (t, J=6.9 Hz, 2H), 3.60 (s, 3H), 3.28 (t, J=6.3 Hz, 2H), 2.90-2.80 (m, 1H), 2.54-2.52 (m, 1H), 2.30-2.15 (m, 2H), 1.99-1.95 (m, 1H), 1.75-1.55 (m, 3H), 1.44 (t, J=11.7 Hz, 1H), 1.22-1.10 (m, 2H), 1.06 (s, 3H), 0.84 (s, 3H); m/z=525.1 (M+H)$^+$; 523.0 (M−H)$^+$.

Example 122

Preparation of Compounds 329-336

Compound 329

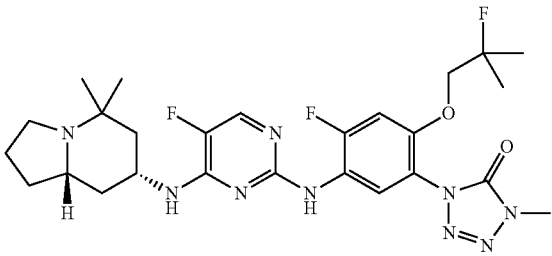

single diastereomer;
single enantiomer

Compound 330

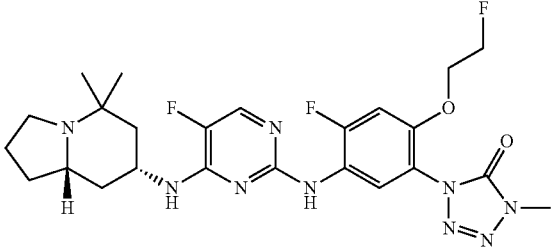

single diastereomer;
single enantiomer

Compound 331

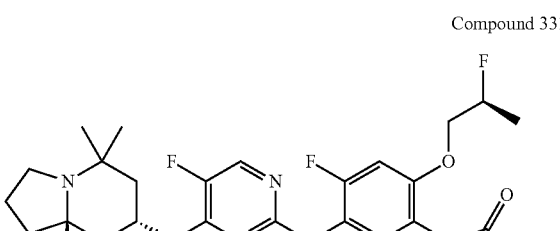

single diastereomer;
single enantiomer

Compound 332

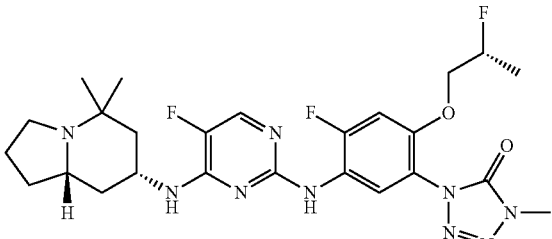

single diastereomer;
single enantiomer

-continued

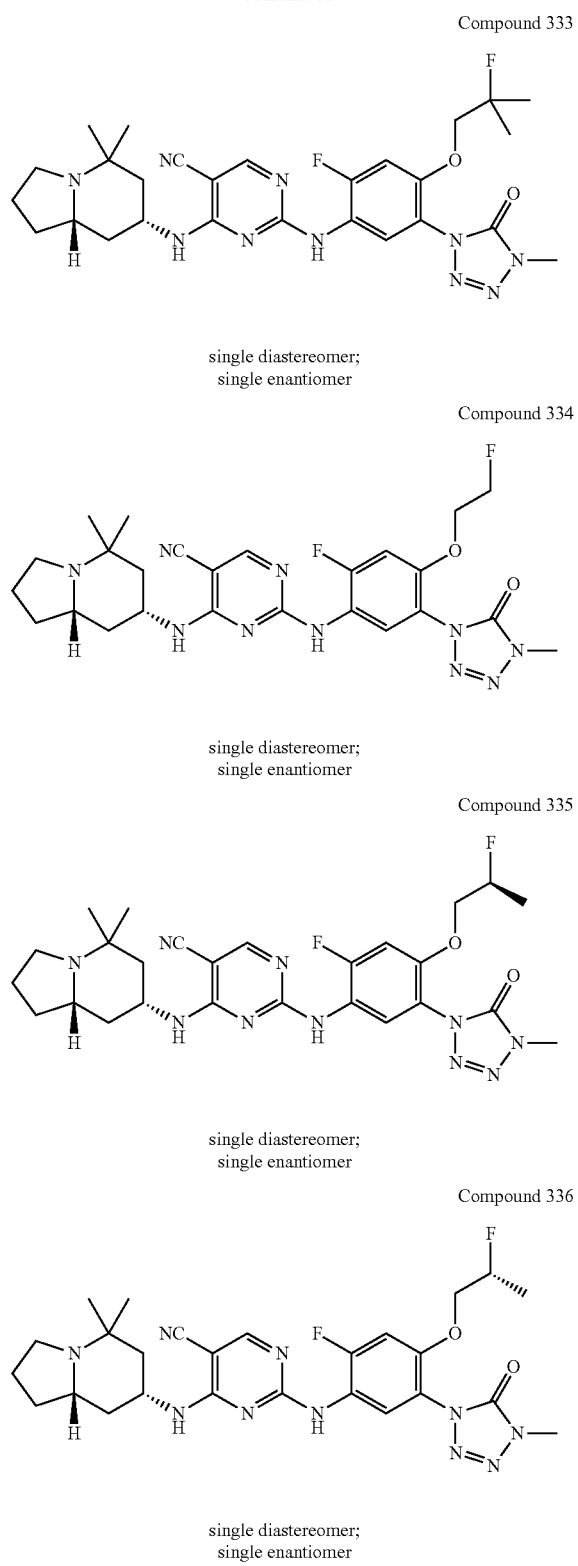

Compound 333
single diastereomer;
single enantiomer

Compound 334
single diastereomer;
single enantiomer

Compound 335
single diastereomer;
single enantiomer

Compound 336
single diastereomer;
single enantiomer

Compounds 329-336 can be prepared as is known to those of skill in the art analogously to examples set forth above, such as in the general scheme for late stage alkylation (See Example 107 above). For example, Compound 333 can be prepared according to the synthetic scheme shown below.

Preparation of 4-(((7R,8aS)-5,5-dimethyloctahydroindolizin-7-yl)amino)-2-((2-fluoro-4-(2-fluoro-2-methylpropoxy)-5-(4-methyl-5-oxo-4,5-dihydro-1H-tetrazol-1-yl)phenyl)amino)pyrimidine-5-carbonitrile (Compound 333)

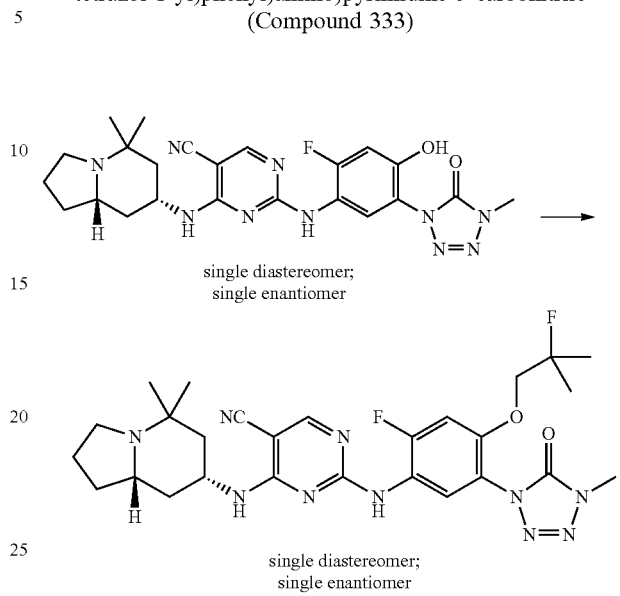

single diastereomer;
single enantiomer single diastereomer;
single enantiomer

Similarly, the following compounds can be prepared as described above:

Compound 329: 1-(5-(4-((7R,8aS)-5,5-dimethyloctahydroindolizin-7-ylamino)-5-fluoropyrimidin-2-ylamino)-4-fluoro-2-(2-fluoro-2-methylpropoxy)phenyl)-4-methyl-1H-tetrazol-5(4H)-one;

Compound 330: 1-(5-(4-((7R,8aS)-5,5-dimethyloctahydroindolizin-7-ylamino)-5-fluoropyrimidin-2-ylamino)-4-fluoro-2-(2-fluoroethoxy)phenyl)-4-methyl-1H-tetrazol-5(4H)-one;

Compound 331: 1-(5-(4-((7R,8aS)-5,5-dimethyloctahydroindolizin-7-ylamino)-5-fluoropyrimidin-2-ylamino)-4-fluoro-2-((S)-2-fluoropropoxy)phenyl)-4-methyl-1H-tetrazol-5(4H)-one;

Compound 332: 1-(5-(4-((7R,8aS)-5,5-dimethyloctahydroindolizin-7-ylamino)-5-fluoropyrimidin-2-ylamino)-4-fluoro-2-((R)-2-fluoropropoxy)phenyl)-4-methyl-1H-tetrazol-5(4H)-one;

Compound 334: 4-((7R,8aS)-5,5-dimethyloctahydroindolizin-7-ylamino)-2-(2-fluoro-4-(2-fluoroethoxy)-5-(4-methyl-5-oxo-4,5-dihydro-1H-tetrazol-1-yl)phenylamino)pyrimidine-5-carbonitrile;

Compound 335: 4-((7R,8aS)-5,5-dimethyloctahydroindolizin-7-ylamino)-2-(2-fluoro-4-((S)-2-fluoropropoxy)-5-(4-methyl-5-oxo-4,5-dihydro-1H-tetrazol-1-yl)phenylamino)pyrimidine-5-carbonitrile; and Compound 336: 4-((7R,8aS)-5,5-dimethyloctahydroindolizin-7-ylamino)-2-(2-fluoro-4-((R)-2-fluoropropoxy)-5-(4-methyl-5-oxo-4,5-dihydro-1H-tetrazol-1-yl)phenylamino)pyrimidine-5-carbonitrile.

BIOLOGICAL EXAMPLES

Example 123

PKC Assay

The inhibition of PKC-alpha, PKC-beta, PKC-delta, PKC epsilon and PKC-theta activity is determined via ELISA as follows: NUNC MAXISORP (#436110) or Costar High Binding (#3922) plates are coated with 0.01 mg/ml Neutravidin (Pierce #PI-31000) in 1×PBS (100 µL/well) for 18-24 hours at 4° C. When ready to be used, plates are washed with 1×PBST and then blocked with 2% BSA in 1×PBST (100 µL/well) for a minimum of 1 hour at room temperature. The reactions are conducted in a volume of 60 µL/well. When ready to begin, the plates are washed with 1×PBST to remove the 2% BSA blocking solution. Reaction solution containing the necessary buffer components as well as the appropriate concentrations of ATP and peptide substrate is then added to each well (see Table 3). Appropriate concentrations of test compound is then added—with the volume added should taking into consideration the DMSO tolerance of the kinases being about 0.2%. The reaction is then initiated by the addition of kinase—the approximate final concentration of which is listed in Table 3 (note that this will vary depending on the batch to batch variability in the activity of enzymes). After allowing the reaction to stand at room temperature for 20 minutes, the plates are then washed with 1×PBST.

minutes period of incubation, the amount of phosphorylated peptide generated is measured by fluorescence polarization (Ex=485 nm, Em=535 nm) using a Tecan Polarian instrument.

TABLE 4

| Peptide substrate | SEQ ID | Enzyme source | Typical enzyme concentration |
|---|---|---|---|
| PKC theta | RFARKGSLR QKNV | Seq ID No. 1 | Upstate Biotechnologies, Temecula, CA, cat. #14-444 | 40 ng/ml |
| PKC epsilon | RFARKGSLR QKNV | Seq ID No. 1 | Upstate Biotechnologies, Temecula, CA, cat. #14-518 | 50 ng/ml |

TABLE 3

| Kinase | Buffer components | [ATP] (uM) | [peptide] (uM) | Time (min) | 1° and 2° antibodies | Notes |
|---|---|---|---|---|---|---|
| PKCs<br>α: ~8 ng/ml<br>β: ~16 ng/ml<br>δ: ~13 ng/ml<br>ε: ~13 ng/ml<br>θ: ~8 ng/ml | 20 mM Hepes pH 7.4<br>5 mM MgCl$_2$<br>0.2 mM CaCl$_2$<br>1 mM DTT<br>0.05% Chaps | 1 µM | 1 µM PKC peptide (biotin-RFARKGSLRQKNV) (Invitrogen #P2760) | 20 min | Rabbit pSer PKC substrate Ab (Cell Signaling #2261); HRP-goat a-rabbit (Jackson Immunoresearch #111-035-003) | 0.15 mg/ml DAG (Sigma #D0138)<br>0.75 mg/ml Phosphoserine (Sigma #P6641)<br>DMSO tolerance ~0.2% |

After removal of the reaction mixture from the plate and washing with 1×PBST, an antibody developing solution containing a 1:10,000 dilution of the appropriate primary and secondary antibodies (Table 3) in a 0.1% BSA solution in 1×PBST is then added to each well (100 µL/well). This is then allowed to stand at room temperature for a minimum of 1 hour. After this time, the plates are once again washed with 1×PBST. The SuperSignal ELISA Pico Chemiluminescent substrate (Pierce #PI-37069) is then added (100 µL/well) and the plate is read on a luminescence plate reader.

Example 124

PKC Assay

Alternatively, the inhibition of PKC activity is measured by monitoring the production of phosphorylated peptide by fluorescence polarization at different concentrations of the inhibitor. Reactions are carried out in 96-well plate format with a total volume of 20 µL containing 20 mM HEPES, pH 7.4, 5 mM MgCl$_2$, 0.2 mM CaCl$_2$, 1 mM DTT, 0.02% Brij-35, 0.1 mg/ml phosphatidylserine, 0.02 mg/ml dioleoyl-sn-glycerol and 5 µM each of ATP and the peptide substrate. Compounds are first diluted serially in DMSO and then transferred to a solution containing the above concentrations of HEPES, MgCl$_2$, CaCl$_2$, DTT, and Brij-35 to yield 5× compound solutions in 2% DMSO, which is then added to the reaction solution. Reactions are initiated by the addition of PKC at a typical concentration as described in Table 4, and then allowed to incubate at room temperature for 20 minutes. At the end of this time, a combination of quench (EDTA) and detection (peptide tracer and antibody) reagents is added using the protocol of Invitrogen P2748. After a 30

Example 125

Calcium Influx

HEK-FLPTREX cells are stably transfected with pcDNA5/FRT/TO+hTRPV4a, rat TRPV1-HA or rTRPA 1-HA are grown in Dulbecco's Modified Eagle's Medium (DMEM) containing 10% tetracycline-free fetal bovine serum, hygromycin (50 µg/ml) and blasticidin (10 µg/ml). Cells are treated with tetracycline (0.1 µg/ml, 20 h) to induce TRP expression. DRG from thoracic and lumbar spinal cord of rats or mice are minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 minutes. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing Ca2+ and Mg2+, 20 mM HEPES buffer, 0.1% BSA, 100 U/ml penicillin, 100 µg/ml streptomycin, with 2.5-5 µM Fura-2AM (Invitrogen) for 20-45 minutes at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

Example 126

In Vivo Hyperplasia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 μl intraplantar injection) and paw withdrawal measurements repeated at different time point. To assess PAR2 TRPV1, TRPV4 and TRPA1 mediated hyperalgesia and potentiation of TRPV-mediated responses, mice are treated with PAR2-AP for 15 minutes followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4αPDD).

Formalin induced hyperalgeisa is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-minutes interval is calculated as the weighted average of the number of seconds spent in each behavior. 2.5% solution of formalin is administered by intraplantar injection and thermal and mechanical pain measured as described above after 30-60 minutes. To assess the role of protein kinases, antagonists or their vehicles (control) are injected into the right paws 20-30 minutes before formalin. Nociceptive behavior will be scored for each rats and compared to control.

Exemplary compounds exhibited in vivo activity in one or more disease models. For example Compound 17 had an ED50 of 30 mg/kg in both pretreatment and treatment dosing in an PLP induced experimental autoimmune encephalomyelitis (EAE) model in SJL mice. As is known to those of skill in the art, EAE is considered to be a model of multiple sclerosis in humans. Other exemplary compounds demonstrated in vivo efficacy in rodents in contact dermatitis and/or adjuvant induced arthritis models.

Example 127

IL-2 ELISA, Human Primary T Cell, Anti CD3+CD28+

Compounds 1-328 were tested in a whole cell functional assay for PKC mediated IL-2 production as follows. Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 minutes at 4° C. at 1750 rpm. The cells at the serum: ficoll interface were recovered and washed twice with 5 volumes of PBS. These freshly isolated human peripheral blood mononuclear cells were cultured in Yssel's medium containing 40 U/ml IL2 in a flask pre-coated with 1 μm/ml αCD3 and 5 μg/ml αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/ml IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hour at 37° C. Cells were then stimulated by transferring them to round-bottom 96-well plates pre-coated with 1 μm/ml αCD3 and 5 μg/ml αCD28. For counter assay, cells were instead stimulated by adding 8× stock solutions of PMA and ionomycin in Yssels (for final concentrations of 0.5 ng/ml PMA and 0.1 uM ionomycin, both from Calbiochem). Cells were incubated at 37° C. for 24 hours before 100 μL supernatants were harvested for quantification of IL-2 by ELISA using Human IL-2 Duoset ELISA Kit from R and D Systems, Cat. # DY202E. Compounds 1-29, 31-138, 140-170, 172-184, 186-215, 218-233, 235-238, 240-256, 258-259, 261-271, 273-276, 278-285, and 287-328 blocked IL-2 production with an EC50 of less than 10 micromolar.

Table 5 shows the EC50 values of Compounds 1-328 according to the above assay. In Table 5, an EC50 of A is less than 0.1 μM, B<0.5 μM, C<1 μM, D<10 μM, and E>10 μM.

TABLE 5

| Compound | EC50 (μM) |
|---|---|
| 1 | B |
| 2 | A |
| 3 | C |
| 4 | D |
| 5 | B |
| 6 | B |
| 7 | D |
| 8 | C |
| 9 | B |
| 10 | B |
| 11 | D |
| 12 | C |
| 13 | A |
| 14 | A |
| 15 | B |

TABLE 5-continued

| Compound | EC50 (μM) |
|---|---|
| 16 | A |
| 17 | A |
| 18 | C |
| 19 | C |
| 20 | D |
| 21 | D |
| 22 | B |
| 23) | A |
| 24 | B |
| 25 | D |
| 26 | D |
| 27 | D |
| 28 | A |
| 29 | D |
| 30 | E |
| 31 | D |
| 32 | D |
| 33 | D |
| 34 | D |
| 35 | D |
| 36 | D |
| 37 | D |
| 38 | B |
| 39 | B |
| 40 | A |
| 41 | B |
| 42 | D |
| 43 | D |
| 44 | D |
| 45 | D |
| 46 | C |
| 47 | A |
| 48 | A |
| 49 | A |
| 50 | A |
| 51 | B |
| 52 | B |
| 53 | A |
| 54 | A |
| 55 | B |
| 56 | A |
| 57 | B |
| 58 | D |
| 59 | B |
| 60 | B |
| 61 | C |
| 62 | B |
| 63 | B |
| 64 | B |
| 65 | D |
| 66 | A |
| 67 | B |
| 68 | B |
| 69 | C |
| 70 | D |
| 71 | C |
| 72 | C |
| 73 | B |
| 74 | B |
| 75 | B |
| 76 | A |
| 77 | A |
| 78 | A |
| 79 | A |
| 80 | A |
| 81 | A |
| 82 | A |
| 83 | A |
| 84 | B |
| 85 | B |
| 86 | A |
| 87 | A |
| 88 | B |
| 89 | D |
| 90 | A |
| 91 | A |
| 92 | A |
| 93 | B |

TABLE 5-continued

| Compound | EC50 (μM) |
|---|---|
| 94 | B |
| 95 | A |
| 96 | A |
| 97 | B |
| 98 | B |
| 99 | A |
| 100 | B |
| 101 | B |
| 102 | B |
| 103 | B |
| 104 | B |
| 105 | C |
| 106 | B |
| 107 | B |
| 108 | A |
| 109 | B |
| 110 | B |
| 111 | B |
| 112 | B |
| 113 | B |
| 114 | C |
| 115 | C |
| 116 | B |
| 117 | D |
| 118 | B |
| 119 | A |
| 120 | B |
| 121 | A |
| 122 | B |
| 123 | A |
| 124 | B |
| 125 | D |
| 126 | A |
| 127 | A |
| 128 | B |
| 129 | A |
| 130 | C |
| 131 | A |
| 132 | A |
| 133 | B |
| 134 | B |
| 135 | A |
| 136 | A |
| 137 | A |
| 138 | A |
| 139 | E |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | B |
| 154 | A |
| 155 | A |
| 156 | D |
| 157 | D |
| 158 | B |
| 159 | B |
| 160 | D |
| 161 | C |
| 162 | B |
| 163 | A |
| 164 | A |
| 165 | C |
| 166 | B |
| 167 | B |
| 168 | D |
| 169 | D |
| 170 | B |
| 171 | E |

TABLE 5-continued

| Compound | EC50 (μM) |
|---|---|
| 172 | B |
| 173 | B |
| 174 | C |
| 175 | C |
| 176 | B |
| 177 | B |
| 178 | B |
| 179 | B |
| 180 | B |
| 181 | B |
| 182 | A |
| 183 | D |
| 184 | B |
| 185 | E |
| 186 | A |
| 187 | B |
| 188 | C |
| 189 | B |
| 190 | B |
| 191 | D |
| 192 | B |
| 193 | B |
| 194 | B |
| 195 | C |
| 196 | B |
| 197 | B |
| 198 | D |
| 199 | C |
| 200 | A |
| 201 | B |
| 202 | A |
| 203 | A |
| 204 | C |
| 205 | A |
| 206 | A |
| 207 | A |
| 208 | D |
| 209 | B |
| 210 | A |
| 211 | D |
| 212 | D |
| 213 | B |
| 214 | B |
| 215 | A |
| 216 | E |
| 217 | E |
| 218 | A |
| 219 | B |
| 220 | A |
| 221 | A |
| 222 | B |
| 223 | A |
| 224 | A |
| 225 | B |
| 226 | B |
| 227 | B |
| 228 | B |
| 229 | D |
| 230 | B |
| 231 | C |
| 232 | C |
| 233 | B |
| 234 | E |
| 235 | A |
| 236 | A |
| 237 | A |
| 238 | C |
| 239 | E |
| 240 | A |
| 241 | B |
| 242 | A |
| 243 | C |
| 248 | B |
| 249 | A |
| 250 | D |
| 251 | D |
| 252 | D |
| 253 | D |
| 254 | D |
| 255 | A |
| 256 | D |
| 257 | E |
| 258 | D |
| 259 | D |
| 260 | E |
| 261 | A |
| 262 | A |
| 263 | B |
| 264 | D |
| 265 | B |
| 266 | A |
| 267 | B |
| 268 | D |
| 269 | C |
| 270 | C |
| 271 | A |
| 272 | E |
| 273 | A |
| 274 | A |
| 275 | B |
| 276 | A |
| 277 | E |
| 278 | A |
| 279 | A |
| 280 | C |
| 281 | A |
| 282 | A |
| 283 | B |
| 284 | A |
| 285 | B |
| 286 | E |
| 287 | D |
| 288 | D |
| 289 | A |
| 290 | B |
| 291 | B |
| 292 | C |
| 293 | B |
| 294 | C |
| 295 | C |
| 296 | C |
| 297 | B |
| 298 | B |
| 299 | B |
| 300 | B |
| 301 | A |
| 302 | C |
| 303 | B |
| 304 | B |
| 305 | B |
| 306 | B |
| 307 | B |
| 308 | C |
| 309 | B |
| 310 | D |
| 311 | D |
| 312 | B |
| 313 | B |
| 314 | B |
| 315 | D |
| 316 | A |
| 317 | A |
| 318 | C |
| 319 | D |
| 320 | B |
| 321 | B |
| 322 | B |
| 323 | D |
| 324 | C |
| 325 | C |
| 326 | B |
| 327 | C |
| 328 | D |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

$R^{18}$ is H, alkyl, substituted alkyl, acyl, acylamino, —$SO_2$-alkyl, —$SO_2$-aryl, aryl or heteroaryl;

X is halo or azido;

$R^{19}$, $R^{20}$, and $R^{21}$ each independently are selected from alkyl, substituted alkyl, aryl substituted aryl, heteroaryl and substituted heteroaryl; and the compound is optically active.

---

---

What is claimed is:

1. A compound according to the formula (XII):

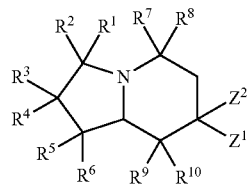

(XII)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$Z^1$ is $OR^{17}$, —$NR^{17}R^{18}$ or X;

$Z^2$ is H, or $Z^1$ and $Z^2$ together form an oxo, =$NR^{19}$ or =$NNR^{20}R^{21}$;

$R^{17}$ is H, alkyl, substituted alkyl, acyl, acylamino, —$SO_2$-alkyl or —$SO_2$-aryl;

2. A method of inhibiting a protein kinase C (PKC) activity comprising contacting a PKC with a compound of formula (VI):

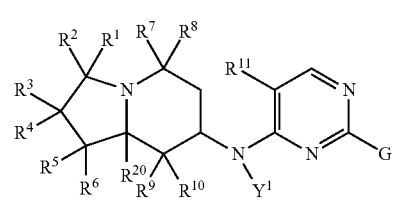

(VI)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;

$R^{11}$ is selected from alkyl, substituted alkyl, cycloalkyl, substituted cycloalkyl, hydroxy, alkoxy, substituted alkoxy, amino, substituted amino, carboxyl, carboxyl ester, cyano, halogen, thiol, thioalkoxy, substituted thioalkoxy, acyl, aminoacyl, nitro, alkenyl, substituted alkenyl, alkynyl, substituted alkynyl, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

$R^{20}$ is selected from hydrogen, alkyl, and substituted alkyl;

G is halogen or —NY$^2$Ar$^1$;

$Y^1$ and $Y^2$ are independently selected from hydrogen, alkyl and substituted alkyl; and Ar$^1$ is selected from aryl, substituted aryl, heteroaryl, and substituted heteroaryl;

or a salt or stereoisomer thereof.

3. The method of claim 2, wherein the inhibition of PKC results in treatment of a disease or disorder that is mediated or sustained through the activity of a PKC activity.

4. The method of claim 3, wherein the disease or disorder is associated with activation of T cells.

5. The method of claim 4, wherein the disease or disorder is an inflammatory disease.

6. The method of claim 4, wherein the disease or disorder is selected from inflammatory bowel disease, Crohn's disease and ulcerative colitis.

7. A method of studying a biological sample known to comprise PKC, the method comprising:
(a) contacting the biological sample with a compound of formula (VI) according to claim 2; and
(b) determining the PKC activity inhibiting effects caused by the compound on the biologic sample.

8. The method of claim 7, wherein the determination step is performed using an assay of inhibition of PKC activity.

9. A method for making a compound according to the formula

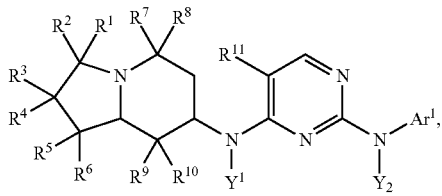

wherein
$R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl and substituted alkyl; and Ar$^1$ is selected from aryl, substituted aryl, heteroaryl, and substituted heteroaryl;

the method comprising contacting a compound of the formula

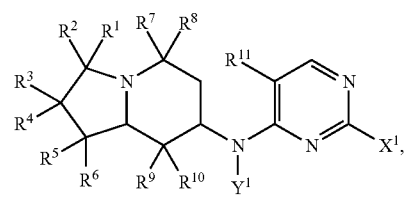

wherein X$^1$ is a halogen;
with a compound of the formula HNY$^2$Ar$^1$.

10. The method of claim 2, wherein G is —NY$^2$Ar$^1$.

11. The method of claim 2, wherein G is halogen.

12. The method of claim 2, wherein Ar$^1$ is aryl or substituted aryl.

13. The method of claim 2, wherein Ar$^1$ is heteroaryl or substituted heteroaryl.

14. The method of claim 2, wherein the compound is a compound according to the formula

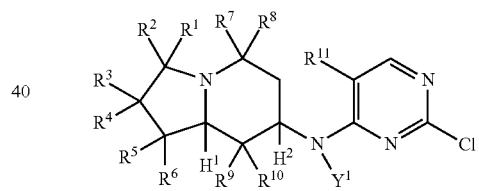

wherein
H$^1$ and H$^2$ are hydrogen.

15. The method of claim 2, wherein the compound is a compound of formula (VII):

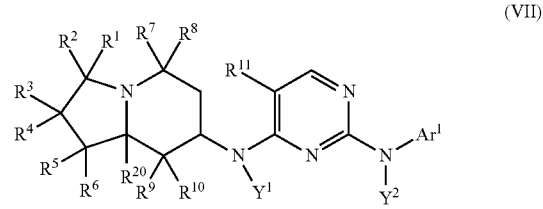

(VII)

wherein
$R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

R$^{20}$ is selected from hydrogen, alkyl, and substituted alkyl;

Y$^1$ and Y$^2$ are independently selected from hydrogen, alkyl and substituted alkyl; and Ar$^1$ is selected from aryl, substituted aryl, heteroaryl, and substituted heteroaryl;

or a salt or stereoisomer thereof.

16. The method of claim 15, wherein the compound is a compound of formula (VIIa):

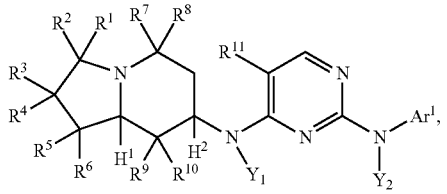

(VIIa)

wherein H$^1$ and H$^2$ are hydrogen with cis relative configuration.

17. The method of claim 15, wherein the compound is a compound of formula (VIIb):

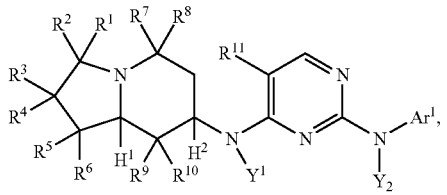

(VIIb)

wherein H$^1$ and H$^2$ are hydrogen with trans relative configuration.

18. The method of claim 15, wherein the compound is optically active.

19. The method of claim 18, wherein the compound has an enantiomeric excess of 90% or more.

20. The method of claim 19, wherein the enantiomeric excess is 95% or more.

21. The method of claim 19, wherein the enantiomeric excess is 99% or more.

22. The method of claim 2, wherein the compound is of formula (VIII):

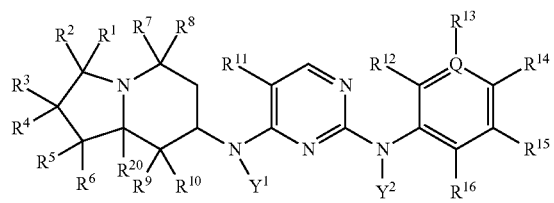

(VIII)

wherein

R$^1$, R$^2$, R$^3$, R$^4$, R$^5$, and R$^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^1$ and R$^2$ together form an oxo group; or R$^3$ and R$^4$ together form an oxo group; or R$^5$ and R$^6$ together form an oxo group;

R$^7$, R$^8$, R$^9$, and R$^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or R$^7$ and R$^8$ together form an oxo group; or R$^9$ and R$^{10}$ together form an oxo group;

R$^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

R$^{20}$ is selected from hydrogen, alkyl, and substituted alkyl;

Y$^1$ and Y$^2$ are independently selected from hydrogen, alkyl and substituted alkyl;

Q is C or N; and

R$^{12}$, R$^{13}$, R$^{14}$, R$^{15}$, and R$^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or R$^{14}$ and R$^{15}$ together with the carbon atoms to which they are attached form aryl, substituted aryl, heteroaryl, substituted heteroaryl, heterocyclyl, or substituted heterocyclyl;

or a salt or stereoisomer thereof.

23. The method of claim 22, wherein Q is C.

24. The method of claim 22, wherein Q is N.

25. The method of claim 22, wherein $R^{12}$, $R^{13}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

26. The method of claim 22, wherein the compound is of formula (VIIIa):

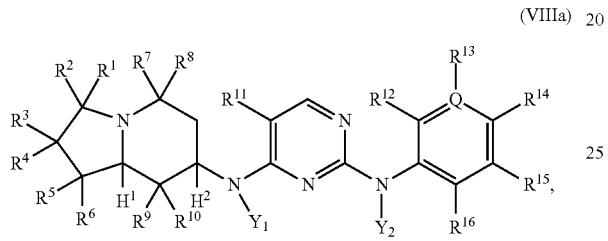

(VIIIa)

wherein $H^1$ and $H^2$ are hydrogen with cis relative configuration.

27. The method of claim 22, wherein the compound is of formula (VIIIb):

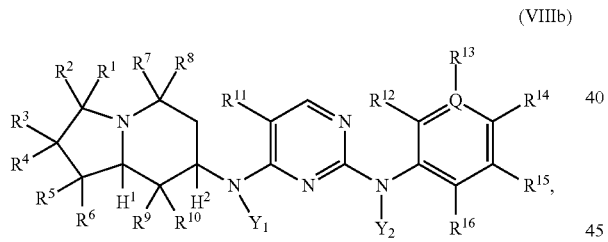

(VIIIb)

wherein $H^1$ and $H^2$ are hydrogen with trans relative configuration.

28. The method of claim 2, wherein the compound is of formula (IX)

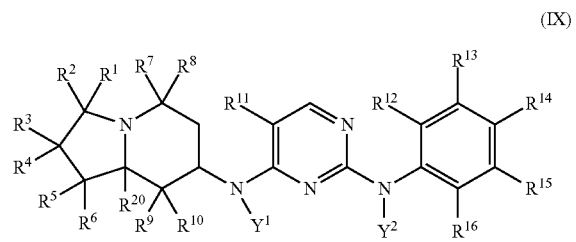

(IX)

wherein $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^1$ and $R^2$ together form an oxo group; or $R^3$ and $R^4$ together form an oxo group; or $R^5$ and $R^6$ together form an oxo group;

$R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or $R^7$ and $R^8$ together form an oxo group; or $R^9$ and $R^{10}$ together form an oxo group;

$R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$R^{20}$ is selected from hydrogen, alkyl, and substituted alkyl;

$Y^1$ and $Y^2$ are independently selected from hydrogen, alkyl and substituted alkyl; and $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

29. The method of claim 28, wherein $R^{12}$, $R^{13}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

30. The method of claim 2, wherein the compound is of formula (X)

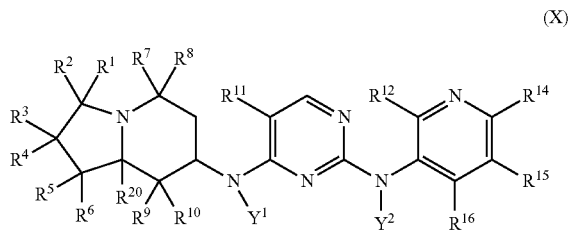

wherein
- $R^1$, $R^2$, $R^3$, $R^4$, $R^5$, and $R^6$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^1$ and $R^2$ together form an oxo group; or $R^3$ and $R^4$ together form an oxo group; or $R^5$ and $R^6$ together form an oxo group;
- $R^7$, $R^8$, $R^9$, and $R^{10}$ are independently selected from hydrogen, alkyl, substituted alkyl, alkoxy, substituted alkoxy, acyl, acylamino, acyloxy, amino, substituted amino, aminoacyl, aminoacyloxy, oxyaminoacyl, azido, cyano, halogen, hydroxyl, carboxyl, carboxylalkyl, thiol, thioalkoxy, substituted thioalkoxy, aryl, aryloxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl; or $R^7$ and $R^8$ together form an oxo group; or $R^9$ and $R^{10}$ together form an oxo group;
- $R^{11}$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;
- $R^{20}$ is selected from hydrogen, alkyl, and substituted alkyl;
- $Y^1$ and $Y^2$ are independently selected from hydrogen, alkyl and substituted alkyl; and
- $R^{12}$, $R^{13}$, $R^{14}$, $R^{15}$, and $R^{16}$ are independently selected from hydrogen, alkyl, substituted alkyl, alkenyl, substituted alkenyl, alkynyl, substituted alkynyl, halogen, cyano, hydroxyl, alkoxy, substituted alkoxy, amino, substituted amino, acylamino, aminocarbonylamino, alkoxycarbonylamino, acyl, carboxyl, carboxyl ester, aminoacyl, aminocarbonyloxy, nitro, sulfonyl, sulfonylamino, aminosulfonyl, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl;

or a salt or stereoisomer thereof.

31. The method of claim 30, wherein $R^{12}$, $R^{14}$, $R^{15}$, and $R^{16}$ are independently selected from hydrogen, alkyl, substituted alkyl, halogen, cyano, hydroxyl, alkoxy, substituted alkoxy, amino, substituted amino, acylamino, aminocarbonylamino, acyl, aminoacyl, aminocarbonyloxy, sulfur pentafluoride, aryl, substituted aryl, cycloalkyl, substituted cycloalkyl, heteroaryl, substituted heteroaryl, heterocyclyl, substituted heterocyclyl, heterocyclyloxy, and substituted heterocyclyloxy, or $R^{14}$ and $R^{15}$ together with the carbon atoms to which they are attached form aryl, substituted aryl, heteroaryl, substituted heteroaryl, heterocyclyl, or substituted heterocyclyl.

32. The method of claim 2, wherein $R^1$, $R^2$, $R^3$, $R^4$, $R^5$, and $R^6$ are independently selected from hydrogen, alkyl, substituted alkyl, cyano, halogen, hydroxyl, acyl, aminoacyl, and nitro; or $R^1$ and $R^2$ together form an oxo group; or $R^3$ and $R^4$ together form an oxo group; or $R^5$ and $R^6$ together form an oxo group.

33. The method of claim 2, wherein $R^1$, $R^2$, $R^3$, $R^4$, $R^5$, and $R^6$ are independently selected from hydrogen, alkyl, substituted alkyl, halogen, and hydroxyl; or $R^1$ and $R^2$ together form an oxo group; or $R^3$ and $R^4$ together form an oxo group; or $R^5$ and $R^6$ together form an oxo group.

34. The method of claim 2, wherein $R^1$ and $R^2$ are hydrogen.

35. The method of claim 2, wherein $R^1$ and $R^2$ are alkyl.

36. The method of claim 2, wherein at least one of $R^3$ and $R^4$ is hydrogen.

37. The method of claim 2, wherein at least one of $R^3$ and $R^4$ is halogen or hydroxyl.

38. The method of claim 2, wherein $R^1$ and $R^2$ together form an oxo group; or $R^3$ and $R^4$ together form an oxo group; or $R^5$ and $R^6$ together form an oxo group.

39. The method of claim 2, wherein $R^1$, $R^2$, $R^3$, $R^4$, $R^5$, and $R^6$ are hydrogen.

40. The method of claim 2, wherein $R^7$, $R^8$, $R^9$, and $R^{10}$ are independently selected from hydrogen, alkyl, substituted alkyl, alkoxy, substituted alkoxy, cyano, halogen, acyl, aminoacyl, and nitro; or $R^7$ and $R^8$ together form an oxo group.

41. The method of claim 2, wherein $R^7$, $R^8$, $R^9$, and $R^{10}$ are independently selected from hydrogen, alkyl, substituted alkyl, and halogen; or $R^7$ and $R^8$ together form an oxo group.

42. The method of claim 2, wherein $R^7$ and $R^8$ are hydrogen.

43. The method of claim 2, wherein $R^7$ and $R^8$ are methyl.

44. The method of claim 2, wherein $R^7$ and $R^8$ together form an oxo group.

45. The method of claim 2, wherein $R^9$ and $R^{10}$ are hydrogen.

46. The method of claim 2, wherein at least one of $R^9$ and $R^{10}$ is methyl.

47. The method of claim 2, wherein $R^{11}$ is selected from alkoxy, substituted alkoxy, cyano, halogen, acyl, aminoacyl, and nitro.

48. The method of claim 2, wherein $R^{11}$ is cyano, halogen, acyl, aminoacyl, or nitro.

49. The method of claim 2, wherein $R^{11}$ is fluoro or cyano.

50. The method of claim 2, wherein $R^{11}$ is fluoro.

51. The method of claim 2, wherein $R^{20}$ is hydrogen.

52. The method of claim 2, wherein $Y^1$ and $Y^2$ are hydrogen.

53. The method of claim 2, wherein the compound selected from:

Compounds 16-21: octahydro-5,5-dimethylindolizin-7ylamino)-5-fluoropyrimidin-2-yl-amino)-2-cyclopropyl-4-fluorophenyl)-4-methyl-1H-tetrazol-5(4H)-one;

Compound 17: 1-(5-(4-((7R,8aS)-octahydro-5,5-dimethylindolizin-7ylamino)-5-fluoropyrimidin-2-yl-amino)-2-cyclopropyl-4-fluorophenyl)-4-methyl-1H-tetrazol-5(4H)-one; and Compound 18: 1-(5-(4-((7S,8aR)-octahydro-5,5-dimethylindolizin-7ylamino)-5-fluoropyrimidin-2-yl amino)-2-cyclopropyl-4-fluorophenyl)-4-methyl-1H-tetrazol-5(4H)-one.

54. The method of claim 2, wherein the compound selected from:

Compounds 1-4: N2-(4,4-dimethyl-4H-benzo[b]tetrazolo[1,5-d][1,4]oxazin-8-yl)-5-fluoro-N4-(octahydro-5,5-dimethylindolizin-7-amine)pyrimidine-2,4-diamine;

Compound 5: N2-(4,4-dimethyl-4H-benzo[b]tetrazolo[1,5-d][1,4]oxazin-8-yl)-5-fluoro-N4-(octahydro-5,5-dimethylindolizin-7-yl)pyrimidine-2,4-diamine;

Compounds 6-10: (R/S,S/R,R/R,S/S)—$N^2$-(4-(1-isopropylpiperidin-4-yloxy)-3-(difluoromethoxy)phenyl)-5-fluoro-$N^4$-(octahydro-5,5-dimethylindolizin-7-yl)pyrimidine-2,4-diamine;

Compounds 11-14: (R/S,S/R,R/R,S/S)-5-fluoro-N4-(octahydro-5,5-dimethylindolizin-7-yl)N2-(3-methoxy-5-(5-methyl-1H-tetrazol-1-yl)phenyl)pyrimidine-2,4-diamine;

Compounds 16-21: octahydro-5,5-dimethylindolizin-7ylamino)-5-fluoropyrimidin-2-yl-amino)-2-cyclopropyl-4-fluorophenyl)-4-methyl-1H-tetrazol-5(4H)-one;

Compound 17: 1-(5-(4-((7R,8aS)-octahydro-5,5-dimethylindolizin-7ylamino)-5-fluoropyrimidin-2-yl-amino)-2-cyclopropyl-4-fluorophenyl)-4-methyl-1H-tetrazol-5(4H)-one;

Compound 18: 1-(5-(4-((7S,8aR)-octahydro-5,5-dimethylindolizin-7ylamino)-5-fluoropyrimidin-2-yl amino)-2-cyclopropyl-4-fluorophenyl)-4-methyl-1H-tetrazol-5(4H)-one;

Compound 22: 1-(5-(4-((7R,8aS)-5,5-dimethyl-octahydroindolizin-7ylamino)-5-fluoropyrimidin-2-ylamino)-4-fluoro-2-methoxyphenyl)-4-methyl-1H-tetrazol-5(4H)-one;

Compound 23: 1-(5-(4-((7R,8aS)-5,5-dimethyl-octahydroindolizin-7ylamino)-5-fluoropyrimidin-2-ylamino)-4-fluoro-2-isopropoxyphenyl)-4-methyl-1H-tetrazol-5(4H)-one;

Compound 24: (±)-$N^2$-(4-cyclopropyl-2-fluoro-5-(1H-tetrazol-1-yl)phenyl)-5-fluoro-n⁴-(octahydroindolizin-7-yl)pyrimidine-2,4-diamine;

Compound 26: N2-(4-cyclopropyl-2-fluoro-5-(4,5-dihydro-4-methyl-5-oxotetrazol-yl)phenylamino)-5-fluoro-N4-(octahydro-5,5-dimethylindolizin-7-ylamino) pyrimidine-2,4-diamine;

Compound 27: (±)-1-(5-(5-fluoro-4-(octahydroindolizin-7-ylamino)pyrimidin-2-ylamino)-2-cyclopropyl-4-fluorophenyl)-4-methyl-1H-tetrazol-5(4H)one;

Compound 28: (±)-$N^2$-(4-cyclopropyl-2-fluoro-5-(5-methyl-1H-tetrazol-1-yl)phenyl)-5-fluoro-n⁴-(octahydroindolizin-7-yl)pyrimidine-2,4-diamine;

Compound 30: N2-{4-cyclopropyl-6-fluoro-[3-(4-methyl)-1,2,3,4-tetrazol-5-one-1-yl]}phenyl-5-fluoro-N4(7-amino-hexahydro-3,3-dimethylindolizin-5 (1H)-one))2,4-pyrimidinediamine;

Compounds 31-33: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 31: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 32: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one;

Compound 33: 1-(5-(5-fluoro-4-(hexahydro-5,5-dimethylindolizin-3(5H)-one-7-ylamino)pyrimidin-2-ylamino)-2-cyclopropyl-4-fluorophenyl)-4-methyl-1H-tetrazol-5(4H)-one formate;

Compounds 34 and 35: 1-(5-(5-fluoro-4-(octahydro-3,3-dimethylindolizin-7-ylamino)pyrimidin-2-ylamino)-2-cyclopropyl-4-fluorophenyl)-4-methyl-1H-tetrazol-5(4H)-one;

Compound 38: 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one;

Compounds 39-40: 1-(5-(5-fluoro-4-(octahydro-5,5-dimethylindolizin-7-ylamino)pyrimidin-2-ylamino)-2-(oxetan-3-yloxy)phenyl)-4-methyl-1H-tetrazol-5(4H)-one;

Compound 41: 5-(5-fluoro-4-(octahydro-5,5-dimethylindolizin-7-ylamino)pyrimidin-2-ylamino)-2-(tetrahydro-2H-pyran-4-yloxy)benzonitrile;

Compound 42: 1-(5-(4-((7S,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 43: $N^2$-(4-cyclopropyl-2-fluoro-5-(1H-tetrazol-1-yl)phenyl)-5-fluoro-$N^4$-((7S,8aR)-2,2-difluorooctahydro-5,5-dimethylindolizin-7-yl)pyrimidine-2,4-diamine;

Compound 44: (4-((7S,8aR)-2,2-difluoro-octahydro-5,5-dimethylindolizin-7-ylamino)-5-fluoropyrimidin-2-ylamino)-2-methylbenzonitrile;

Compound 45: 1-(5-(4-((7R,8aR)-2,2-difluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 46: $N^2$-(4-cyclopropyl-2-fluoro-5-(1H-tetrazol-1-yl)phenyl)-5-fluoro-$N^4$-((7R,8aR)-2,2-difluorooctahydro-5,5-dimethylindolizin-7-yl)pyrimidine-2,4-diamine;

Compound 47: 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 48: 1-(2-((R)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 49: 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 50: 1-(2-((S)-tetrahydrofuran-3-yloxy)-5-(5-fluoro-4-(octahydro-5,5-dimethylindolizin-7-ylamino)pyrimidin-2-ylamino)phenyl)-4-methyl-1H-tetrazol-5(4H)-one;

Compound 51: 1-(5-(5-fluoro-4-(octahydro-5,5-dimethylindolizin-7-ylamino)pyrimidin-2-ylamino)-2-(tetrahydro-2H-pyran-4-oxy)phenyl)-4-methyl-1H-tetrazol-5(4H)-one;

Compound 52: 1-(5-(5-fluoro-4-(octahydro-5,5-dimethylindolizin-7-ylamino)pyrimidin-2-ylamino)-2-(tetrahydro-2H-pyran-4-yloxy)phenyl)-4-methyl-1H-tetrazol-5(4H)-one;

Compound 53: (±)-N$^2$-(4-cyclopropyl-2-fluoro-5-(1H-tetrazol-1-yl)phenyl)-5-fluoro-n$^4$-(octahydro-5,5-dimethylindolizin-7-yl)pyrimidine-2,4-diamine;

Compounds 54 and 55: (±)-N$^2$-(4-cyclopropyl-2-fluoro-5-(1H-tetrazol-1-yl)phenyl)-5-fluoro-n$^4$-(octahydro-5,5-dimethylindolizin-7-yl)pyrimidine-2,4-diamine;

Compound 56: (±)-2-(4-cyclopropyl-2-fluoro-5-(1H-tetrazol-1-yl)phenylamino)-4-(octahydro-5,5-dimethylindolizin-7-ylamino)pyrimidine-5-carbonitrile;

Compound 57: 2-((R)-tetrahydrofuran-3-yloxy)-5-(5-fluoro-4-(octahydro-5,5-dimethylindolizin-7-ylamino)pyrimidin-2-ylamino)benzonitrile;

Compounds 58-59: 2-((R)-tetrahydrofuran-3-yloxy)-5-(5-fluoro-4-(octahydro-5,5-dimethylindolizin-7-ylamino)pyrimidin-2-ylamino)benzonitrile;

Compound 60: 2-((S)-tetrahydrofuran-3-yloxy)-5-(5-fluoro-4-(octahydro-5,5-dimethylindolizin-7-ylamino)pyrimidin-2-ylamino)benzonitrile;

Compounds 61-62: 2-((S)-tetrahydrofuran-3-yloxy)-5-(5-fluoro-4-(octahydro-5,5-dimethylindolizin-7-ylamino)pyrimidin-2-ylamino)benzonitrile;

Compound 63: 5-(5-fluoro-4-(octahydro-5,5-dimethylindolizin-7-ylamino)pyrimidin-2-ylamino)-2-(oxetan-3-yloxy)benzonitrile;

Compound 64: 1-(5-(4-((2R,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 65: 1-(5-(4-((2R,7S,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 66: 4-((R/S,S/R)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile;

Compound 67: 1-(5-(4-((2S,7R,8aR)-2-fluoro-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compound 68: 1-(5-(4-((2R,7R,8aR)-2-hydroxy-octahydro-5,5-dimethylindolizin-7-ylamino)-5-fluoropyrimidin-2-ylamino)-2-cyclopropyl-4-fluorophenyl)-4-methyl-1H-tetrazol-5(4H)-one;

Compounds 69-70: 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine;

Compound 69: 1-(5-(5-Fluoro-4-(octahydro-5,5,8-trimethylindolizin-7-ylamino)pyrimidin-2-ylamino)-2-cyclopropyl-4-fluorophenyl)-4-methyl-1H-tetrazol-5(4H)-one;

Compound 70: 5-Fluoro-N2-(4-fluoro-3-(5-methyl-1H-tetrazol-1-yl)phenyl)-N4-(octahydro-5,5,8-trimethylindolizin-7-yl)pyrimidine-2,4-diamine;

Compound 76: 4-(R,S)-Octahydro-5,5-dimethylindolizin-7-ylamino)-2-(4-cyclopropyl-2-fluoro-5-(4,5-dihydro-4-methyl-5-oxotetrazol-yl)phenylamino)pyrimidine-5-carbonitrile;

Compound 91: 1-(5-(4-(((7R,8aS)-octahydro-5,5-dimethylindolizin-7-ylamino)-5-fluoropyrimidin-2-ylamino)-2-bromo-4-fluorophenyl)-4-methyl-1H-tetrazol-5(4H)-one;

Compound 92: 1-(5-(4-(((7R,8aS)-octahydro-5,5-dimethylindolizin-7-ylamino)-5-fluoropyrimidin-2-ylamino)-4-fluoro-2-vinylphenyl)-4-methyl-1H-tetrazol-5(4H)-one;

Compound 93: 1-(5-(4-(((7R,8aS)-octahydro-5,5-dimethylindolizin-7-ylamino)-5-fluoropyrimidin-2-ylamino)-4-fluoro-2-(2-hydroxyethyl)phenyl)-4-methyl-1H-tetrazol-5(4H)-one;

Compound 94: 1-(5-(4-(((7R,8aS)-octahydro-5,5-dimethylindolizin-7-ylamino)-5-fluoropyrimidin-2-ylamino)-4-fluoro-2-(1-hydroxyethyl)phenyl)-4-methyl-1H-tetrazol-5(4H)-one;

Compound 95: 1-(5-(4-(((7R,8aS)-octahydro-5,5-dimethylindolizin-7-ylamino)-5-fluoropyrimidin-2-ylamino)-2-ethyl-4-fluorophenyl)-4-methyl-1H-tetrazol-5(4H)-one;

Compound 96: 1-(5-(4-(((7R,8aS)-octahydro-5,5-dimethylindolizin-7-ylamino)-5-fluoropyrimidin-2-ylamino)-4-fluoro-2-(3-hydroxyprop-1-ynyl)phenyl)-4-methyl-1H-tetrazol-5(4H)-one;

Compound 97: 1-(5-(4-(((7R,8aS)-octahydro-5,5-dimethylindolizin-7-ylamino)-5-fluoropyrimidin-2-ylamino)-4-fluoro-2-(3-hydroxypropyl)phenyl)-4-methyl-1H-tetrazol-5(4H)-one;

Compound 98: 4-(4-(((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)benzonitrile;

Compound 99: 1-(2-((R)-1-hydroxypropan-2-yloxy)-5-(4-((7R,8aS)-octahydro-5,5-dimethylindolizin-7-ylamino)-5-fluoropyrimidin-2-ylamino)-4-fluorophenyl)-4-methyl-1H-tetrazol-5(4H)-one;

Compound 100: 5-(4-((7R,8aS)-5,5-dimethyloctahydroindolizin-7-ylamino)-5-fluoropyrimidin-2-ylamino)-2-(2-oxa-7-azaspiro[3.5]nonan-7-yl)benzonitrile;

Compound 101: 5-(4-((7R,8aS)-5,5-dimethyloctahydroindolizin-7-ylamino)-5-fluoropyrimidin-2-ylamino)-2-(2-oxa-6-azaspiro[3.3]heptan-6-yl)benzonitrile;

Compound 102: N2-(4,4-dimethyl-4H-benzo[b]tetrazolo[1,5-d][1,4]oxazin-8-yl)-N4-((7S,8aR)-5,5-dimethyl-octahydroindolizin-7-yl)-5-fluoropyrimidine-2,4-diamine;

Compound 103: 5-((4-(((7R,8aS)-5,5-Dimethyloctahydroindolizin-7-yl)amino)-5-fluoropyrimidin-2-yl)amino)-2-(4-(methylsulfonyl)piperazin-1-yl)benzonitrile;

Compound 104: 4-(cyclopropylmethyl)-7-((4-(((7R,8aS)-5,5-dimethyloctahydroindolizin-7-yl)amino)-5-fluoropyrimidin-2-yl)amino)-2H-benzo[b][1,4]oxazin-3(4H)-one;

Compound 105: 4-(cyclopropylmethyl)-7-((4-(((7R,8aS)-5,5-dimethyloctahydroindolizin-7-yl)amino)-5-fluoropyrimidin-2-yl)amino)-2,2-dimethyl-2H-benzo[b][1,4]oxazin-3(4H)-one;

Compound 106: 5-((4-(((7R,8aS)-5,5-dimethyloctahydroindolizin-7-yl)amino)-5-fluoropyrimidin-2-yl)amino)-2-morpholinobenzonitrile;

Compound 107: 5-((4-(((7R,8aS)-5,5-dimethyloctahydroindolizin-7-yl)amino)-5-fluoropyrimidin-2-yl)amino)-2-(4-hydroxypiperidin-1-yl)benzonitrile;

Compound 108: 5-((4-(((7R,8aS)-5,5-dimethyloctahydroindolizin-7-yl)amino)-5-fluoropyrimidin-2-yl)amino)-2-(4-methylpiperazin-1-yl)benzonitrile, formate salt;

Compound 109: 1-(5-((4-(((7R,8aS)-5,5-dimethyloctahydroindolizin-7-yl)amino)-5-fluoropyrimidin-2-yl)amino)-4-fluoro-2-(((R)-tetrahydrofuran-3-yl)oxy)phenyl)-4-methyl-1,4-dihydro-5H-tetrazol-5-one;

Compound 110: 1-(5-((4-(((7R,8aS)-5,5-dimethyloctahydroindolizin-7-yl)amino)-5-fluoropyrimidin-2-yl)amino)-4-fluoro-2-(((S)-tetrahydrofuran-3-yl)oxy)phenyl)-4-methyl-1,4-dihydro-5H-tetrazol-5-one;

Compound 111: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-(((R)-tetrahydrofuran-3-yl)oxy)phenyl)amino)pyrimidine-5-carbonitrile;

Compound 112: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-(((S)-tetrahydrofuran-3-yl)oxy)phenyl)amino)pyrimidine-5-carbonitrile;

Compound 113: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-(oxetan-3-yloxy)phenyl)amino)pyrimidine-5-carbonitrile;

Compound 114: 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)oxy)phenyl)-4-methyl-1,4-dihydro-5H-tetrazol-5-one;

Compound 115: 4-(((7R,8aS)-5,5-dimethyloctahydroindolizin-7-yl)amino)-2-((2-fluoro-5-(4-methyl-5-oxo-4,5-dihydro-1H-tetrazol-1-yl)-4-((tetrahydro-2H-pyran-4-yl)oxy)phenyl)amino)pyrimidine-5-carbonitrile;

Compound 116: 5-((4-(((7R,8aS)-5,5-dimethyloctahydroindolizin-7-yl)amino)-5-fluoropyrimidin-2-yl)amino)-2-(4-(oxetan-3-yl)piperazin-1-yl)benzonitrile;

Compound 117: 1-(5-((4-(((7R,8aS)-5,5-dimethyloctahydroindolizin-7-yl)amino)-5-fluoropyrimidin-2-yl)amino)-2-(4-(oxetan-3-yl)piperazin-1-yl)phenyl)-4-methyl-1,4-dihydro-5H-tetrazol-5-one;

Compound 118: $N^4$-((7R,8aS)-5,5-dimethyloctahydroindolizin-7-yl)-5-fluoro-$N^2$-(4-(piperidin-4-yloxy)-3-(trifluoromethyl)phenyl)pyrimidine-2,4-diamine;

Compound 119: $N^4$-((7R,8aS)-5,5-dimethyloctahydroindolizin-7-yl)-5-fluoro-$N^2$-(4-(((3R,4R)-3-fluoropiperidin-4-yl)oxy)-3-(trifluoromethyl)phenyl)pyrimidine-2,4-diamine;

Compound 120: $N^4$-((7R,8aS)-5,5-dimethyloctahydroindolizin-7-yl)-5-fluoro-$N^2$-(4-((1-(oxetan-3-yl)piperidin-4-yl)oxy)-3-(trifluoromethyl)phenyl)pyrimidine-2,4-diamine;

Compound 121: $N^4$-((7R,8aS)-5,5-dimethyloctahydroindolizin-7-yl)-5-fluoro-$N^2$-(4-(((3S,4S)-3-fluoropiperidin-4-yl)oxy)-3-(trifluoromethyl)phenyl)pyrimidine-2,4-diamine;

Compound 122: $N^4$-((7R,8aS)-5,5-dimethyloctahydroindolizin-7-yl)-5-fluoro-$N^2$-(4-(((3R,4R)-3-fluoro-1-(oxetan-3-yl)piperidin-4-yl)oxy)-3-(trifluoromethyl)phenyl)pyrimidine-2,4-diamine;

Compound 123: $N^2$-(3-chloro-4-(((3S,4S)-3-fluoropiperidin-4-yl)oxy)phenyl)-$N^4$-((7R,8aS)-5,5-dimethyloctahydroindolizin-7-yl)-5-fluoropyrimidine-2,4-diamine;

Compound 124: 4-(2-chloro-4-((4-(((7R,8aS)-5,5-dimethyloctahydroindolizin-7-yl)amino)-5-fluoropyrimidin-2-yl)amino)phenoxy)piperidin-3-ol;

Compound 125: 8-((4-(((7R,8aS)-5,5-dimethyloctahydroindolizin-7-yl)amino)-5-fluoropyrimidin-2-yl)amino)-4H-benzo[b]tetrazolo[1,5-d][1,4]oxazine-4,4-diyl)dimethanol;

Compound 126: 9-(4-((7R,8aS)-5,5-dimethyloctahydroindolizin-7-ylamino)-5-fluoropyrimidin-2-ylamino)-4-methyl-4,5-dihydrobenzo[b]tetrazolo[1,5-d][1,4]oxazepin-4-ol;

Compound 127: 9-((4-(((7R,8aS)-5,5-dimethyloctahydroindolizin-7-yl)amino)-5-fluoropyrimidin-2-yl)amino)-4-methyl-4,5-dihydrobenzo[b]tetrazolo[1,5-d][1,4]oxazepin-4-ol;

Compound 128: $N^2$-(3-(difluoromethoxy)-4-(piperidin-4-yloxy)phenyl)-$N^4$-((7R,8aS)-5,5-dimethyloctahydroindolizin-7-yl)-5-fluoropyrimidine-2,4-diamine;

Compound 129: 2-(2-(5-cyclopropyl-1H-tetrazol-1-yl)-4-((4-(((7R,8aS)-5,5-dimethyloctahydroindolizin-7-yl)amino)-5-fluoropyrimidin-2-yl)amino)phenoxy)ethan-1-ol;

Compound 130: 2-(4-((4-(((7R,8aS)-5,5-dimethyloctahydroindolizin-7-yl)amino)-5-fluoropyrimidin-2-yl)amino)-2-fluorophenoxy)ethan-1-ol;

Compound 131: 2-(4-((4-(((7R,8aS)-5,5-dimethyloctahydroindolizin-7-yl)amino)-5-fluoropyrimidin-2-yl)amino)-2-(trifluoromethyl)phenoxy)ethan-1-ol;

Compound 132: 1-(5-((4-(((7R,8aS)-5,5-dimethyloctahydroindolizin-7-yl)amino)-5-fluoropyrimidin-2-yl)amino)-2-(2-hydroxyethoxy)phenyl)-4-methyl-1,4-dihydro-5H-tetrazol-5-one;

Compound 133: 2-(2-chloro-4-((4-(((7R,8aS)-5,5-dimethyloctahydroindolizin-7-yl)amino)-5-fluoropyrimidin-2-yl)amino)phenoxy)ethan-1-ol;

Compound 134: 2-(4-((4-(((7R,8aS)-5,5-dimethyloctahydroindolizin-7-yl)amino)-5-fluoropyrimidin-2-yl)amino)-2-(methyl)phenoxy)ethan-1-ol;

Compound 135: 1-(5-((4-(((7R,8aS)-5,5-dimethyloctahydroindolizin-7-yl)amino)-5-fluoropyrimidin-2-yl)amino)-2-(((S)-1-hydroxypropan-2-yl) oxy)phenyl)-4-methyl-1,4-dihydro-5H-tetrazol-5-one;

Compound 136: N2-(4,4-dimethyl-4H-benzo[b]tetrazolo[1,5-d][1,4]oxazin-8-yl)-N4-((7R,8aS)-5,5-dimethyl-octahydroindolizin-7-yl)-5-fluoropyrimidine-2,4-diamine;

Compound 137: N4-((7R,8aS)-5,5-dimethyloctahydroindolizin-7-yl)-5-fluoro-N2-(2',3',5',6'-tetrahydrospiro[benzo[b]tetrazolo[1,5-d][1,4]oxazine-4,4'-pyran]-8-yl)pyrimidine-2,4-diamine, formate salt;

Compound 138: 5-(4-(((7R,8aS)-octahydro-5,5-dimethylindolizin-7-ylamino)-5-fluoropyrimidin-2-ylamino)-2-(4-isopropylpiperazin-1-yl)benzonitrile;

Compound 139: 1-(5-(4-(((7R,8aS)-5,5-dimethyloctahydroindolizin-7-yl)(2-hydroxy-2-methylpropyl)amino)-5-fluoropyrimidin-2-ylamino)-4-fluoro-2-(2-hydroxy-2-methylpropoxy)phenyl)-4-methyl-1H-tetrazol-5(4H)-one;

Compound 140: N4-((7R,8aS)-5,5-dimethyloctahydroindolizin-7-yl)-5-fluoro-N2-(4-methoxy-3-(5-methyl-1H-tetrazol-1-yl)phenyl)pyrimidine-2,4-diamine, bis-formate salt;

Compound 141: N4-((7R,8aS)-5,5-dimethyloctahydroindolizin-7-yl)-5-fluoro-N2-(4-fluoro-3-(5-methyl-1H-tetrazol-1-yl)phenyl)pyrimidine-2,4-diamine, bis-formate salt;

Compound 142: N4-((7R,8aS)-5,5-dimethyloctahydroindolizin-7-yl)-5-fluoro-N2-(2-fluoro-5-(5-methyl-1H-tetrazol-1-yl)phenyl)pyrimidine-2,4-diamine, formate salt;

Compound 143: N2-(3-(5-cyclopropyl-1H-tetrazol-1-yl)-4-fluorophenyl)-N4-((7R,8aS)-5,5-dimethyloctahydroindolizin-7-yl)-5-fluoropyrimidine-2,4-diamine, bis-formate salt;

Compound 144: N2-(5-(5-cyclopropyl-1H-tetrazol-1-yl)-2-fluorophenyl)-N4-((7R,8aS)-5,5-dimethyloctahydroindolizin-7-yl)-5-fluoropyrimidine-2,4-diamine, bis-formate salt;

Compound 145: N2-(4-chloro-3-(5-cyclopropyl-1H-tetrazol-1-yl)phenyl)-N4-((7R,8aS)-5,5-dimethyloctahydroindolizin-7-yl)-5-fluoropyrimidine-2,4-diamine, bis-formate salt;

Compound 146: 5-chloro-N2-(4-cyclopropyl-2-fluoro-5-(1H-tetrazol-1-yl)phenyl)-N4-((7R,8aS)-5,5-dimethyloctahydroindolizin-7-yl)pyrimidine-2,4-diamine, bis-formate salt;

Compound 147: 5-chloro-N4-((7R,8aS)-5,5-dimethyloctahydroindolizin-7-yl)-N2-(4-methyl-3-(1H-tetrazol-1-yl)phenyl)pyrimidine-2,4-diamine, bis-formate salt;

Compound 148: 1-(5-((5-chloro-4-(((7R,8aS)-5,5-dimethyloctahydroindolizin-7-yl)amino)pyrimidin-2-yl)amino)-2-cyclopropyl-4-fluorophenyl)-4-methyl-1,4-dihydro-5H-tetrazol-5-one, formate salt;

Compound 149: 5-chloro-N4-((7R,8aS)-5,5-dimethyloctahydroindolizin-7-yl)-N2-(4-fluoro-3-(5-methyl-1H-tetrazol-1-yl)phenyl)pyrimidine-2,4-diamine, bis-formate salt;

Compound 150: 5-chloro-N4-((7R,8aS)-5,5-dimethyloctahydroindolizin-7-yl)-N2-(2-fluoro-5-(5-methyl-1H-tetrazol-1-yl)phenyl)pyrimidine-2,4-diamine, bis-formate salt;

Compound 151: 5-chloro-N4-((7R,8aS)-5,5-dimethyloctahydroindolizin-7-yl)-N2-(4-methoxy-3-(5-methyl-1H-tetrazol-1-yl)phenyl)pyrimidine-2,4-diamine, bis-formate salt;

Compound 152: 5-chloro-N4-((7R,8aS)-5,5-dimethyloctahydroindolizin-7-yl)-N2-(3-methoxy-5-(5-methyl-1H-tetrazol-1-yl)phenyl)pyrimidine-2,4-diamine, bis-formate salt;

Compound 153: 3-((5-chloro-4-(((7R,8aS)-5,5-dimethyloctahydroindolizin-7-yl)amino)pyrimidin-2-yl)amino)benzonitrile;

Compound 154: 5-((5-chloro-4-(((7R,8aS)-5,5-dimethyloctahydroindolizin-7-yl)amino)pyrimidin-2-yl)amino)-2-methylbenzonitrile;

Compound 155: 5-((5-chloro-4-(((7R,8aS)-5,5-dimethyloctahydroindolizin-7-yl)amino)pyrimidin-2-yl)amino)-2-cyclopropylbenzonitrile;

Compound 156: N4-((7R,8aS)-5,5-dimethyloctahydroindolizin-7-yl)-5-fluoro-N2-(3,4,5-trimethoxyphenyl)pyrimidine-2,4-diamine;

Compound 157: N2-(2,2-dimethylbenzo[d][1,3]dioxol-5-yl)-N4-((7R,8aS)-5,5-dimethyloctahydroindolizin-7-yl)-5-fluoropyrimidine-2,4-diamine;

Compound 158: 1-(5-((4-(((7R,8aS)-5,5-dimethyloctahydroindolizin-7-yl)amino)-5-fluoropyrimidin-2-yl)amino)-4-fluoro-2-(2-methoxyethoxy)phenyl)-4-methyl-1,4-dihydro-5H-tetrazol-5-one;

Compound 159: 1-(5-((4-(((7R,8aS)-5,5-dimethyloctahydroindolizin-7-yl)amino)-5-fluoropyrimidin-2-yl)amino)-4-fluoro-2-((3-methyloxetan-3-yl)methoxy)phenyl)-4-methyl-1,4-dihydro-5H-tetrazol-5-one;

Compound 160: N4-((7R,8aS)-5,5-dimethyloctahydroindolizin-7-yl)-5-fluoro-N2-(2-fluoro-3,4-bis(2-methoxyethoxy)phenyl)pyrimidine-2,4-diamine, bis-TFA salt;

Compound 161: N2-(3,5-dimethoxyphenyl)-N4-((7R,8aS)-5,5-dimethyloctahydroindolizin-7-yl)-5-fluoropyrimidine-2,4-diamine, bis-TFA salt;

Compound 162: 5-chloro-N2-(3,5-dimethoxyphenyl)-N4-((7R,8aS)-5,5-dimethyloctahydroindolizin-7-yl)pyrimidine-2,4-diamine, bis-TFA salt;

Compound 163: 5-chloro-N2-(3-(5-cyclopropyl-1H-tetrazol-1-yl)-4-fluorophenyl)-N4-((7R,8aS)-5,5-dimethyloctahydroindolizin-7-yl)pyrimidine-2,4-diamine, bis-TFA salt;

Compound 164: 5-chloro-N2-(5-(5-cyclopropyl-1H-tetrazol-1-yl)-2-fluorophenyl)-N4-((7R,8aS)-5,5-dimethyloctahydroindolizin-7-yl)pyrimidine-2,4-diamine, bis-formate salt;

Compound 165: 1-(5-((4-(((7R,8aS)-5,5-dimethyloctahydroindolizin-7-yl)amino)-5-fluoropyrimidin-2-yl)amino)-4-fluoro-2-((3-(hydroxymethyl)oxetan-3-yl)methoxy)phenyl)-4-methyl-1,4-dihydro-5H-tetrazol-5-one, bis-formate salt;

Compound 166: 1-(5-((4-(((7R,8aS)-5,5-dimethyloctahydroindolizin-7-yl)amino)-5-fluoropyrimidin-2-yl)amino)-4-fluoro-2-(oxetan-3-ylmethoxy)phenyl)-4-methyl-1,4-dihydro-5H-tetrazol-5-one, bis-formate salt;

Compound 167: 1-(5-((4-(((7R,8aS)-5,5-dimethyloctahydroindolizin-7-yl)amino)-5-fluoropyrimidin-2-yl)amino)-4-fluoro-2-(oxetan-2-ylmethoxy)phenyl)-4-methyl-1,4-dihydro-5H-tetrazol-5-one, bis-formate salt;

Compound 168: 5-((4-(((7R,8aS)-5,5-dimethyloctahydroindolizin-7-yl)amino)-5-fluoropyrimidin-2-yl)amino)-2-hydroxybenzonitrile;

Compound 169: 1-(2-((1,4-dioxan-2-yl)methoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, bis-TFA salt;

Compound 170: 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)methoxy)phenyl)-4-methyl-1,4-dihydro-5H-tetrazol-5-one, bis-TFA salt;

Compound 171: 3-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)-2-oxopropanoic acid, bis-TFA salt;

Compound 172: 5-((4-(((7R,8aS)-5,5-dimethyloctahydroindolizin-7-yl)amino)-5-fluoropyrimidin-2-yl)amino)-2-(2-methoxyethoxy)benzonitrile;

Compound 173: 5-(4-((7R,8aS)-5,5-dimethyloctahydroindolizin-7-ylamino)-5-fluoropyrimidin-2-ylamino)-2-((3-methyloxetan-3-yl)methoxy)benzonitrile;

Compound 174: 5-(4-((7R,8aS)-5,5-dimethyloctahydroindolizin-7-ylamino)-5-fluoropyrimidin-2-ylamino)-2-((3-(hydroxymethyl)oxetan-3-yl)methoxy)benzonitrile;

Compound 175: 5-(4-((7R,8aS)-5,5-dimethyloctahydroindolizin-7-ylamino)-5-fluoropyrimidin-2-ylamino)-2-(oxetan-3-ylmethoxy)benzonitrile;

Compound 176: 5-(4-((7R,8aS)-5,5-dimethyloctahydroindolizin-7-ylamino)-5-fluoropyrimidin-2-ylamino)-2-(oxetan-2-ylmethoxy)benzonitrile;

Compound 177: 2-((1,4-dioxan-2-yl)methoxy)-5-(4-((7R,8aS)-5,5-dimethyloctahydroindolizin-7-ylamino)-5-fluoropyrimidin-2-ylamino)benzonitrile;

Compound 178: 5-(4-(((7R,8aS)-5,5-dimethyloctahydroindolizin-7-ylamino)-5-fluoropyrimidin-2-ylamino)-2-((tetrahydro-2H-pyran-4-yl)methoxy)benzonitrile;

Compound 179: 5-(4-(((7R,8aS)-5,5-dimethyloctahydroindolizin-7-ylamino)-5-fluoropyrimidin-2-ylamino)-2-(oxetan-3-yloxy)benzonitrile, formate salt;

Compound 180: 2-bromo-5-((4-(((7R,8aS)-5,5-dimethyloctahydroindolizin-7-yl)amino)-5-fluoropyrimidin-2-yl)amino)benzonitrile;

Compound 181: 5-((5-chloro-4-(((7R,8aS)-5,5-dimethyloctahydroindolizin-7-yl)amino)pyrimidin-2-yl)amino)-2-cyclopropyl-4-fluorobenzonitrile;

Compound 182: 5-chloro-N2-(4-chloro-3-(5-cyclopropyl-1H-tetrazol-1-yl)phenyl)-N4-((7R,8aS)-5,5-dimethyloctahydroindolizin-7-yl)pyrimidine-2,4-diamine;

Compound 183: 5-chloro-N4-((7R,8aS)-5,5-dimethyloctahydroindolizin-7-yl)-N2-(3,4,5-trimethoxyphenyl)pyrimidine-2,4-diamine;

Compound 184: ethyl 2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)propanoate;

Compound 185: 1-(5-((4-(((7R,8aS)-5,5-dimethyloctahydroindolizin-7-yl)amino)-5-fluoropyrimidin-2-yl)amino)-4-fluoro-2-((2-oxotetrahydrofuran-3-yl)oxy)phenyl)-4-methyl-1,4-dihydro-5H-tetrazol-5-one, formate salt;

Compound 186: 1-(5-((4-(((7R,8aS)-5,5-dimethyloctahydroindolizin-7-yl)amino)-5-fluoropyrimidin-2-yl)amino)-4-fluoro-2-(2-hydroxyethoxy)phenyl)-4-methyl-1,4-dihydro-5H-tetrazol-5-one, formate salt;

Compound 187: 1-(5-((4-(((7R,8aS)-5,5-dimethyloctahydroindolizin-7-yl)amino)-5-fluoropyrimidin-2-yl)amino)-4-fluoro-2-((tetrahydro-2H-pyran-4-yl)methoxy)phenyl)-4-methyl-1,4-dihydro-5H-tetrazol-5-one, TFA salt;

Compound 188: 1-(2-((R)-2,3-dihydroxypropoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, TFA salt;

Compound 189: 5-((4-(((7R,8aS)-5,5-dimethyloctahydroindolizin-7-yl)amino)-5-fluoropyrimidin-2-yl)amino)-2-(2-hydroxyethoxy)benzonitrile, formate salt;

Compound 190: 5-((4-(((7R,8aS)-5,5-dimethyloctahydroindolizin-7-yl)amino)-5-fluoropyrimidin-2-yl)amino)-2-(2-(2-methoxyethoxy)ethoxy)benzonitrile, formate salt;

Compound 191: (3S,4R,5R)-2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)tetrahydro-2H-pyran-3,4,5-triyl triacetate;

Compound 192: 1-(2-(2-(dimethylamino)ethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 193: 1-(2-(2-(dimethylamino)ethyl)(2-(dimethylamino)ethyl)(4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 194: 1-(2-(2-(diethylamino)ethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, TFA salt;

Compound 195: 1-(5-((4-(((7R,8aS)-5,5-dimethyloctahydroindolizin-7-yl)amino)-5-fluoropyrimidin-2-yl)amino)-4-fluoro-2-(2-morpholinoethoxy)phenyl)-4-methyl-1,4-dihydro-5H-tetrazol-5-one;

Compound 196: 4-((4-(((7R,8aS)-5,5-dimethyloctahydroindolizin-7-yl)amino)-5-fluoropyrimidin-2-yl)amino)-2-(1H-tetrazol-1-yl)phenol;

Compound 197: (3S,4R,5R)-2-(2-cyano-44(4-(((7R,8aS)-5,5-dimethyloctahydroindolizin-7-yl)amino)-5-fluoropyrimidin-2-yl)amino)phenoxy)tetrahydro-2H-pyran-3,4,5-triyl triacetate;

Compound 198: 1-(5-((4-(((7R,8aS)-5,5-dimethyloctahydroindolizin-7-yl)amino)-5-fluoropyrimidin-2-yl)amino)-4-fluoro-2-(2-(2-methoxyethoxy)ethoxy)phenyl)-4-methyl-1,4-dihydro-5H-tetrazol-5-one, TFA salt;

Compound 199: 1-(2-(2,3-dihydroxypropoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, bis-TFA salt;

Compound 200: 1-(5-((4-(((7R,8aS)-5,5-dimethyloctahydroindolizin-7-yl)amino)-5-fluoropyrimidin-2-yl)amino)-4-fluoro-2-(2-hydroxypropoxy)phenyl)-4-methyl-1,4-dihydro-5H-tetrazol-5-one, TFA salt;

Compound 201: 5-((4-(((7R,8aS)-5,5-dimethyloctahydroindolizin-7-yl)amino)-5-fluoropyrimidin-2-yl)amino)-2-(2-hydroxypropoxy)benzonitrile, formate salt;

Compound 202: N4-((7R,8aS)-5,5-dimethyloctahydroindolizin-7-yl)-5-fluoro-N2-(4-(2-methoxyethoxy)-3-(1H-tetrazol-1-yl)phenyl)pyrimidine-2,4-diamine, formate salt;

Compound 203: N4-((7R,8aS)-5,5-dimethyloctahydroindolizin-7-yl)-5-fluoro-N2-(4-((3-methyloxetan-3-yl)methoxy)-3-(1H-tetrazol-1-yl)phenyl)pyrimidine-2,4-diamine, formate salt;

Compound 204: (3-((4-((4-(((7R,8aS)-5,5-dimethyloctahydroindolizin-7-yl)amino)-5-fluoropyrimidin-2-yl)amino)-2-(1H-tetrazol-1-yl)phenoxy)methyl)oxetan-3-yl)methanol, formate salt;

Compound 205: 2-(4-((4-(((7R,8aS)-5,5-dimethyloctahydroindolizin-7-yl)amino)-5-fluoropyrimidin-2-yl)amino)-2-(1H-tetrazol-1-yl)phenoxy)ethan-1-ol;

Compound 206: 1-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-2-ol, formate salt;

Compound 207: N4-((7R,8aS)-5,5-dimethyloctahydroindolizin-7-yl)-5-fluoro-N2-(4-(2-(2-methoxyethoxy)ethoxy)-3-(1H-tetrazol-1-yl)phenyl)pyrimidine-2,4-diamine;

Compound 208: 4-((4-(((7R,8aS)-5,5-dimethyloctahydroindolizin-7-yl)amino)-5-fluoropyrimidin-2-yl)amino)-2-methoxyphenol;

Compound 209: 5-((4-(((7R,8aS)-5,5-dimethyloctahydroindolizin-7-yl)amino)-5-fluoropyrimidin-2-yl)amino)-2-(3,3,3-trifluoro-2-hydroxy-2-(trifluoromethyl)propoxy)benzonitrile, formate salt;

Compound 210: 5-((4-(((7R,8aS)-5,5-dimethyloctahydroindolizin-7-yl)amino)-5-fluoropyrimidin-2-yl)amino)-2-(2-hydroxyethoxy-1,1,2,2-d4)benzonitrile, formate salt;

Compound 211: 2-(2,3-dihydroxypropoxy)-5-((4-((2,3-dihydroxypropyl)((7R,8aS)-5,5-dimethyloctahydroindolizin-7-yl)amino)-5-fluoropyrimidin-2-yl)amino) benzonitrile, TFA salt;

Compound 212: 2-(2,3-dihydroxypropoxy)-5-((4-((((7R,8aS)-5,5-dimethyloctahydroindolizin-7-yl)amino)-5-fluoropyrimidin-2-yl)amino)benzonitrile, TFA salt;

Compound 213: 5-((4-(((7R,8aS)-5,5-dimethyloctahydroindolizin-7-yl)amino)-5-fluoropyrimidin-2-yl)amino)-2-(3-hydroxypropoxy)benzonitrile, TFA salt;

Compound 214: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propane-1,2-diol, TFA salt;

Compound 215: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol, TFA salt;

Compound 216: 2-(4-((4-(((7R,8aS)-5,5-dimethyloctahydroindolizin-7-yl)amino)-5-fluoropyrimidin-2-yl)amino)-2-methoxyphenoxy)ethan-1-ol;

Compound 217: 2-(4-((4-(((7R,8aS)-5,5-dimethyloctahydroindolizin-7-yl)amino)-5-fluoropyrimidin-2-yl)amino)-2-methoxyphenoxy)ethan-1,1,2,2-d4-1-ol;

Compound 218: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol;

Compound 219: 5-((4-(((7R,8aS)-5,5-dimethyloctahydroindolizin-7-yl)amino)-5-fluoropyrimidin-2-yl)amino)-2-(2-hydroxyethoxy-1,1,2,2-d4)benzonitrile;

Compound 220: 1-(5-((4-(((7R,8aS)-5,5-dimethyloctahydroindolizin-7-yl)amino)-5-fluoropyrimidin-2-yl)amino)-4-fluoro-2-(2-hydroxypropoxy)phenyl)-4-methyl-1,4-dihydro-5H-tetrazol-5-one;

Compound 221: 1-(5-((4-(((7R,8aS)-5,5-dimethyloctahydroindolizin-7-yl)amino)-5-fluoropyrimidin-2-yl)amino)-4-fluoro-2-(2-hydroxyethoxy-1,1,2,2-d4)phenyl)-4-methyl-1,4-dihydro-5H-tetrazol-5-one;

Compound 222: 1-(5-((4-(((7R,8aS)-5,5-dimethyloctahydroindolizin-7-yl)amino)-5-fluoropyrimidin-2-yl)amino)-4-fluoro-2-((R)-3-hydroxy-2-methylpropoxy)phenyl)-4-methyl-1,4-dihydro-5H-tetrazol-5-one;

Compound 223: 2-(4-((5-chloro-4-(((7R,8aS)-5,5-dimethyloctahydroindolizin-7-yl)amino)pyrimidin-2-yl)amino)-2-(1H-tetrazol-1-yl)phenoxy)ethan-1-ol;

Compound 224: 3-(4-((4-(((7R,8aS)-5,5-dimethyloctahydroindolizin-7-yl)amino)-5-fluoropyrimidin-2-yl)amino)-2-(1H-tetrazol-1-yl)phenoxy)propan-1-ol, formate salt;

Compound 225: 1-(2-(3-(benzyloxy)cyclobutoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 226: tert-butyl (2-(4-((4-(((7R,8aS)-5,5-dimethyloctahydroindolizin-7-yl)amino)-5-fluoropyrimidin-2-yl)amino)-5-fluoro-2-(4-methyl-5-oxo-4,5-dihydro-1H-tetrazol-1-yl)phenoxy)ethyl)carbamate;

Compound 227: 1-(5-((4-(((7R,8aS)-5,5-dimethyloctahydroindolizin-7-yl)amino)-5-fluoropyrimidin-2-yl)amino)-4-fluoro-2-(3-hydroxycyclobutoxy)phenyl)-4-methyl-1,4-dihydro-5H-tetrazol-5-one;

Compound 228: 1-(2-(2-aminoethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one;

Compound 229: 5-((5-chloro-4-(((7R,8aS)-5,5-dimethyloctahydroindolizin-7-yl)amino)pyrimidin-2-yl)amino)-2-(2-hydroxypropoxy)benzonitrile, formate salt;

Compound 230: 1-(5-((4-(((7R,8aS)-5,5-dimethyloctahydroindolizin-7-yl)amino)-5-fluoropyrimidin-2-yl)amino)-4-fluoro-2-(3,3,3-trifluoro-2-hydroxypropoxy)phenyl)-4-methyl-1,4-dihydro-5H-tetrazol-5-one, formate salt;

Compound 231: 1-(2-(2-aminoethoxy)-5-((4-(((7R,8aS)-5,5-dimethyloctahydroindolizin-7-yl)amino)-5-fluoropyrimidin-2-yl)amino)-4-fluorophenyl)-4-methyl-1,4-dihydro-5H-tetrazol-5-one, formate salt;

Compound 232: 1-(5-((5-chloro-4-(((7R,8aS)-5,5-dimethyloctahydroindolizin-7-yl)amino)pyrimidin-2-yl)amino)-4-fluoro-2-hydroxyphenyl)-4-methyl-1,4-dihydro-5H-tetrazol-5-one;

Compound 233: 1-(5-((4-(((7R,8aS)-5,5-dimethyloctahydroindolizin-7-yl)amino)-5-fluoropyrimidin-2-yl)amino)-4-fluoro-2-((S)-2-methoxypropoxy)phenyl)-4-methyl-1,4-dihydro-5H-tetrazol-5-one;

Compound 234: 1-(5-((4-(((7R,8aS)-5,5-dimethyloctahydroindolizin-7-yl)((S)-2-methoxypropyl)amino)-5-fluoropyrimidin-2-yl)amino)-4-fluoro-2-((S)-2-methoxypropoxy)phenyl)-4-methyl-1,4-dihydro-5H-tetrazol-5-one;

Compound 235: 1-(5-((5-chloro-4-(((7R,8aS)-5,5-dimethyloctahydroindolizin-7-yl)amino)pyrimidin-2-yl)amino)-4-fluoro-2-((S)-2-hydroxypropoxy)phenyl)-4-methyl-1,4-dihydro-5H-tetrazol-5-one, formate salt;

Compound 236: 1-(5-((5-chloro-4-(((7R,8aS)-5,5-dimethyloctahydroindolizin-7-yl)amino)pyrimidin-2-yl)amino)-4-fluoro-2-(2-hydroxypropoxy)phenyl)-4-methyl-1,4-dihydro-5H-tetrazol-5-one, formate salt, mixture of diastereomers;

Compound 237: 1-(5-((5-chloro-4-(((7R,8aS)-5,5-dimethyloctahydroindolizin-7-yl)amino)pyrimidin-2-yl)amino)-4-fluoro-2-(2-hydroxyethoxy)phenyl)-4-methyl-1,4-dihydro-5H-tetrazol-5-one, formate salt;

Compound 238: 1-(5-((5-chloro-4-(((7R,8aS)-5,5-dimethyloctahydroindolizin-7-yl)amino)pyrimidin-2-yl)amino)-4-fluoro-2-((S)-2-methoxypropoxy)phenyl)-4-methyl-1,4-dihydro-5H-tetrazol-5-one, formate salt;

Compound 239: 1-(5-((5-chloro-4-(((7R,8aS)-5,5-dimethyloctahydroindolizin-7-yl)((S)-2-methoxypropyl)amino)pyrimidin-2-yl)amino)-4-fluoro-2-((S)-2-methoxypropoxy)phenyl)-4-methyl-1,4-dihydro-5H-tetrazol-5-one, formate salt;

Compound 240: 1-(5-((5-chloro-4-(((7R,8aS)-5,5-dimethyloctahydroindolizin-7-yl)amino)pyrimidin-2-yl)amino)-4-fluoro-2-(2-hydroxy-2-methylpropoxy)phenyl)-4-methyl-1,4-dihydro-5H-tetrazol-5-one;

Compound 241: 5-fluoro-N2-(2-fluoro-5-methoxy-3-(5-methyl-1H-tetrazol-1-yl)phenyl)-N4-((7R,8aS)-octahydro-5,5-dimethylindolizin-7-yl)pyrimidine-2,4-diamine, TFA salt;

Compound 242: 5-fluoro-N2-(2-fluoro-3-methoxy-5-(5-methyl-1H-tetrazol-1-yl)phenyl)-N4-((7R,8aS)-octahydro-5,5-dimethylindolizin-7-yl)pyrimidine-2,4-diamine, TFA salt;

Compound 243: 5-fluoro-N2-(2,6-difluoro-3-methoxy-5-(5-methyl-1H-tetrazol-1-yl)phenyl)-N4-((7R,8aS)-octahydro-5,5-dimethylindolizin-7-yl)pyrimidine-2,4-diamine, TFA salt;

Compound 248: 5-fluoro-N2-(1H-2,4-dihydron-2,4,4-trimethyl-[1,2,4]triazolo[3,4-c][1,4]benzoxazin-1-one- Compound 248: ... 8-yl)-N4-((7R,8aS)-octahydro-5,5-dimethylindolizin-7-yl)pyrimidine-2,4-diamine;

Compound 249: 5-fluoro-N2-(2-fluoro-5-(5-methyl-1H-tetrazol-1-yl)-4-(oxetan-3-yloxy)phenyl)-N4-((7R,8aS)-octahydro-5,5-dimethylindolizin-7-yl)pyrimidine-2,4-diamine;

Compound 250: 5-fluoro-N2-(1H-2,4-dihydron-4,4-dimethyl-2-(3-chloropropanol-2-yl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 251: 5-fluoro-N2-(1H-2,4-dihydron-4,4-dimethyl-2-(oxetan-3-yl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 252: 4-(4-((7R,8aS)-octahydro-5,5-dimethylindolizin-7-ylamino)-5-fluoropyrimidin-2-ylamino)-5-fluoro-2-(5-methyl-1H-tetrazol-1-yl)phenol, besylate salt;

Compound 253: N5-(4-((7R,8aS)-octahydro-5,5-dimethylindolizin-7-ylamino)-5-fluoropyrimidin-2-yl)-6-fluoro-N2-methylbenzo[d]oxazole-2,5-diamine, formate salt;

Compound 254: N5-(4-((7R,8aS)-octahydro-5,5-dimethylindolizin-7-ylamino)-5-fluoropyrimidin-2-yl)-6-fluoro-N2-methylbenzo[d]oxazole-2,5-diamine, besylate salt;

Compound 255: N2-(5-(5-cyclopropyl-1H-tetrazol-1-yl)-2-fluoro-4-(oxetan-3-yloxy)phenyl)-5-fluoro-N4-((7R,8aS)-octahydro-5,5-dimethylindolizin-7-yl)pyrimidine-2,4-diamine;

Compound 256: 4-(4-((7R,8aS)-octahydro-5,5-dimethylindolizin-7-ylamino)-5-fluoropyrimidin-2-ylamino)-2-(5-cyclopropyl-1H-tetrazol-1-yl)-5-fluorophenol, TFA salt;

Compound 257: N2-(5-(5-cyclopropyl-1H-tetrazol-1-yl)-2-fluoro-4-isopropoxyphenyl)-5-fluoro-N4-((7R,8aS)-octahydro-5,5-dimethylindolizin-7-yl)pyrimidine-2,4-diamine, TFA salt;

Compound 258: 5-fluoro-N2-(2-fluoro-5-(5-(methylamino)-1H-tetrazol-1-yl)-4-(oxetan-3-yloxy)phenyl)-N4-((7R,8aS)-octahydro-5,5-dimethylindolizin-7-yl)pyrimidine-2,4-diamine;

Compound 259: 1-(3-(4-((7R,8aS)-octahydro-5,5-dimethylindolizin-7-ylamino)-5-fluoropyrimidin-2-ylamino)phenyl)-1H-tetrazole-5-thiol, formate salt;

Compound 260: 1-(3-(4-((7R,8aS)-octahydro-5,5-dimethylindolizin-7-ylamino)-5-fluoropyrimidin-2-ylamino)phenyl)-1H-tetrazol-5(4H)-one;

Compound 261: 5-fluoro-N4-((7R,8aS)-octahydro-5,5-dimethylindolizin-7-yl)-N2-(3-(5-(methylthio)-1H-tetrazol-1-yl)phenyl)pyrimidine-2,4-diamine;

Compound 262: 5-fluoro-N4-((7R,8aS)-octahydro-5,5-dimethylindolizin-7-yl)-N2-(3-(5-(oxetan-3-ylthio)-1H-tetrazol-1-yl)phenyl)pyrimidine-2,4-diamine;

Compound 263: 2-(1-(3-(4-((7R,8aS)-octahydro-5,5-dimethylindolizin-7-ylamino)-5-fluoropyrimidin-2-ylamino)phenyl)-1H-tetrazol-5-ylthio)propane-1,3-diol;

Compound 264: 2-(1-(3-(4-((7R,8aS)-octahydro-5,5-dimethylindolizin-7-ylamino)-5-fluoropyrimidin-2-ylamino)phenyl)-1H-tetrazol-5-ylthio)-3-aminopropan-1-ol, besylate salt;

Compound 265: 1-(3-(4-((7R,8aS)-octahydro-5,5-dimethylindolizin-7-ylamino)-5-fluoropyrimidin-2-ylamino)phenyl)-4-(oxetan-3-yl)-1H-tetrazol-5(4H)-one, formate salt;

Compound 266: 2-(1-(3-(4-((7R,8aS)-octahydro-5,5-dimethylindolizin-7-ylamino)-5-fluoropyrimidin-2-ylamino)phenyl)-1H-tetrazol-5-ylthio)ethanol, besylate salt;

Compound 267: 1-(3-(4-((7R,8aS)-octahydro-5,5-dimethylindolizin-7-ylamino)-5-fluoropyrimidin-2-ylamino)phenyl)-4-(2-hydroxyethyl)-1H-tetrazol-5(4H)-one, formate salt;

Compound 268: 5-fluoro-N2-(1H-2,4-dihydron-2-(2-hydroxyethyl)-4,4-dimethyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 269: 5-fluoro-N4-((7R,8aS)-octahydro-5,5-dimethylindolizin-7-yl)-N2-(3-(5-(methylsulfonyl)-1H-tetrazol-1-yl)phenyl)pyrimidine-2,4-diamine, TFA salt;

Compound 270: 5-fluoro-N4-((7R,8aS)-octahydro-5,5-dimethylindolizin-7-yl)-N2-(3-(5-(methylsulfinyl)-1H-tetrazol-1-yl)phenyl)pyrimidine-2,4-diamine, TFA salt;

Compound 271: 2-(1-(3-(4-((7R,8aS)-octahydro-5,5-dimethylindolizin-7-ylamino)-5-fluoropyrimidin-2-ylamino)phenyl)-1H-tetrazol-5-ylthio)ethanol;

Compound 272: 1-(5-(4-((7R,8aS)-octahydro-5,5-dimethylindolizin-7-ylamino)-5-fluoropyrimidin-2-ylamino)-2-methylphenyl)-1H-tetrazol-5(4H)-one, besylate salt;

Compound 273: 1-(5-(4-((7R,8aS)-octahydro-5,5-dimethylindolizin-7-ylamino)-5-fluoropyrimidin-2-ylamino)-2-methylphenyl)-4-methyl-1H-tetrazol-5(4H)-one, HCl salt;

Compound 274: 1-(5-(4-((7R,8aS)-octahydro-5,5-dimethylindolizin-7-ylamino)-5-fluoropyrimidin-2-ylamino)-2-methylphenyl)-4-methyl-1H-tetrazol-5(4H)-one;

Compound 275: 1-(5-(4-((7R,8aS)-octahydro-5,5-dimethylindolizin-7-ylamino)-5-fluoropyrimidin-2-ylamino)-2-methylphenyl)-4-(2-hydroxyethyl)-1H-tetrazol-5(4H)-one;

Compound 276: 1-(5-(4-((7R,8aS)-octahydro-5,5-dimethylindolizin-7-ylamino)-5-fluoropyrimidin-2-ylamino)-2-methylphenyl)-4-(oxetan-3-yl)-1H-tetrazol-5(4H)-one, formate salt;

Compound 277: 1-(5-(4-((7R,8aS)-octahydro-5,5-dimethylindolizin-7-ylamino)-5-fluoropyrimidin-2-ylamino)-2-methoxyphenyl)-1H-tetrazol-5(4H)-one;

Compound 278: 1-(5-(4-((7R,8aS)-octahydro-5,5-dimethylindolizin-7-ylamino)-5-fluoropyrimidin-2-ylamino)-2-methoxyphenyl)-4-methyl-1H-tetrazol-5(4H)-one, HCl salt;

Compound 279: 1-(5-(4-((7R,8aS)-octahydro-5,5-dimethylindolizin-7-ylamino)-5-fluoropyrimidin-2-ylamino)-2-methoxyphenyl)-4-methyl-1H-tetrazol-5(4H)-one;

Compound 280: 1-(5-(4-((7R,8aS)-octahydro-5,5-dimethylindolizin-7-ylamino)-5-fluoropyrimidin-2-ylamino)-2-methoxyphenyl)-4-(2-hydroxyethyl)-1H-tetrazol-5(4H)-one;

Compound 281: 5-fluoro-N4-((7R,8aS)-octahydro-5,5-dimethylindolizin-7-yl)-N2-(4-methyl-3-(5-(methylthio)-1H-tetrazol-1-yl)phenyl)pyrimidine-2,4-diamine;

Compound 282: 2-(1-(5-(4-((7R,8aS)-octahydro-5,5-dimethylindolizin-7-ylamino)-5-fluoropyrimidin-2-ylamino)-2-methylphenyl)-1H-tetrazol-5-ylthio)ethanol;

Compound 283: 5-fluoro-N2-(1H-2,4-dihydron-spiro(2H-1,4-benzoxazine-4,4'-[4H]pyran)-2-methyl-[1,2,4]triazolo[3,4-c][1,4]benzoxazin-1-one-8-yl)-N4-((7R, 8aS)-octahydro-5,5-dimethylindolizin-7-yl)pyrimidine-2,4-diamine, TFA salt;

Compound 284: 5-fluoro-N4-((7R,8aS)-octahydro-5,5-dimethylindolizin-7-yl)-N2-(4-methoxy-3-(5-(oxetan-3-yloxy)-1H-tetrazol-1-yl)phenyl)pyrimidine-2,4-diamine, formate salt;

Compound 285: 1-(5-(4-((7R,8aS)-octahydro-5,5-dimethylindolizin-7-ylamino)-5-fluoropyrimidin-2-ylamino)-2-methoxyphenyl)-4-(oxetan-3-yl)-1H-tetrazol-5(4H)-one, formate salt;

Compound 286: 5-fluoro-N4-((7R,8aS)-octahydro-5,5-dimethylindolizin-7-yl)-N2-(4-methyl-3-(5-(methylsulfonyl)-1H-tetrazol-1-yl)phenyl)pyrimidine-2,4-diamine, TFA salt;

Compound 287: 5-fluoro-N2-(1H-2,4-dihydron-4-(hydroxymethyl)-4-(((1,1-dimethylethyl)dimethylsilyl)oxymethyl)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, besylate salt;

Compound 288: 5-fluoro-N2-(1H-2,4-dihydron-4,4-di(hydroxymethyl)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine, besylate salt;

Compound 289: 1-(5-(4-((7R,8aS)-octahydro-5,5-dimethylindolizin-7-ylamino)-5-fluoropyrimidin-2-ylamino)-2-methylphenyl)-4-(2-hydroxy-2-methylpropyl)-1H-tetrazol-5(4H)-one, formate salt;

Compound 290: 1-(5-(4-((7R,8aS)-octahydro-5,5-dimethylindolizin-7-ylamino)-5-fluoropyrimidin-2-ylamino)-2-methoxyphenyl)-4-(2-hydroxy-2-methylpropyl)-1H-tetrazol-5(4H)-one;

Compound 291: 5-fluoro-N2-(1H-2,4-dihydron-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 292: 5-fluoro-N2-(1H-2,3,4,5-tetrahydron-2,4-dimethyl-4-hydroxy-[1,2,4]triazolo[4,5-c][1,5]benzoxazepin-1-one-9-yl)-N4-((7R,8aS)-octahydro-5,5-dimethylindolizin-7-yl)pyrimidine-2,4-diamine;

Compound 293: 5-fluoro-N2-(1H-2,4-dihydron-spiro(2H-1,4-benzoxazine-4,3'-[3H]oxetan)-2-methyl-[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 294: 5-fluoro-N2-(1H-2,3,4,5-tetrahydron-2,4-dimethyl-4-hydroxy-[1,2,4]triazolo[4,5-c][1,5]benzoxazepin-1-one-9-yl)-N4-((7R,8aS)-octahydro-5,5-dimethylindolizin-7-yl)pyrimidine-2,4-diamine;

Compound 295: 5-fluoro-N2-(1H-2,3,4,5-tetrahydron-2,4-dimethyl-4-hydroxy-[1,2,4]triazolo[4,5-c][1,5]benzoxazepin-1-one-9-yl)-N4-((7R,8aS)-octahydro-5,5-dimethylindolizin-7-yl)pyrimidine-2,4-diamine;

Compound 296: 5-fluoro-N2-(1H-2,4-dihydron-2-methyl-4,4-di(methoxymethyl)[1,2,4]triazolo[3,4-c][1,4]benzoxazin-1-one-8-yl)-N4-((7R,8aS)-octahydro-5,5-dimethylindolizin-7-yl)pyrimidine-2,4-diamine;

Compound 297: N2-(3-(Difluoromethoxy)-4-morpholinophenyl)-N4-((7S,8aS)-3,3-dimethyloctahydroindolizin-7-yl)-5-fluoropyrimidine-2,4-diamine;

Compound 298: N2-(3-(Difluoromethoxy)-4-(oxetan-3-yloxy)phenyl)-N4-((7S,8aS)-3,3-dimethyloctahydroindolizin-7-yl)-5-fluoropyrimidine-2,4-diamine, formate salt;

Compound 299: N2-(3-(Difluoromethoxy)-4-methoxyphenyl)-N4-((7S,8aS)-3,3-dimethyloctahydroindolizin-7-yl)-5-fluoropyrimidine-2,4-diamine;

Compound 300: N2-(3-(Difluoromethoxy)-4-(2,6-dimethylmorpholino)phenyl)-N4-((7S,8aS)-3,3-dimethyloctahydroindolizin-7-yl)-5-fluoropyrimidine-2,4-diamine;

Compound 301: N2-(4-Cyclopropyl-2-fluoro-5-(5-(oxetan-3-yl)-1H-tetrazol-1-yl)phenyl)-N4-((7S,8aS)-3,3-dimethyloctahydroindolizin-7-yl)-5-fluoropyrimidine-2,4-diamine, formate salt;

Compound 302: N2-(3-(Difluoromethoxy)-4-(2-oxa-6-azaspiro[3.3]heptan-6-yl)phenyl)-N4-((7S,8aS)-3,3-dimethyloctahydroindolizin-7-yl)-5-fluoropyrimidine-2,4-diamine, formate salt;

Compound 303: 2-(2-(Difluoromethoxy)-4-((4-(((7S,8aS)-3,3-dimethyloctahydroindolizin-7-yl)amino)-5-fluoropyrimidin-2-yl)amino)phenoxy)ethan-1-ol, formate salt;

Compound 304: 5-((4-(((7S,8aS)-3,3-Dimethyloctahydroindolizin-7-yl)amino)-5-fluoropyrimidin-2-yl)amino)-2-(3-hydroxycyclobutoxy)benzonitrile, formate salt;

Compound 305: 3-(4-((4-(((7S,8aS)-3,3-Dimethyloctahydroindolizin-7-yl)amino)-5-fluoropyrimidin-2-yl)amino)-2-(trifluoromethyl)phenoxy)cyclobutan-1-ol, formate salt;

Compound 306: 3-(2-(Difluoromethoxy)-4-((4-(((7S,8aS)-3,3-dimethyloctahydroindolizin-7-yl)amino)-5-fluoropyrimidin-2-yl)amino)phenoxy)cyclobutan-1-ol, formate salt;

Compound 307: 3-(2-(Difluoromethoxy)-4-((4-(((7S,8aS)-3,3-dimethyloctahydroindolizin-7-yl)amino)-5-fluoropyrimidin-2-yl)amino)phenoxy)propan-1-ol, formate salt;

Compound 308: 1-(2-(Difluoromethoxy)-4-((4-(((7S,8aS)-3,3-dimethyloctahydroindolizin-7-yl)amino)-5-fluoropyrimidin-2-yl)amino)phenyl)azetidin-3-ol, formate salt;

Compound 309: 1-(5-((4-(((7S,8aS)-3,3-Dimethyloctahydroindolizin-7-yl)amino)-5-fluoropyrimidin-2-yl)amino)-2-(3-hydroxycyclobutoxy-1-d)phenyl)-4-methyl-1,4-dihydro-5H-tetrazol-5-one, formate salt;

Compound 310: N2-(4-(3-(Benzyloxy)cyclobutoxy)-3-chlorophenyl)-N4-((7S,8aS)-3,3-dimethyloctahydroindolizin-7-yl)-5-fluoropyrimidine-2,4-diamine;

Compound 311: N2-(4-(3-(benzyloxy)cyclobutoxy-1-d)-3-chlorophenyl)-N4-((7S,8aS)-3,3-dimethyloctahydroindolizin-7-yl)-5-fluoropyrimidine-2,4-diamine;

Compound 312: 3-(2-Chloro-4-((4-(((7S,8aS)-3,3-dimethyloctahydroindolizin-7-yl)amino)-5-fluoropyrimidin-2-yl)amino)phenoxy)cyclobutan-1-ol, formate salt;

Compound 313: 3-(2-Chloro-4-((4-(((7S,8aS)-3,3-dimethyloctahydroindolizin-7-yl)amino)-5-fluoropyrimidin-2-yl)amino)phenoxy)cyclobutan-3-d-1-ol, formate salt;

Compound 314: 4-((7R,8aS)-octahydro-5,5-dimethylindolizin-7-ylamino)-2-(4-((R)-2-hydroxypropoxy)-2-fluoro-5-(4,5-dihydro-4-methyl-5-oxotetrazol-1-yl)phenylamino)pyrimidine-5-carbonitrile, formate salt;

Compound 315: 4-methyl-N-(5-(4-((7R,8aS)-octahydro-5,5-dimethylindolizin-7-ylamino)-5-fluoropyrimidin-2-ylamino)-2H-1,4-benzoxazine-3(4H)-one, formate salt;

Compound 316: N²-(4,5-dihydro-4,4-bis(methoxymethyl)tetrazolo[5,1-c][1,4]benzoxazin-8-yl)-N⁴-((7R,8aS)-octahydro-5,5-dimethylindolizin-7-yl)-5-fluoropyrimidin-2,4-diamine;

Compound 317: N²-(4,5-dihydro-4,4-bis(methoxymethyl)tetrazolo[5,1-c][1,4]benzoxazin-8-yl)-N⁴-((7R,8aS)-octahydro-5,5-dimethylindolizin-7-yl)-5-fluoropyrimidin-2,4-diamine, formate salt;

Compound 318: 2,2,4-trimethyl-N-(5-(4-(((7R,8aS)-octahydro-5,5-dimethylindolizin-7-ylamino)-5-fluoropyrimidin-2-ylamino)-2H-1,4-benzoxazine-3(4H)-one, p-toluene sulfonic salt;

Compound 319: 4N-(1-methoxyethyl)-2,2-dimethyl-N-(5-(4-(((7R,8aS)-octahydro-5,5-dimethylindolizin-7-ylamino)-5-fluoropyrimidin-2-ylamino)-2H-1,4-benzoxazine-3(4H)-one, p-toluene sulfonic salt;

Compound 320: methyl 2-trifluoromethyl-N-(5-(4-(((7R,8aS)-octahydro-5,5-dimethylindolizin-7-ylamino)-5-fluoropyrimidin-2-ylamino)benzoate, formate salt;

Compound 321: 1-(4-(4-(((7R,8aS)-octahydro-5,5-dimethylindolizin-7-ylamino)-5-fluoropyrimidin-2-ylamino)-2-(trifluoromethyl)phenylamino)-3-chloropropa-2-ol, formate salt;

Compound 322: 2-(4-(4-(((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)phenoxy)acetamide, formate salt;

Compound 323: isopropyl 2-(4-(4-(((7R,8aS)-octahydro-5,5-dimethylindolizin-7-ylamino)-5-fluoropyrimidin-2-ylamino)-5-fluoro-2-(4,5-dihydro-4-methyl-5-oxotetrazol-1-yl)phenoxy)acetate, p-toluene sulfonic salt;

Compound 324: 1-(4-(4-(((7R,8aS)-octahydro-5,5-dimethylindolizin-7-ylamino)-5-fluoropyrimidin-2-ylamino)-2-(trifluoromethyl)phenyl)azetidine-3-carboxamide, formate salt;

Compound 325: 1-(4-(4-(((7R,8aS)-octahydro-5,5-dimethylindolizin-7-ylamino)-5-fluoropyrimidin-2-ylamino)-2-((2-trifluoromethylphenylamino)methyl)-3-chloropropanamide, p-toluene sulfonic salt;

Compound 326: 1-(4-(4-(((7R,8aS)-octahydro-5,5-dimethylindolizin-7-ylamino)-5-fluoropyrimidin-2-ylamino)-2-(trifluoromethyl)phenyl)azetidin-3-ol, formate salt;

Compound 327: 4-(4-(((7R,8aS)-octahydro-5,5-dimethylindolizin-7-ylamino)-5-fluoropyrimidin-2-ylamino)-2-chloro-N-methylbenzamide, p-toluene sulfonic salt; and Compound 328: 1-(5-(4-(((7R,8aS)-octahydro-5,5-dimethylindolizin-7-ylamino)-5-fluoropyrimidin-2-ylamino)-2-(3-hydroxyazetidin-1-yl)phenyl)-4-methyl-1H-tetrazol-5(4H)-one.

55. The method of claim 2, wherein the compound is selected from:

Compound 329: 1-(5-(4-(((7R,8aS)-5,5-dimethyloctahydroindolizin-7-ylamino)-5-fluoropyrimidin-2-ylamino)-4-fluoro-2-(2-fluoro-2-methylpropoxy)phenyl)-4-methyl-1H-tetrazol-5(4H)-one;

Compound 330: 1-(5-(4-(((7R,8aS)-5,5-dimethyloctahydroindolizin-7-ylamino)-5-fluoropyrimidin-2-ylamino)-4-fluoro-2-(2-fluoroethoxy)phenyl)-4-methyl-1H-tetrazol-5(4H)-one;

Compound 331: 1-(5-(4-(((7R,8aS)-5,5-dimethyloctahydroindolizin-7-ylamino)-5-fluoropyrimidin-2-ylamino)-4-fluoro-2-((S)-2-fluoropropoxy)phenyl)-4-methyl-1H-tetrazol-5(4H)-one;

Compound 332: 1-(5-(4-(((7R,8aS)-5,5-dimethyloctahydroindolizin-7-ylamino)-5-fluoropyrimidin-2-ylamino)-4-fluoro-2-((R)-2-fluoropropoxy)phenyl)-4-methyl-1H-tetrazol-5(4H)-one;

Compound 333: 4-(((7R,8aS)-5,5-dimethyloctahydroindolizin-7-yl)amino)-2-((2-fluoro-4-(2-fluoro-2-methylpropoxy)-5-(4-methyl-5-oxo-4,5-dihydro-1H-tetrazol-1-yl)phenyl)amino)pyrimidine-5-carbonitrile;

Compound 334: 4-((7R,8aS)-5,5-dimethyloctahydroindolizin-7-ylamino)-2-(2-fluoro-4-(2-fluoroethoxy)-5-(4-methyl-5-oxo-4,5-dihydro-1H-tetrazol-1-yl)phenylamino)pyrimidine-5-carbonitrile;

Compound 335: 4-((7R,8aS)-5,5-dimethyloctahydroindolizin-7-ylamino)-2-(2-fluoro-4-((S)-2-fluoropropoxy)-5-(4-methyl-5-oxo-4,5-dihydro-1H-tetrazol-1-yl)phenylamino)pyrimidine-5-carbonitrile; and Compound 336: 4-((7R,8aS)-5,5-dimethyloctahydroindolizin-7-ylamino)-2-(2-fluoro-4-((R)-2-fluoropropoxy)-5-(4-methyl-5-oxo-4,5-dihydro-1H-tetrazol-1-yl)phenylamino)pyrimidine-5-carbonitrile.

\* \* \* \* \*

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 1

Arg Phe Ala Arg Lys Gly Ser Leu Arg Gln Lys Asn Val
1               5                   10